US012528820B2

(12) United States Patent
Jin

(10) Patent No.: US 12,528,820 B2
(45) **Date of Patent: *Jan. 20, 2026**

(54) LUMINESCENCE DEVICE AND POLYCYCLIC COMPOUND FOR LUMINESCENCE DEVICE

(71) Applicant: Samsung Display Co., LTD., Yongin-si (KR)

(72) Inventor: XiuLan Jin, Yokohama (JP)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 594 days.

This patent is subject to a terminal disclaimer.

(21) Appl. No.: 16/935,413

(22) Filed: Jul. 22, 2020

(65) Prior Publication Data

US 2021/0104675 A1 Apr. 8, 2021

(30) Foreign Application Priority Data

Oct. 7, 2019 (KR) ........................ 10-2019-0123810

(51) Int. Cl.
*H01L 51/00* (2006.01)
*C07D 491/04* (2006.01)
(Continued)

(52) U.S. Cl.
CPC ....... *C07D 491/04* (2013.01); *C07D 491/048* (2013.01); *C07D 495/04* (2013.01);
(Continued)

(58) Field of Classification Search
CPC ............. C07D 491/048; H10K 85/633; H10K 85/657; H10K 85/6574; H10K 85/6576; C09K 2211/1018
See application file for complete search history.

(56) References Cited

U.S. PATENT DOCUMENTS

| | | | |
|---|---|---|---|
| 9,893,293 B2 | 2/2018 | Sasaki et al. |
| 10,115,907 B2 | 10/2018 | Shin et al. |

(Continued)

FOREIGN PATENT DOCUMENTS

| | | |
|---|---|---|
| CN | 105655492 A | 6/2016 |
| CN | 108774236 A | 11/2018 |

(Continued)

OTHER PUBLICATIONS

KR20160122974 machine translation, downloaded on Oct. 22, 2022 from Google patents.*

(Continued)

*Primary Examiner* — Alexander C Kollias
(74) *Attorney, Agent, or Firm* — CANTOR COLBURN LLP

(57) ABSTRACT

The present disclosure herein relates to a luminescence device including a polycyclic compound represented by Formula 1 below in at least one functional layer and achieving a low driving voltage, high efficiency, and long life, and a polycyclic compound represented by Formula 1 below.

Formula 1

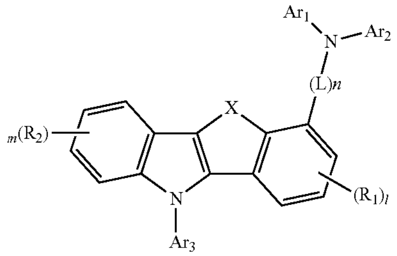

17 Claims, 2 Drawing Sheets

(51) Int. Cl.

| | |
|---|---|
| ***C07D 491/048*** | (2006.01) |
| ***C07D 495/04*** | (2006.01) |
| ***C09K 11/06*** | (2006.01) |
| ***H10K 85/60*** | (2023.01) |
| *H10K 50/11* | (2023.01) |
| *H10K 50/15* | (2023.01) |

(52) U.S. Cl.

CPC ............ *C09K 11/06* (2013.01); *H10K 85/633* (2023.02); *H10K 85/636* (2023.02); *C09K 2211/1018* (2013.01); *H10K 50/11* (2023.02); *H10K 50/15* (2023.02); *H10K 85/615* (2023.02); *H10K 85/657* (2023.02); *H10K 85/6574* (2023.02); *H10K 85/6576* (2023.02)

(56) References Cited

U.S. PATENT DOCUMENTS

| | | | | |
|---|---|---|---|---|
| 2013/0200350 | A1 | 8/2013 | Sawada et al. | |
| 2021/0104676 | A1 * | 4/2021 | Jin ........................ | C07D 495/04 |

FOREIGN PATENT DOCUMENTS

| | | | | |
|---|---|---|---|---|
| EP | 3029752 | A2 | 6/2016 | |
| JP | 2010270084 | A | 12/2010 | |
| JP | 2016111065 | A | 6/2016 | |
| KR | 1020140046771 | A | 4/2014 | |
| KR | 20150042386 | A | 4/2015 | |
| KR | 1020150058625 | A | 5/2015 | |
| KR | 1020150145131 | A | 12/2015 | |
| KR | 1020160082209 | A | 7/2016 | |
| KR | 20160122974 | A | 10/2016 | |
| KR | 1020170091470 | A | 8/2017 | |
| KR | 1020150145463 | A | 2/2019 | |
| KR | 1020190011463 | A | 2/2019 | |
| WO | 2012035934 | A1 | 3/2012 | |
| WO | WO-2014058183 | A1 * | 4/2014 | ........... C09D 209/56 |
| WO | 2019022435 | A1 | 1/2019 | |

OTHER PUBLICATIONS

English language translation of WO2014058183, pp. 1-47, Sep. 19, 2023.*

English langauge translation of KR 102343602, Sep. 19, 2023.*

English language translation of JP 2010270084, pp. 1-31, Mar. 24, 2025.*

Extended European Search Report dated Jan. 22, 2021, issued from the European Patent Office in respect of European Patent Application No. 20193076 which corresponds to the above-identified U.S. application.

General synthesis, structure, and optical properties of benzothiophene-fused benzoheteroles containing Group 15 and 16 elements, Tetrahedron 72 (2016) 8085-8090, Aichi Gakuin University.

Examination report Aug. 5, 2023 from the Chinese Patent Office in respect of the Chinese Patent Application Serial No. 202011059371.9, 7 pp.

* cited by examiner

LUMINESCENCE DEVICE AND POLYCYCLIC COMPOUND FOR LUMINESCENCE DEVICE

CROSS-REFERENCE TO RELATED APPLICATIONS

This U.S. non-provisional patent application claims priority under 35 U.S.C. § 119 to Korean Patent Application No. 10-2019-0123810, filed on Oct. 7, 2019, the entire contents of which are hereby incorporated by reference.

BACKGROUND

The present disclosure herein relates to a luminescence device and a polycyclic compound used therein.

There has been an increased interest in the development of an electroluminescence display as an image display. The electroluminescence display may include an organic electroluminescence display as an example. The organic electroluminescence display is different from a liquid crystal display and is a self-luminescent display in which a light-emitting material included in an emission layer emits light to produce a display by recombining holes and electrons injected from a first electrode and a second electrode in an emission layer.

In the application of a luminescence device to a display, an increase of the efficiency and life of the luminescence device is desirable. Therefore, there is a need for materials with improved properties such as driving voltage and emission efficiency for a luminescence device.

SUMMARY

The present disclosure provides a luminescence device having a low driving voltage, high efficiency, and long life.

The present disclosure also provides a polycyclic compound which may be applied to a luminescence device to accomplish a low driving voltage, high efficiency, and long life.

A luminescence device according to an embodiment may include a first electrode, a second electrode disposed on the first electrode, and at least one functional layer disposed between the first electrode and the second electrode. The at least one functional layer may include a polycyclic compound represented by the following Formula 1:

Formula 1

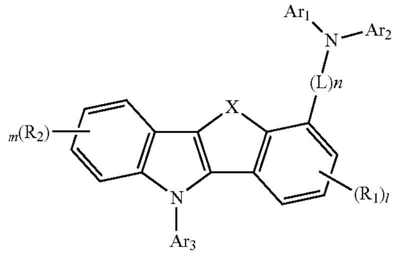

In Formula 1, X may be O, or S. $R_1$ and $R_2$ may each independently be a hydrogen atom, a deuterium atom, a halogen atom, a substituted or unsubstituted alkyl group of 1 to 20 carbon atoms, a substituted or unsubstituted aryl group of 6 to 30 ring carbon atoms, or a substituted or unsubstituted heteroaryl group of 2 to 30 ring carbon atoms. $Ar_1$ to $Ar_3$ may be each independently a substituted or unsubstituted aryl group of 6 to 30 ring carbon atoms, or a substituted or unsubstituted heteroaryl group of 2 to 30 ring carbon atoms. L may be a direct linkage, a substituted or unsubstituted arylene group of 6 to 30 ring carbon atoms, or a substituted or unsubstituted heteroarylene group of 2 to 30 ring carbon atoms. l may be an integer of 0 to 3. m may be an integer of 0 to 4. n may be an integer of 0 to 3.

In an embodiment, the at least one functional layer may include a hole transport region disposed on the first electrode, an emission layer disposed on the hole transport region, and an electron transport region disposed on the emission layer. The hole transport region may include the polycyclic compound.

In an embodiment, the hole transport region may further include a hole injection layer disposed on the first electrode, and a hole transport layer disposed between the hole injection layer and the emission layer. The hole transport layer may include the polycyclic compound.

In an embodiment, Formula 1 may include one acyclic amine.

In an embodiment, Formula 1 may be represented by the following Formula 1-1 or Formula 1-2:

Formula 1-1

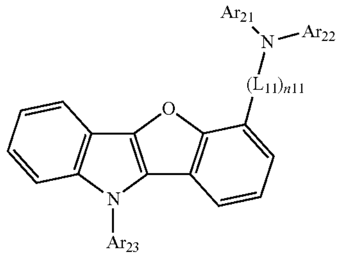

Formula 1-2

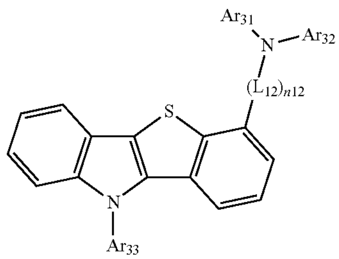

In Formula 1-1 and Formula 1-2, $Ar_{21}$ to $Ar_{23}$, and $Ar_{31}$ to $Ar_{33}$ may be each independently a substituted or unsubstituted aryl group of 6 to 30 ring carbon atoms, or a substituted or unsubstituted heteroaryl group of 2 to 30 ring carbon atoms. $L_{11}$, and $L_{12}$ may be each independently a direct linkage, a substituted or unsubstituted arylene group of 6 to 30 ring carbon atoms, or a substituted or unsubstituted heteroarylene group of 2 to 30 ring carbon atoms. n11, and n12 may be each independently an integer of 0 to 3.

In an embodiment, Formula 1 may be represented by the following Formula 1-3:

Formula 1-3

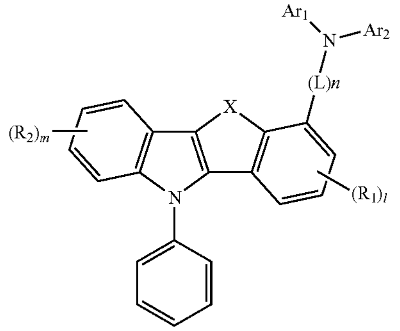

In Formula 1-3, X, $R_1$, $R_2$, $Ar_1$, $Ar_2$, L, and 1 to n may be the same as defined in Formula 1.

In an embodiment, Formula 1 may be represented by the following Formula 1-4:

Formula 1-4

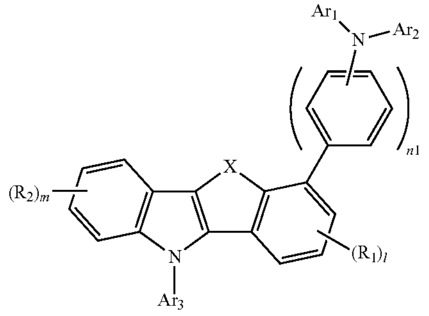

In Formula 1-4, n1 may be 0 or 1. X, $R_1$, $R_2$, $Ar_1$ to $Ar_3$, 1, and m may be the same as defined in Formula 1.

In an embodiment, $Ar_1$ and $Ar_2$ may be each independently represented by the following Formula 2:

$$*\text{—}(Ar_{11})_p\text{—}Ar_{12} \qquad \text{Formula 2}$$

In Formula 2, $Ar_n$ may be a substituted or unsubstituted phenylene group, a substituted or unsubstituted divalent biphenyl group, a substituted or unsubstituted divalent terphenyl group, a substituted or unsubstituted phenanthrylene group, a substituted or unsubstituted fluorenylene group, a substituted or unsubstituted naphthylene group, a substituted or unsubstituted carbazolylene group, a substituted or unsubstituted dibenzofuranylene group, or a substituted or unsubstituted dibenzothiophenylene group. $Ar_{12}$ may be a substituted or unsubstituted phenyl group, a substituted or unsubstituted biphenyl group, a substituted or unsubstituted terphenyl group, a substituted or unsubstituted phenanthryl group, a substituted or unsubstituted fluorenyl group, a substituted or unsubstituted naphthyl group, a substituted or unsubstituted carbazolyl group, a substituted or unsubstituted dibenzofuranyl group, or a substituted or unsubstituted dibenzothiophenyl group. p may be 0 or 1.

In an embodiment, $Ar_1$ and $Ar_2$ may be each independently represented by the following 1-1 to 1-10:

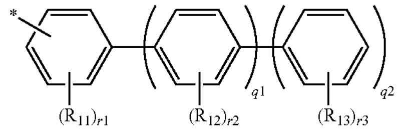

1-1

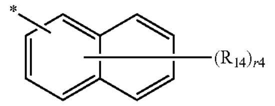

1-2

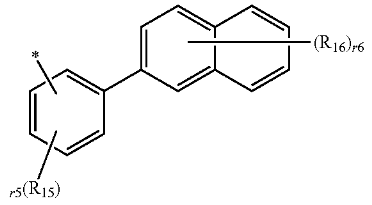

1-3

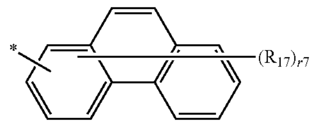

1-4

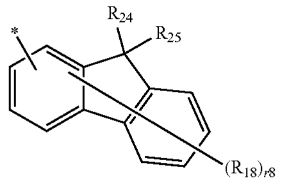

1-5

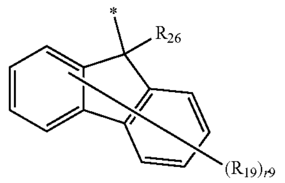

1-6

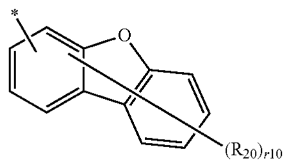

1-7

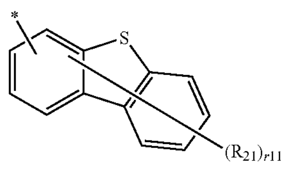

1-8

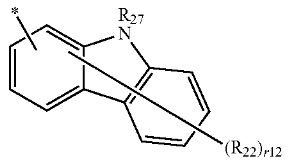

1-9

-continued 1-10

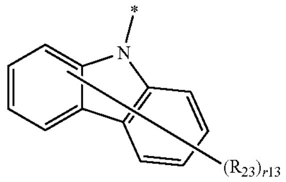

In 1-1 to 1-10 above, $R_{11}$ to $R_{27}$ may be each independently a hydrogen atom, a deuterium atom, a halogen atom, a substituted or unsubstituted alkyl group of 1 to 20 carbon atoms a substituted or unsubstituted aryl group of 6 to 30 ring carbon atoms, or a substituted or unsubstituted heteroaryl group of 2 to 30 ring carbon atoms. r1, r2, and r5 may be each independently an integer of 0 to 4. r3 may be an integer of 0 to 5. r4, r6, and r8 to r12 may be each independently an integer of 0 to 7. r7 may be an integer of 0 to 9. r13 may be an integer of 0 to 8. q1 and q2 may be each independently 0 or 1.

In an embodiment, Formula 1 may be represented by the following Formula 1-5:

Formula 1-5

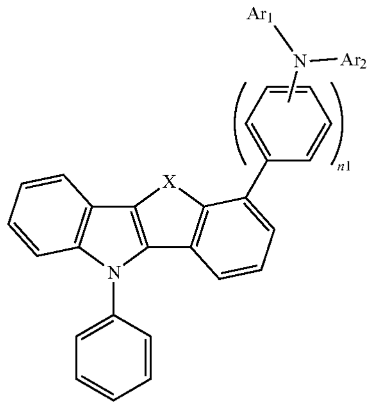

In Formula 1-5, n1 may be 0 or 1. X, $Ar_1$, and $Ar_2$ may be the same as defined in Formula 1.

According to an embodiment, a polycyclic compound represented by Formula 1 above may be provided.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
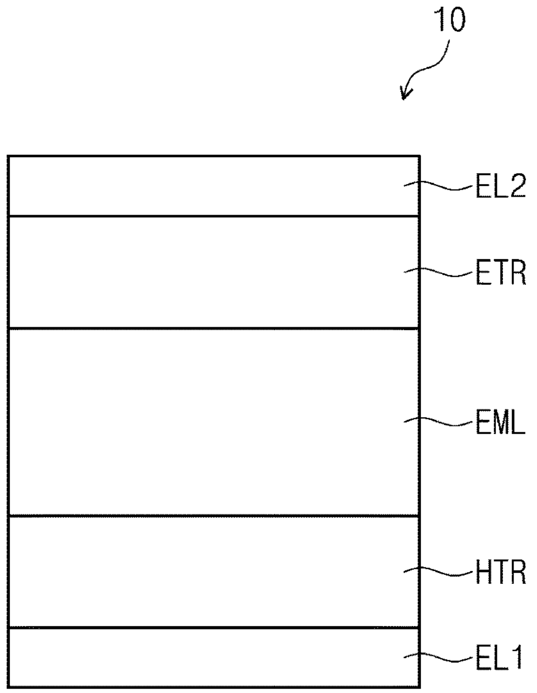
FIG. 1 is a cross-sectional view schematically illustrating a luminescence device according to an exemplary embodiment of the inventive concept.

The inventive concept may have various modifications and may be embodied in different forms, and example embodiments will be explained in detail with reference to the accompany drawings. The inventive concept may, however, be embodied in different forms and should not be construed as limited to the embodiments set forth herein. Rather, all modifications, equivalents, and substituents which are included in the spirit and technical scope of the inventive concept should be included in the inventive concept.

Like reference numerals refer to like elements throughout. In the drawings, the dimensions of structures are exaggerated for clarity of illustration. It will be understood that, although the terms first, second, etc. may be used herein to describe various elements, these elements should not be limited by these terms. These terms are only used to distinguish one element from another element. Thus, a first element could be termed a second element without departing from the teachings of the present invention. Similarly, a second element could be termed a first element. As used herein, the singular forms are intended to include the plural forms as well, unless the context clearly indicates otherwise.

It will be further understood that the terms "comprises" and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof.

It will also be understood that when a layer, a film, a region, a plate, etc. is referred to as being "on" or "above" another part, it can be "directly on" the other part, or intervening layers may also be present. On the contrary, it will also be understood that when a layer, a film, a region, a plate, etc. is referred to as being "under" or "below" another part, it can be "directly under" the other part, or intervening layers may also be present. Also, when an element is referred to as being disposed "on" another element, it can be disposed under the other element.

In the description, a substituent of a substituted group is at least one of a deuterium atom, a halogen atom, a cyano group, a nitro group, an amino group, a silyl group, an alkoxy group, an aryloxy group, a alkylthio group, an arylthio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. In addition, each of the substituents may be substituted or unsubstituted. For example, a biphenyl group may be interpreted as an aryl group or a phenyl group substituted with a phenyl group.

In the description, the term "adjacent group" means a pair of substituent groups where the first substituent is connected to an atom that is directly connected to another atom substituted with the second substituent, a pair of substituent groups connected to the same atom and different from each other, or a substituent sterically positioned at the nearest position to a corresponding substituent. For example, in 1,2-dimethylbenzene, two methyl groups may be interpreted as "adjacent groups" to each other, and in 1,1-diethylcyclopentane, two ethyl groups may be interpreted as "adjacent groups" to each other.

In the description, the halogen atom may be a fluorine atom, a chlorine atom, a bromine atom or an iodine atom.

In the description, the alkyl may be a linear, branched or cyclic type. The carbon number of the alkyl may be 1 to 50, 1 to 30, 1 to 20, 1 to 10, or 1 to 6. Examples of the alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, the hydrocarbon ring group means an optional functional group or substituent derived from an aliphatic hydrocarbon ring. The hydrocarbon ring group may be a saturated hydrocarbon ring group of 5 to 20 ring carbon atoms.

In the description, the aryl group means an optional functional group or substituent derived from an aromatic hydrocarbon ring. The aryl group may be a monocyclic aryl group or a polycyclic aryl group. The ring carbon number in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinquephenyl, sexiphenyl, triphenylenyl, pyrenyl, benzofluoranthenyl, chrysenyl, etc., without limitation.

In the description, the fluorenyl group may be substituted, and two substituents may be combined with each other to form a spiro structure. Examples of a substituted fluorenyl group are as follows. However, an embodiment of the inventive concept is not limited thereto.

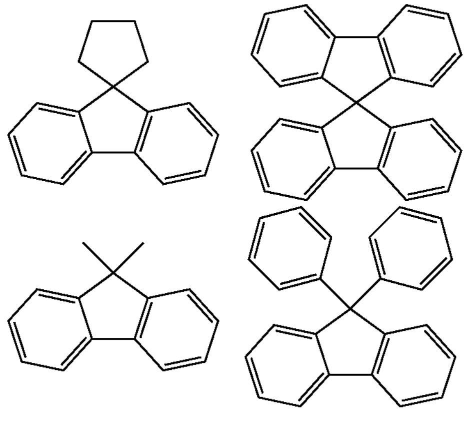

In the description, the heterocyclic group may include one or more among B, O, N, P, Si, Se, Ge, and S as heteroatoms. If the heterocyclic group includes two or more heteroatoms, two or more heteroatoms may be the same or different. The heterocyclic group may be a monocyclic heterocyclic group or a polycyclic heterocyclic group, and has a concept including a heteroaryl group. The ring carbon number of the heterocyclic group may be 2 to 30, 2 to 20, or 2 to 10.

In the description, the aliphatic heterocyclic group may include one or more among B, O, N, P, Si, Se, Ge, and S as heteroatoms. The ring carbon number of the aliphatic heterocyclic group may be 2 to 30, 2 to 20, or 2 to 10. Examples of the aliphatic heterocyclic group may include an oxirane group, a thiirane group, a pyrrolidine group, a piperidine group, a tetrahydrofuran group, a tetrahydrothiophene group, a thiane group, a tetrahydropyran group, a 1,4-dioxane group, etc., without limitation.

In the description, the heteroaryl group may include one or more among B, O, N, P, Si, Se, Ge, and S as heteroatoms. If the heteroaryl group includes two or more heteroatoms, two or more heteroatoms may be the same or different. The heteroaryl group may be a monocyclic heteroaryl group or polycyclic heteroaryl group. The carbon number for forming a ring of the heteroaryl group may be 2 to 30, 2 to 20, or 2 to 10. Examples of the heteroaryl group may include thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, isooxazole, oxadiazole, thiadiazole, phenothiazine, dibenzosilole, dibenzofuran, etc., without limitation.

In the description, the aryl group may be applied to the arylene group except that the arylene group is a divalent group. The explanation on the heteroaryl group may be applied to the heteroarylene group except that the heteroarylene group is a divalent group.

In the description, the alkenyl group may be a linear chain or a branched chain. The carbon number is not specifically limited but may be 2 to 30, 2 to 20, or 2 to 10. Examples of the alkenyl group may include a vinyl group, a 1-butenyl group, a 1-pentenyl group, a 1,3-butadienyl aryl group, a styrenyl group, a styrylvinyl group, etc., without limitation.

In the description, the alkoxy group may be a linear, branched or cyclic chain. The carbon number of the alkoxy group is not specifically limited but may be, for example, 1 to 20 or 1 to 10. Examples of the alkoxy group may include methoxy, ethoxy, n-propoxy, isopropoxy, butoxy, pentyloxy, hexyloxy, octyloxy, nonyloxy, decyloxy, etc. However, an embodiment of the inventive concept is not limited thereto.

In the description, the carbon number for forming a ring of the aryl oxy group is not specifically limited, but for example, may be 6 to 30, 6 to 20, or 6 to 15.

In the description, the alkylthio group may be a linear, branched or cyclic chain. The carbon number of the alkylthio group is not specifically limited but may be, for example, 1 to 20 or 1 to 10. Examples of the alkylthio group may include —S-methyl, —S-ethyl, —S-n-propyl, —S-isopropyl, and the like. However, an embodiment of the inventive concept is not limited thereto.

In the description, the carbon number for forming a ring of the aryl thio group is not specifically limited, but for example, may be 6 to 30, 6 to 20, or 6 to 15.

In the description, the carbon number of the amine group is not specifically limited, but may be 1 to 30. The amine group may include an alkyl amine group and an aryl amine group. Examples of the amine group include a methylamine group, a dimethylamine group, a phenylamine group, a diphenylamine group, a naphthylamine group, a 9-methyl-anthracenylamine group, a triphenylamine group, etc., without limitation.

The aryl amine group is defined as an amine group in which at least one of an aryl group or a heteroaryl group is substituted at a nitrogen atom.

In the description, the direct linkage may mean a single bond.

Meanwhile, in the description, "*—" means a connected position.

FIG. 1 is a cross-sectional view schematically showing a luminescence device 10 according to an embodiment of the inventive concept. The luminescence device 10 according to an embodiment may include a first electrode EL1, a hole transport region HTR, an emission layer EML, an electron transport region ETR, and a second electrode EL2 stacked in order. The luminescence device 10 may be an organic electroluminescence device including an organic light-emitting material, but an embodiment of the inventive concept is not limited thereto. Hereinafter, the explanation will be based on that the luminescence device 10 is an organic electroluminescence device.

FIGS. 1 to 4 are cross-sectional views schematically showing luminescence devices 10 according to exemplary embodiments of the inventive concept. Referring to FIGS. 1 to 4, in a luminescence device 10 according to an embodiment, a first electrode EL1 and a second electrode EL2 are oppositely disposed, and between the first electrode EL1 and the second electrode EL2, an emission layer EML may be disposed.

In addition, the luminescence device 10 of an embodiment further includes a plurality of functional layers between the first electrode EL1 and the second electrode EL2 in addition to the emission layer EML. The plurality of the functional layers may include a hole transport region HTR and an electron transport region ETR. That is, the luminescence device 10 of an embodiment may include a first electrode EL1, a hole transport region HTR, an emission layer EML, an electron transport region ETR, and a second electrode, stacked in order. In addition, the luminescence device 10 of an embodiment may include a capping layer CPL which is disposed on the second electrode EL2.

The luminescence device 10 of an embodiment may include a compound of an embodiment, which will be explained later, in the emission layer EML which is disposed between the first electrode EL1 and the second electrode EL2. However, an embodiment of the inventive concept is not limited thereto, and the luminescence device 10 of an embodiment may include a polycyclic compound of an embodiment, which will be explained later, in the hole transport region HTR or the electron transport region ETR, which are functional layers disposed between the first electrode EL1 and the second electrode EL2, or include a polycyclic compound of an embodiment, which will be explained later, in the capping layer CPL disposed on the second electrode EL2, in addition to the emission layer EML.

Figure 2:
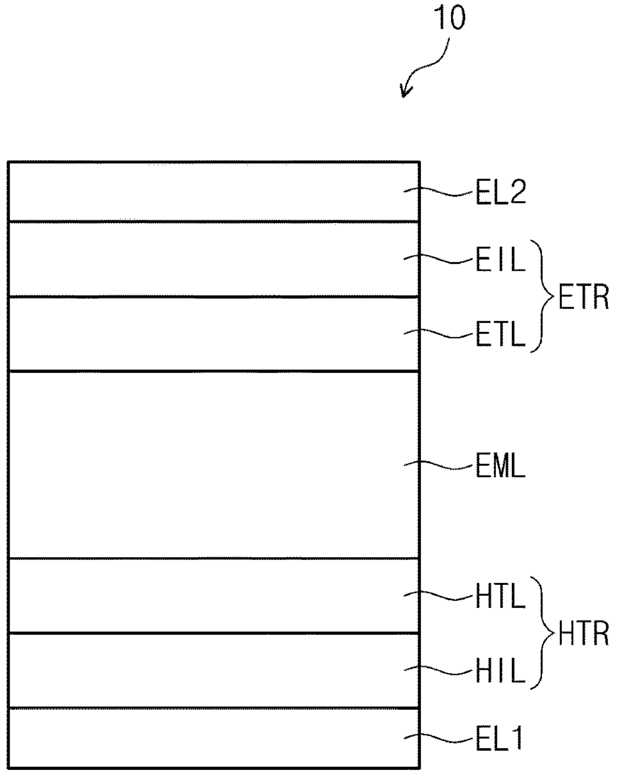
FIG. 2 is a cross-sectional view schematically illustrating a luminescence device according to an embodiment of the inventive concept.
Figure 3:
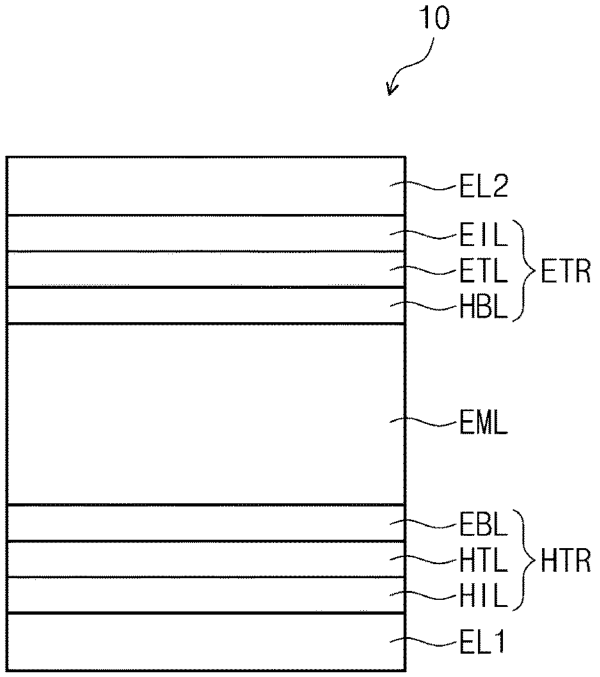
FIG. 3 is a cross-sectional view schematically illustrating a luminescence device according to an embodiment of the inventive concept.
Figure 4:
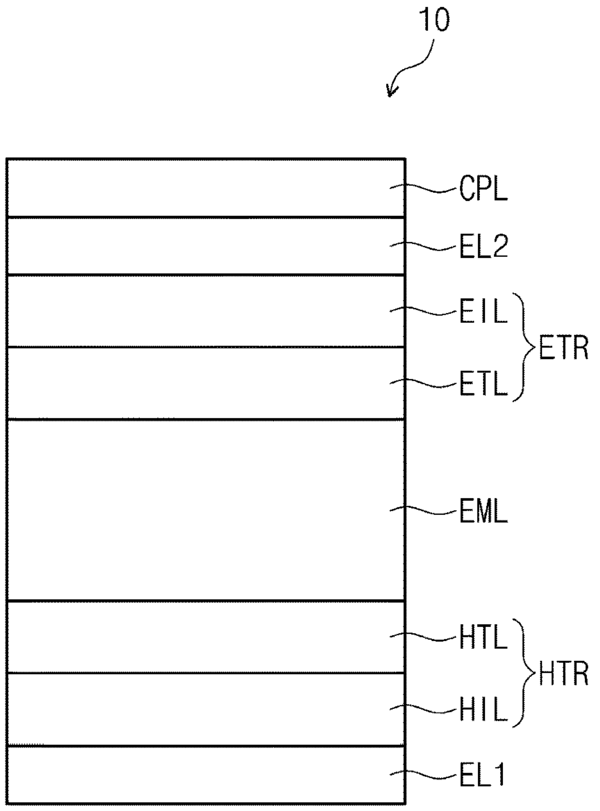
FIG. 4 is a cross-sectional view schematically illustrating a luminescence device according to an embodiment of the inventive concept.

Meanwhile, when compared with FIG. 1, FIG. 2 shows the cross-sectional view of a luminescence device 10 of an embodiment, wherein a hole transport region HTR includes a hole injection layer HIL and a hole transport layer HTL, and an electron transport region ETR includes an electron injection layer EIL and an electron transport layer ETL. In addition, when compared with FIG. 1, FIG. 3 shows the cross-sectional view of a luminescence device 10 of an embodiment, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. When compared with FIG. 2, FIG. 4 shows the cross-sectional view of a luminescence device 10 of an embodiment, including a capping layer CPL disposed on the second electrode EL2.

At least one functional layer may include a polycyclic compound represented by the following Formula 1:

Formula 1

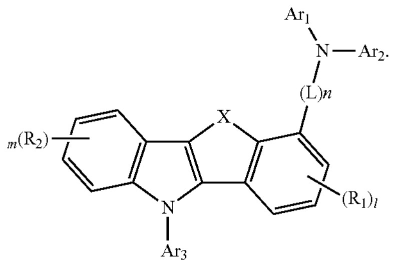

In Formula 1, X may be O, or S. $R_1$ and $R_2$ may be each independently a hydrogen atom, a deuterium atom, a halogen atom, an alkyl group, an aryl group, or a heteroaryl group. The alkyl group may be a substituted or unsubstituted alkyl group of 1 to 20 carbon atoms. The aryl group may be a substituted or unsubstituted aryl group of 6 to 30 ring carbon atoms. The heteroaryl group may be a substituted or unsubstituted heteroaryl group of 2 to 30 ring carbon atoms.

$Ar_1$ to $Ar_3$ may be each independently an aryl group, or a heteroaryl group. The aryl group may be a substituted or unsubstituted aryl group of 6 to 30 ring carbon atoms. The heteroaryl group may be a substituted or unsubstituted heteroaryl group of 2 to 30 ring carbon atoms.

For example, $Ar_3$ may be a substituted or unsubstituted phenyl group.

L may be a direct linkage, an arylene group, or a heteroarylene group. The arylene group may be a substituted or unsubstituted arylene group of 6 to 30 ring carbon atoms. The heteroarylene group may be a substituted or unsubstituted heteroarylene group of 2 to 30 ring carbon atoms. For example, L may be a substituted or unsubstituted phenylene group.

In case where $Ar_1$ to $Ar_3$, and L are substituted groups, they may be substituted with, for example, halogen atoms. The halogen atom may be, for example, a fluorine atom which has high inductive effect and small electron donor properties because of the resonance effect.

1 may be an integer of 0 to 3. m may be an integer of 0 to 4. n may be an integer of 0 to 3. If 1 is an integer of 2 or more, a plurality of $R_1$ groups may be the same or different. If 1 is an integer of 2 or more, at least one $R_1$ may not be a hydrogen atom. If m is an integer of 2 or more, a plurality of $R_2$ groups may be the same or different. If m is an integer of 2 or more, at least one $R_2$ may not be a hydrogen atom. If n is an integer of 2 or more, a plurality of L groups may be the same or different. If n is an integer of 2 or more, at least one L may not be a direct linkage.

The polycyclic compound of an embodiment may include one acyclic amine. The polycyclic compound of an embodiment may not include a cyclic amine. That is, the polycyclic compound represented by Formula 1 may not include any acyclic amine excluding *—$NAr_1Ar_2$.

$Ar_1$ and $Ar_2$ may be each independently represented by the following Formula 2:

$$*-(Ar_{11})_p-Ar_{12}$$ Formula 2

In Formula 2, $Ar_{11}$ may be a substituted or unsubstituted phenylene group, a substituted or unsubstituted divalent biphenyl group, a substituted or unsubstituted divalent terphenyl group, a substituted or unsubstituted phenanthrylene group, a substituted or unsubstituted fluorenylene group, a substituted or unsubstituted naphthylene group, a substituted or unsubstituted carbazolylene group, a substituted or unsubstituted dibenzofuranylene group, or a substituted or unsubstituted dibenzothiophenylene group.

$Ar_{12}$ may be a substituted or unsubstituted phenyl group, a substituted or unsubstituted biphenyl group, a substituted or unsubstituted terphenyl group, a substituted or unsubstituted phenanthryl group, a substituted or unsubstituted fluorenyl group, a substituted or unsubstituted naphthyl group, a substituted or unsubstituted carbazolyl group, a substituted or unsubstituted dibenzofuranyl group, or a substituted or unsubstituted dibenzothiophenyl group.

p may be 0 or 1.

$Ar_1$ and $Ar_2$ may be each independently represented by the following 1-1 to 1-10:

1-1

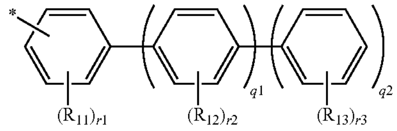

1-2

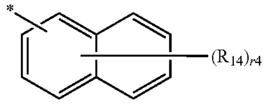

1-3

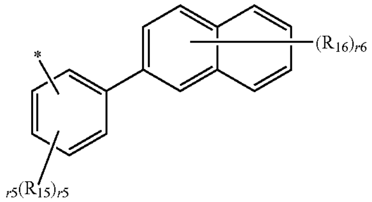

1-4

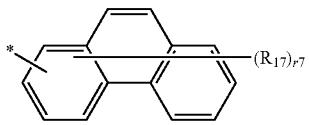

1-5

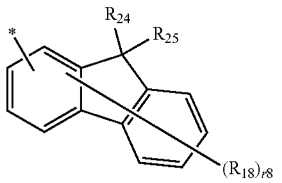

1-6

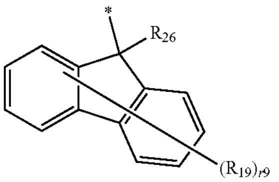

-continued 1-7

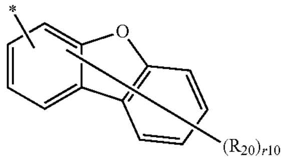

1-8

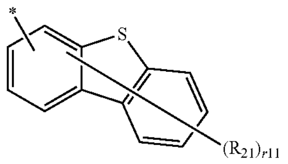

1-9

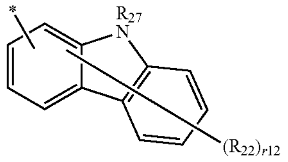

1-10

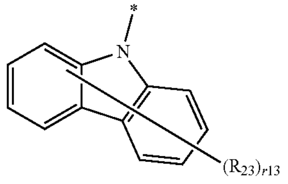

In 1-1 to 1-10 above, $R_{11}$ to $R_{27}$ may be each independently a hydrogen atom, a deuterium atom, an alkyl group, a halogen atom, an aryl group, or a heteroaryl group. The alkyl group may be a substituted or unsubstituted alkyl group of 1 to 20 carbon atoms. The aryl group may be a substituted or unsubstituted aryl group of 6 to 30 ring carbon atoms. The heteroaryl group may be a substituted or unsubstituted heteroaryl group of 2 to 30 ring carbon atoms. For example, $R_{11}$ to $R_{27}$ may be each independently a hydrogen atom, a halogen atom, or a substituted or unsubstituted phenyl group.

r1, r2, and r5 may be each independently an integer of 0 to 4. r3 may be an integer of 0 to 5. r4, r6, and r8 to r12 may be each independently an integer of 0 to 7. r7 may be an integer of 0 to 9. r13 may be an integer of 0 to 8. q1 and q2 may be each independently 0 or 1. For example, r1 to r13 may be each independently 0, or 1. Otherwise, all r1 to r13 may be 0.

If r1 is an integer of 2 or more, a plurality of $R_{11}$ groups may be the same or different. The same explanation may be applied to r2 to r13.

Formula 1 may be represented by the following Formula 1-1 or Formula 1-2:

Formula 1-1

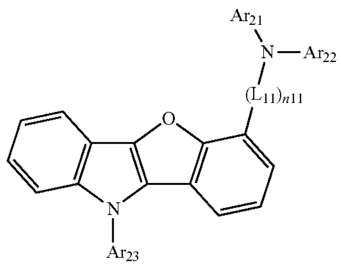

-continued

Formula 1-2

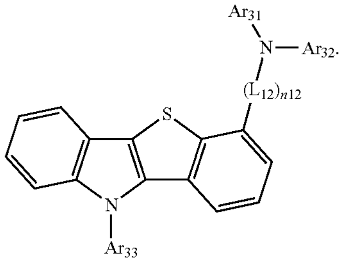

Formula 1-1 corresponds to Formula 1, wherein X, and 1 are embodied. Formula 1-2 corresponds to Formula 1, wherein X, and m are embodied.

$Ar_{21}$ to $Ar_{23}$, and $Ar_{31}$ to $Ar_{33}$ may be each independently an aryl group, or a heteroaryl group. The aryl group may be a substituted or unsubstituted aryl group of 6 to 30 ring carbon atoms. The heteroaryl group may be a substituted or unsubstituted heteroaryl group of 2 to 30 ring carbon atoms.

$L_{11}$, and $L_{12}$ may be each independently a direct linkage, an arylene group, or a heteroarylene group. The arylene group may be a substituted or unsubstituted arylene group of 6 to 30 ring carbon atoms. The heteroarylene group may be a substituted or unsubstituted heteroarylene group of 2 to 30 ring carbon atoms.

n11, and n12 may be each independently an integer of 0 to 3.

Formula 1 may be represented by the following Formula 1-3:

Formula 1-3

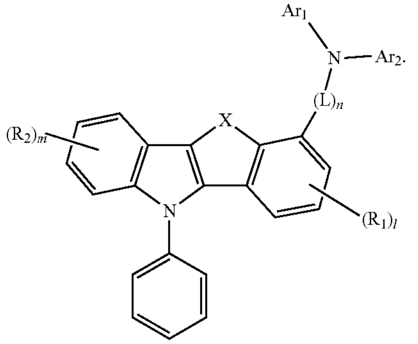

Formula 1-3 corresponds to Formula 1, wherein $Ar_3$ is an unsubstituted phenyl group. In Formula 1-3, X, $R_1$, $R_2$, $Ar_1$, $Ar_2$, L, and 1 to n may be the same as defined in Formula 1.

Formula 1 may be represented by the following Formula 1-4:

Formula 1-4

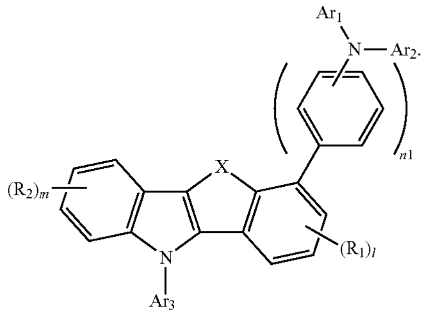

Formula 1-4 corresponds to Formula 1, wherein L is a direct linkage, or an unsubstituted phenylene group. In Formula 1-4, n1 may be 0 or 1. In Formula 1-4, X, $R_1$, $R_2$, $Ar_1$ to $Ar_3$, 1, and m may be the same as defined in Formula 1.

Formula 1 may be represented by the following Formula 1-5:

Formula 1-5

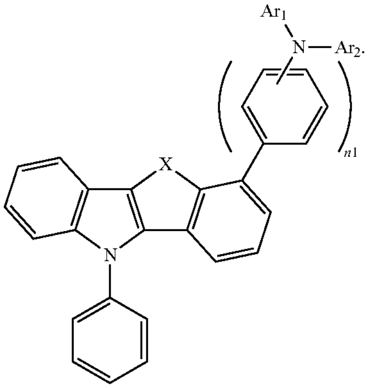

Formula 1-5 corresponds to Formula 1, wherein $Ar_3$ is an unsubstituted phenyl group, and L is a direct linkage, or an unsubstituted phenylene group. In Formula 1-5, n1 may be 0 or 1. X, $Ar_1$, and $Ar_2$ may be the same as defined in Formula 1.

The polycyclic compound of an embodiment may be any one among Compound Group 1 and Compound Group 2:

Control Group 1

A1

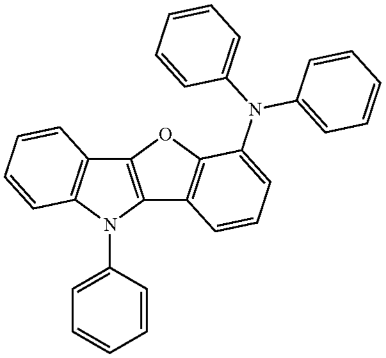

-continued
A2
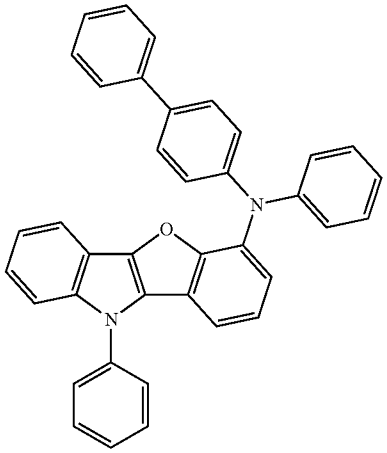
A3
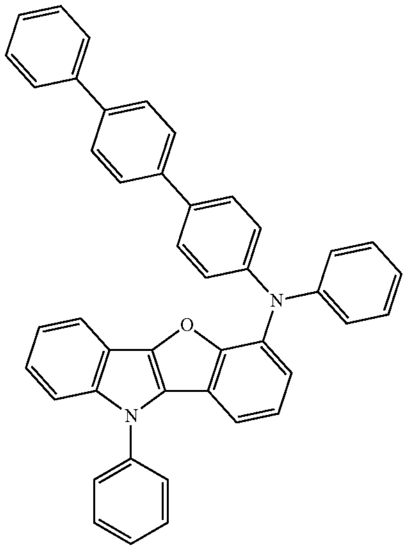
A4
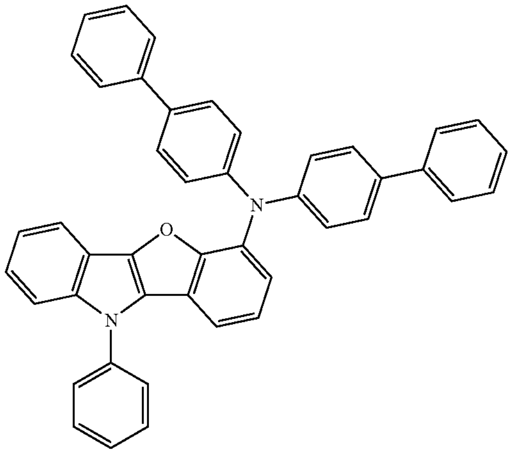
-continued
A5
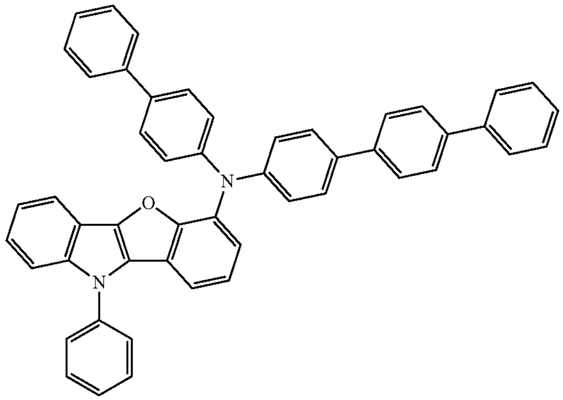
A6
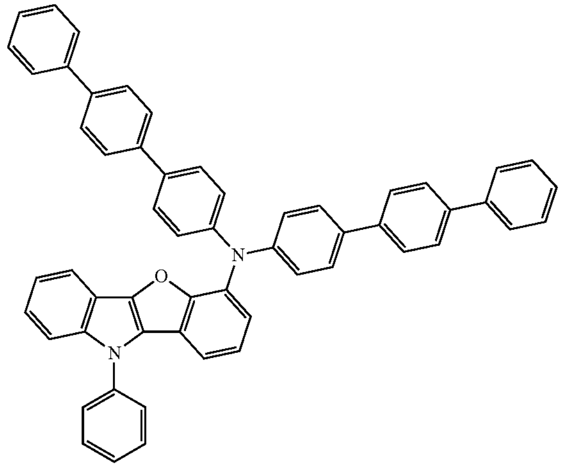
A7
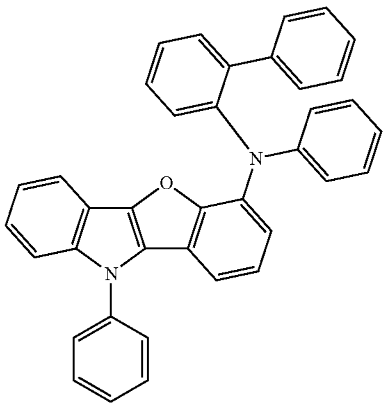

-continued
A8
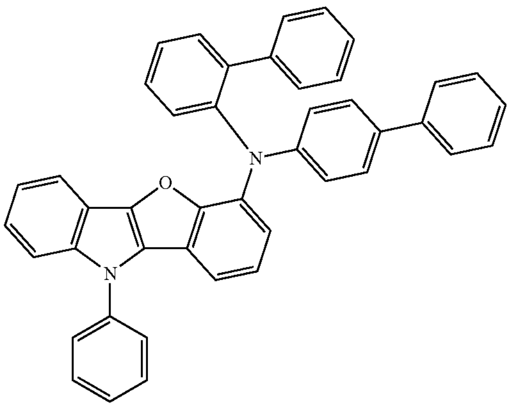
A9
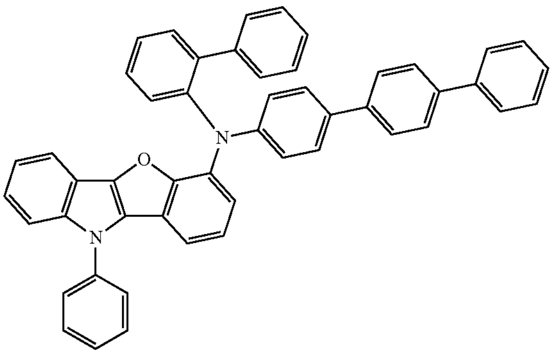
A10
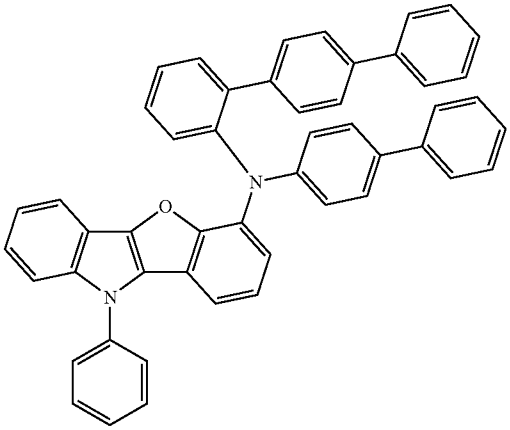
-continued
A11
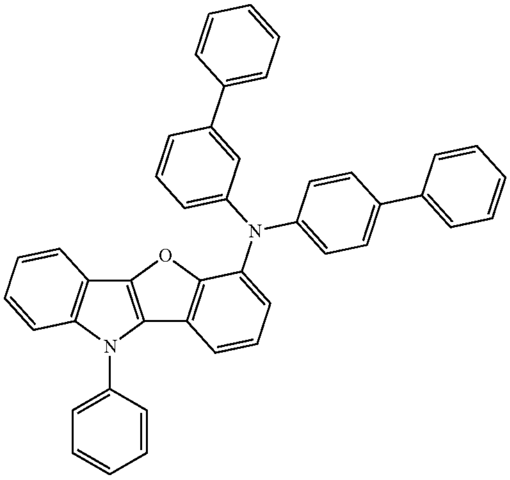
A12
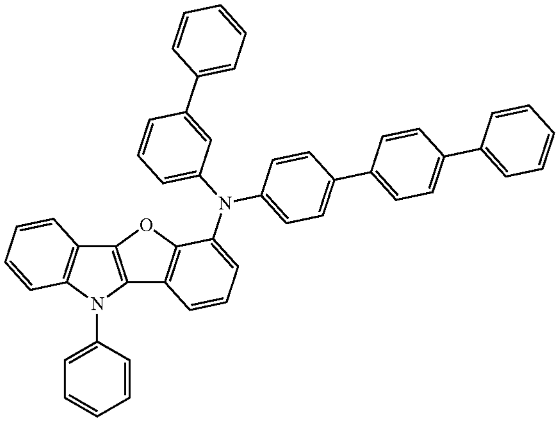
A13
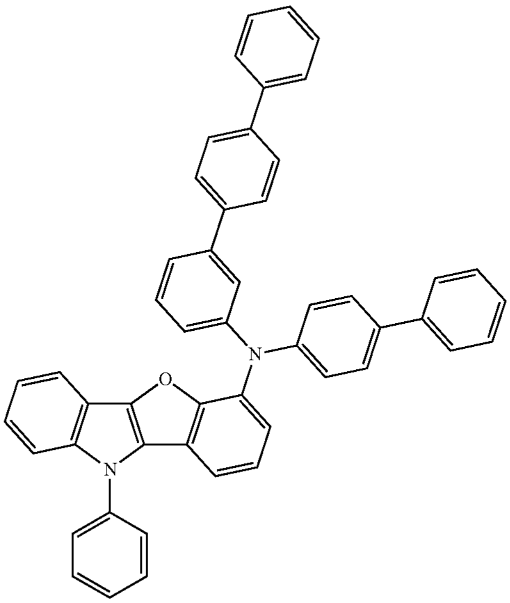

-continued
A14
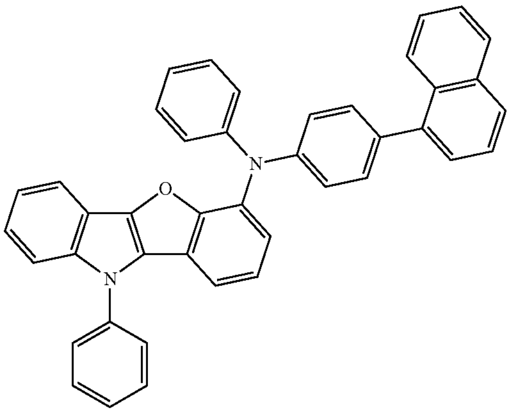
A15
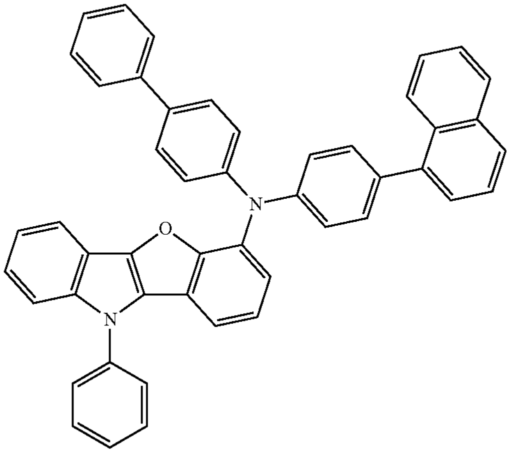
A16
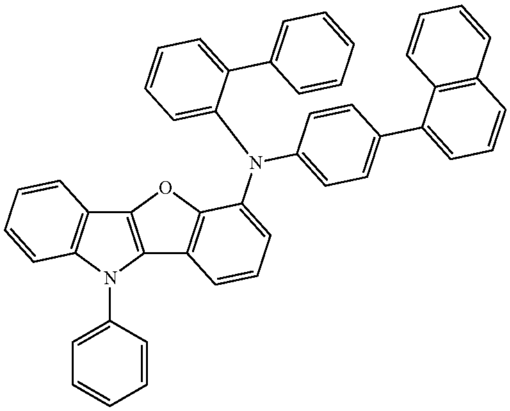
-continued
A17
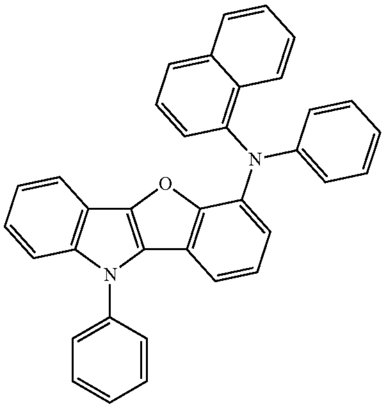
A18
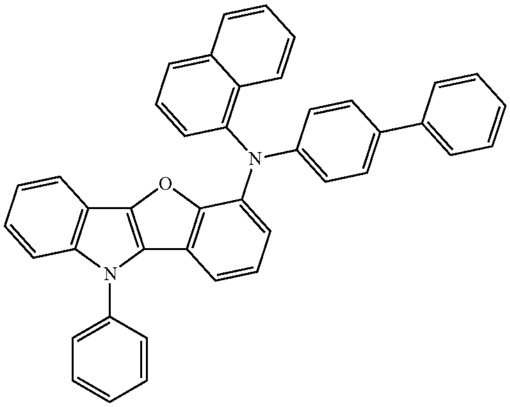
A19
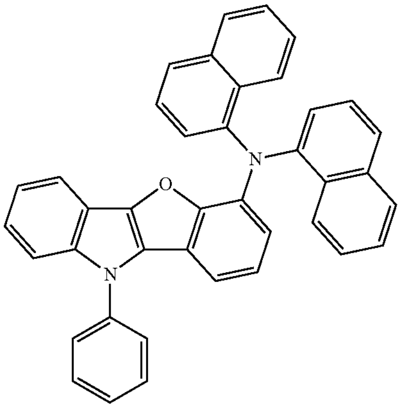

-continued
A20
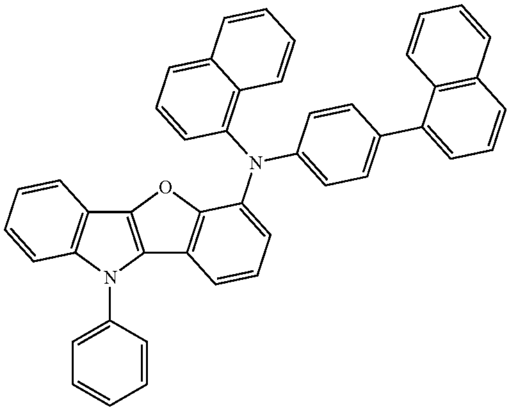
A21
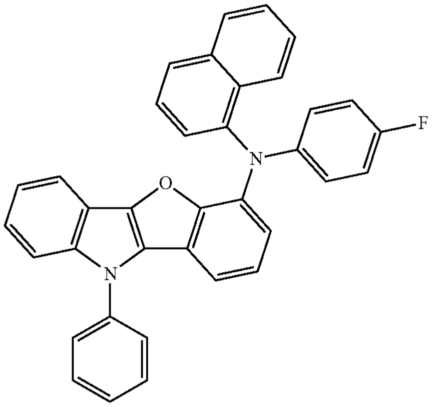
A22
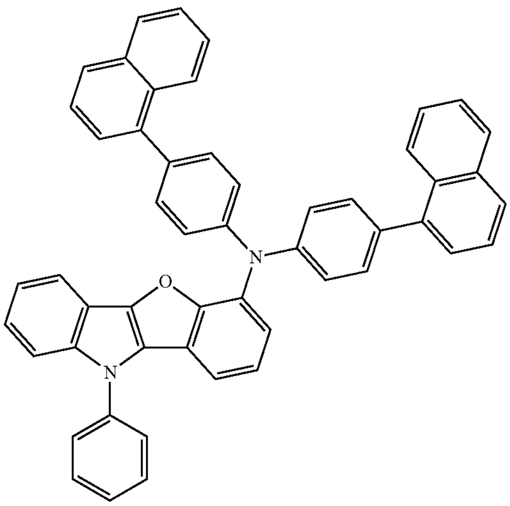
-continued
A23
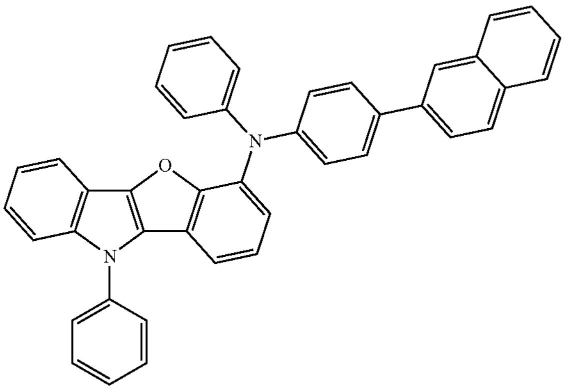
A24
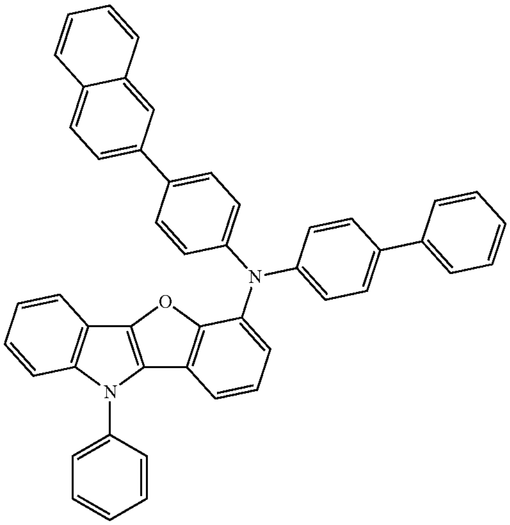
A25
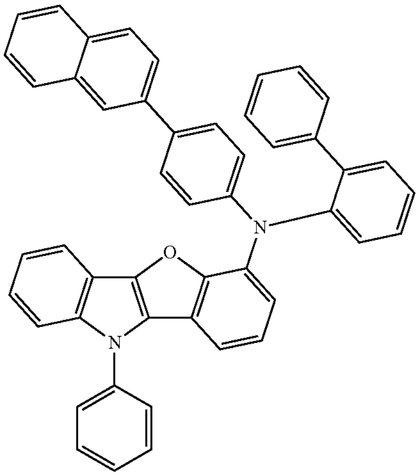

-continued
A26
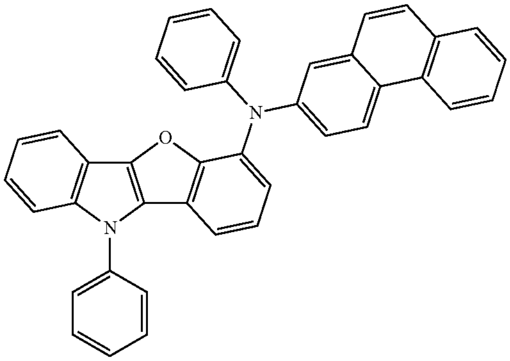
A27
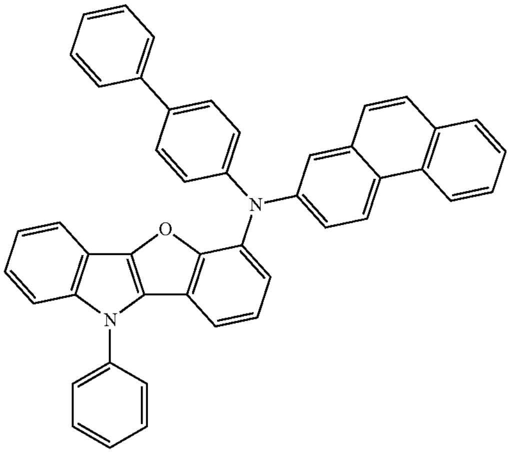
A28
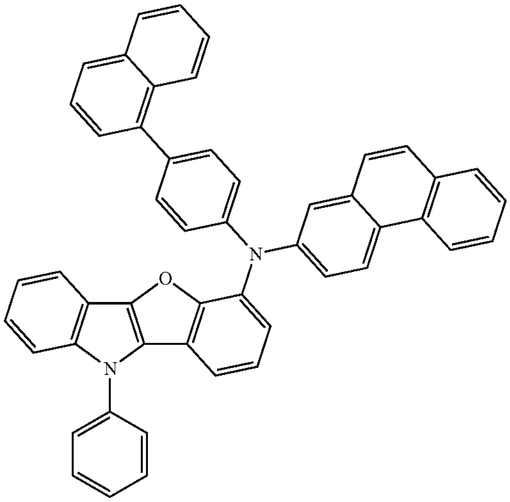
-continued
A29
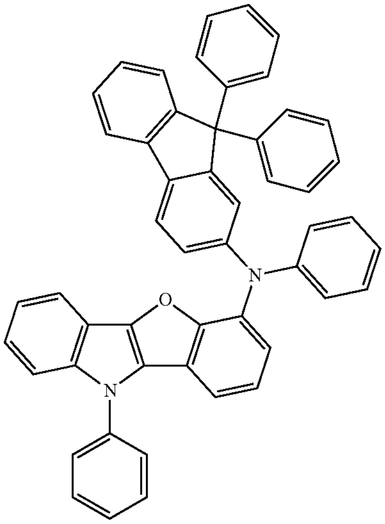
A30
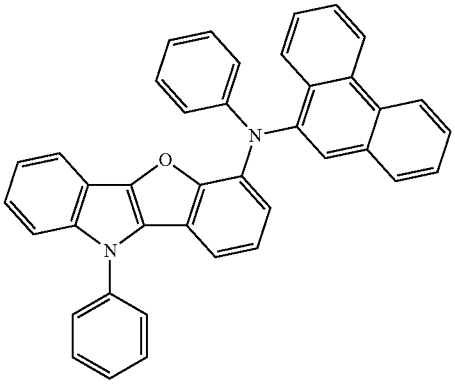
A31
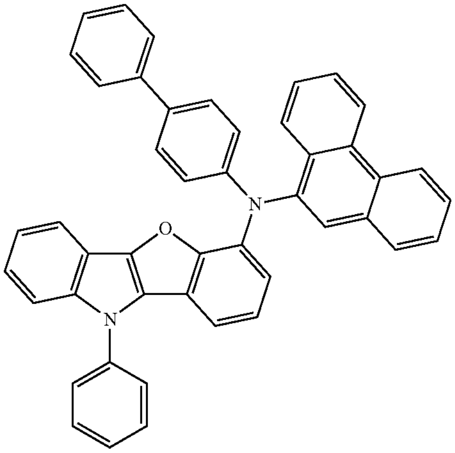

-continued
A32
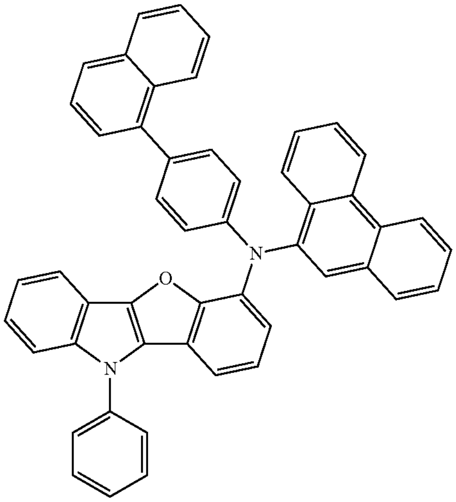
A33
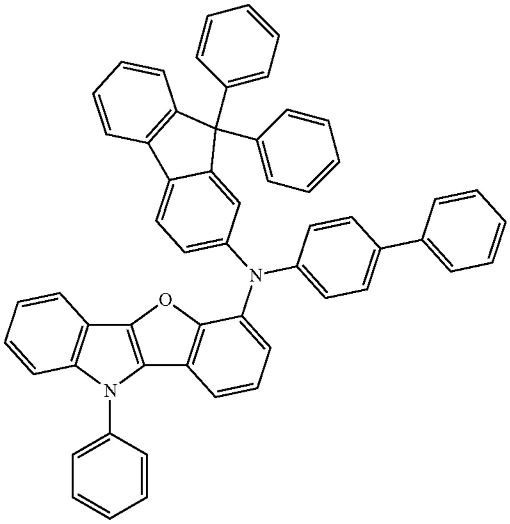
A34
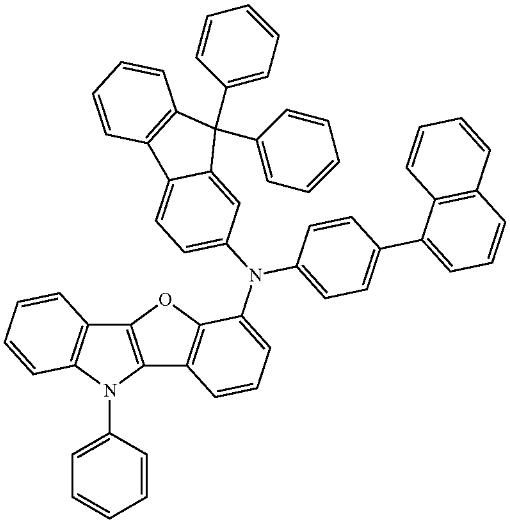
-continued
A35
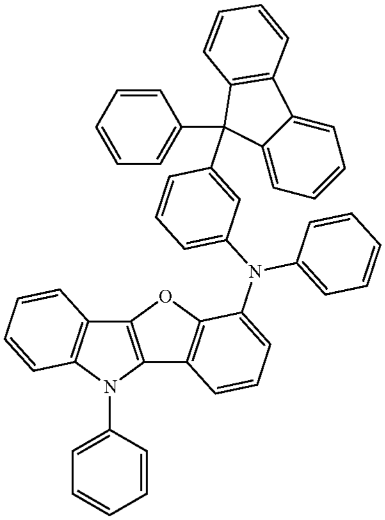
A36
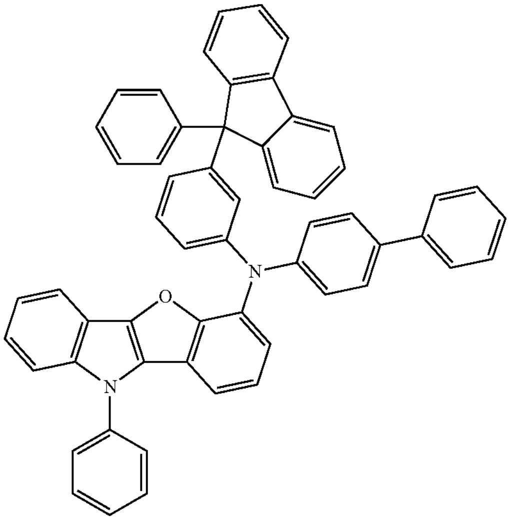
A37
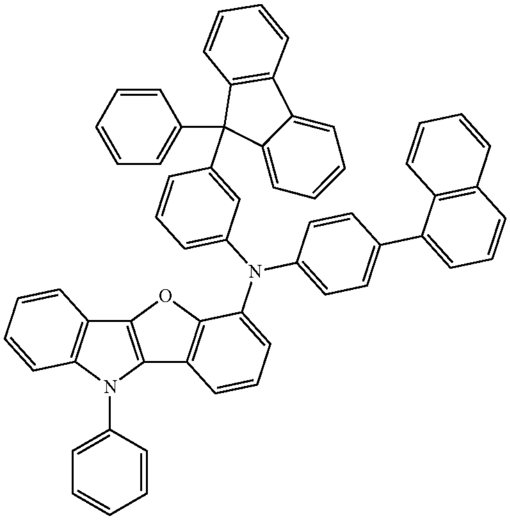

-continued
A38
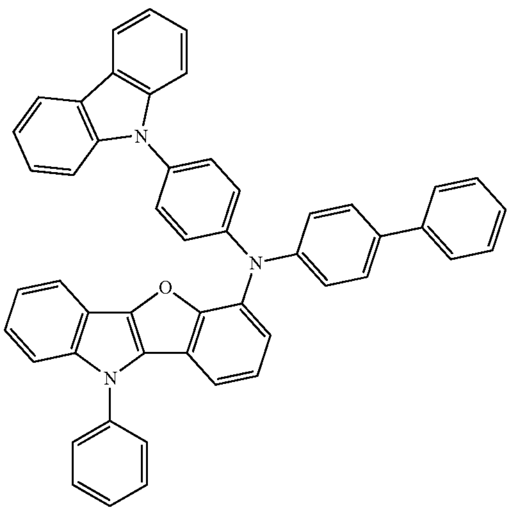
A39
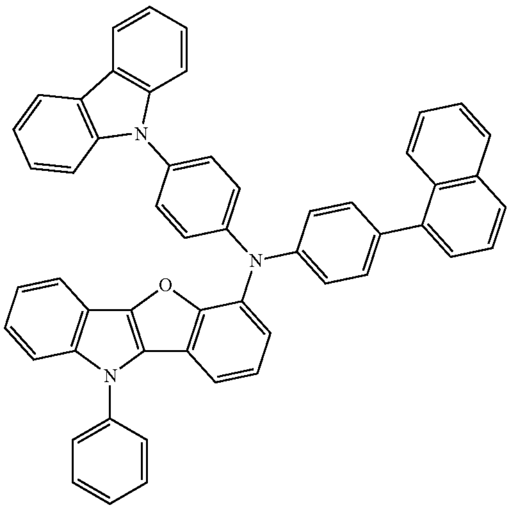
A40
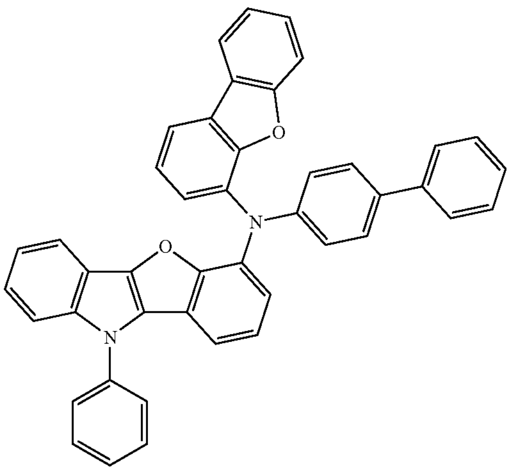
-continued
A41
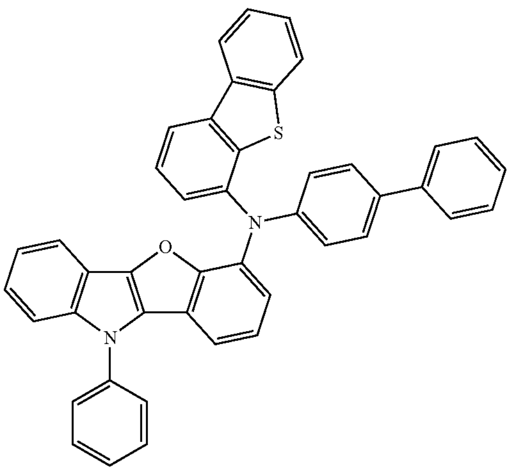
A42
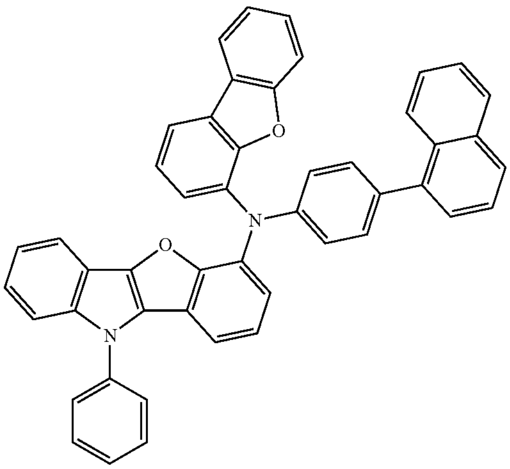
A43
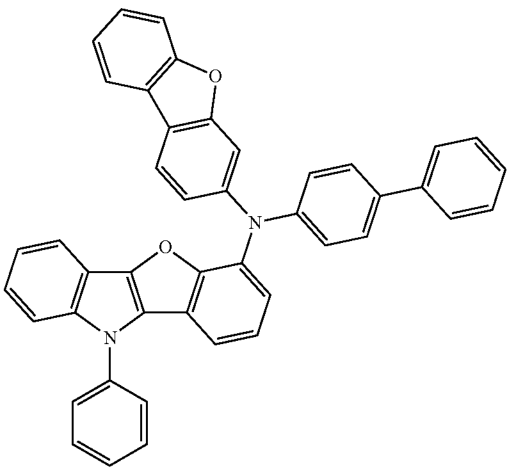

-continued
A44
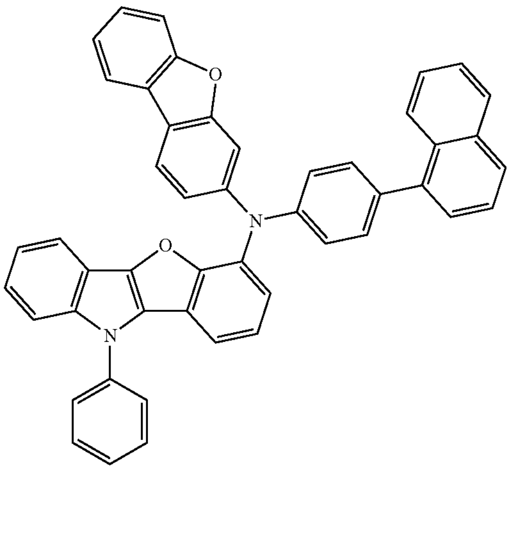
A45
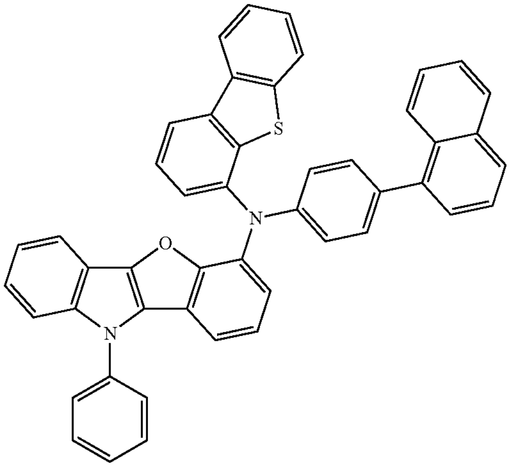
A46
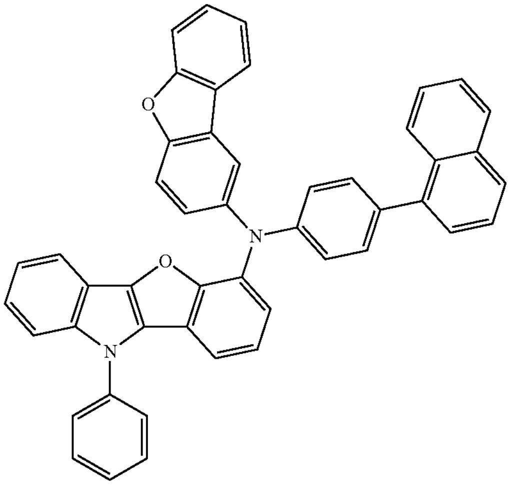
-continued
A47
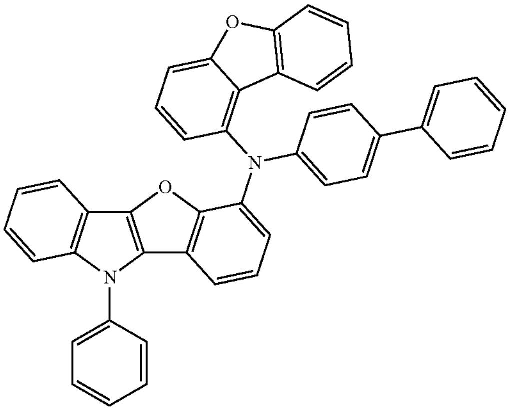
A48
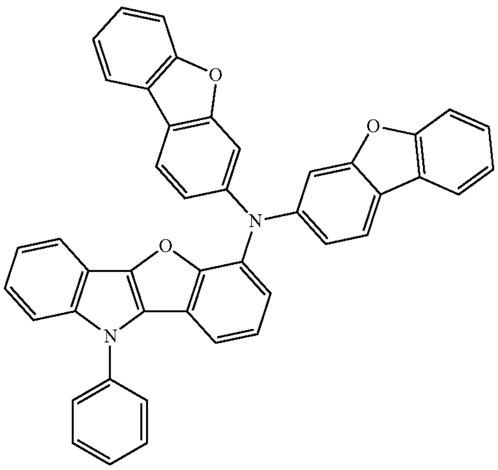
A49
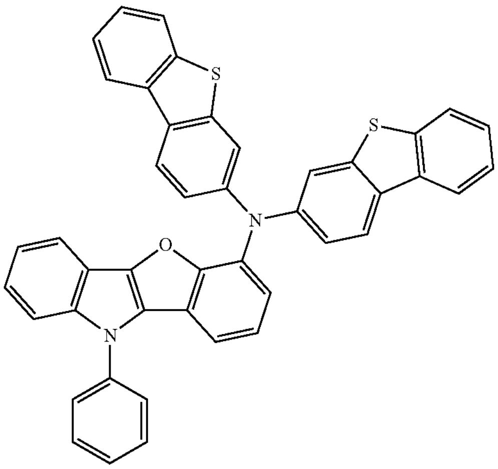

-continued
A50
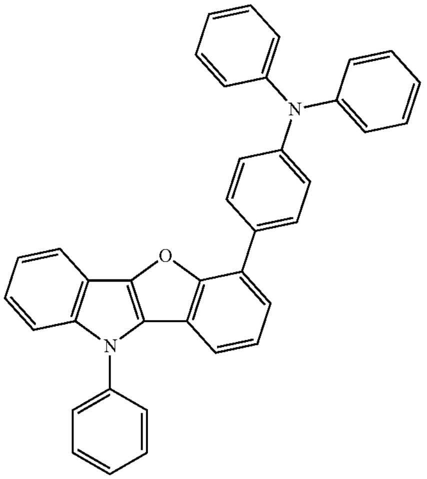
A51
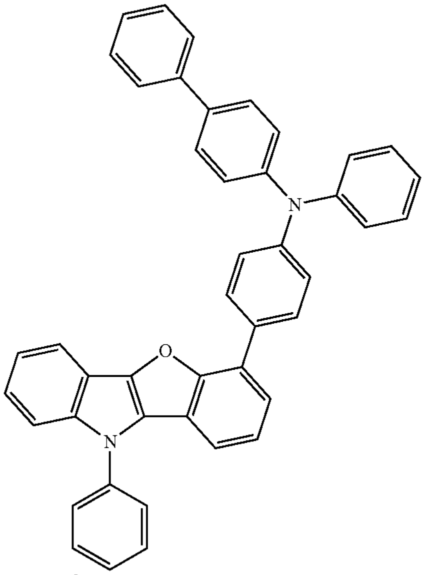
A52
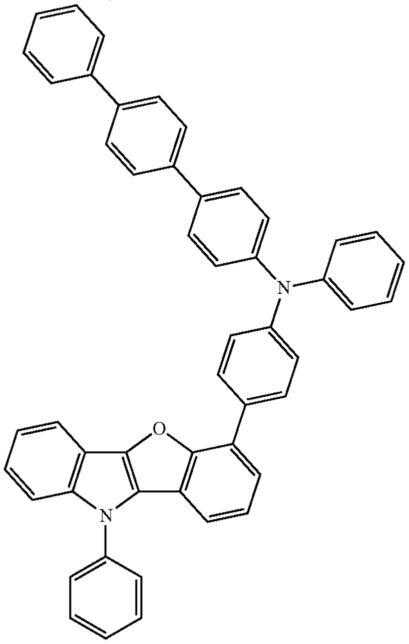
-continued
A53
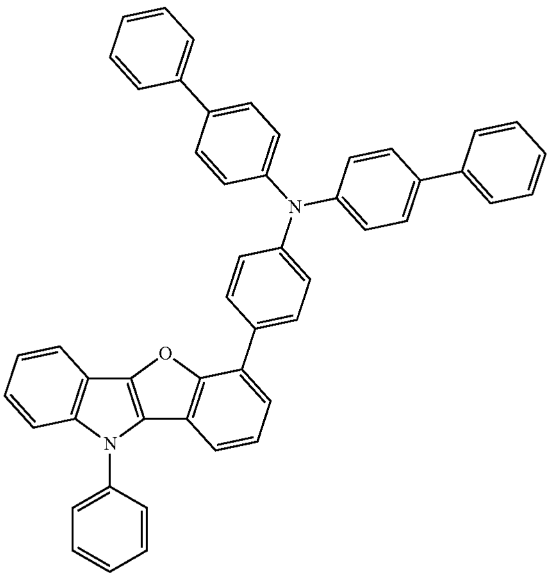
A54
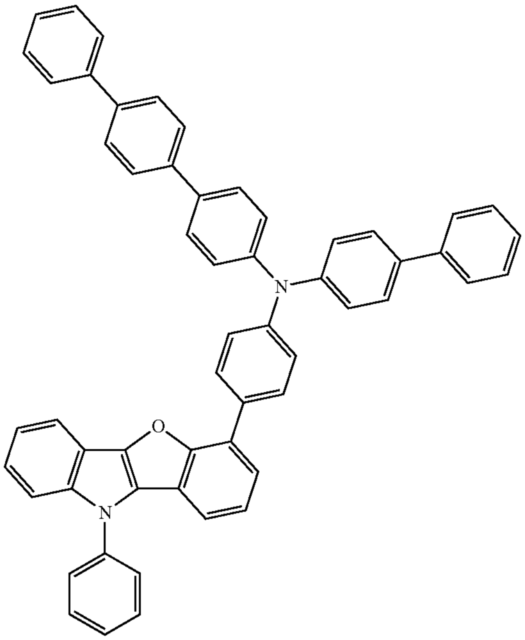

-continued
A55
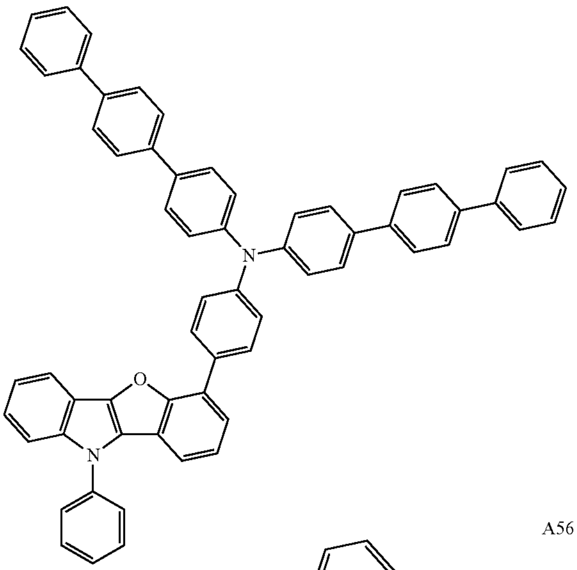
A56
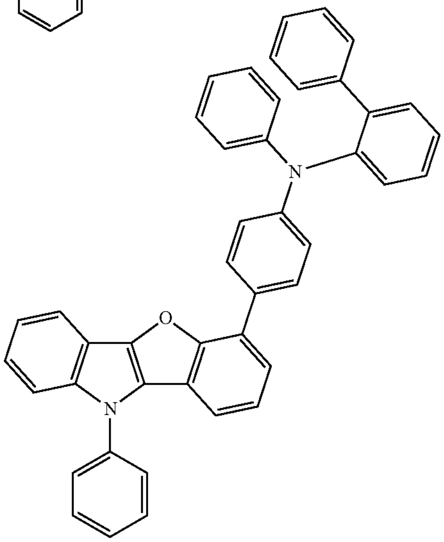
A57
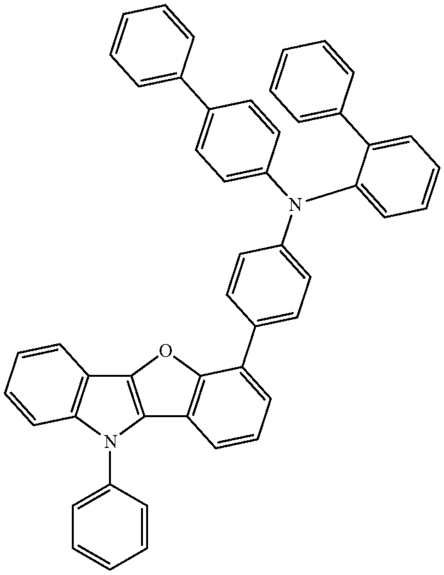
-continued
A58
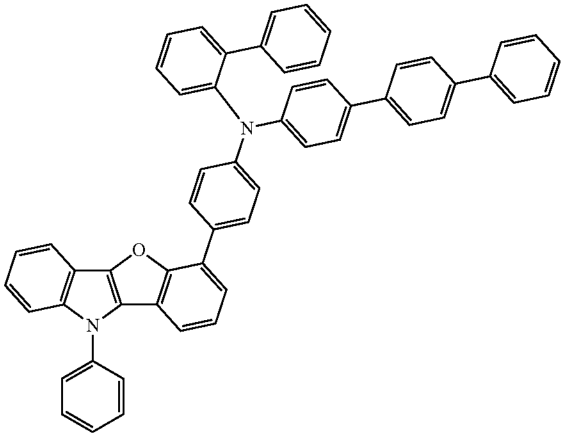
A59
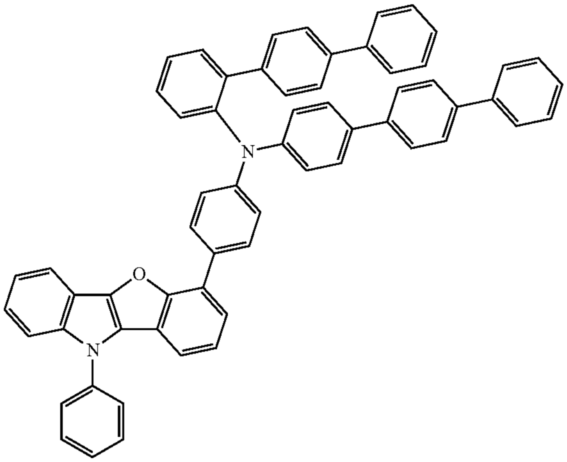
A60
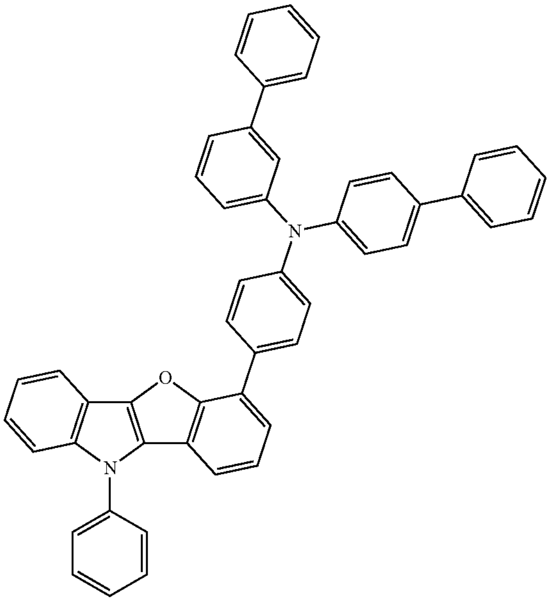

-continued
A61
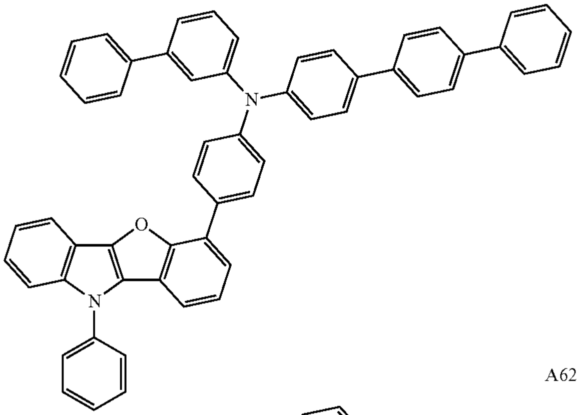
A62
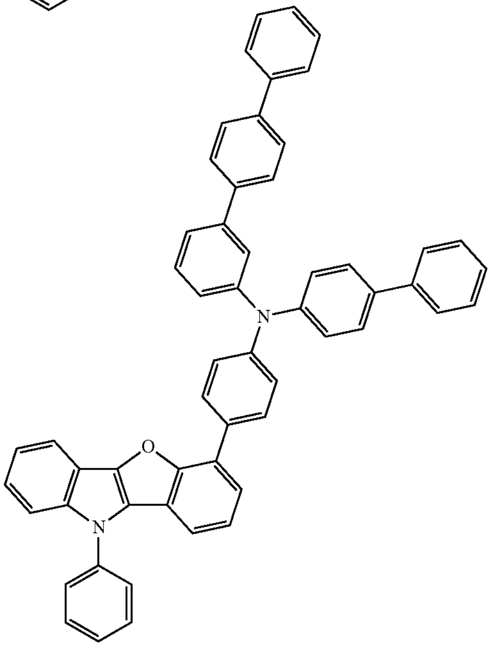
A63
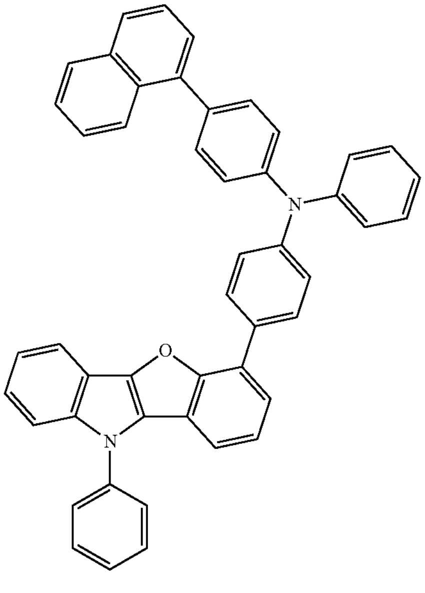
-continued
A64
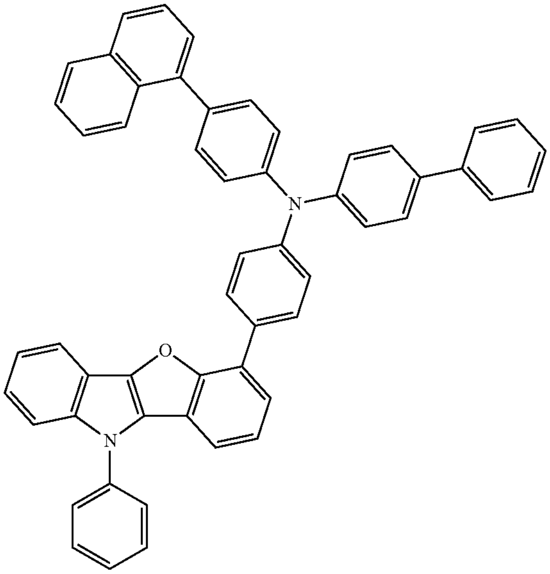
A65
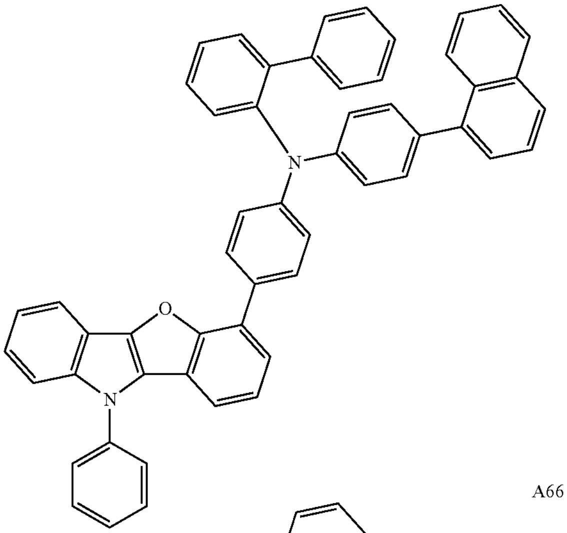
A66
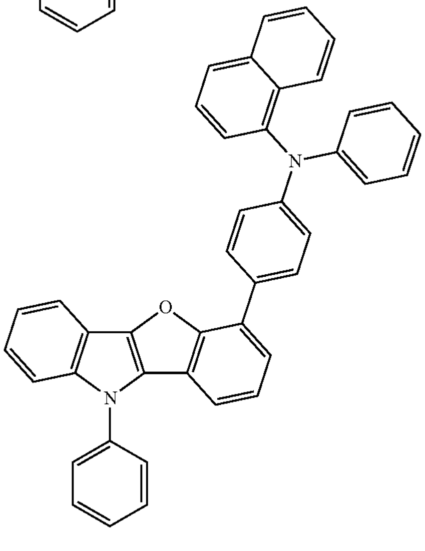

-continued
A67
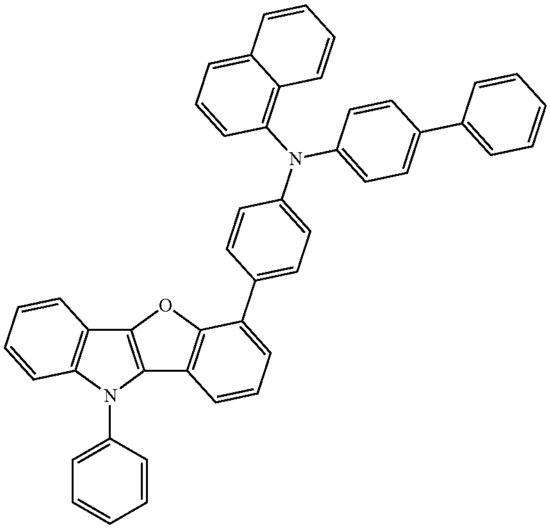
A68
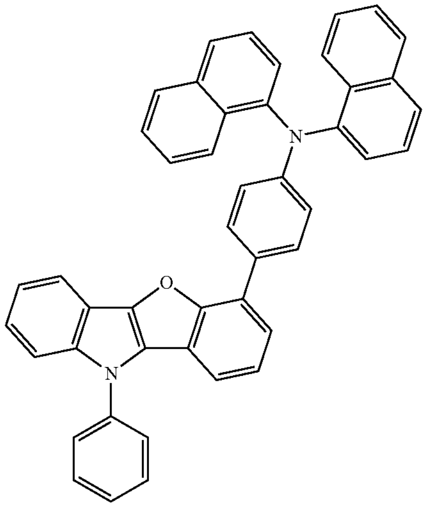
A69
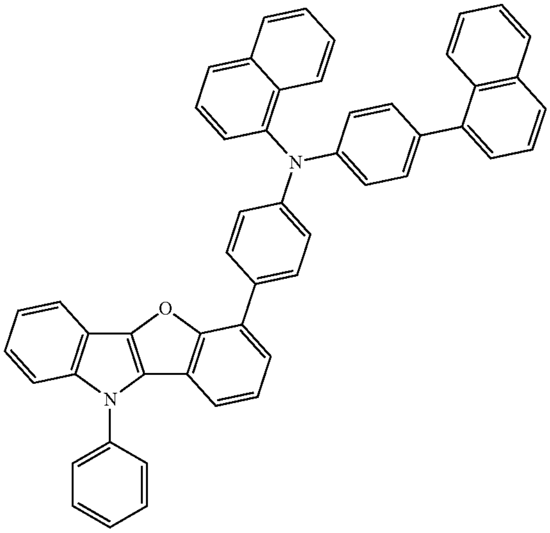
-continued
A70
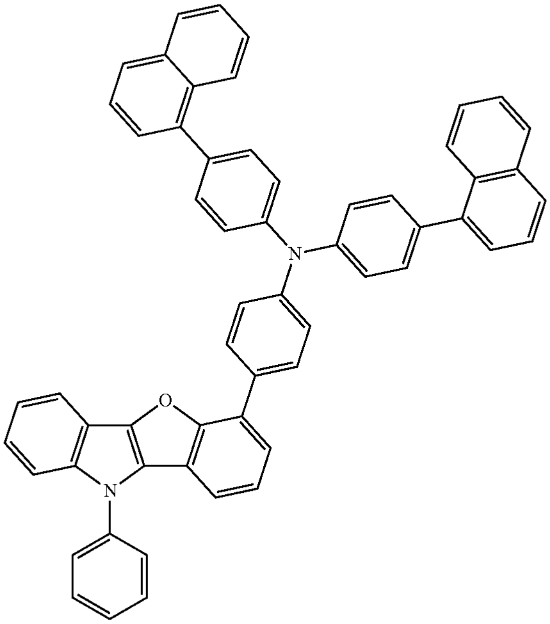
A71
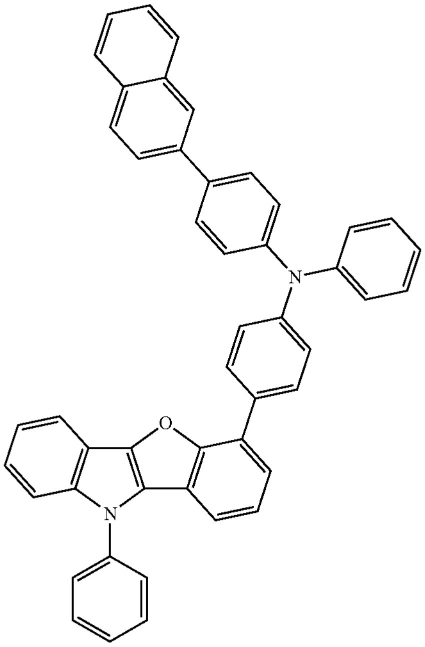

-continued
A72
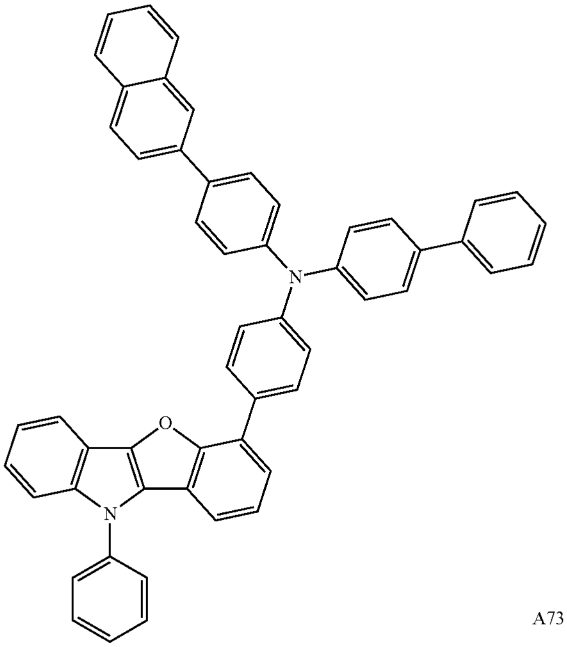
A73
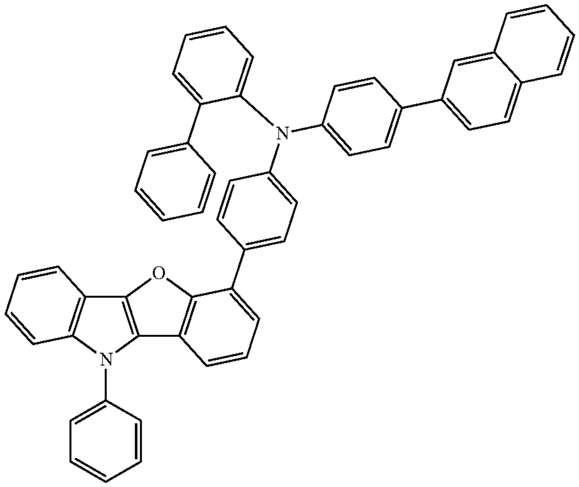
A74
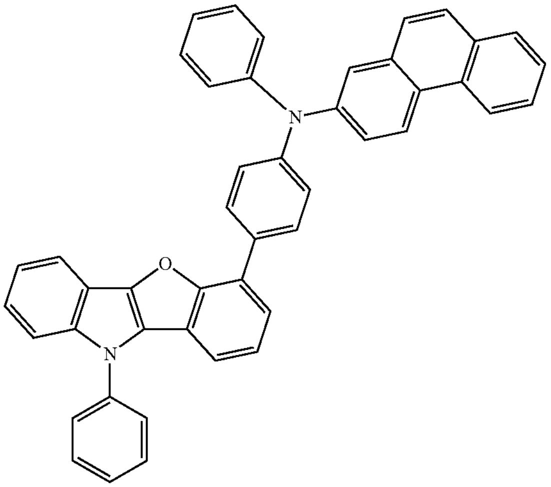
-continued
A75
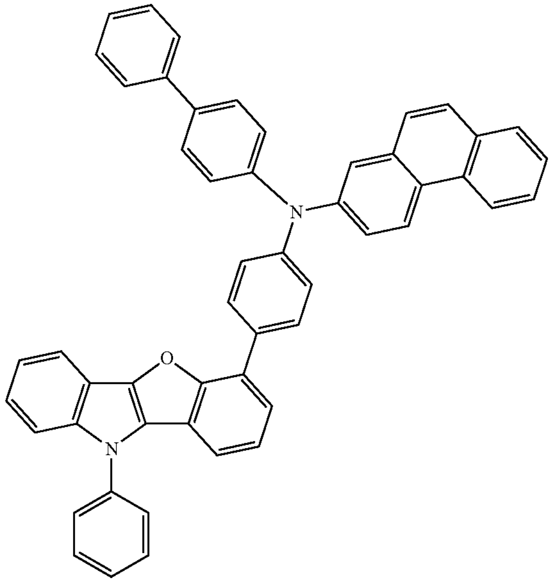
A76
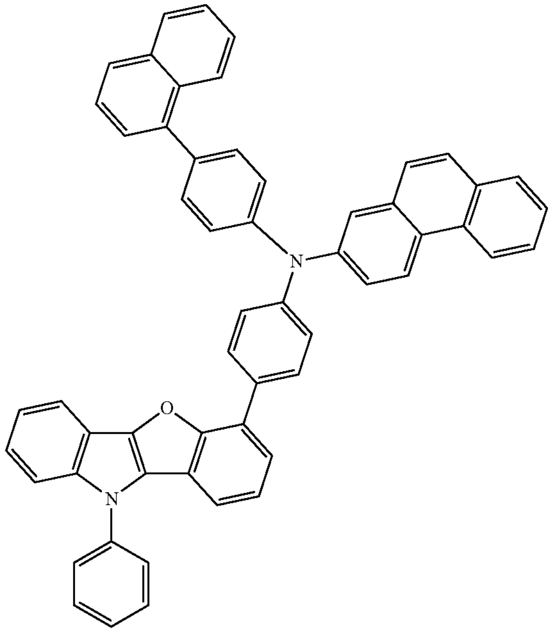

A77
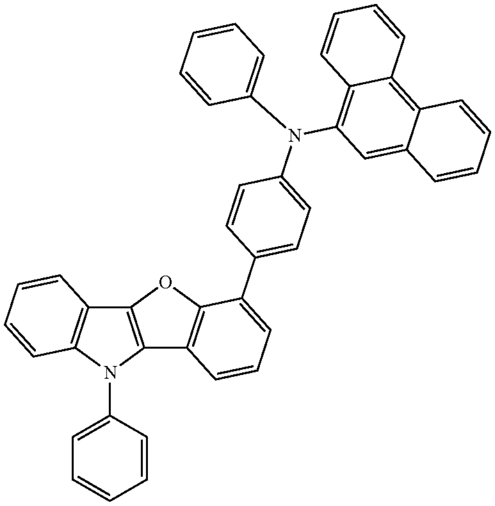
A78
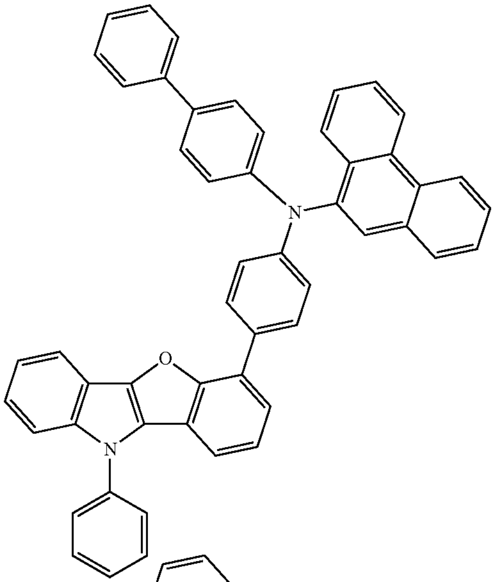
A79
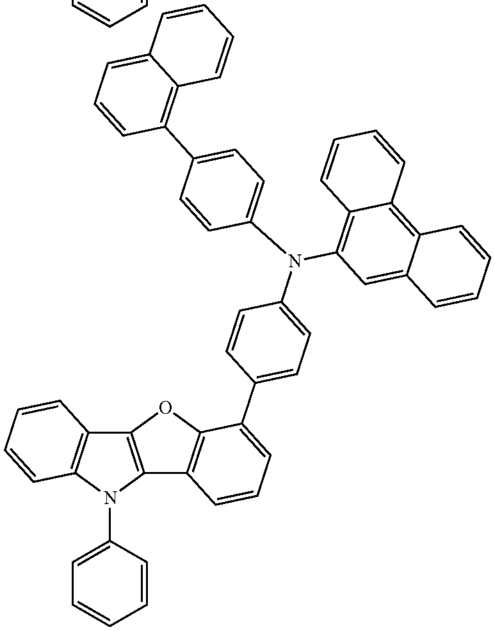
A80
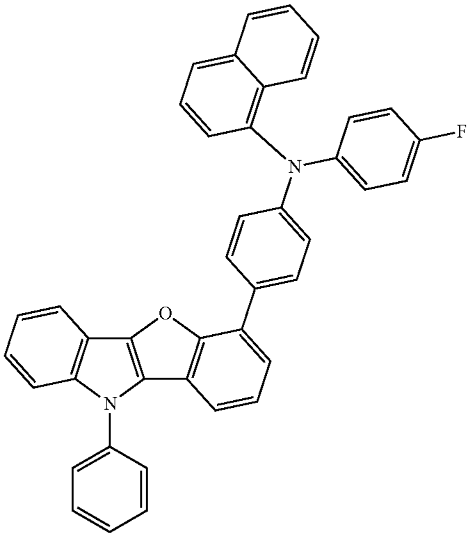
A81
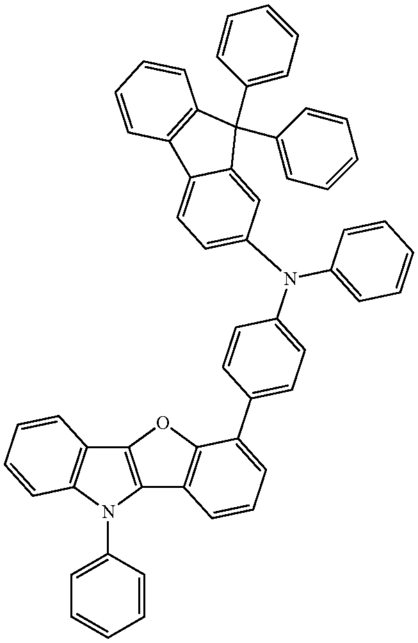

A82
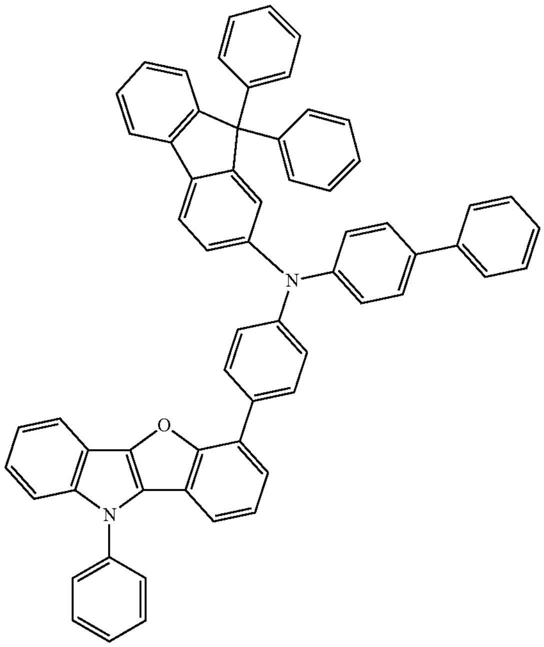
A84
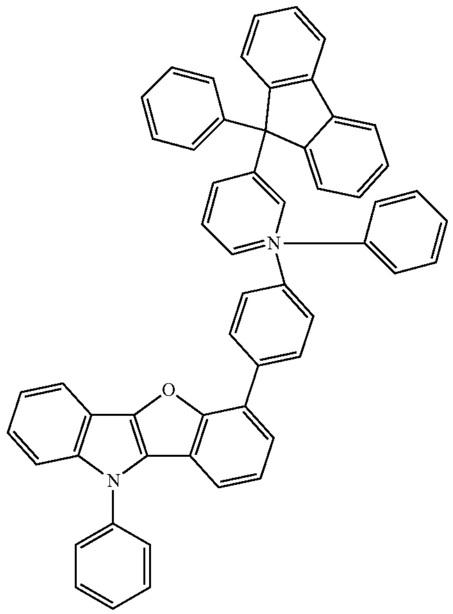
A83
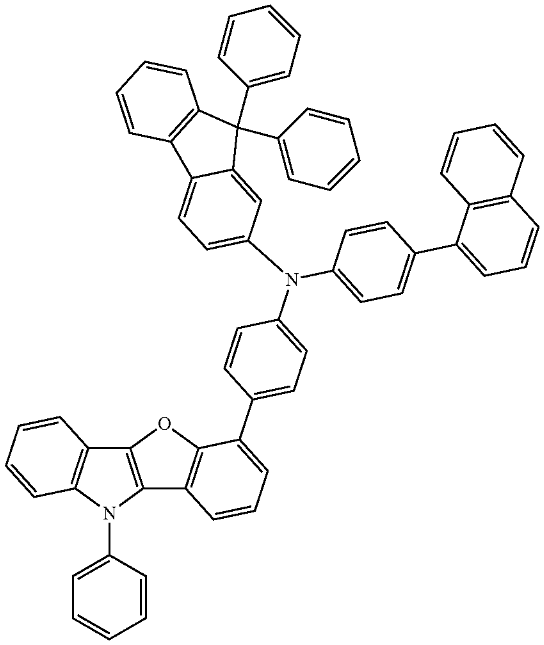
A85
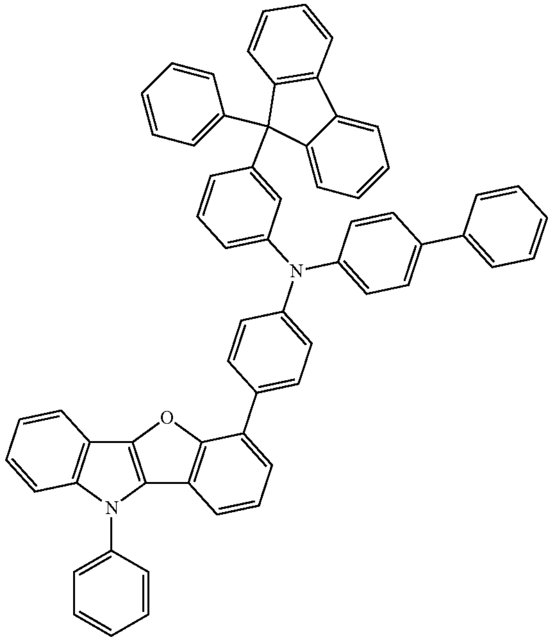

-continued
A86
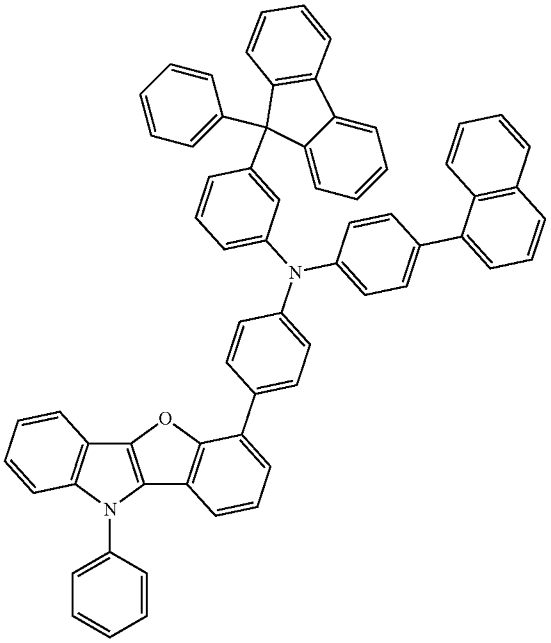
A87
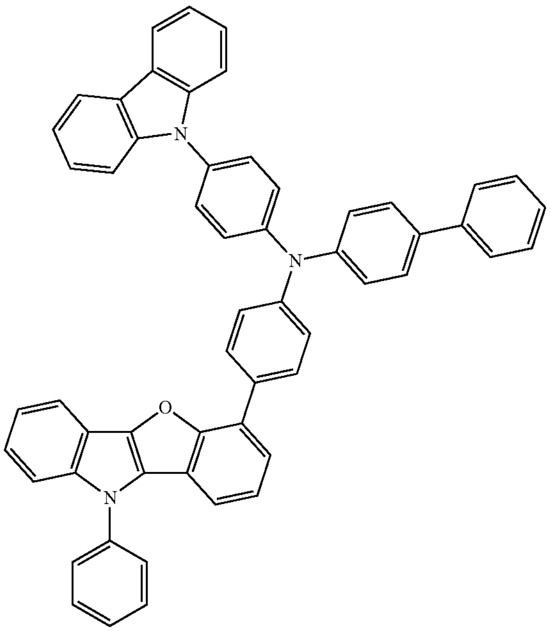
-continued
A88
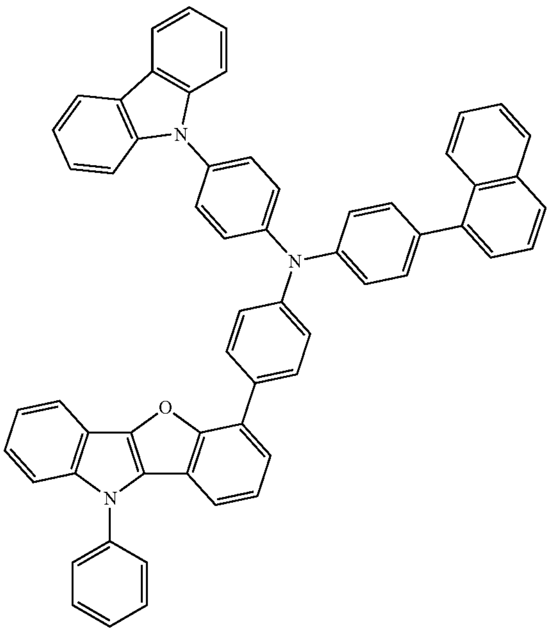
A89
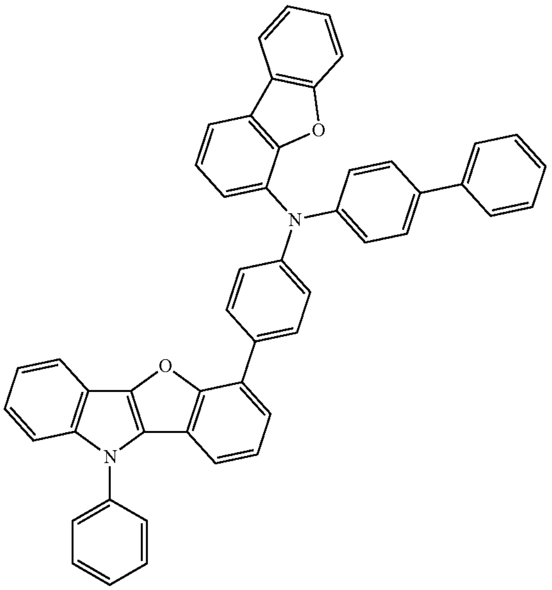

-continued
A90
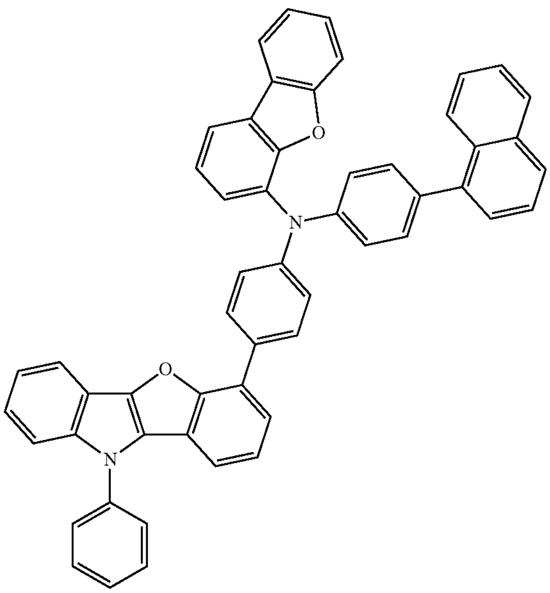
A91
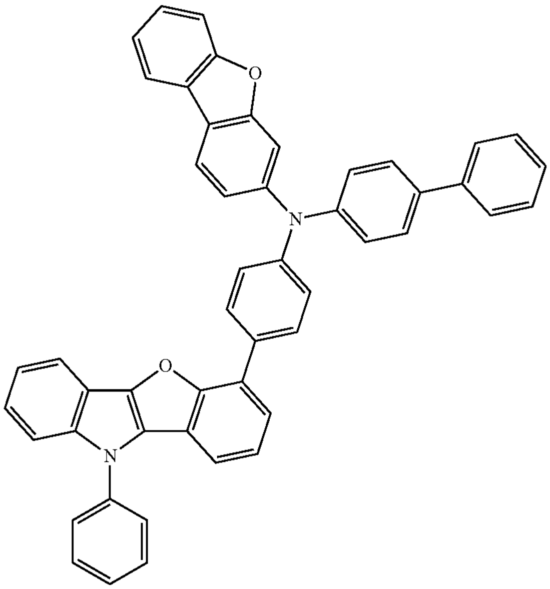
-continued
A92
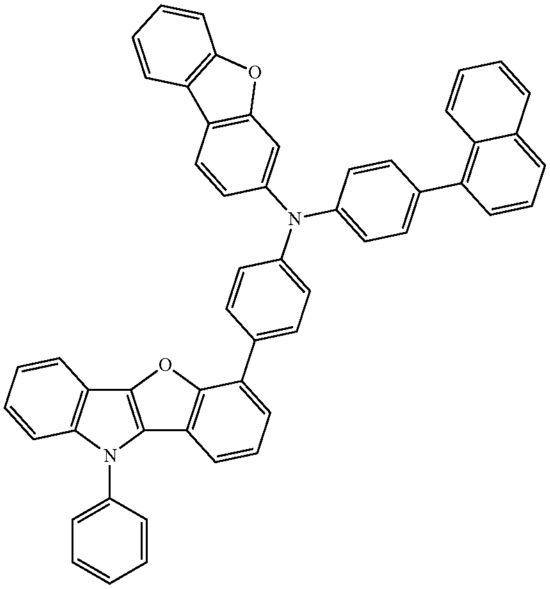
A93
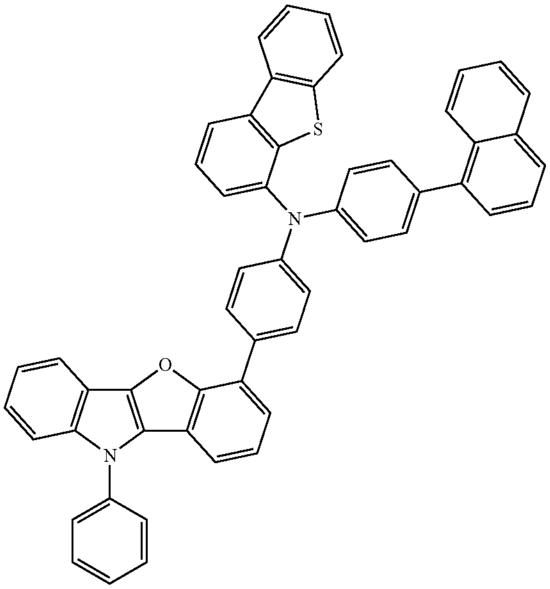

-continued
A94
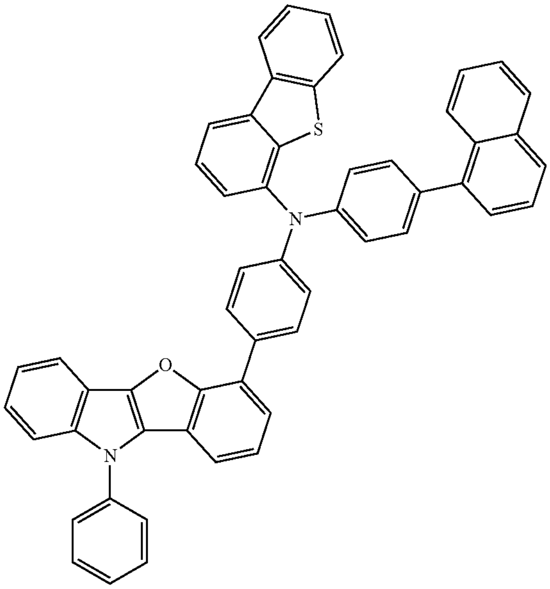
A95
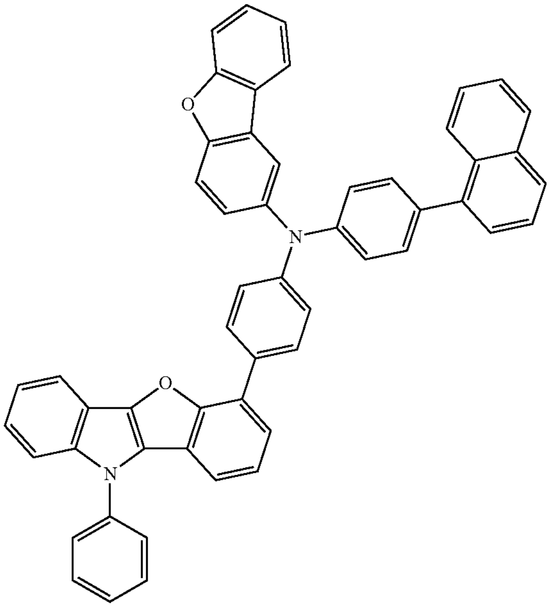
-continued
A96
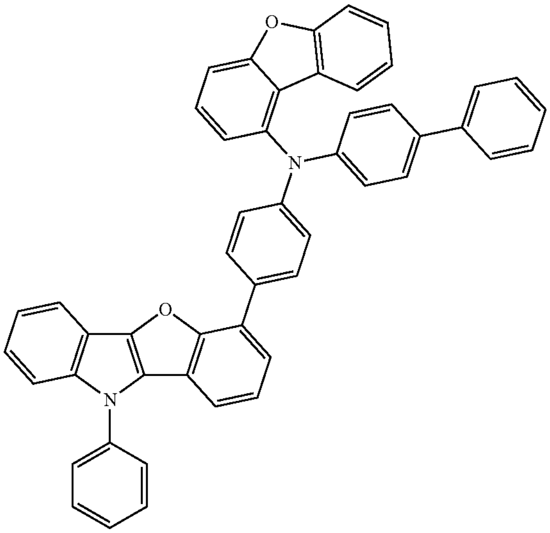
A97
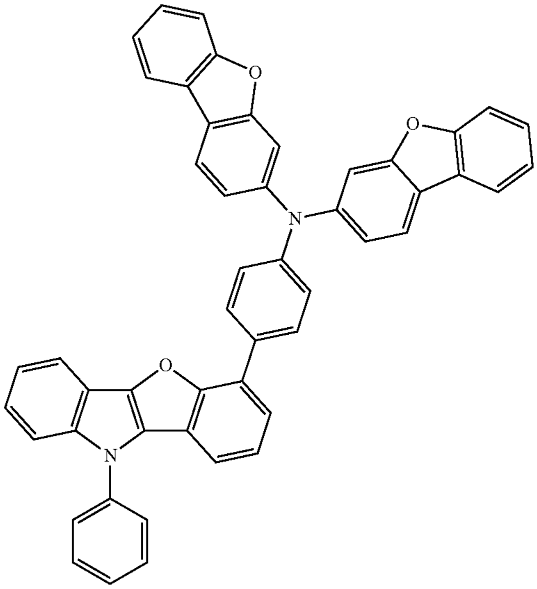

-continued
A98
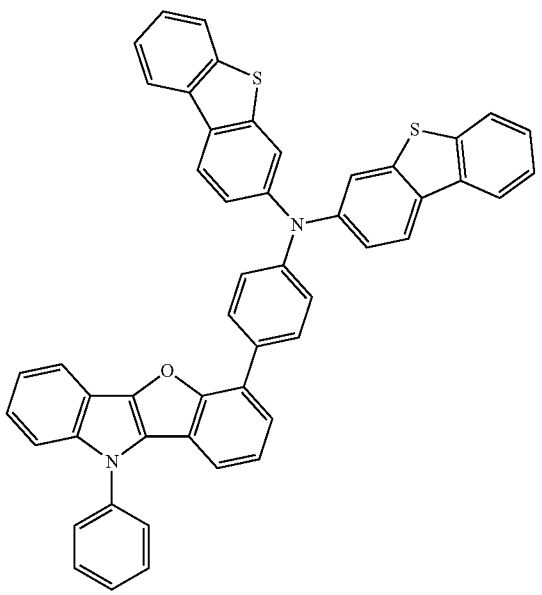
A99
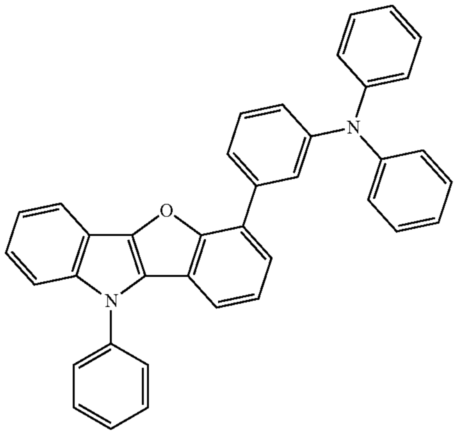
A100
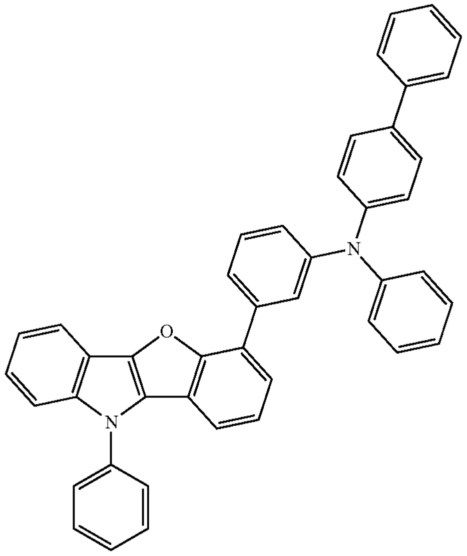
-continued
A101
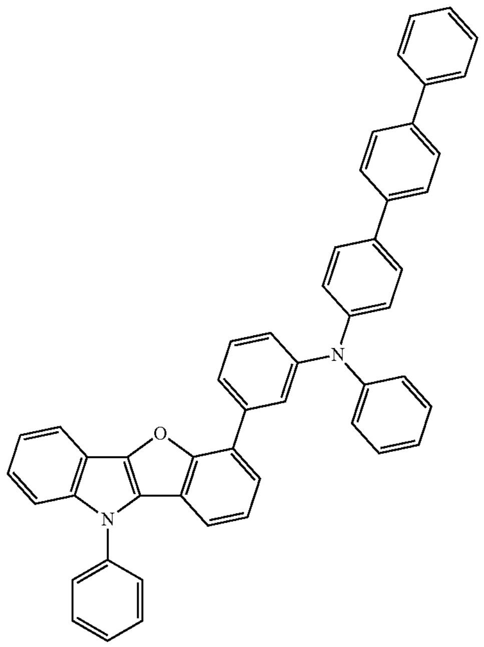
A102
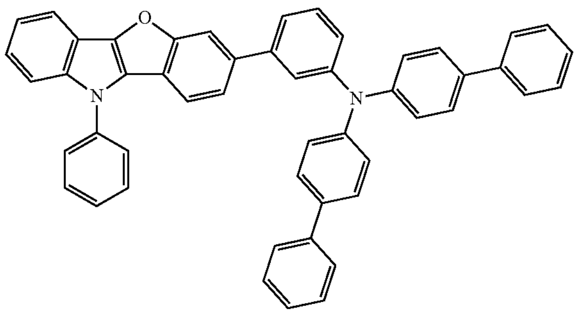
A103
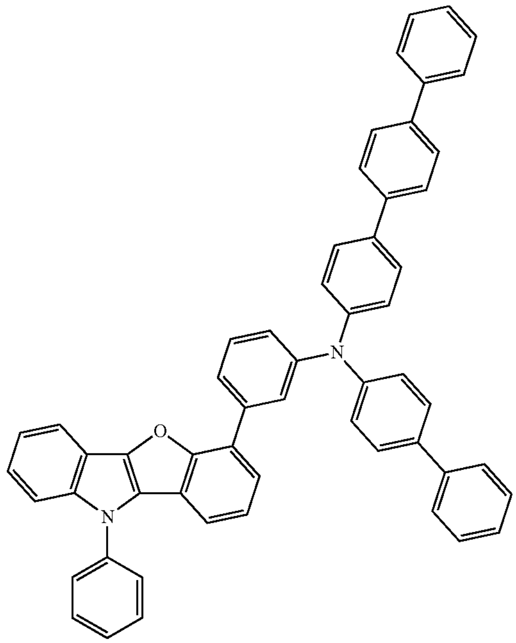

-continued
A104
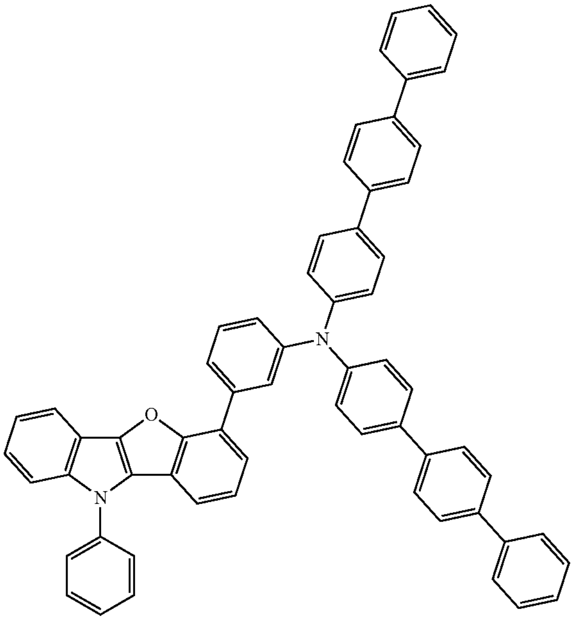
A105
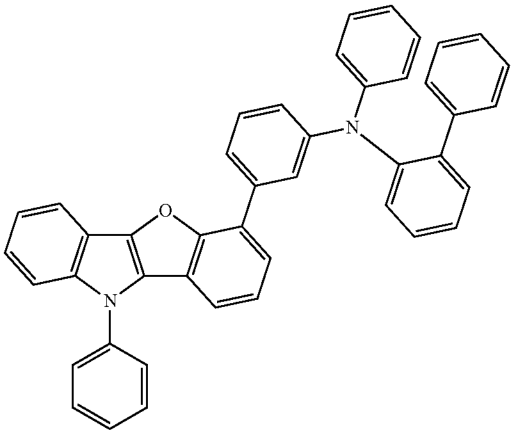
A106
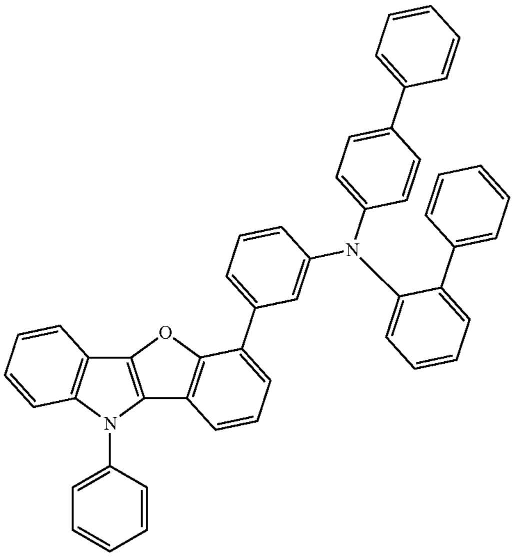
-continued
A107
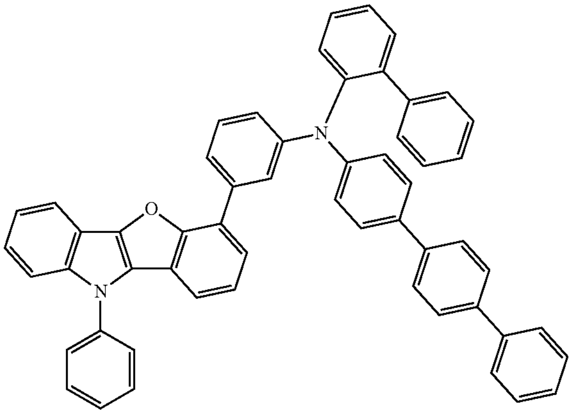
A108
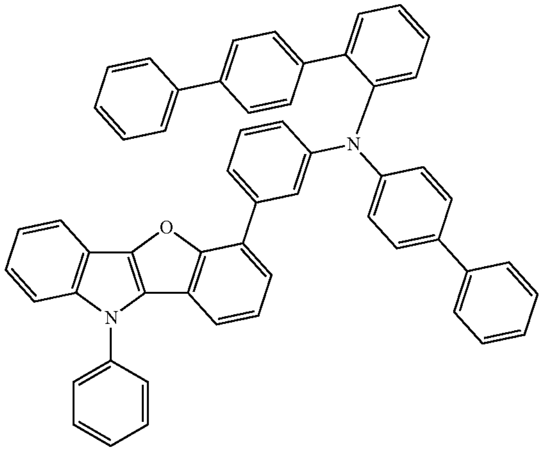
A109
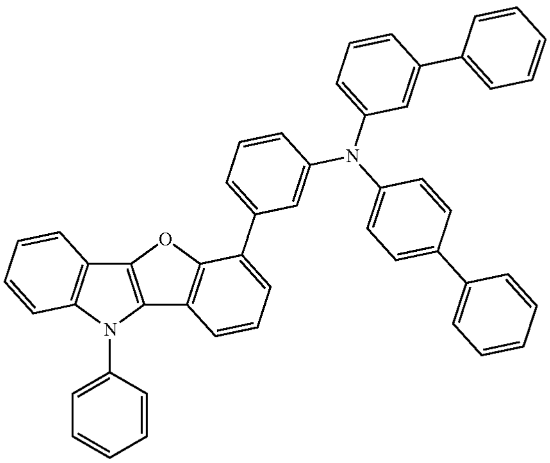

-continued
A110
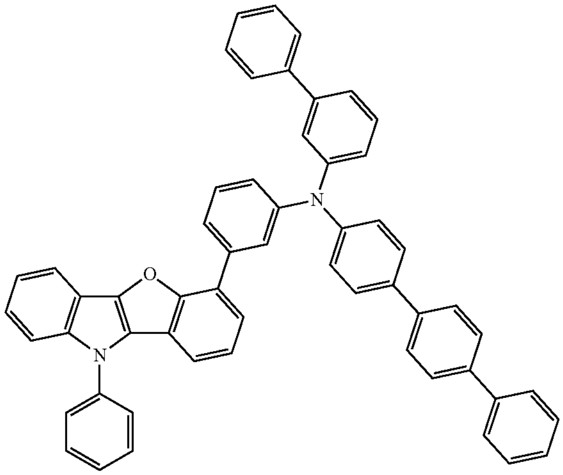
A111
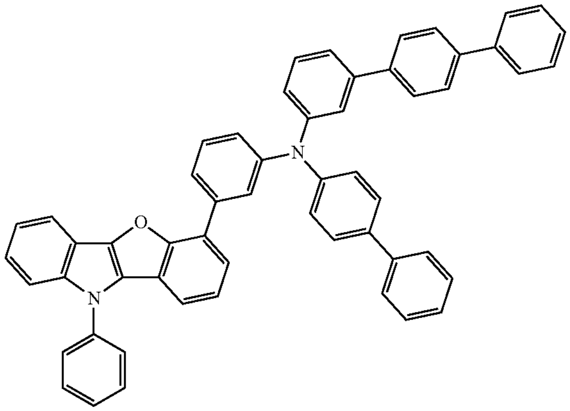
A112
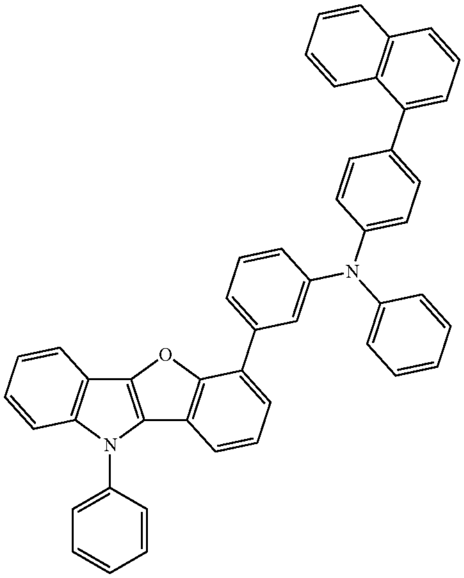
-continued
A113
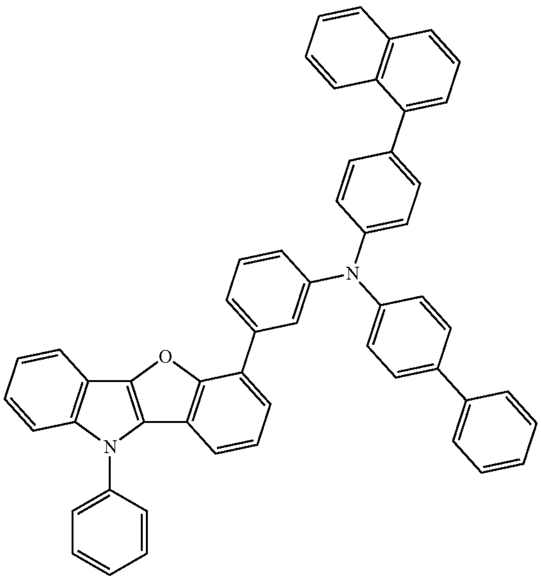
A114
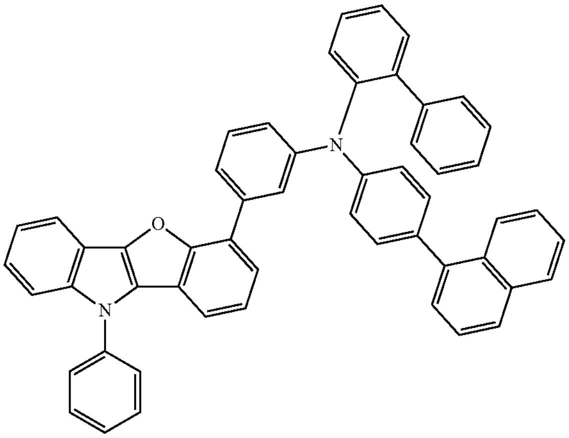
A115
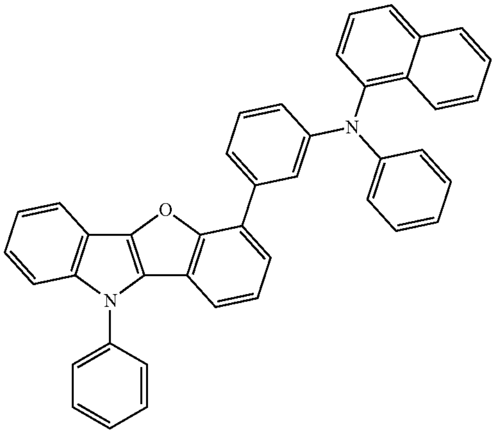

-continued
A116
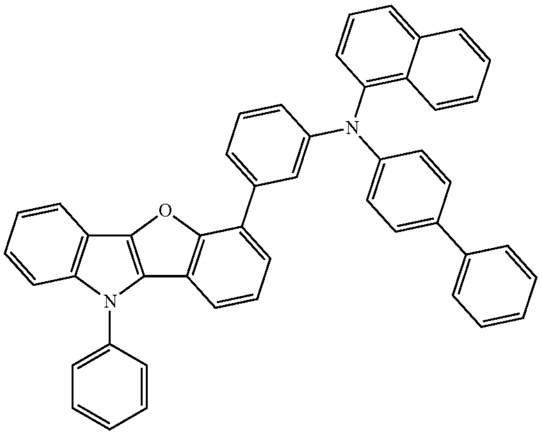
A117
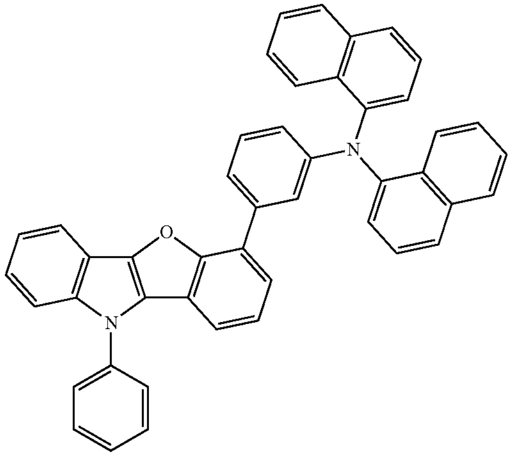
A118
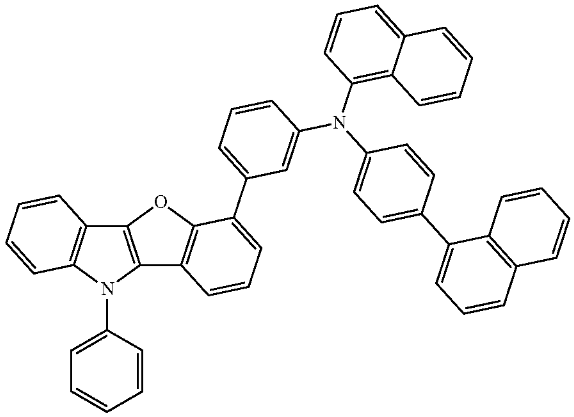
-continued
A119
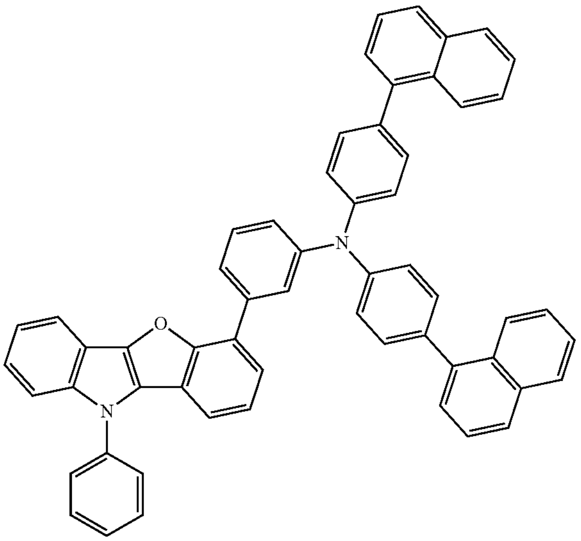
A120
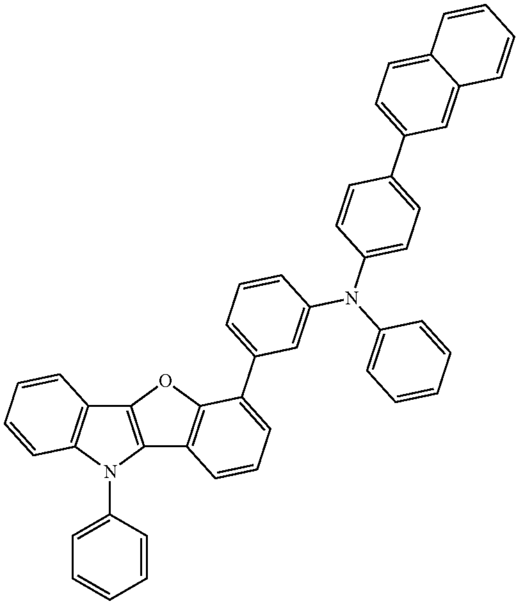

-continued
A121
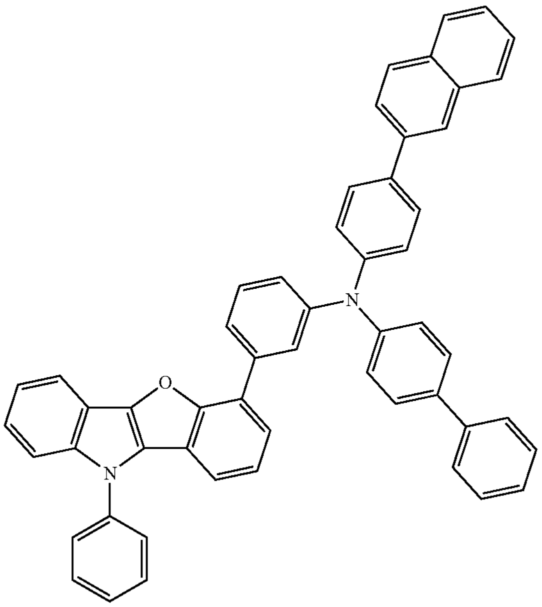
A122
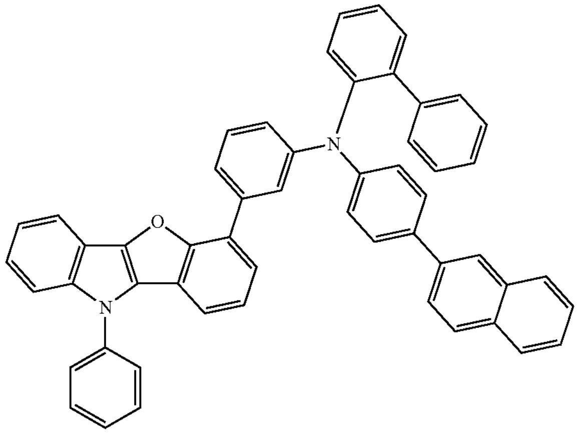
A123
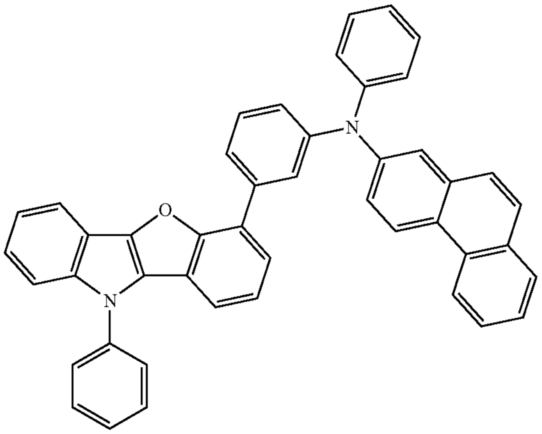
-continued
A124
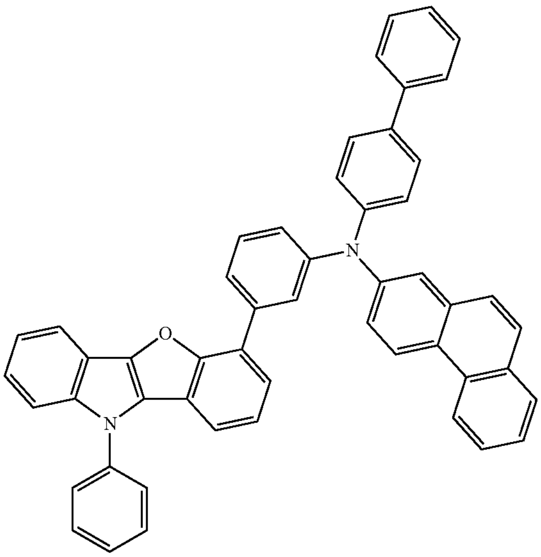
A125
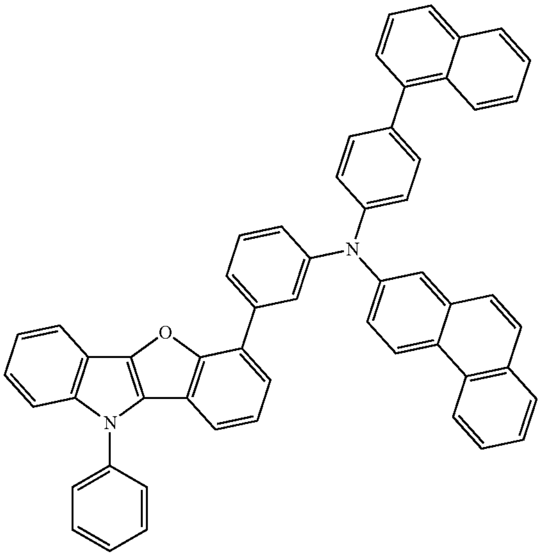
A126
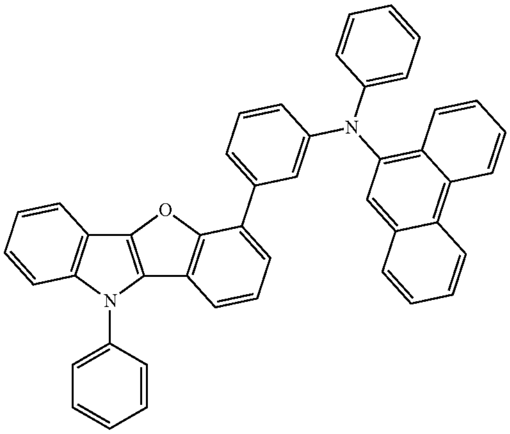

-continued
A127
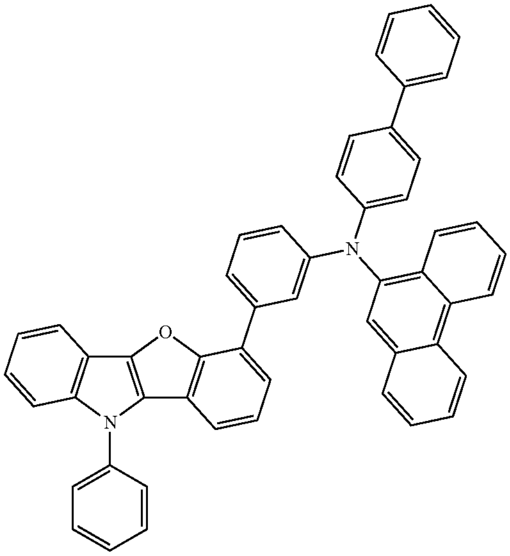
A128
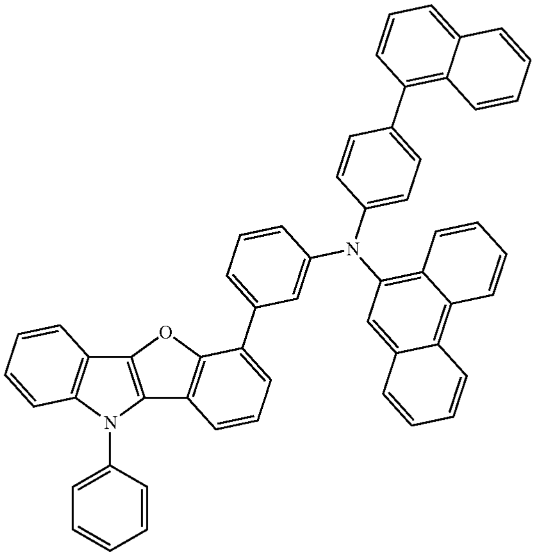
A129
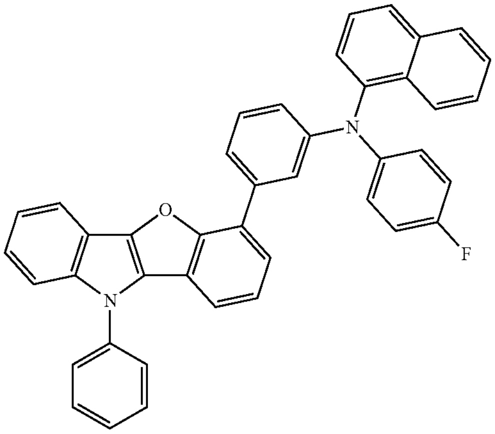
-continued
A130
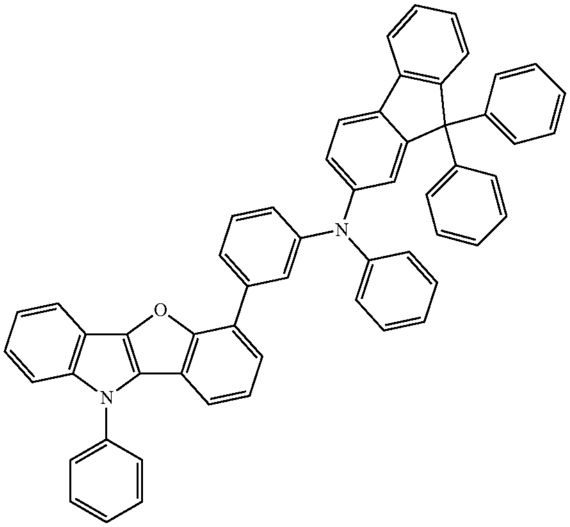
A131
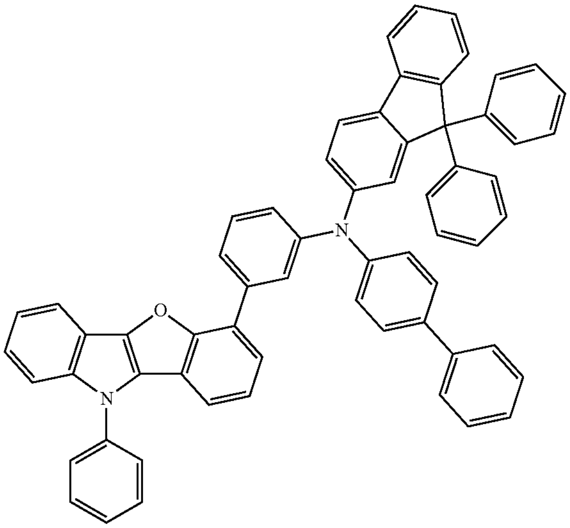
A132
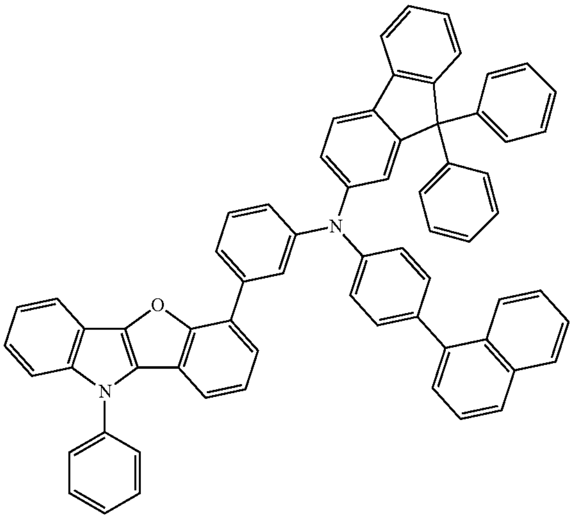

A133
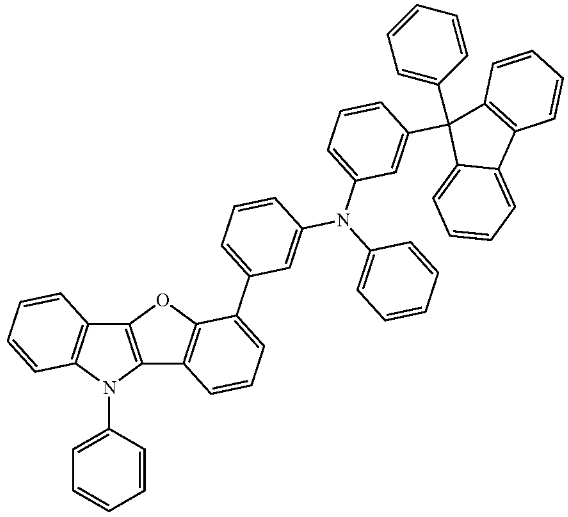
A134
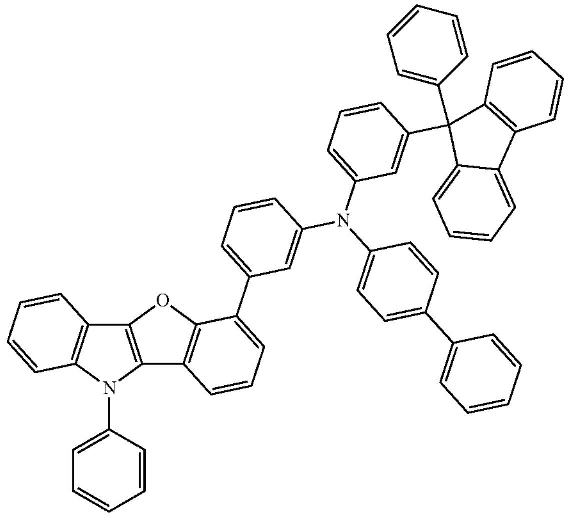
A135
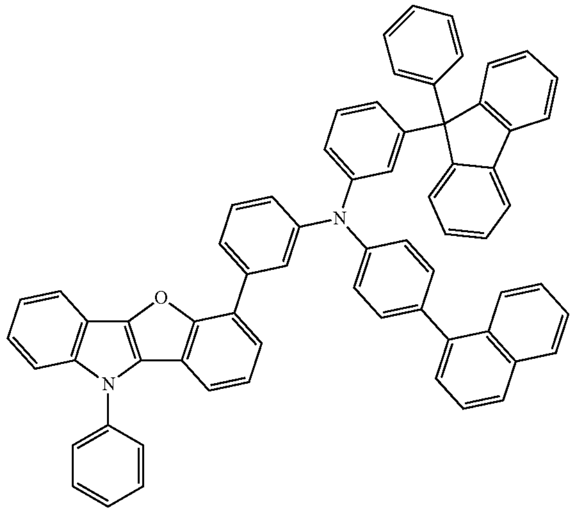
A136
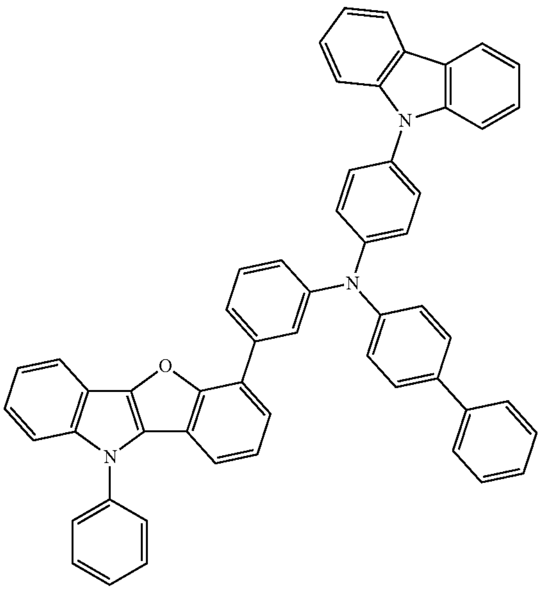
A137
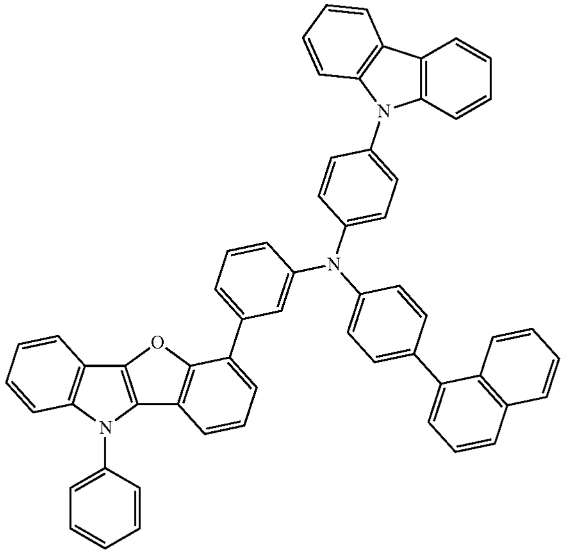
A138
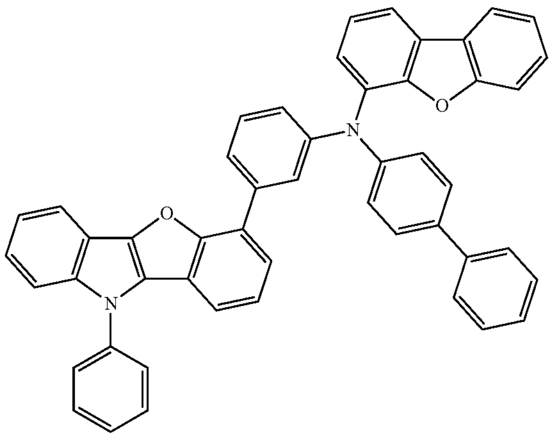

-continued
A139
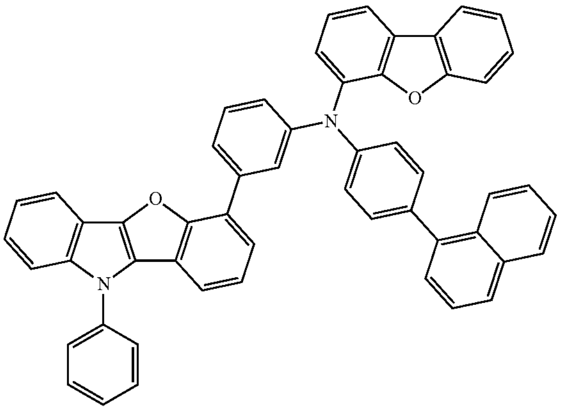
A140
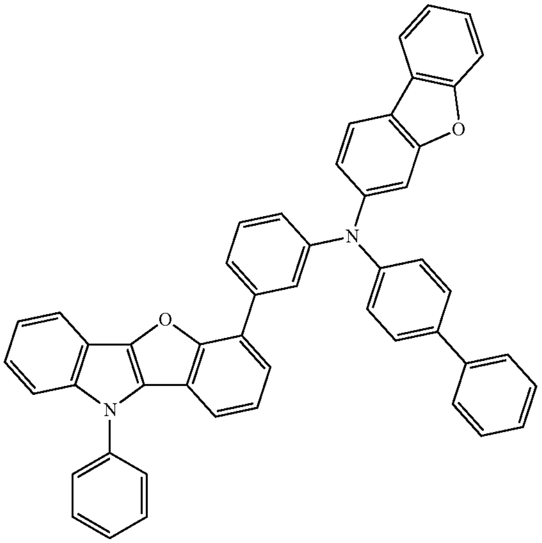
A141
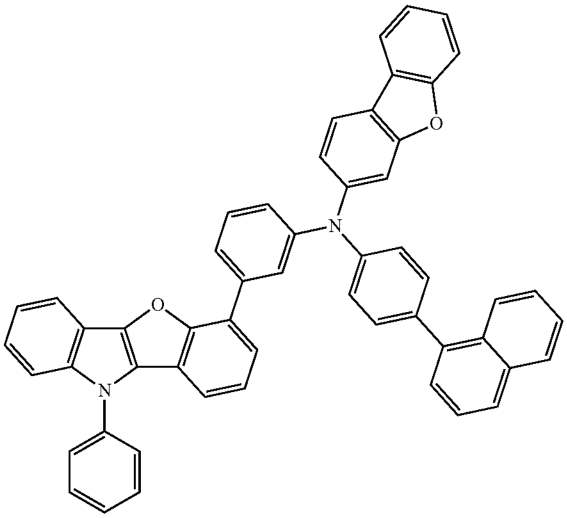
-continued
A142
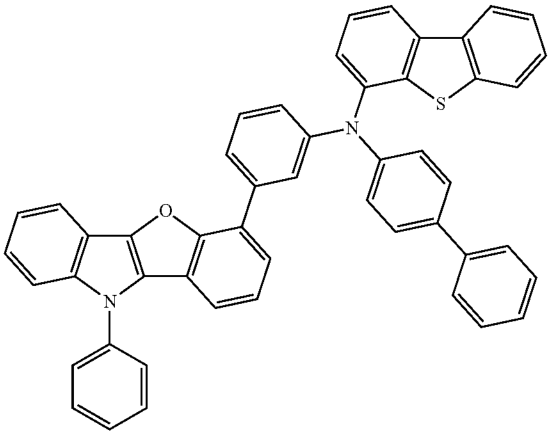
A143
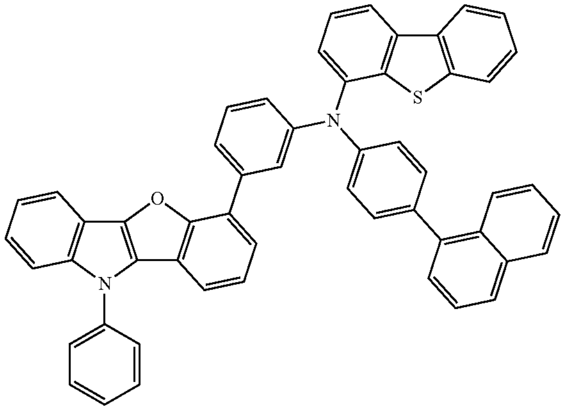
A144
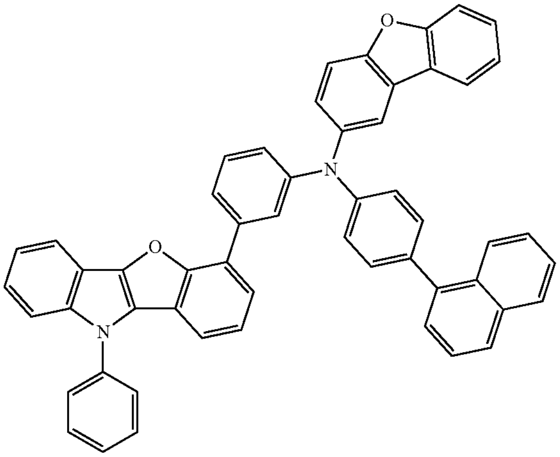

-continued
A145
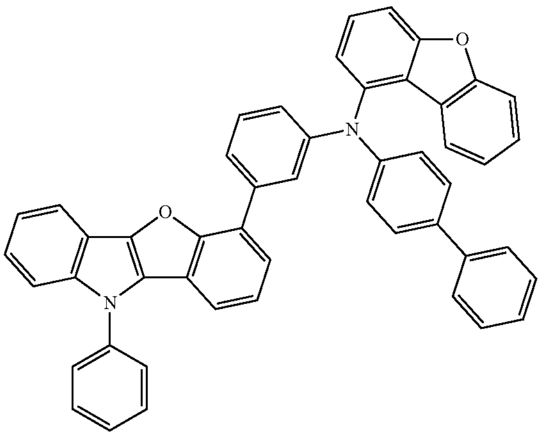
A146
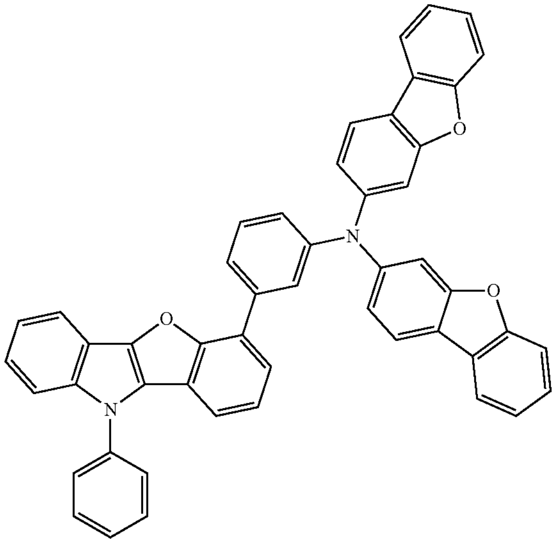
A147
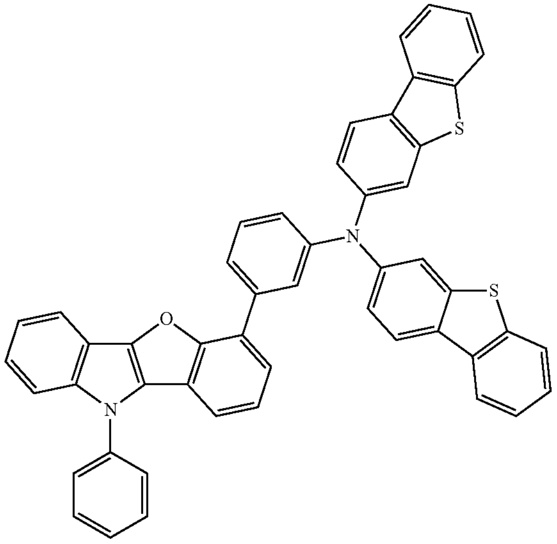
-continued
A148
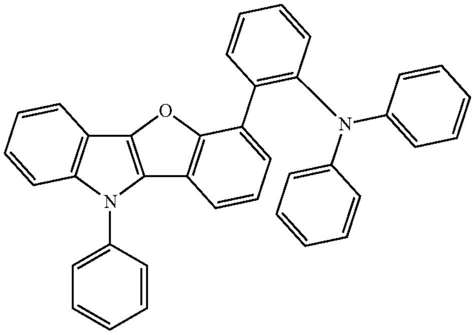
A149
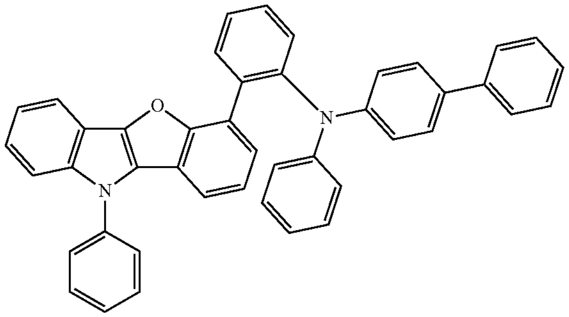
A150
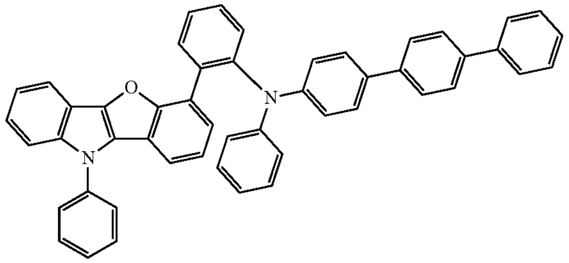
A151
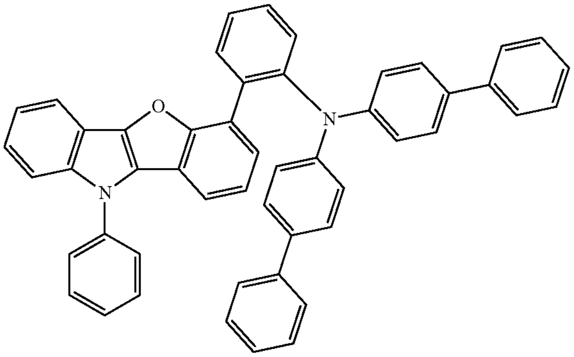

-continued
A152
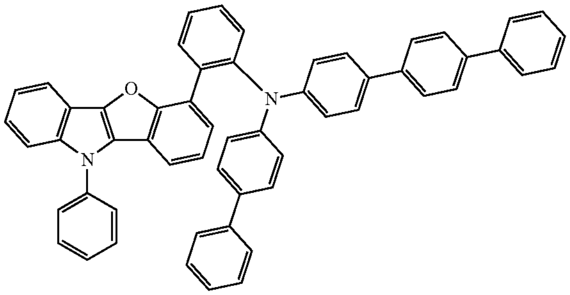
A153
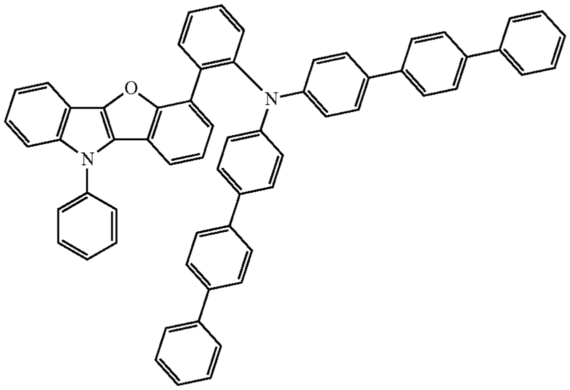
A154
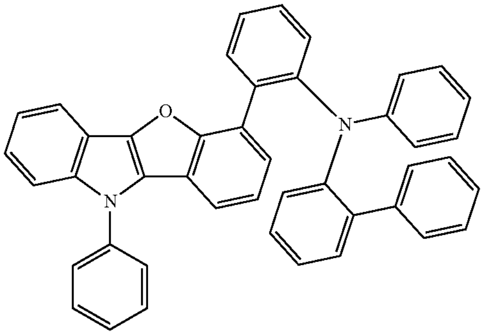
A155
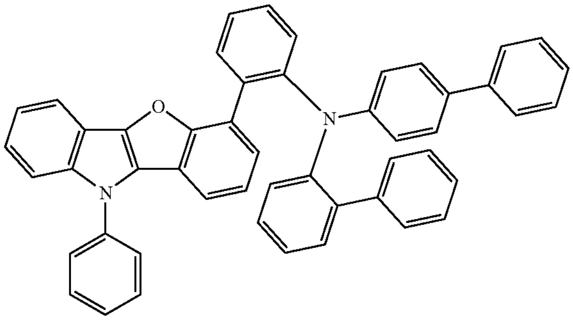
-continued
A156
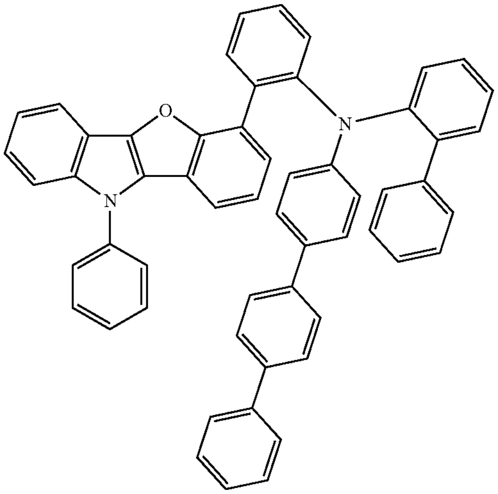
A157
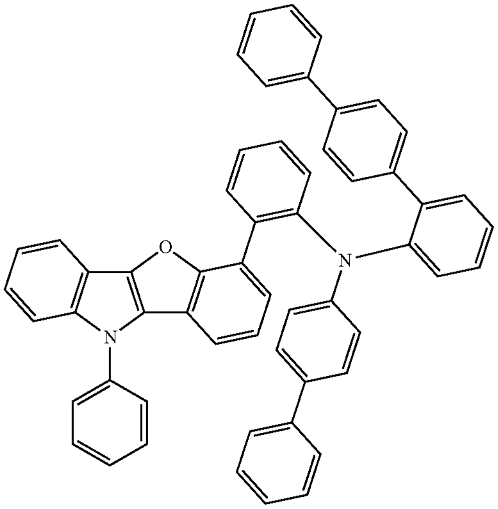
A158
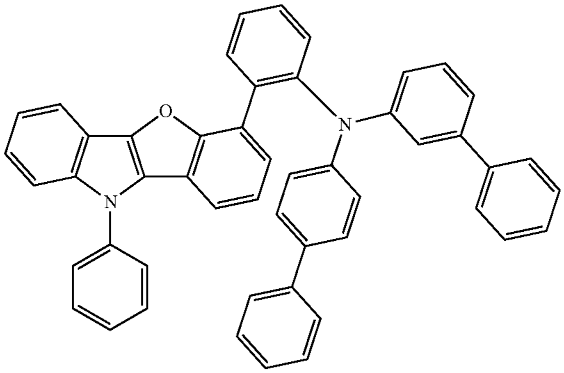

-continued
A159
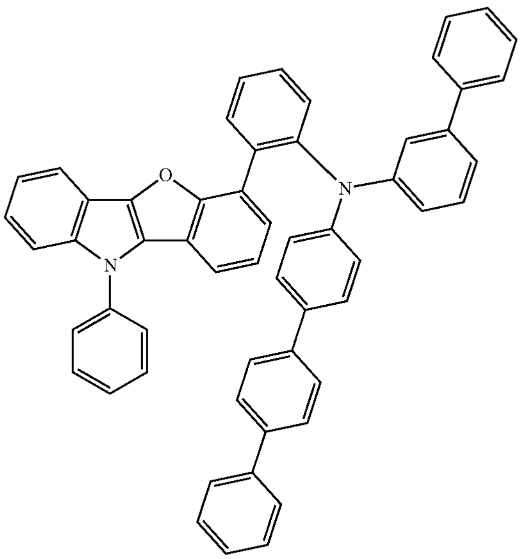
A160
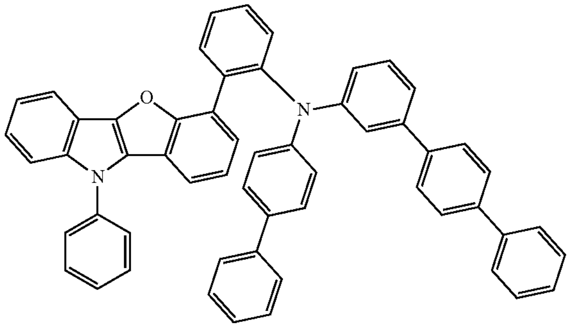
A161
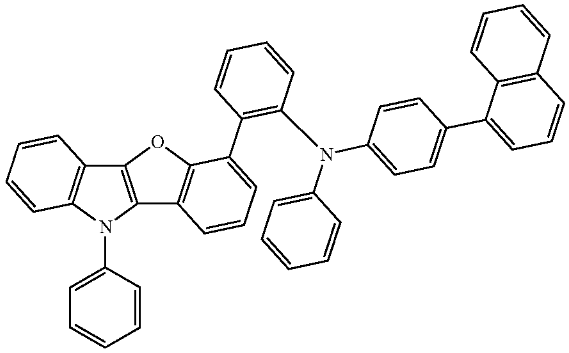
-continued
A162
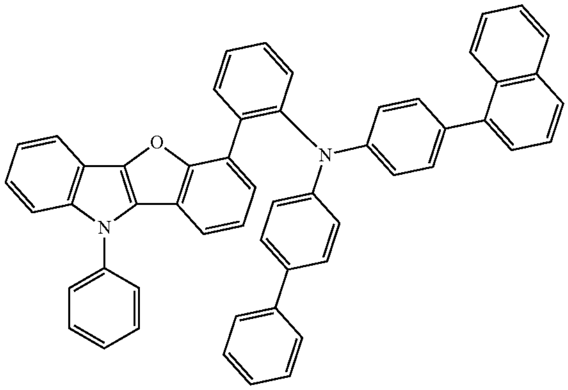
A163
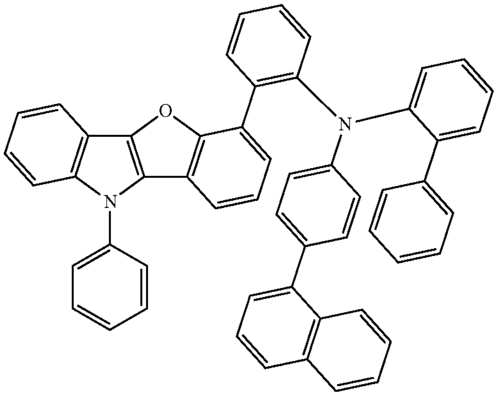
A164
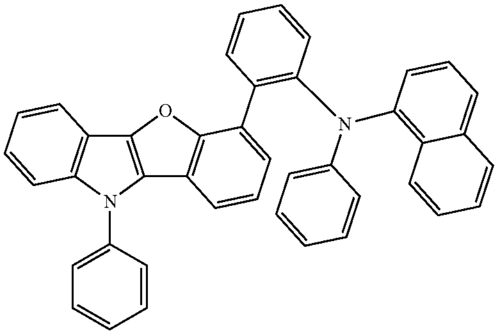
A165
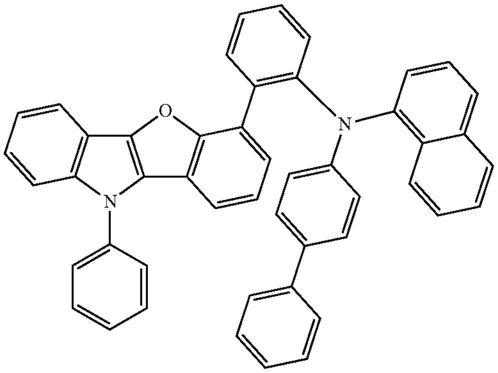

-continued
A166
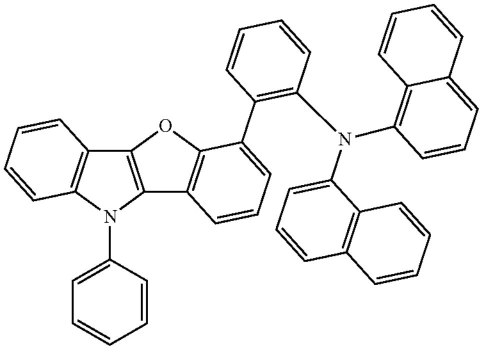
A167
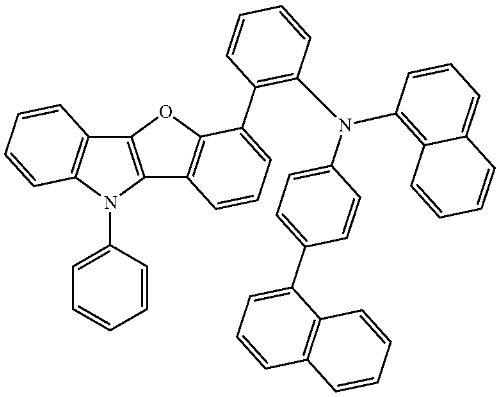
A168
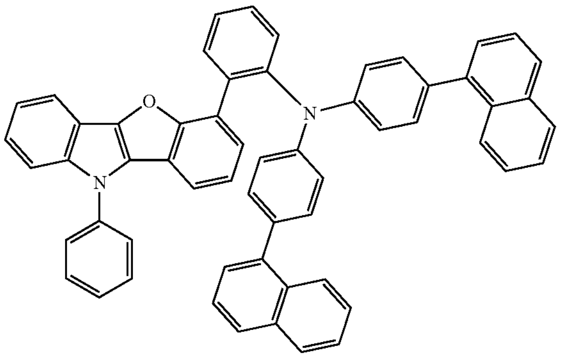
A169
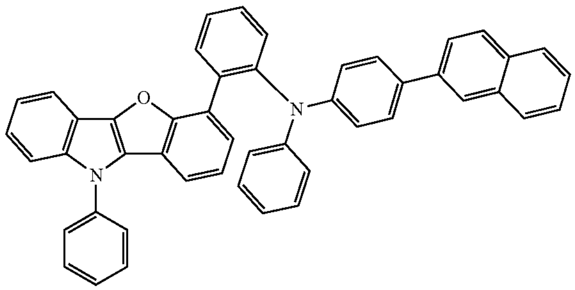
-continued
A170
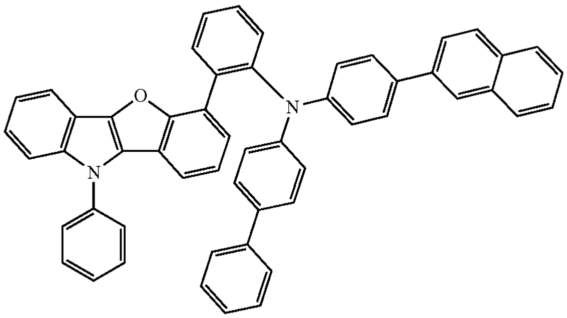
A171
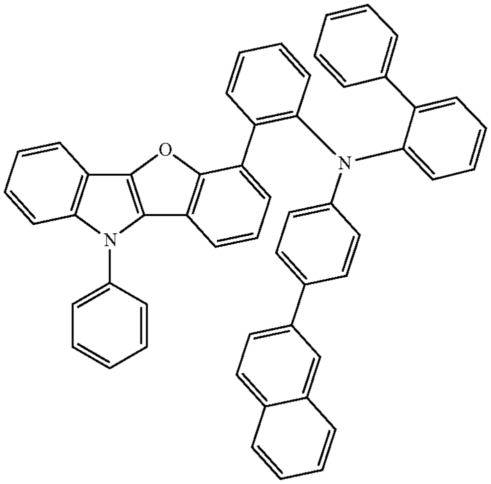
A172
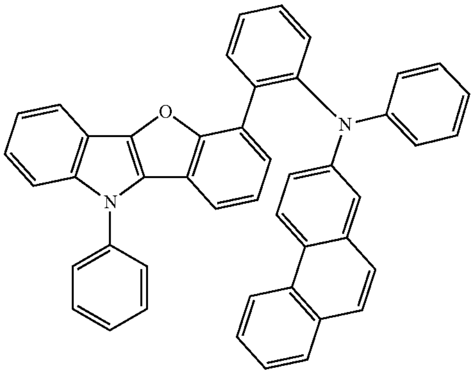
A173
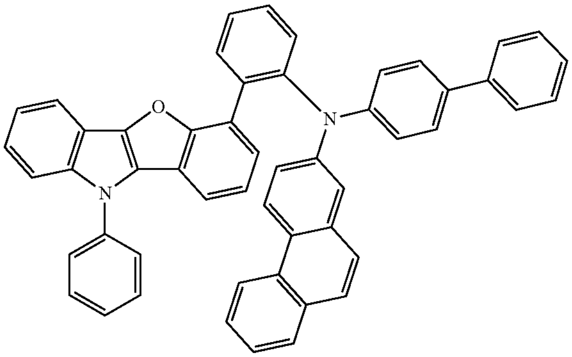

-continued
A174
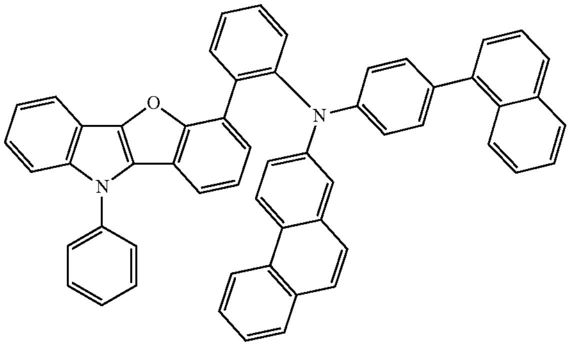
A175
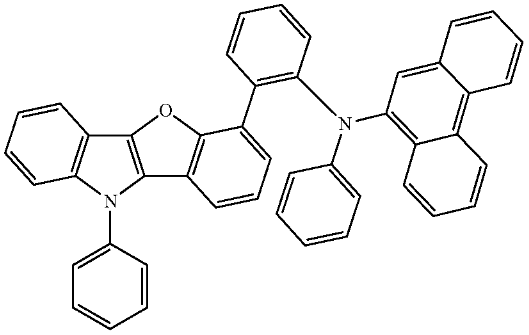
A176
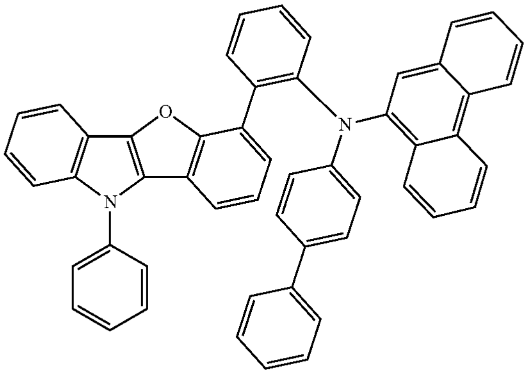
A177
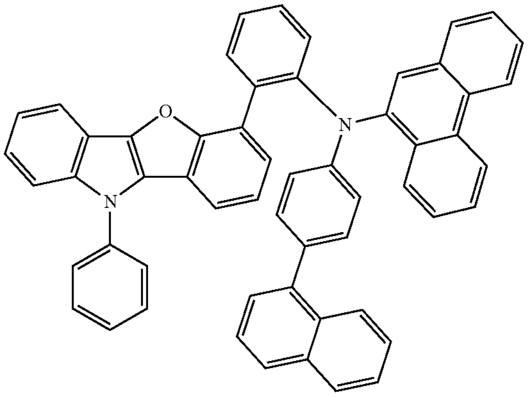
-continued
A178
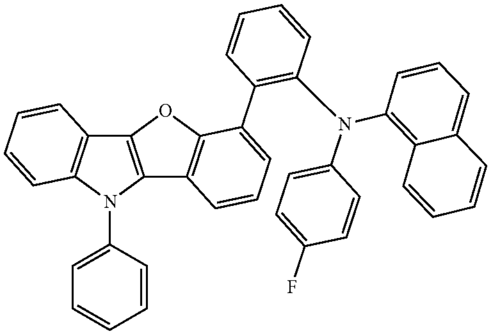
A179
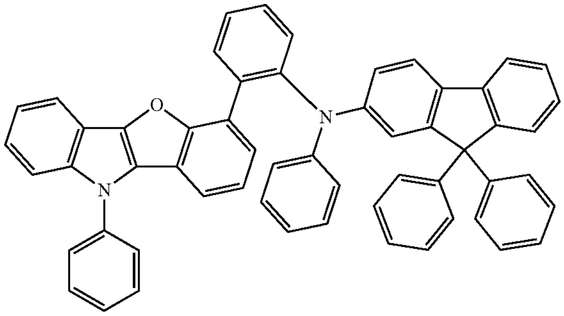
A180
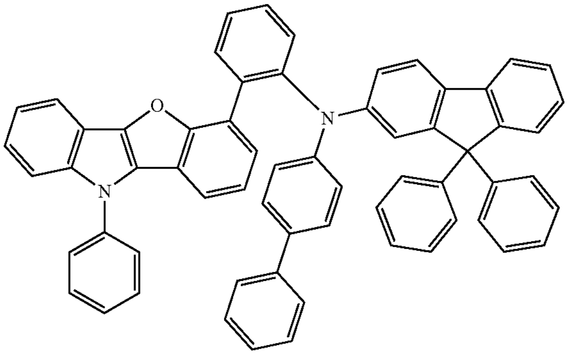
A181
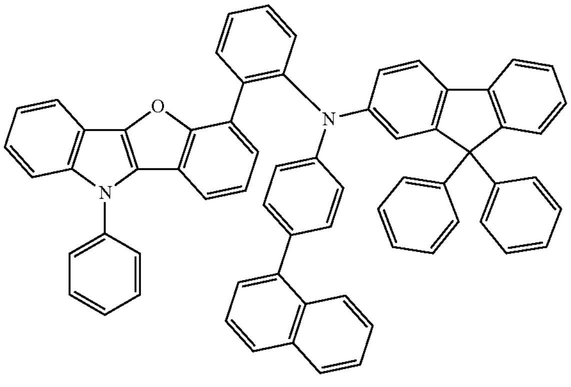

-continued
A182
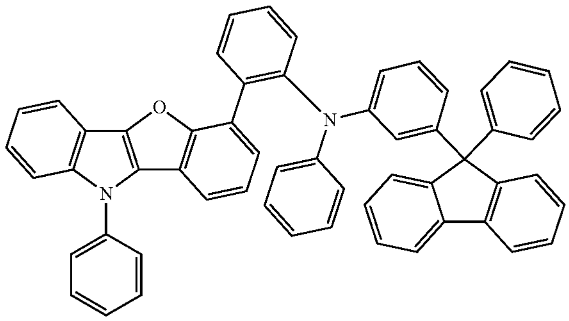
A183
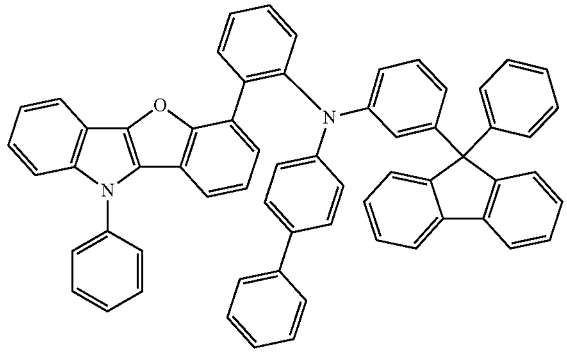
A184
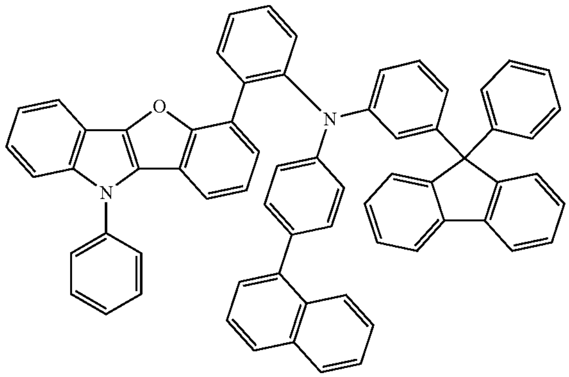
A185
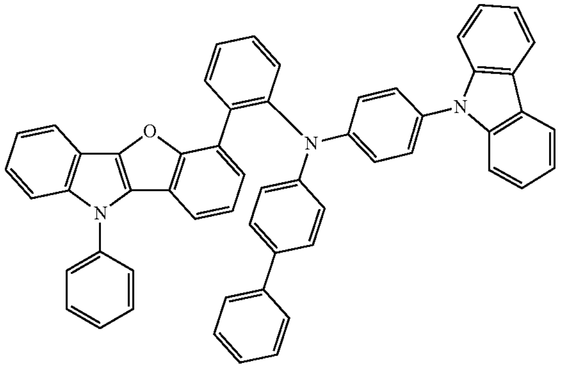
-continued
A186
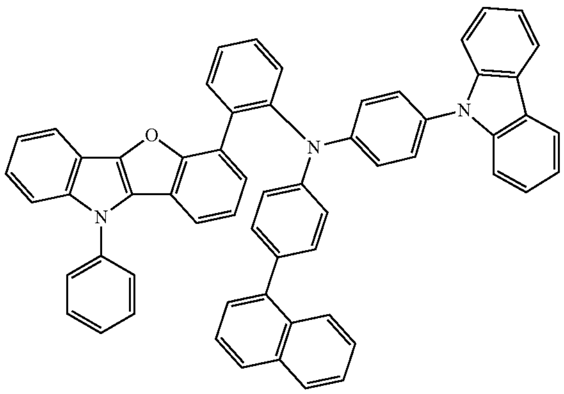
A187
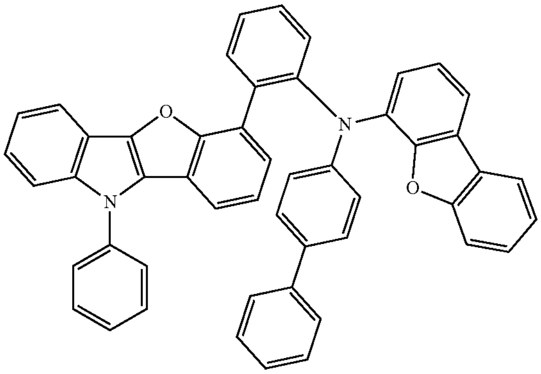
A188
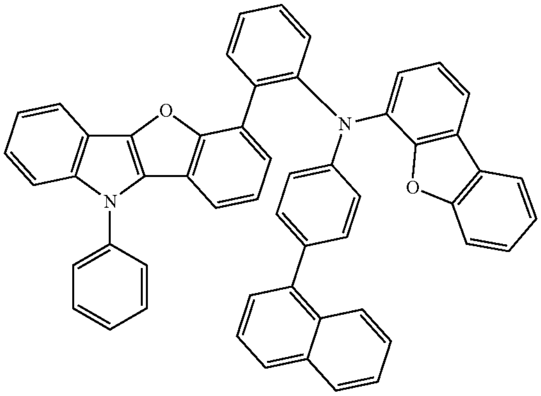
A189
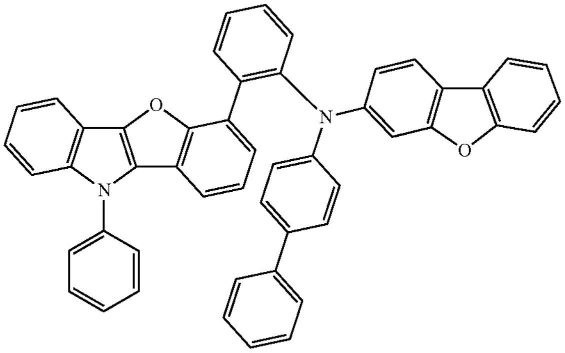

-continued
A190
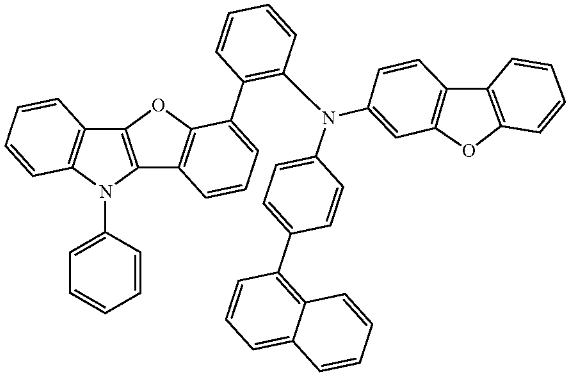
A191
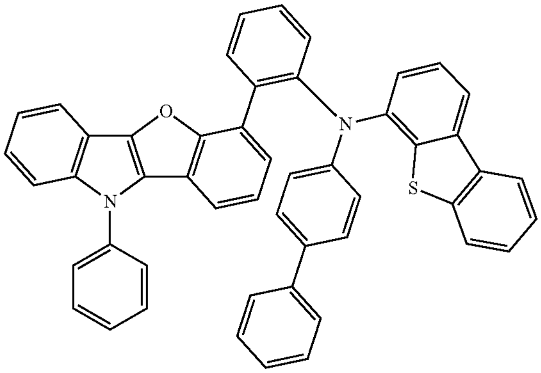
A192
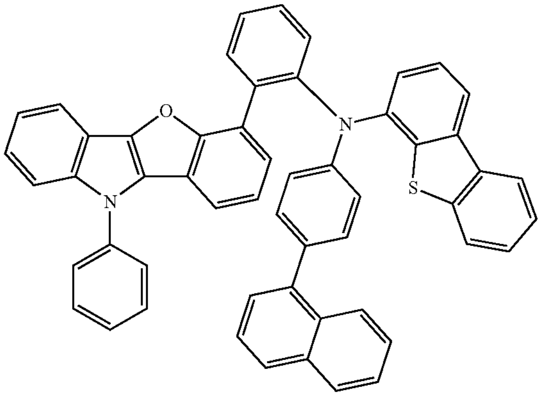
A193
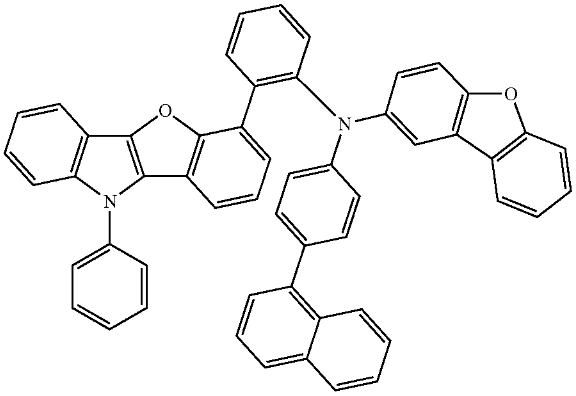
-continued
A194
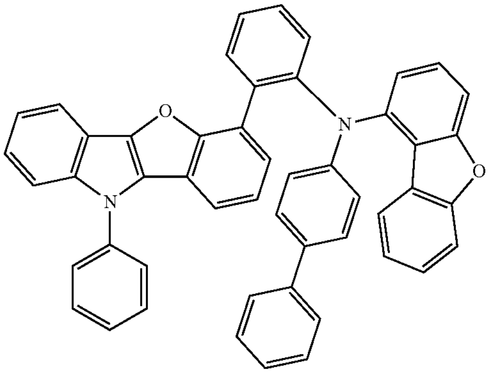
A195
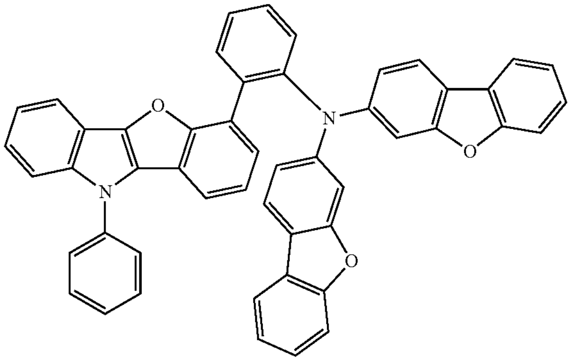
A196
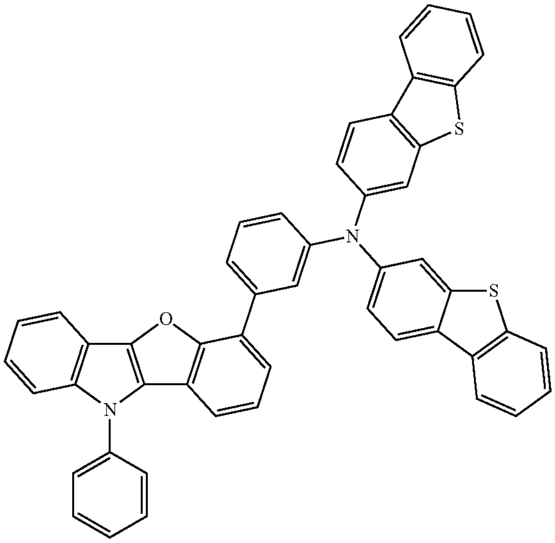

-continued
A197
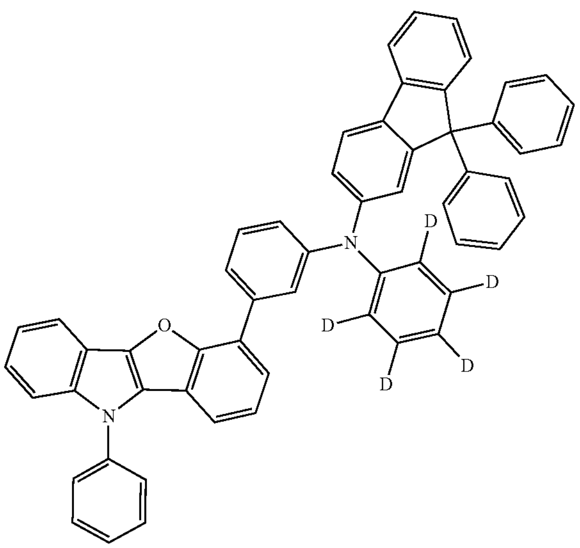
A198
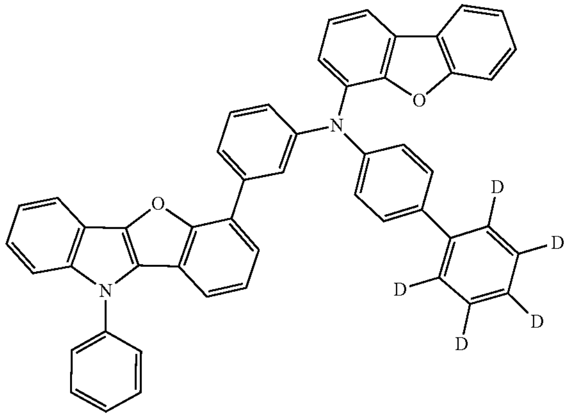
A199
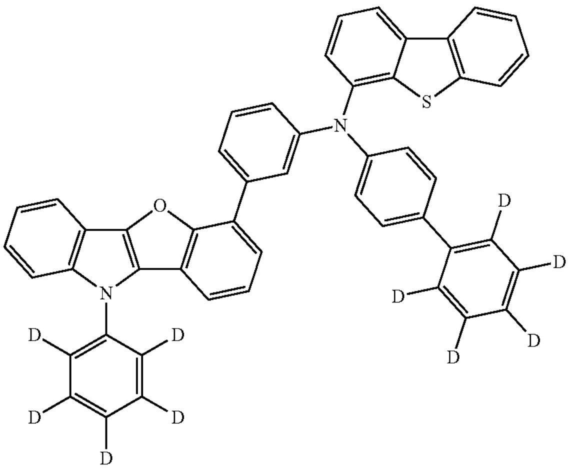
-continued
A200
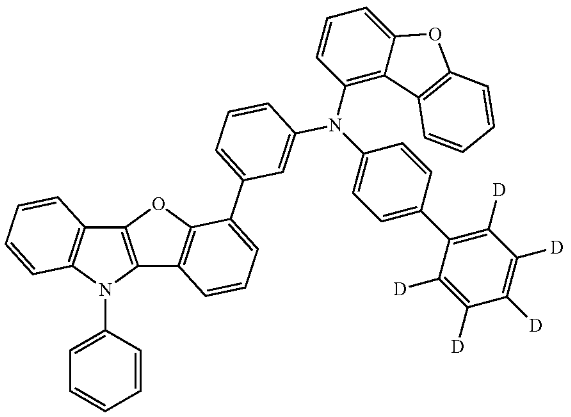
A201
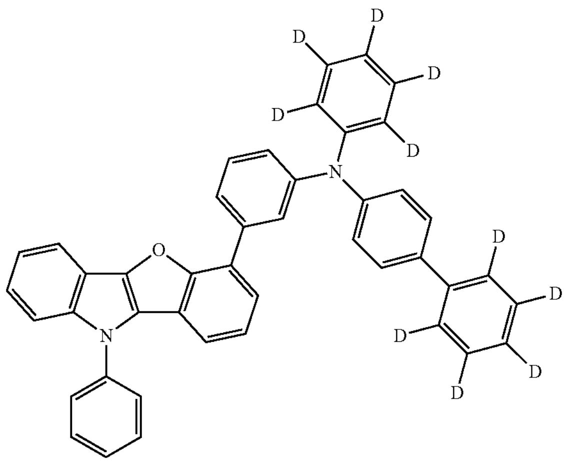
Compound Group 2
B1
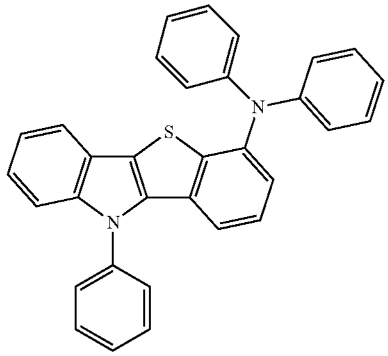

-continued
B2
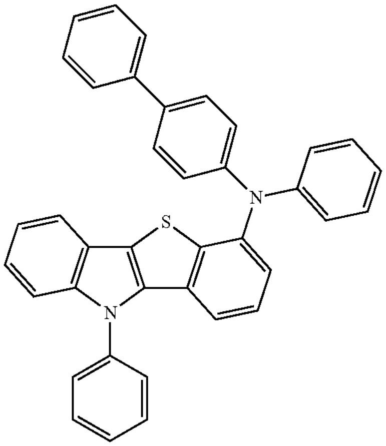
B3
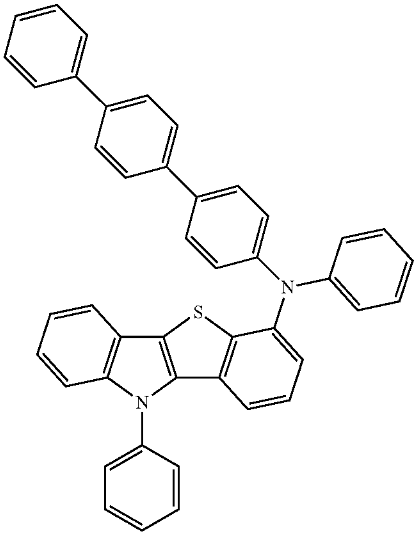
B4
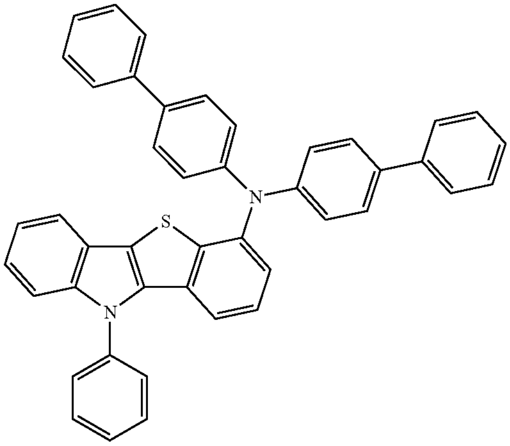
-continued
B5
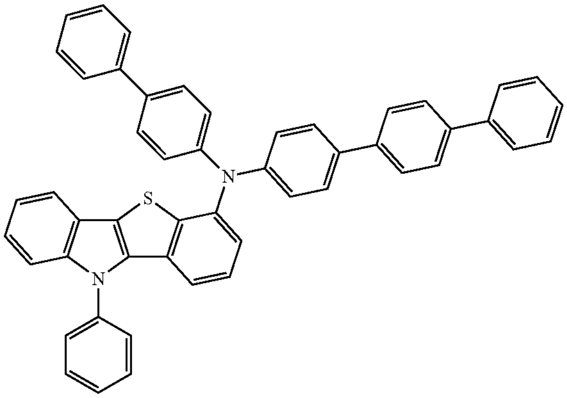
B6
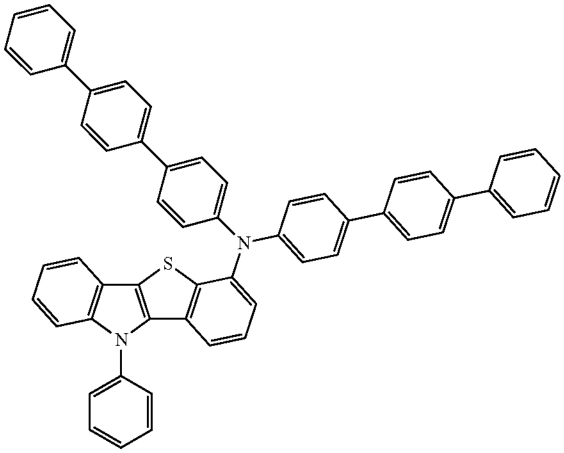
B7
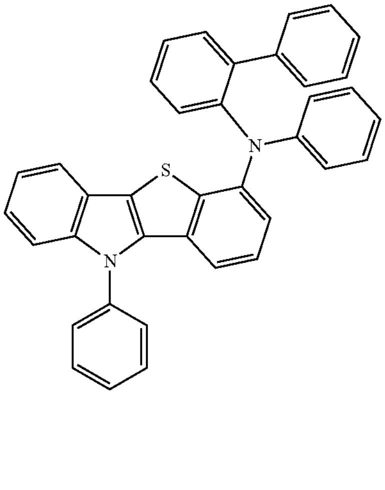

-continued
B8
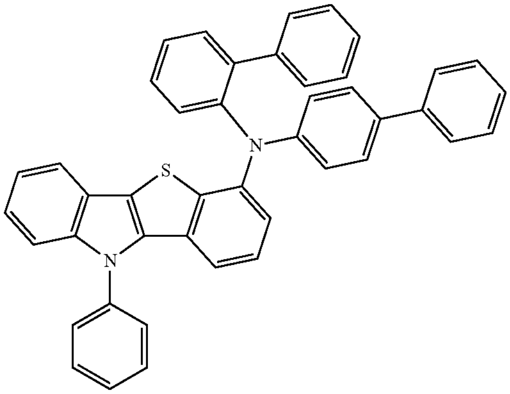
B9
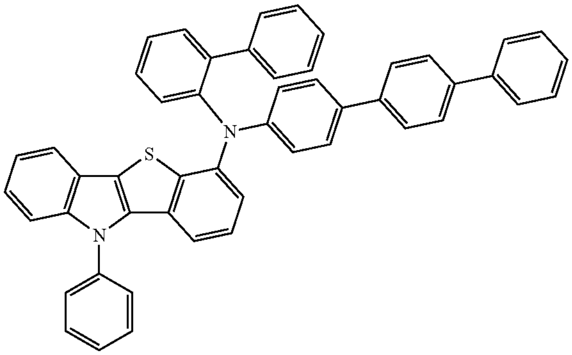
B10
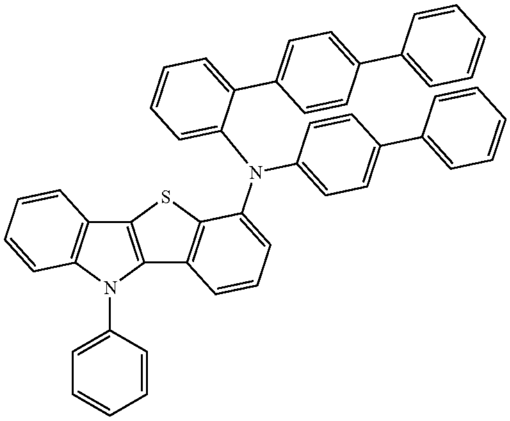
-continued
B11
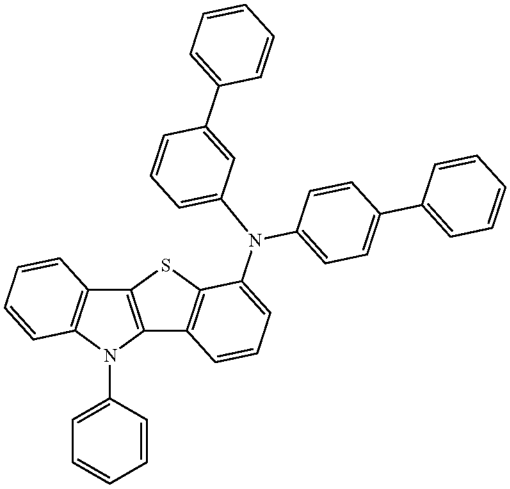
B12
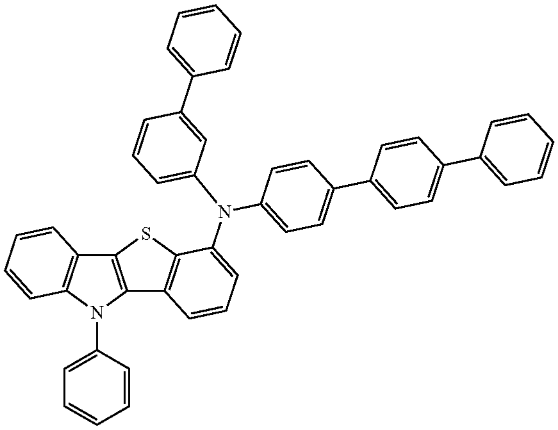
B13
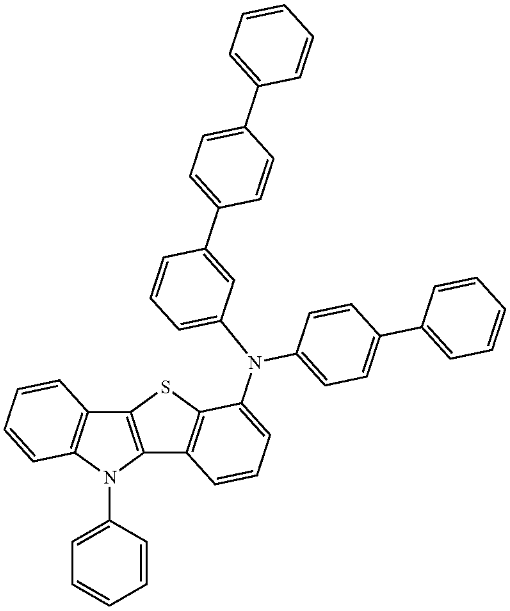

-continued
B14
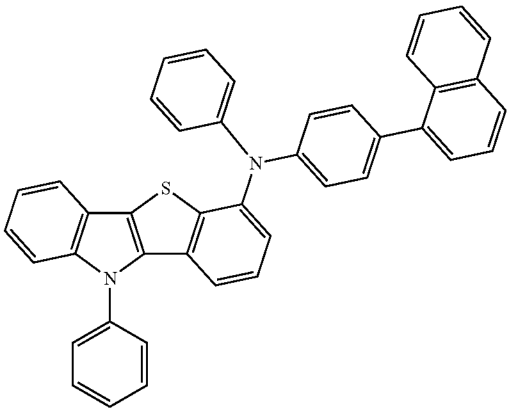
B15
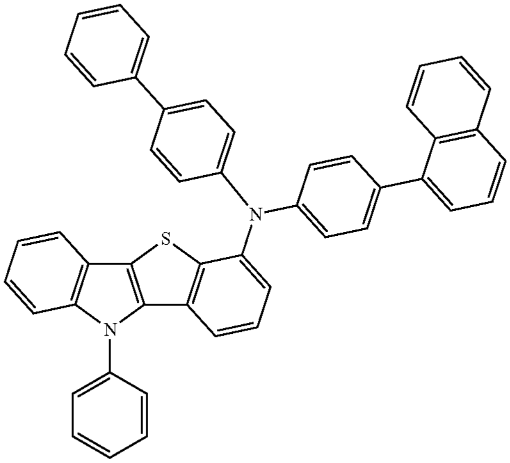
B16
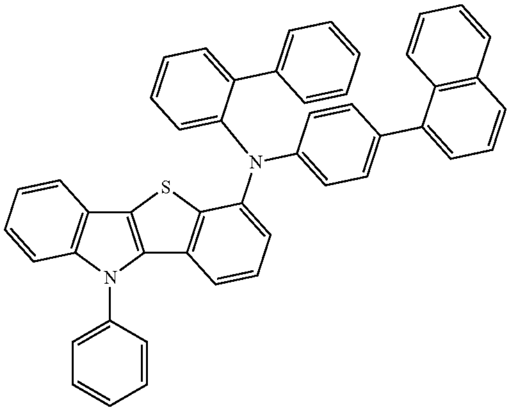
-continued
B17
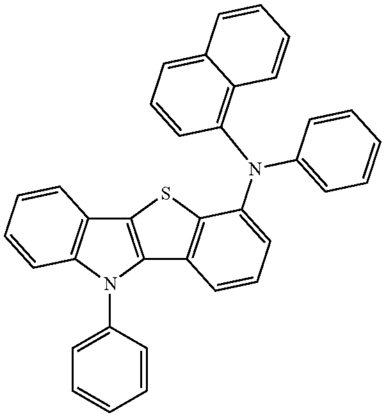
B18
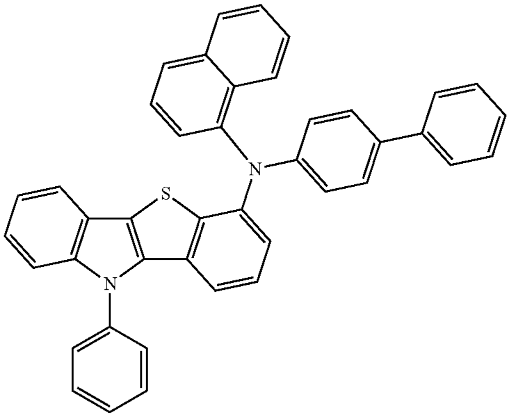
B19
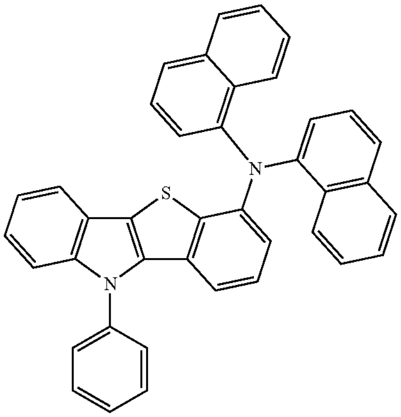

-continued
B20
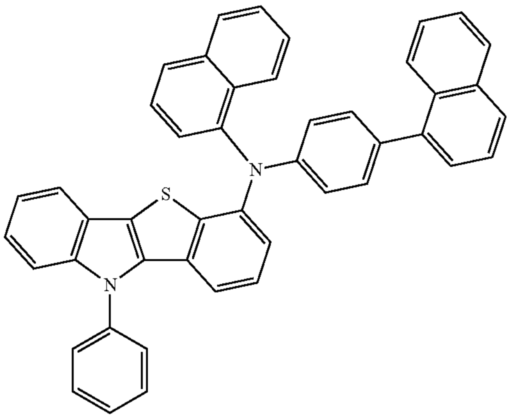
B21
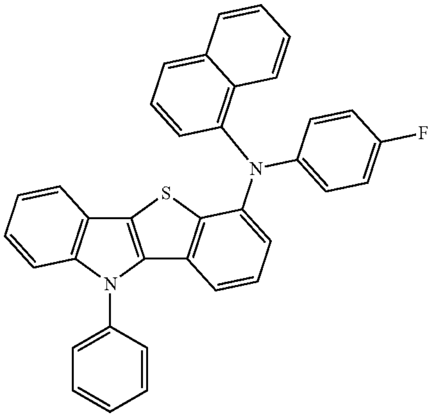
B22
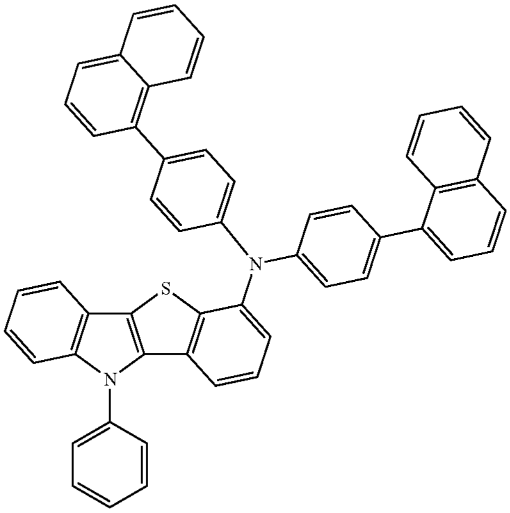
-continued
B23
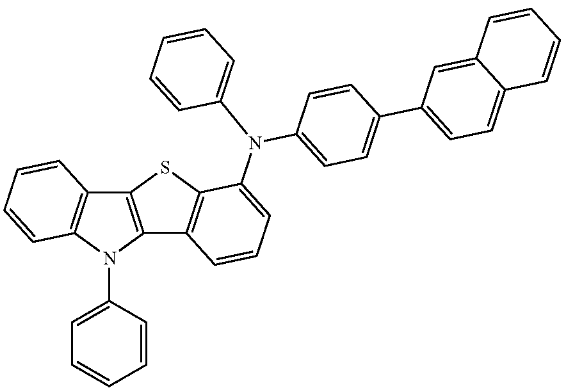
B24
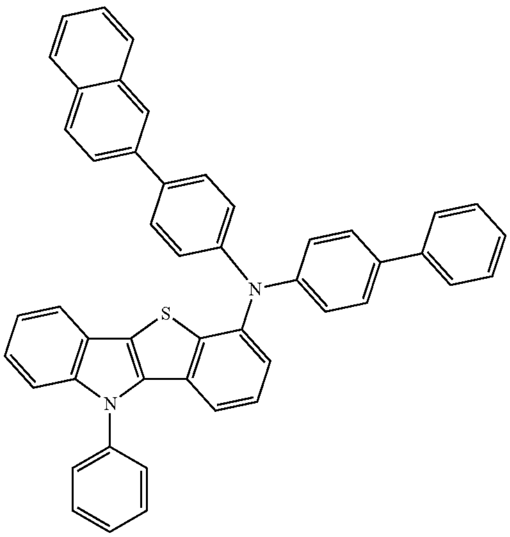
B25
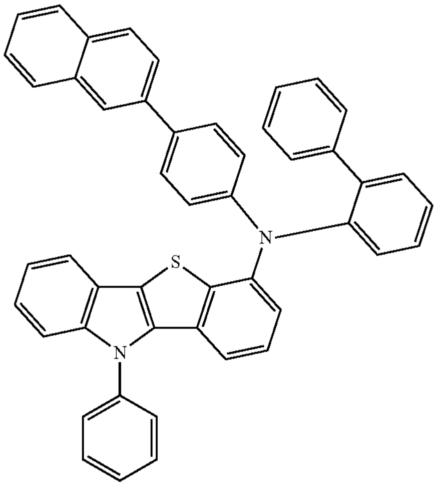

-continued
B26
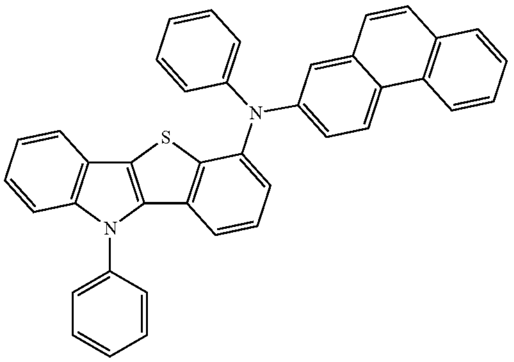
B27
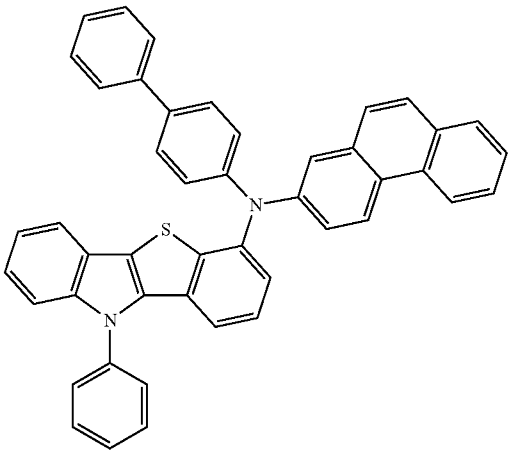
B28
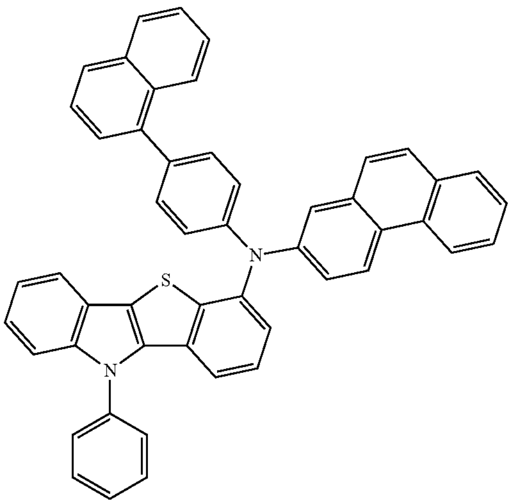
-continued
B29
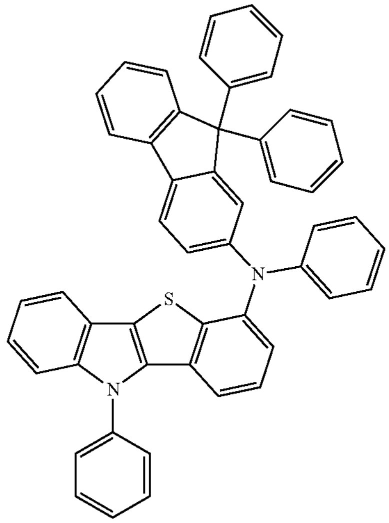
B30
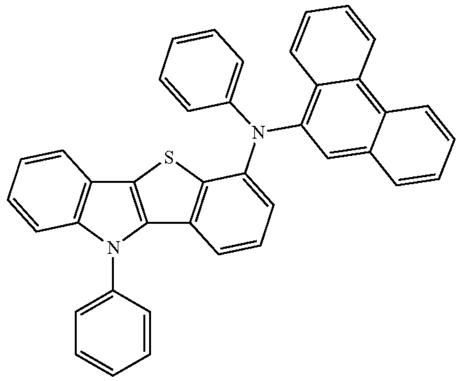
B31
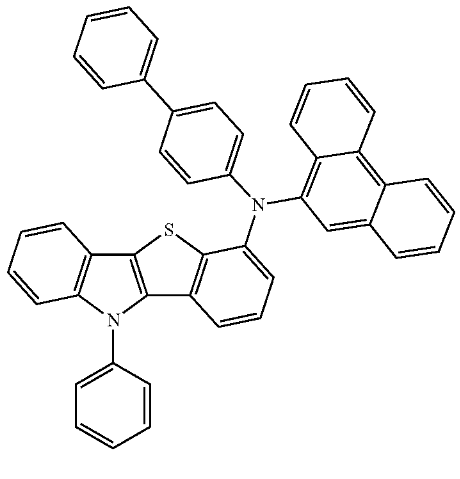

-continued
B32
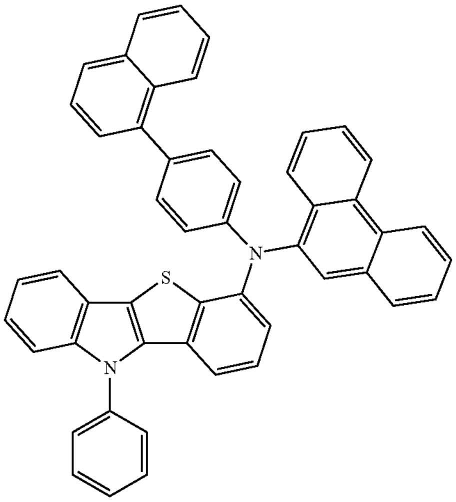
B33
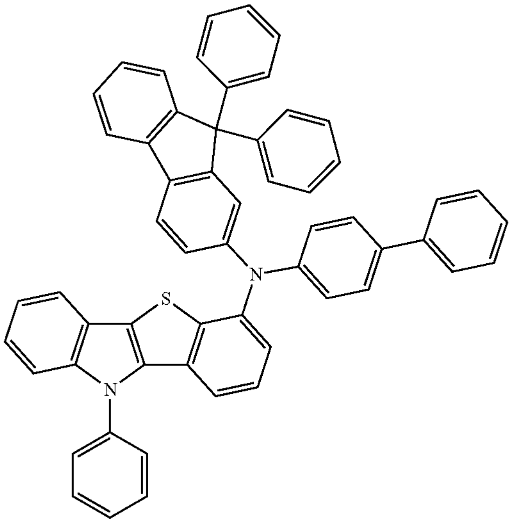
B34
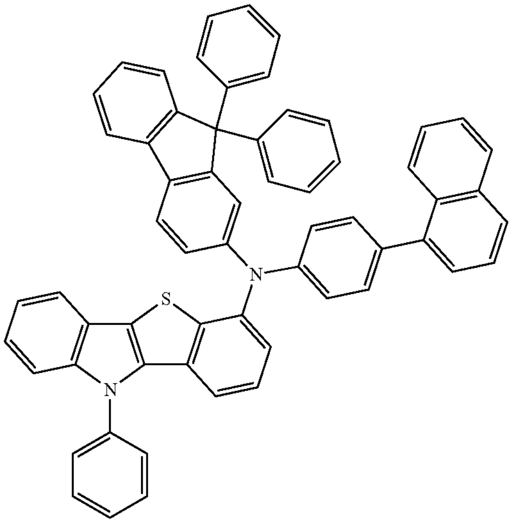
-continued
B35
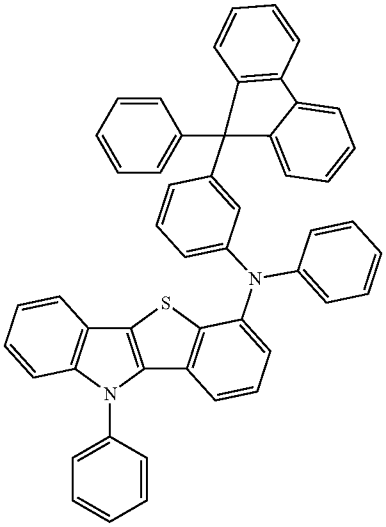
B36
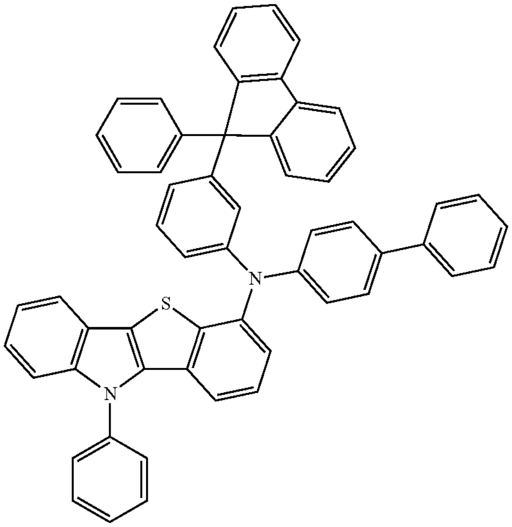
B37
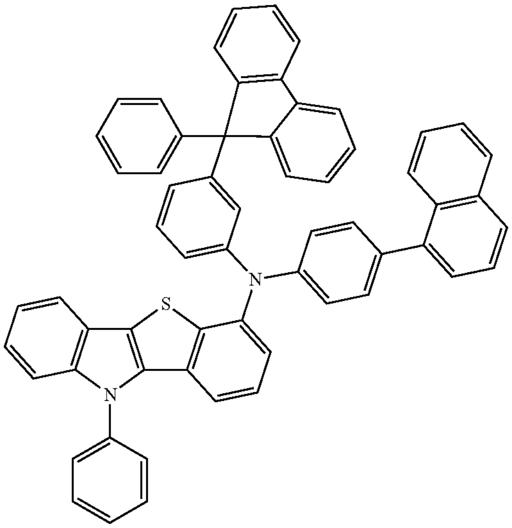

-continued
B38
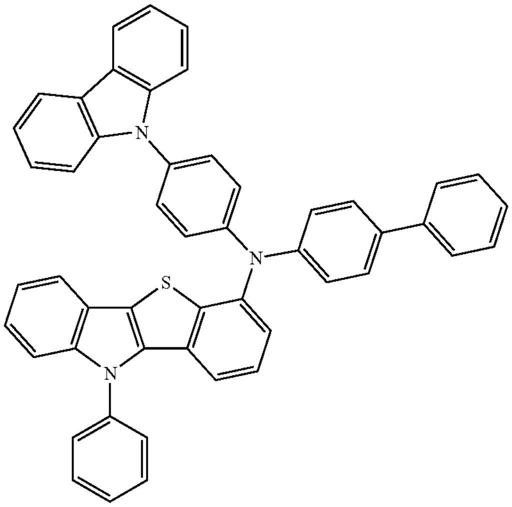
B39
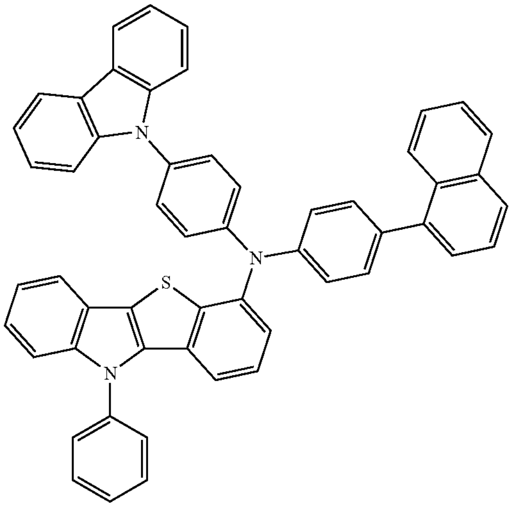
B40
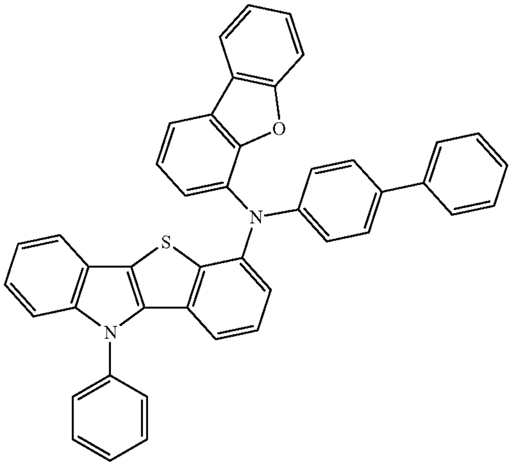
-continued
B41
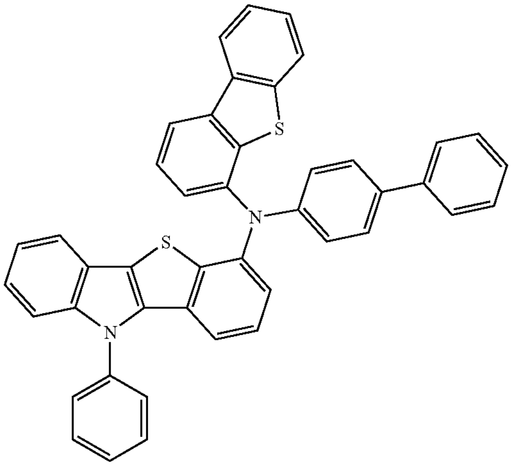
B42
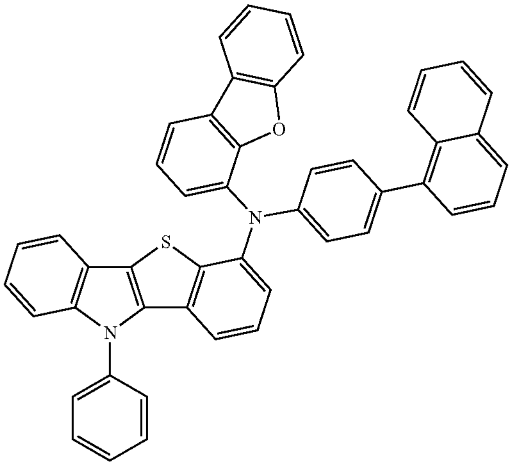
B43
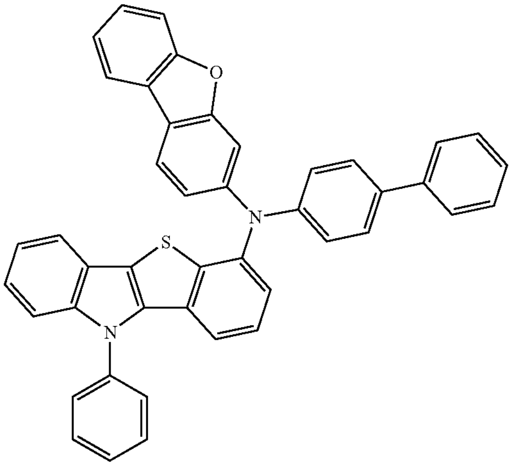

-continued
B44
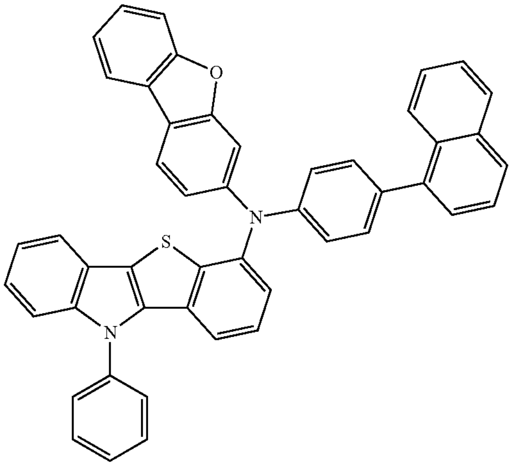
B45
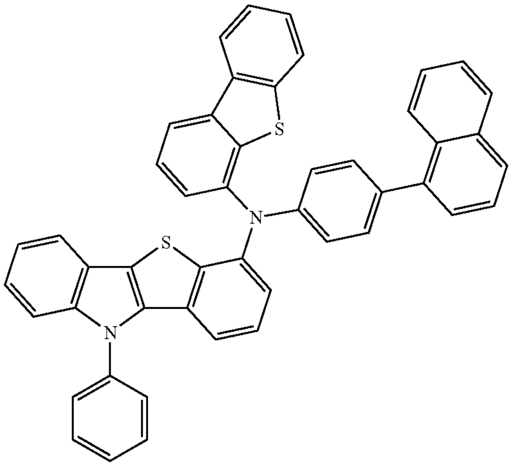
B46
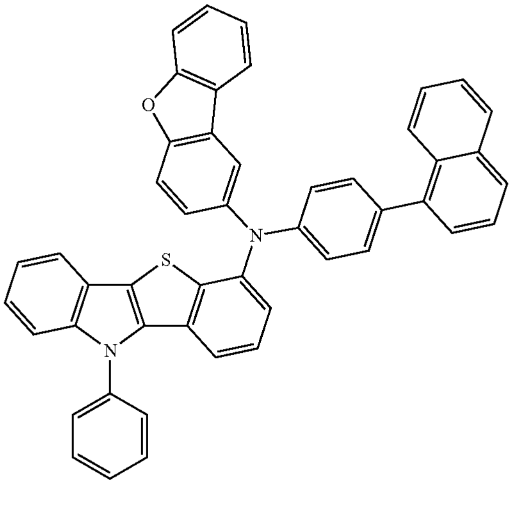
-continued
B47
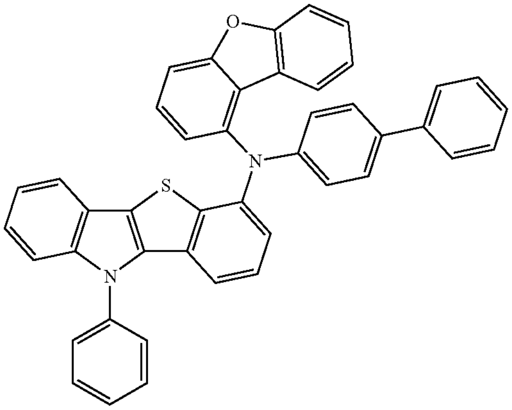
B48
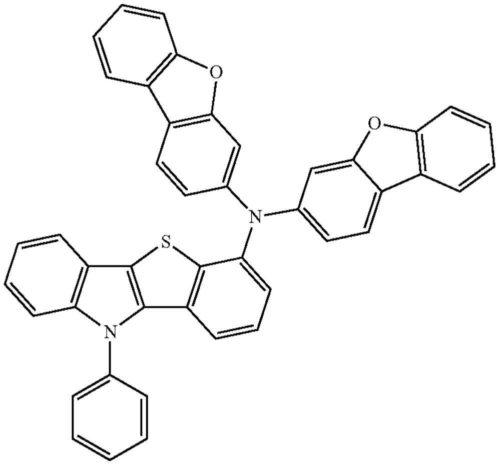
B49
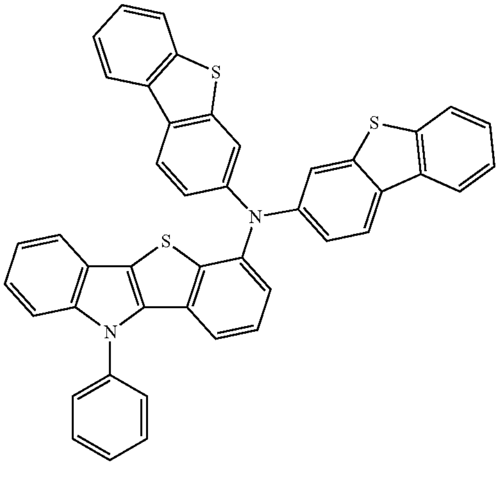

-continued
B50
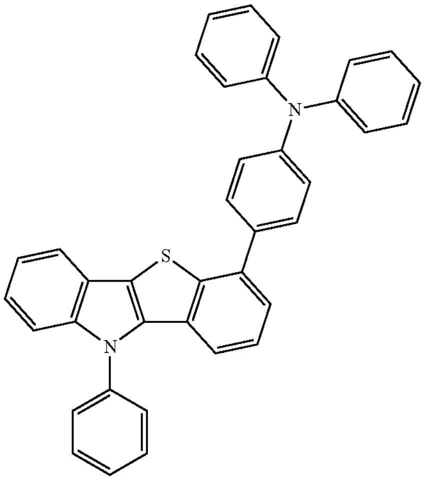
B51
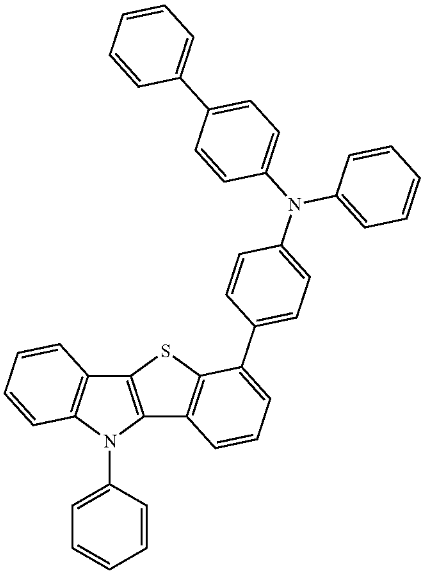
B52
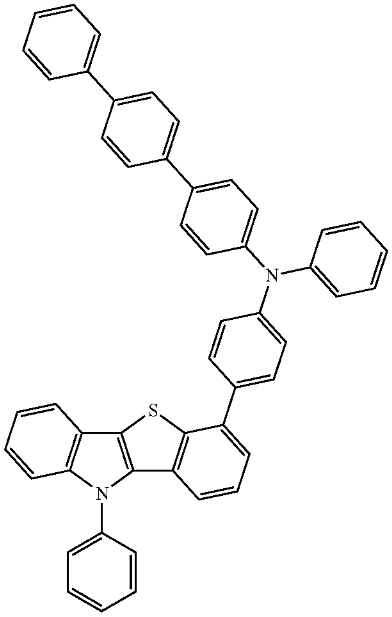
B53
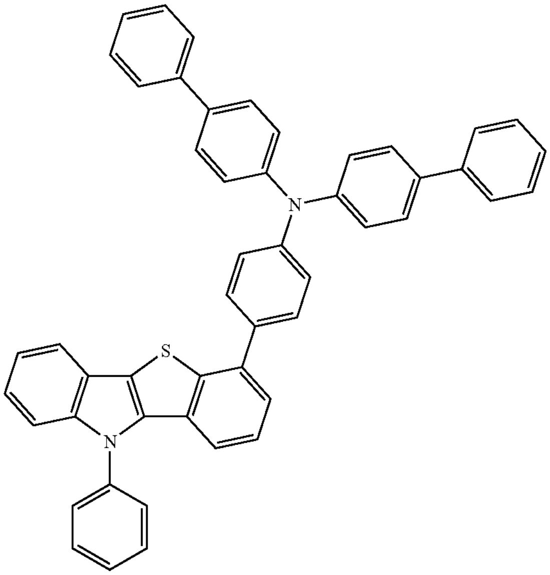
B54
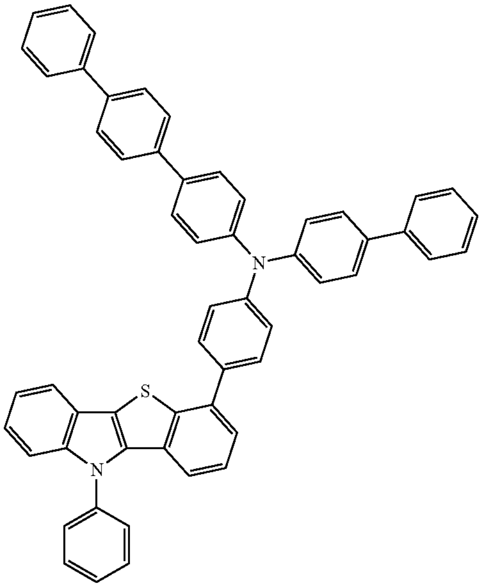

-continued
B55
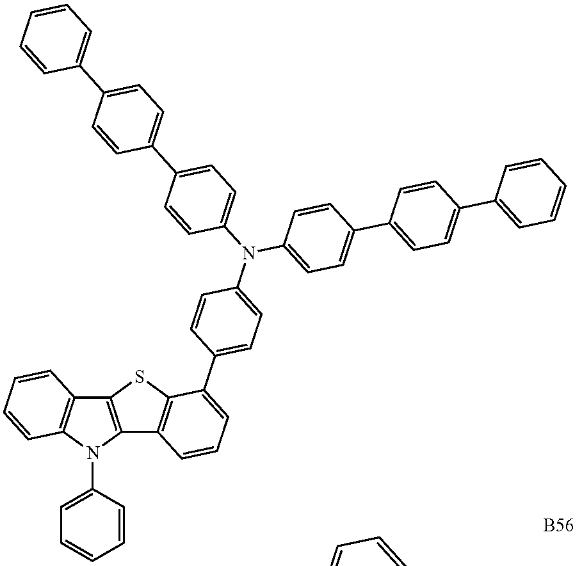
B56
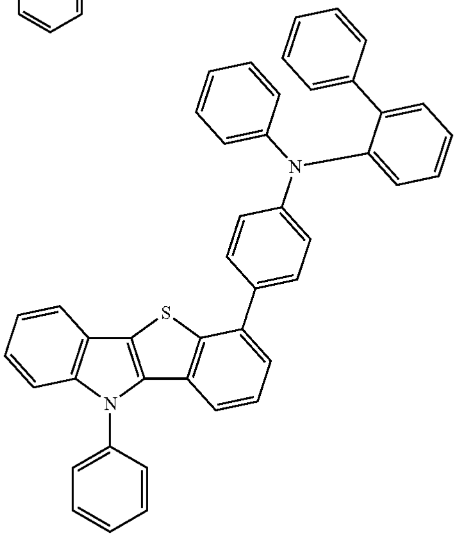
B57
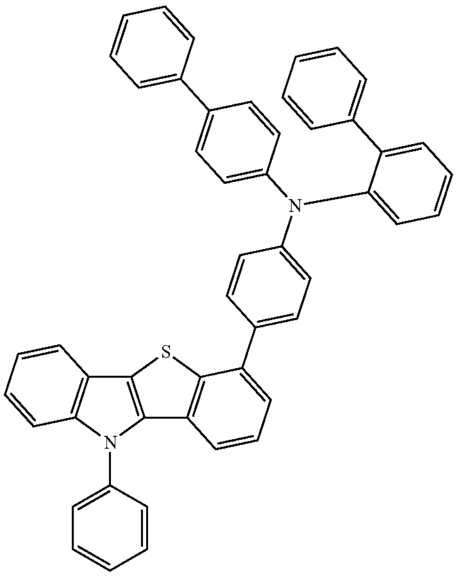
-continued
B58
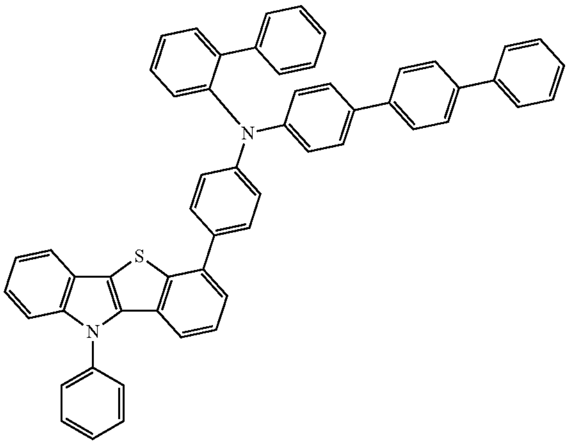
B59
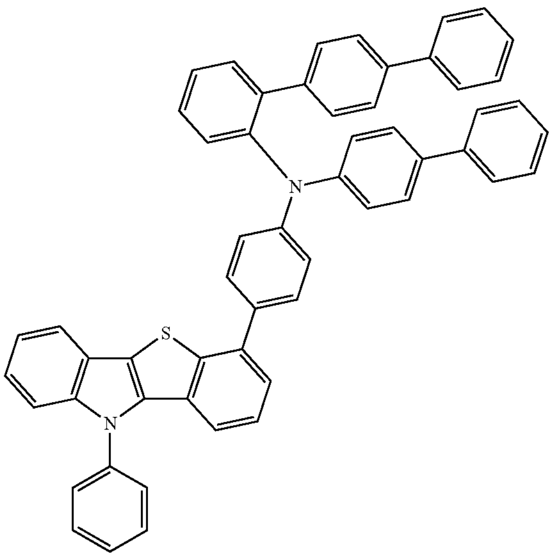
B60
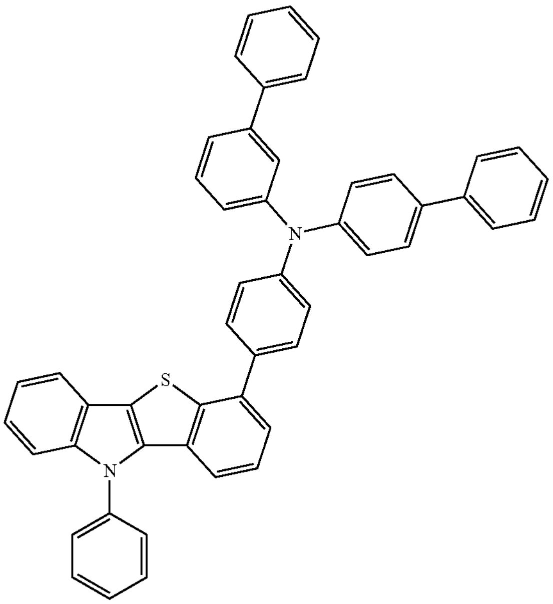

-continued
B61
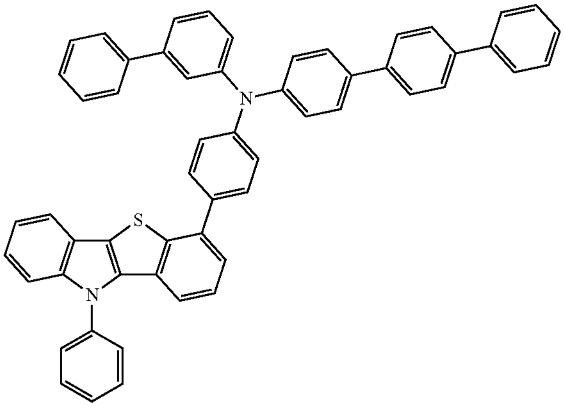
B62
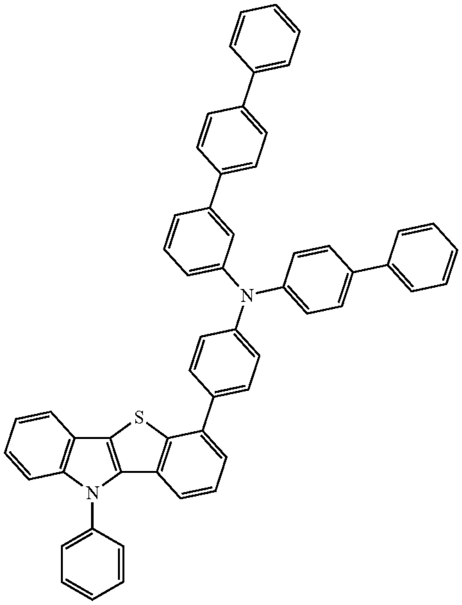
B63
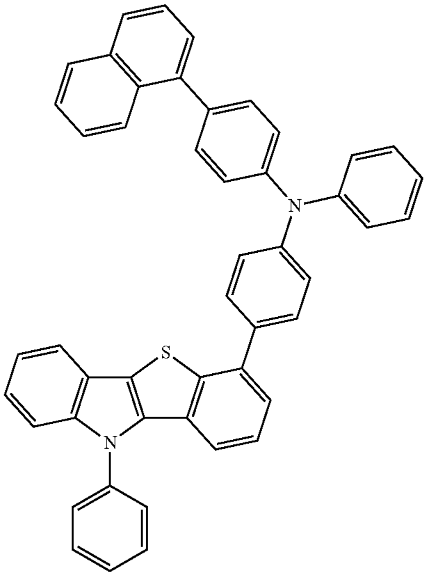
-continued
B64
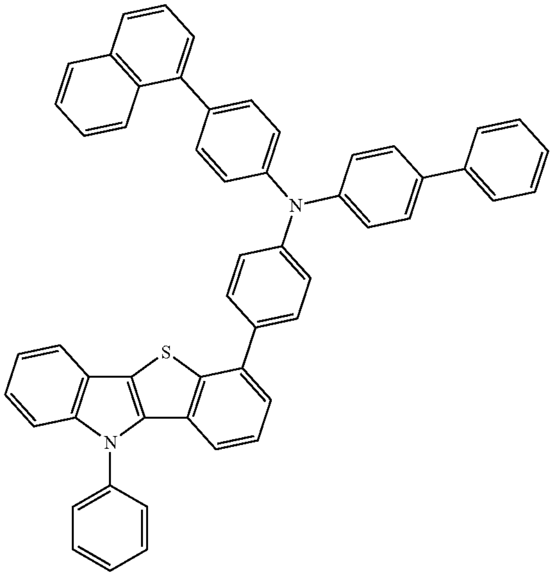
B65
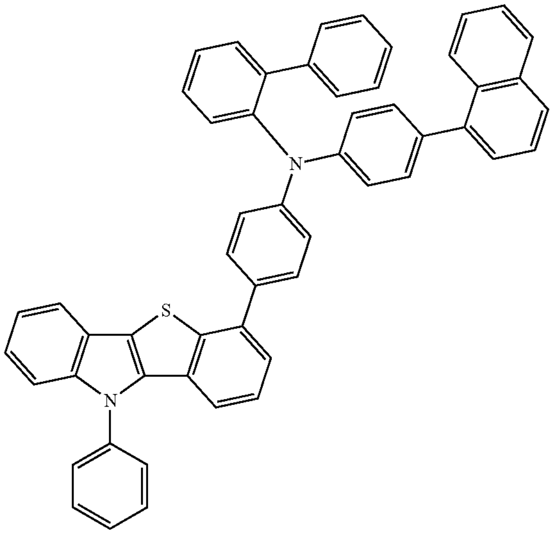

-continued
B66
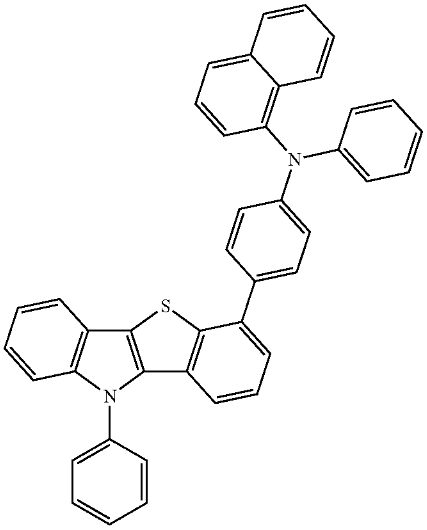
B67
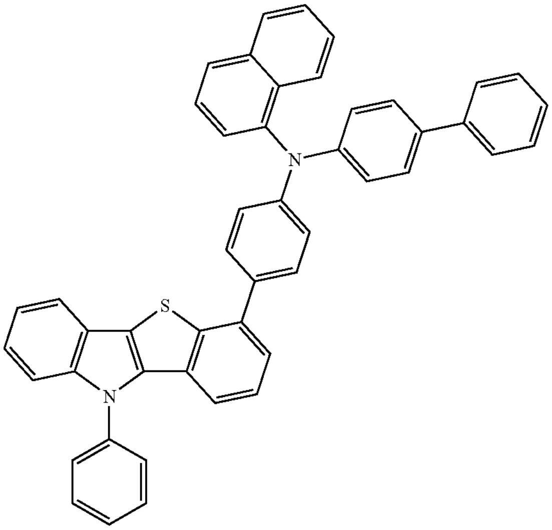
B68
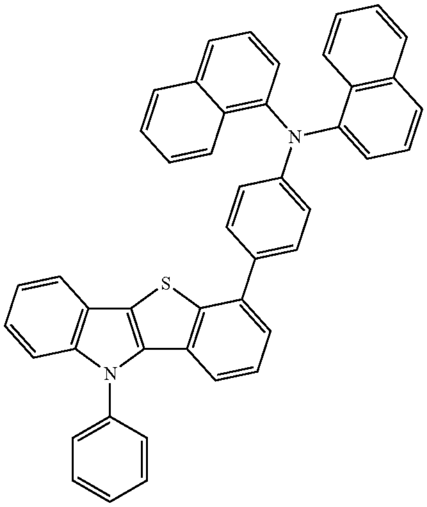
-continued
B69
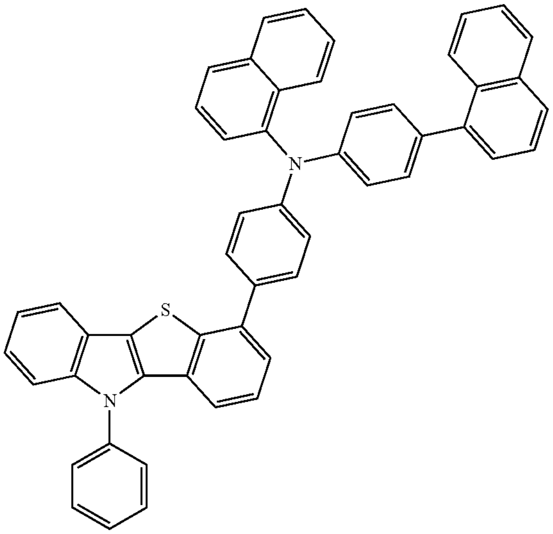
B70
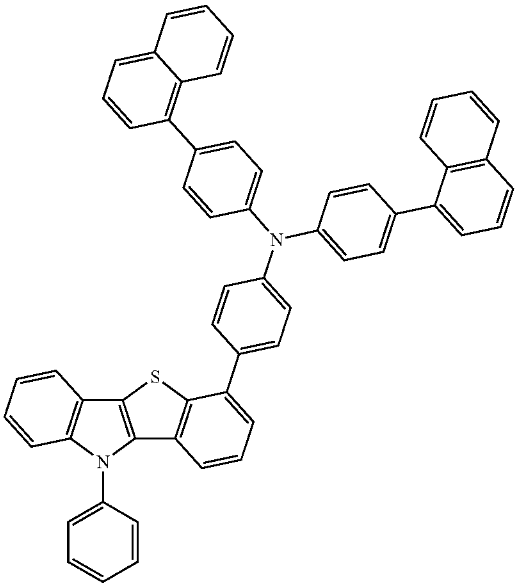

-continued
B71
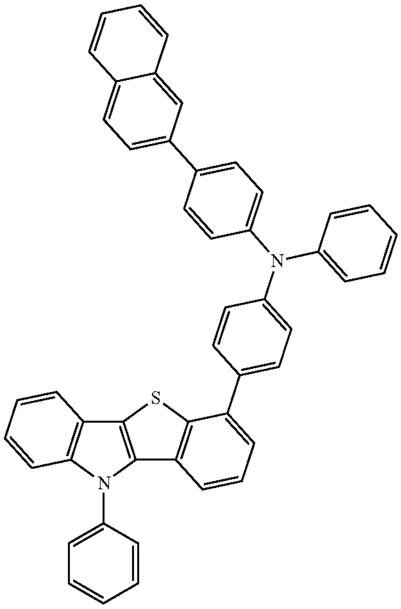
B72
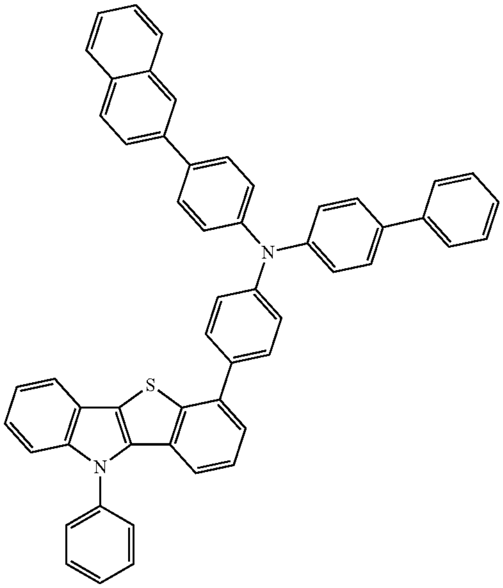
-continued
B73
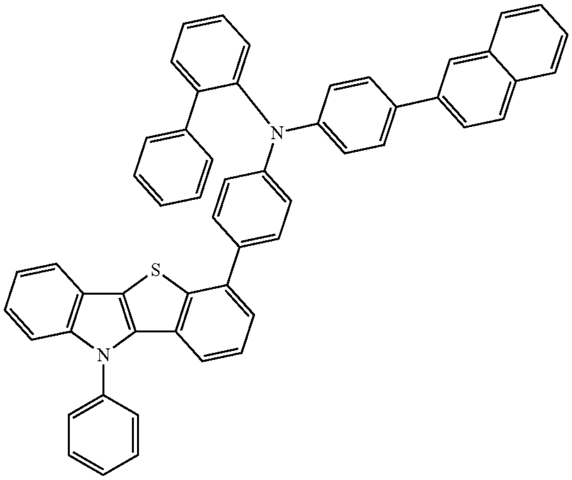
B74
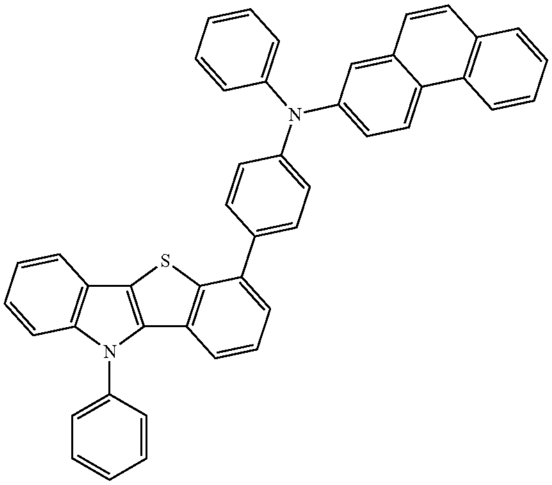
B75
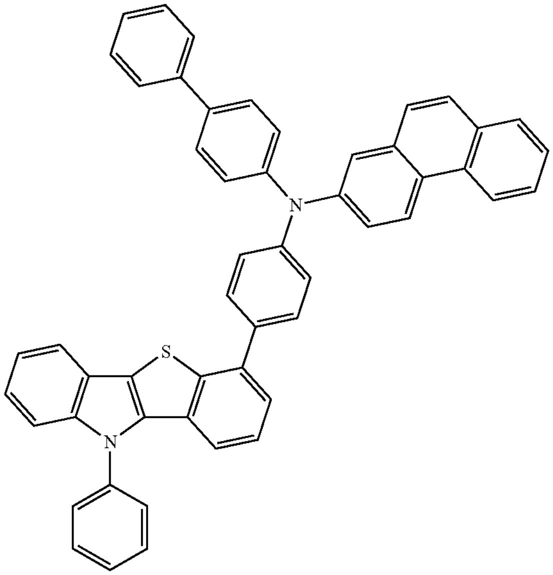

-continued
B76
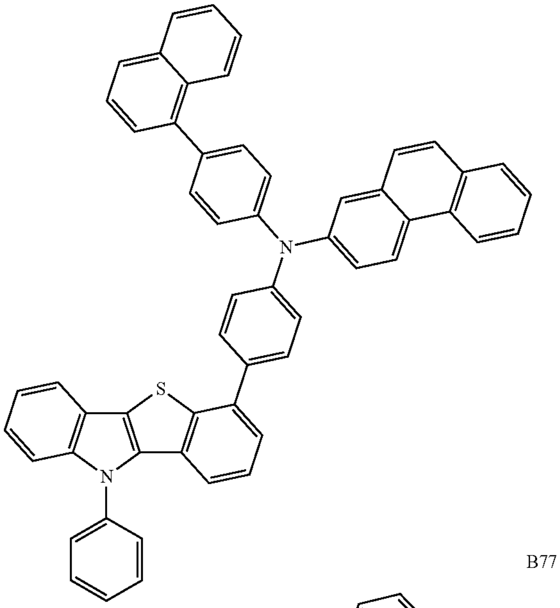
B77
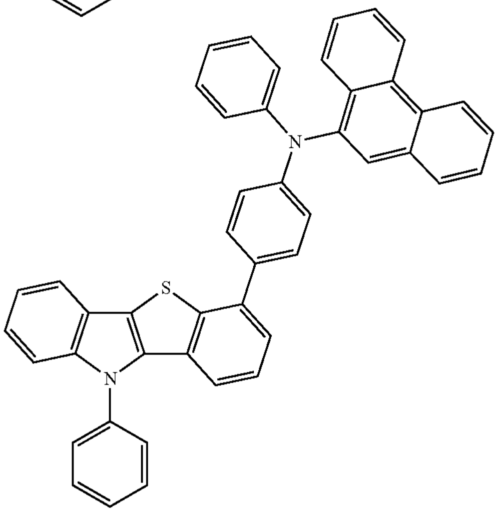
B78
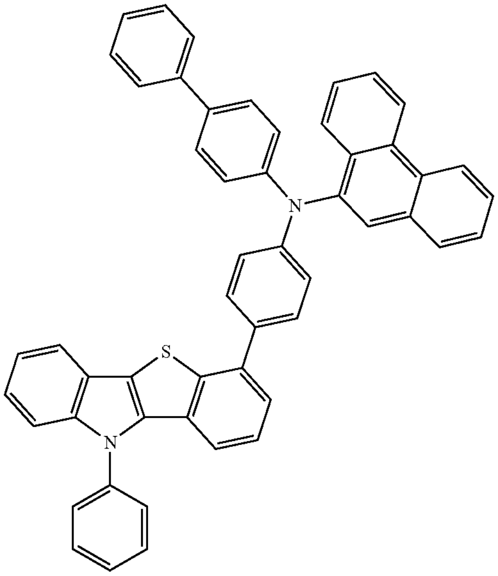
-continued
B79
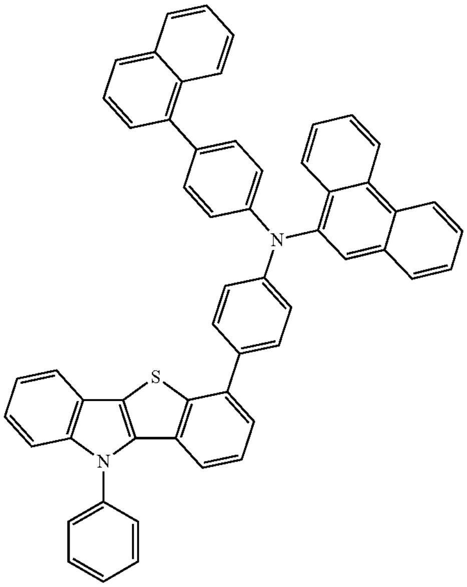
B80
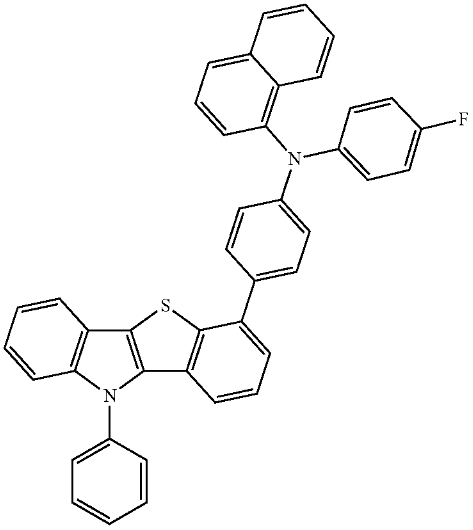

-continued
B81
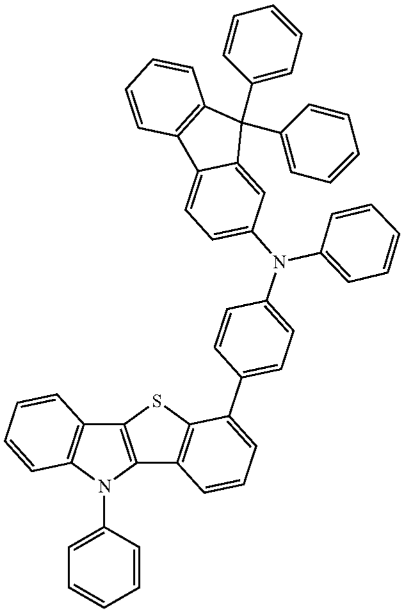
B82
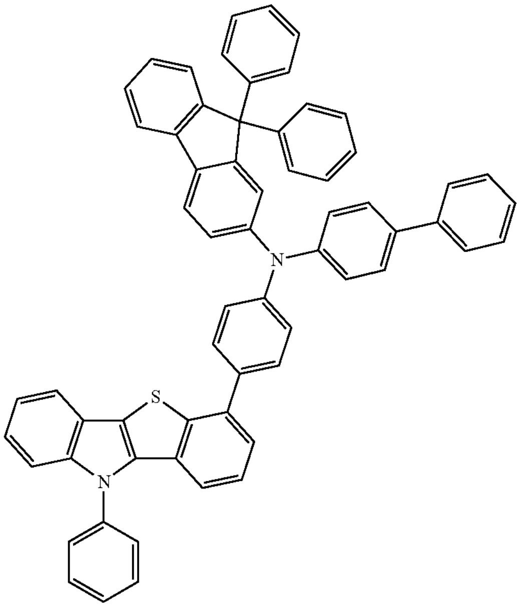
-continued
B83
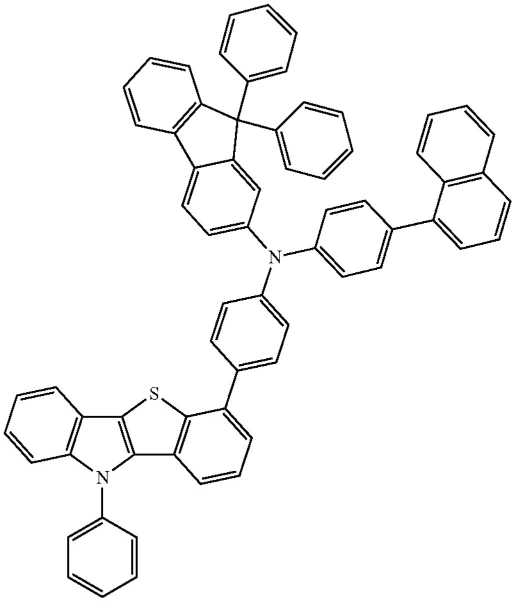
B84
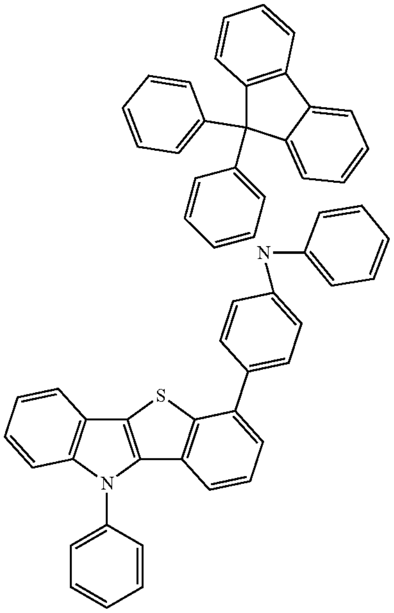

B85
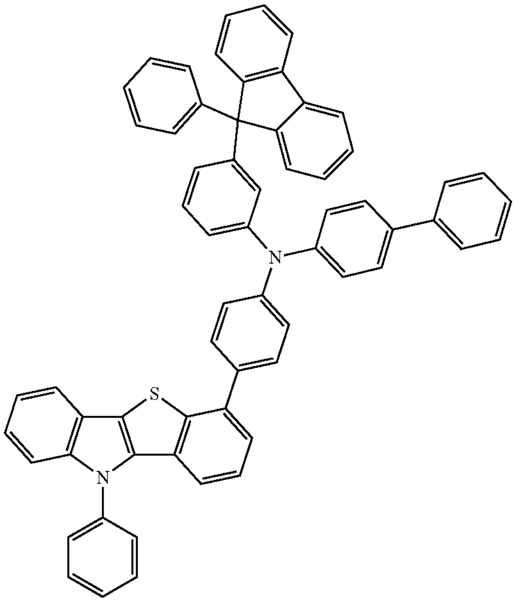
B86
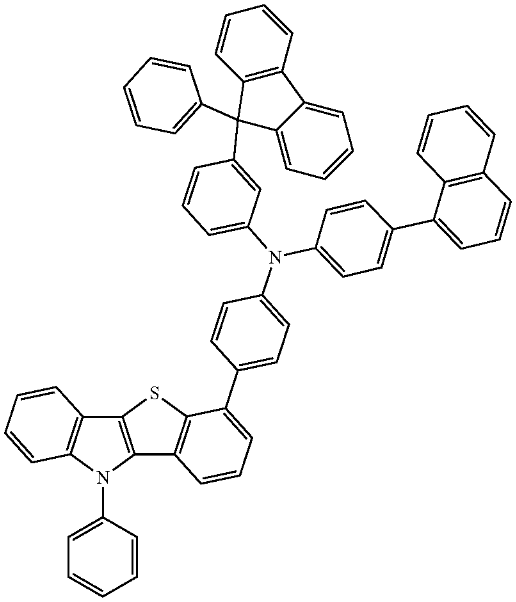
B87
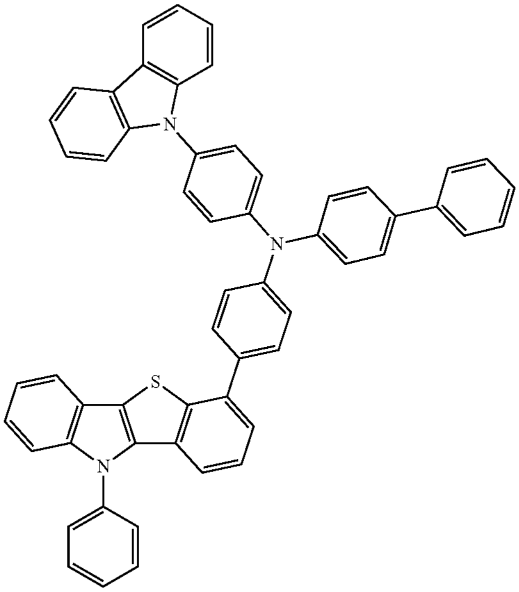
B88
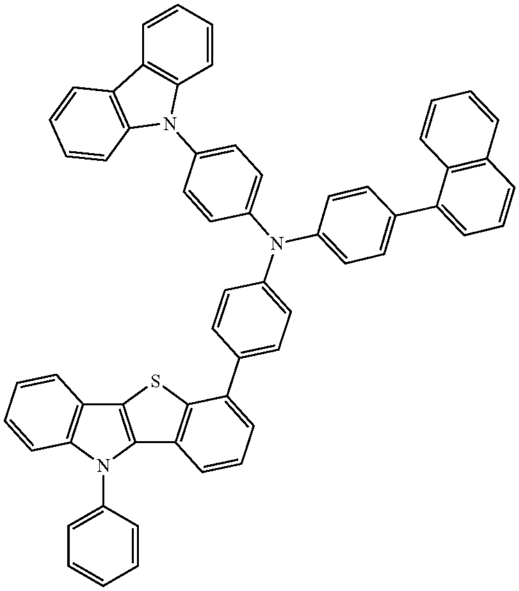

-continued
B89
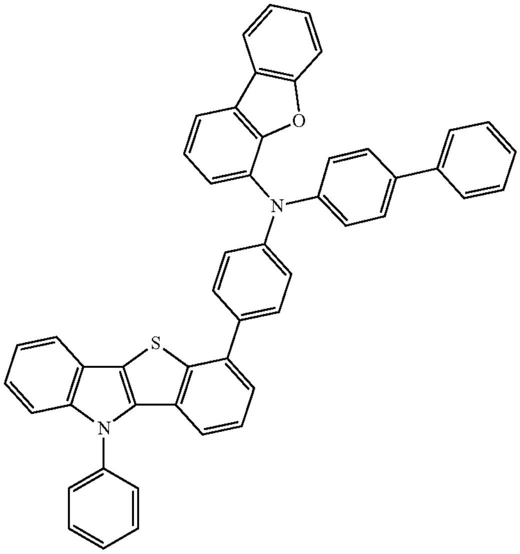
B90
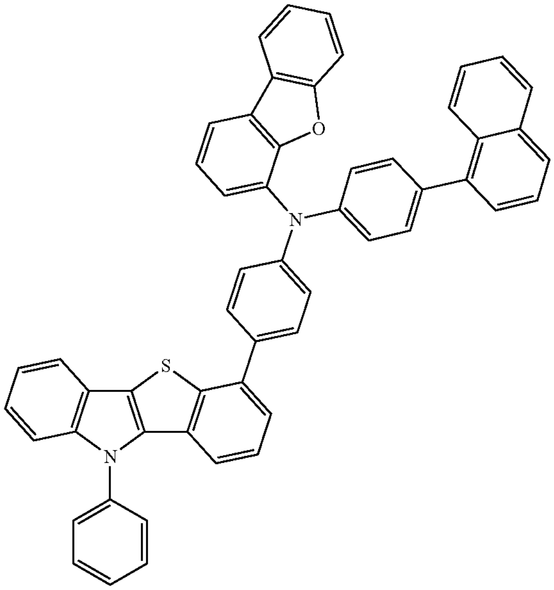
-continued
B91
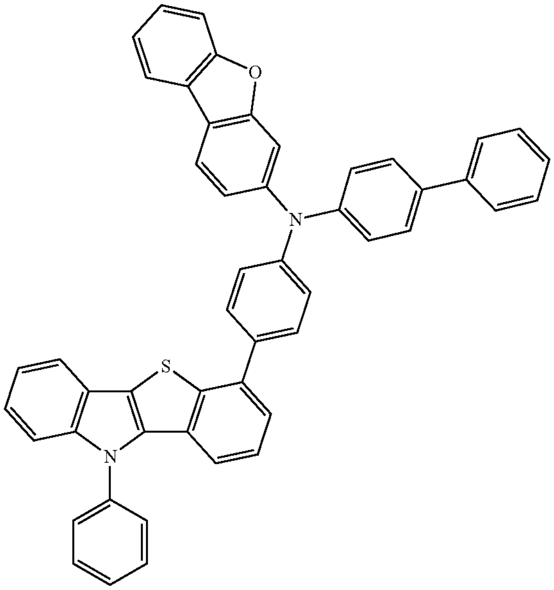
B92
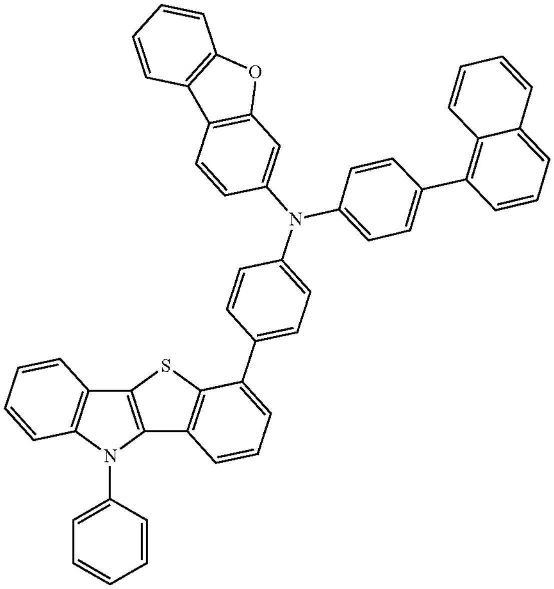

-continued
B93
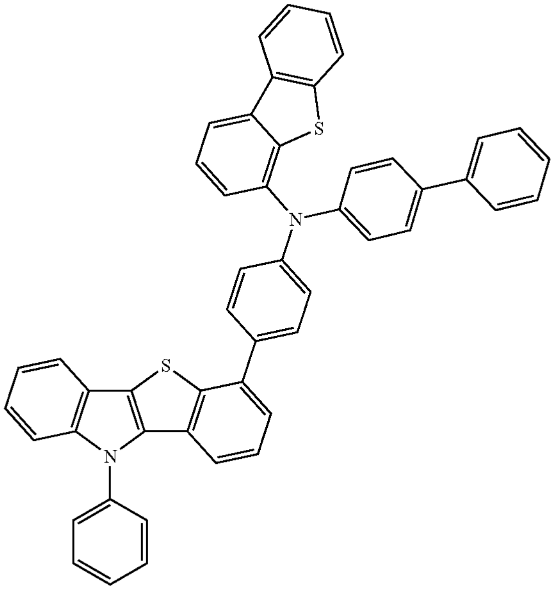
B94
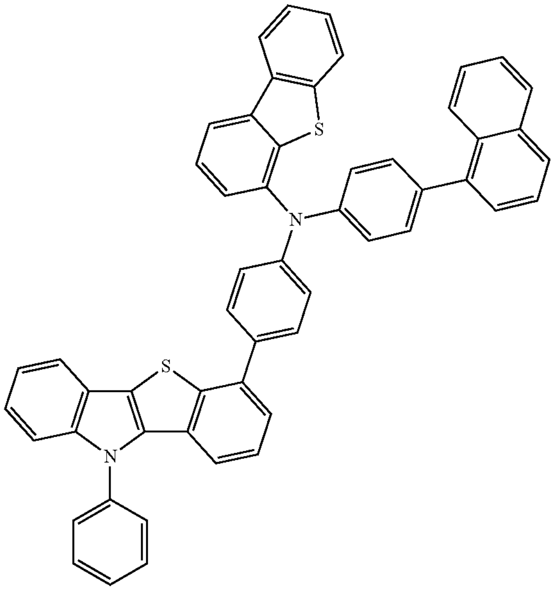
-continued
B95
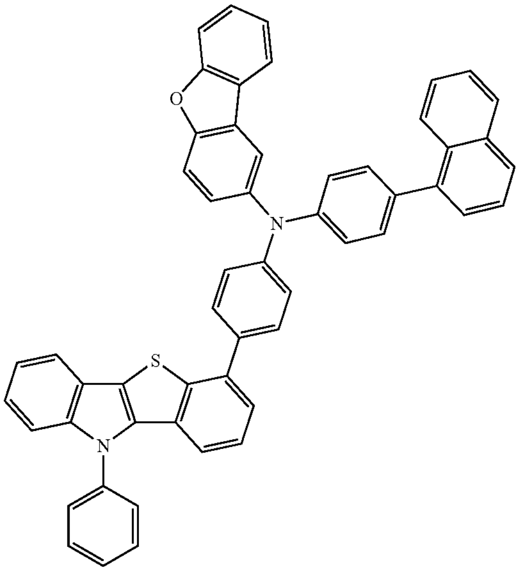
B96
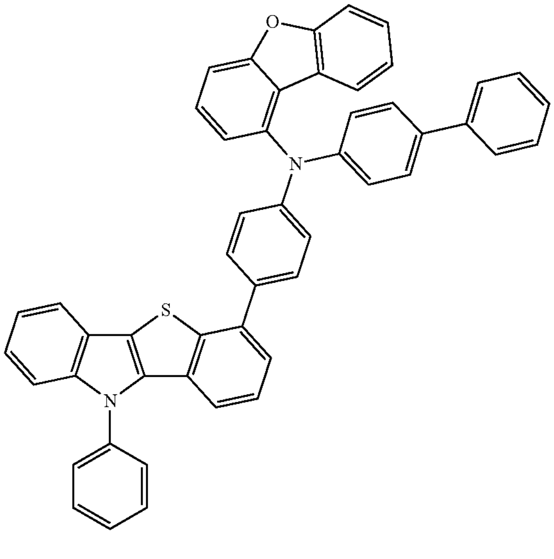

-continued
B97
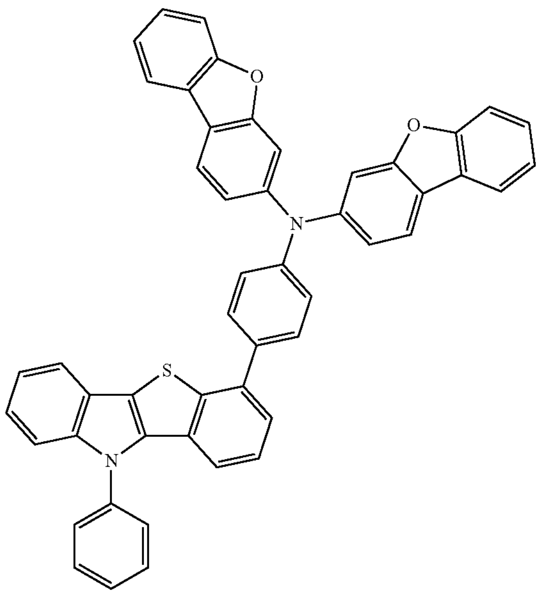
B98
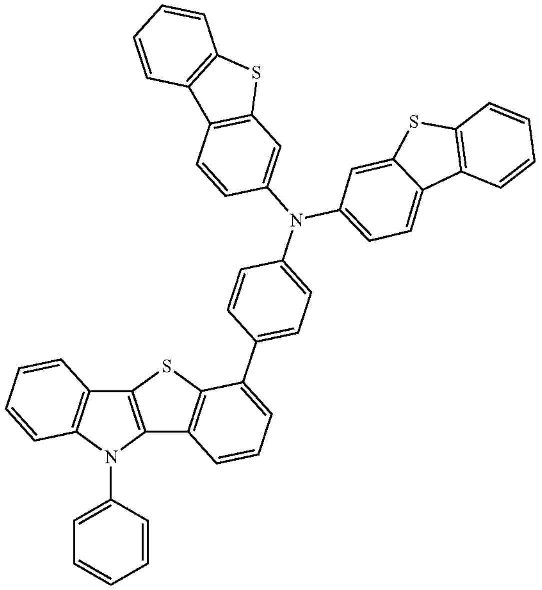
B99
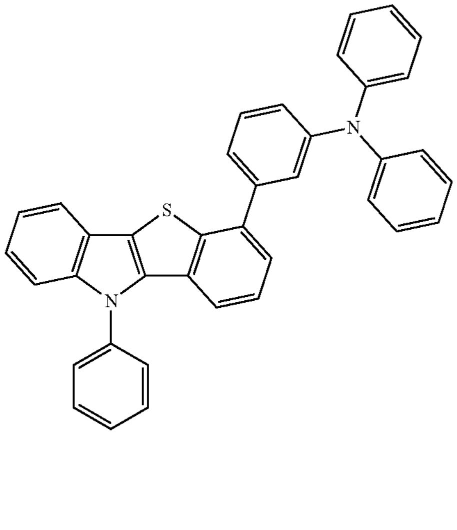
-continued
B100
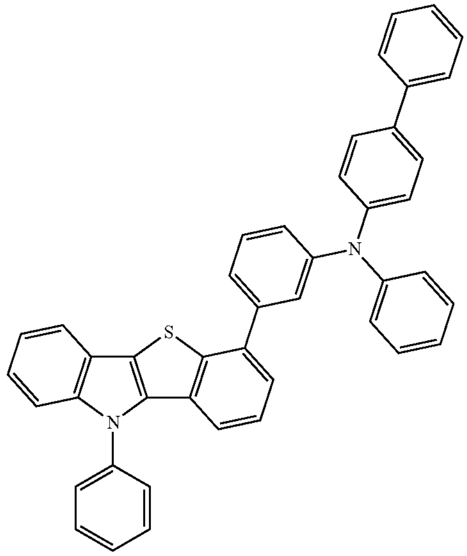
B101
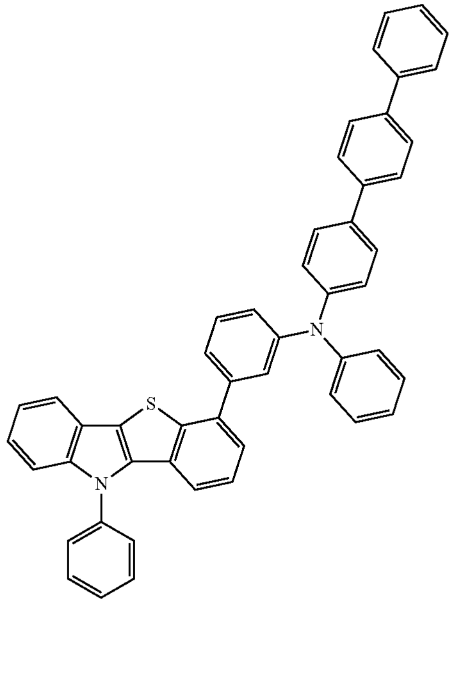

-continued
B102
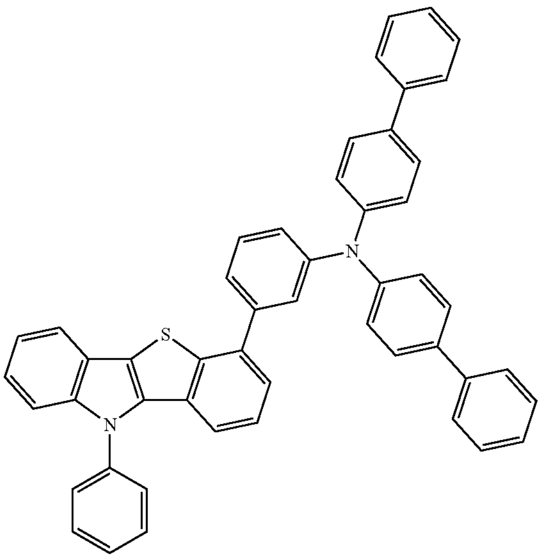
B103
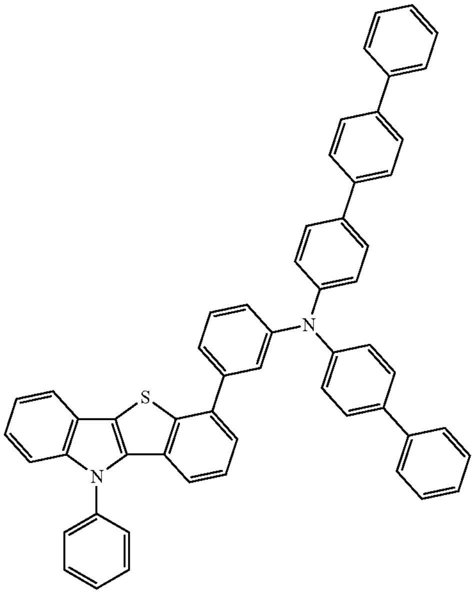
-continued
B104
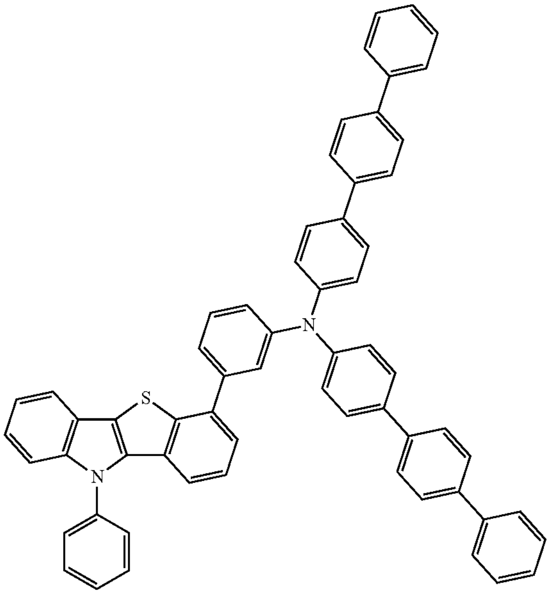
B105
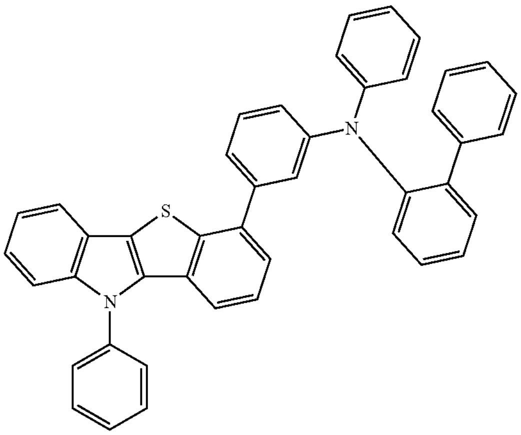
B106
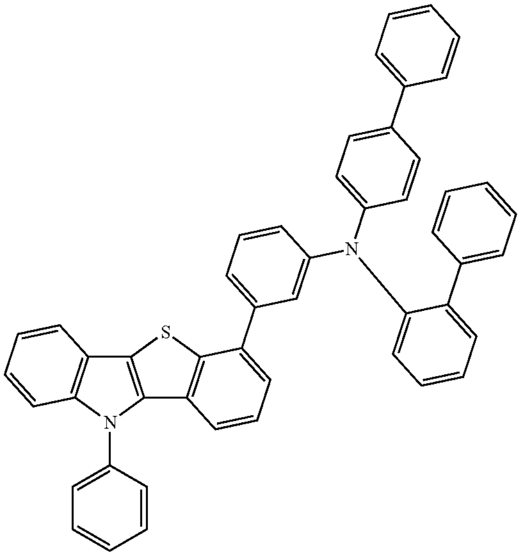

-continued
B107
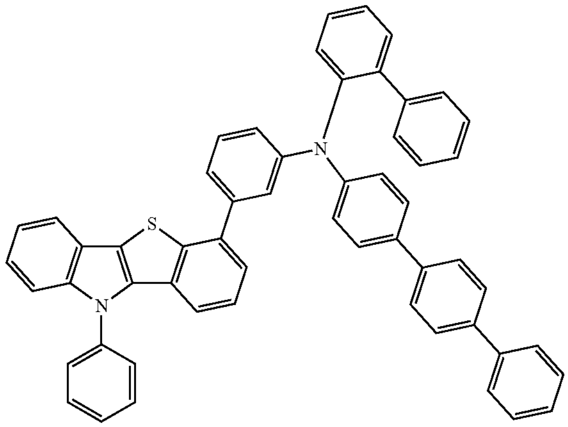
B108
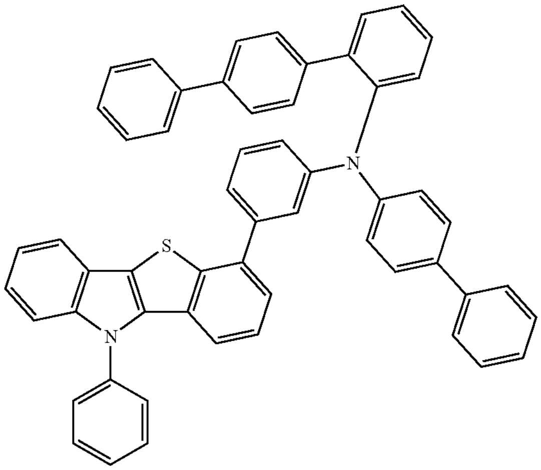
B109
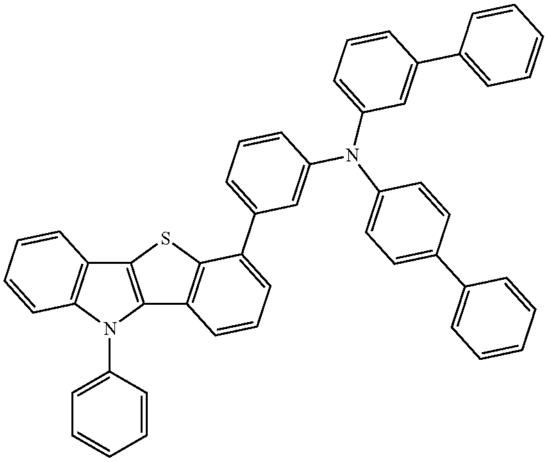
-continued
B110
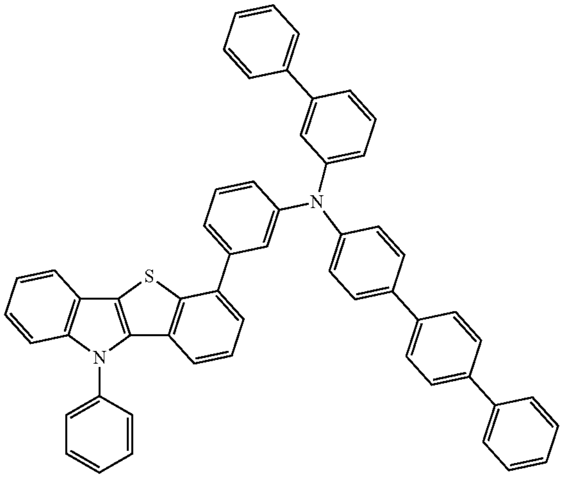
B111
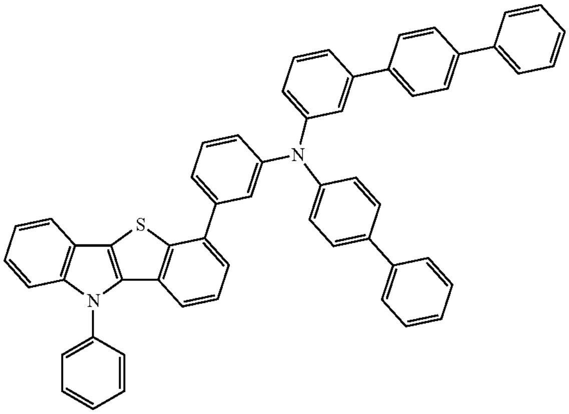
B112
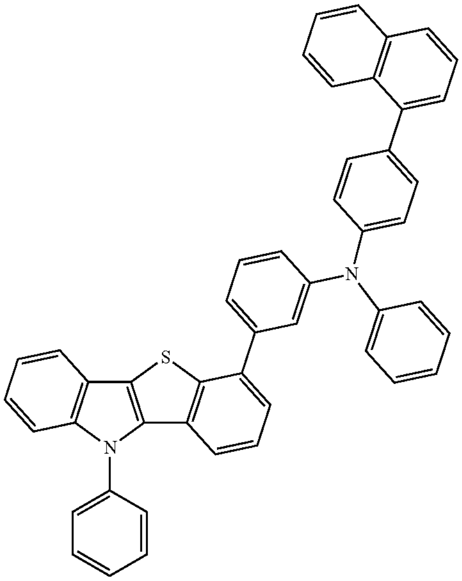

-continued
B113
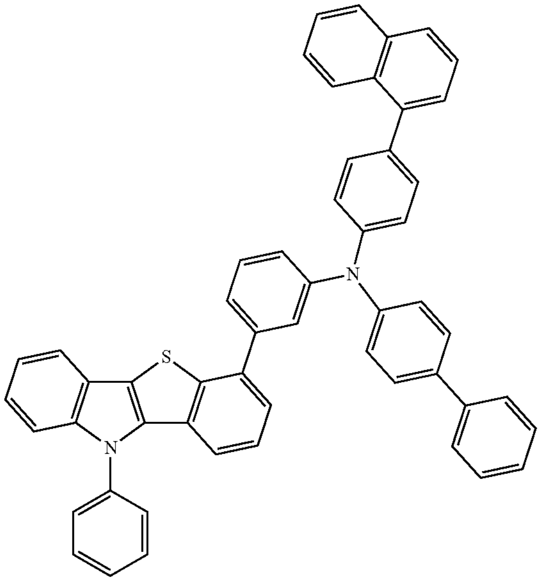
B114
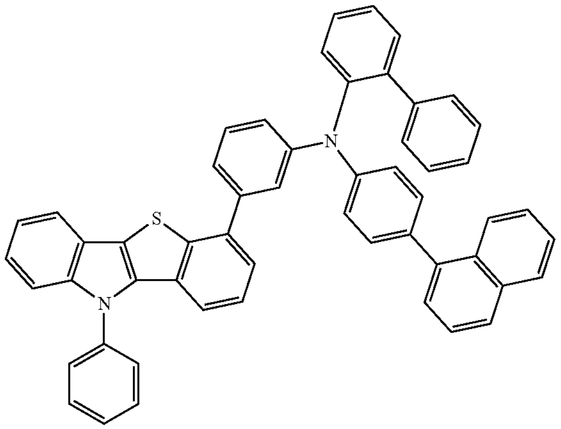
B115
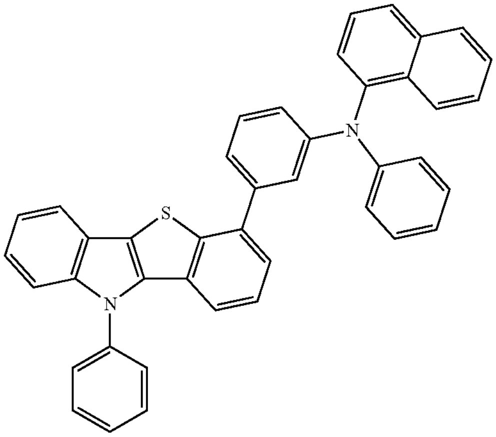
-continued
B116
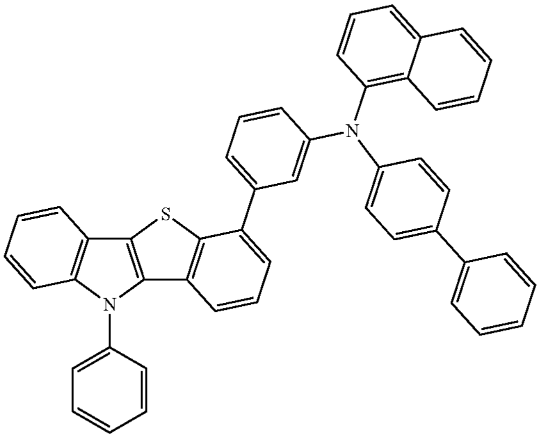
B117
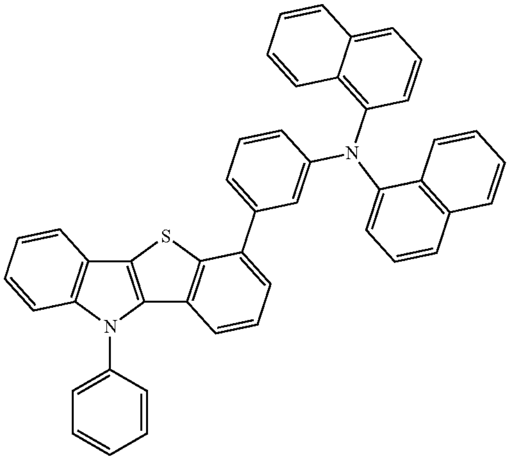
B118
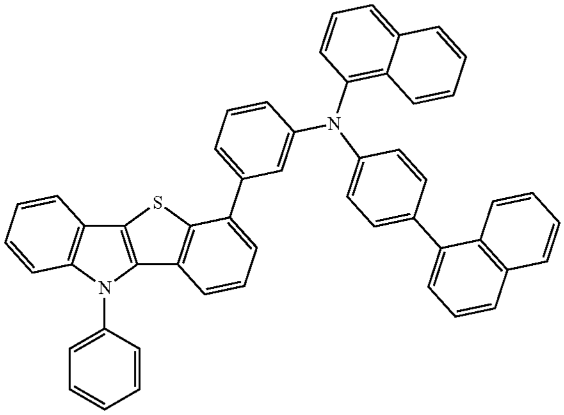

-continued
B119
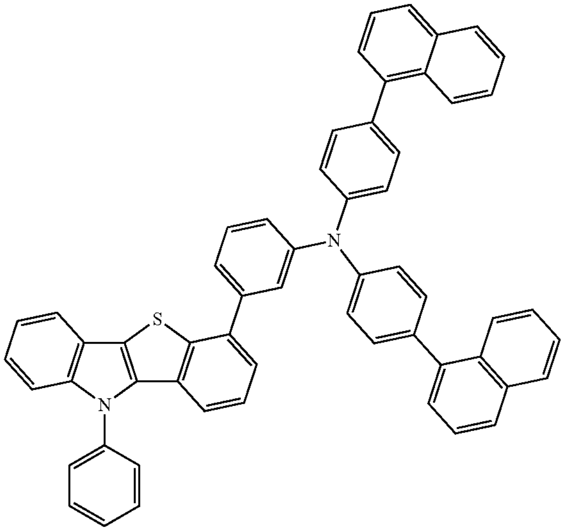
B120
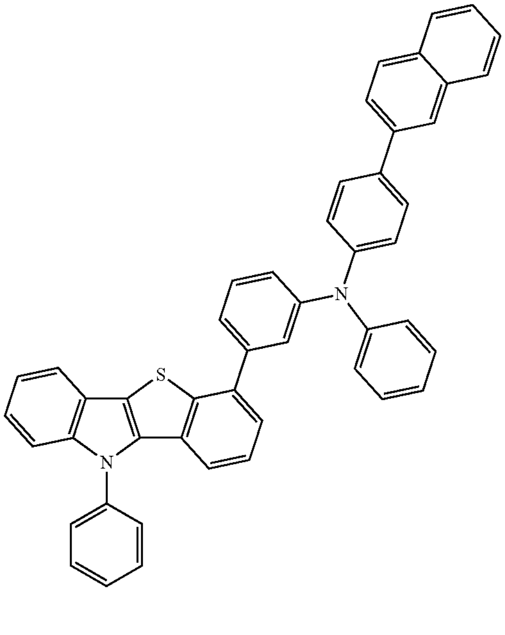
-continued
B121
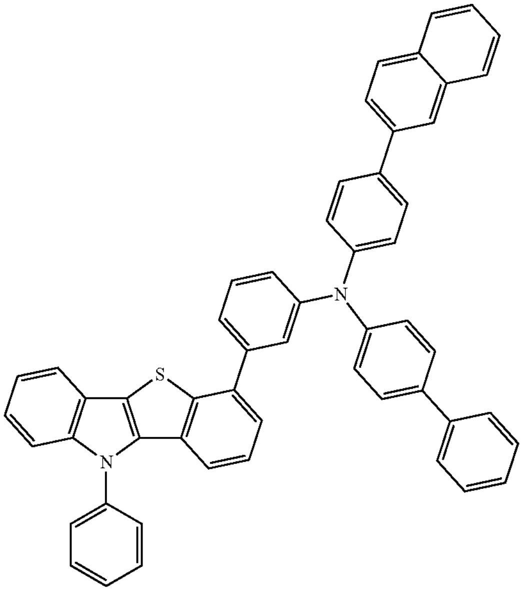
B122
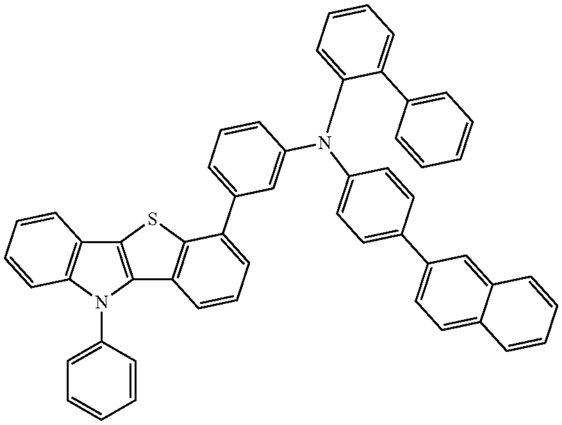
B123
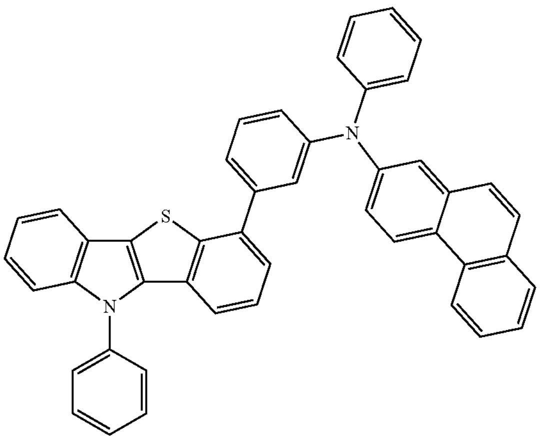

B124
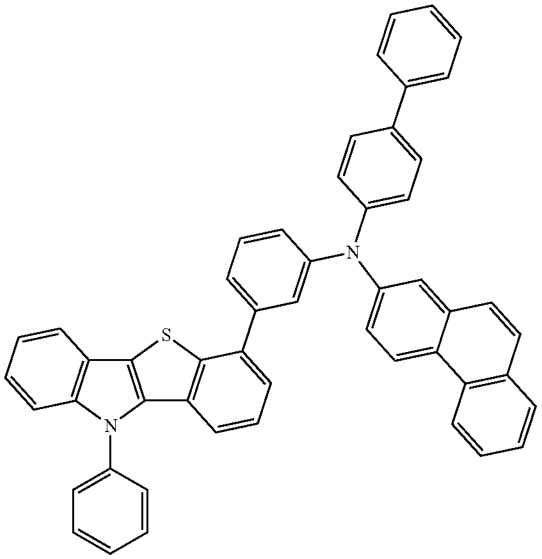
B125
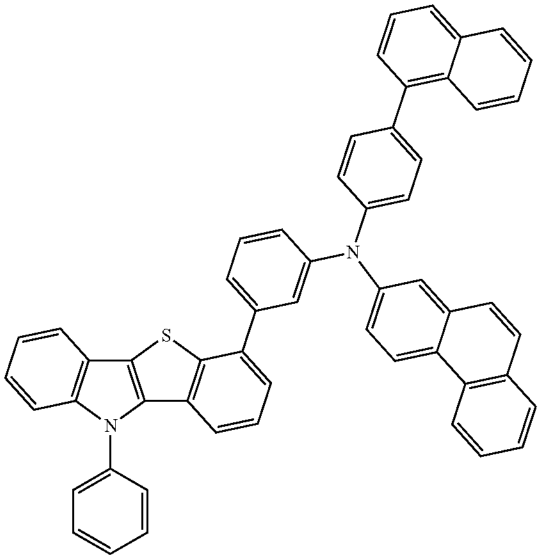
B126
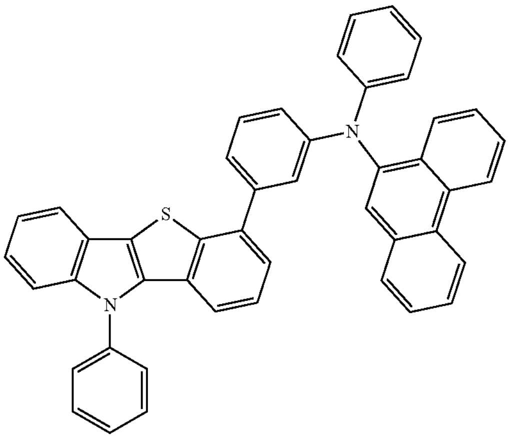
B127
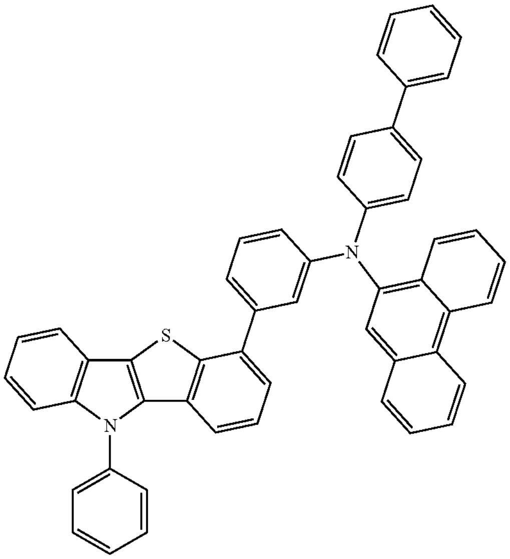
B128
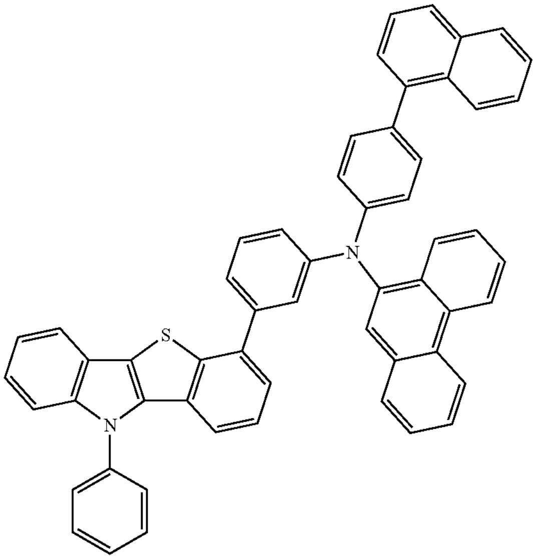
B129
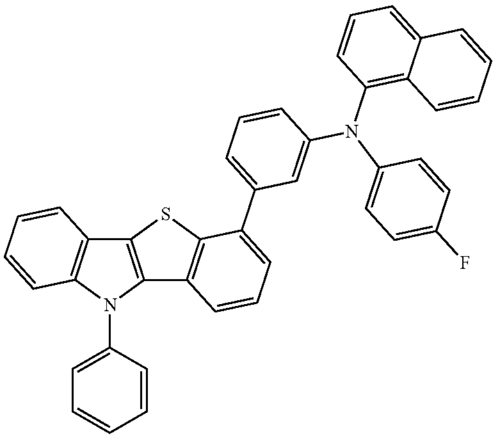

-continued
B130
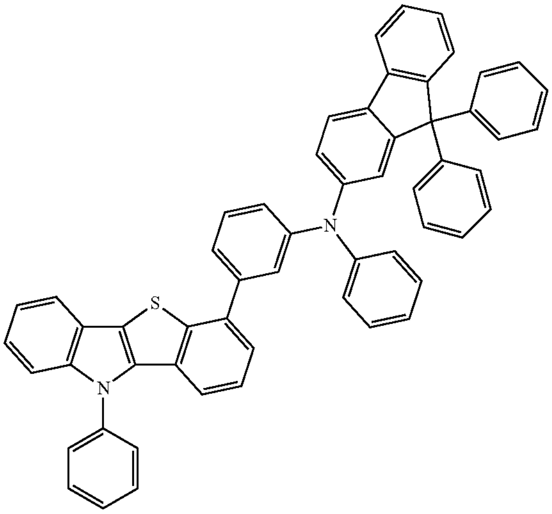
B131
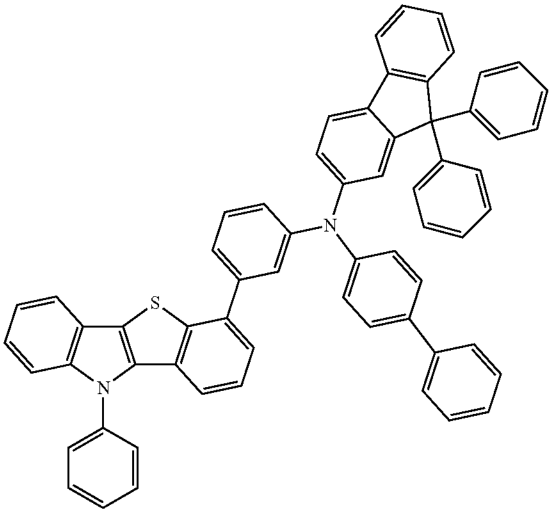
B132
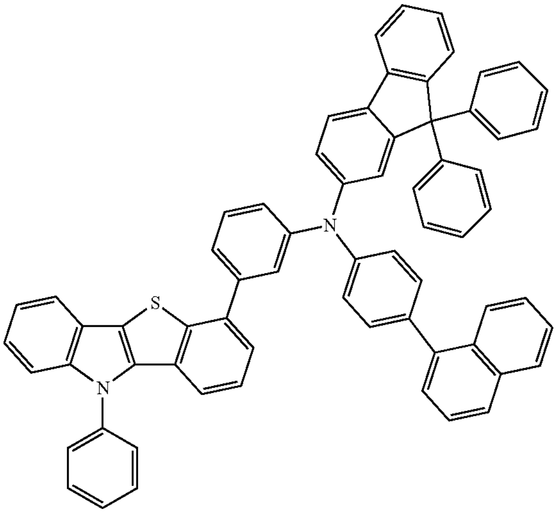
-continued
B133
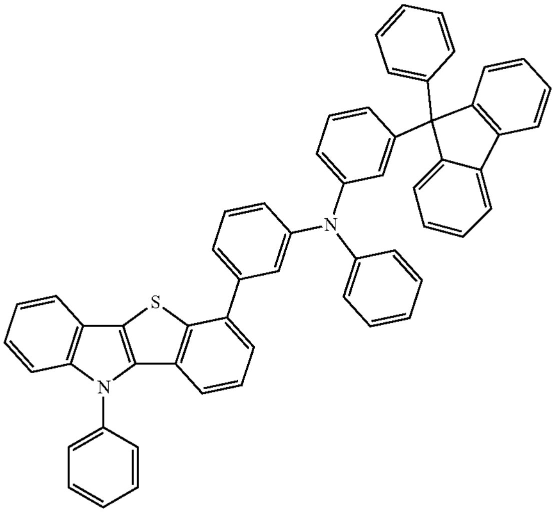
B134
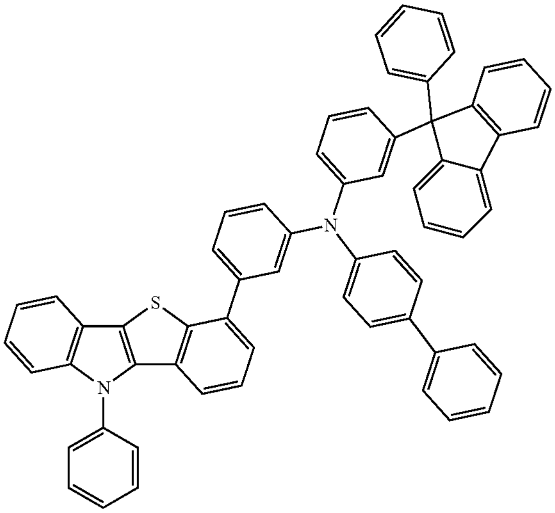
B135
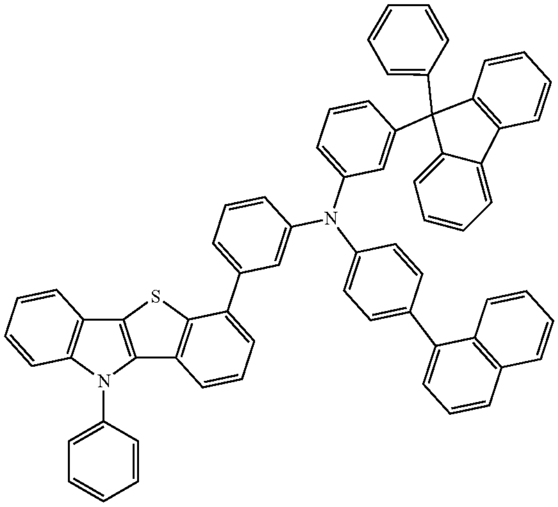

-continued
B136
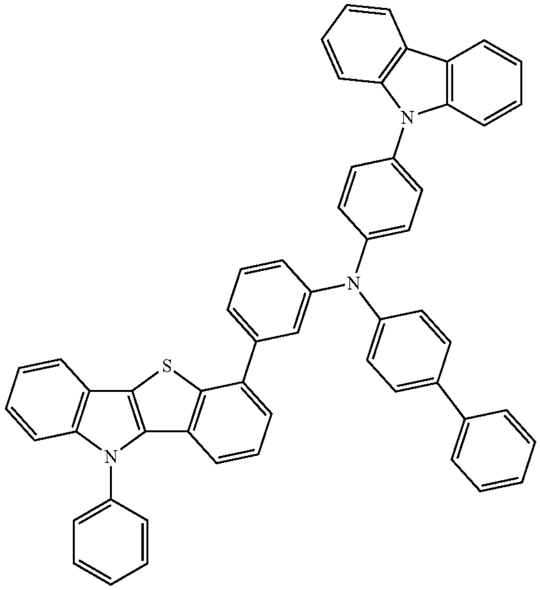
B137
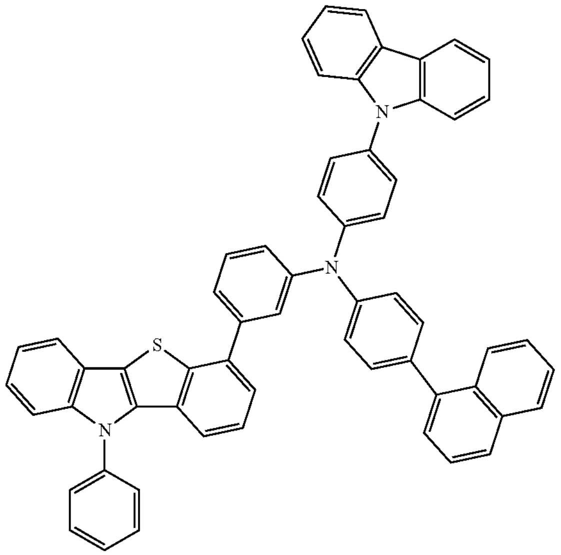
B138
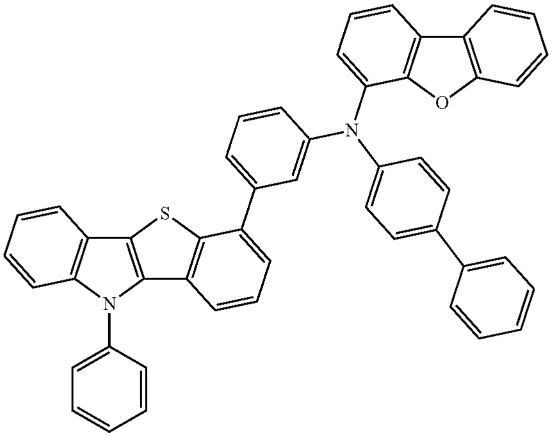
-continued
B139
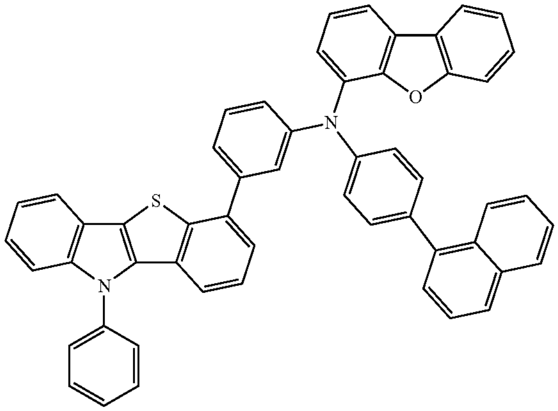
B140
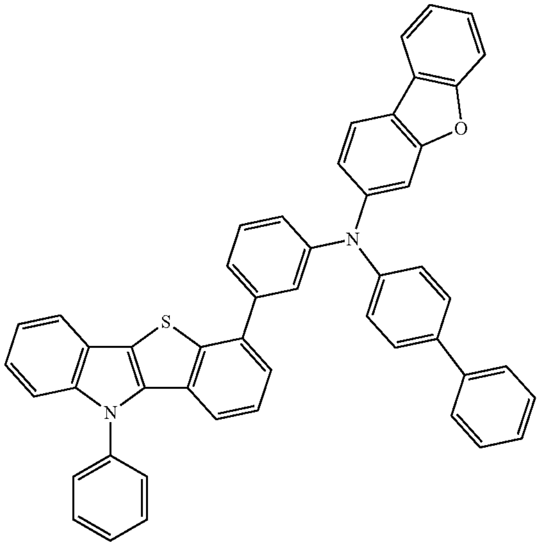
B141
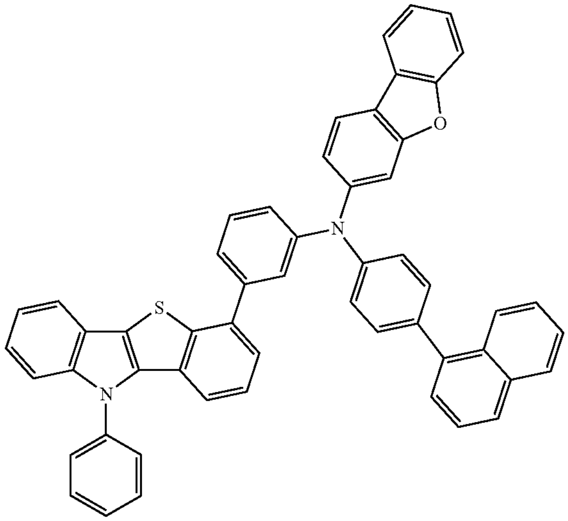

-continued
B142
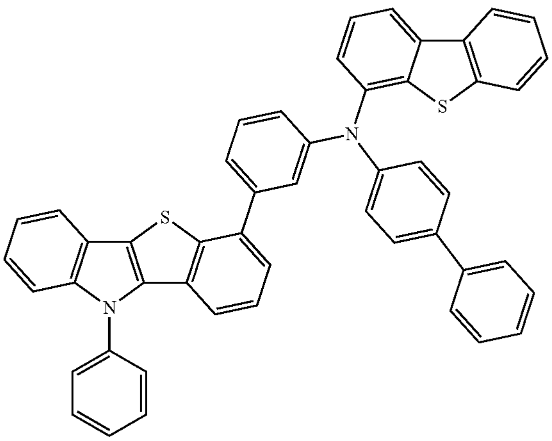
B143
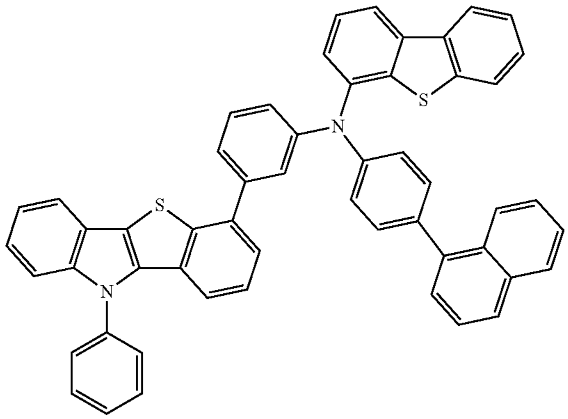
B144
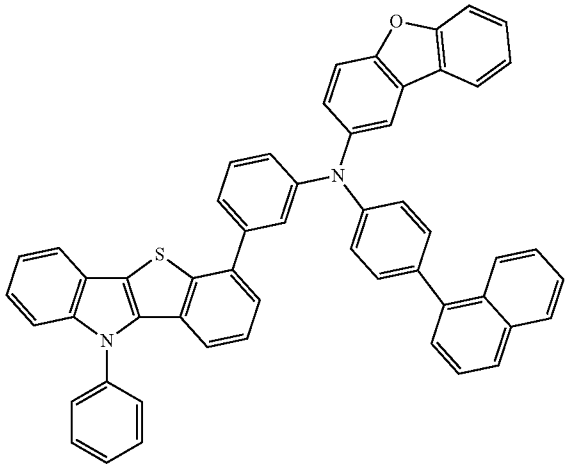
-continued
B145
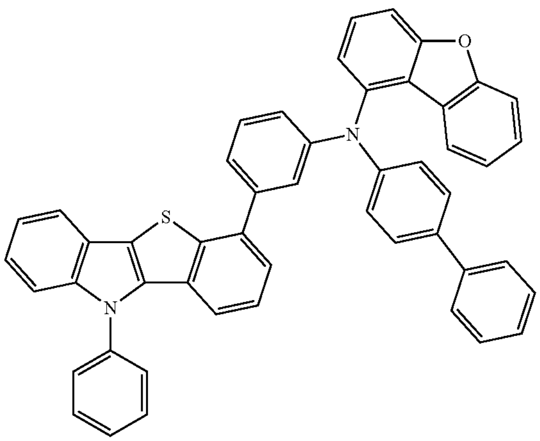
B146
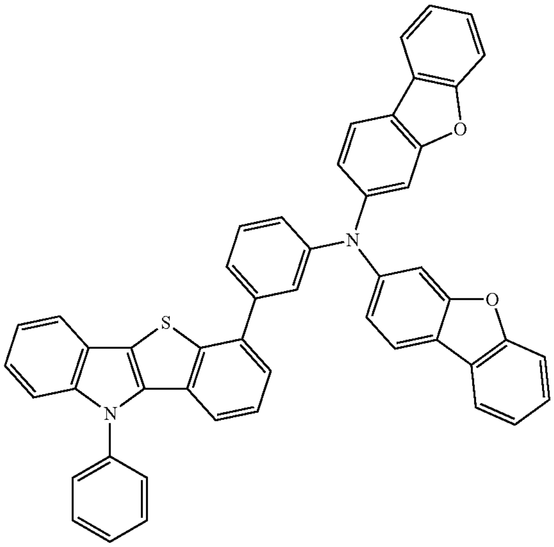
B147
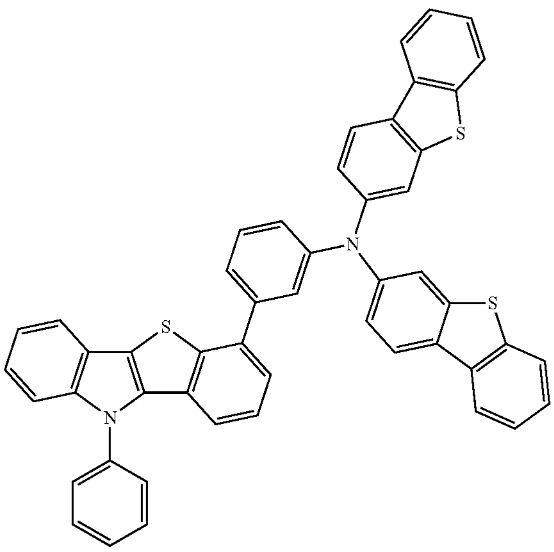

-continued
B148
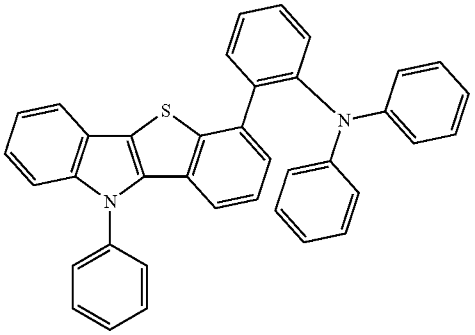
B149
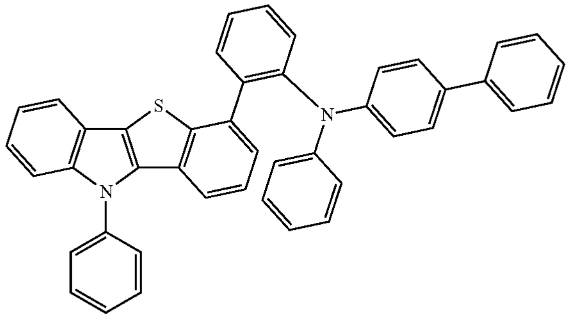
B150
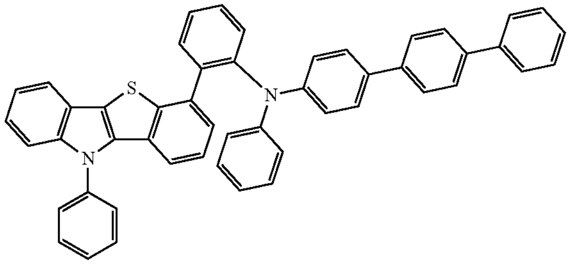
B151
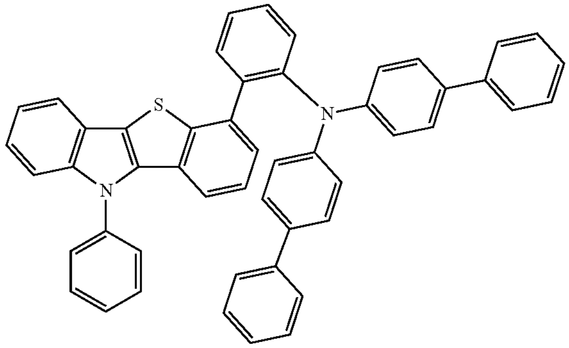
-continued
B152
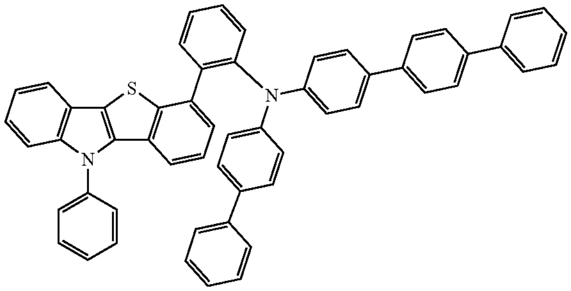
B153
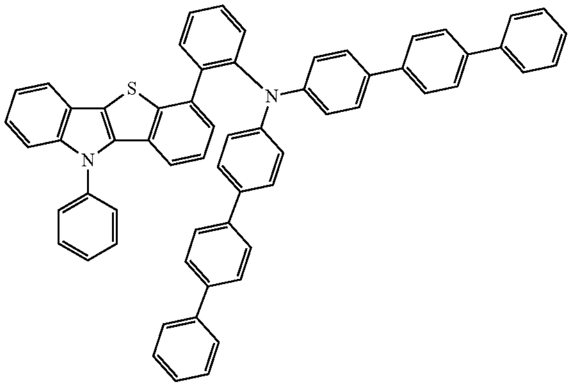
B154
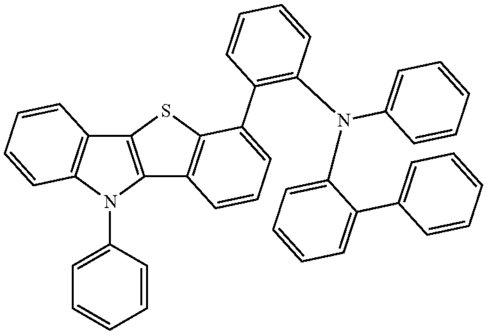
B155
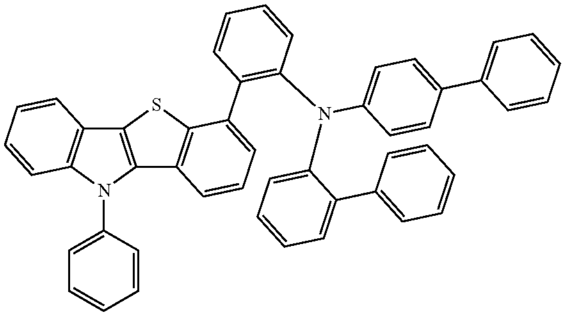

-continued
B156
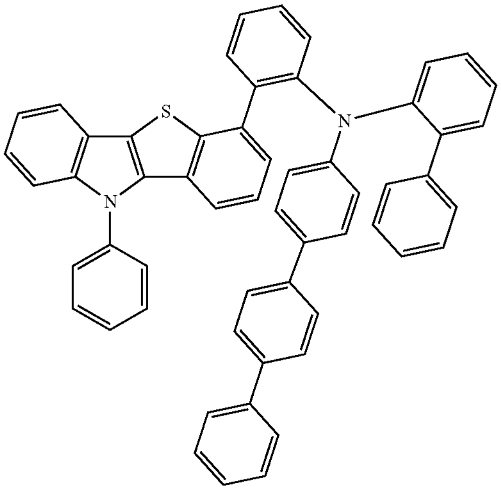
B157
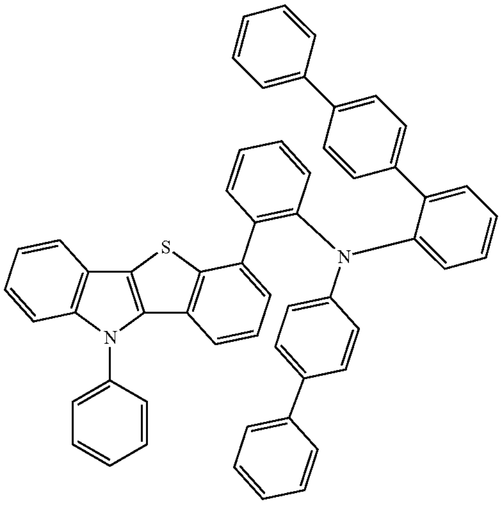
B158
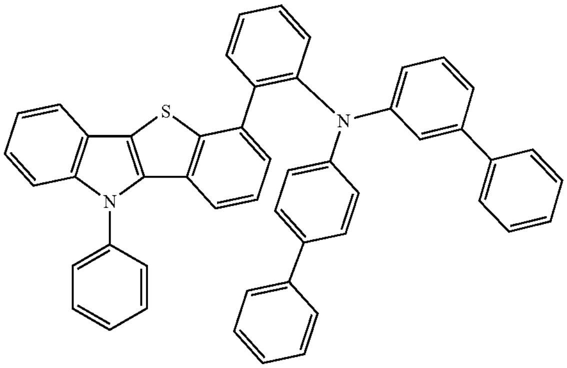
-continued
B159
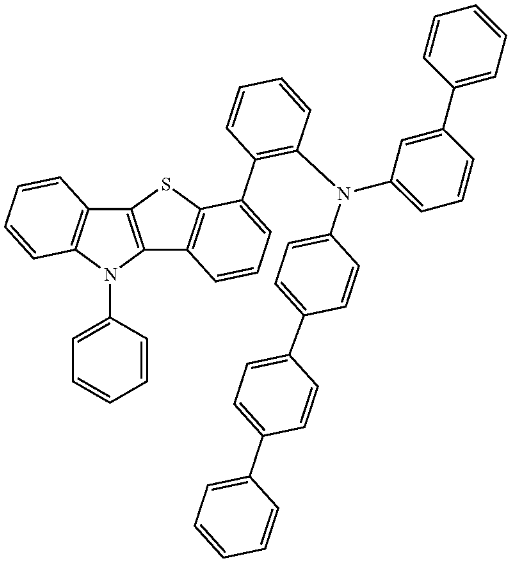
B160
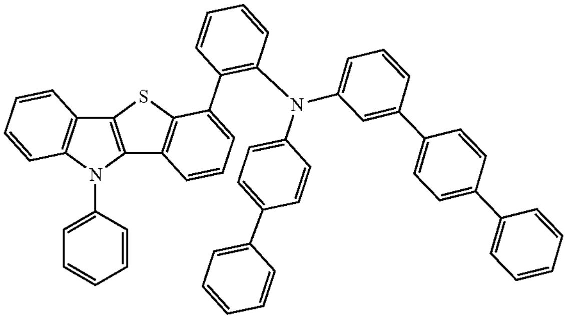
B161
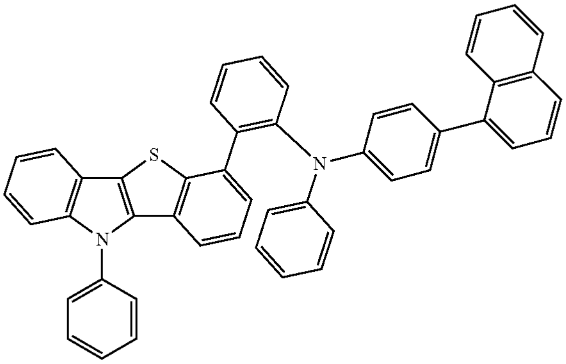

-continued
B162
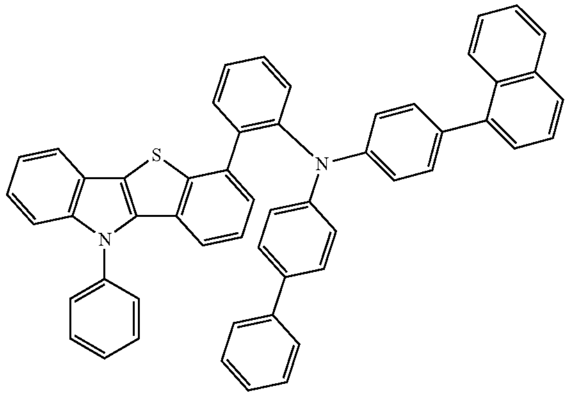
B163
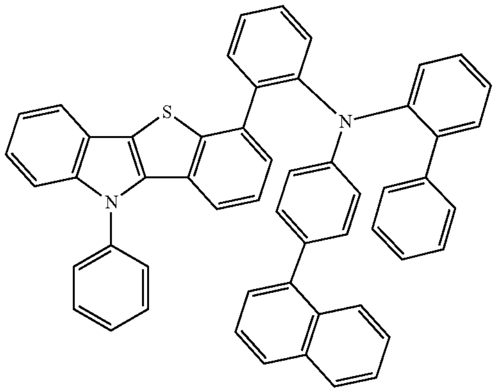
B164
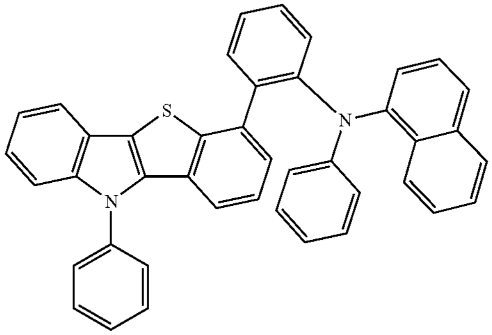
B165
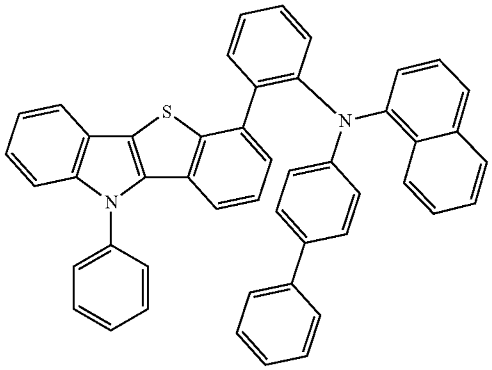
-continued
B166
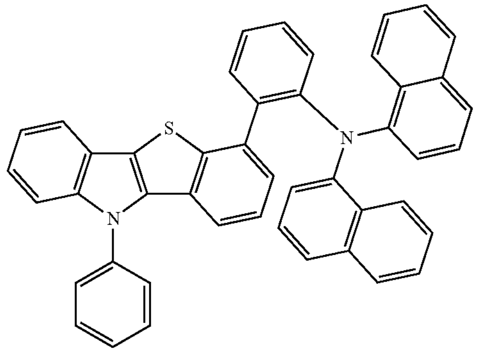
B167
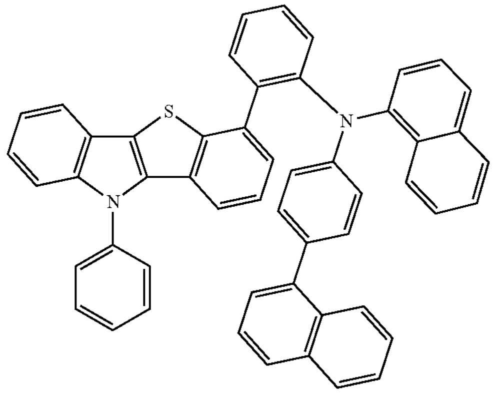
B168
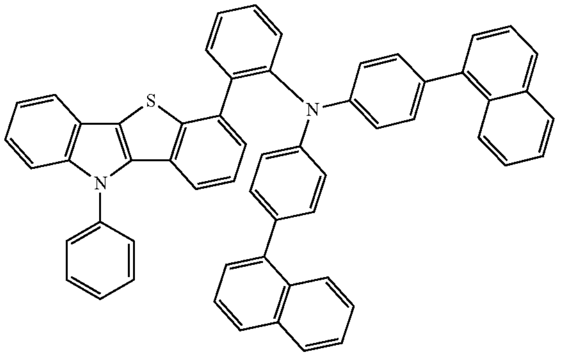
B169
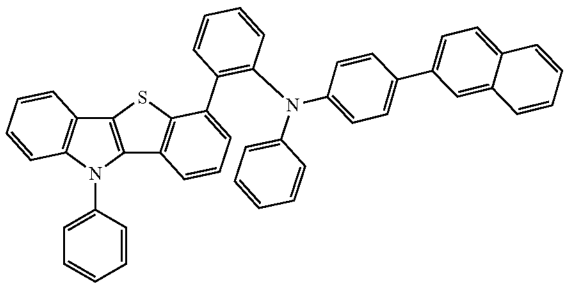

-continued
B170
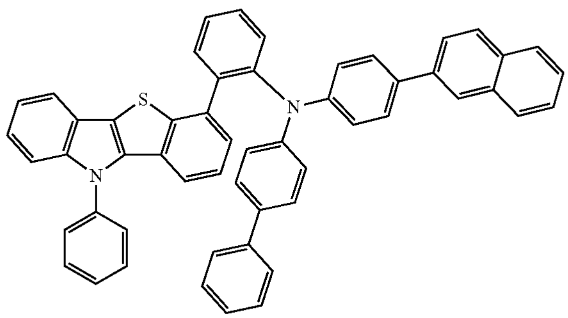
B171
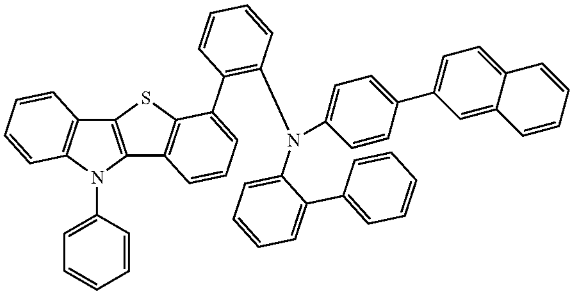
B172
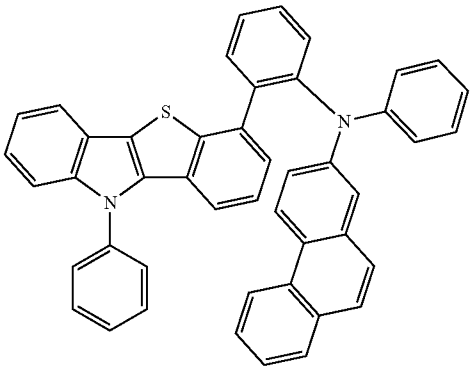
B173
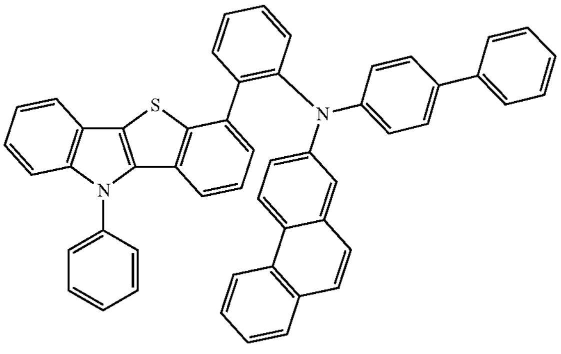
-continued
B174
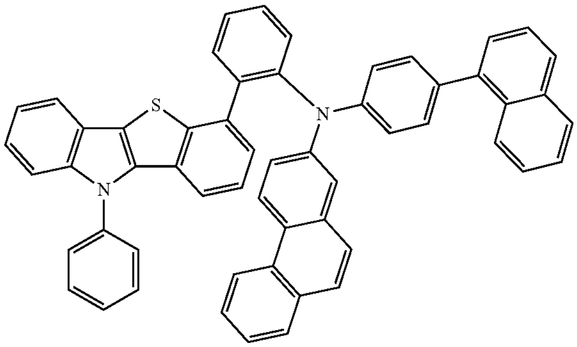
B175
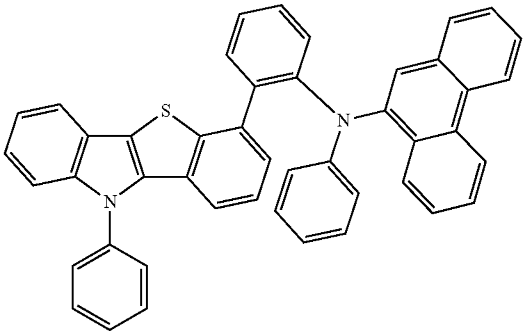
B176
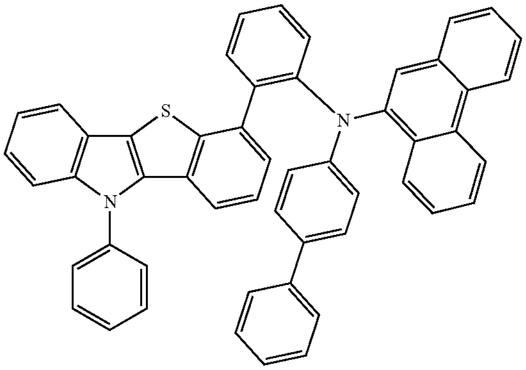
B177
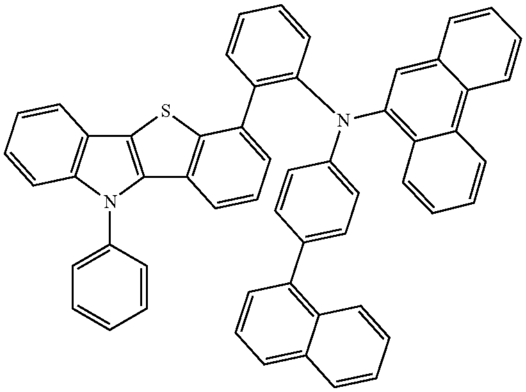

-continued
B178
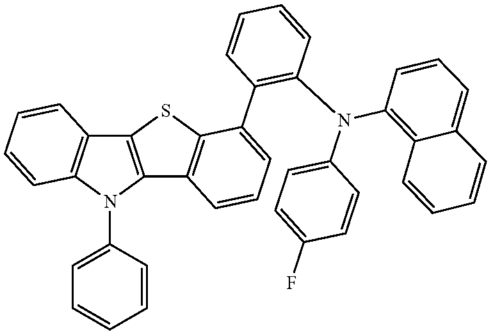
B179
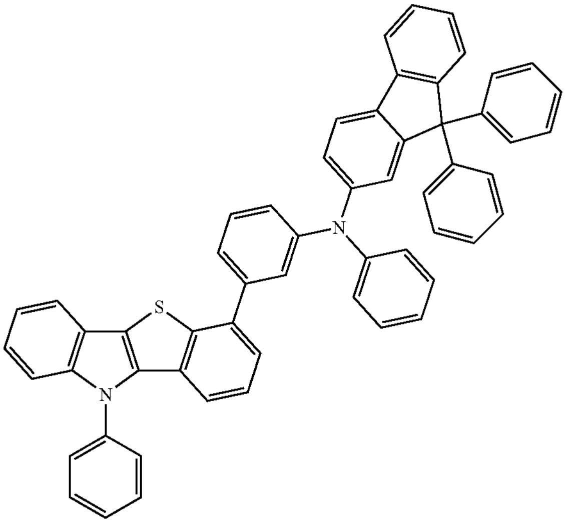
B180
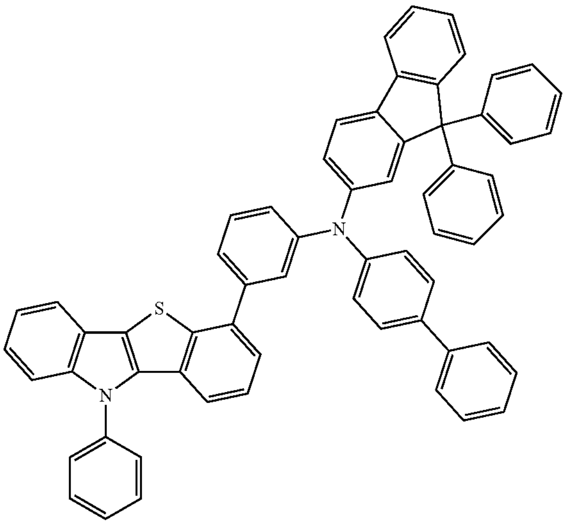
-continued
B181
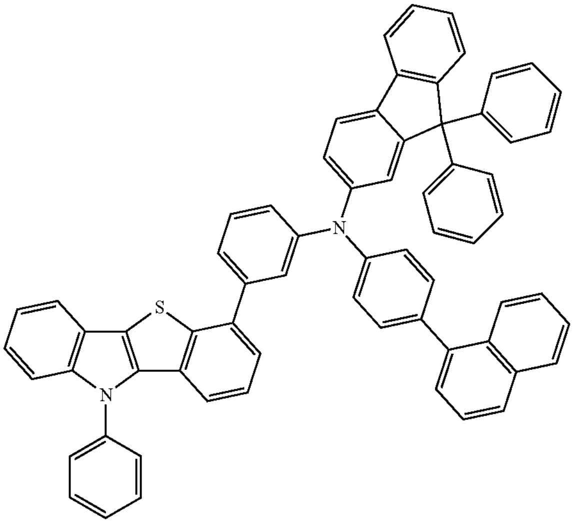
B182
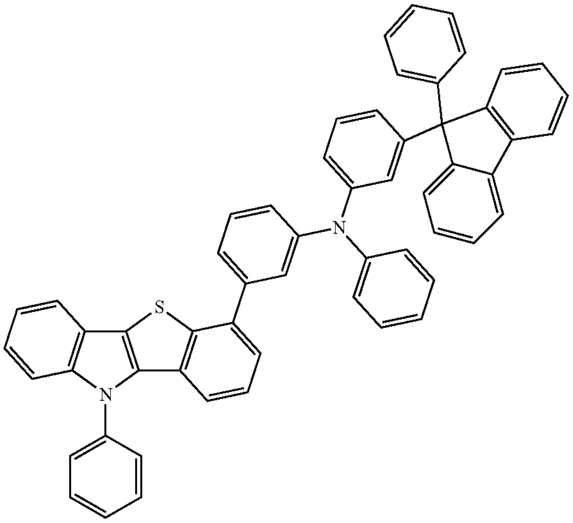
B183
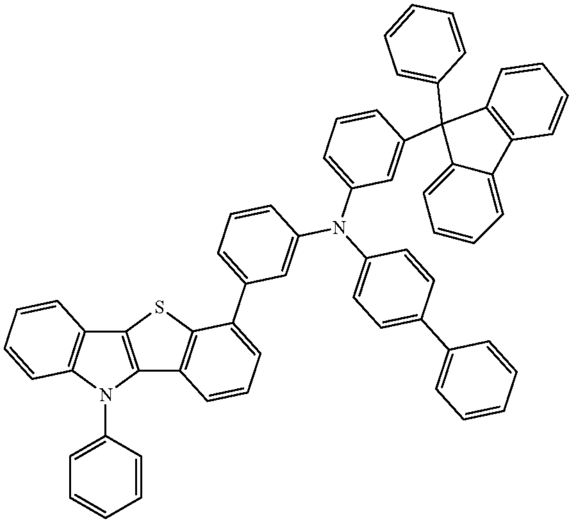

-continued
B184
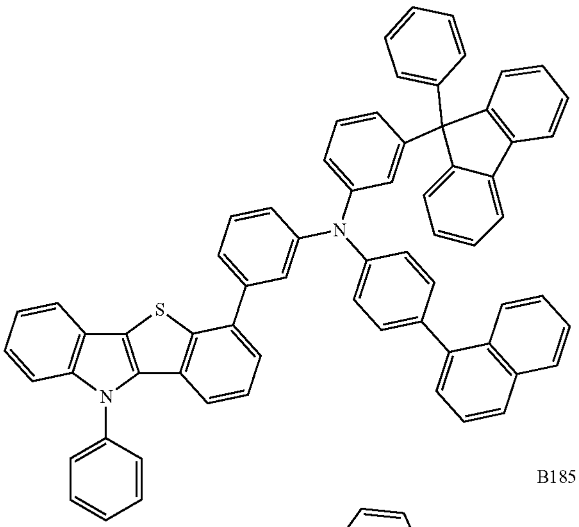
B185
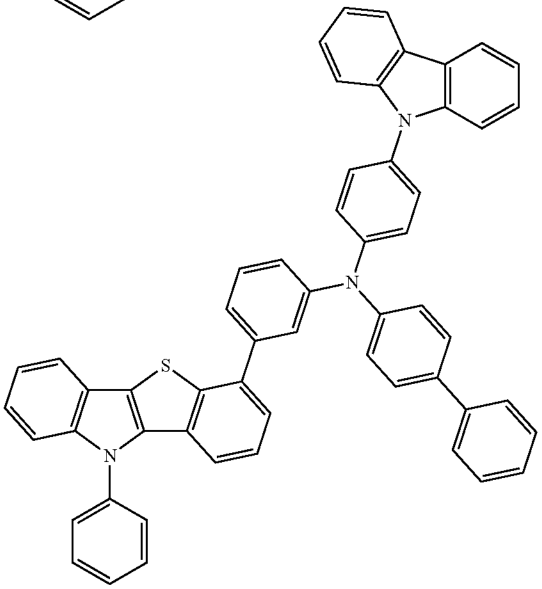
B186
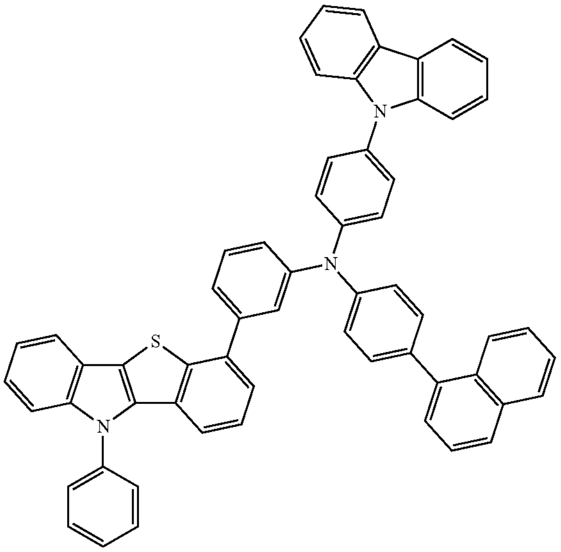
-continued
B187
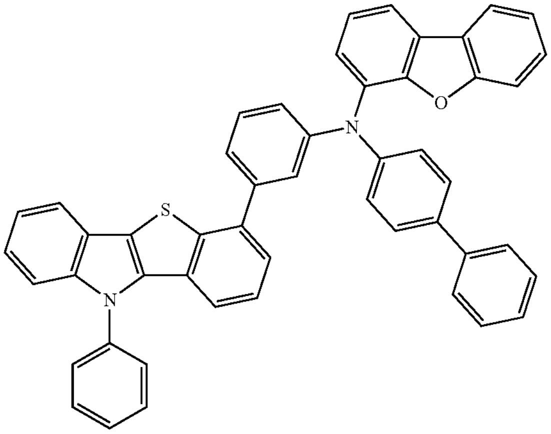
B188
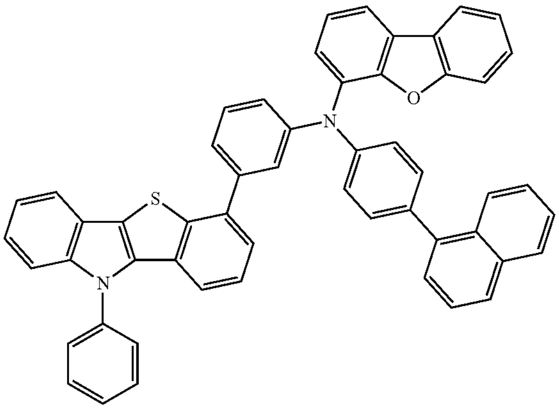
B189
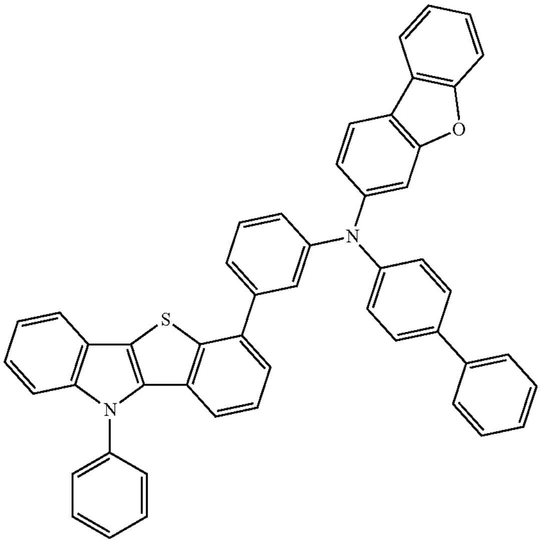

-continued
B190
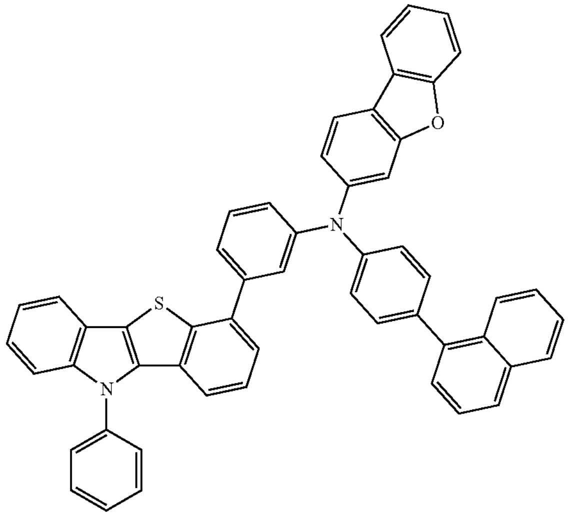
B191
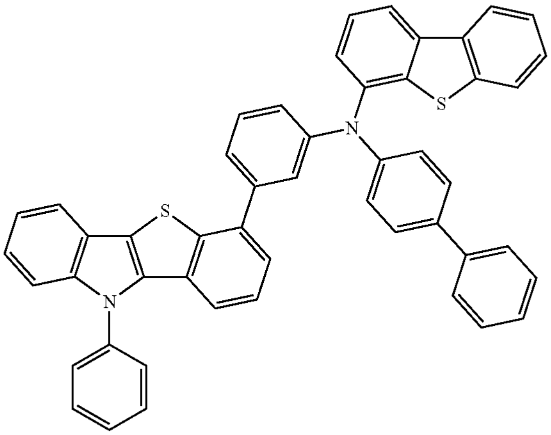
B192
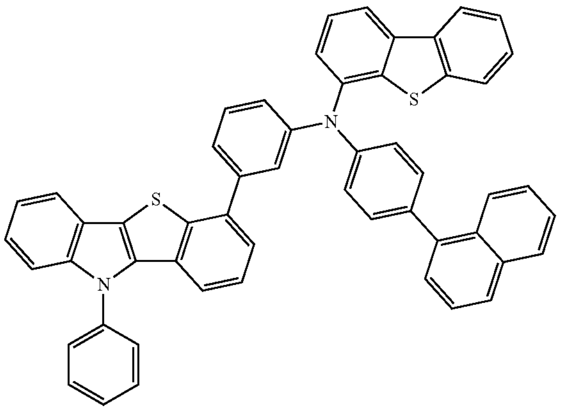
-continued
B193
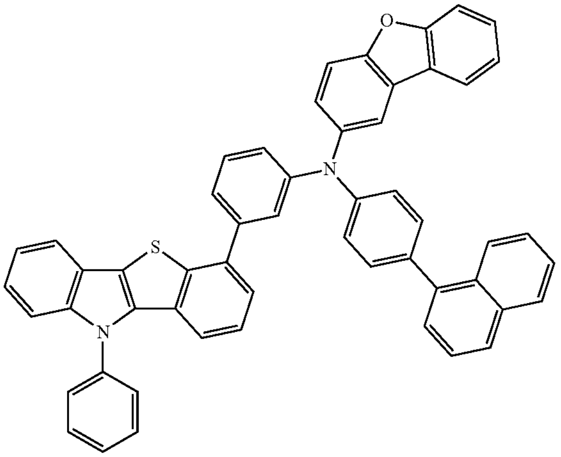
B194
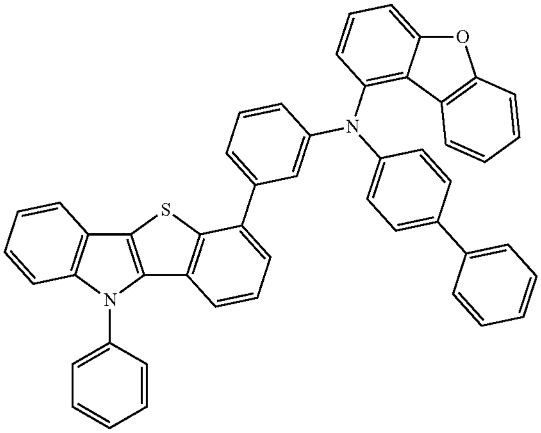
B195
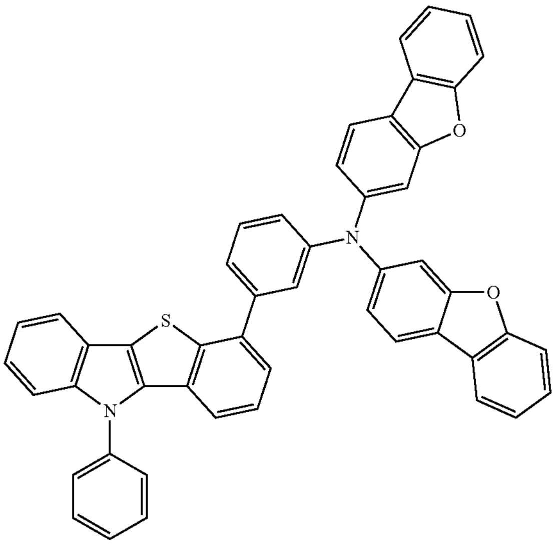

-continued

B196

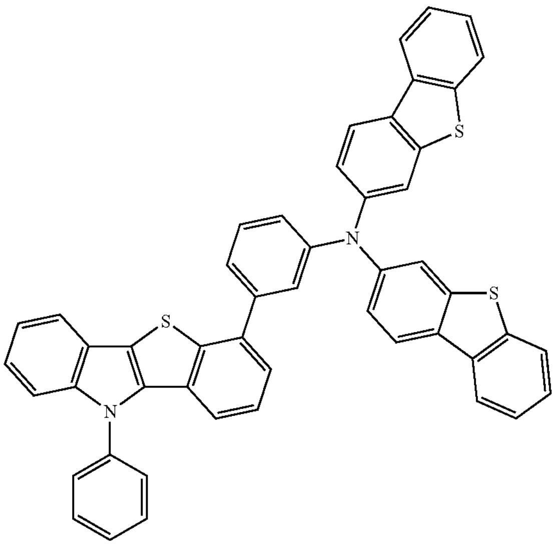

B197

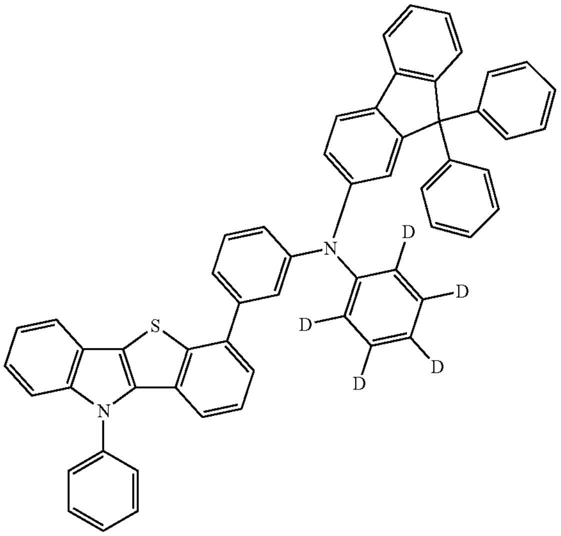

B198

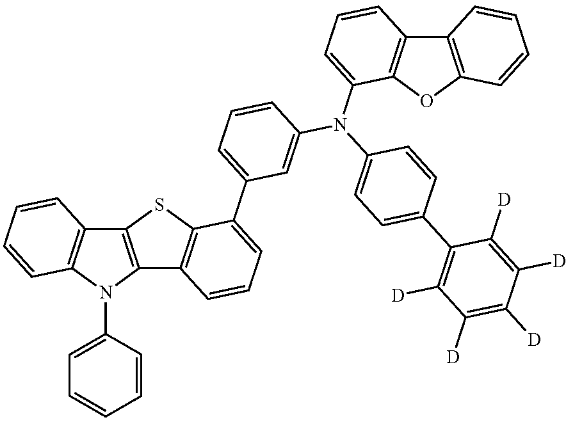

-continued

B199

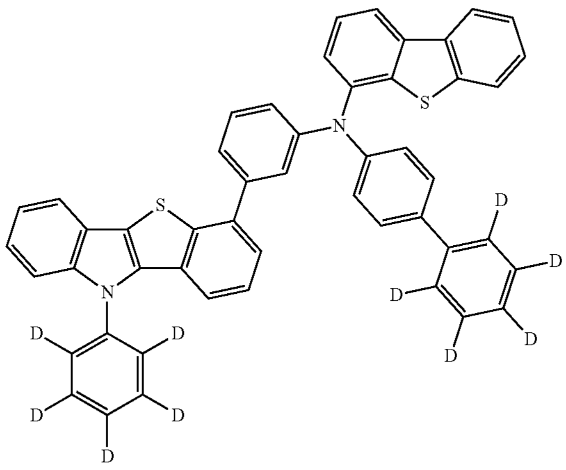

B200

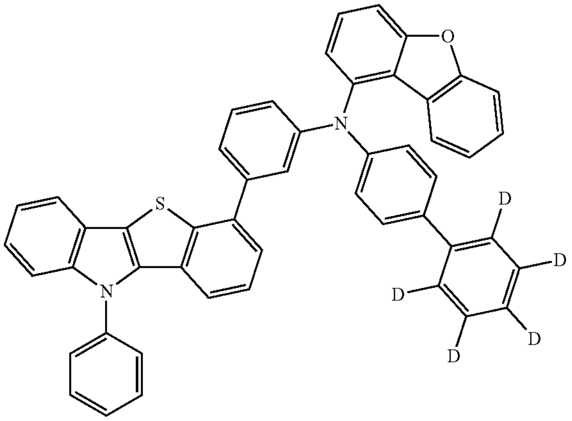

B201

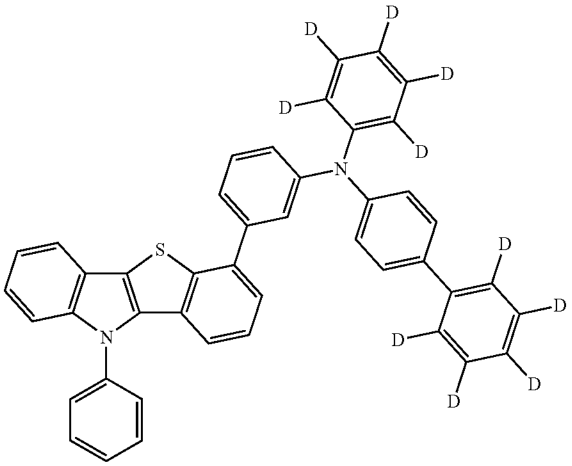

A hole transport region of an embodiment may include the above-described polycyclic compound of an embodiment, as explained later.

The first electrode EL1 has conductivity. The first electrode EL1 may be formed using a metal alloy or a conductive compound. The first electrode EL1 may be an anode. Also, the first electrode EL1 may be a pixel electrode. The first electrode EL1 may be a transmissive electrode, a transflective electrode, or a reflective electrode. If the first electrode EL1 is a transmissive electrode, the first electrode EL1 may include a transparent metal oxide, for example, indium tin oxide (ITO), indium zinc oxide (IZO), zinc oxide (ZnO), and indium tin zinc oxide (ITZO), etc. If the first electrode EL1 is a transflective electrode or a reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Alternatively, the first electrode EL1 may have a structure including a plurality of layers including a reflective layer or a transflective layer formed using the above materials, and a transmissive conductive layer formed using ITO, IZO, ZnO, ITZO, etc. For example, the first electrode EL1 may include a three-layer structure of ITO/Ag/ITO. However, an embodiment of the inventive concept is not limited thereto. The thickness of the first electrode EL1 may be from about 1,000 Å to about 10,000 Å, for example, from about 1,000 Å to about 3,000 Å.

The hole transport region HTR is disposed on the first electrode EL1. The hole transport region HTR may include at least one of a hole injection layer HIL, a hole transport layer HTL, a hole buffer layer (not shown), or an electron blocking layer EBL.

The hole transport region HTR may have a single layer formed using a single material, a single layer formed using a plurality of different materials, or a multilayer structure including a plurality of layers formed using a plurality of different materials.

For example, the hole transport region HTR may have a single layer structure of the hole injection layer HIL or the hole transport layer HTL, or a single layer structure formed using a hole injection material and a hole transport material. In addition, the hole transport region HTR may have a structure of a single layer formed using a plurality of different materials, or a structure stacked from the first electrode EL1 of hole injection layer HIL/hole transport layer HTL, hole injection layer HIL/hole transport layer HTL/hole buffer layer (not shown), hole injection layer HIL/hole buffer layer (not shown), hole transport layer HTL/hole buffer layer, or hole injection layer HIL/hole transport layer HTL/electron blocking layer EBL, without limitation.

The hole transport region HTR may include the polycyclic compound in an embodiment. For example, at least one layer among a hole injection layer HIL, a hole transport layer HTL, a hole buffer layer (not shown), or an electron blocking layer EBL may include the polycyclic compound in an embodiment.

In the polycyclic compound of an embodiment, an aryl amine group which has high hole tolerance is connected with a benzofuranoindole skeleton, or a benzothienoindole skeleton. Accordingly, the polycyclic compound of an embodiment may maintain long life.

Particularly, in the polycyclic compound of an embodiment, the aryl amine group may be substituted at an ortho position with respect to an oxygen atom of the benzofuranoindole skeleton, or substituted at an ortho position with respect to a sulfur atom of the benzothienoindole skeleton. Accordingly, structural asymmetric properties in a molecule may increase, the crystallinity of the molecule may be restrained, and hole transport capacity may be improved.

In the polycyclic compound of an embodiment, an aryl amine group is in an ortho position with respect to a sulfur atom or an oxygen atom, and the disposition of partial negative charge in a resonance structure is different when the aryl amine group is in a meta position with respect to a sulfur atom or an oxygen atom. Accordingly, the polycyclic compound of an embodiment has specific electrical properties according to the substitution position of the aryl amine group. Due to such specific electrical properties of the compound of an embodiment, improved hole transport capacity may be achieved.

In conclusion, the polycyclic compound of an embodiment may be included in a hole transport region HTR to show excellent hole transport capacity. The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL may include in addition to the polycyclic compound of an embodiment, for example, a phthalocyanine compound such as copper phthalocyanine, N,N'-diphenyl-N,N'-bis-[4-(phenyl-m-tolyl-amino)-phenyl]-biphenyl-4,4'-diamine (DNTPD), 4,4',4"-tris(3-methylphenylphenylamino) triphenylamine (m-MTDATA), 4,4',4"-tris(N,N-diphenylamino)triphenylamine (TDATA), 4,4',4"-tris{N-2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(1-naphthalene-1-yl)-N,N'-diphenyl-benzidine (NPB), triphenylamine-containing polyetherketone (TPAPEK), 4-isopropyl-4'-methyldiphenyliodonium tetrakis(pentafluorophenyl)borate, and dipyrazino[2,3-f:2',3'-h]quinoxaline-2,3,6,7,10,11-hexacarbonitrile (HAT-CN).

The hole transport layer HTL may include in addition to the polycyclic compound of an embodiment, for example, carbazole derivatives such as N-phenyl carbazole and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4"-tris(carbazol-9-yl)triphenylamine (TCTA), N,N'-di(naphthalene-1-yl)-N,N'-diphenyl-benzidine (NPB), 4,4'-bis[N,N-bis(4-methylphenyl)benzeneamine] (TAPC), 4,4'-bis[N,N'-(3-tolyl)amino]-3,3'-dimethylbiphenyl (HMTPD), 1,3-bis(N-carbazolyl)benzene (mCP), 9-(4-tert-butylphenyl)-3,6-bis(triphenylsilyl)-9H-carbazole (CzSi), etc.

The thickness of the hole transport region HTR may be from about 100 Å to about 10,000 Å, for example, from about 100 Å to about 5,000 Å. The thickness of the hole injection layer HIL may be, for example, from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. If the thicknesses of the hole transport region HTR, the hole injection layer HIL, the hole transport layer HTL and the electron blocking layer EBL satisfy the above-described ranges, satisfactory hole transport properties may be achieved without substantial increase of a driving voltage.

The hole transport region HTR may further include a charge generating material to increase conductivity in addition to the above-described materials. The charge generating material may be dispersed uniformly or non-uniformly in the hole transport region HTR. The charge generating material may be, for example, a p-dopant. The p-dopant may be one of quinone derivatives, metal oxides, or cyano group-containing compounds, without limitation. For example, non-limiting examples of the p-dopant may include quinone derivatives such as tetracyanoquinodimethane (TCNQ) and 2,3,5,6-tetrafluoro-7,7,8,8-tetracyanoquinodimethane (F4-

TCNQ), metal oxides such as tungsten oxide and molybdenum oxide, etc., without limitation.

As described above, the hole transport region HTR may further include at least one of a hole buffer layer (not shown) or an electron blocking layer EBL in addition to the hole injection layer HIL and the hole transport layer HTL. The hole buffer layer (not shown) may compensate an optical resonance distance according to the wavelength of light emitted from an emission layer EML to increase light emission efficiency. Materials which may be included in the hole transport region HTR may be used as materials included in the hole buffer layer (not shown). The electron blocking layer EBL is a layer playing the role of preventing the electron injection from the electron transport region ETR to the hole transport region HTR.

The emission layer EML is disposed on the hole transport region HTR. The emission layer EML may have a thickness of, for example, about 100 Å to about 1,000 Å or about 100 Å to about 300 Å. The emission layer EML may have a single layer formed using a single material, a single layer formed using a plurality of different materials, or a multi-layer structure having a plurality of layers formed using a plurality of different materials.

In the luminescence device 10 of an embodiment, the emission layer EML may include anthracene derivatives, pyrene derivatives, fluoranthene derivatives, chrysene derivatives, dihydrobenzanthracene derivatives, or triphenylene derivatives. Particularly, the emission layer EML may include anthracene derivatives or pyrene derivatives.

The emission layer EML may include an anthracene derivative represented by the following Formula A:

Formula A

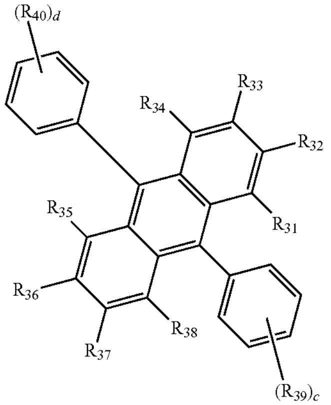

In the above formula, $R_{31}$ to $R_{40}$ may be each independently a hydrogen atom, a deuterium atom, a halogen atom, a substituted or unsubstituted silyl group, a substituted or unsubstituted alkyl group of 1 to 10 carbon atoms, a substituted or unsubstituted aryl group of 6 to 30 ring carbon atoms, or a substituted or unsubstituted heteroaryl group of 2 to 30 ring carbon atoms, or combined with an adjacent group to form a ring. Meanwhile, $R_{31}$ to $R_{40}$ may be combined with adjacent groups from each other to form saturated hydrocarbon rings or unsaturated hydrocarbon ring.

In the above formula, c and d may be each independently an integer of 0 to 5.

The above formula may be represented by any one among Compound 3-1 to Compound 3-16:

3-1

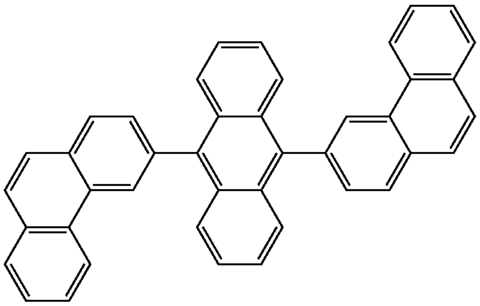

3-2

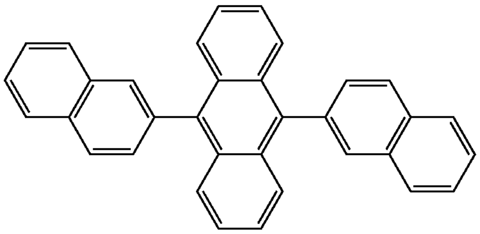

3-3

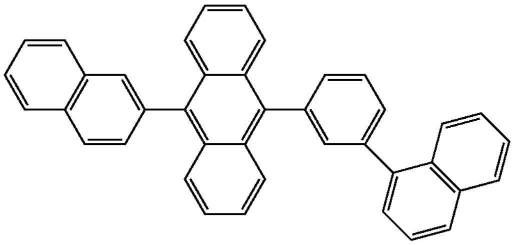

3-4

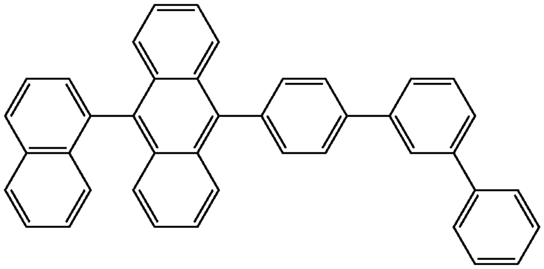

3-5

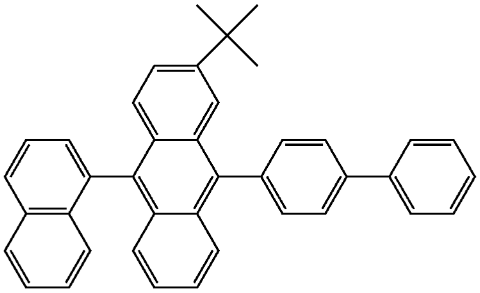

-continued
3-6
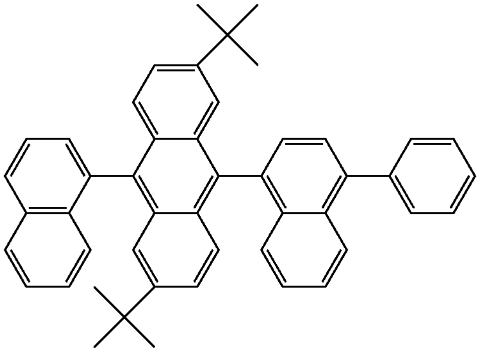
3-7
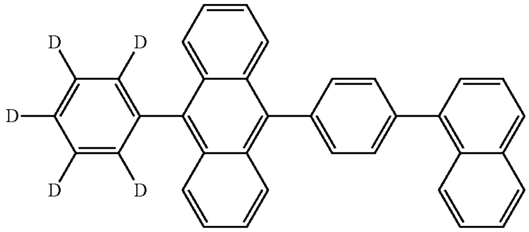
3-8
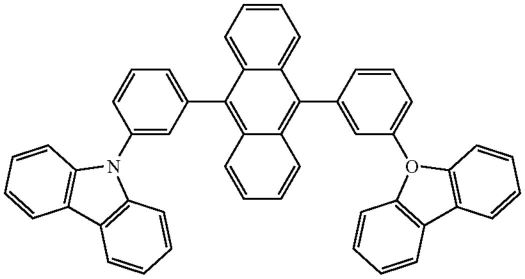
3-9
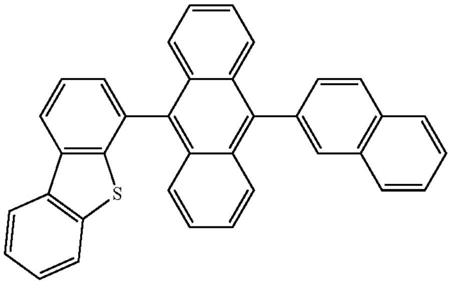
3-10
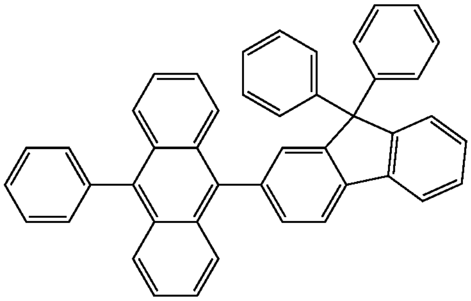
-continued
3-11
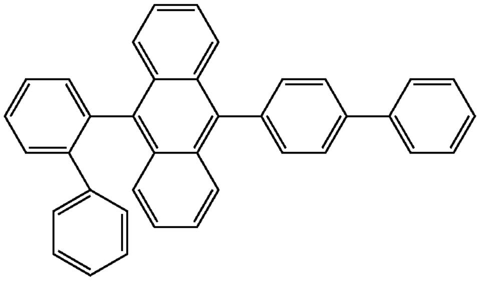
3-12
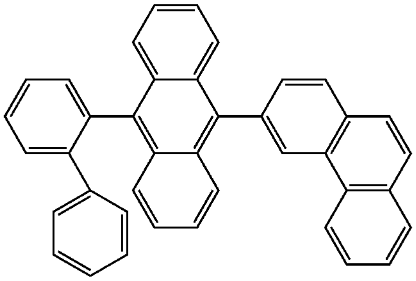
3-13
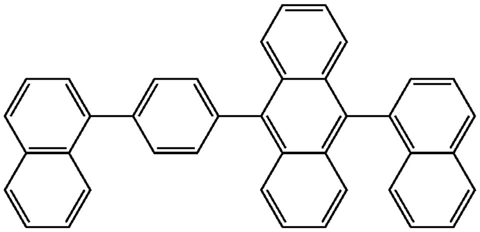
3-14
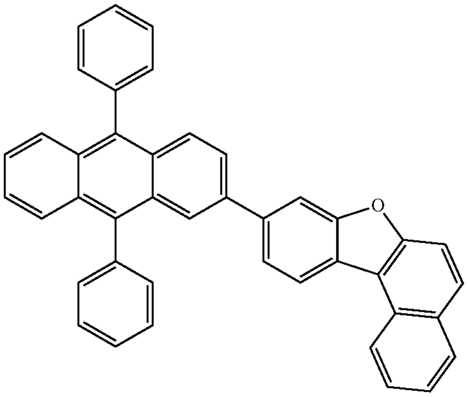

-continued 3-15

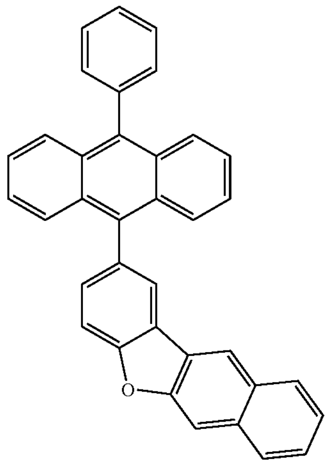

3-16

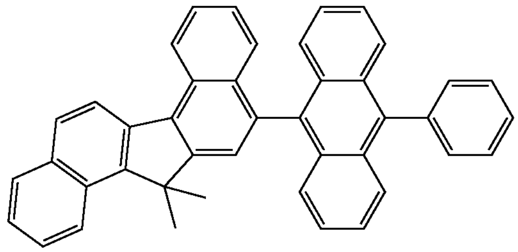

In the luminescence devices 10 of exemplary embodiments as shown in FIG. 1 to FIG. 4, the emission layer EML may include a host and a dopant, and the emission layer EML may include the compounds represented by the above-described chemical formulae as host or dopant materials.

The emission layer EML may further include commonly used materials well known as the host material in the art. For example, the emission layer EML may include as a host material, at least one of bis[2-(diphenylphosphino)phenyl] ether oxide (DPEPO), 4,4'-bis(carbazol-9-yl)biphenyl (CBP), 1,3-bis(carbazol-9-yl)benzene (mCP), 2,8-bis(diphenylphosphoryl)dibenzo[b,d]furan (PPF), 4,4',4"-tris (carbazol-9-yl) triphenylamine or 1,3,5-tris(1-phenyl-1H-benzo[d] imidazol-2-yl)benzene (TPBi). However, an embodiment of the inventive concept is not limited thereto. For example, tris(8-hydroxyquinolino)aluminum ($Alq_3$), 4,4'-bis(N-carbazolyl)-1,1'-biphenyl (CBP), poly(N-vinylcarbazole) (PVK), 9,10-di(naphthalene-2-yl)anthracene (ADN), 2-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis (triphenylsilyl)benzene (UGH2), hexaphenylcyclotrisiloxane ($DPSiO_3$), octaphenylcyclotetra siloxane ($DPSiO_4$), 2,8-bis(diphenylphosphoryl)dibenzofuran (PPF), 9-(4-tert-butylphenyl)-3,6-bis(triphenylsilyl)-9H-carbazole (CzSi), etc. may be used as the host material.

In an embodiment, the emission layer EML may include as the dopant material, styryl derivatives (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino) styryl)naphthalen-2-yl)vinyl)phenyl)-N-phenylbenzenamine (N-BDAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino)pyrene), etc.

The explanation has been based on that the emission layer EML included an organic light-emitting material, but an embodiment of the inventive concept is not limited thereto. For example, the emission layer EML may include an inorganic material of a quantum dot, or a quantum rod.

In the luminescence devices 10 of embodiments as shown in FIGS. 1 to 4, the electron transport region ETR is disposed on the emission layer EML. The electron transport region ETR may include at least one of a hole blocking layer HBL, an electron transport layer ETL or an electron injection layer EIL. However, an embodiment of the inventive concept is not limited thereto.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material or an electron transport material. Also, the electron transport region ETR may have a single layer structure formed using a plurality of different materials, or a structure stacked from the emission layer EML of electron transport layer ETL/electron injection layer EIL, or hole blocking layer HBL/electron transport layer ETL/electron injection layer EIL, without limitation. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

If the electron transport region ETR includes an electron transport layer ETL, the electron transport region ETR may include an anthracene-based compound. An embodiment of the inventive concept is not limited thereto, but the electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazole-1-yl) phenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,08)-(1,1'-biphenyl-4-olato) aluminum (BAlq), berylliumbis(benzoquinolin-10-olate ($Bebq_2$), 9,10-di(naphthalene-2-yl)anthracene (ADN), 1,3-bis[3,5-di(pyridine-3-yl)phenyl]benzene (BmPyPhB), or a mixture thereof. The thickness of the electron transport layer ETL may be from about 100 Å to about 1,000 Å and may be, for example, from about 150 Å to about 500 Å. If the thickness of the electron transport layer ETL satisfies the above-described range, satisfactory electron transport properties may be obtained without substantial increase of a driving voltage.

If the electron transport region ETR includes the electron injection layer EIL, the electron transport region ETR may use a metal halide such as LiF, NaCl, CsF, RbCl, RbI, and CuI, a metal in lanthanoides such as Yb, a metal oxide such as $Li_2O$ and BaO, or lithium quinolate (LiQ). However, an embodiment of the inventive concept is not limited thereto. The electron injection layer EIL may also be formed using a mixture material of an electron transport material and an insulating organo metal salt. The organo metal salt may be a material having an energy band gap of about 4 eV or more. Particularly, the organo metal salt may include, for example, metal acetates, metal benzoates, metal acetoacetates, metal acetylacetonates, or metal stearates. The thickness of the electron injection layer EIL may be from about 1 Å to about 100 Å, and from about 3 Å to about 90 Å. If the thickness of the electron injection layer EIL satisfies the above described range, satisfactory electron injection properties may be obtained without inducing substantial increase of a driving voltage.

The electron transport region ETR may include a hole blocking layer HBL as described above. The hole blocking layer HBL may include, for example, at least one of 2,9-dimethyl-4,7-diphenyl-1,10-phenanthroline (BCP), or 4,7-diphenyl-1,10-phenanthroline (Bphen). However, an embodiment of the inventive concept is not limited thereto.

The second electrode EL2 is disposed on the electron transport region ETR. The second electrode EL2 may be a common electrode or a cathode. The second electrode EL2 may be a transmissive electrode, a transflective electrode or a reflective electrode. If the second electrode EL2 is the transmissive electrode, the second electrode EL2 may be formed using a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Alternatively, the second electrode EL2 may have a multilayered structure including a reflective layer or a transflective layer formed using the above-described materials and a transparent conductive layer formed using ITO, IZO, ZnO, ITZO, etc.

Though not shown, the second electrode EL2 may be connected with an auxiliary electrode. If the second electrode EL2 is connected with the auxiliary electrode, the resistance of the second electrode EL2 may decrease.

A capping layer (CPL) may be further disposed on the second electrode EL2 of the luminescence device 10 of an embodiment. The capping layer CPL may include, for example, α-NPD, NPB, TPD, m-MTDATA, $Alq_3$, CuPc, N4,N4,N4',N4'-tetra(biphenyl-4-yl) biphenyl-4,4'-diamine (TPD15), 4,4',4"-tris(carbazol-9-yl)triphenylamine (TCTA), N,N'-bis(naphthalen-1-yl), etc.

The above-described compound of an embodiment may be included in a functional layer other than the hole transport region HTR as a material for the luminescence device 10. The luminescence device 10 according to an embodiment of the inventive concept may include the above-described compound in at least one functional layer disposed between the first electrode EL1 and the second electrode EL2, or in the capping layer (CPL) disposed on the second electrode EL2.

In the luminescence device 10, according to the application of voltages to the first electrode EL1 and second electrode EL2, respectively, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to produce excitons, and the excitons may emit light via transition from an excited state to a ground state.

Hereinafter, the compound according to an embodiment of the inventive concept and the luminescence device 10 of an embodiment including the compound of an embodiment will be particularly explained referring to embodiments and comparative embodiments. The following embodiments are only illustrations to assist the understanding of the inventive concept, and the scope of the inventive concept is not limited thereto.

1. Synthetic Examples

The polycyclic compound of an embodiment may be synthesized, for example, by the following. However, the synthetic method of the polycyclic compound of an embodiment is not limited thereto.

1-1. Synthesis of Intermediate A-4

Intermediate A-4 for synthesizing the compound of an embodiment may be synthesized, for example, by the following Scheme 1:

Scheme 1

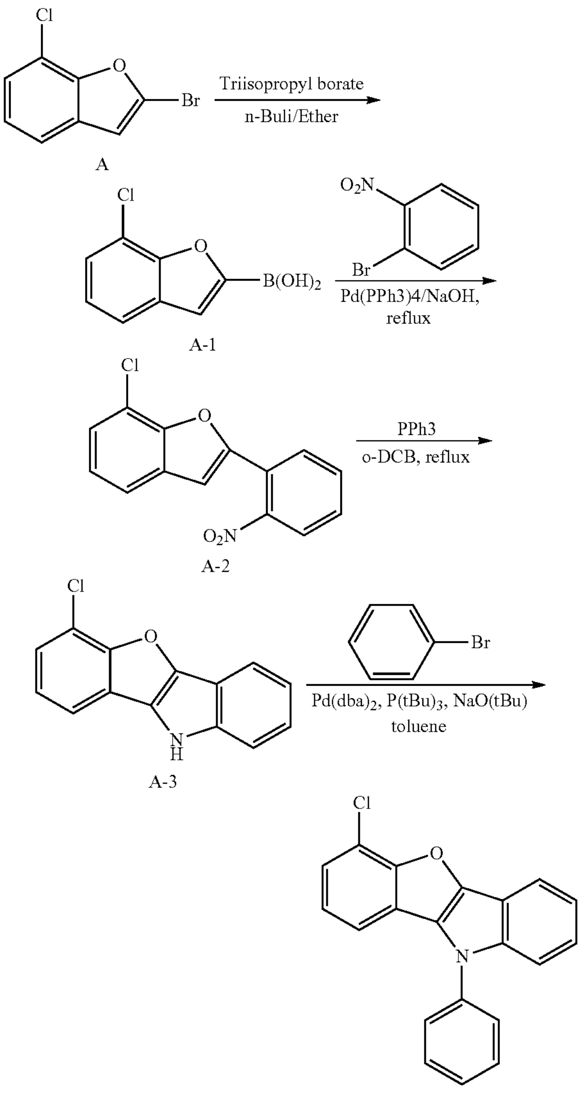

A
A-1
A-2
A-3
A-4

Synthesis of Intermediate A-1

Under an argon atmosphere, to a 500 ml, three-neck flask, Reactant A (11.57 g, 50 mmol), and diethyl ether (250 ml) were added, and the temperature was decreased to about −78° C. Then, n-BuLi (74.07 g, 120 mmol) was added thereto dropwise and stirred for about 1 hour. After that, $B(OMe_3)$ (15.59 g, 150 mmol) was added thereto dropwise, and the reaction temperature was elevated back to room temperature, followed by stirring for about 3 hours. Then, the reaction solution was neutralized with 1 M (1 molar concentration) HCl, extracted with $CH_2Cl_2$, dried with $MgSO_4$, and concentrated. The crude product thus obtained was separated by silica gel column chromatography to obtain a white solid compound (7.07 g, yield 72%).

The molecular ion peak (m/z) of Intermediate A-1 measured by a FAB-MS measurement method was 196.

Synthesis of Intermediate A-2

Under an argon atmosphere, to a 500 ml, three-neck flask, 2-nitrobromobenzene (6.0 g, 29.6 mmol), Intermediate A-1 (7.00 g, 35.6 mmol), $K_3PO_4$ (12.8 g, 60.5 mmol), toluene (138.6 ml), ethanol (69.3 ml), and $H_2O$ (34.6 ml) were added in order and then completely mixed. Then, $Pd(PPh_3)_4$ (1.2 g, 1.07 mmol) was added thereto, followed by heating and stirring at about 80° C. for about 4 hours. After cooling to room temperature in the air, reaction solvents were removed by distillation. The crude product thus obtained was separated by silica gel column chromatography to obtain Intermediate A-2 (6.32 g, yield 78%) as a white solid.

The molecular ion peak (m/z) of Intermediate A-2 measured by a FAB-MS measurement method was 273.

Synthesis of Intermediate A-3

Under an argon atmosphere, to a 500 ml, three-neck flask, Intermediate A-2 (6.2 g, 22.6 mmol), $PPh_3$ (14.8 g, 56.5 mmol), and o-dichlorobenzene (105 ml) were added, followed by refluxing and stirring for about 24 hours. After cooling to room temperature in the air, the reaction product was filtered. The filtrate was concentrated and separated by silica gel column chromatography to obtain Intermediate A-3 (2.5 g, yield 45%).

The molecular ion peak (m/z) of Intermediate A-3 measured by a FAB-MS measurement method was 241.

Synthesis of Intermediate A-4

Under an argon atmosphere, to a 500 ml, three-neck flask, Intermediate A-3 (5.0 g, 20.7 mmol), $Pd(dba)_2$ (0.59 g, 0.05 eq, 1.03 mmol), NaOtBu (1.99 g, 1 eq, 20.7 mmol), toluene (194 ml), bromobenzene (4.64 g, 1.1 eq, 22.77 mmol) and $P(tBu)_3$ (0.79 g, 0.2 eq, 4.14 mmol) were added in order, followed by heating, refluxing and stirring for about 6 hours. After cooling in the air to room temperature, water was added to the reaction solvent, and the organic layer was separated. The aqueous layer was extracted with toluene. The combined organic layers were washed with a saline solution and dried with $MgSO_4$. $MgSO_4$ was filtered and removed, and the filtrate was concentrated to obtain a crude product. The crude product thus obtained was separated by silica gel column chromatography to obtain Intermediate A-4 (5.72 g, yield 87%) as a white solid.

The molecular ion peak (m/z) of Intermediate A-4 measured by a FAB-MS measurement method was 317.

1-2. Synthesis of Compound A15

Polycyclic Compound A15 of an embodiment may be synthesized, for example, by the following Scheme 2:

Scheme 2

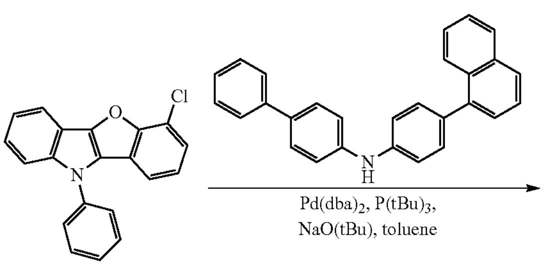

A-4

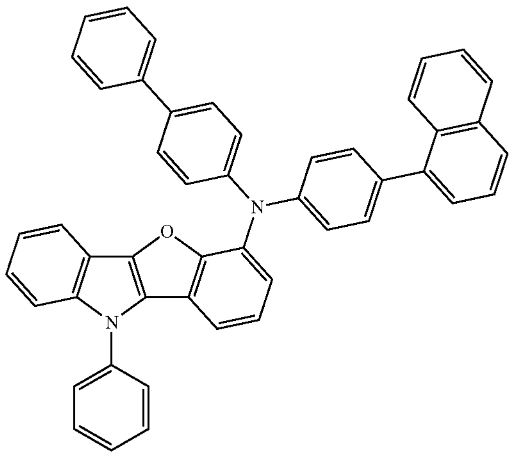

A15

Synthesis of Compound A15

Under an argon atmosphere, to a 300 ml, three-neck flask, Intermediate A-4 (4.8 g, 14.98 mmol), $Pd(dba)_2$ (0.43 g, 0.05 eq, 0.75 mmol), NaOtBu (1.44 g, 1 eq, 14.98 mmol), toluene (164 ml), N,N-(4-biphenyl)-[4-(1-naphthalenyl)phenyl]yl) amine (6.12 g, 1.1 eq, 16.48 mmol) and $P(tBu)_3$ (0.61 g, 0.2 eq, 3.0 mmol) were added in order, followed by heating, refluxing and stirring for about 6 hours. After cooling to room temperature in the air, water was added to a reaction solvent, and the organic layer was separated. The aqueous layer was extracted with toluene. The combined organic layers were collected and then washed with a saline solution and dried with $MgSO_4$. $MgSO_4$ was filtered and removed, and the filtrate was concentrated to obtain a crude product. The crude product was separated by silica gel column chromatography to obtain Intermediate A15 (6.8 g, yield 70%) as a white solid.

The molecular ion peak (m/z) of Intermediate A15 measured by a FAB-MS measurement method was 652.

1-3. Synthesis of Compound A45

Polycyclic Compound A45 of an embodiment may be synthesized, for example, by the following Scheme 3:

Scheme 3

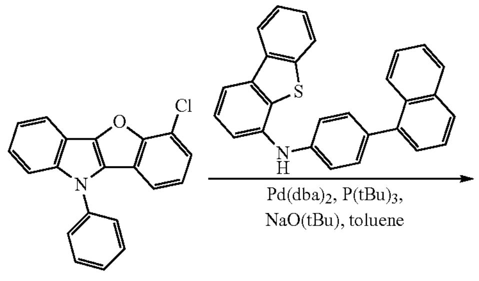

A-4

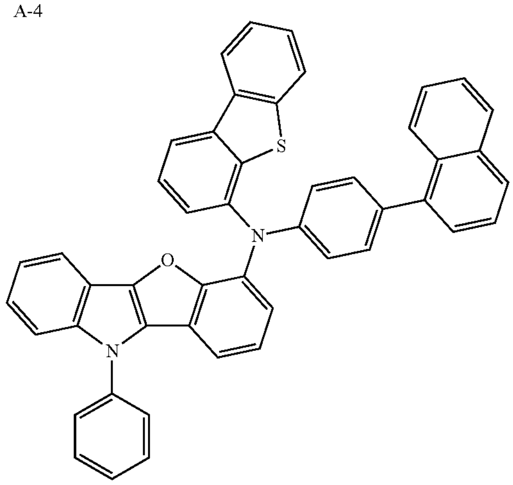

A45

Synthesis of Compound A45

Compound A45 was synthesized by the same method as the synthetic method of Compound A15 except for using N,N-[4-(1-naphthalenyl)phenyl]-4-dibenzothiophenyl-4-amine instead of N,N-(4-biphenyl)-[4-(1-naphthalenyl)phenyl]yl)amine.

The molecular ion peak (m/z) of Compound A45 measured by a FAB-MS measurement method was 682.

1-4. Synthesis of Intermediate B-4

Intermediate B-4 for synthesizing the compound of an embodiment may be synthesized, for example, by the following Scheme 4:

Scheme 4

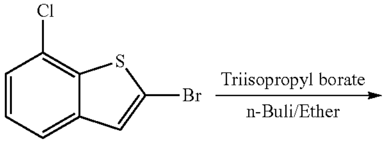

A1

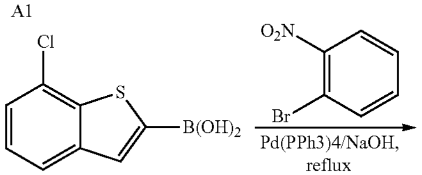

B-1

-continued

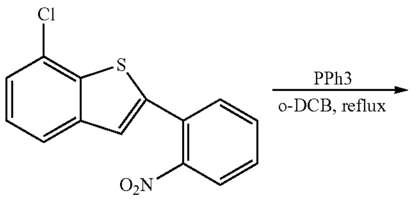

B-2

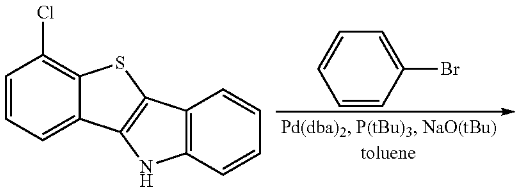

B-3

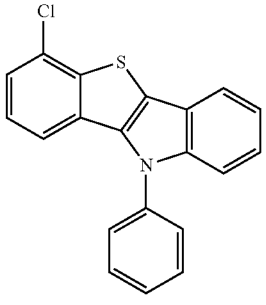

B-4

Synthesis of Intermediate B-1

Under an argon atmosphere, to a 500 ml, three-neck flask, Reactant A1 (12.37 g, 50 mmol), and diethyl ether (250 ml) were added, and the temperature was decreased to about −78° C. Then, n-BuLi (74.07 g, 120 mmol) was added thereto dropwise and stirred for about 1 hour. After that, $B(OMe_3)$ (15.59 g, 150 mmol) was added thereto dropwise, and the reaction temperature was elevated back to room temperature, followed by stirring for about 3 hours. Then, the reaction solution was neutralized with 1 M HCl, extracted with $CH_2Cl_2$, dried with $MgSO_4$, and concentrated. The crude product thus obtained was separated by silica gel column chromatography to obtain a white solid Intermediate B-1 (7.65 g, yield 72%).

The molecular ion peak (m/z) of Intermediate B-1 measured by a FAB-MS measurement method was 212.

1-5. Synthesis of Compound B4

Polycyclic Compound B4 of an embodiment may be synthesized, for example, by the following Scheme 5:

Scheme 5

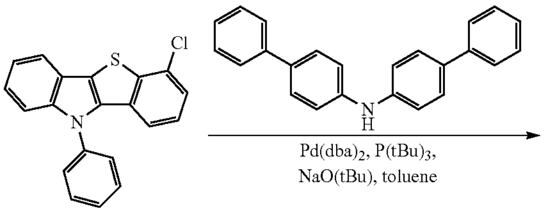

B-4

-continued

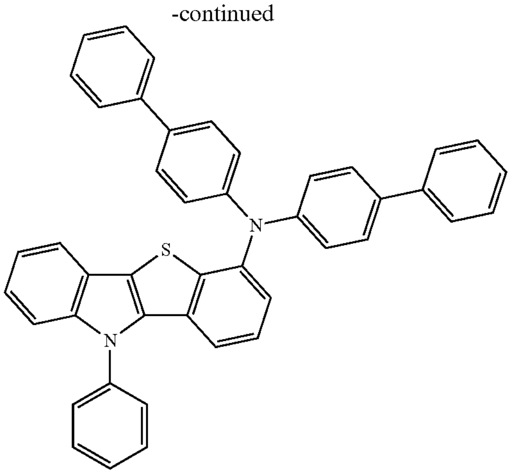

B4

Synthesis of Compound B4

Under an argon atmosphere, to a 300 ml, three-neck flask, Intermediate B-4 (5.0 g, 14.98 mmol), $Pd(dba)_2$ (0.43 g, 0.05 eq, 0.75 mmol), NaOtBu (1.44 g, 1 eq, 14.98 mmol), toluene (164 ml), N,N'-dibiphenylamine (5.30 g, 1.1 eq, 16.48 mmol) and $P(tBu)_3$ (0.61 g, 0.2 eq, 3.0 mmol) were added in order, followed by heating, refluxing and stirring for about 6 hours. After cooling to room temperature in the air, water was added to a reaction solvent, and the organic layer was separated. Then aqueous layer was extracted with toluene. The combined organic layers were washed with a saline solution and dried with $MgSO_4$. $MgSO_4$ was filtered and removed, and the filtrate was concentrated to obtain a crude product. The crude product thus obtained was separated by silica gel column chromatography to obtain Compound B4 (6.5 g, yield 70%) as a white solid.

The molecular ion peak (m/z) of Compound B4 measured by a FAB-MS measurement method was 618.

1-6. Synthesis of Compound B15

Polycyclic Compound B15 of an embodiment may be synthesized, for example, by the following Scheme 6:

Scheme 6

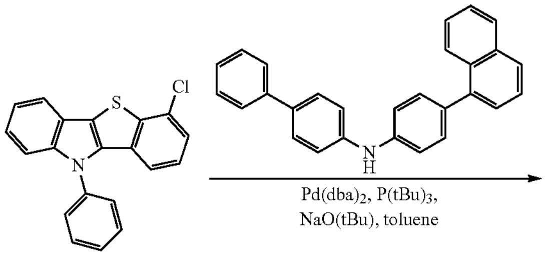

B-4

-continued

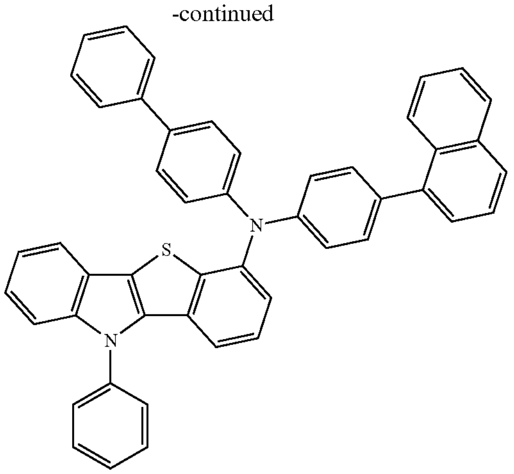

B15

Synthesis of Compound B15

Compound B15 was synthesized by the same method as the synthetic method of Compound B4 except for using N,N-[4-(biphenyl)-]-4-(1-naphthalenyl)phenyl)amine instead of N,N'-dibiphenylamine.

The molecular ion peak (m/z) of Compound B15 measured by a FAB-MS measurement method was 668.

1-7. Synthesis of Compound B44

Polycyclic Compound B44 of an embodiment may be synthesized, for example, by the following Scheme 7:

Scheme 7

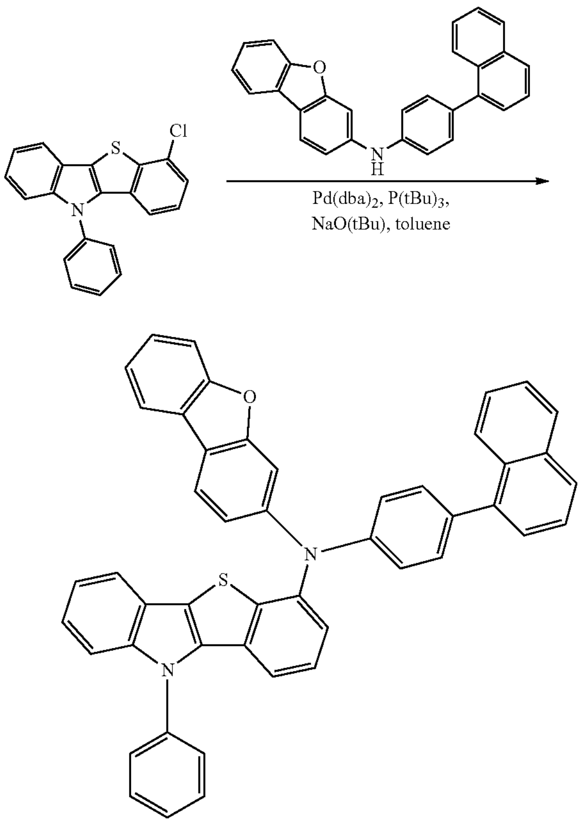

B44

Synthesis of Compound B44

Compound B44 was synthesized by the same method as the synthetic method of Compound B4 except for using N,N-[4-(1-naphthalenyl)phenyl]-3-dibenzofuranphenyl-4-amine instead of N,N'-dibiphenylamine.

The molecular ion peak (m/z) of Compound B44 measured by a FAB-MS measurement method was 682.

1-8. Synthesis of Compound B45

Polycyclic Compound B45 of an embodiment may be synthesized, for example, by the following Scheme 8:

Scheme 8

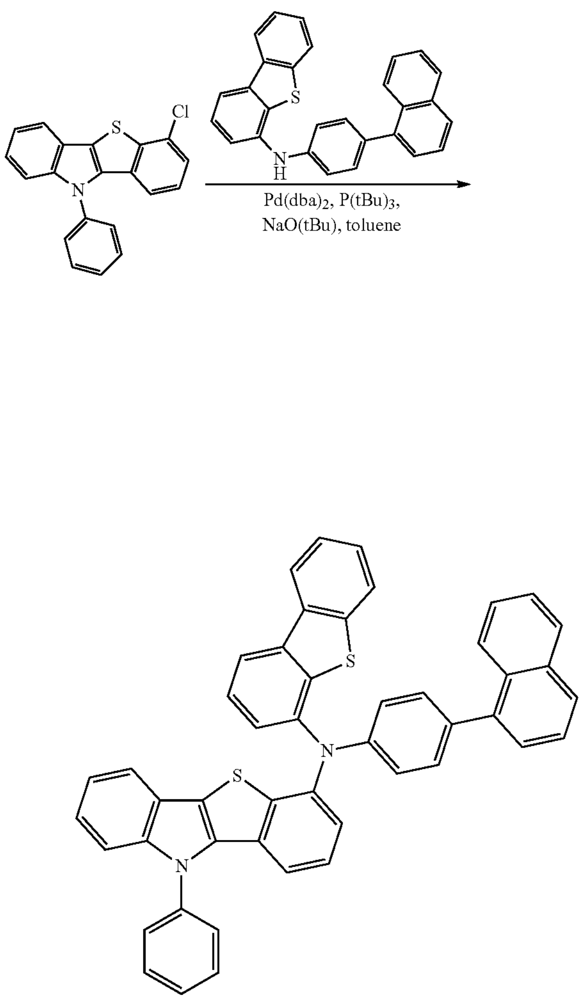

B45

Synthesis of Compound B45

Compound B45 was synthesized by the same method as the synthetic method of Compound B4 except for using N,N-[4-(1-naphthalenyl)phenyl]-4-dibenzothiophenyl-4-amine instead of N,N'-dibiphenylamine.

The molecular ion peak (m/z) of Compound B45 measured by a FAB-MS measurement method was 698.

1-9. Synthesis of Compound B53

Polycyclic Compound B53 of an embodiment may be synthesized, for example, by the following Scheme 9:

Scheme 9

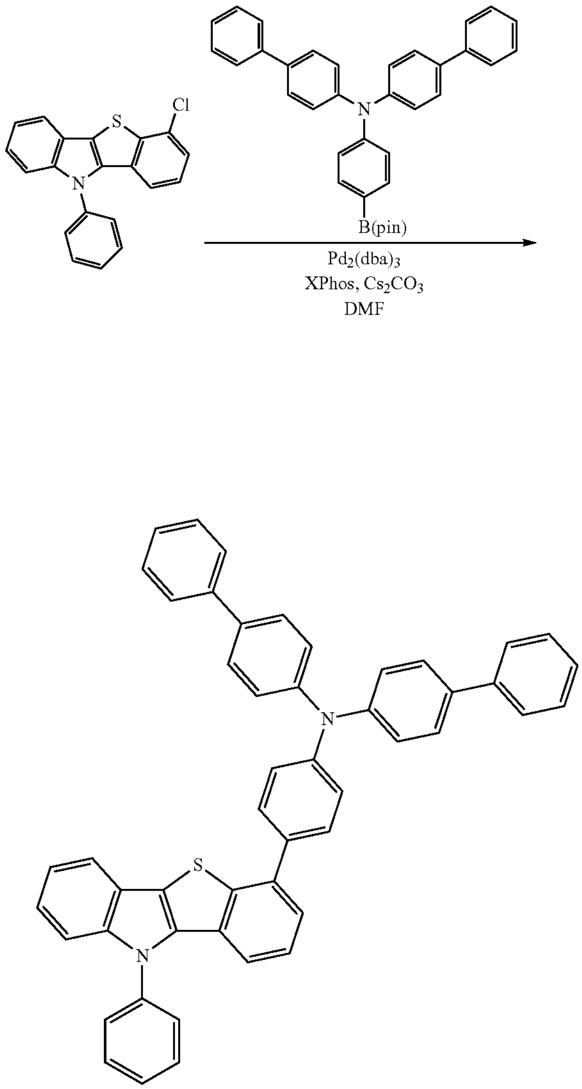

(Synthesis of Compound B53)

Under an argon atmosphere, to a 300 ml, three-neck flask, Intermediate B-4 (5.0 g, 14.98 mmol), N,N-di(4-biphenyl)-4-(4,4,5,5-tetramethyl-1,3,2-dioxaborolan-2-yl)aniline (6.53 g, 1.1 eq, 16.5 mmol), Pd(dba)$_2$ (0.55 g, 0.04 eq, 0.6 mmol), $Cs_2CO_3$ (14.64 g, 3 eq, 44.94 mmol), 2-dicyclohexylphosphino-2',4',6'-triisopropylbiphenyl (XPhos, 0.86 g, 0.12 eq, 1.8 mmol), and N,N-dimethylmethanamide (DMF, 100 ml) were added in order, followed by heating, refluxing and stirring at about 130° C. for about 6 hours. After cooling to room temperature in the air, water was added to a reaction mixture, and an organic layer was separated. Toluene was added to an aqueous layer, and organic layers were additionally extracted by adding $CH_2Cl_2$. The combined organic layers were washed with a saline solution and dried with $MgSO_4$. $MgSO_4$ was filtered and removed, and an organic layer was concentrated to obtain a crude product. The crude product thus obtained was separated by silica gel column chromatography to obtain Compound B53 (7.7 g, yield 68%) as a white solid.

The molecular ion peak (m/z) of Compound B53 measured by a FAB-MS measurement method was 694.

1-10. Synthesis of Compound B72

Polycyclic Compound B72 of an embodiment may be synthesized, for example, by the following Scheme 10:

Scheme 10

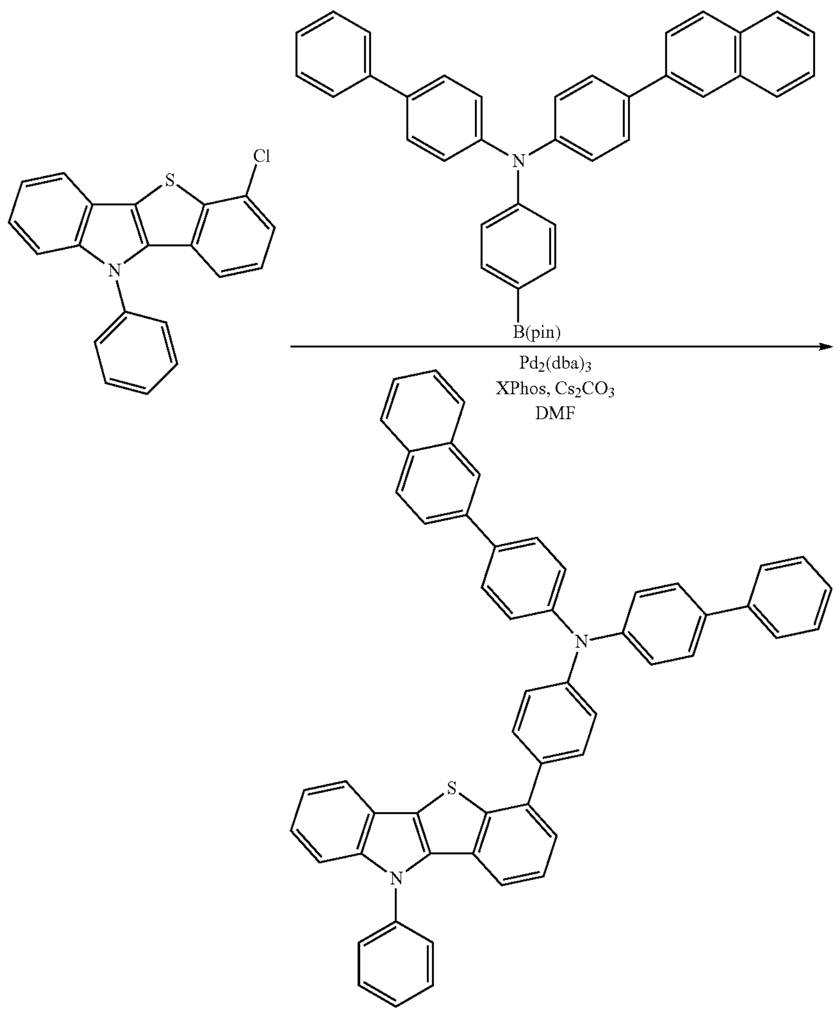

Synthesis of Compound B72

Compound B72 was synthesized by the same method as the synthetic method of Compound B53 except for using N,N-[4-(biphenylyl)-4-(2-naphthyl)phenyldioxaborolan-2-yl]aniline instead of N,N-di(4-biphenyl)-4-(4,4,5,5-tetramethyl-1,3,2-dioxaborolan-2-yl)aniline.

The molecular ion peak (m/z) of Compound B72 measured by a FAB-MS measurement method was 744.

2. Manufacture and Evaluation of Luminescence Device Including Polycyclic Compound 2-1. Example of Luminescence Device Including Polycyclic Compound Luminescence devices of Examples 1 to 6, and Comparative Examples 1 to 4 were manufactured using Example Compounds A15, A45, B4, B15, B44, B45, B53, and B72, and Comparative Compounds C1 to C6 as materials for a hole transport layer.

Example Compounds

A15

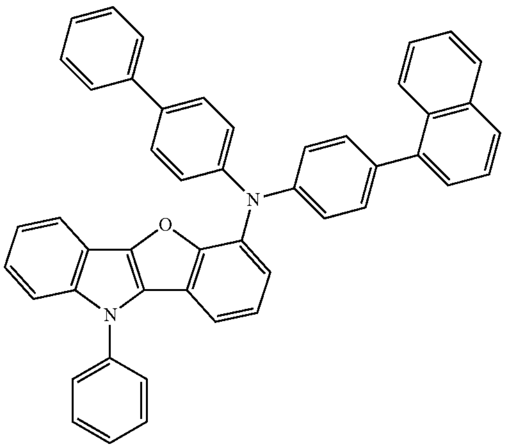

A45
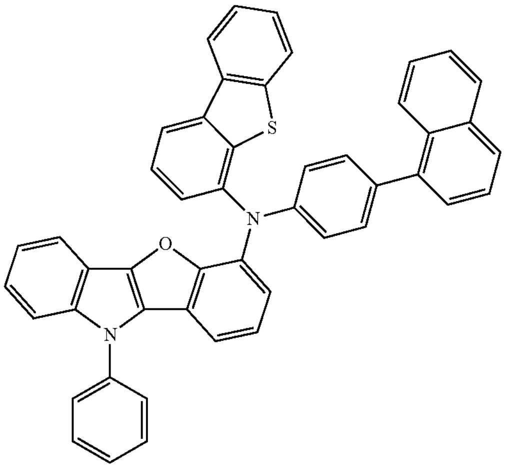
B4
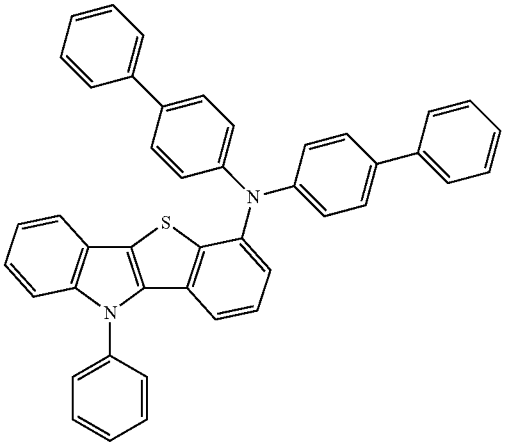
B15
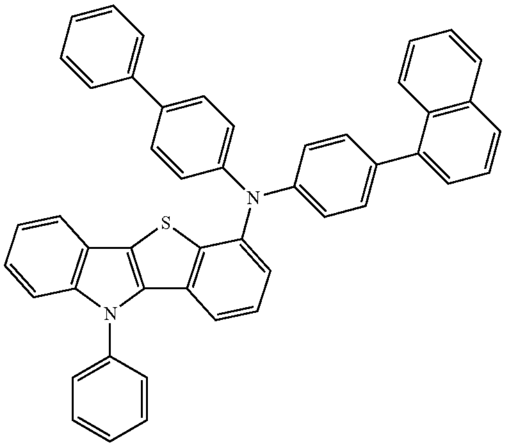
B44
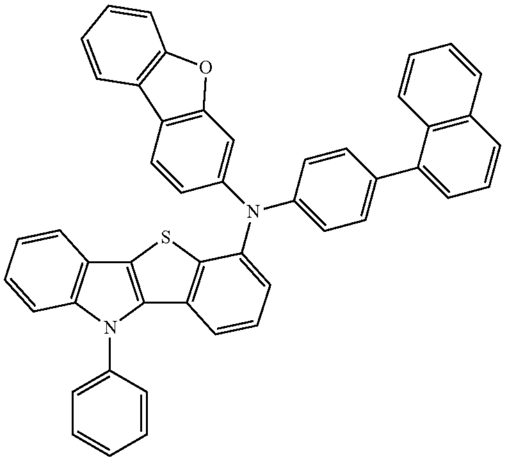
B45
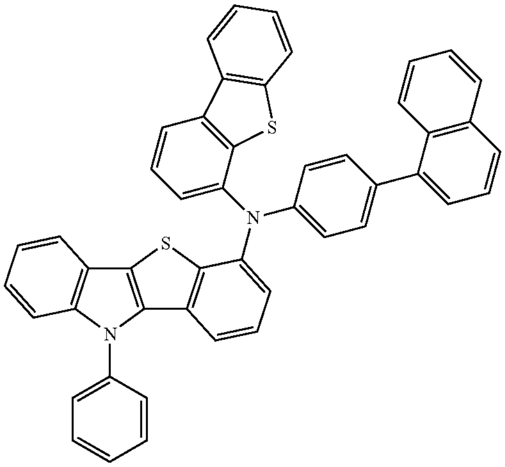
B53
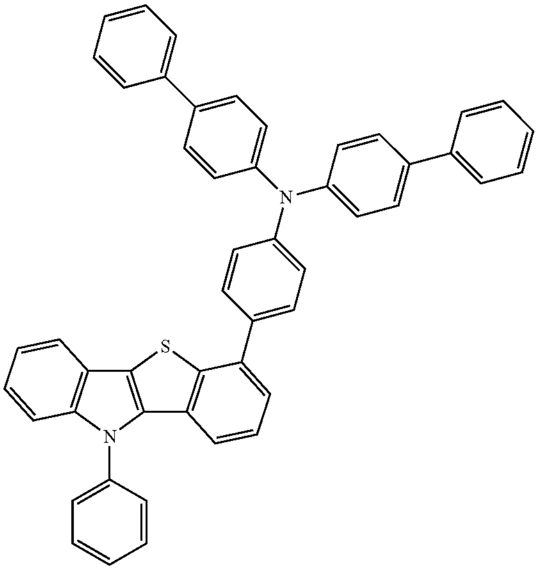

-continued
B72
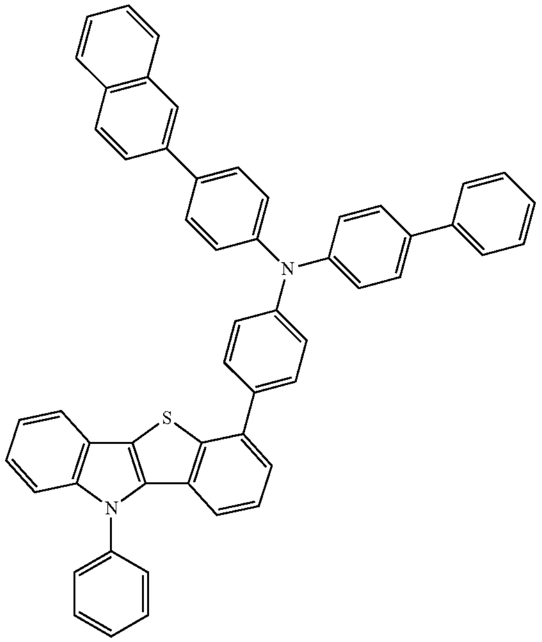
Comparative Compounds
C1
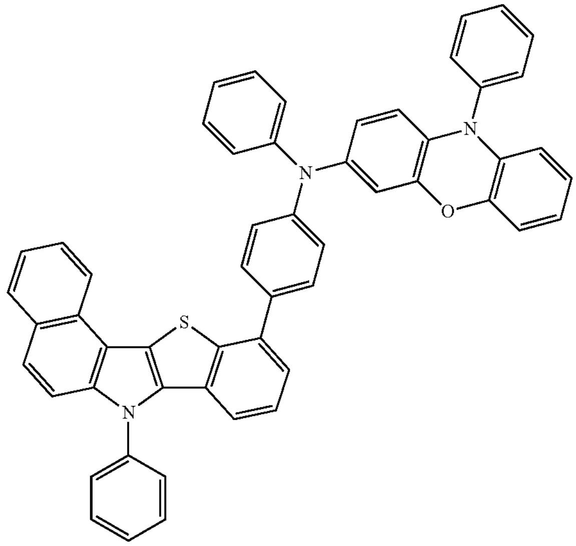
-continued
C2
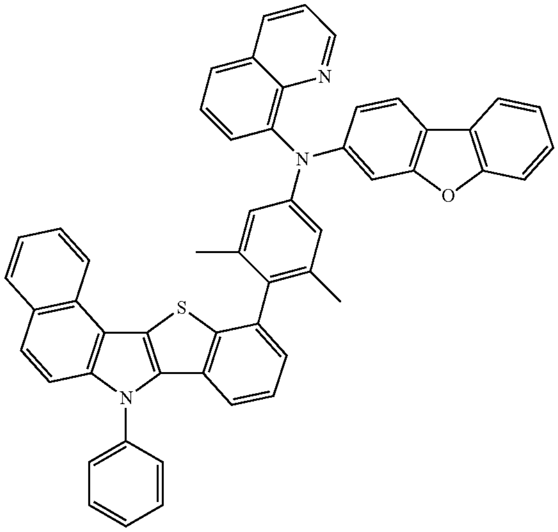
C3
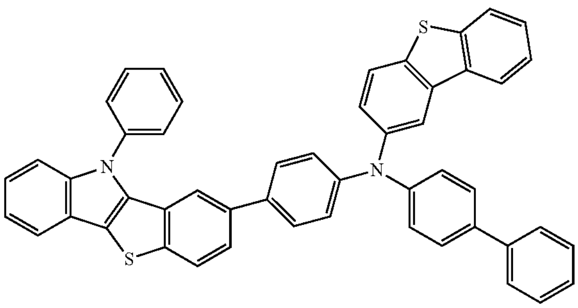
C4
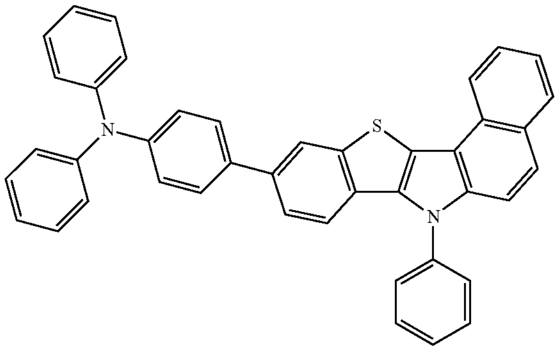
C5
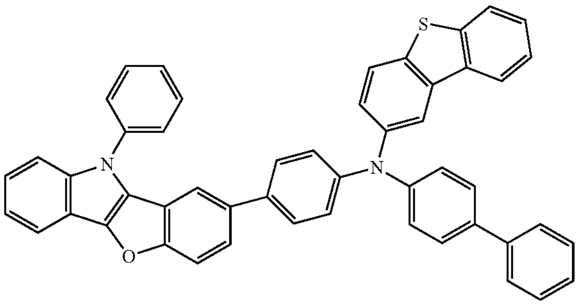

-continued

C6

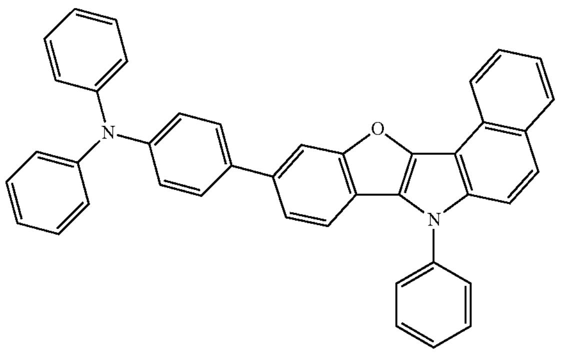

Manufacture of Luminescence Device

Each of the luminescence devices of Examples 1 to 8 and Comparative Examples 1 to 6 was manufactured as follows. A first electrode EL1 with a thickness of about 150 nmt was formed using ITO. A hole injection layer HIL with a thickness of about 60 nmt was formed using 1-TNANA, and a hole transport layer HTL with a thickness of about 30 nmt was formed using the Example Compound or Comparative Compound. An emission layer EML with a thickness of about 25 nm was formed using ADN doped with 3% TBP. An electron transport layer ETL with a thickness of about 25 nmt was formed using $Alq_3$, and an electron injection layer EIL with a thickness of about 1 nmt was formed using LiF. A second electrode EL2 with a thickness of about 100 nmt was formed using A1. All layers were formed by a vacuum deposition method. 1-TNATA, TBP, ADN, and $Alq_3$ were commercial products on the market purchased and were used after performing sublimation and purification.

Evaluation of Properties of Luminescence Device

In order to evaluate the properties of the luminescence devices 10 according to the Examples and Comparative Examples, emission efficiency and luminance half-life were measured. The emission efficiency was a value on a current density of about 10 $mA/cm^2$. The luminance half-life was represented based on a time period required for decreasing luminescence of about 1,000 $cd/m^2$ by 50. The luminance half-life was measured by continuously driving at a current density of about 1.0 $mA/cm^2$. For the evaluation of emission properties of the luminescence devices 10 manufactured, a current density, a driving voltage, and emission efficiency were measured using Source Meter of 2400 Series of Keithley Instruments Co., a luminance colorimeter, CS-200 which is a product of Konica Minolta Co., and LabVIEW8.2 PC program for measurement, which is a product of Japanese National Instruments Co.

TABLE 1

| Device manufacturing example | Hole transport layer material | Driving voltage (V) | Current efficiency (cd/A) | Luminance half-life |
|---|---|---|---|---|
| Example 1 | Example Compound A15 | 5.6 | 8.1 | 2200 |
| Example 2 | Example Compound A45 | 5.5 | 8.3 | 2000 |
| Example 3 | Example Compound B4 | 5.7 | 8.1 | 2100 |
| Example 4 | Example Compound B15 | 5.8 | 8.5 | 2000 |
| Example 5 | Example Compound B44 | 5.6 | 8.4 | 2250 |
| Example 6 | Example Compound B45 | 5.7 | 8.8 | 2200 |
| Example 7 | Example Compound B53 | 5.6 | 8.3 | 2200 |
| Example 8 | Example Compound B72 | 5.8 | 8.0 | 2300 |
| Comparative Example 1 | Comparative Compound C1 | 6.0 | 6.2 | 1700 |
| Comparative Example 2 | Comparative Compound C2 | 6.0 | 6.0 | 1500 |
| Comparative Example 3 | Comparative Compound C3 | 5.9 | 7.4 | 1800 |
| Comparative Example 4 | Comparative Compound C4 | 6.1 | 7.5 | 1900 |
| Comparative Example 5 | Comparative Compound C5 | 6.2 | 6.3 | 1600 |
| Comparative Example 6 | Comparative Compound C6 | 5.9 | 7.2 | 1300 |

Referring to the results of Table 1, it could be found that if the polycyclic compound according to an embodiment of the inventive concept was applied to a luminescence device as a material for a hole transport layer, a low driving voltage, high efficiency and long life could be achieved. Particularly, it was confirmed that Example 1 to Example 8 achieved a lower driving voltage, higher efficiency and longer life when compared with Comparative Example 1 to Comparative Example 6.

When compared with Comparative Compounds C1 and C2, in which a benzene ring is additionally condensed to a benzofuranoindole skeleton or benzothienoindole skeleton, a benzene ring is not additionally condensed in the Example Compounds. Accordingly, improved hole transport capacity could be achieved due to different structural and electrical properties from those of the Comparative Compounds C1 and C2. Accordingly, the Example Compounds are considered to achieve the low driving voltage, high efficiency, and long life of a device.

The compounds of the Examples have different substitution positions of an aryl amine group from Comparative Compounds C3 to C6. Accordingly, improved hole transport capacity could be achieved due to different structural and electrical properties from those of the Comparative Compounds C3 to C6. Accordingly, the Example Compounds are considered to have achieved a low driving voltage, high efficiency, and long life of a device.

The luminescence device of an embodiment includes the polycyclic compound represented by Formula 1. Accordingly, the luminescence device of an embodiment may achieve a low driving voltage, high efficiency and a long life. By applying the polycyclic compound of an embodiment to a luminescence device, a low driving voltage, a high efficiency and a long life of a device may be achieved.

The luminescence device according to an embodiment of the inventive concept may achieve a low driving voltage, a high efficiency, and a long life.

The polycyclic compound according to an embodiment of the inventive concept may be applied to a luminescence device to achieve a low driving voltage, a high efficiency, and a long life.

Although the exemplary embodiments of the present invention have been described, it is understood that the present invention should not be limited to these exemplary embodiments, but various changes and modifications can be made by one ordinary skilled in the art within the spirit and scope of the present invention as hereinafter claimed.

What is claimed is:

1. A luminescence device, comprising:

a first electrode;

a second electrode disposed on the first electrode; and at least one functional layer disposed between the first electrode and the second electrode, wherein the at least one functional layer comprises a hole transport region disposed on the first electrode;

an emission layer disposed on the hole transport region; and an electron transport region disposed on the emission layer, wherein the hole transport region comprises a polycyclic compound represented by Formula 1:

Formula 1

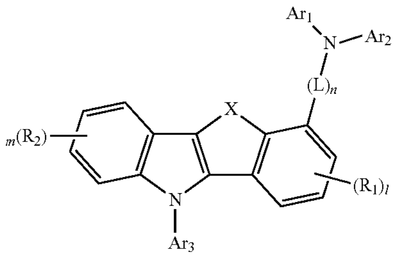

in Formula 1,

X is O, or S, $R_1$ and $R_2$ are each a hydrogen atom, wherein $Ar_1$ and $Ar_2$ are each independently represented by Formula 2:

$$*—(Ar_{11})_p—Ar_{12}$$ Formula 2 in Formula 2, $Ar_{11}$ is an unsubstituted phenylene group or an unsubstituted divalent biphenyl group, $Ar_{12}$ is an unsubstituted phenyl group, an unsubstituted biphenyl group, an unsubstituted terphenyl group, an unsubstituted phenanthryl group, an unsubstituted fluorenyl group, a fluorenyl group substituted with a substituted or unsubstituted aryl group of 6 to 30 ring carbon atoms, an unsubstituted naphthyl group, an unsubstituted carbazolyl group, an unsubstituted dibenzofuranyl group, or an unsubstituted dibenzothiophenyl group, and p is 0 or 1, $Ar_3$ is an unsubstituted aryl group of 6 to 30 ring carbon atoms L is a direct linkage or an unsubstituted arylene group of 6 to 30 ring carbon atoms, l is an integer of 0 to 3, m is an integer of 0 to 4, and n is 0 or 1.

2. The luminescence device of claim 1, wherein the hole transport region further comprises:

a hole injection layer disposed on the first electrode; and a hole transport layer disposed between the hole injection layer and the emission layer, wherein the hole transport layer comprises the polycyclic compound.

3. The luminescence device of claim 1, wherein the polycyclic compound comprises one acyclic amine.

4. The luminescence device of claim 1, wherein Formula 1 is represented by Formula 1-1 or Formula 1-2:

Formula 1-1

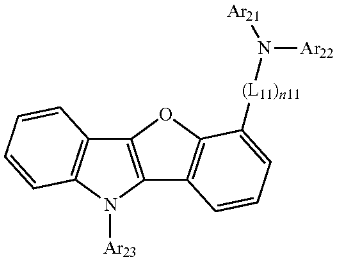

Formula 1-2

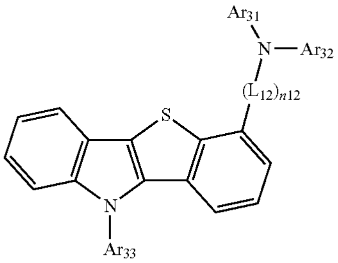

in Formula 1-1 and Formula 1-2, $Ar_{21}$ to $Ar_{23}$, and $Ar_{31}$ to $Ar_{33}$ are each independently represented by Formula 2, $L_{11}$, and $L_{12}$ are each independently a direct linkage or an unsubstituted arylene group of 6 to 30 ring carbon atoms and n11, and n12 are each independently 0 or 1.

5. The luminescence device of claim 1, wherein Formula 1 is represented by Formula 1-3:

Formula 1-3

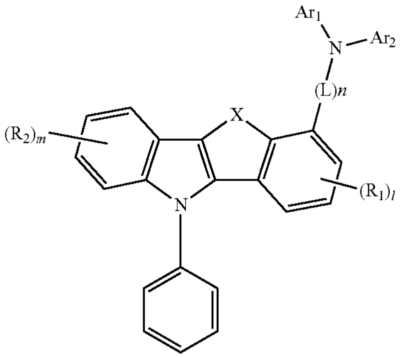

in Formula 1-3,

X, $R_1$, $R_2$, $Ar_1$, $Ar_2$, L, and 1 to n are the same as defined in Formula 1.

6. The luminescence device of claim 1, wherein Formula 1 is represented by Formula 1-4:

Formula 1-4

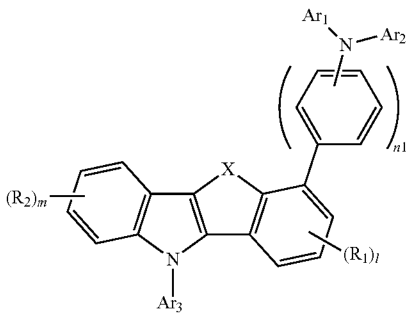

in Formula 1-4, n1 is 0 or 1, and

X, $R_1$, $R_2$, $Ar_1$ to $Ar_3$, 1, and m are the same as defined in Formula 1.

7. The luminescence device of claim 1, wherein $Ar_1$ and $Ar_2$ are each independently represented by 1-1 to 1-8, or 1-10:

1-1

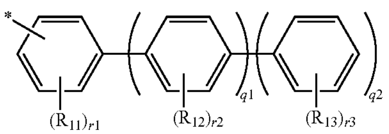

1-2

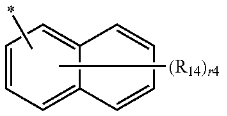

1-3

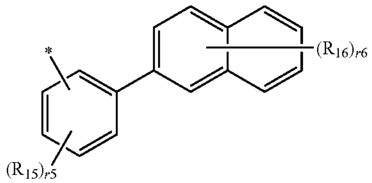

1-4

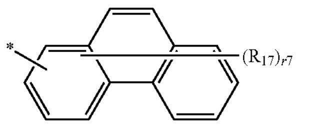

1-5

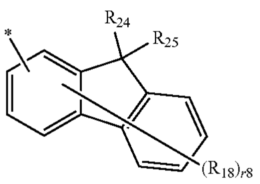

1-6

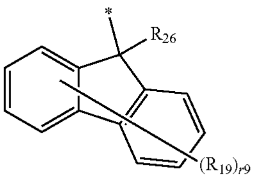

-continued 1-7

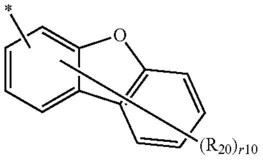

1-8

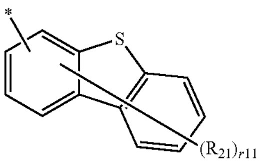

1-10

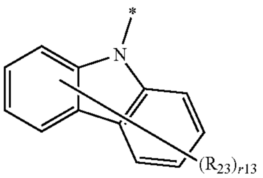

in 1-1 to 1-8 and 1-10 above, $R_{11}$ to $R_{17}$, $R_{20}$, $R_{21}$, and $R_{23}$ are hydrogen atom, $R_{18}$, $R_{19}$, $R_{24}$, $R_{25}$, and $R_{26}$ are each independently a hydrogen atom, or a substituted or unsubstituted aryl group of 6 to 30 ring carbon atoms, r1, r2, and r5 are each independently an integer of 0 to 4, r3 is an integer of 0 to 5, r4, r6, and r8 to r11 are each independently an integer of 0 to 7, r7 is an integer of 0 to 9, r13 is an integer of 0 to 8, and q1 and q2 are each independently 0 or 1.

8. The luminescence device of claim 1, wherein Formula 1 is represented by Formula 1-5:

Formula 1-5

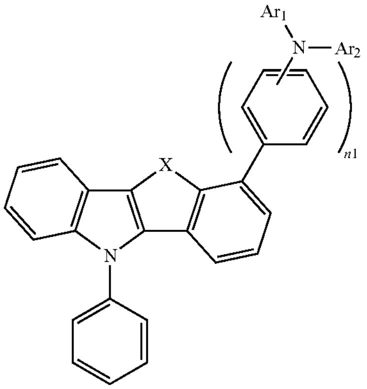

in Formula 1-5, n1 is 0 or 1, and

X, $Ar_1$, and $Ar_2$ are the same as defined in Formula 1.

9. The luminescence device of claim 1, wherein the polycyclic compound comprises at least one among Compound Group 1 or Compound Group 2:

Compound Group 1
A1
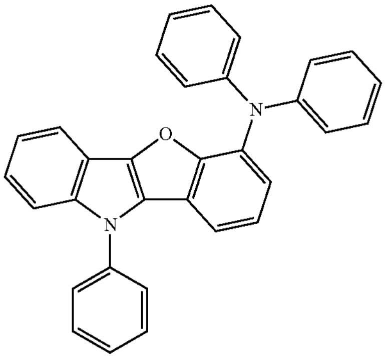
A2
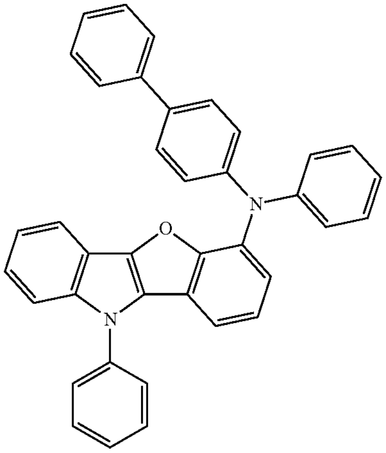
A3
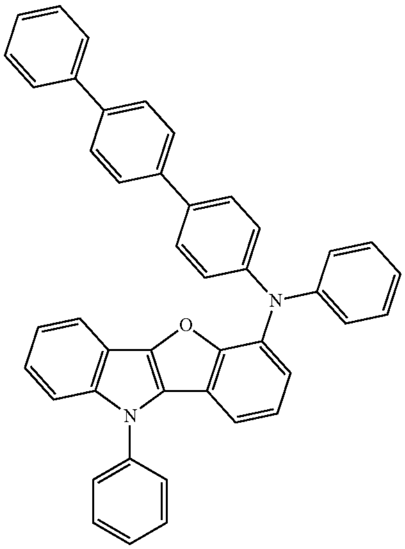
-continued
A4
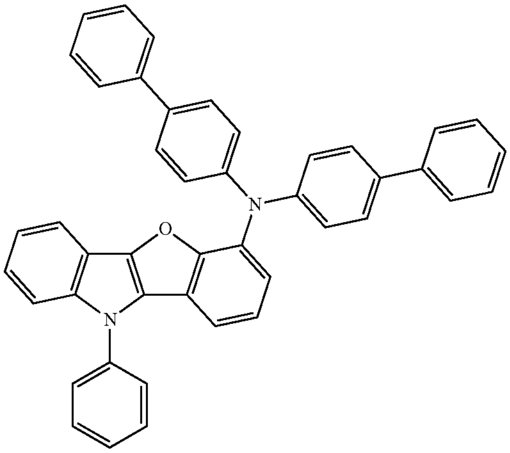
A5
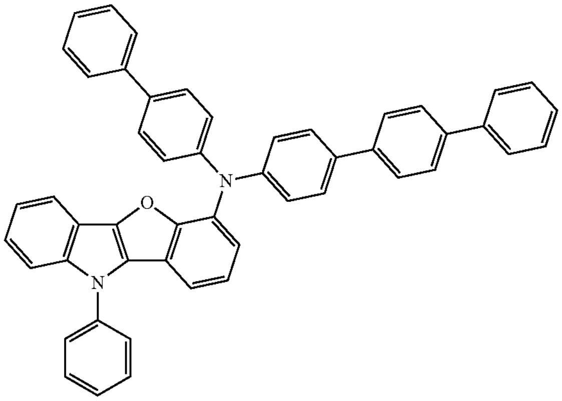
A6
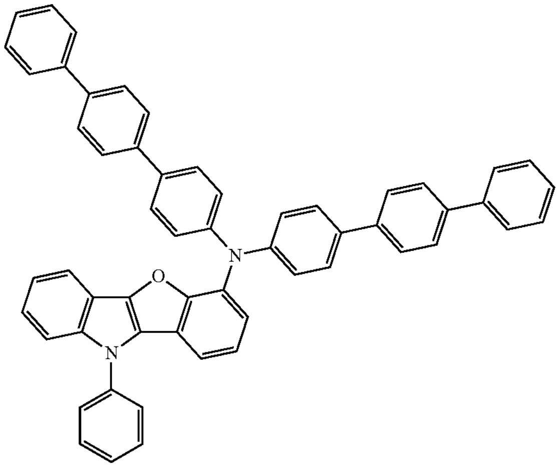

-continued
A7
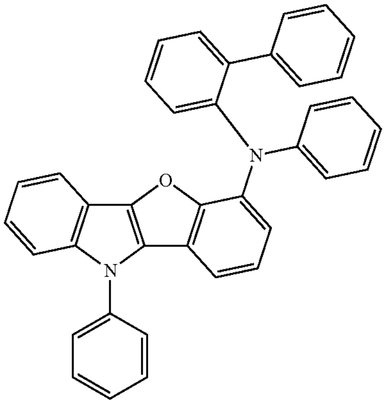
A8
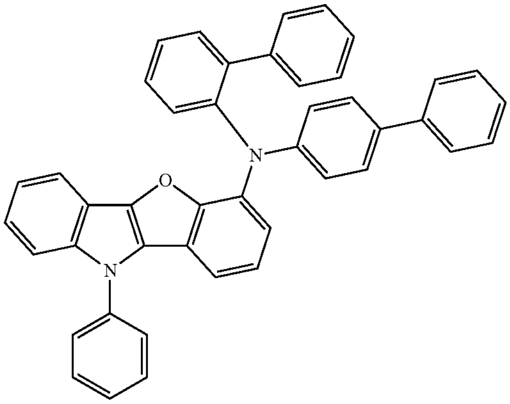
A9
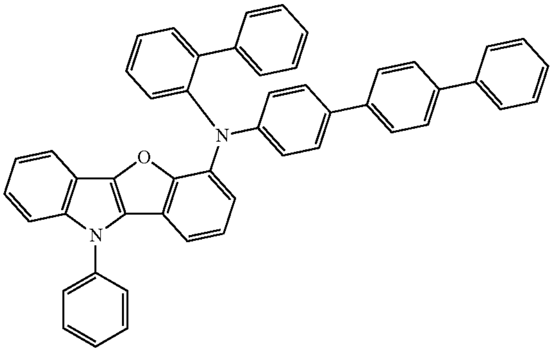
-continued
A10
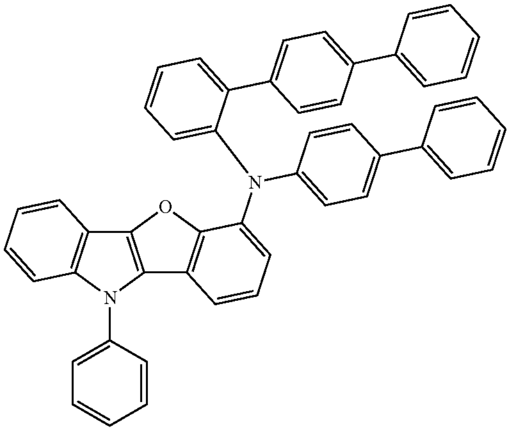
A11
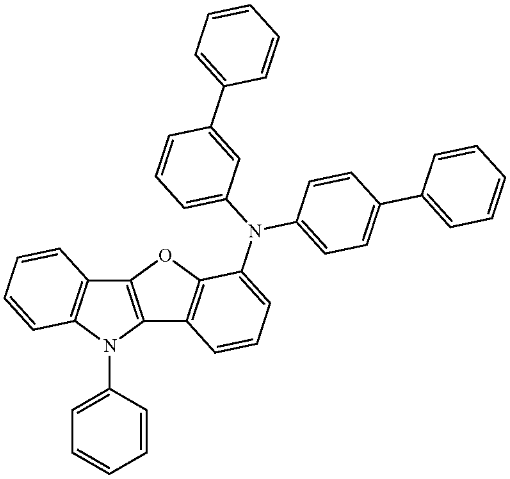
A12
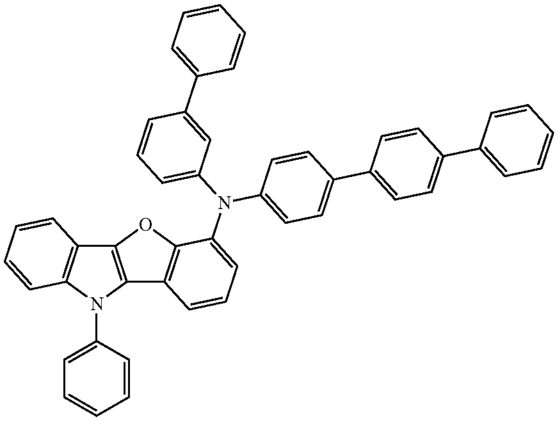

-continued
A13
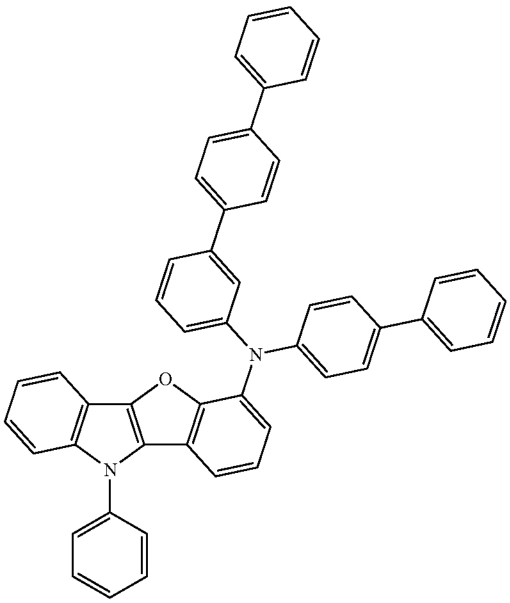
A14
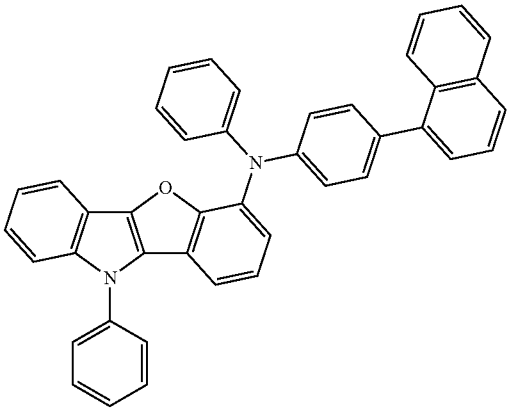
A15
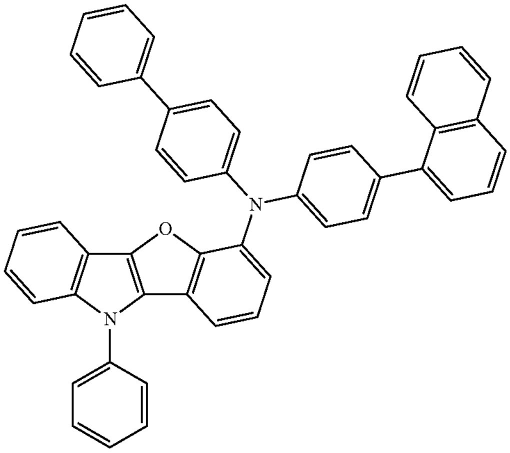
-continued
A16
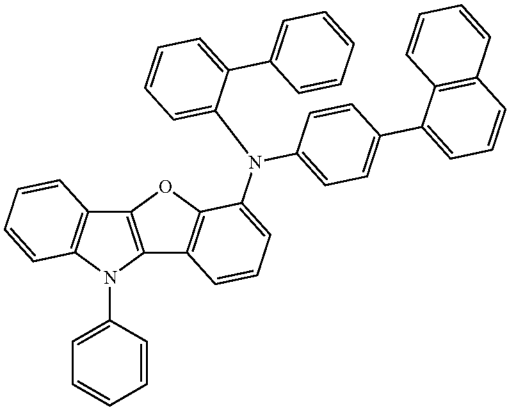
A17
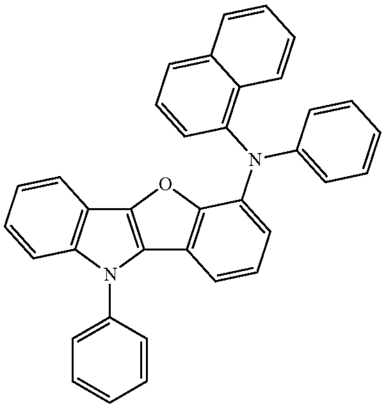
A18
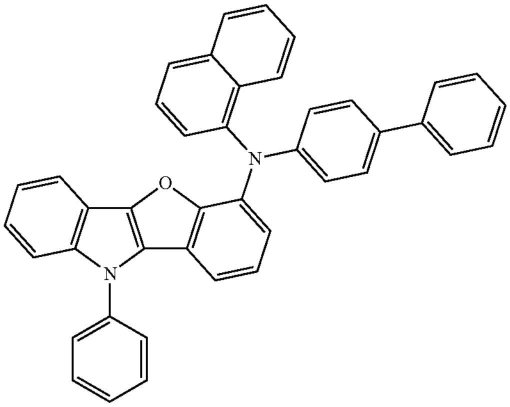

-continued
A19
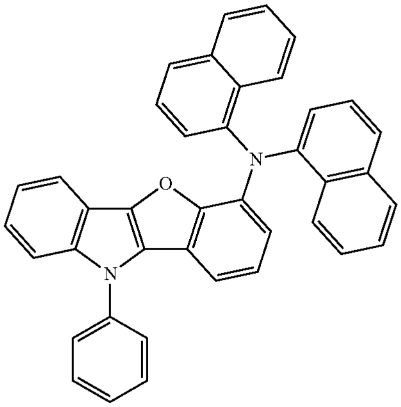
A20
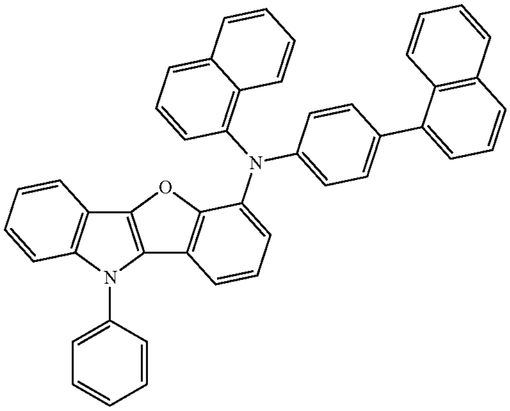
A22
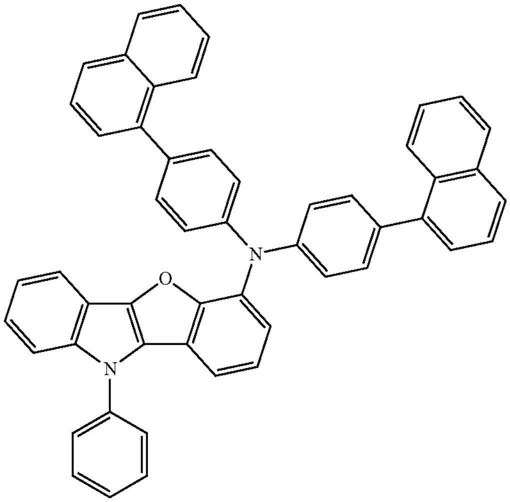
-continued
A23
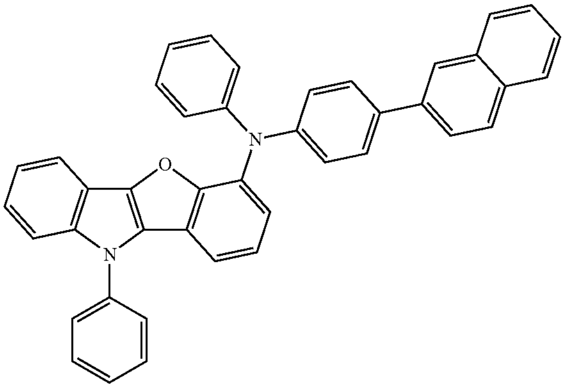
A24
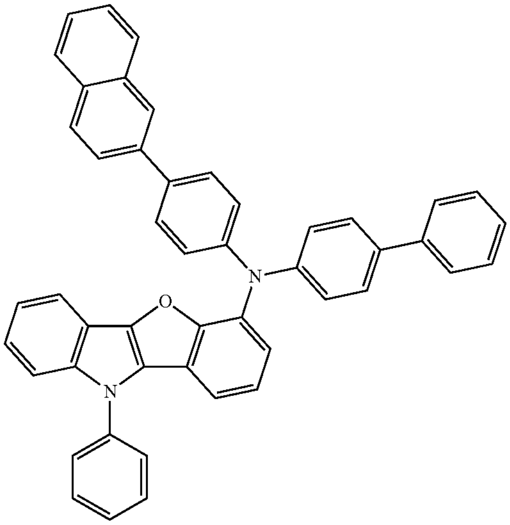
A25
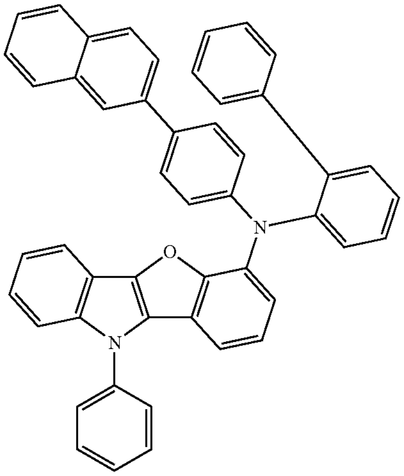

-continued
A26
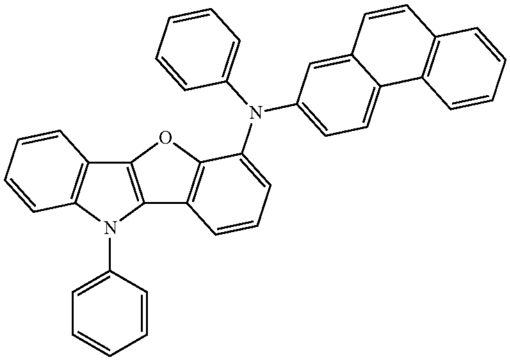
A27
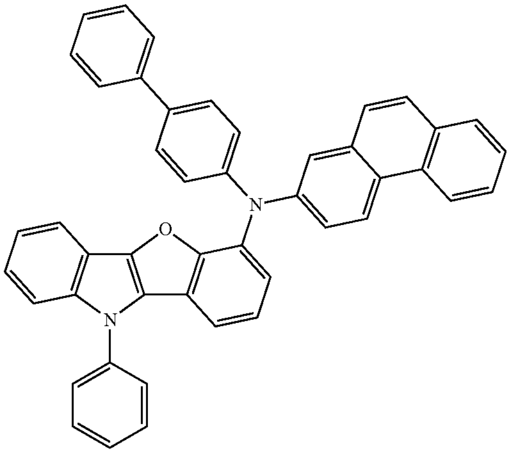
A28
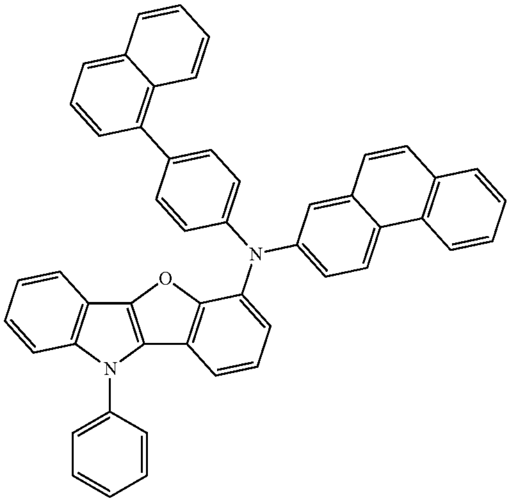
-continued
A29
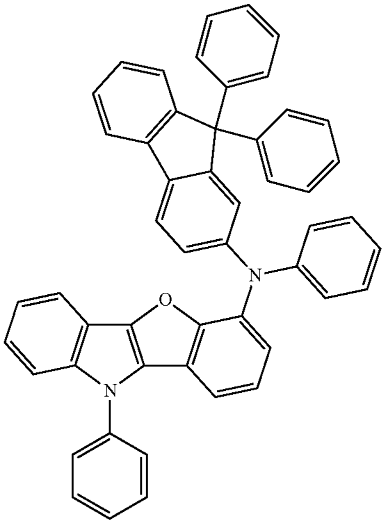
A30
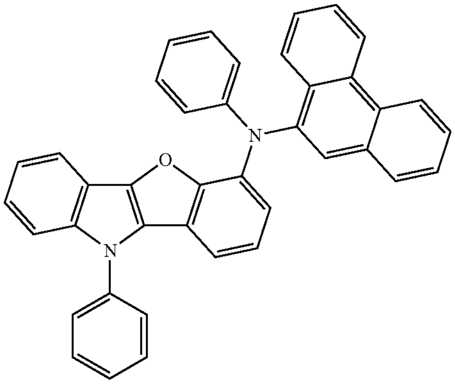
A31
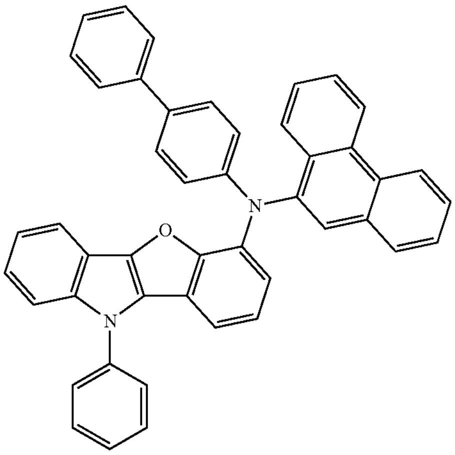

-continued
A32
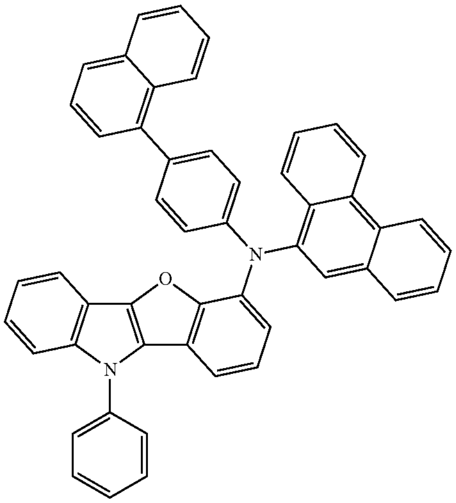
A33
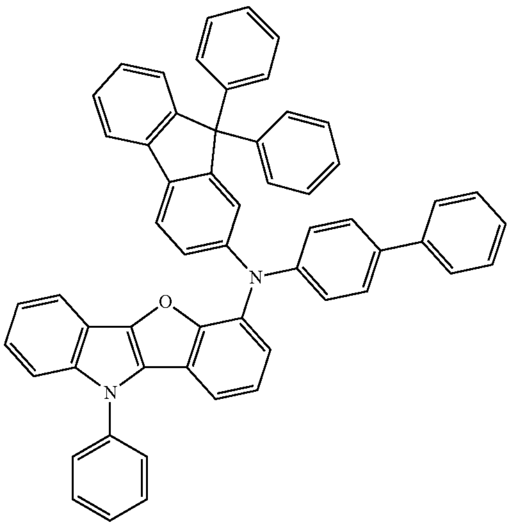
A34
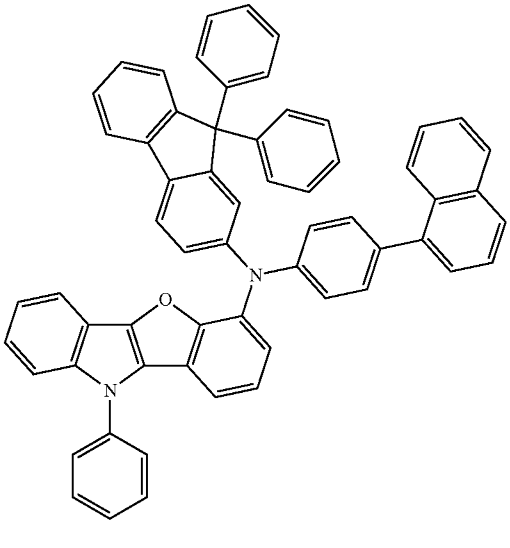
-continued
A35
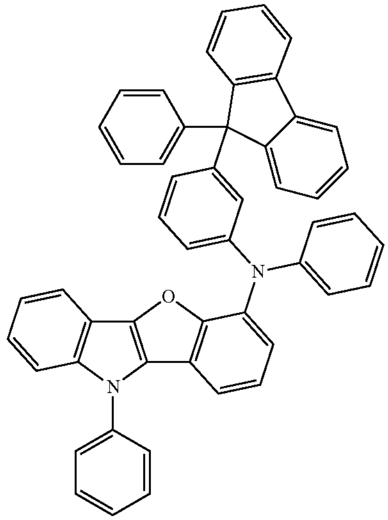
A36
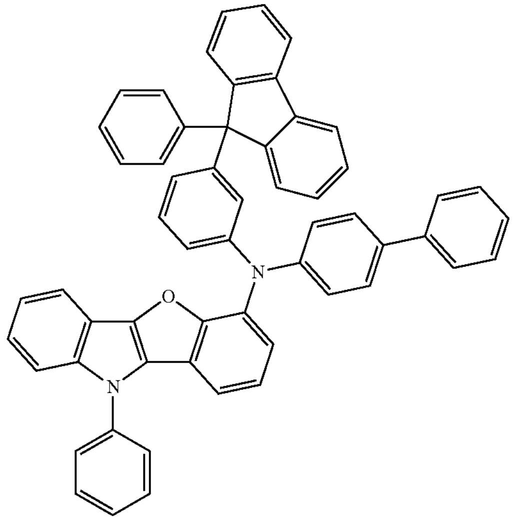
A37
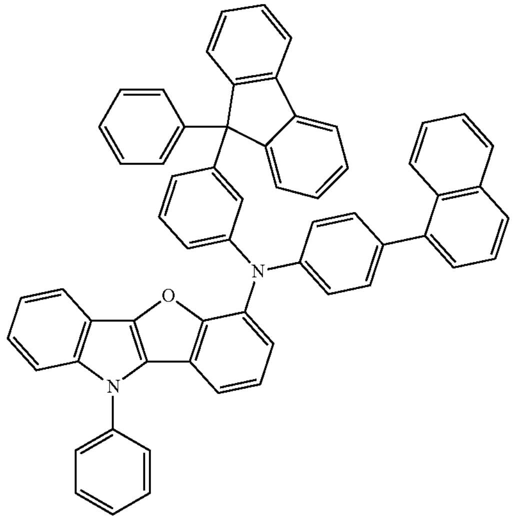

-continued
A38
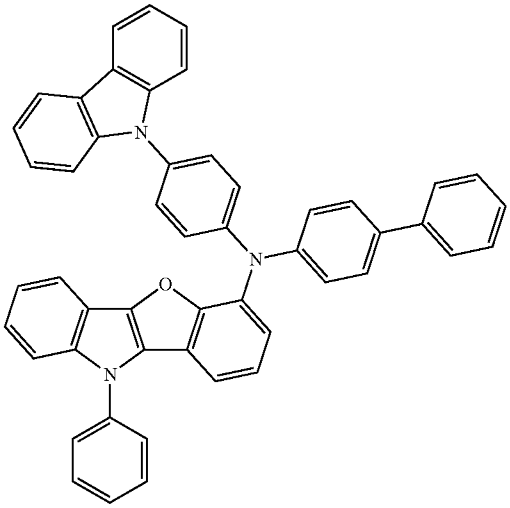
A39
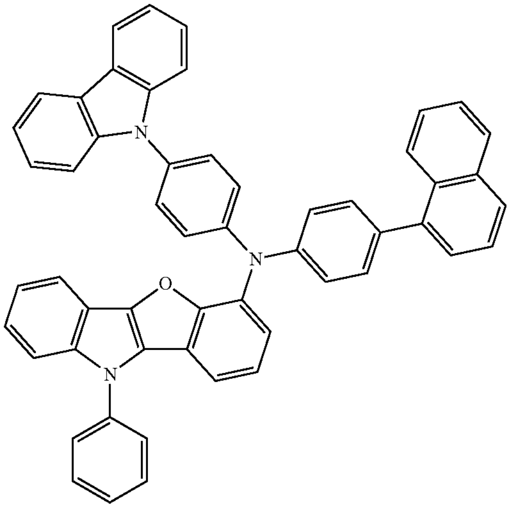
A40
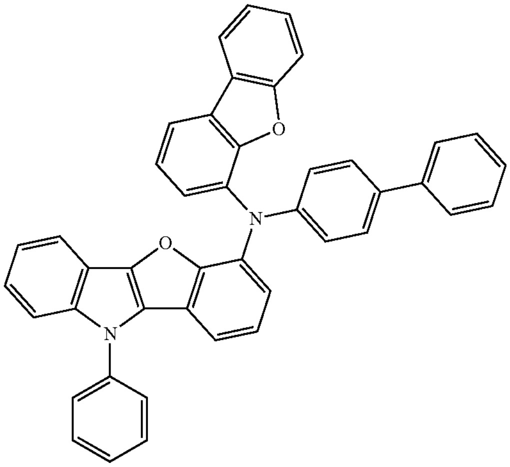
-continued
A41
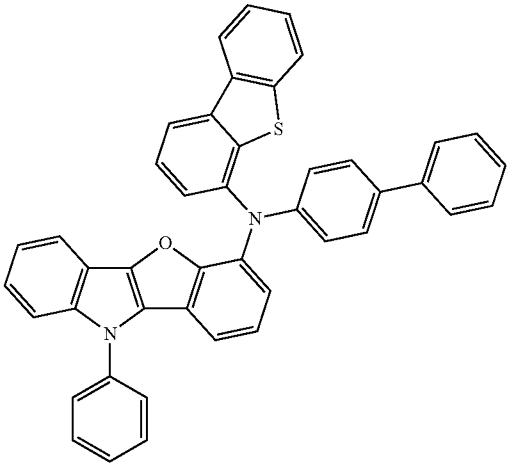
A42
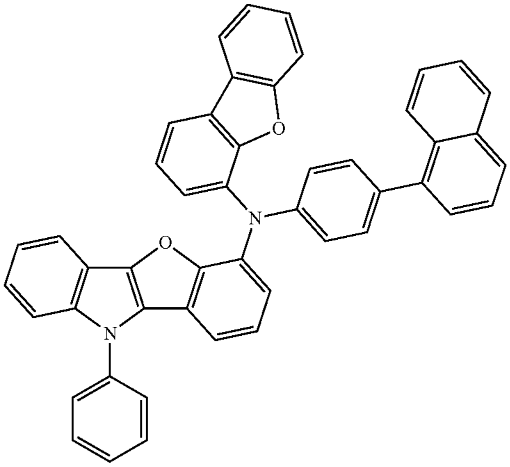
A43
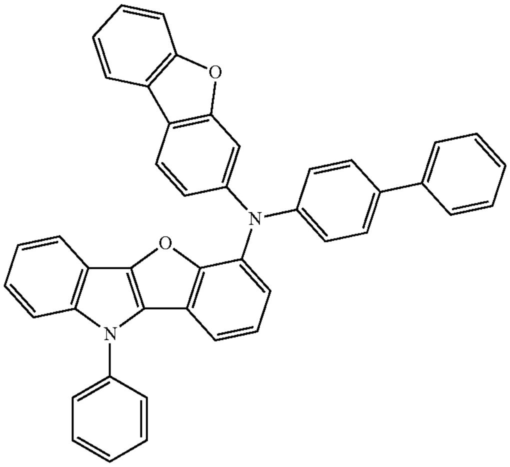

-continued
A44
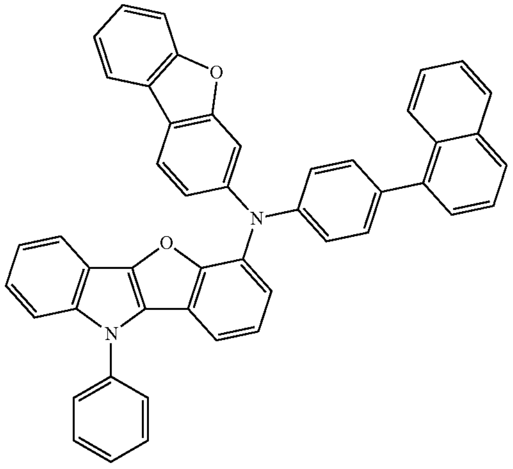
A45
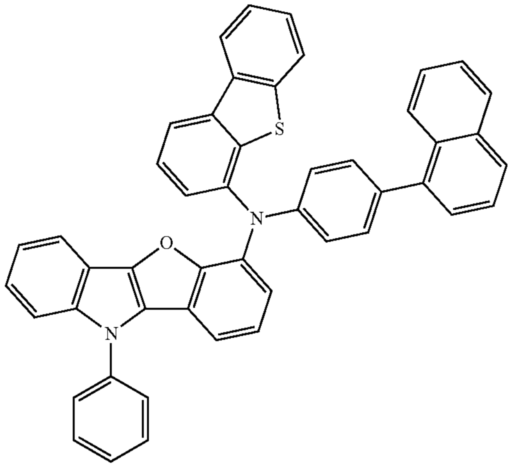
A46
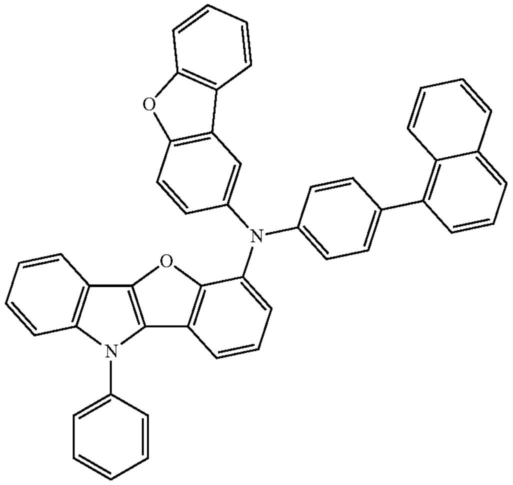
-continued
A47
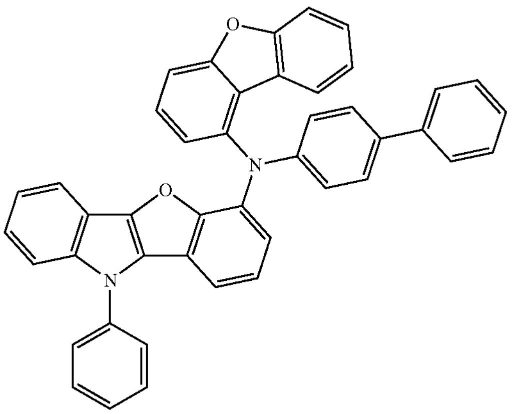
A48
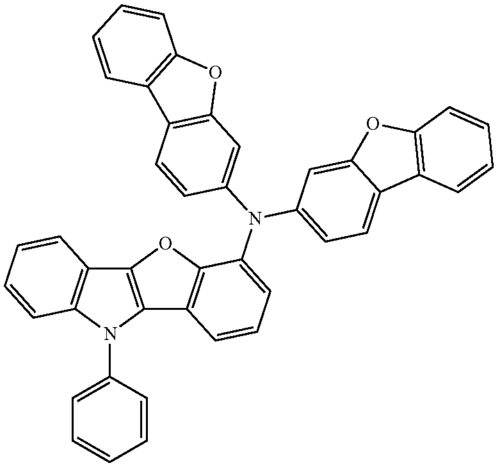
A49
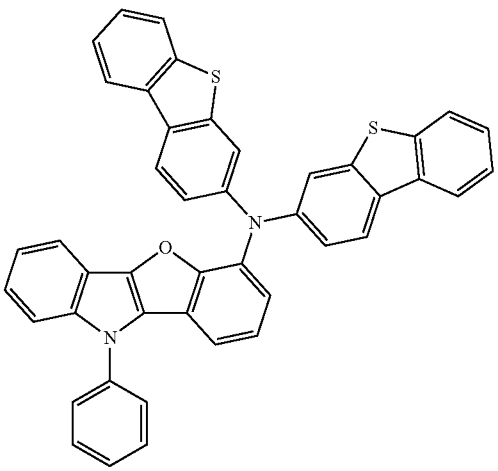

-continued
A50
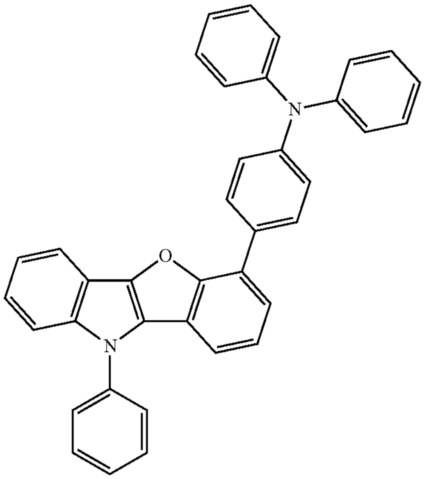
A51
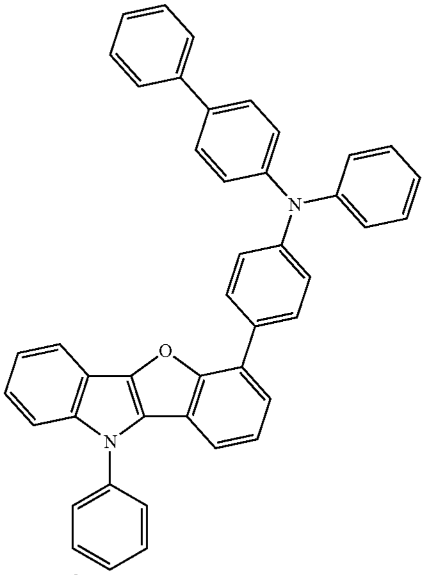
A52
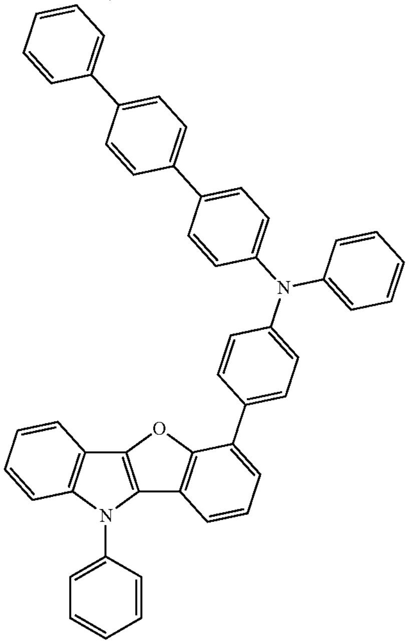
-continued
A53
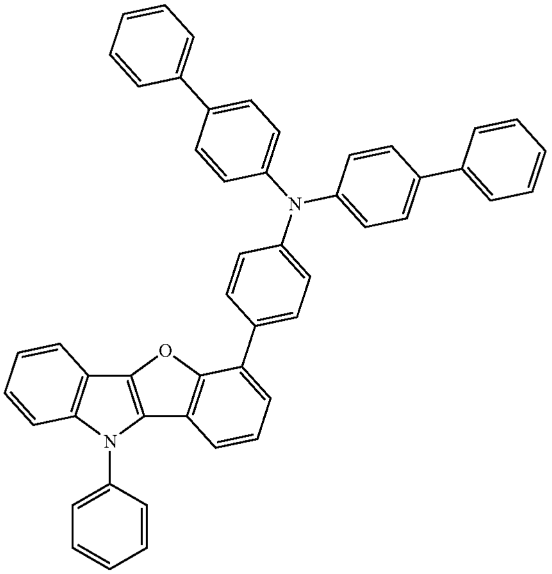
A54
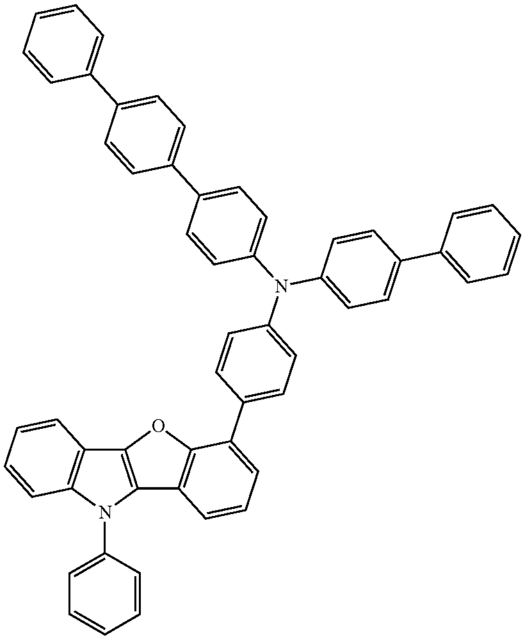

-continued
A55
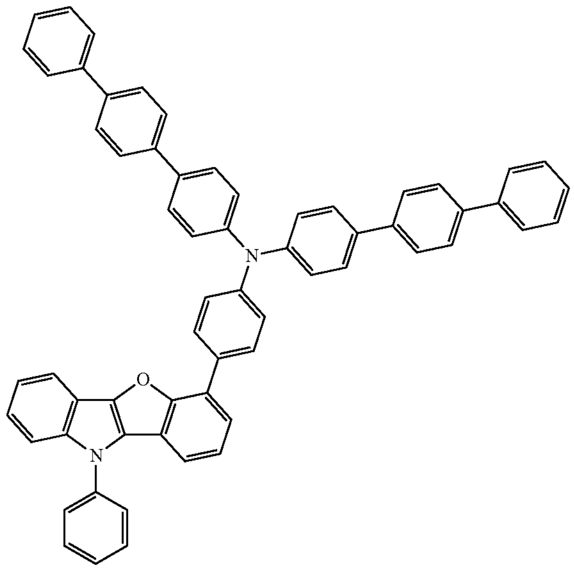
A56
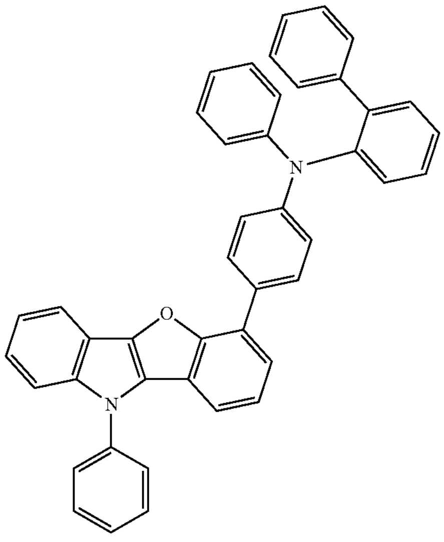
-continued
A57
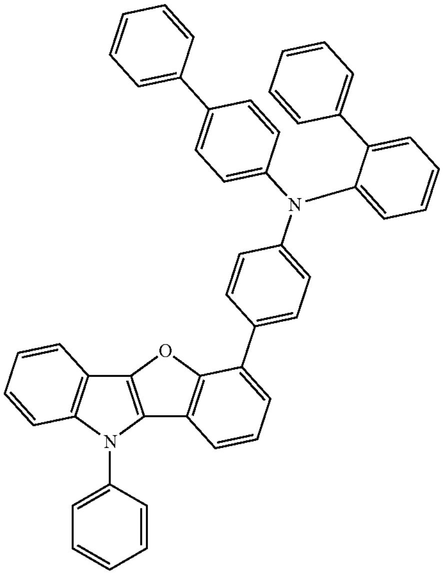
A58
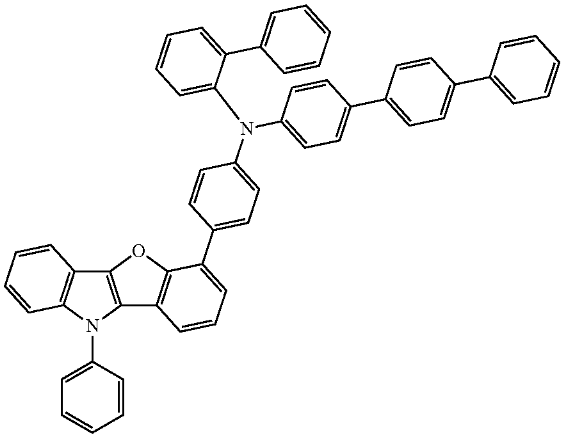
A59
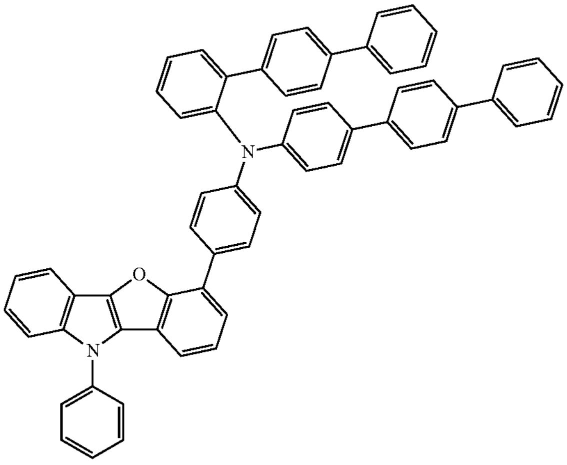

-continued
A60
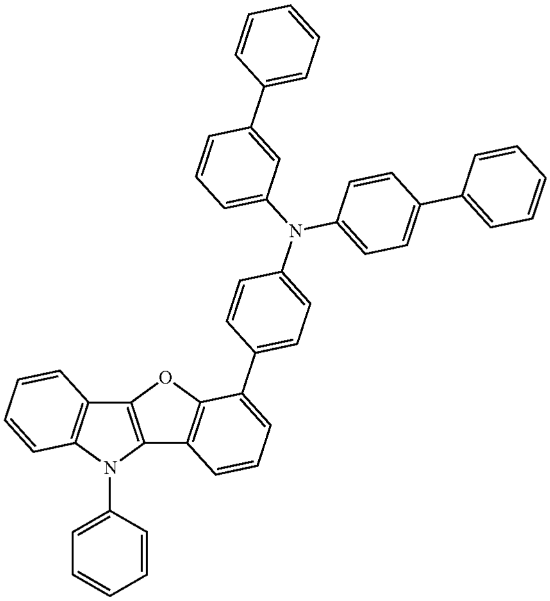
A61
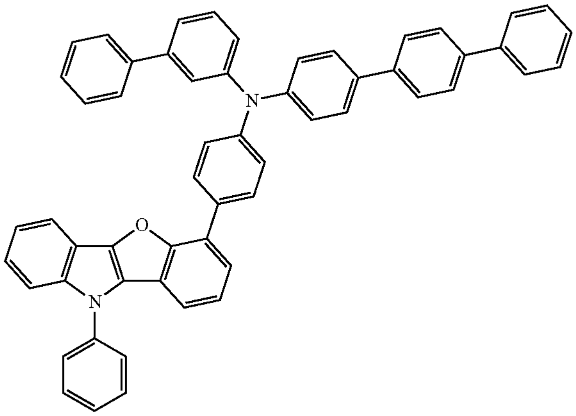
-continued
A62
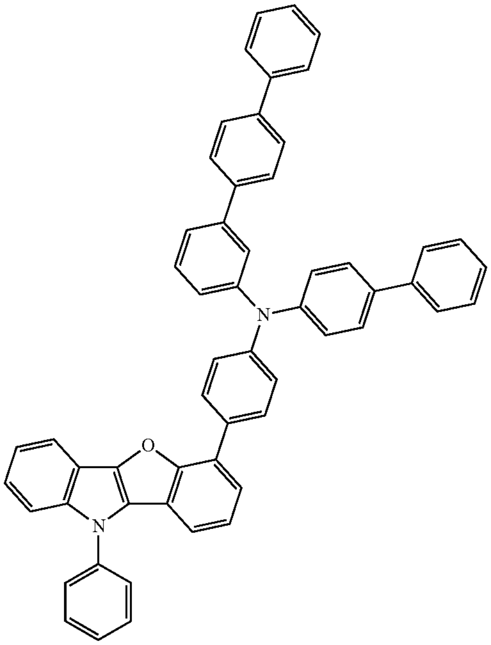
A63
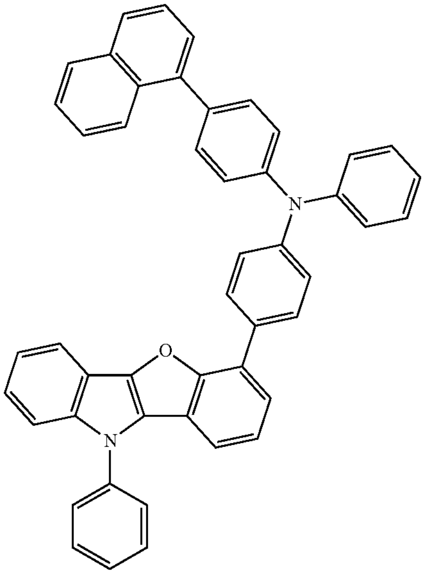

-continued
A64
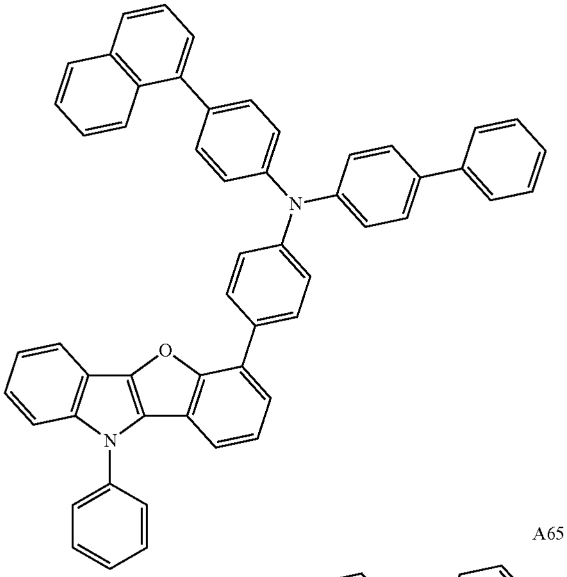
A65
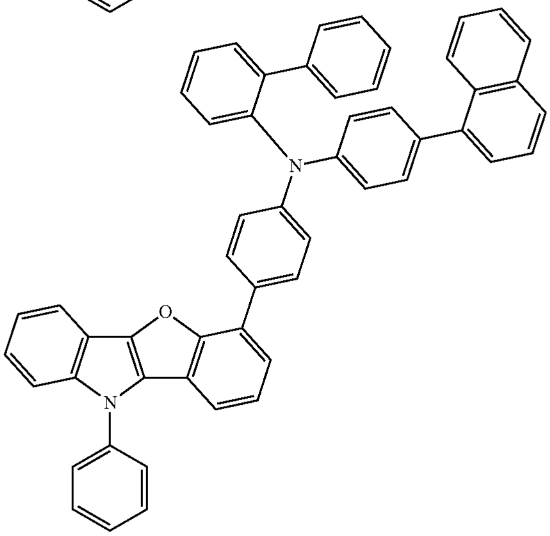
A66
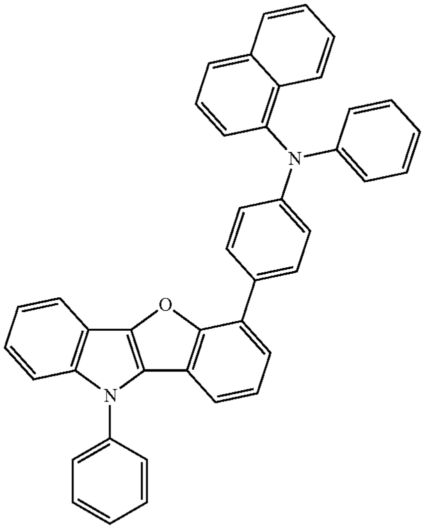
-continued
A67
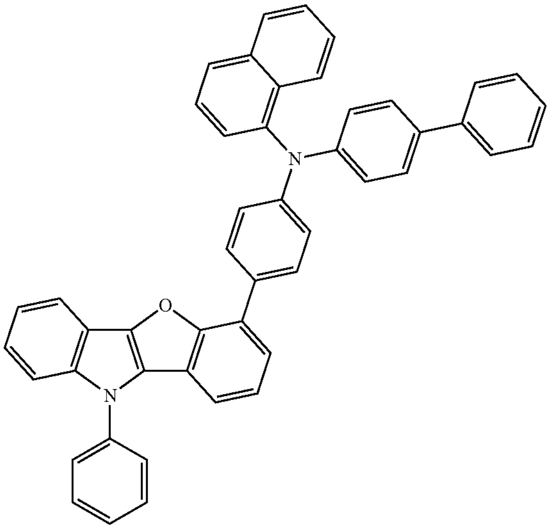
A68
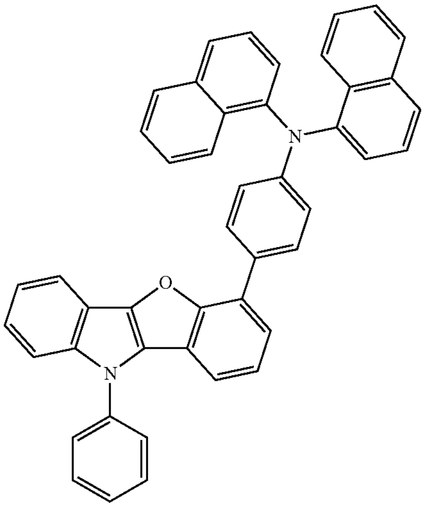
A69
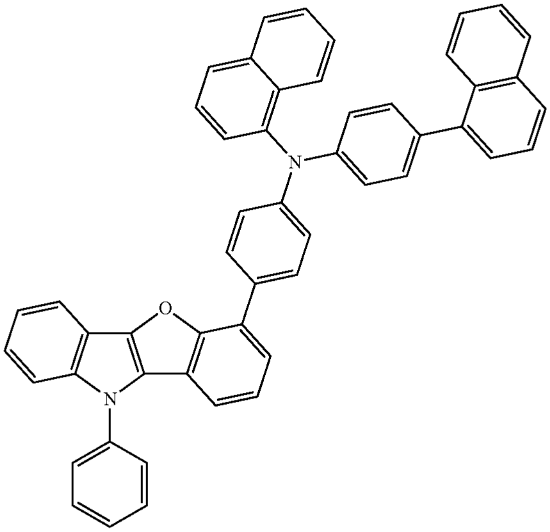

-continued
A70
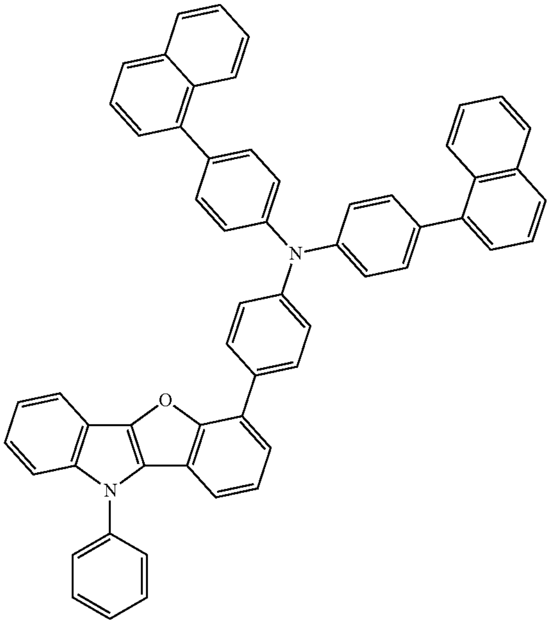
A71
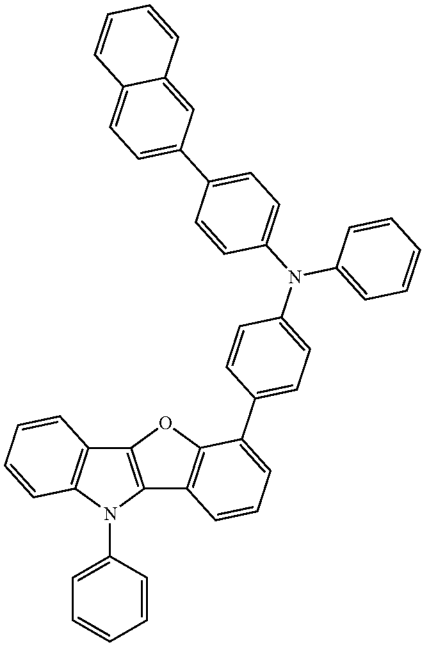
-continued
A72
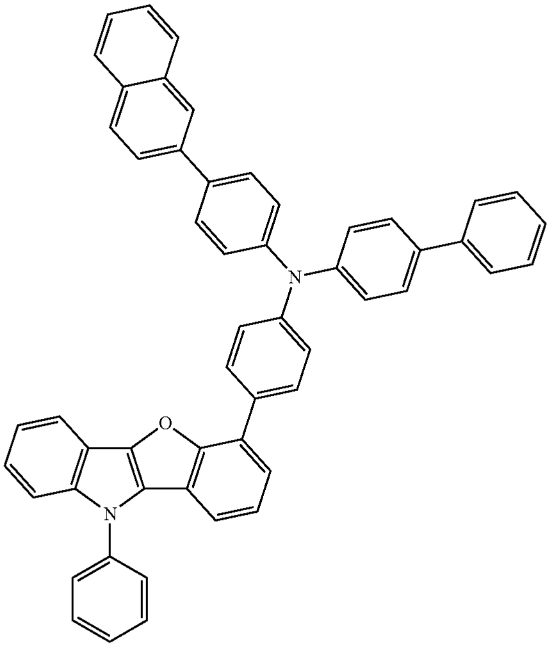
A73
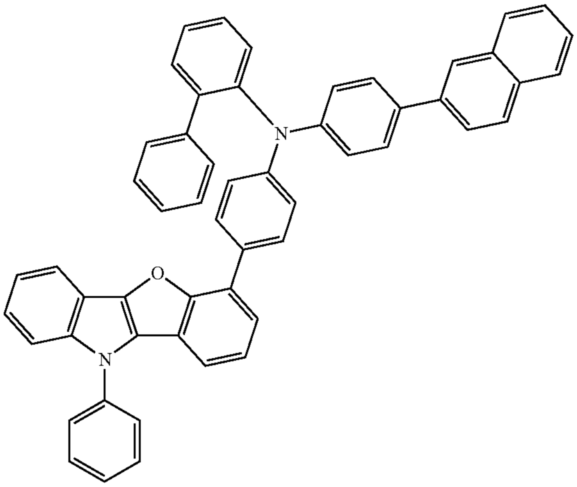

-continued
A74
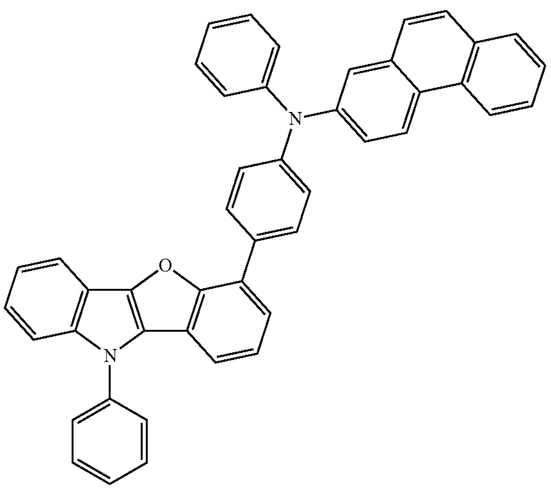
A75
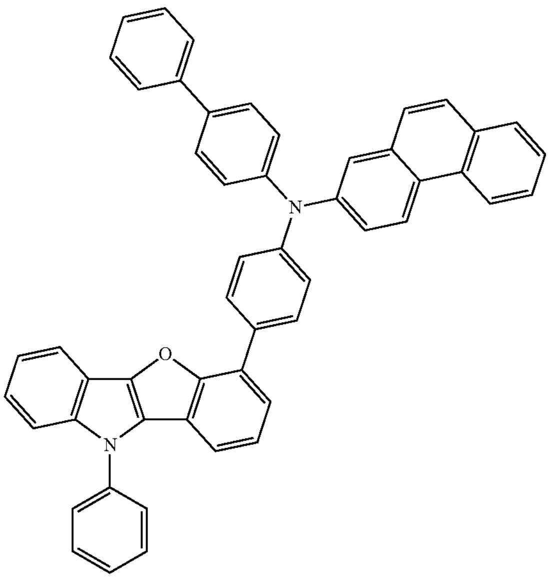
-continued
A76
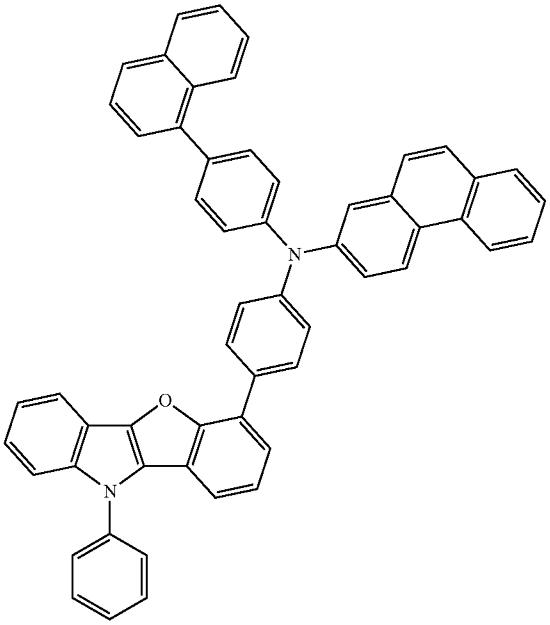
A77
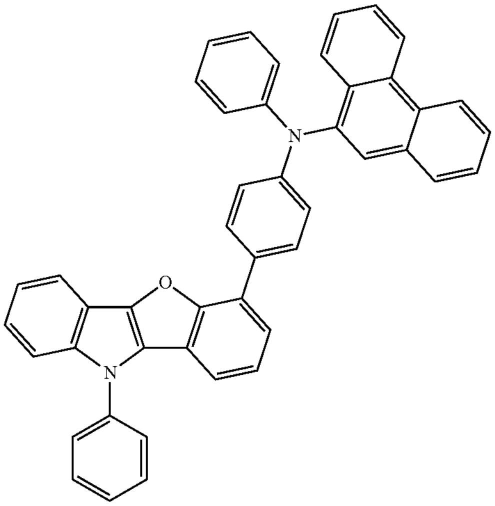

-continued
A78
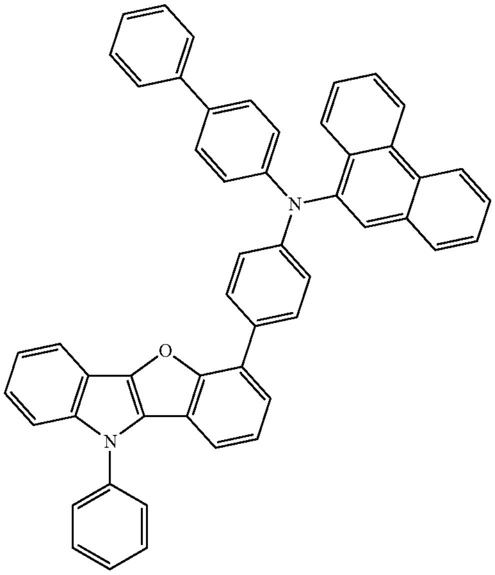
A79
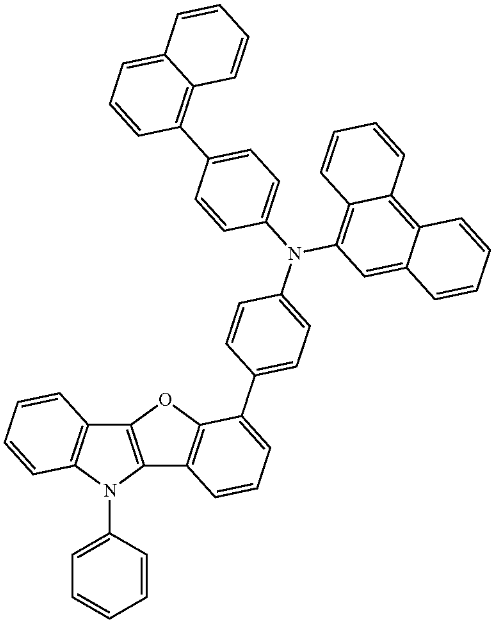
-continued
A81
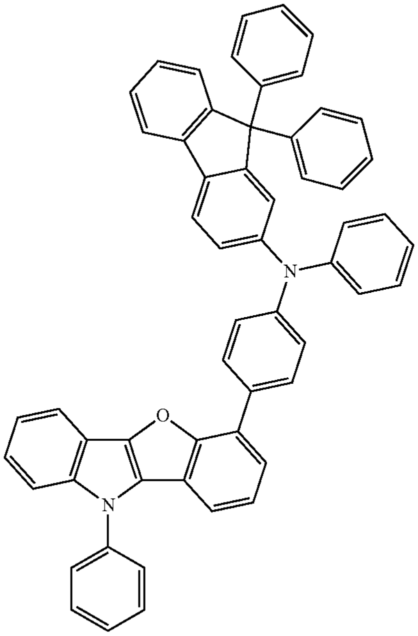
A82
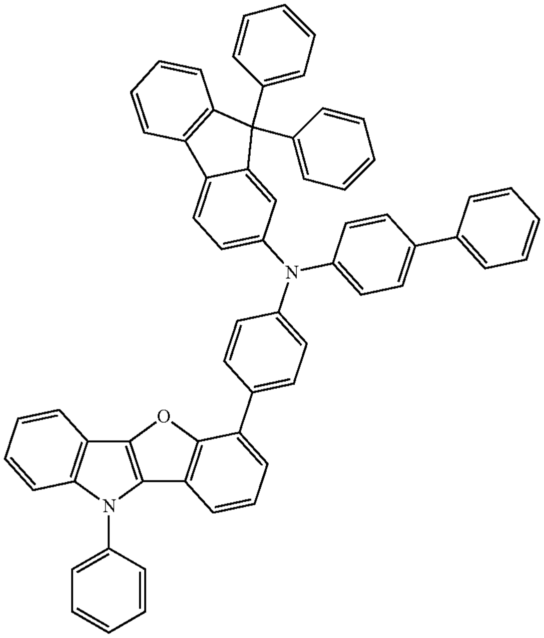

-continued
A83
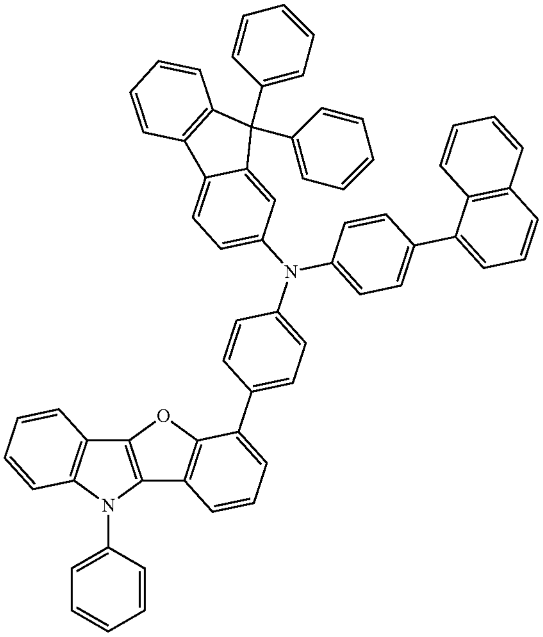
A84
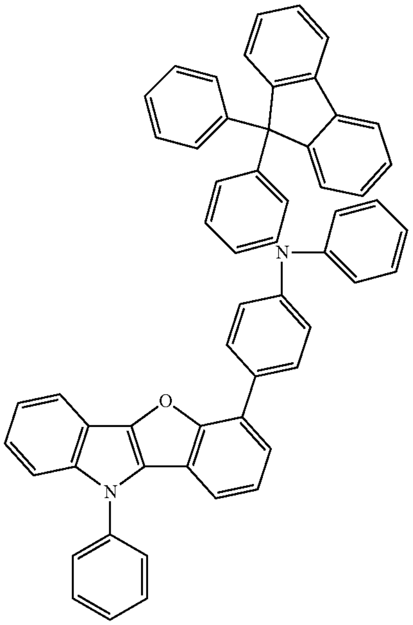
-continued
A85
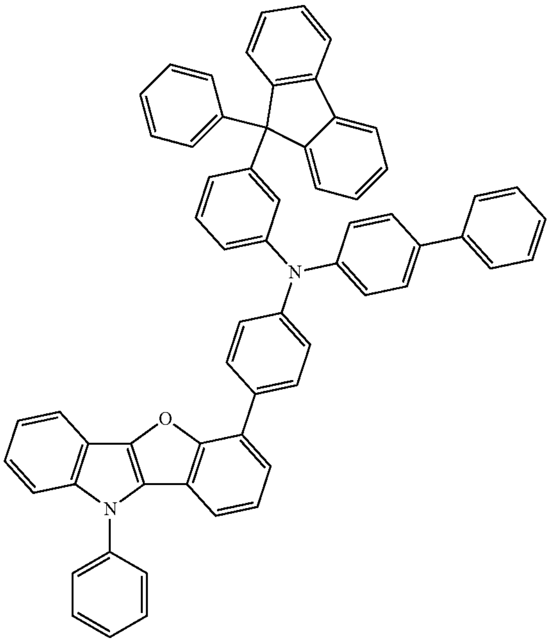
A86
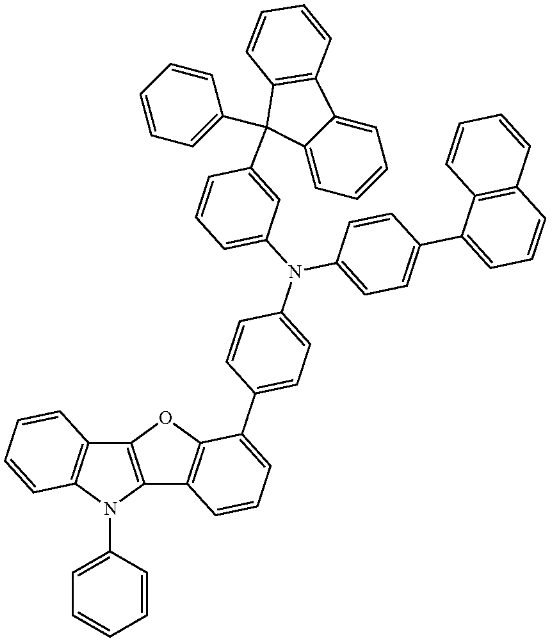

-continued
A87
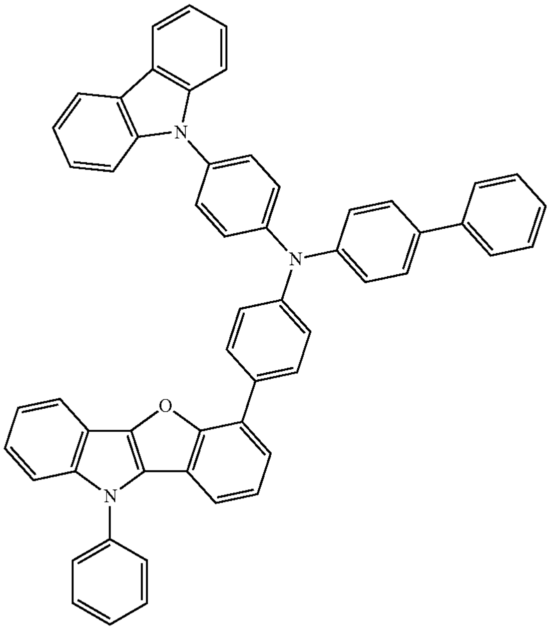
-continued
A89
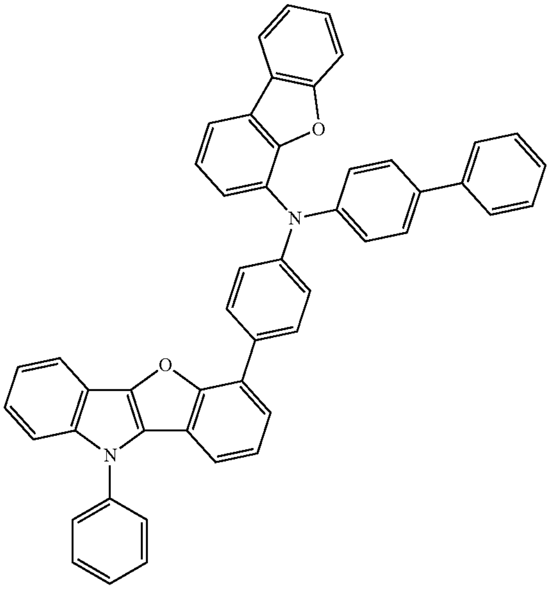
A88
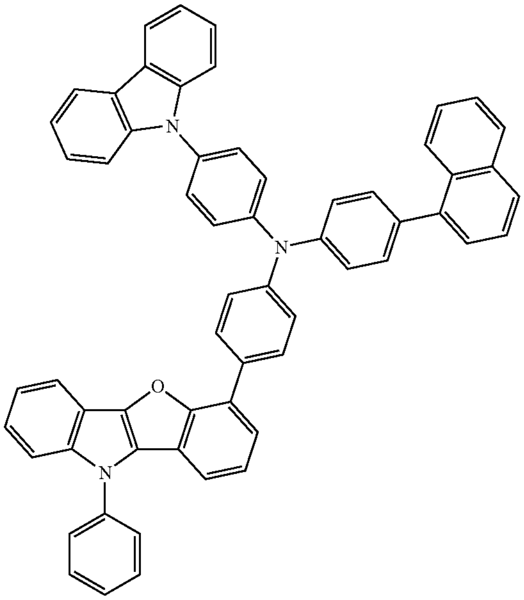
A90
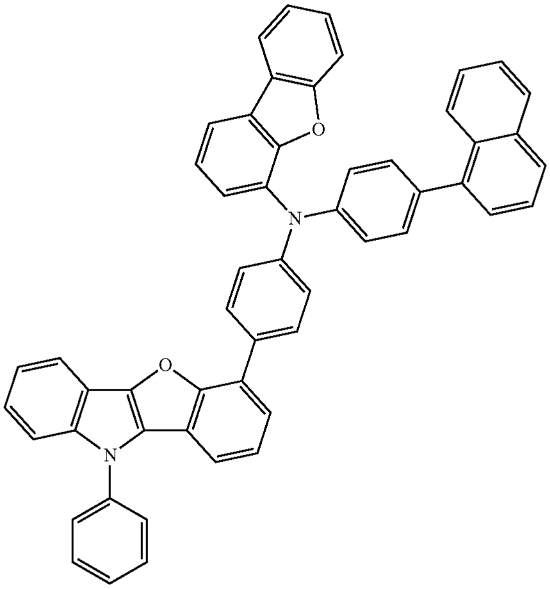

-continued
A91
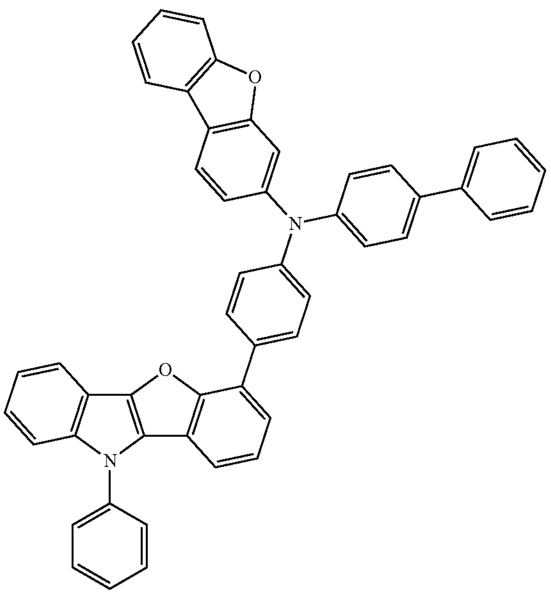
A92
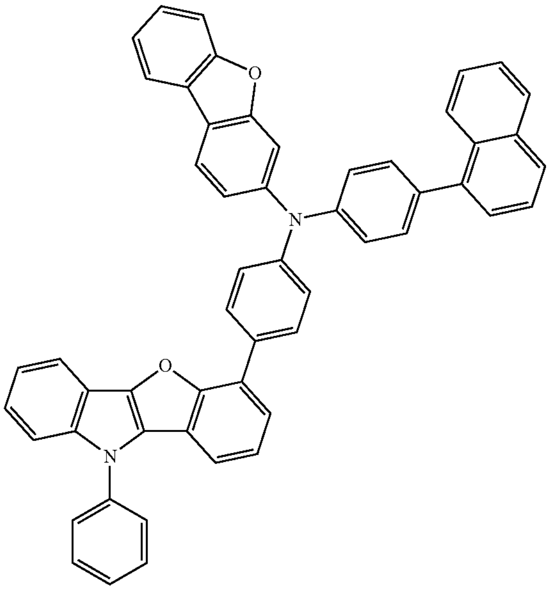
-continued
A93
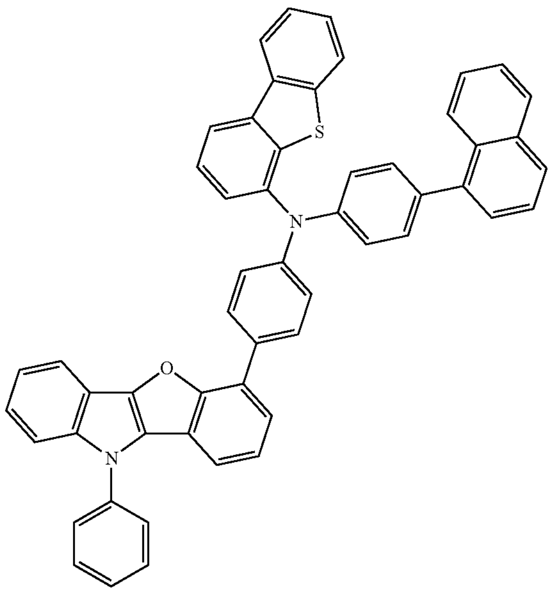
A94
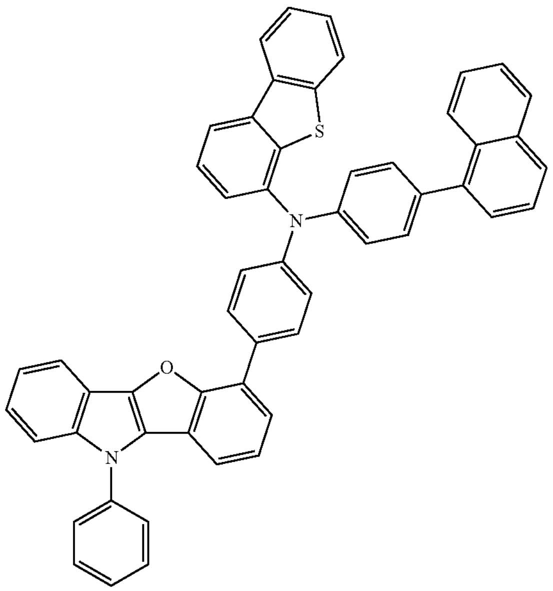

-continued
A95
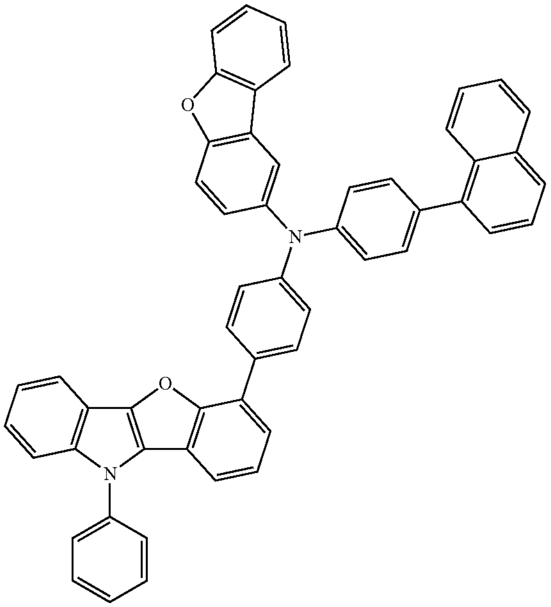
A96
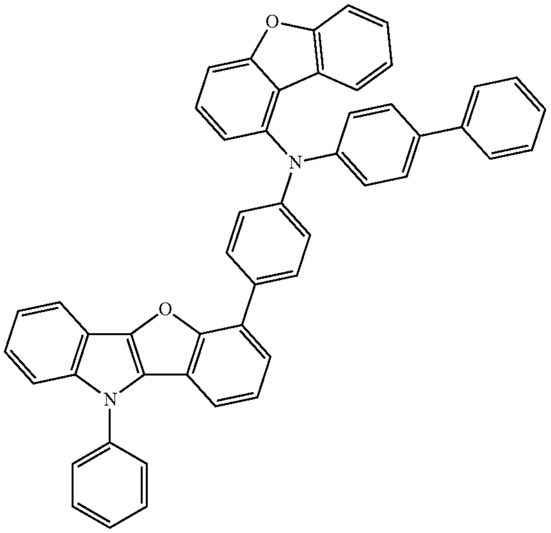
-continued
A97
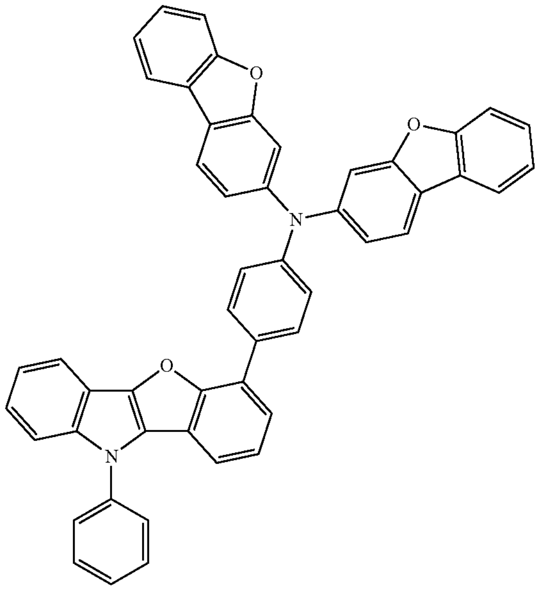
A98
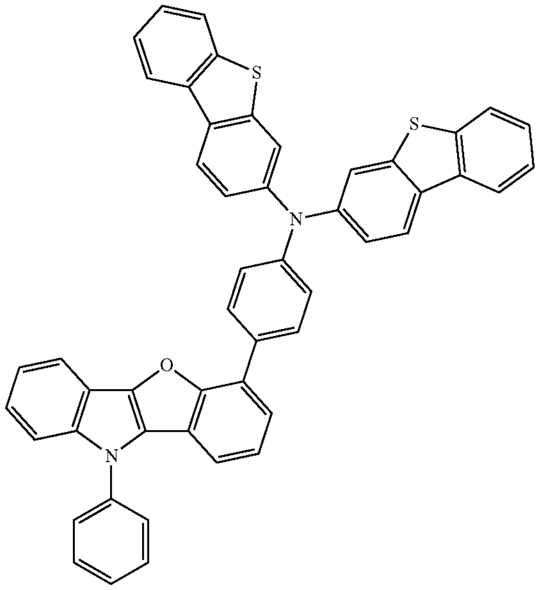
A99
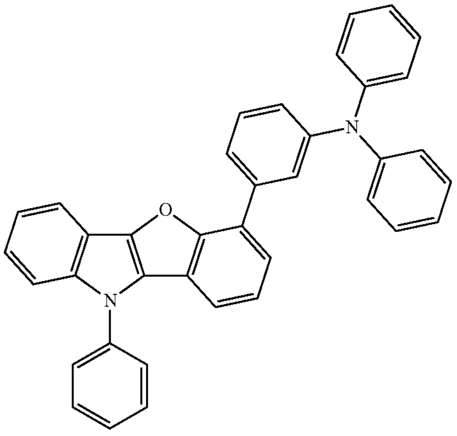

-continued
A100
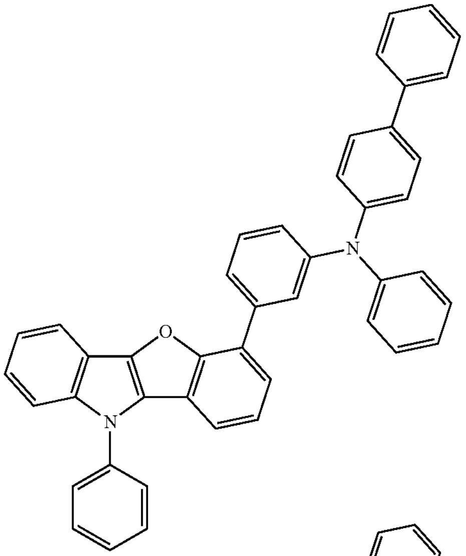
A101
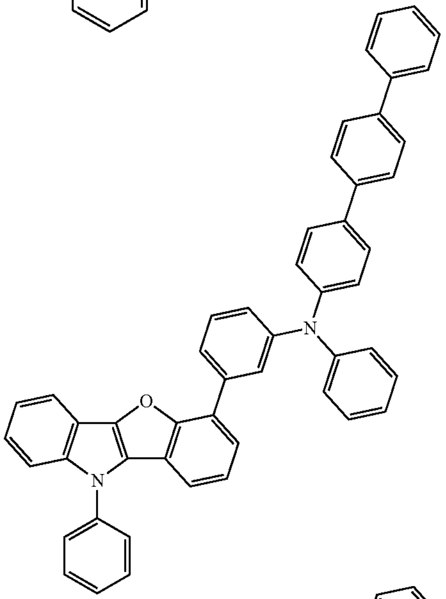
A103
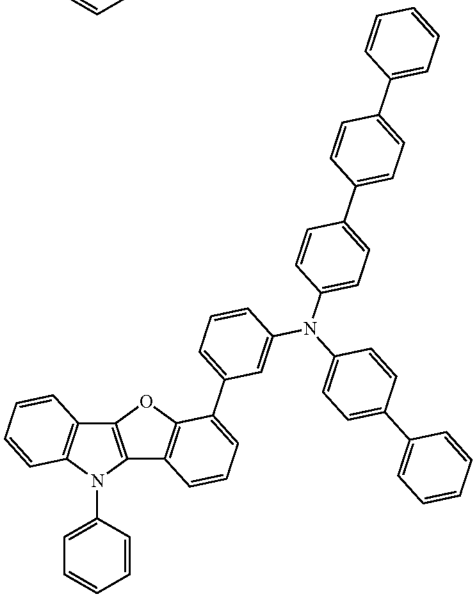
-continued
A104
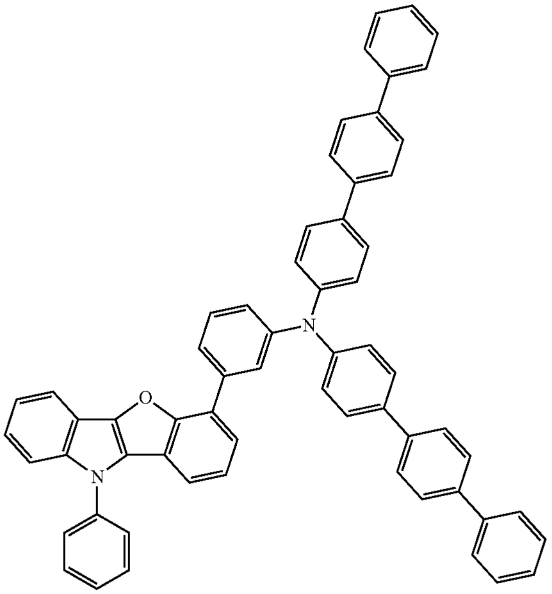
A105
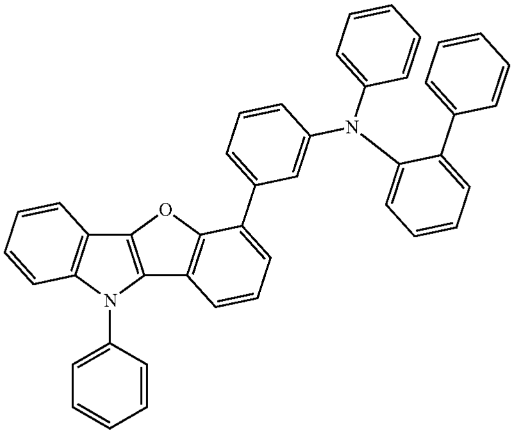
A106
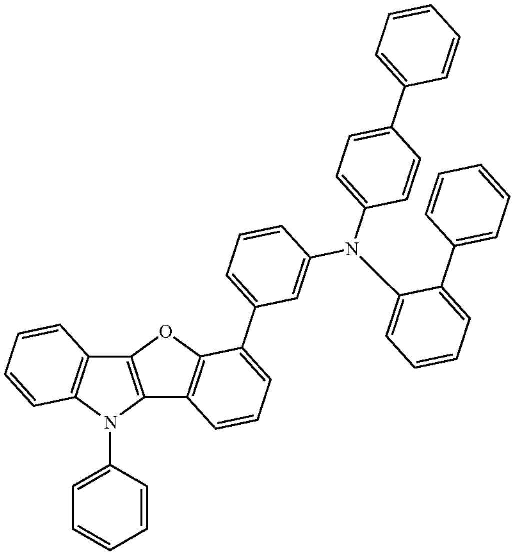

-continued
A107
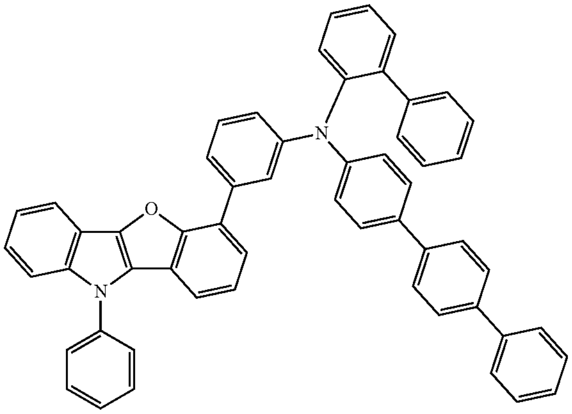
A108
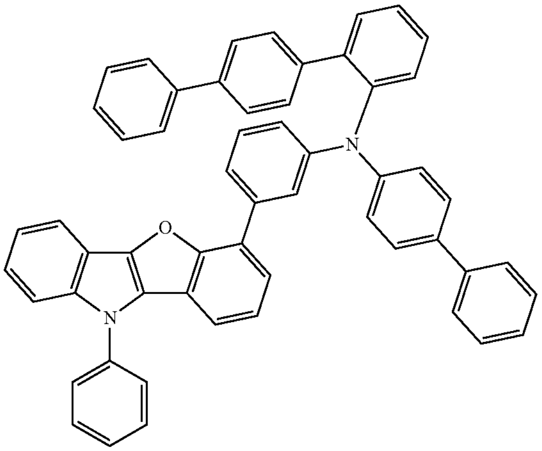
A109
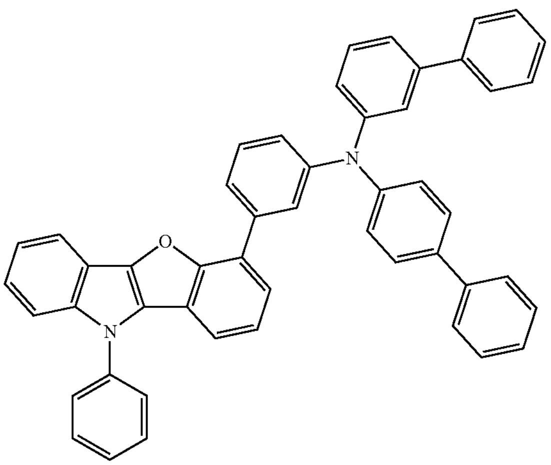
-continued
A110
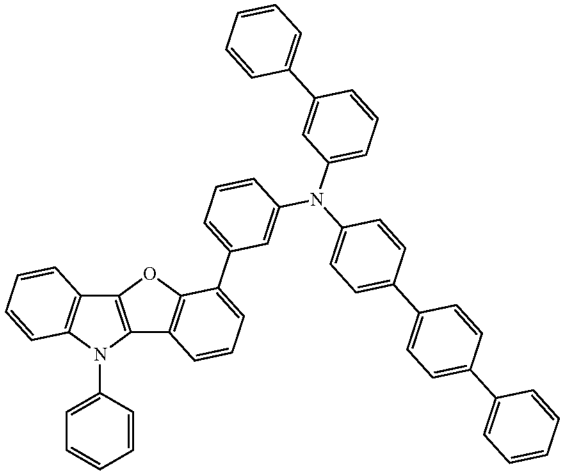
A111
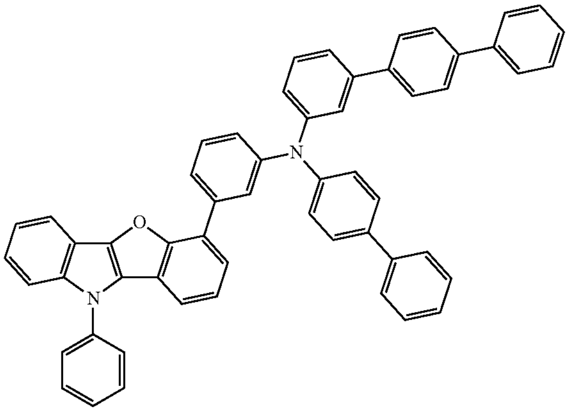
A112
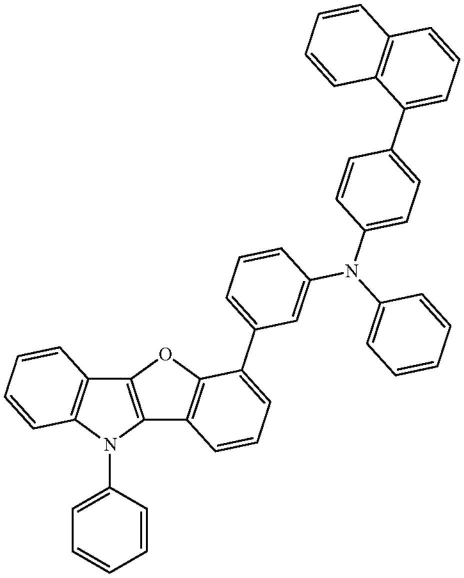

-continued
A113
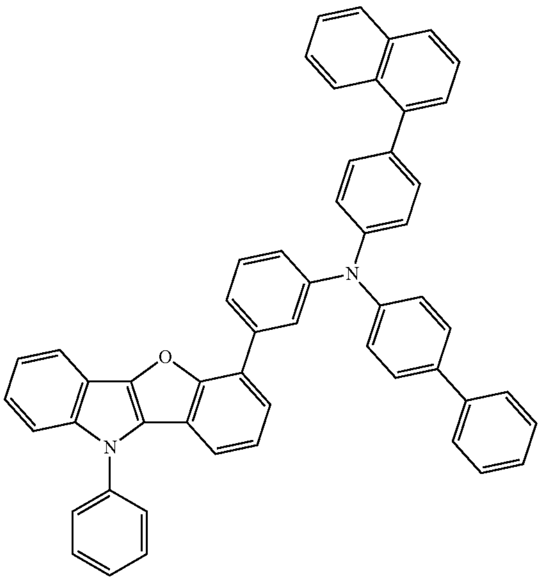
A114
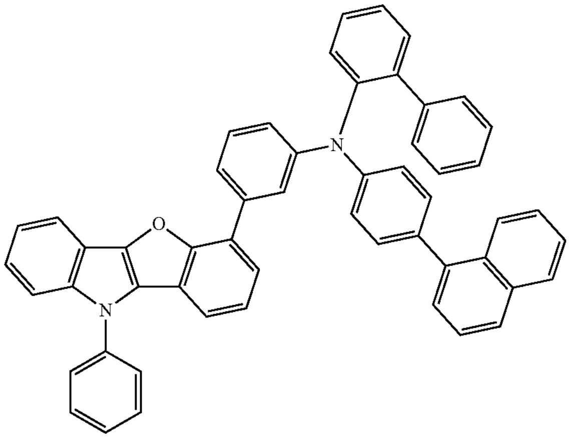
A115
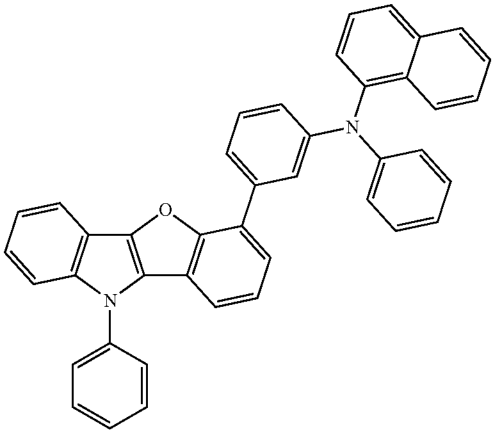
-continued
A116
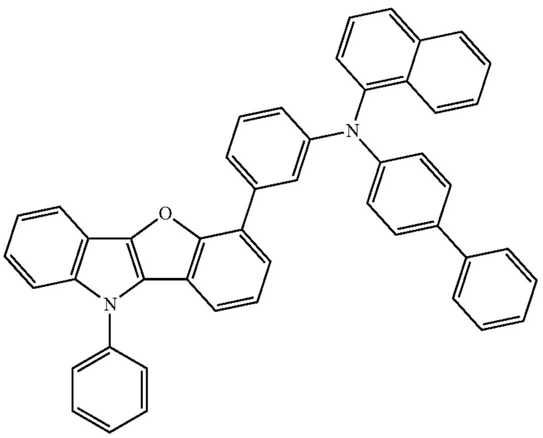
A117
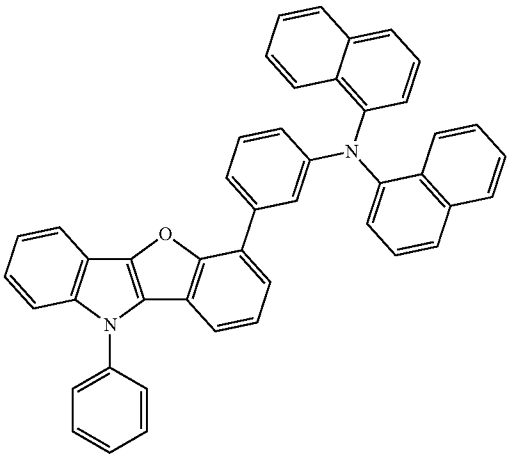
A118
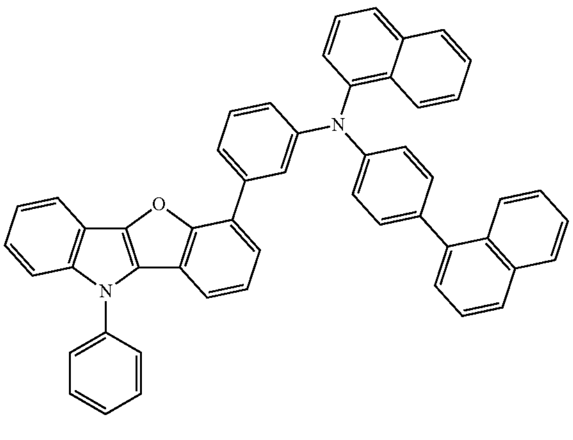

-continued
A119
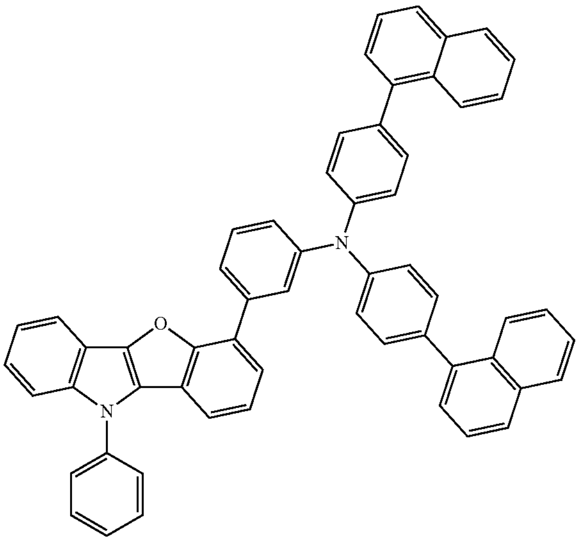
A120
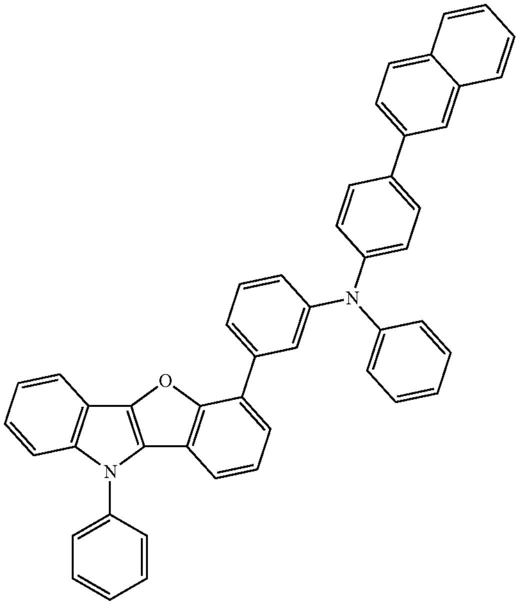
-continued
A121
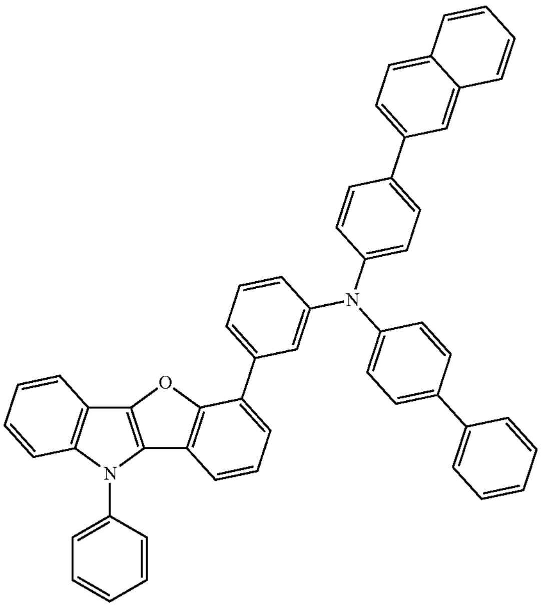
A122
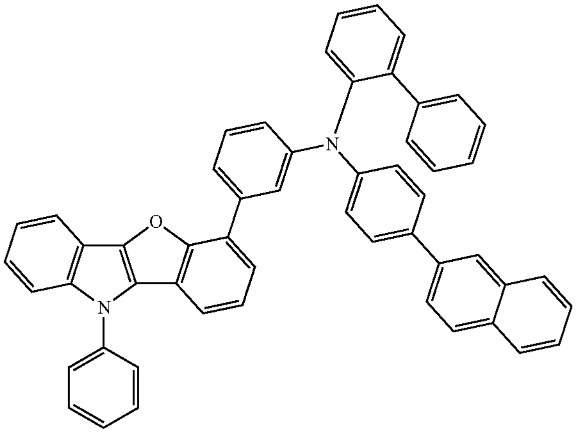
A123
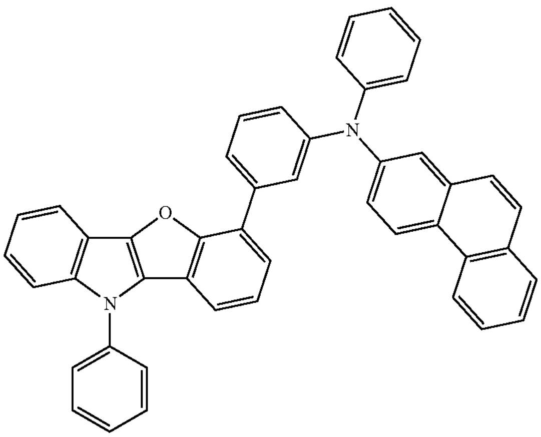

-continued
A124
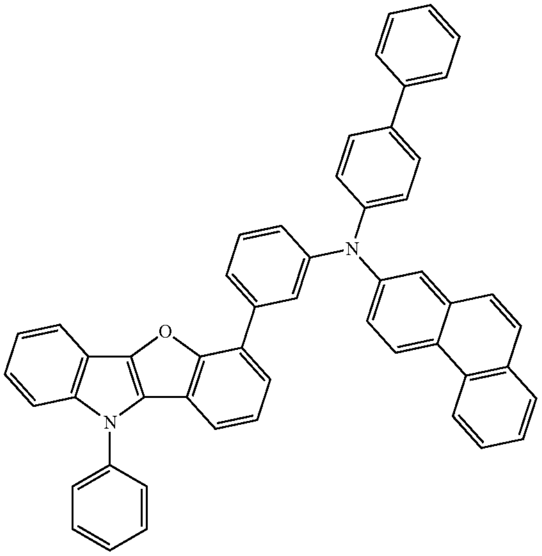
A125
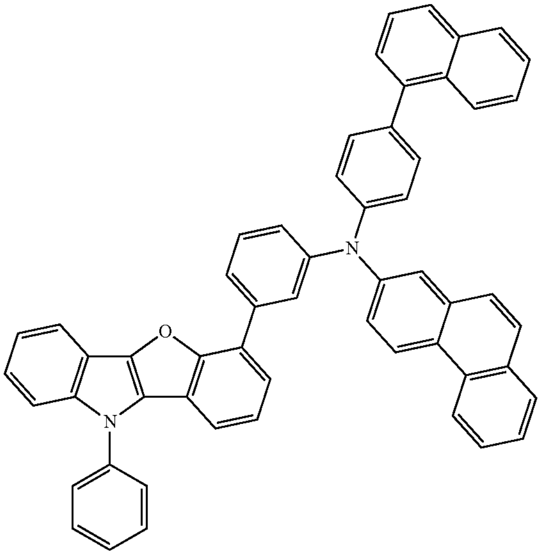
A126
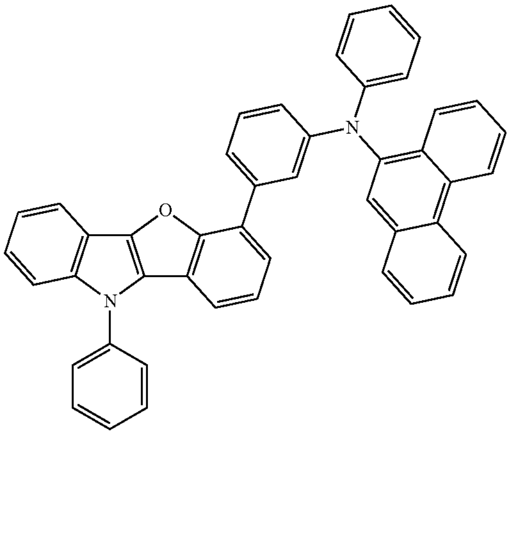
-continued
A127
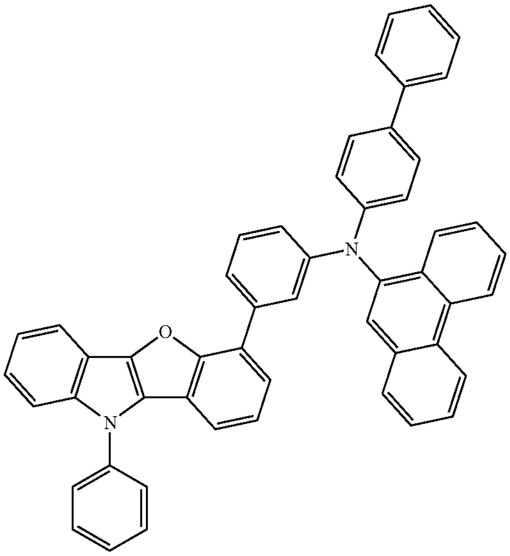
A128
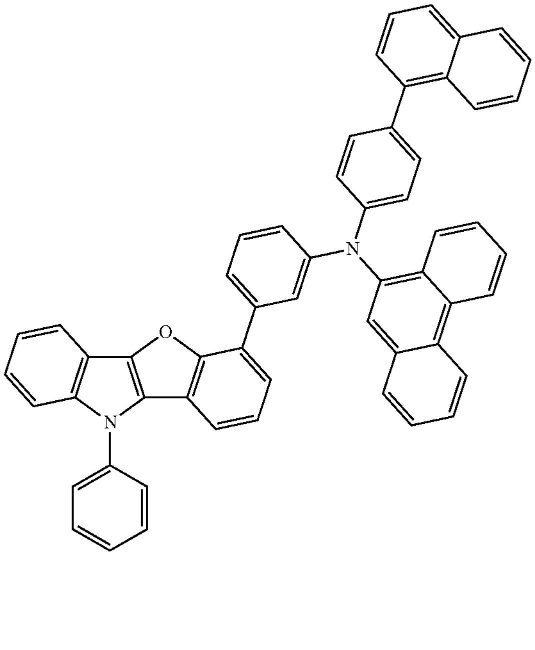

-continued
A130
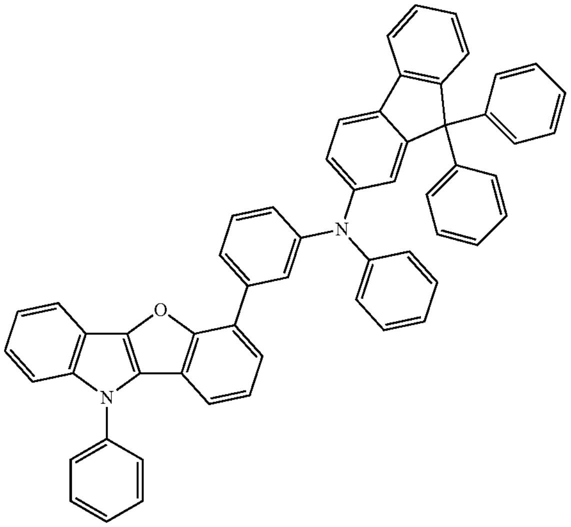
A131
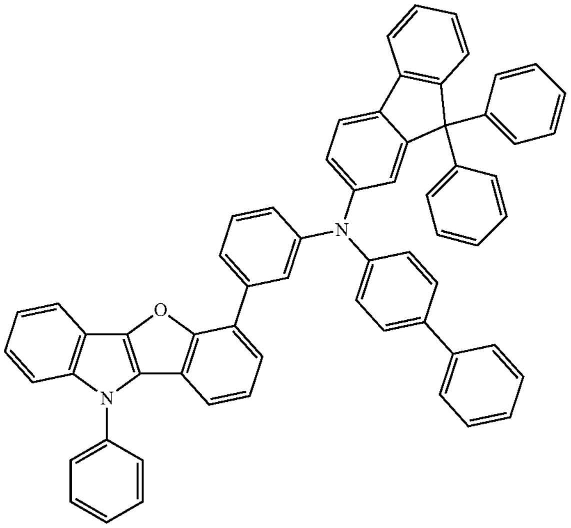
A132
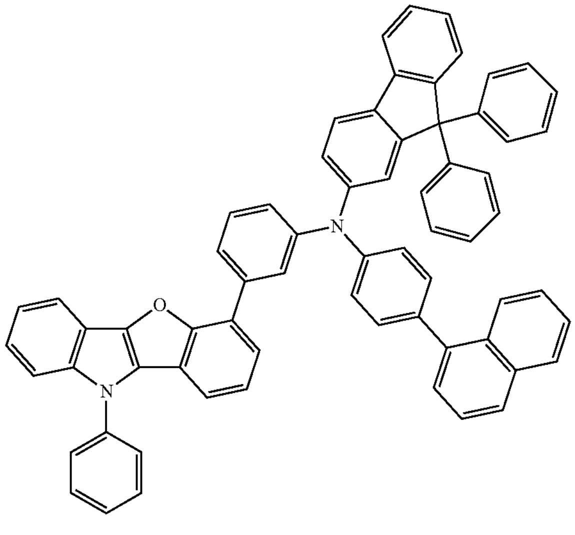
-continued
A133
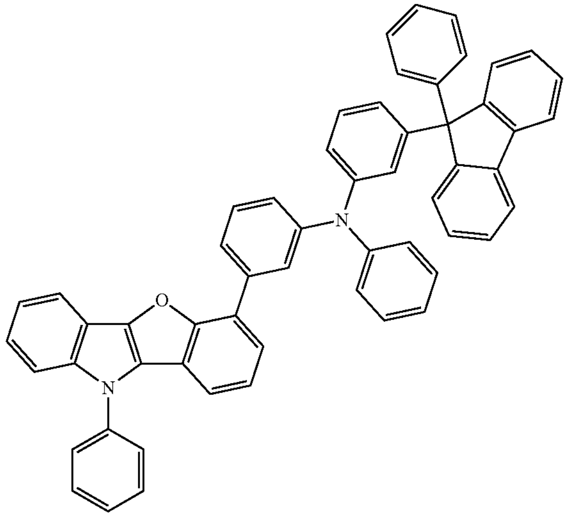
A134
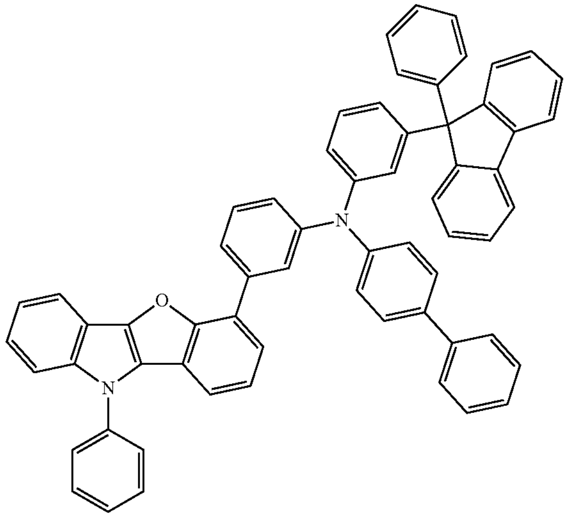
A135
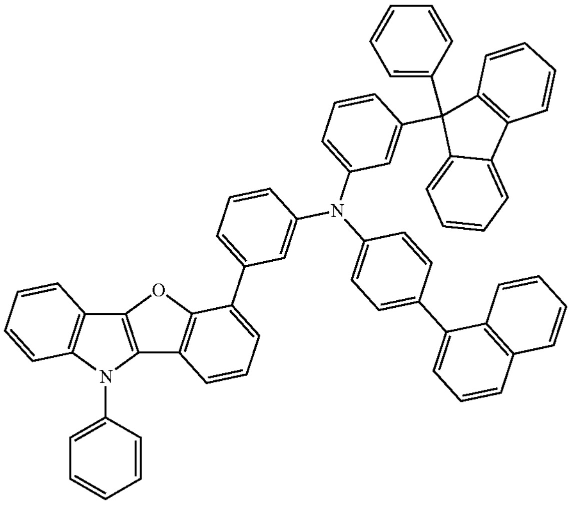

-continued
A136
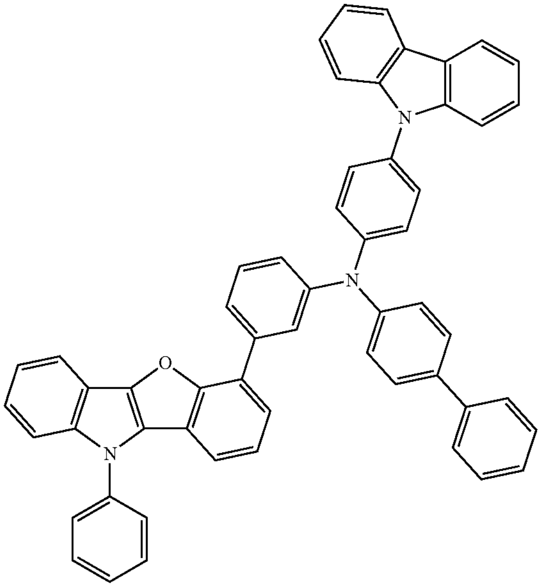
A137
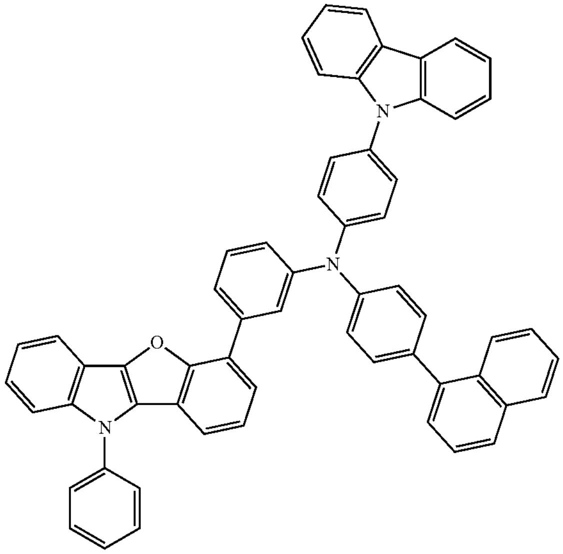
A138
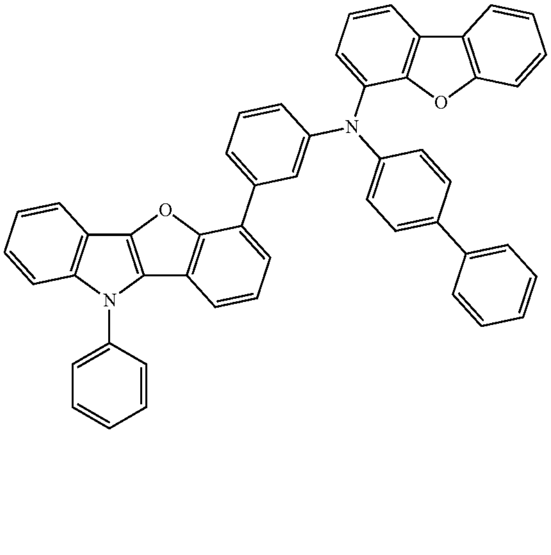
-continued
A139
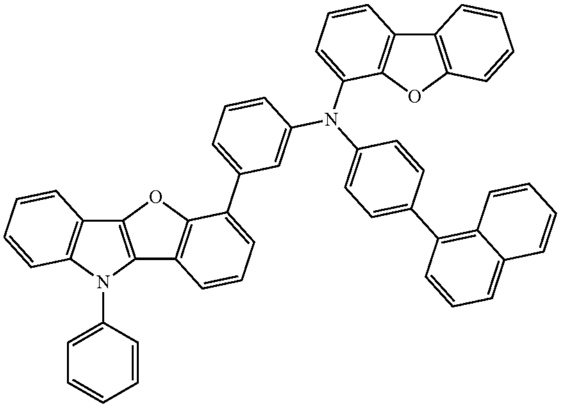
A140
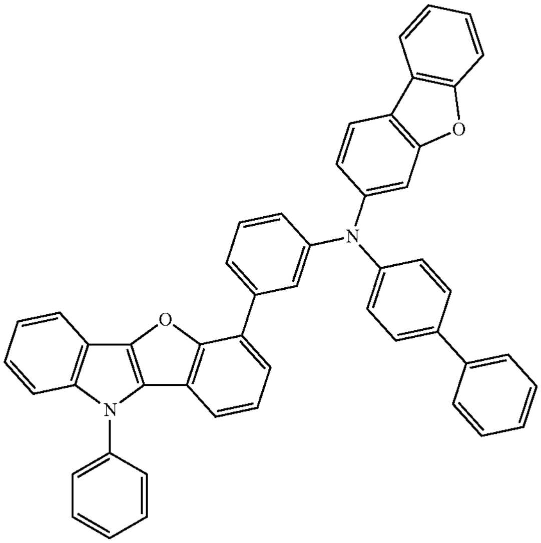
A141
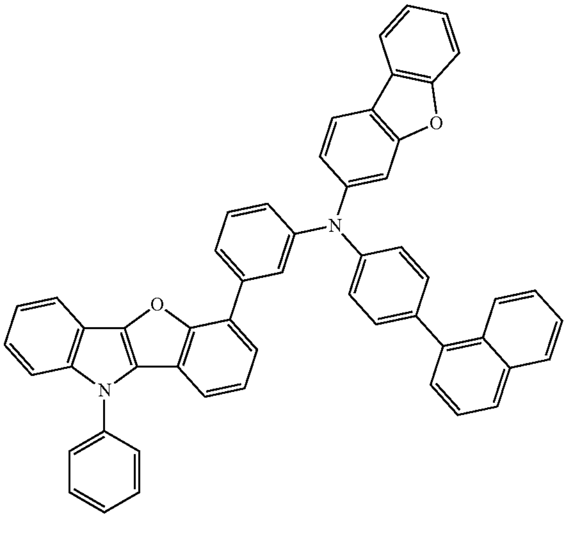

-continued
A142
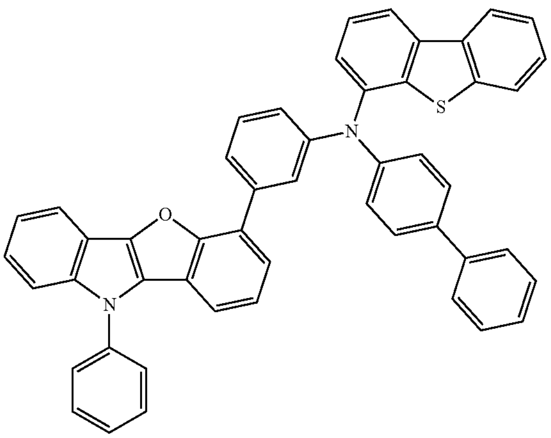
A143
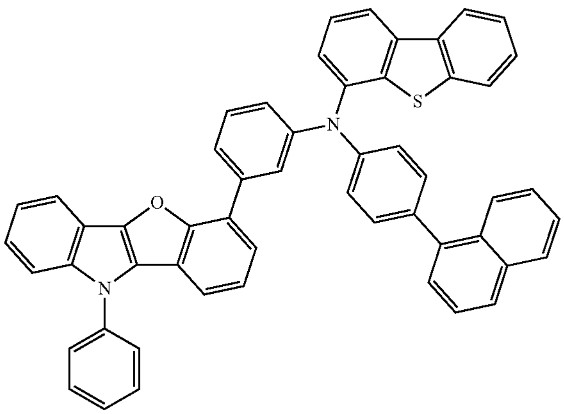
A144
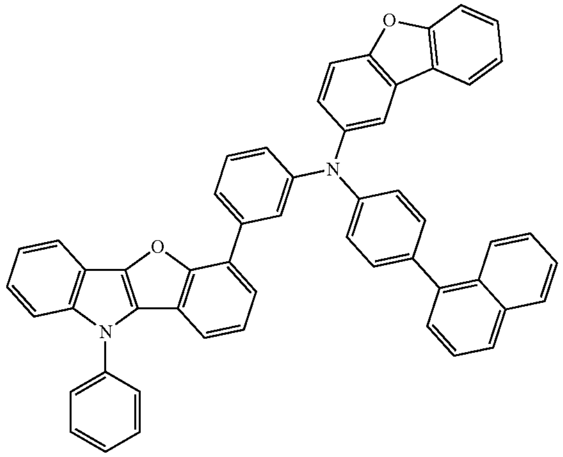
-continued
A145
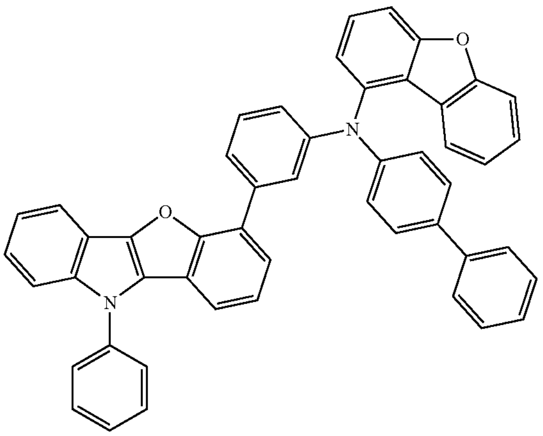
A146
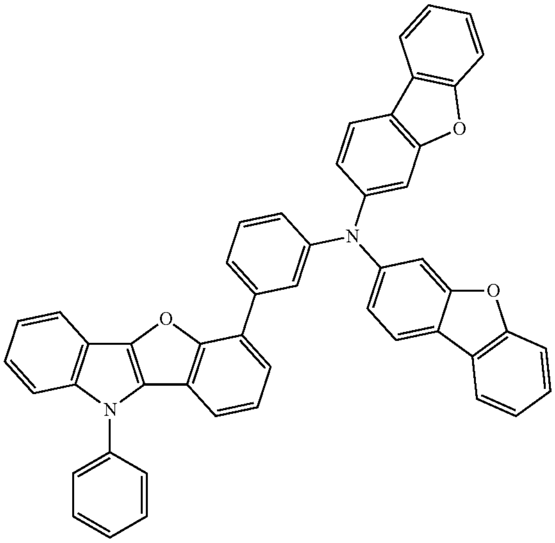
A147
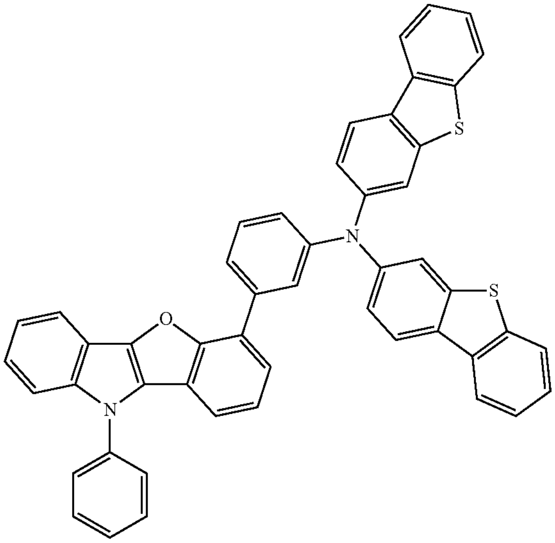

A148
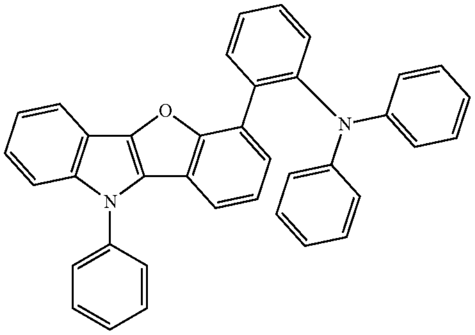
A149
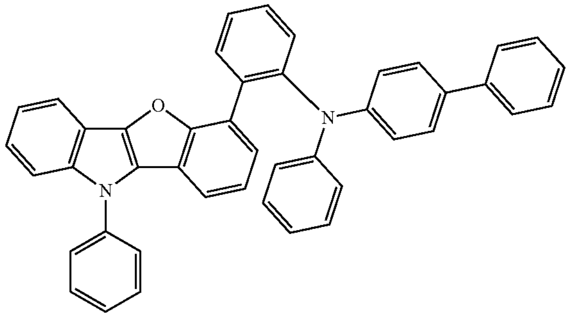
A150
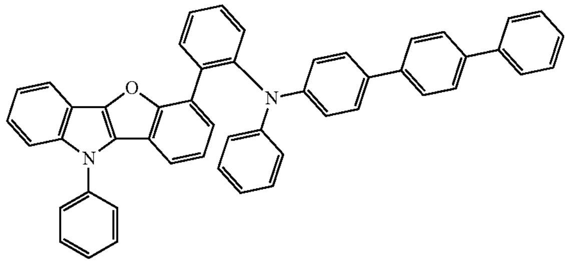
A151
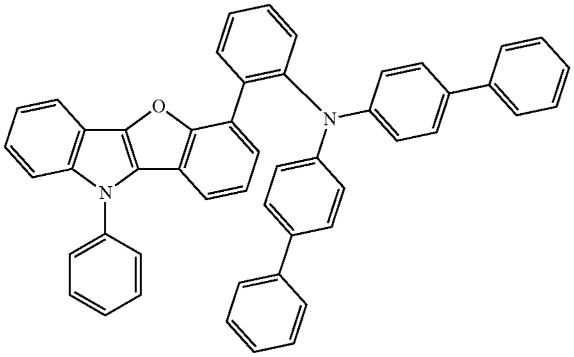
A152
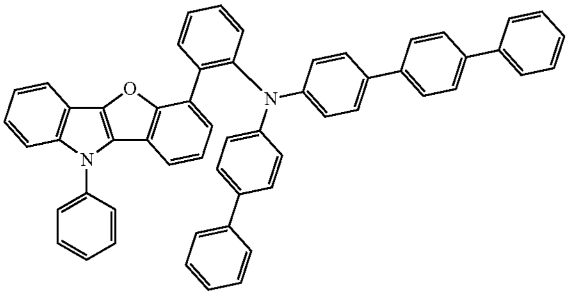
A153
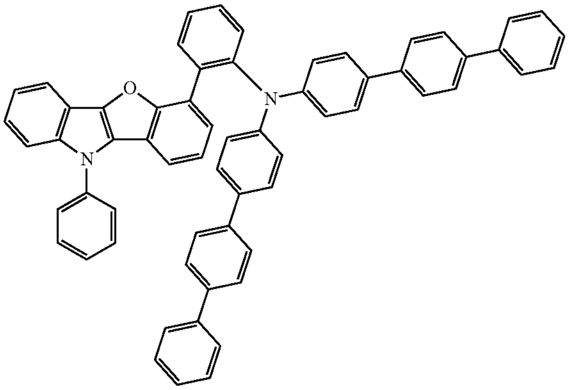
A154
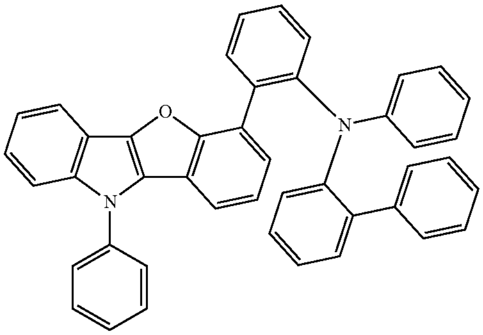
A155
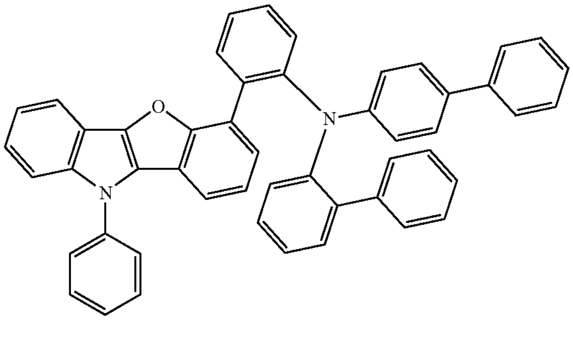

-continued
A156
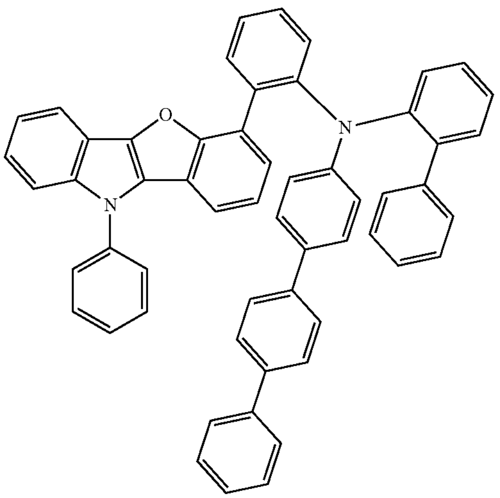
A157
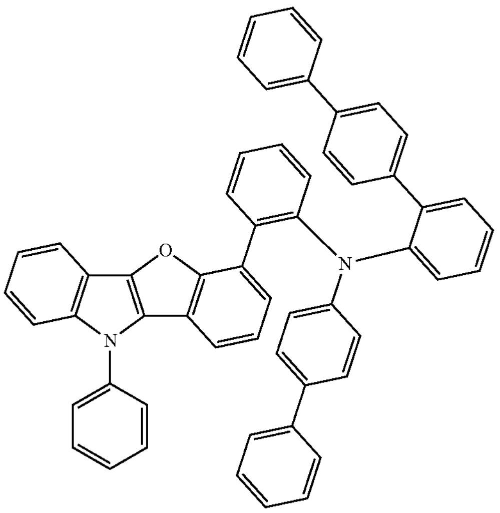
A158
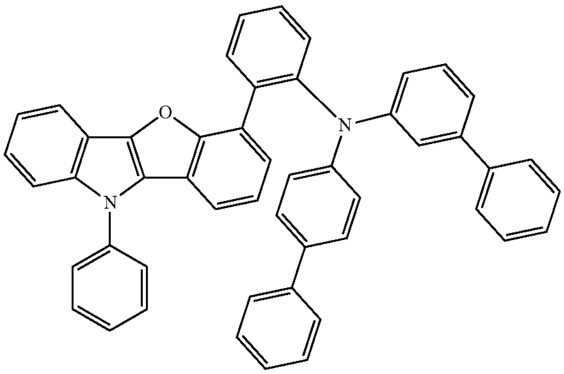
-continued
A159
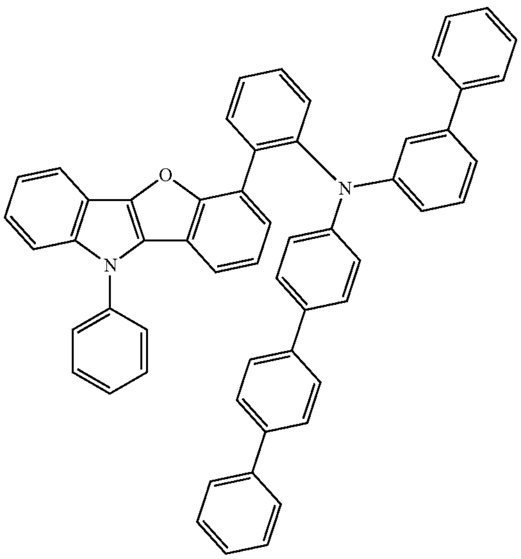
A160
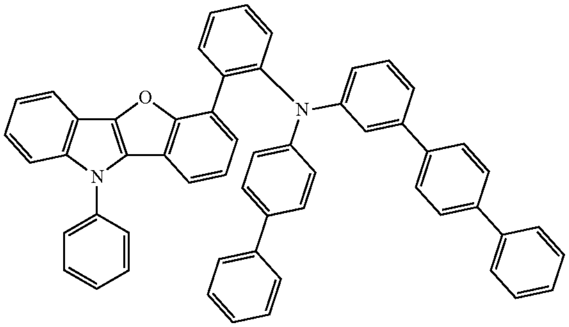
A161
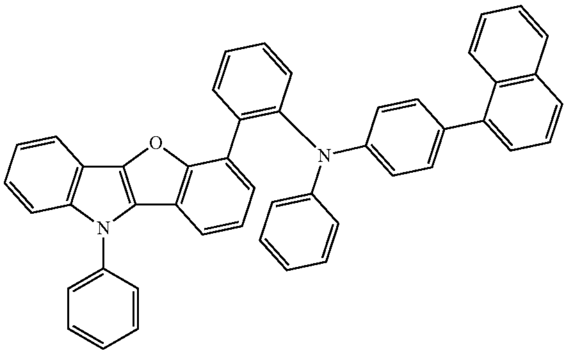

-continued
A162
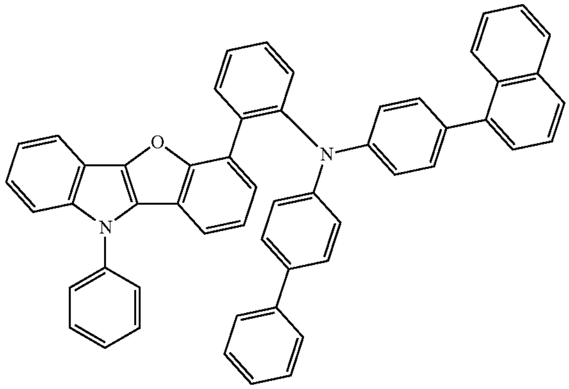
A163
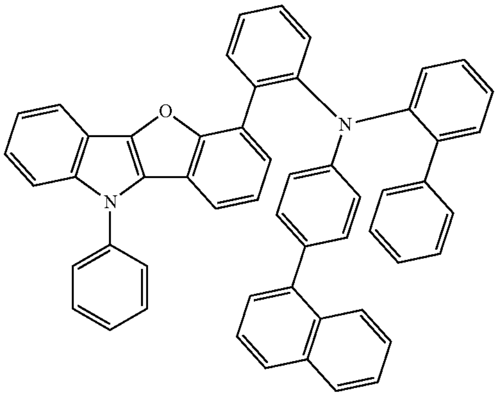
A164
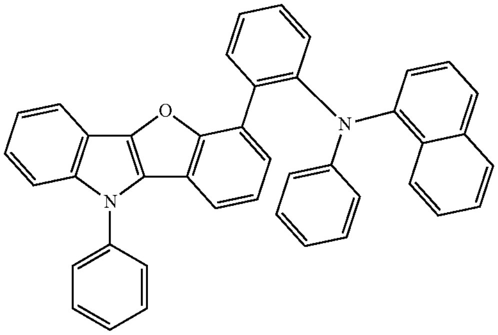
A165
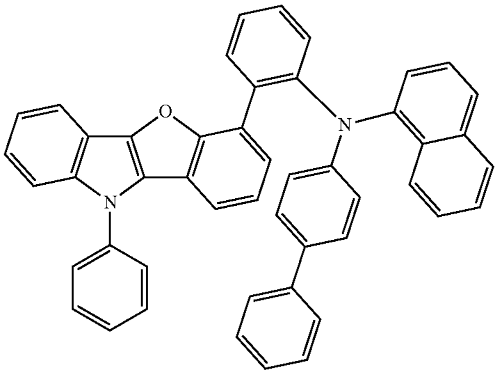
-continued
A166
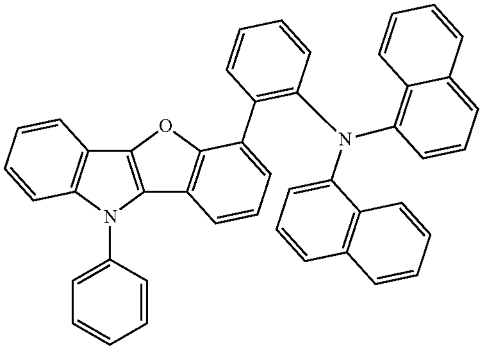
A167
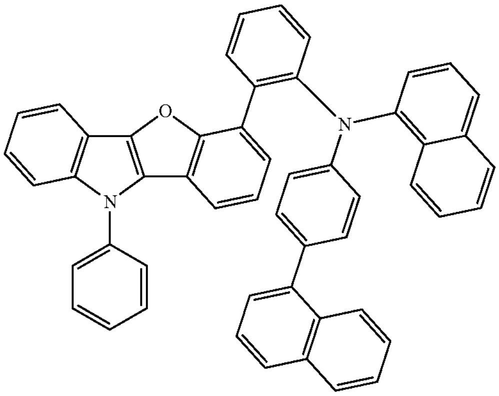
A168
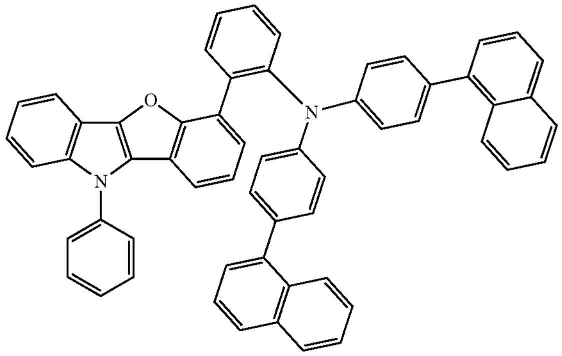
A169
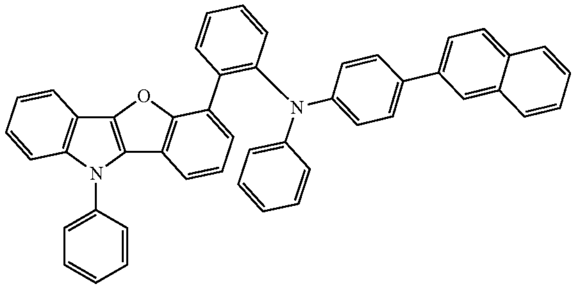

-continued
A170
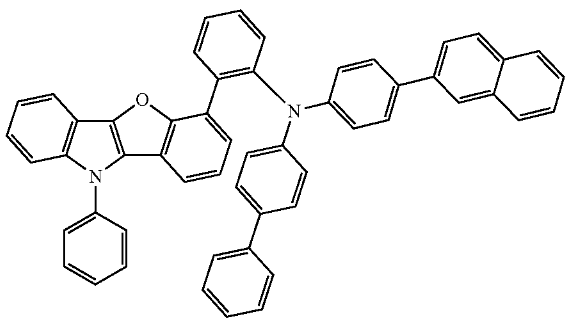
A171
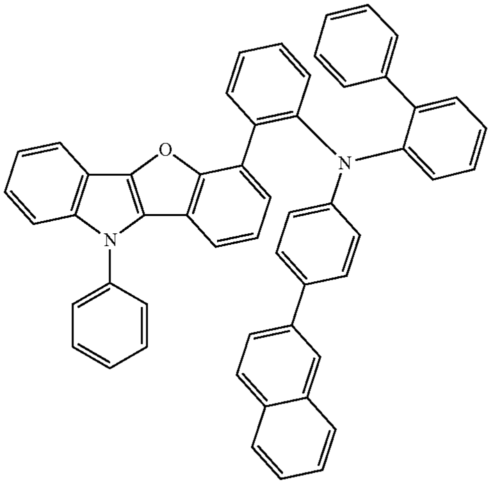
A172
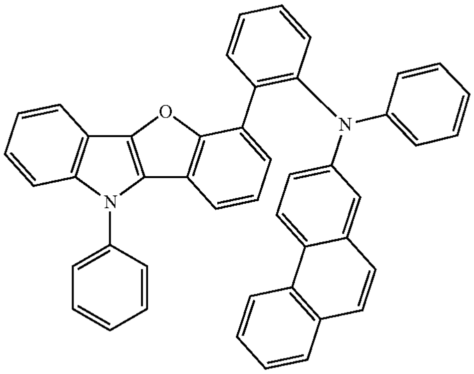
A173
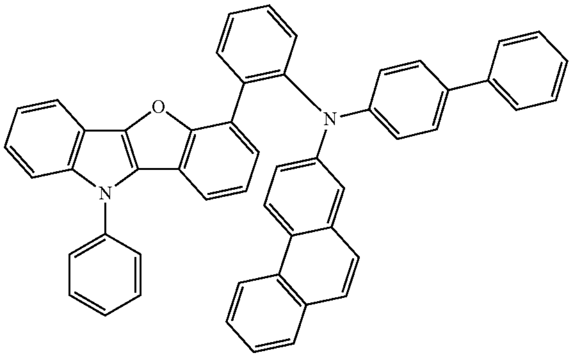
-continued
A174
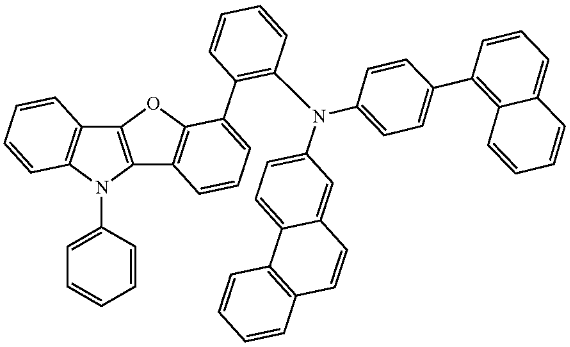
A175
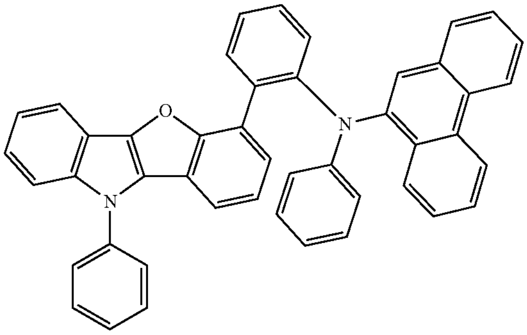
A176
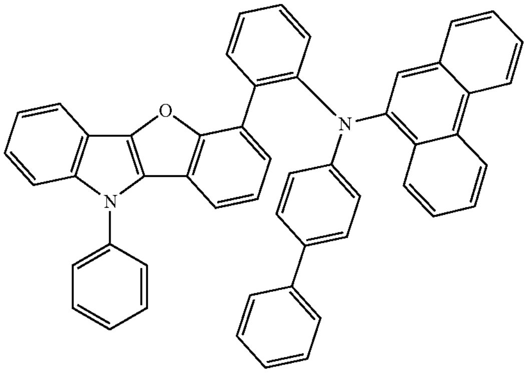
A177
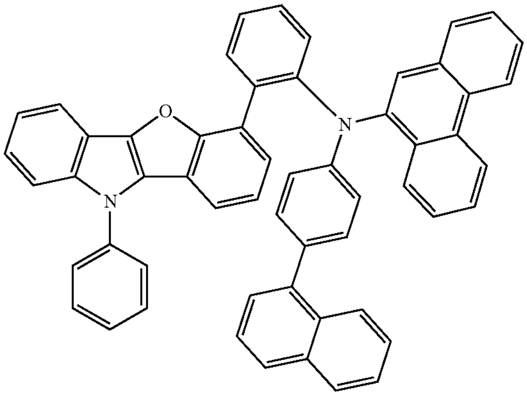

-continued
A179
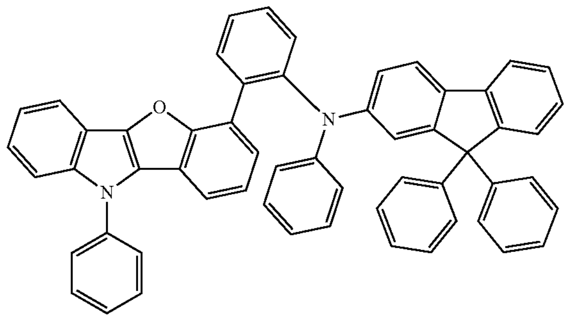
A180
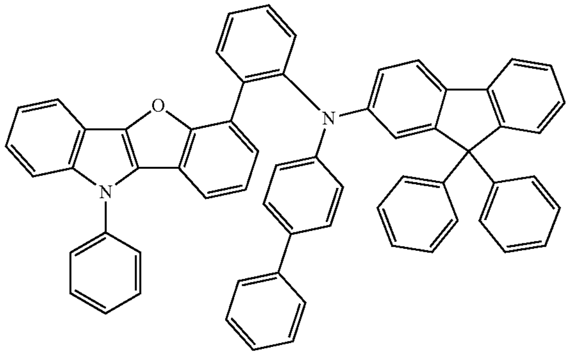
A181
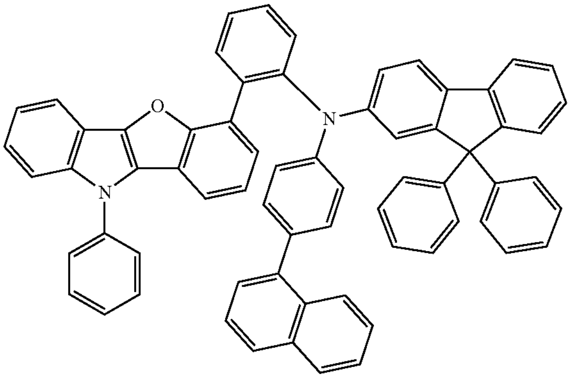
A182
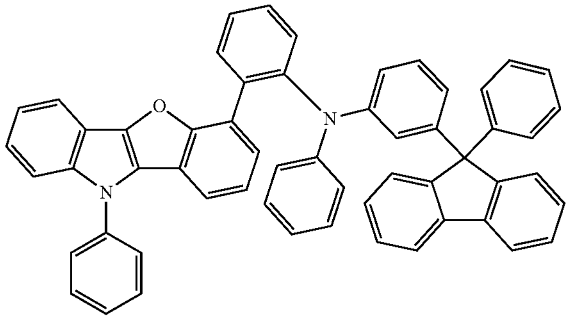
-continued
A183
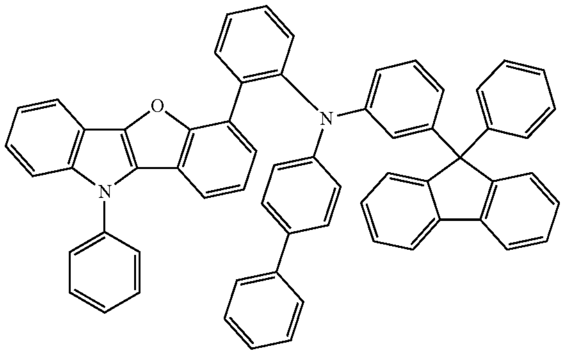
A184
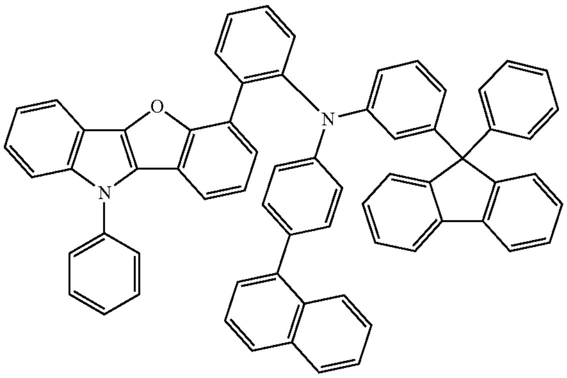
A185
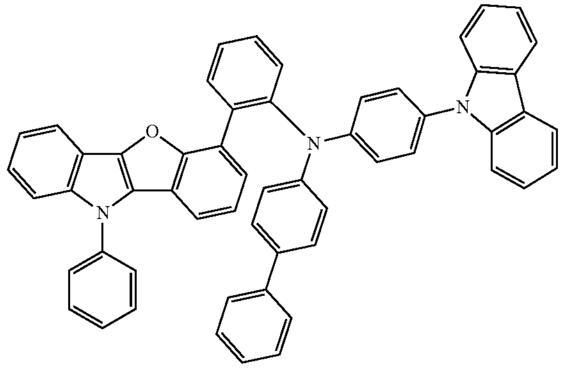
A186
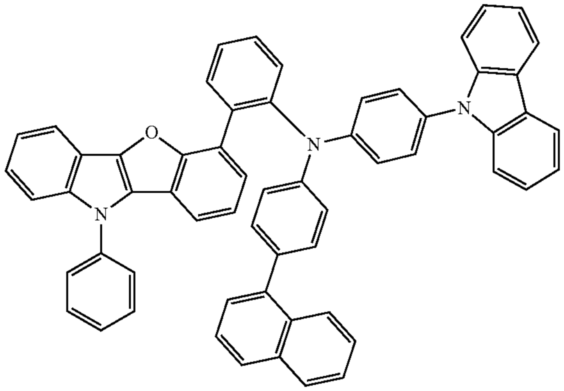

-continued
A187
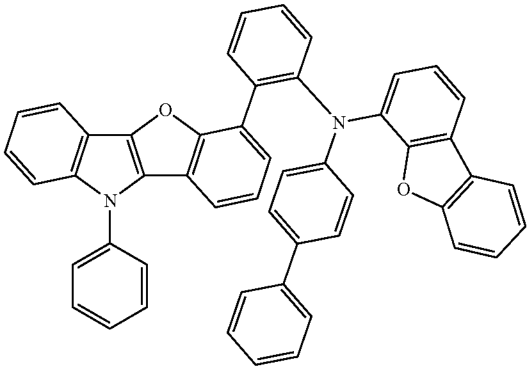
A189
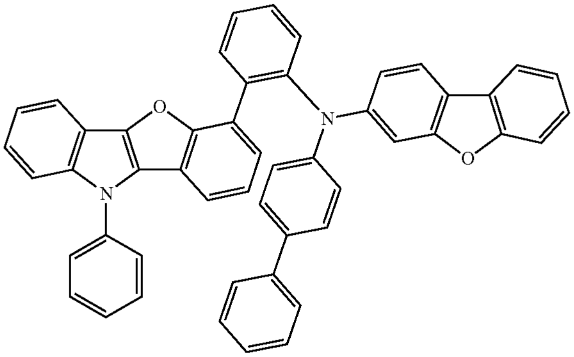
A190
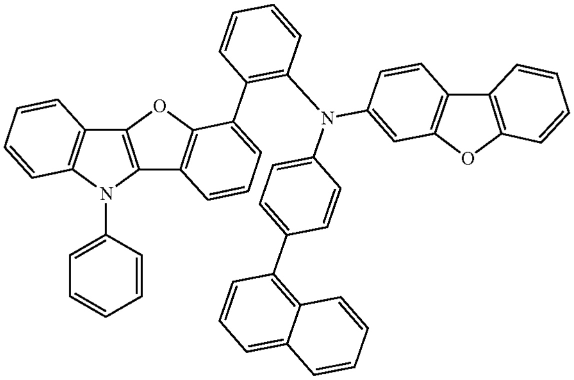
A191
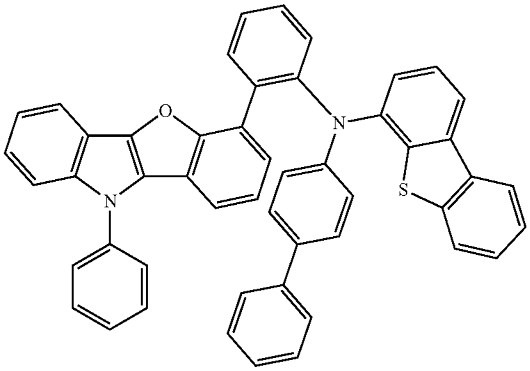
A192
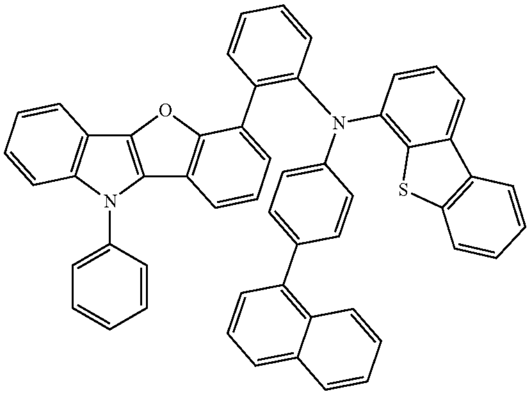
A193
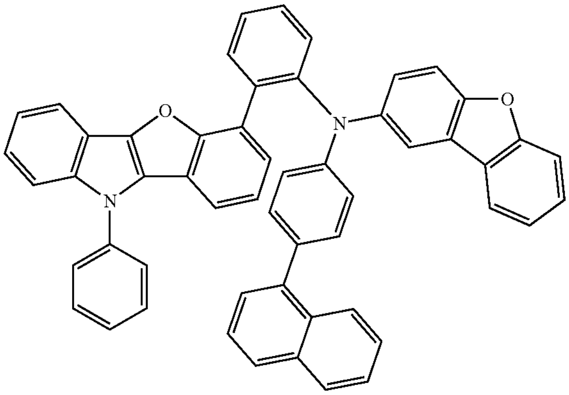
A194
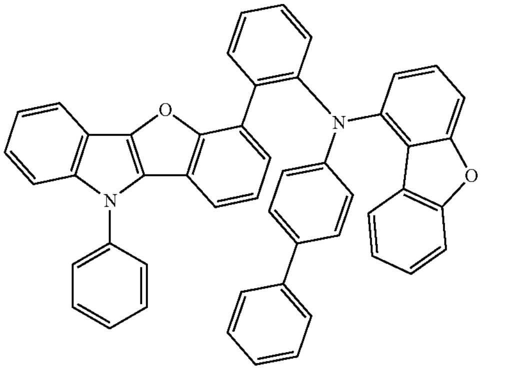
A195
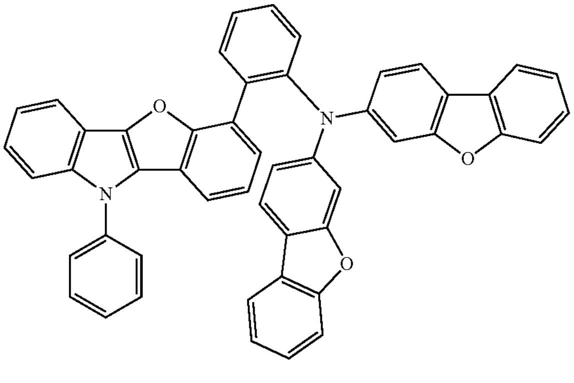

-continued
A196
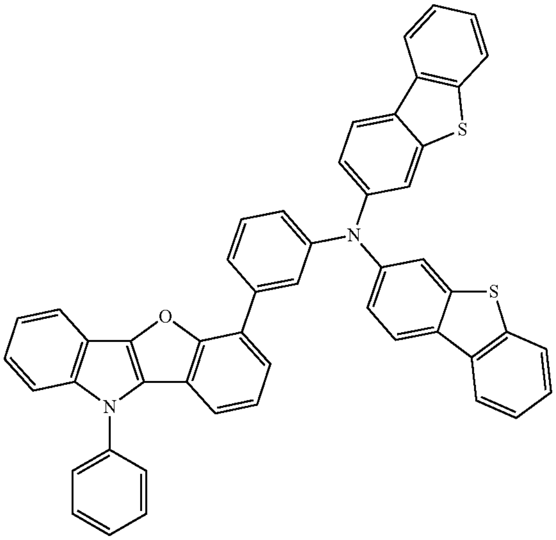
Compound Group 2
B1
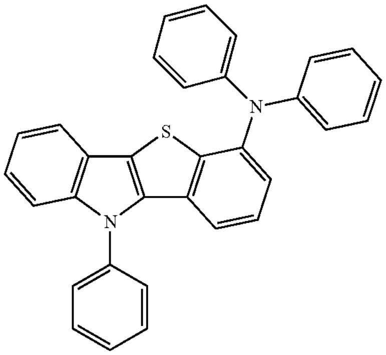
B2
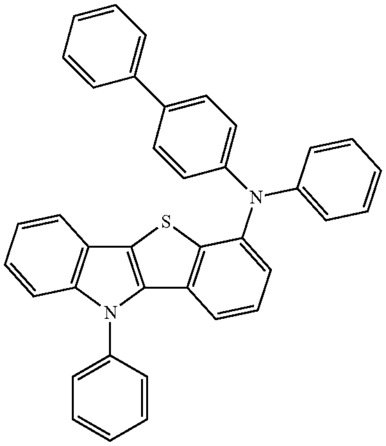
-continued
B3
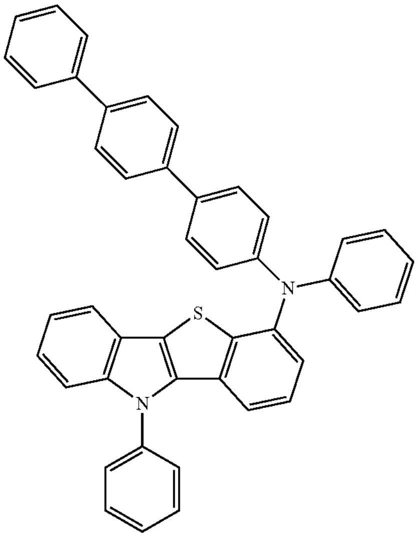
B4
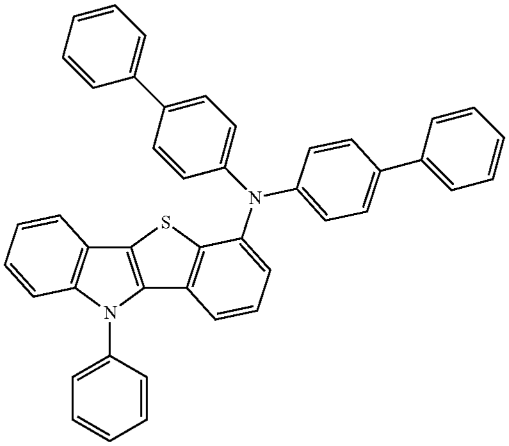
B5
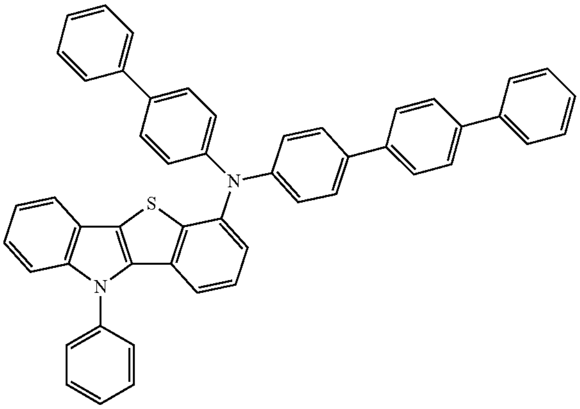

-continued
B6
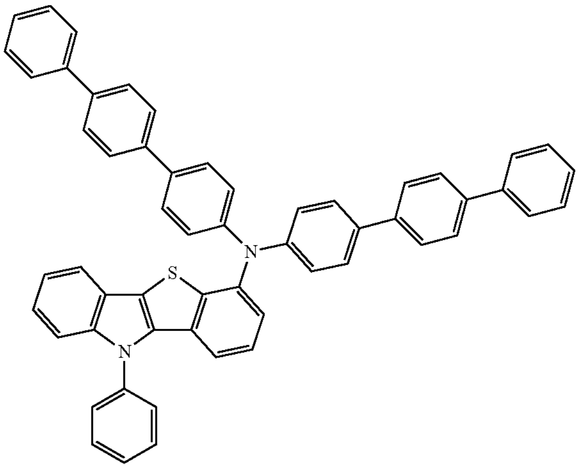
B7
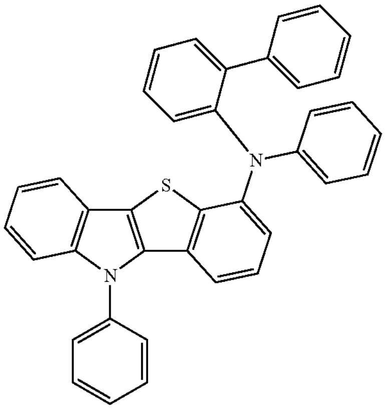
B8
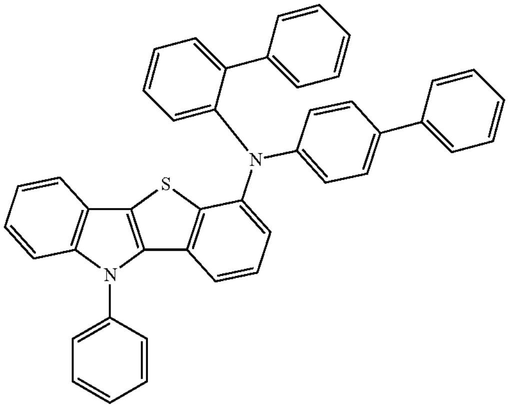
-continued
B9
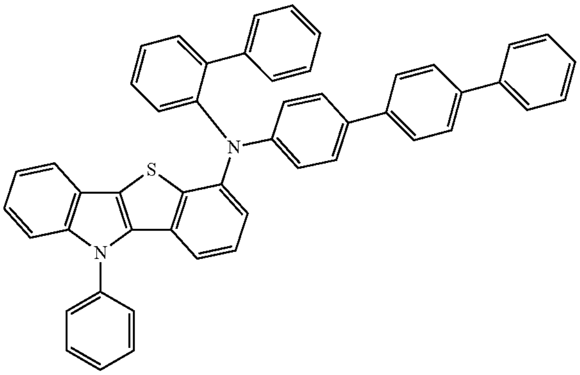
B10
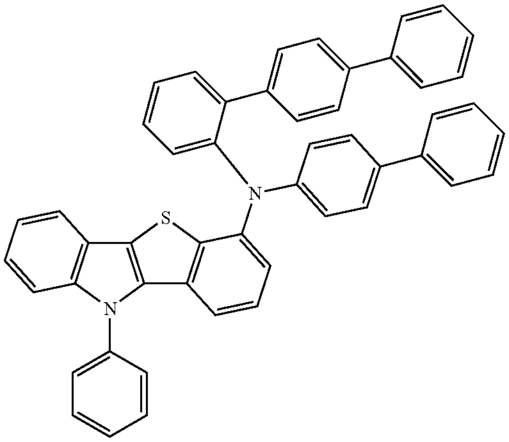
B11
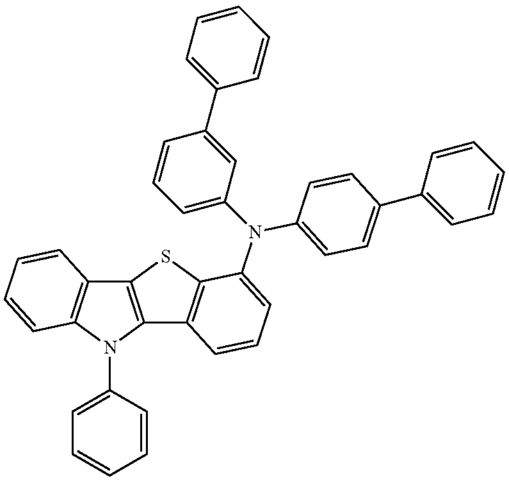

-continued
B12
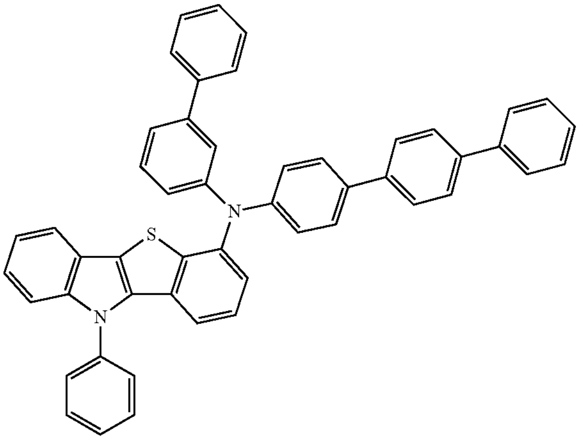
B13
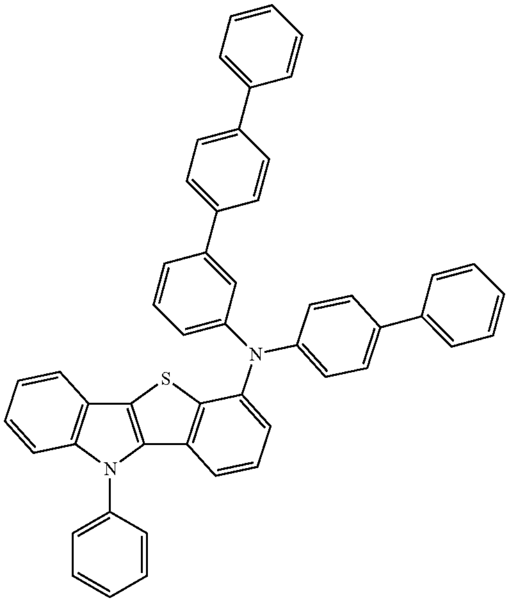
B14
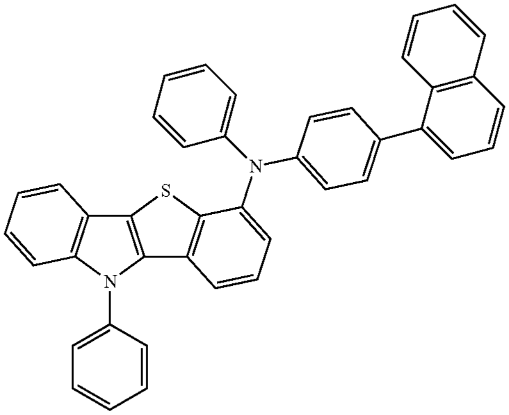
-continued
B15
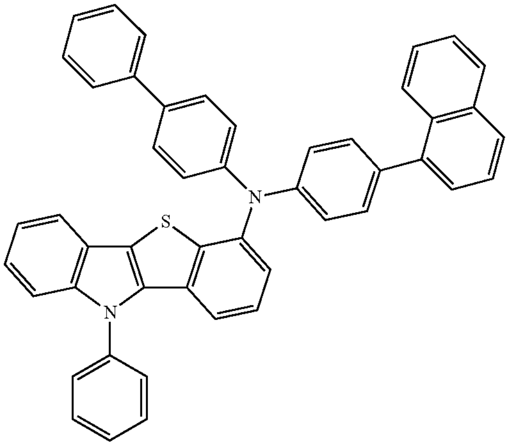
B16
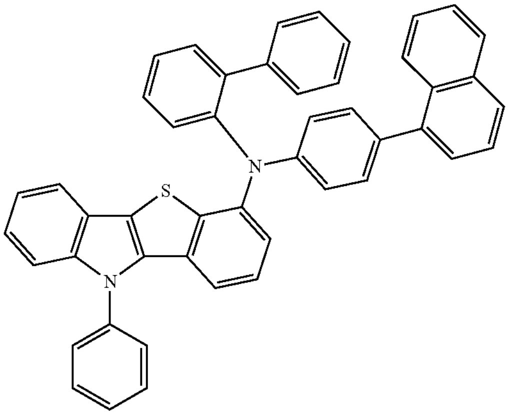
B17
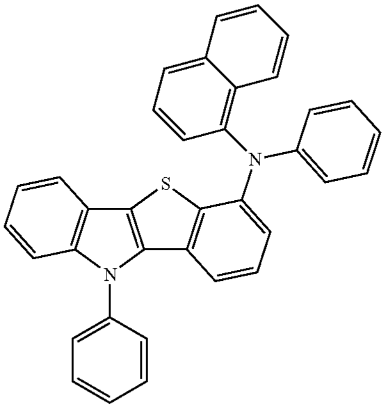

-continued
B18
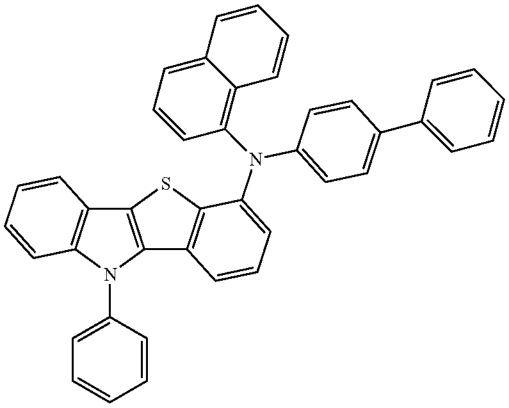
B19
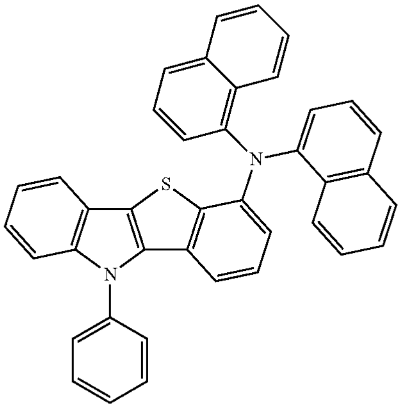
B20
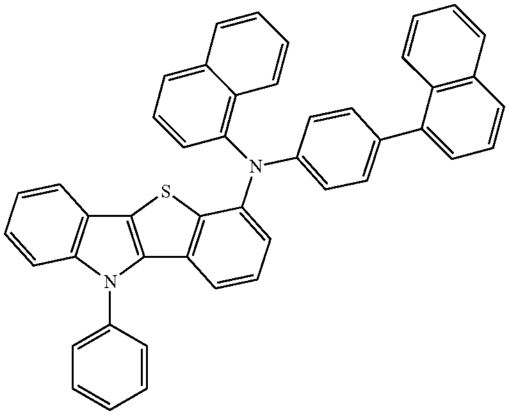
-continued
B22
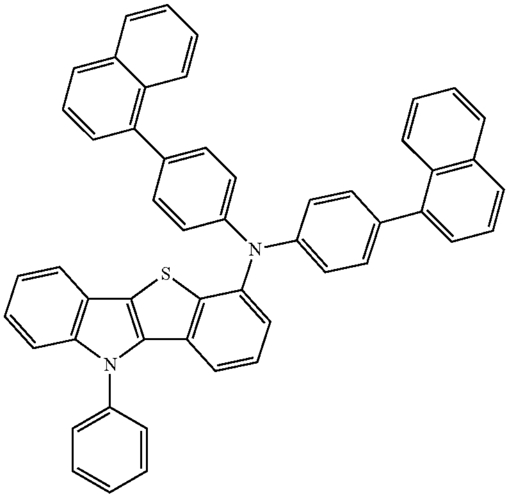
B23
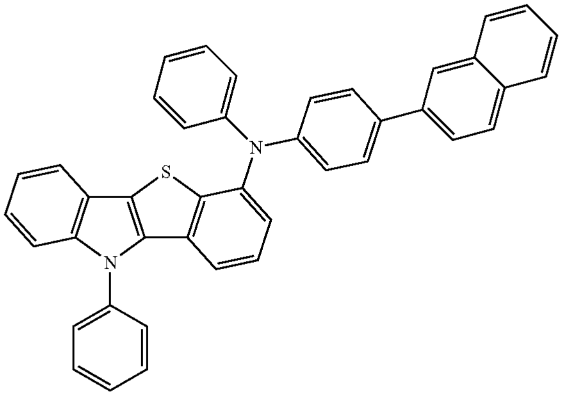
B24
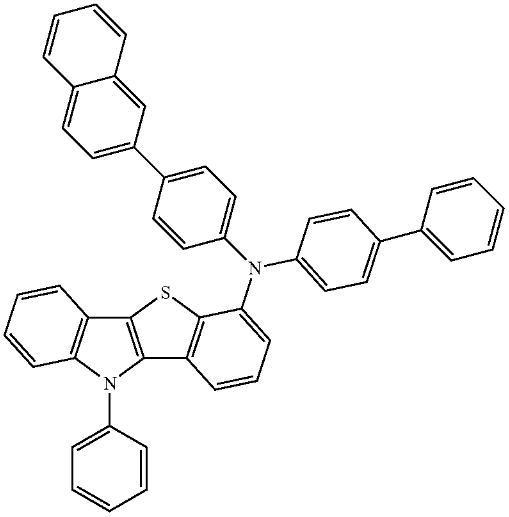

-continued
B25
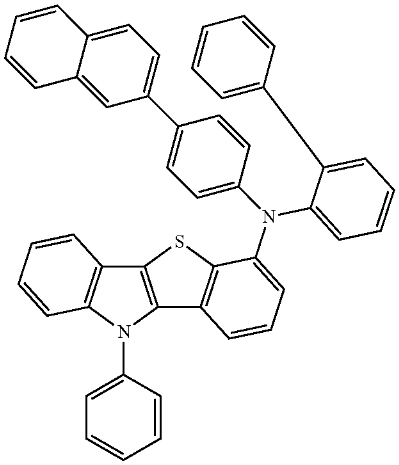
B26
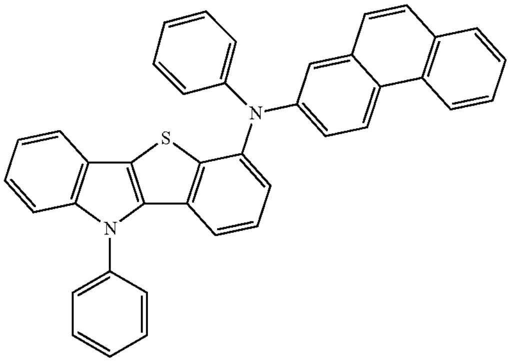
B27
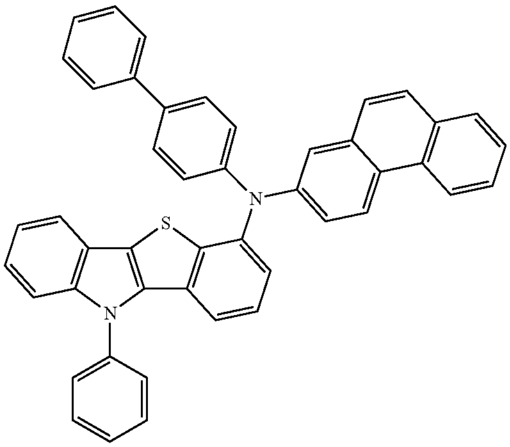
-continued
B28
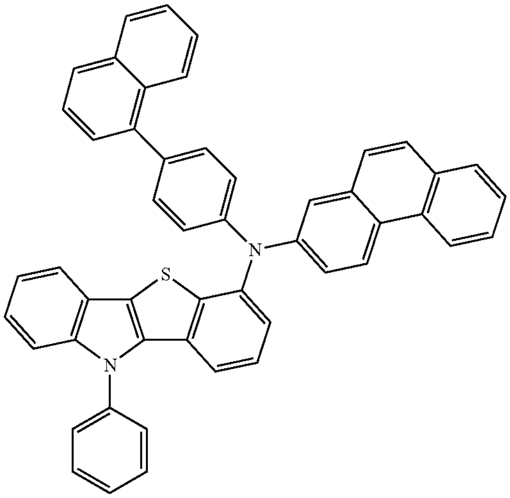
B29
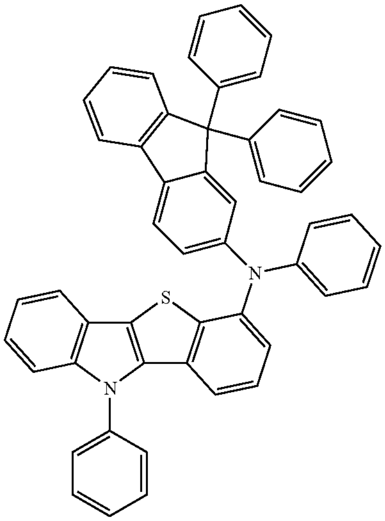
B30
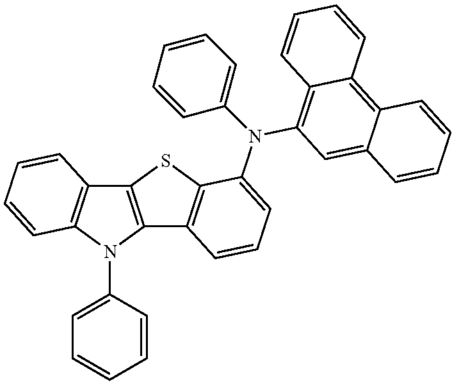

-continued
B31
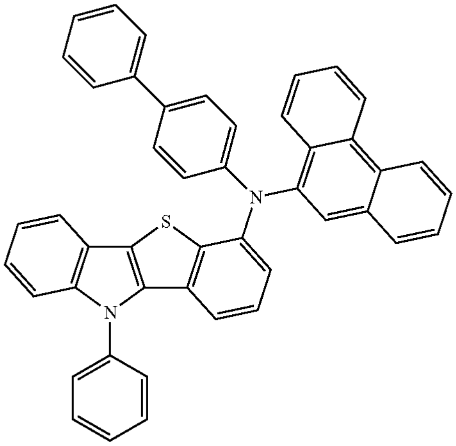
B32
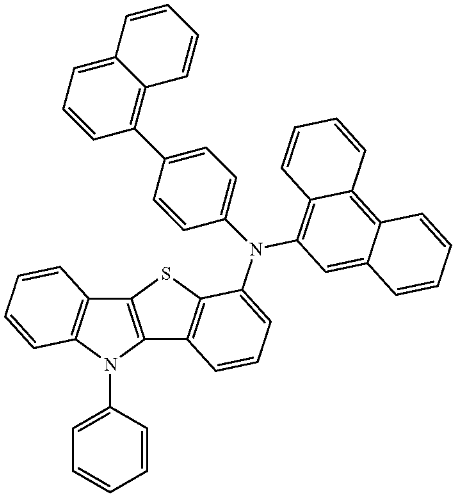
B33
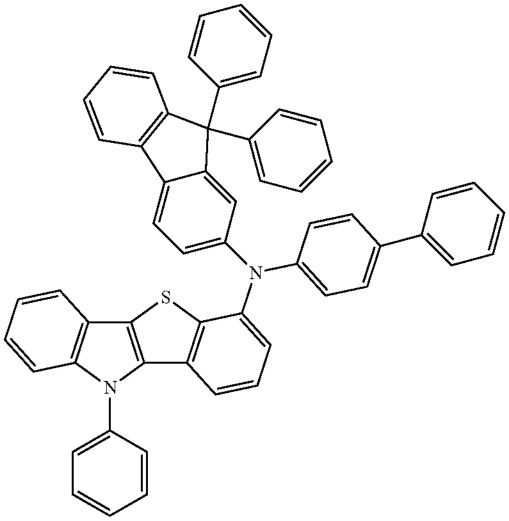
-continued
B34
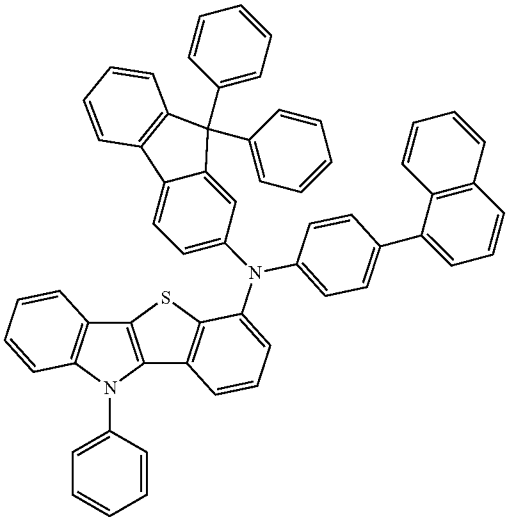
B35
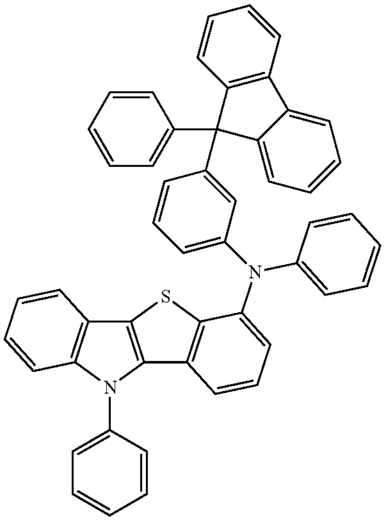
B36
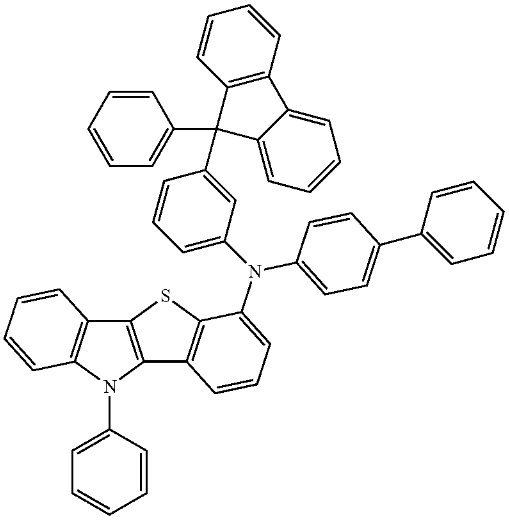

-continued
B37
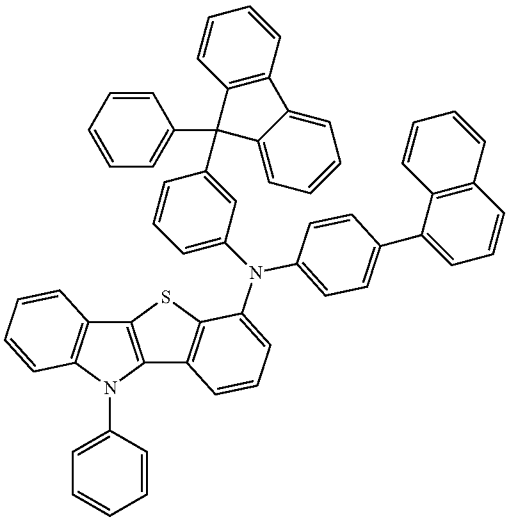
B38
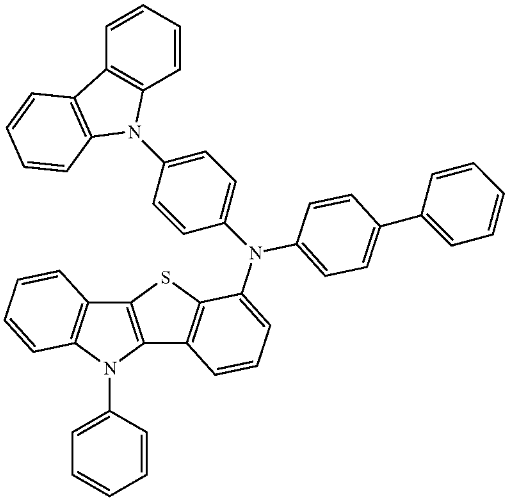
B39
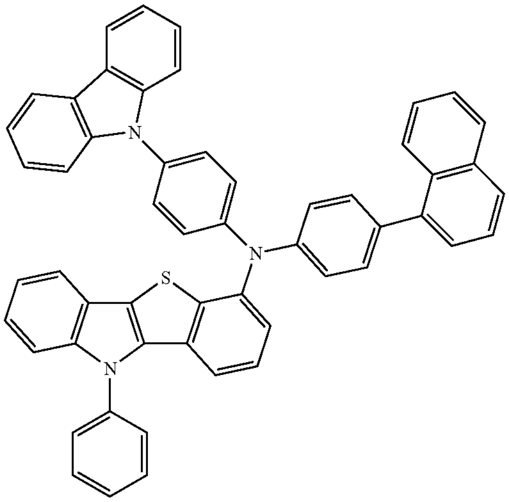
-continued
B40
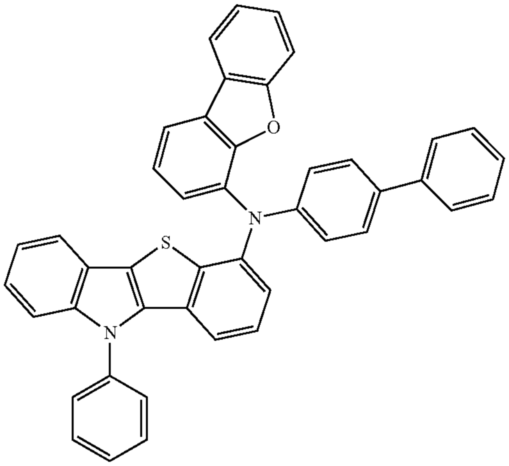
B41
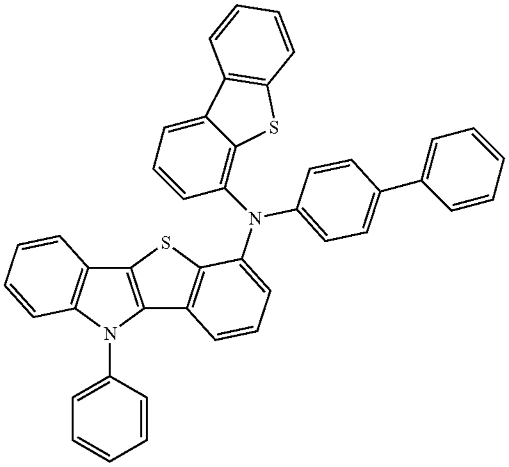
B42
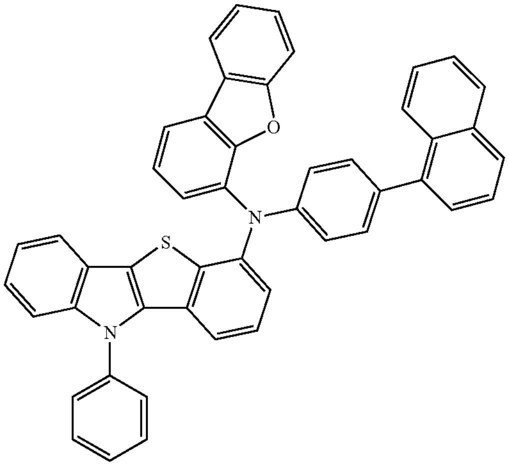

-continued
B43
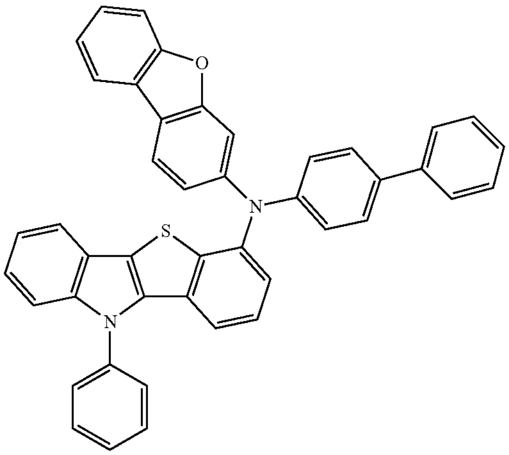
B44
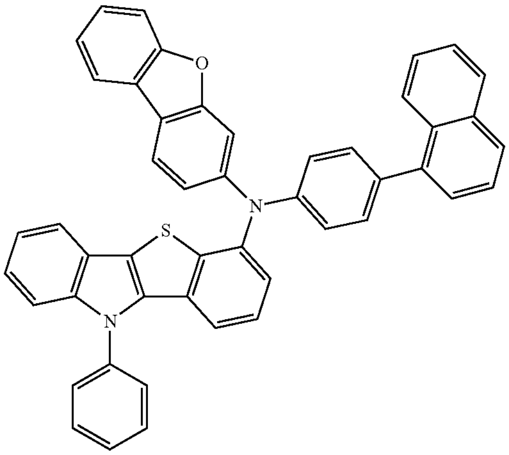
B45
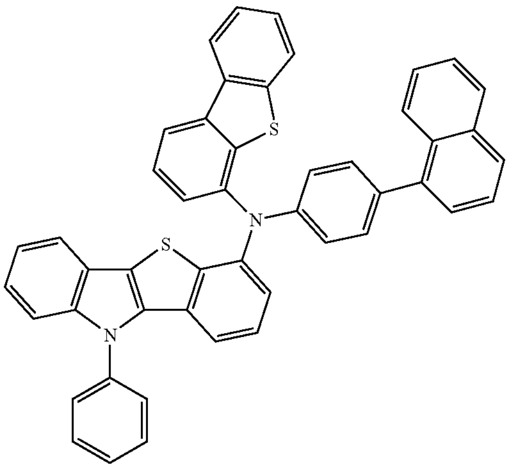
-continued
B46
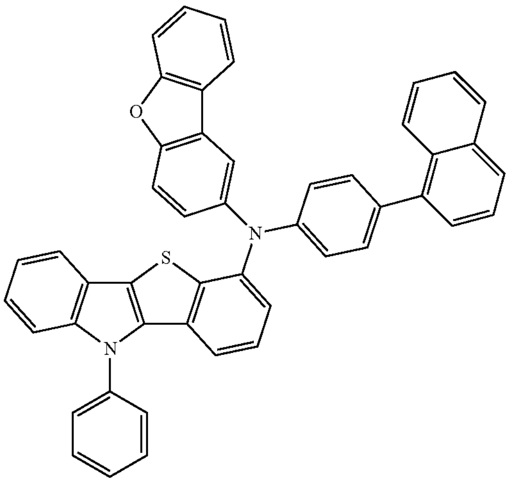
B47
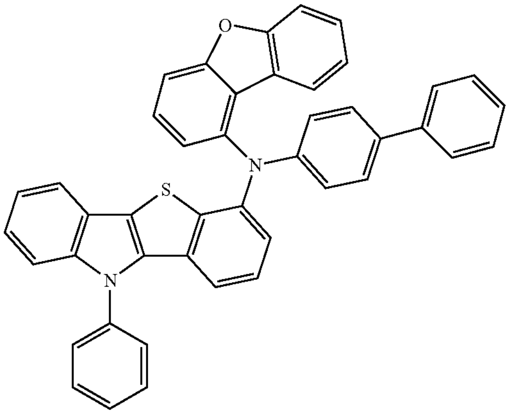
B48
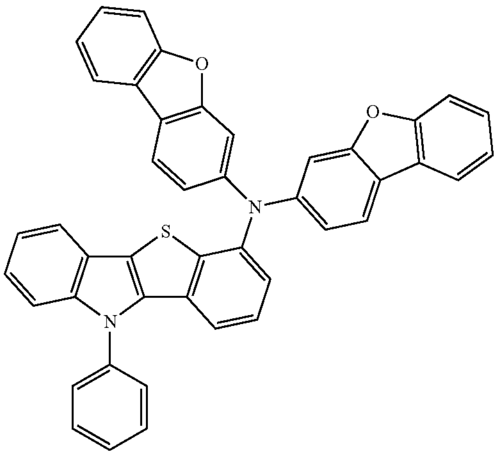

-continued
B49
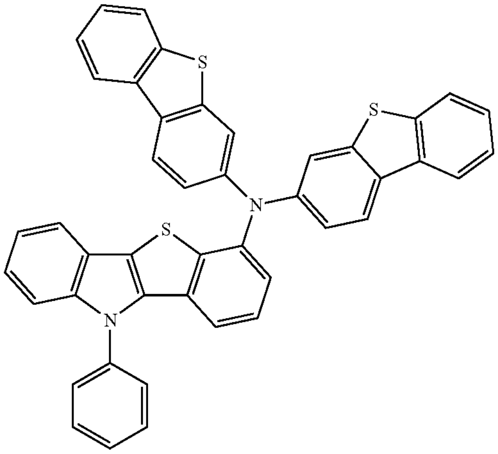
B50
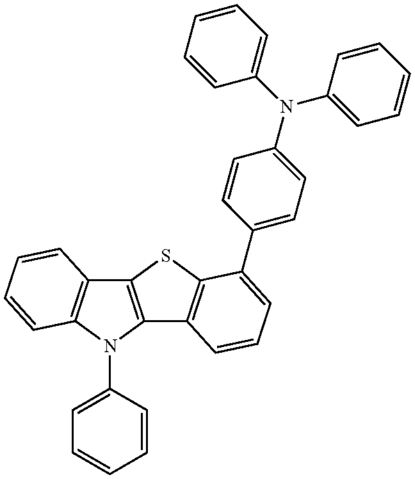
B51
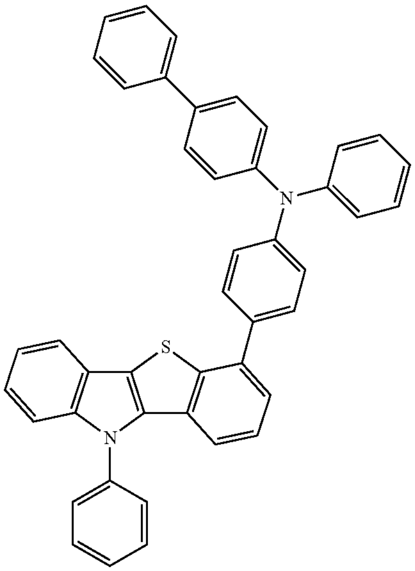
-continued
B52
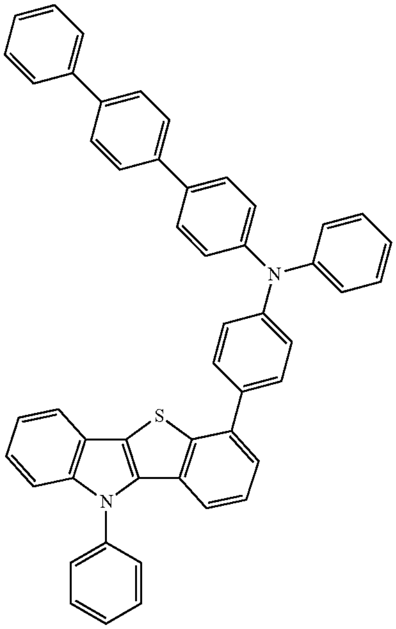
B53
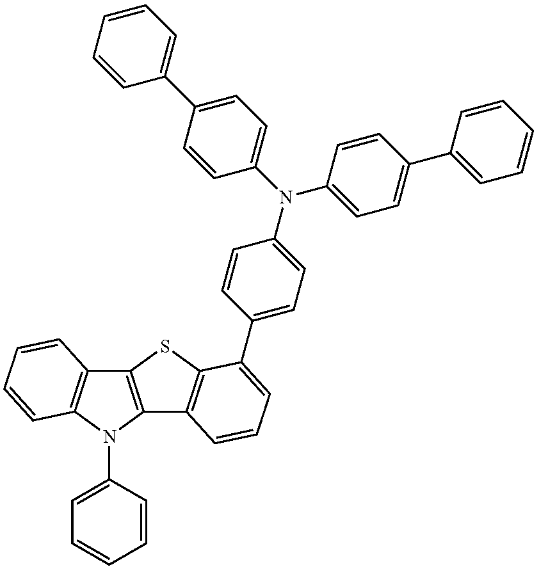

-continued
B54
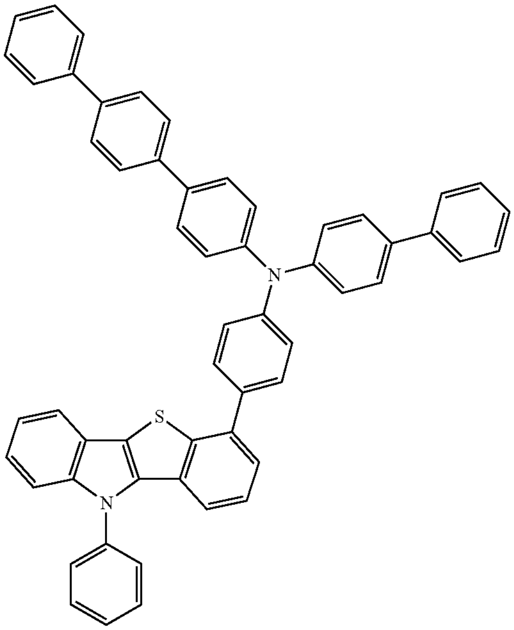
B55
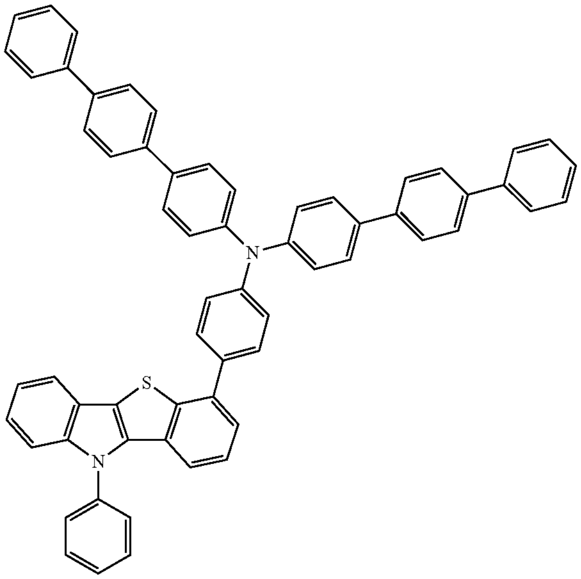
-continued
B56
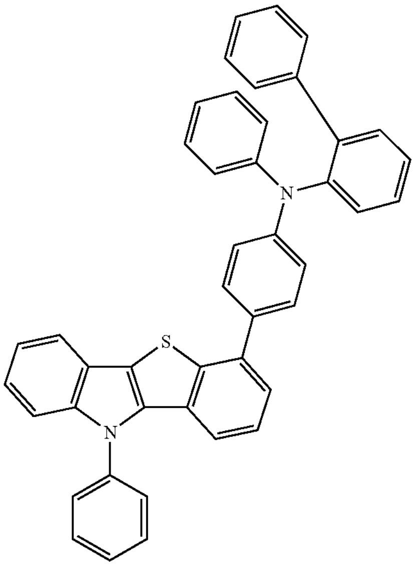
B57
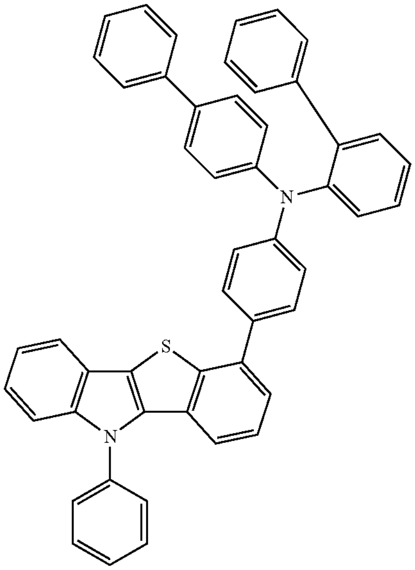
B58
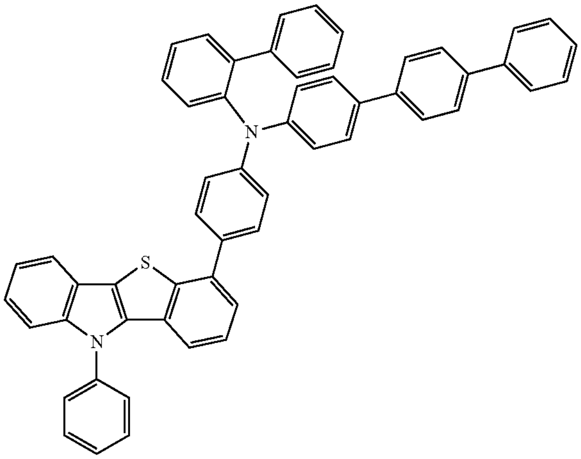

-continued
B59
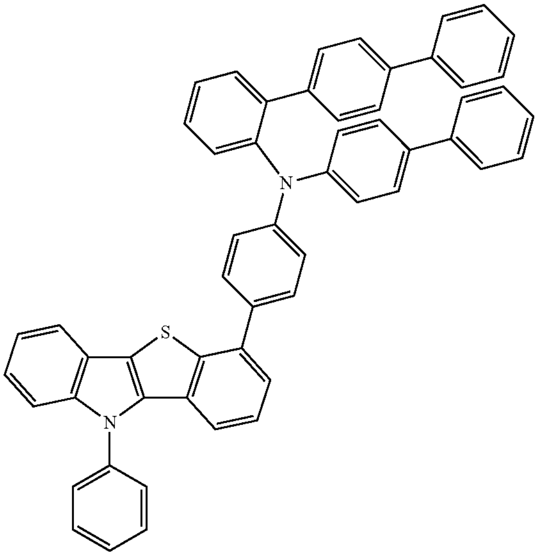
B60
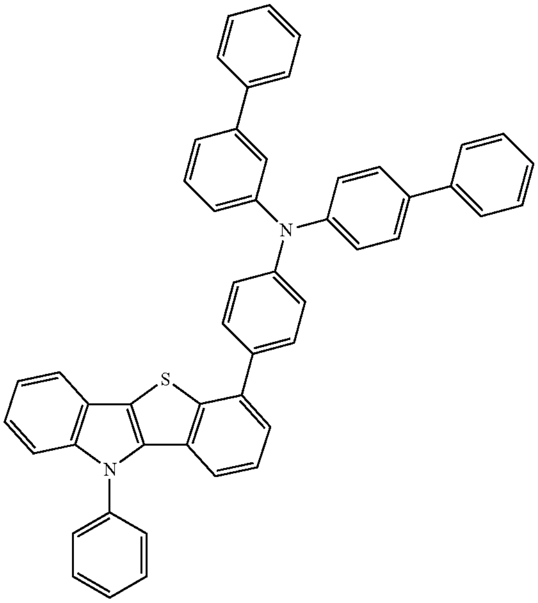
B61
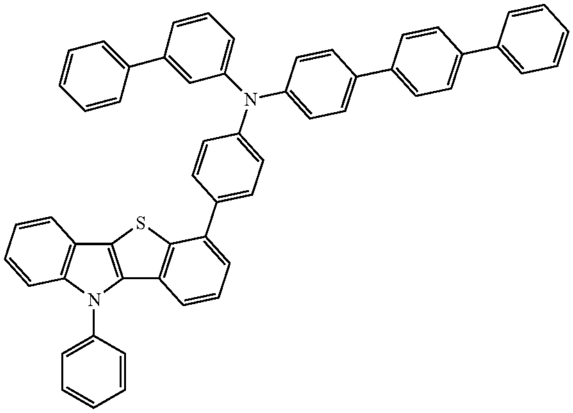
B62
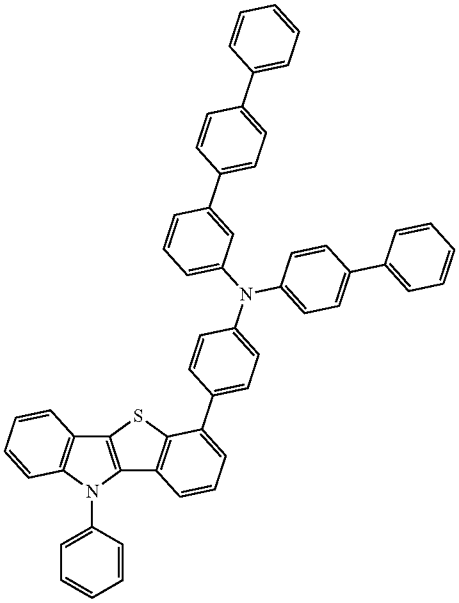
B63
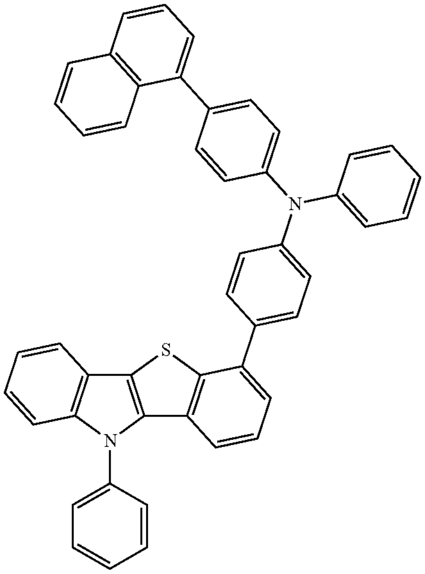

-continued
B64
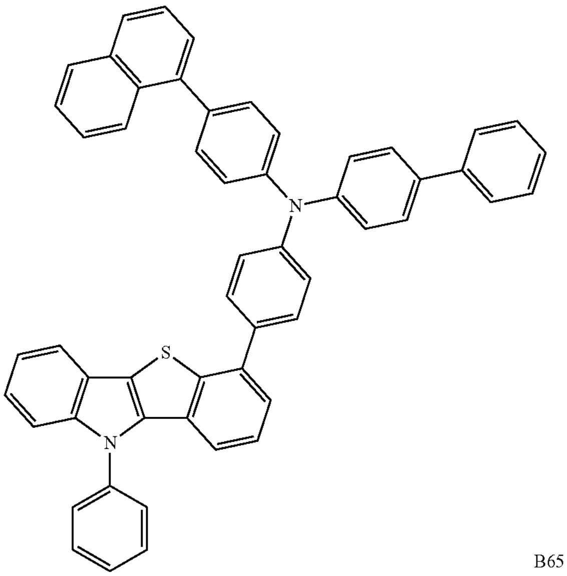
B65
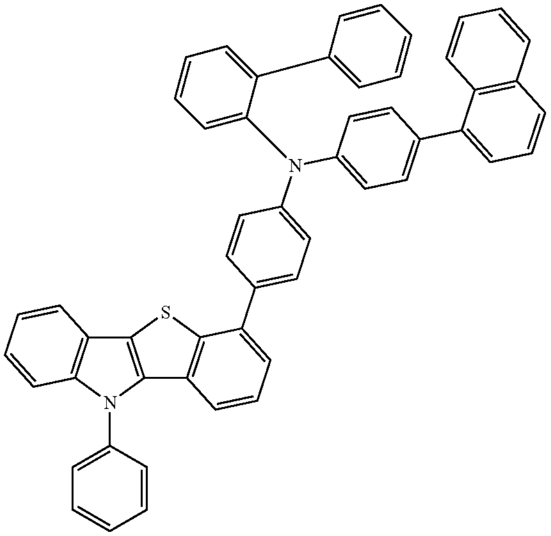
B66
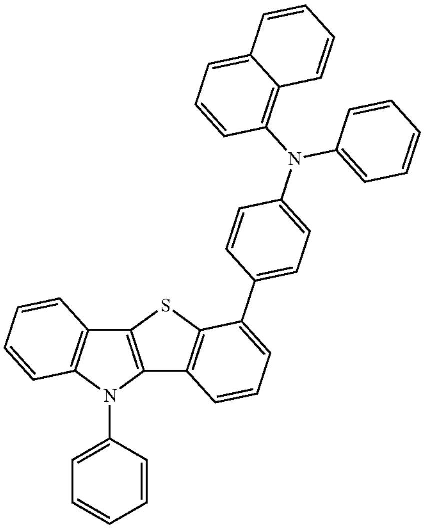
-continued
B67
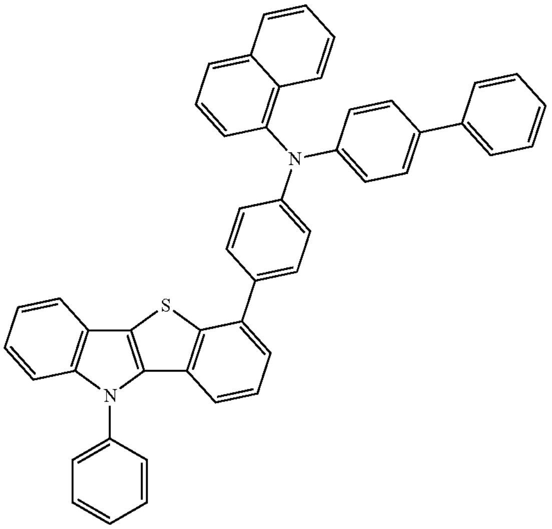
B68
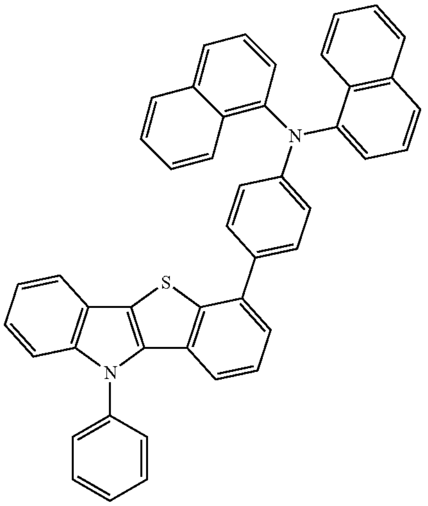
B69
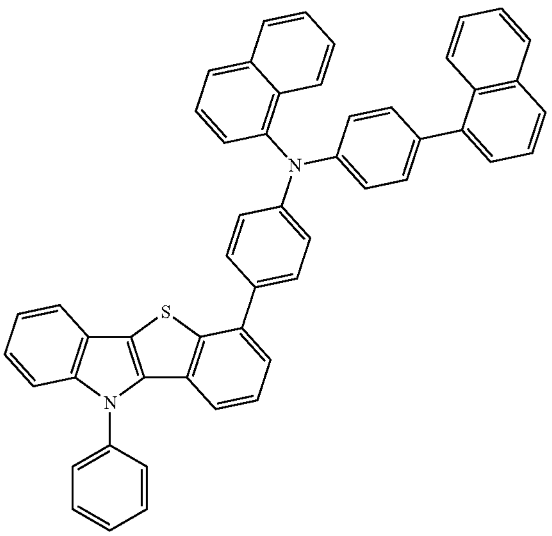

-continued
B70
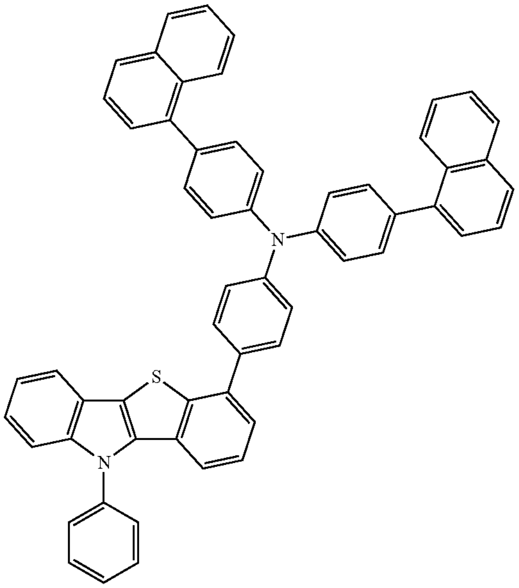
B71
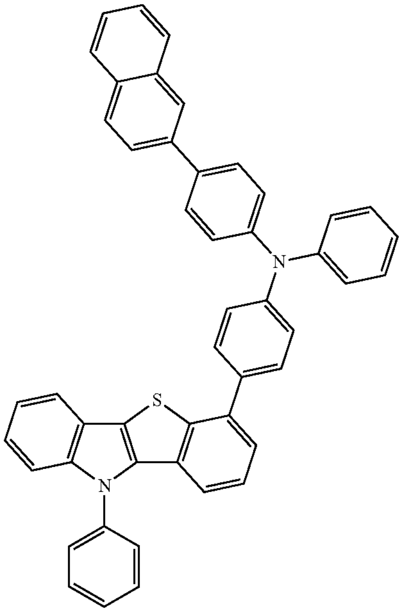
-continued
B72
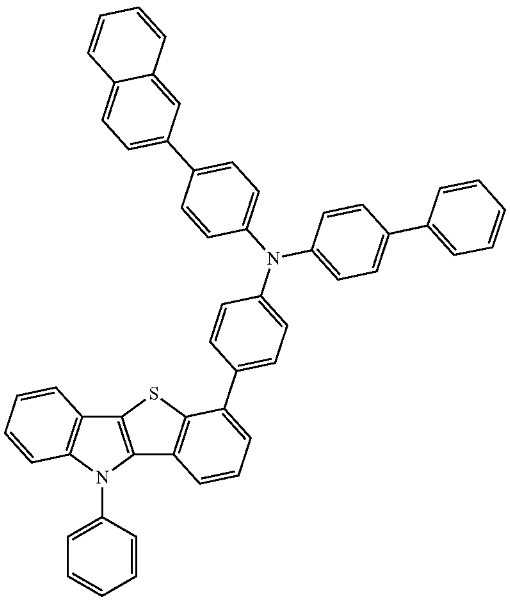
B73
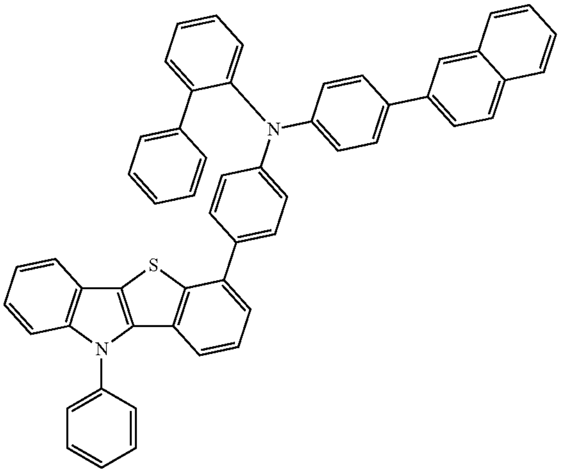
B74
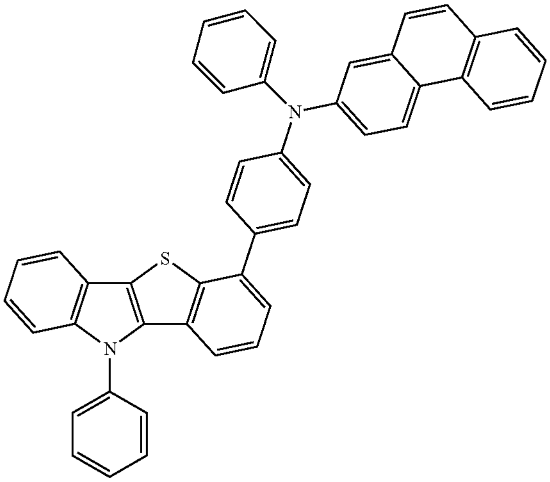

-continued
B75
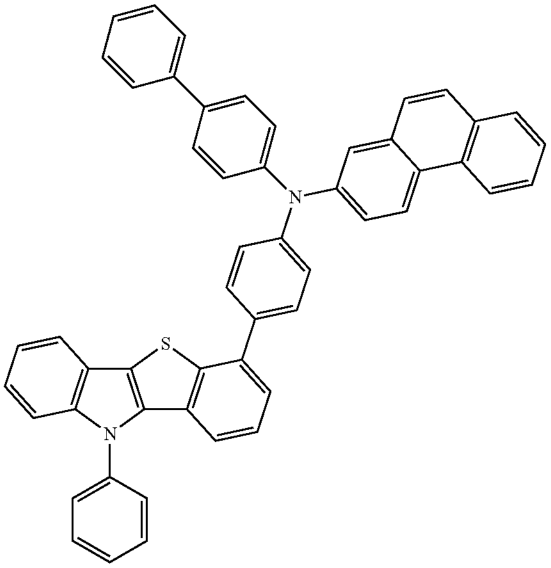
B76
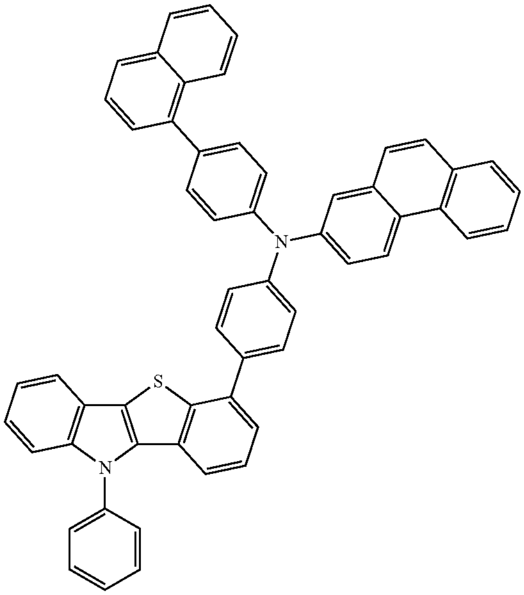
-continued
B77
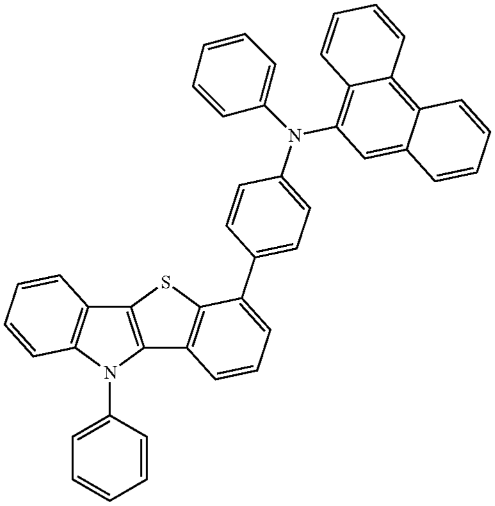
B78
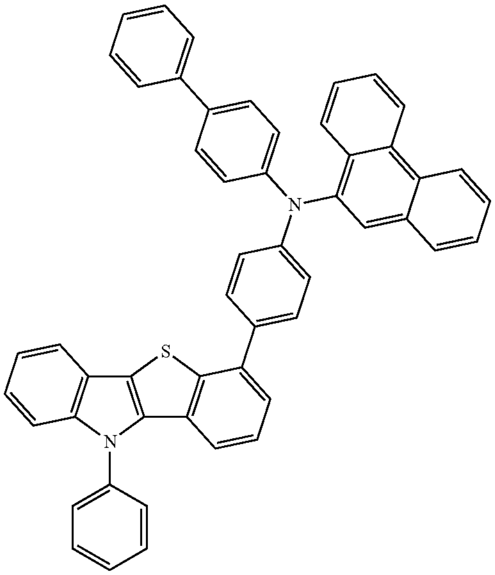

-continued
B79
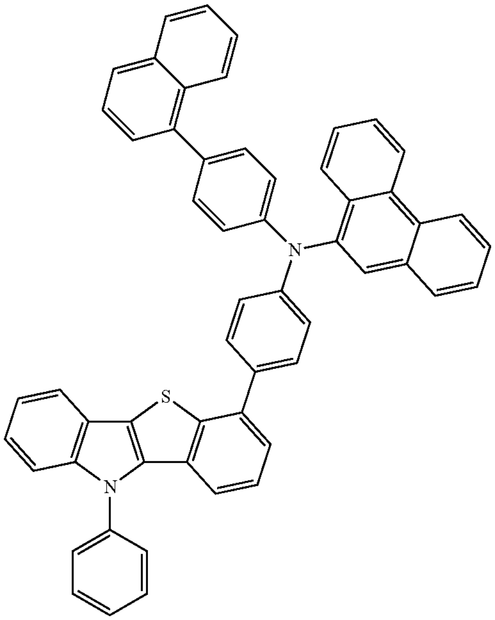
B81
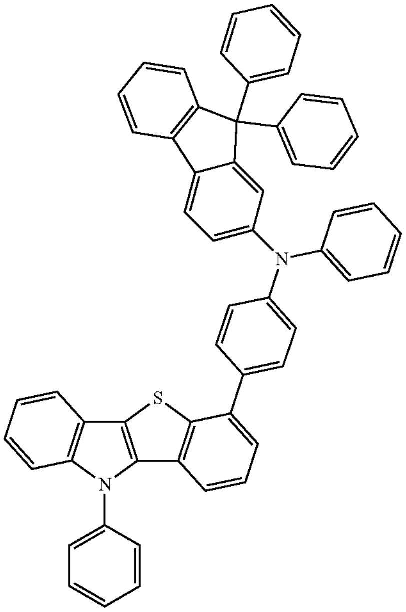
-continued
B82
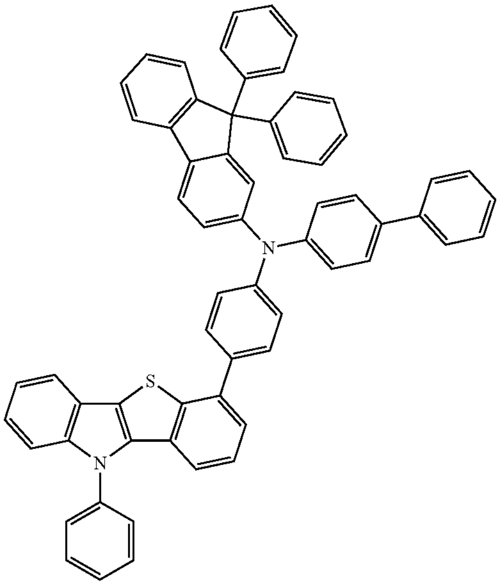
B83
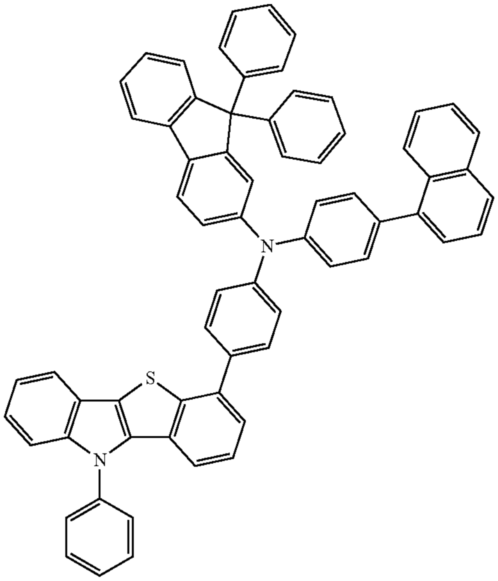

-continued
B84
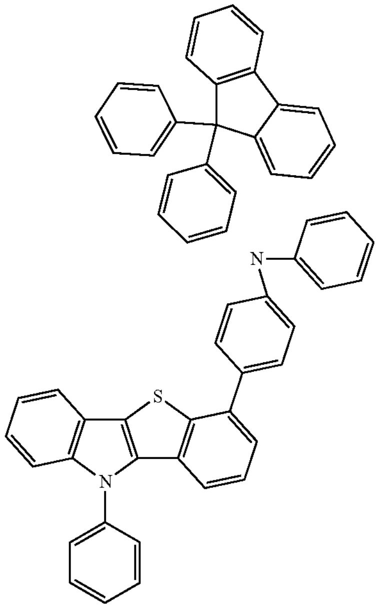
-continued
B86
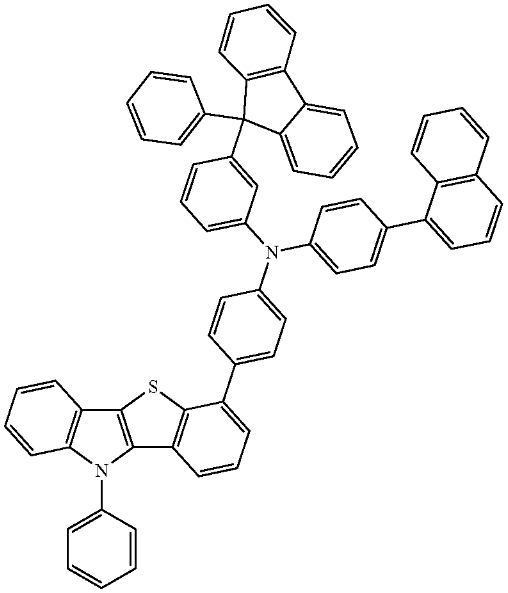
B85
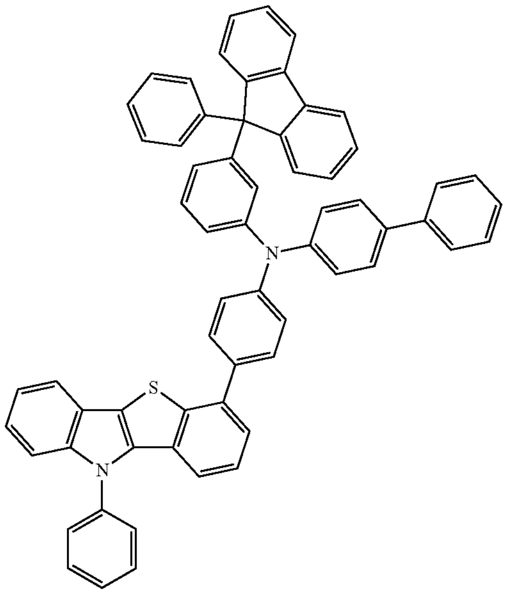
B87
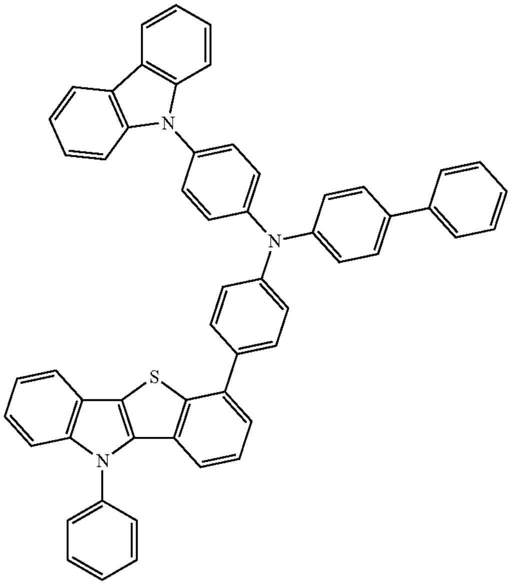

-continued
B88
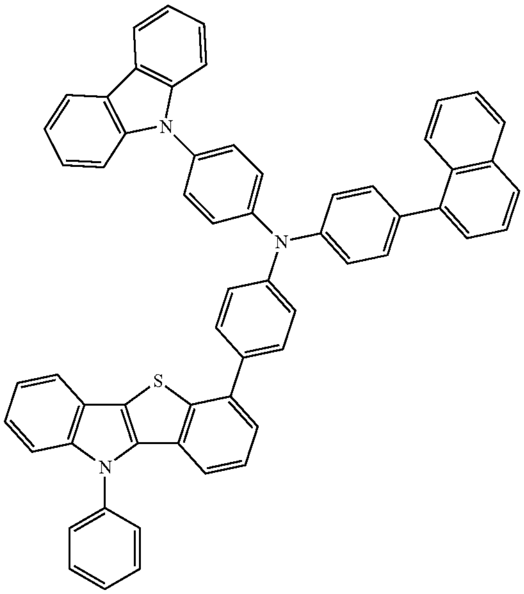
B89
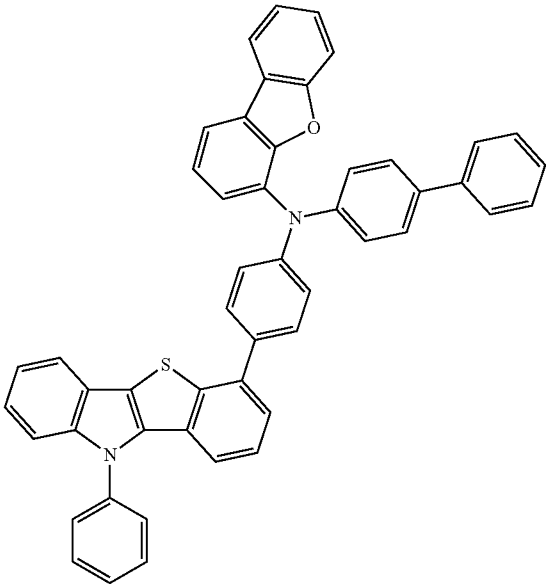
-continued
B90
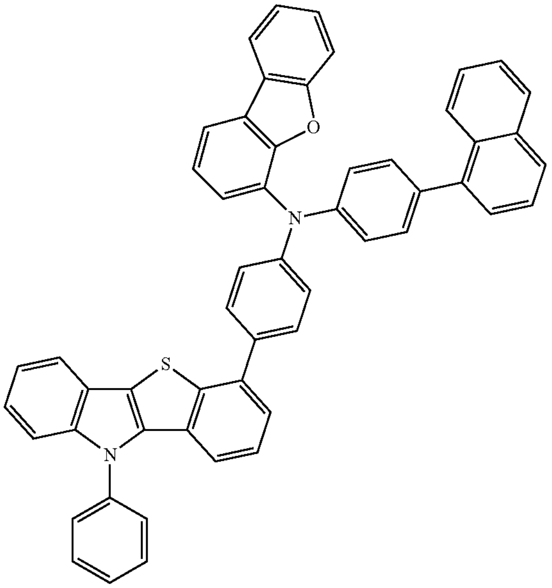
B91
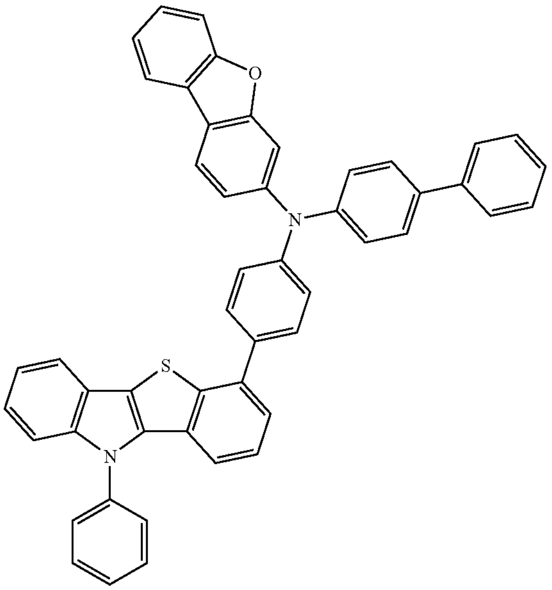

-continued
B92
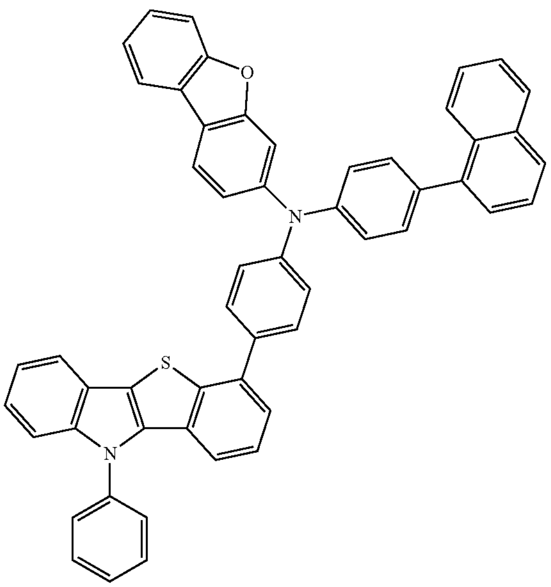
B93
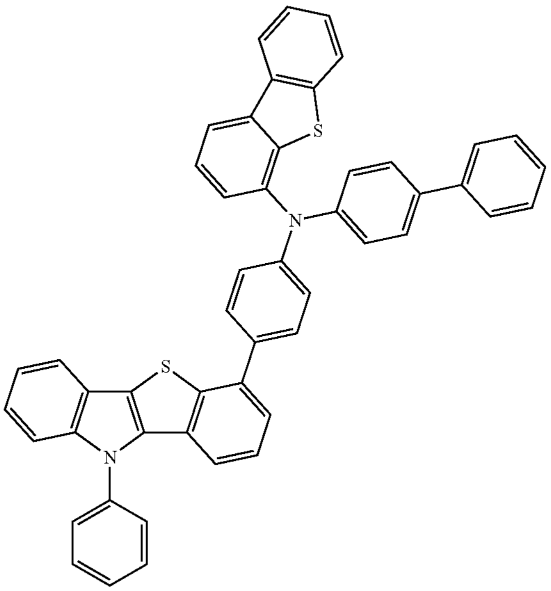
-continued
B94
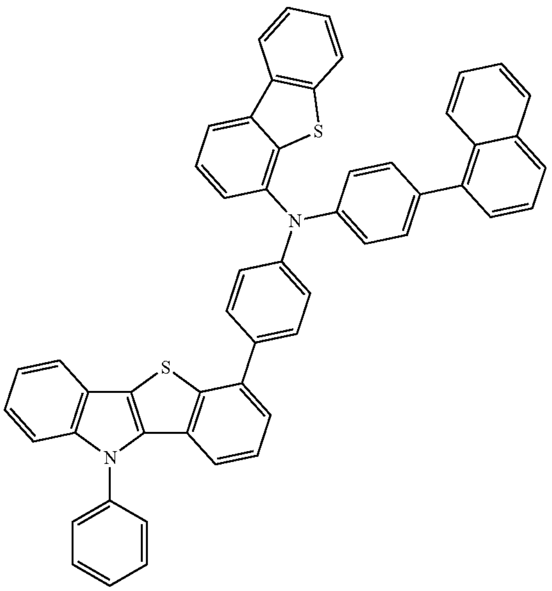
B95
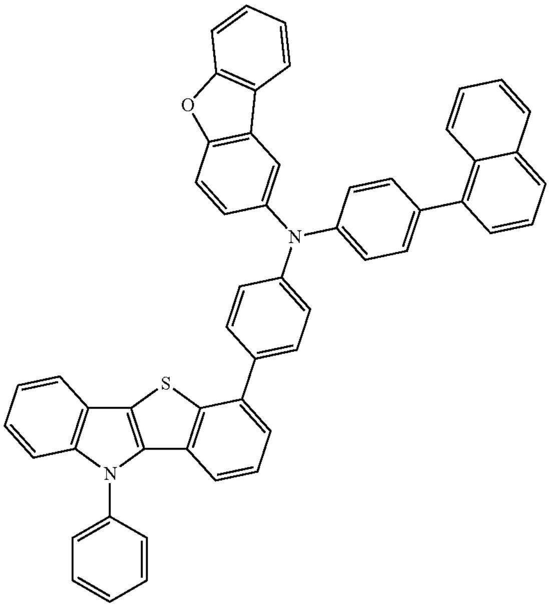

-continued
B96
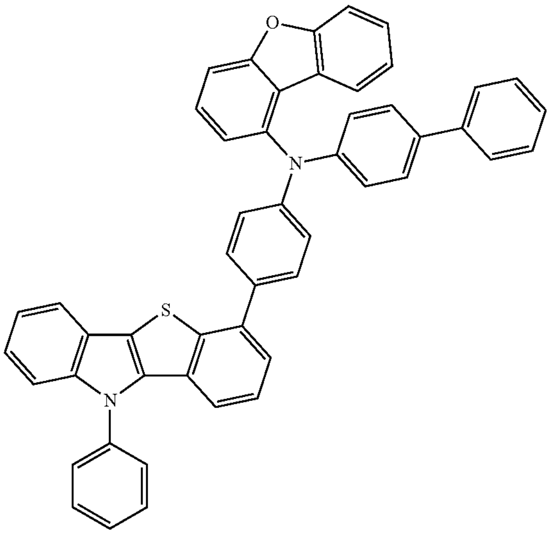
B97
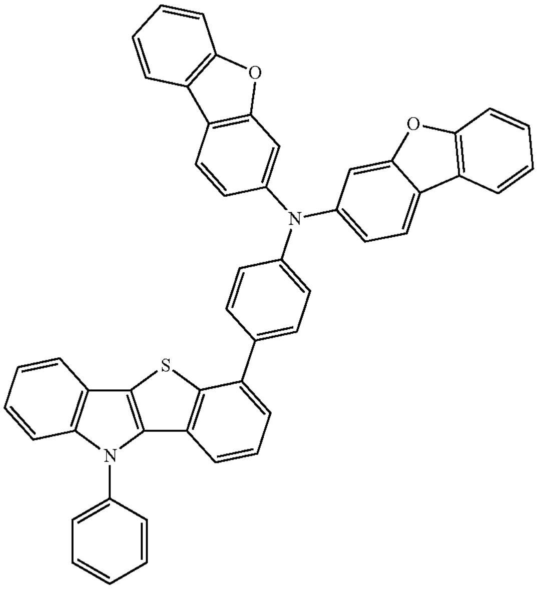
-continued
B98
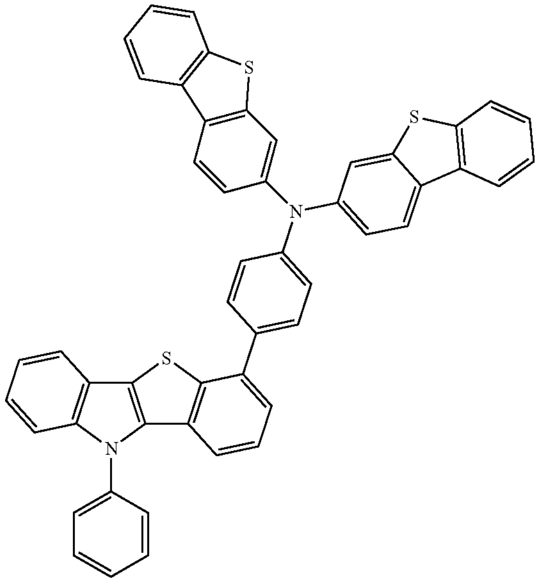
B99
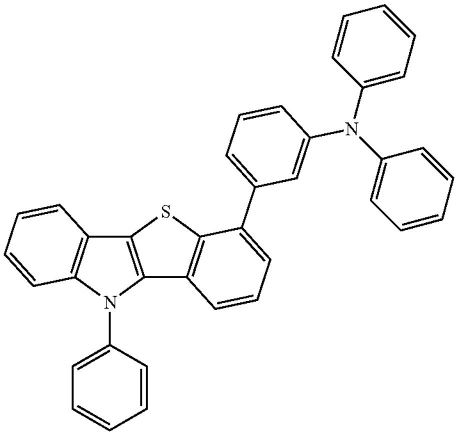
B100
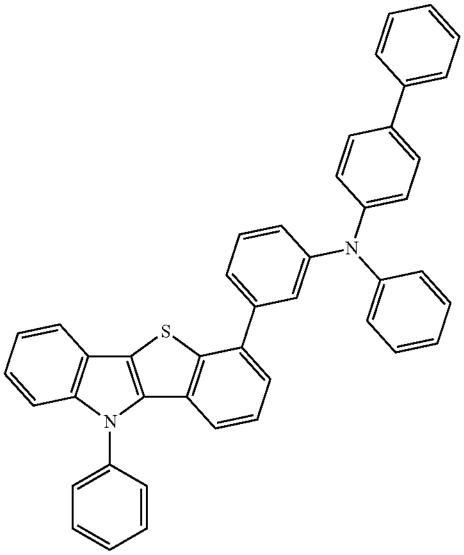

-continued
B101
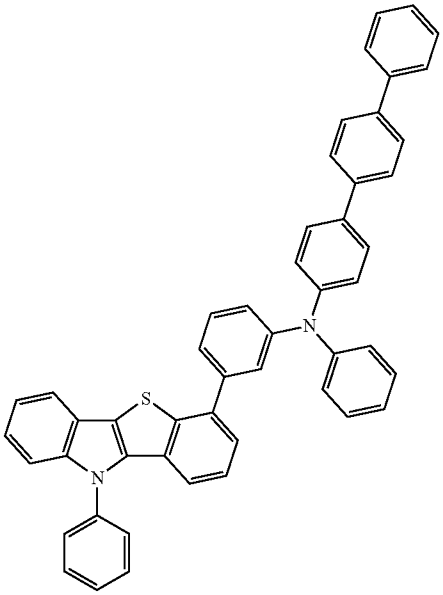
B102
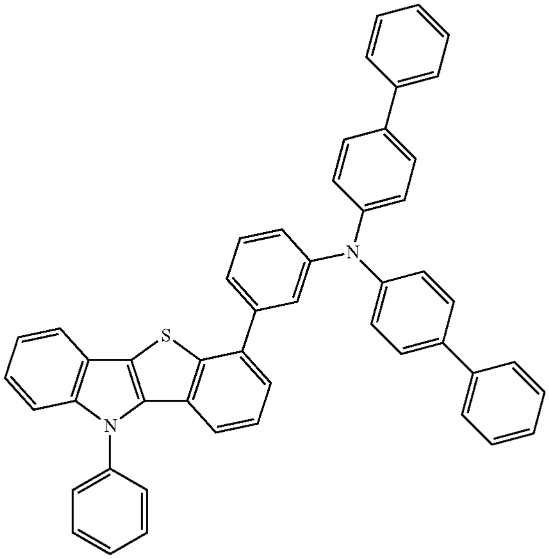
-continued
B103
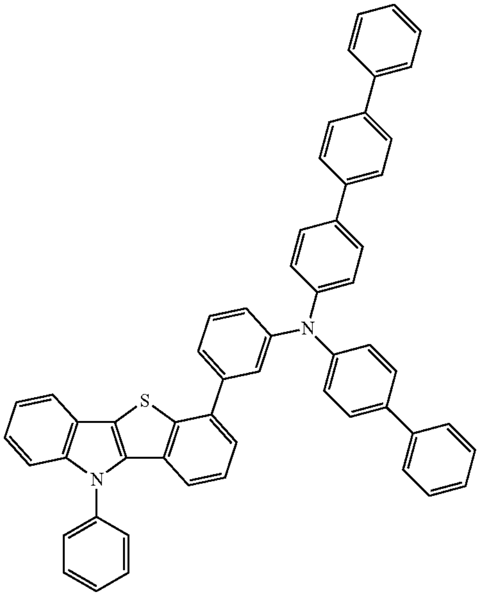
B104
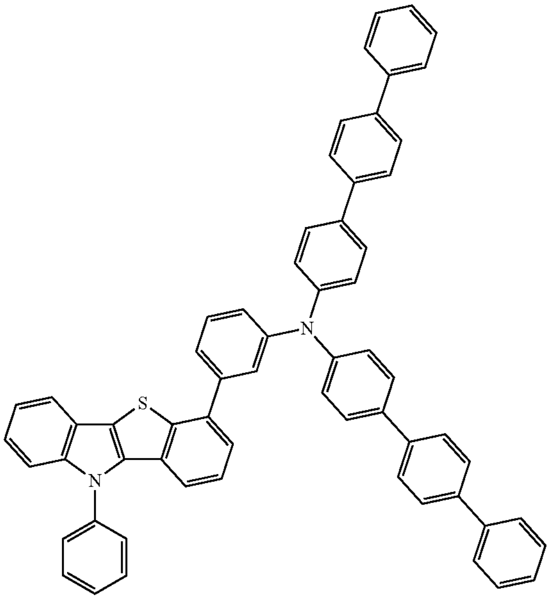

-continued
B105
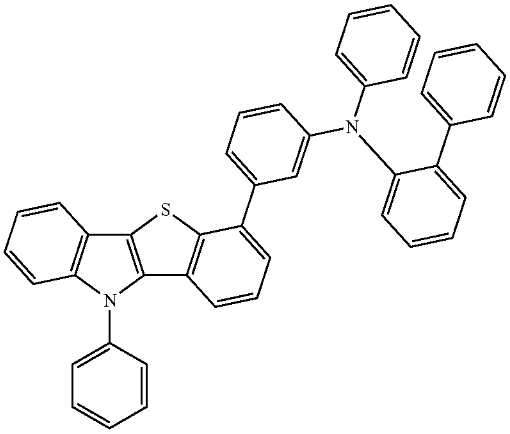
B106
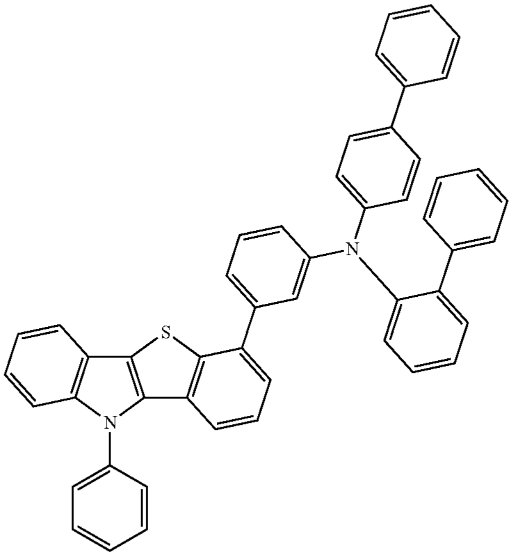
B107
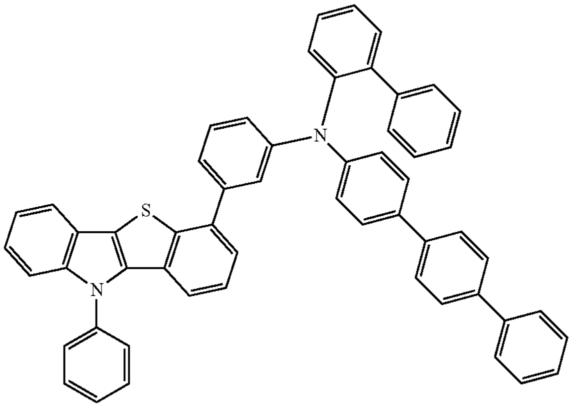
-continued
B108
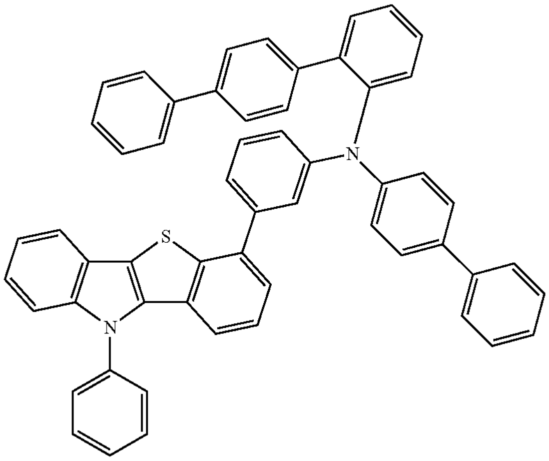
B109
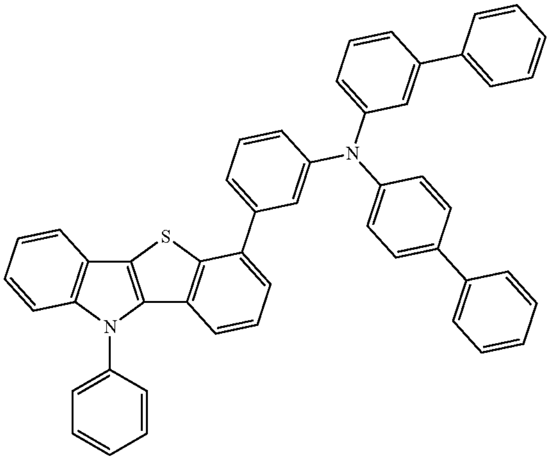
B110
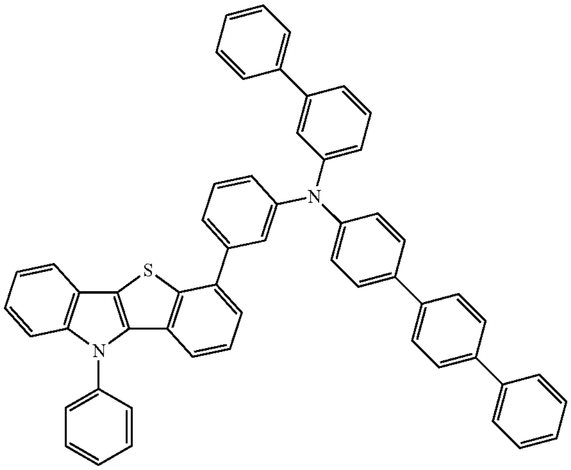

B111
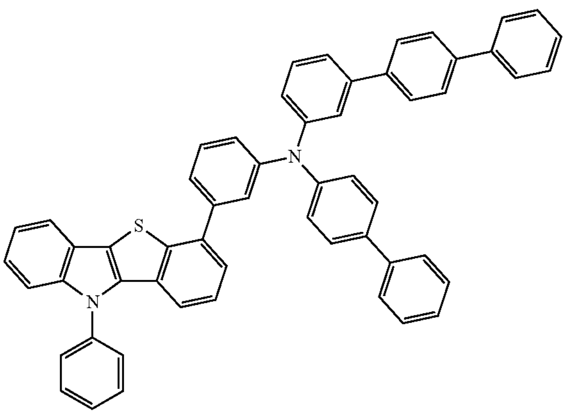
B112
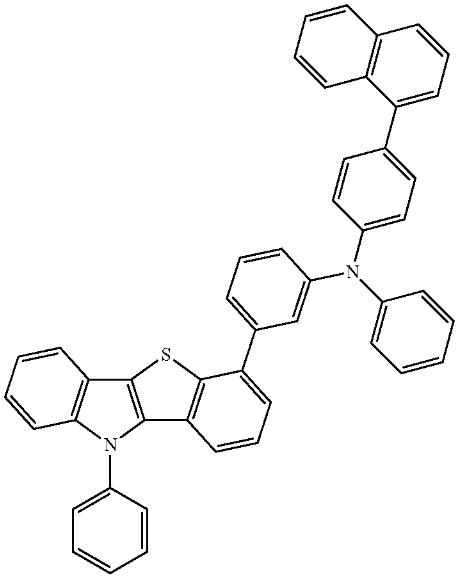
B113
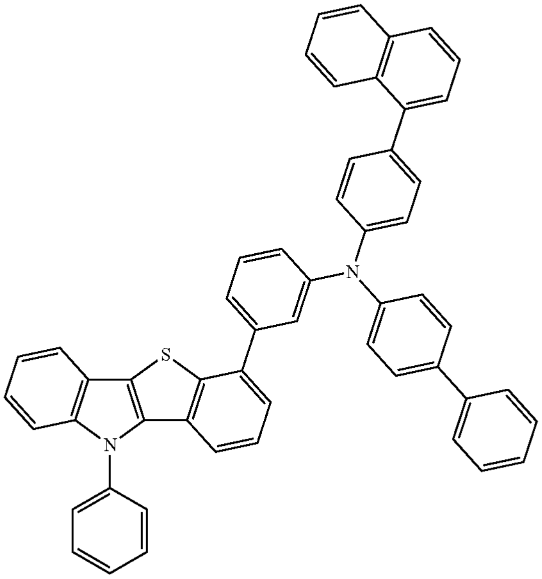
B114
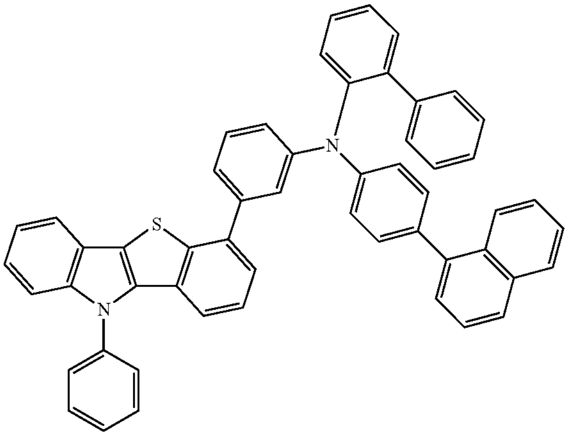
B115
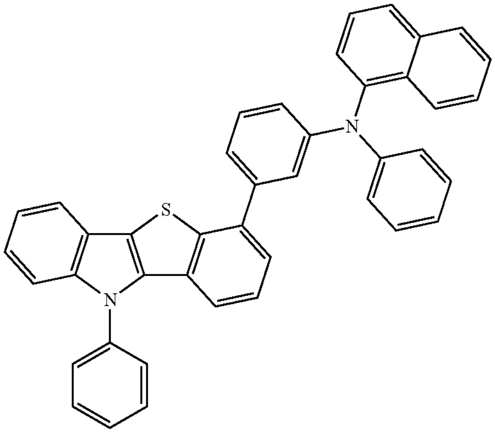
B116
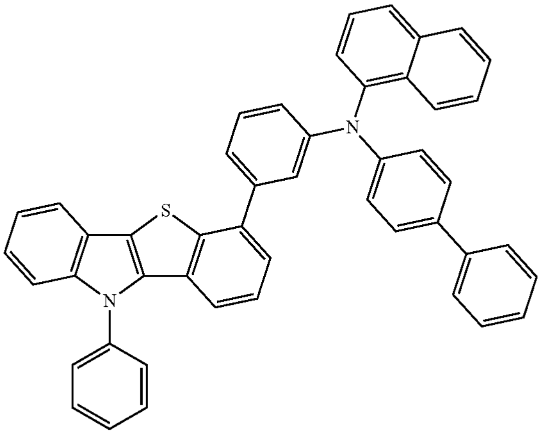

-continued
B117
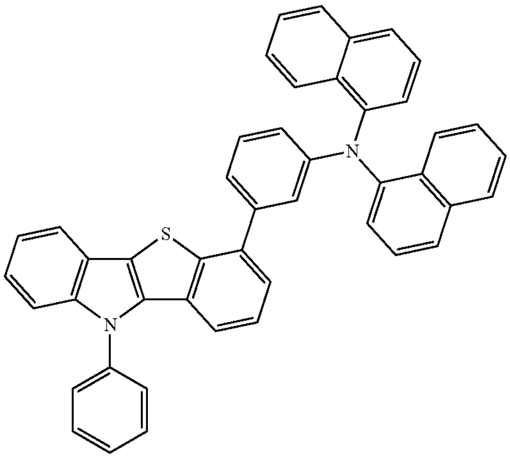
B118
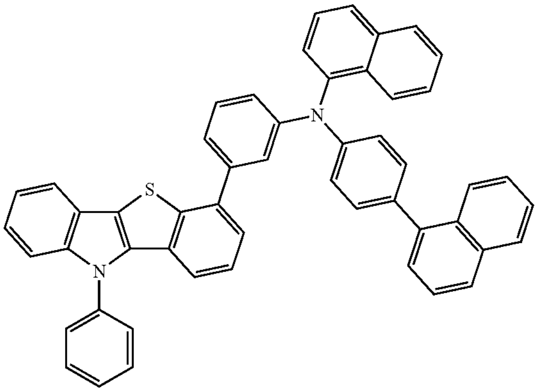
B119
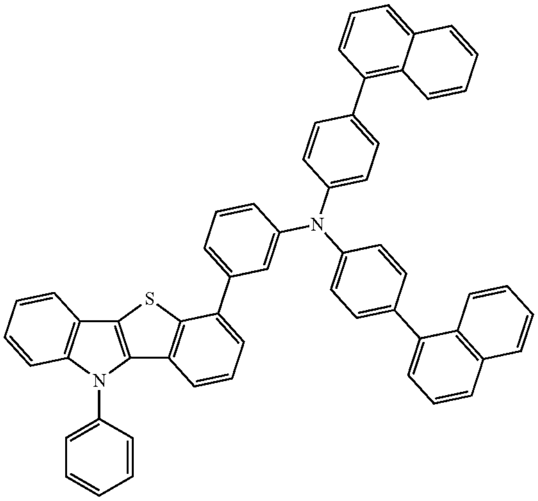
-continued
B120
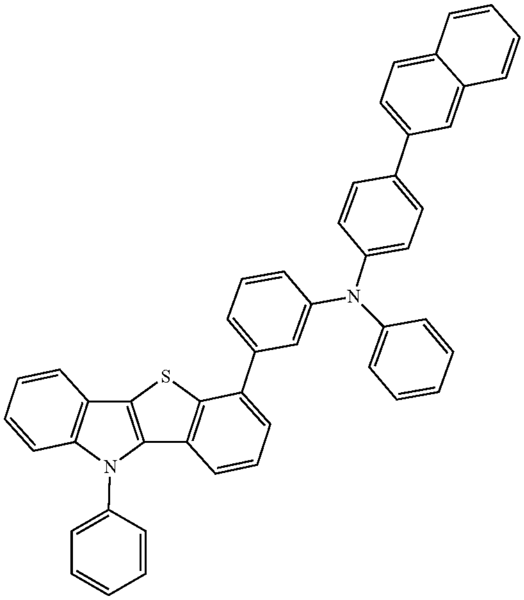
B121
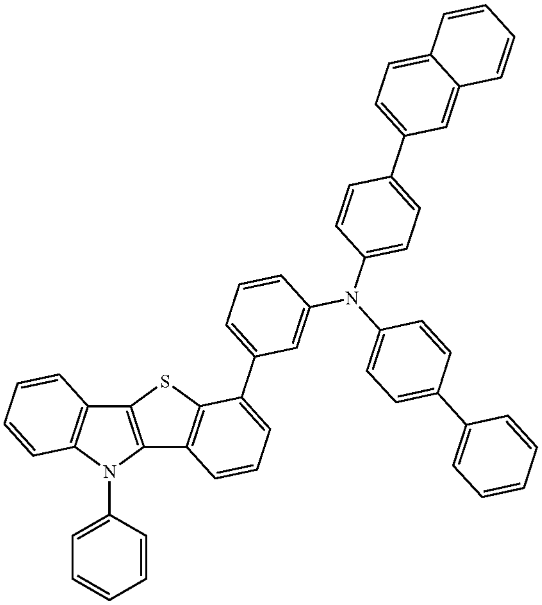

-continued
B122
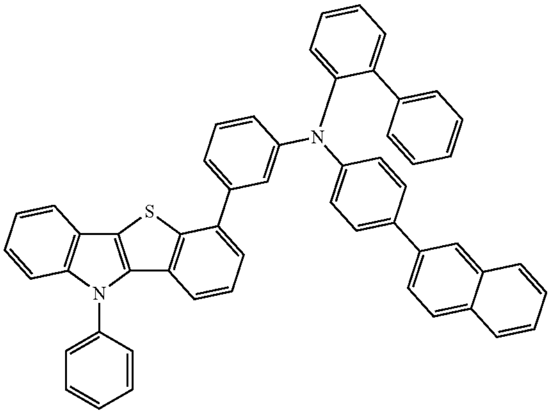
B123
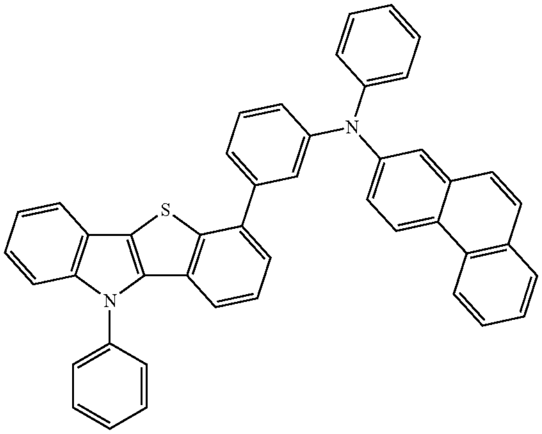
B124
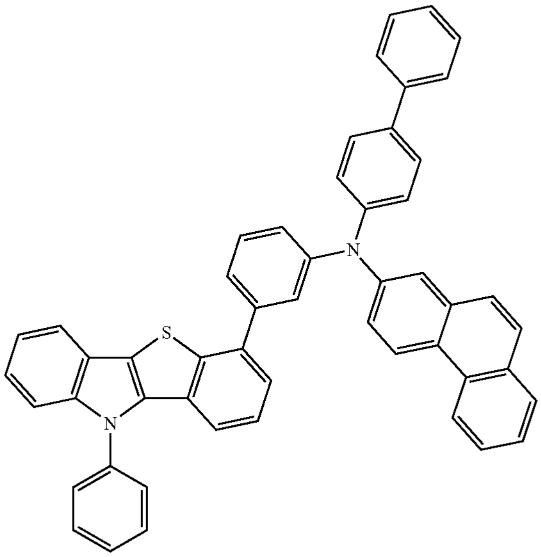
-continued
B125
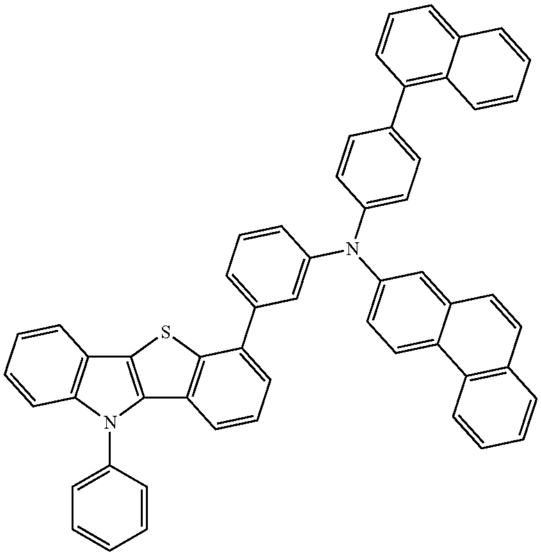
B126
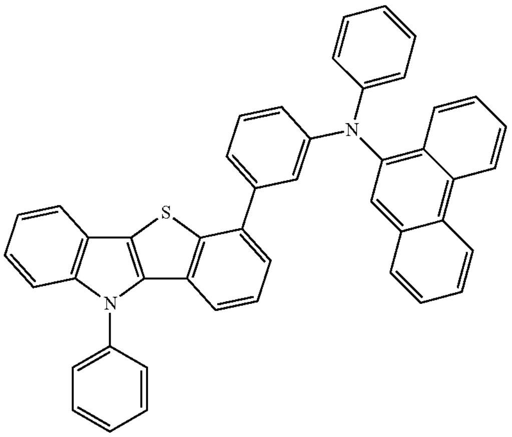
B127
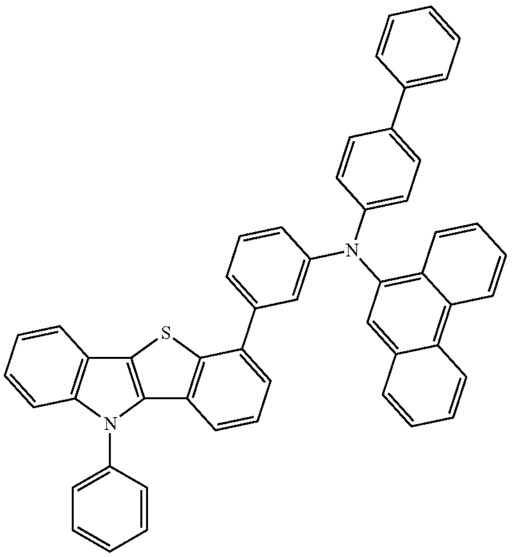

-continued
B128
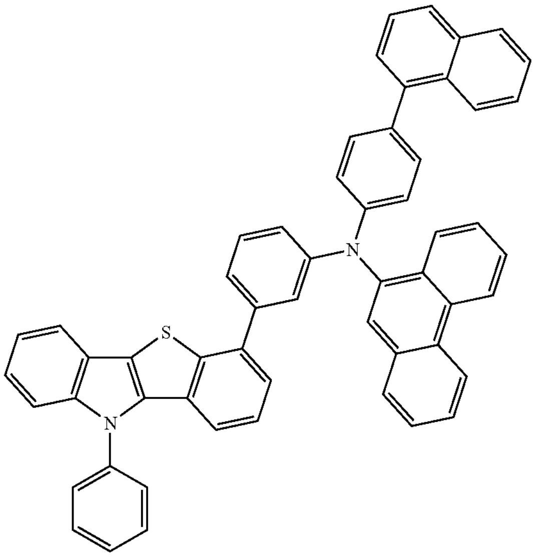
B130
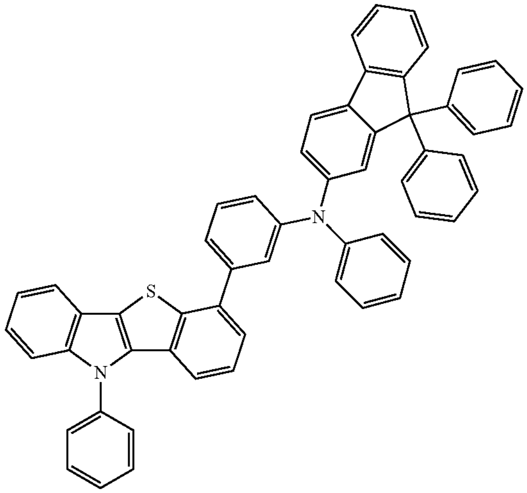
B131
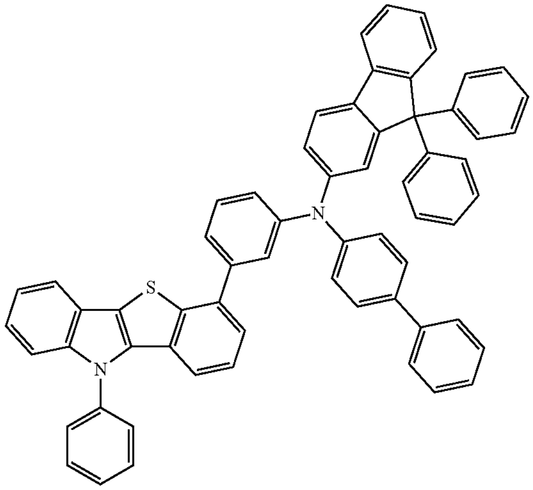
-continued
B132
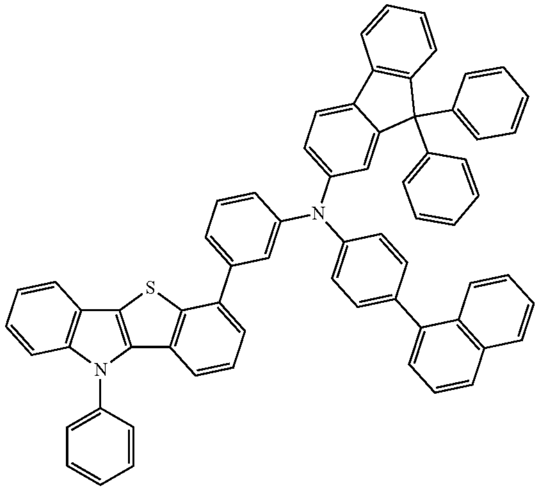
B133
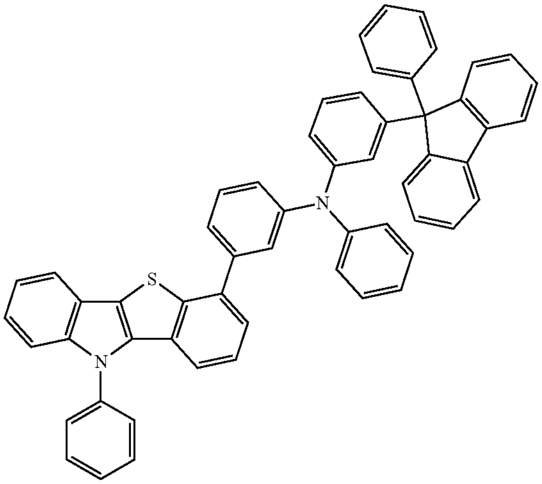
B134
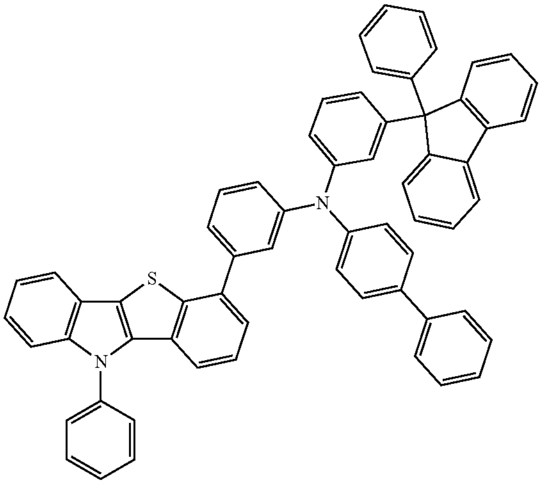

-continued
B135
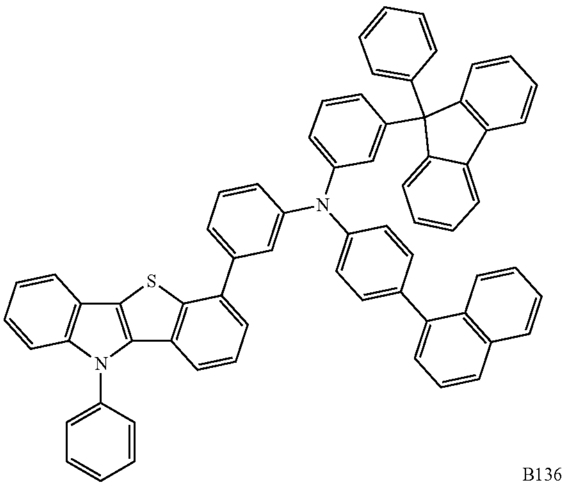
B136
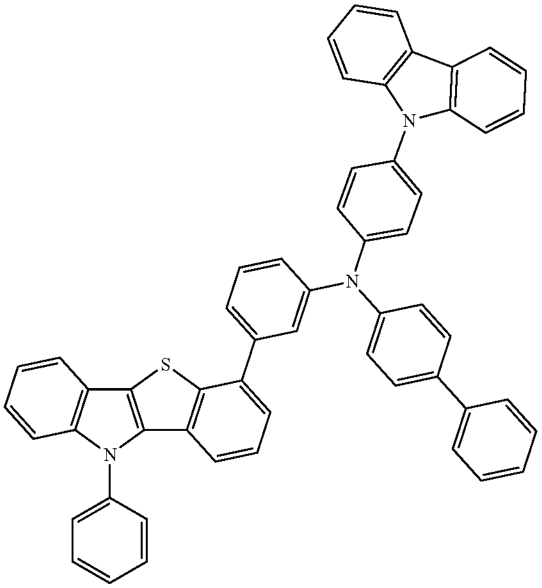
B137
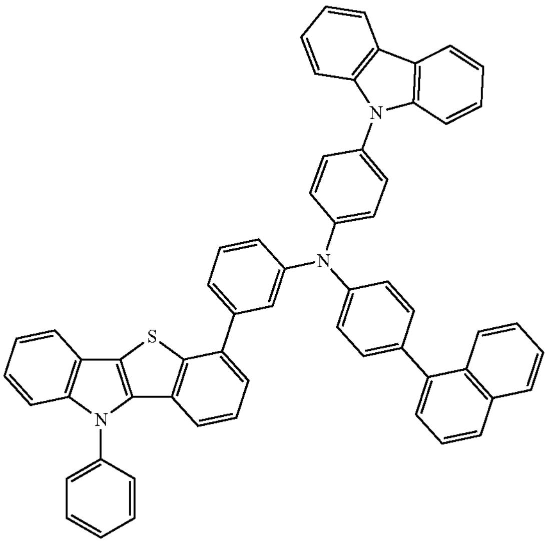
-continued
B138
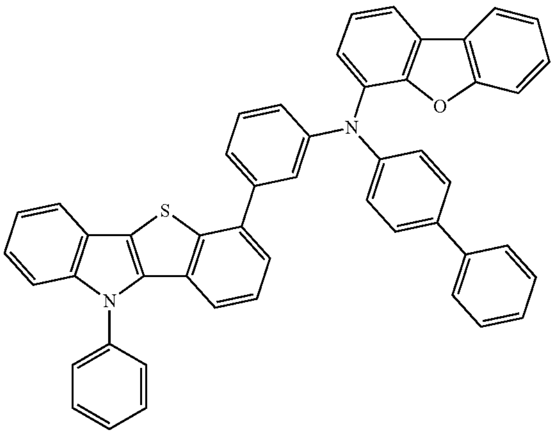
B139
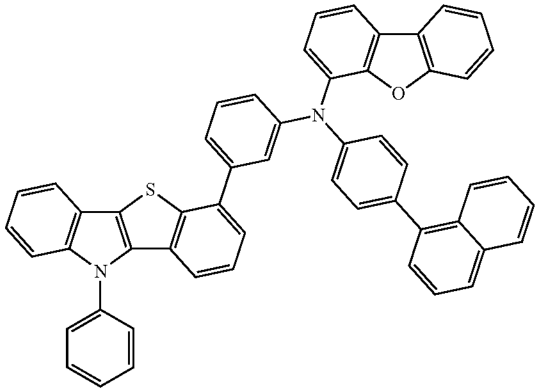
B140
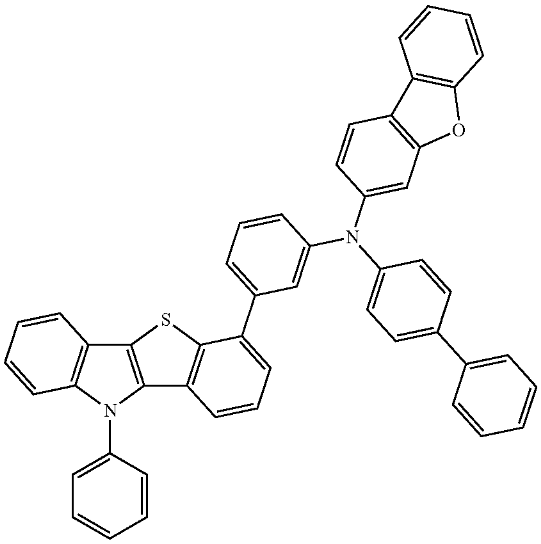

-continued
B141
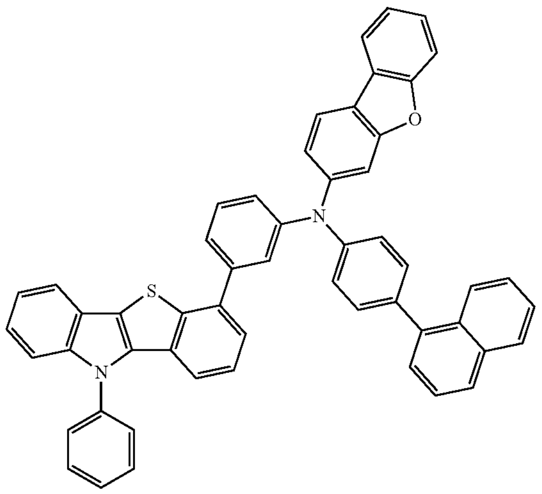
B142
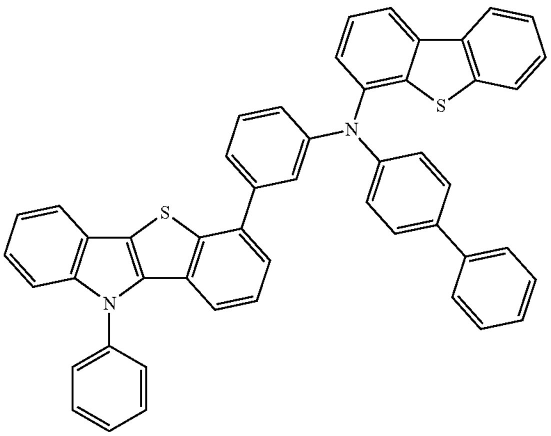
B143
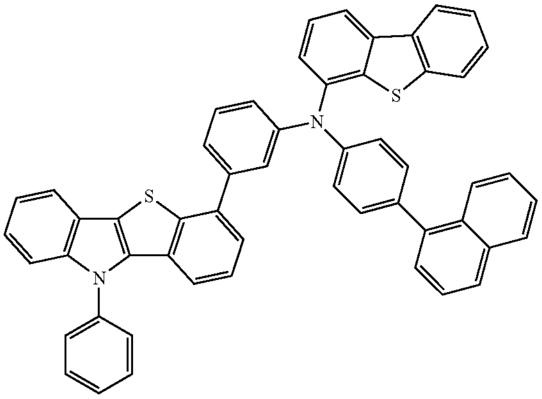
-continued
B144
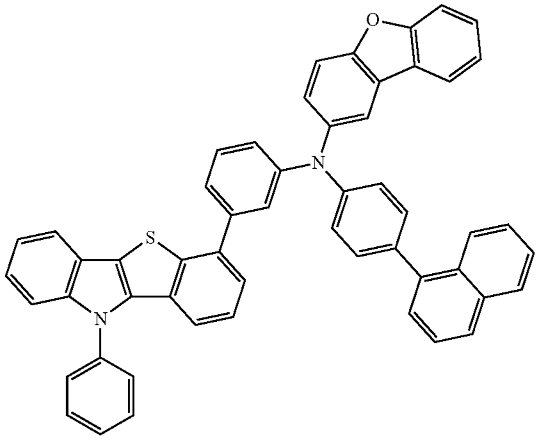
B145
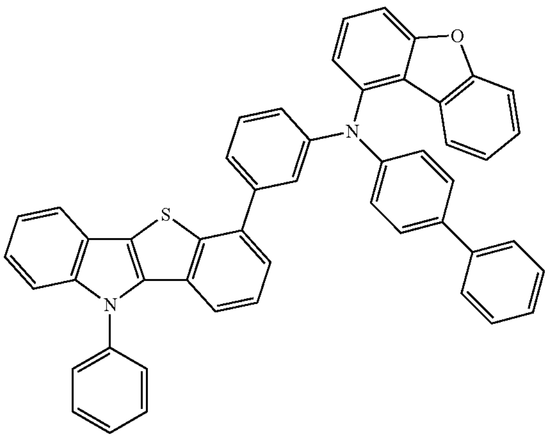
B146
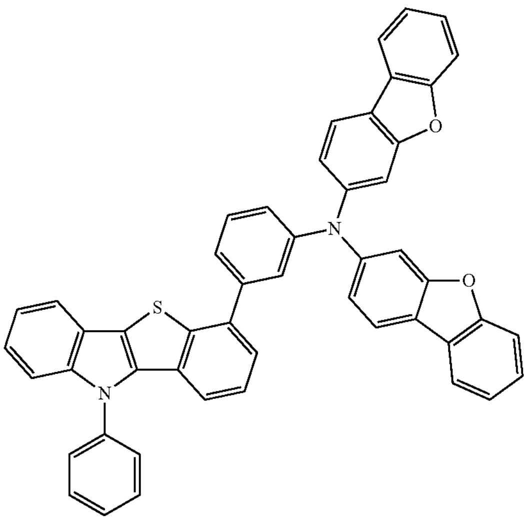

-continued
B147
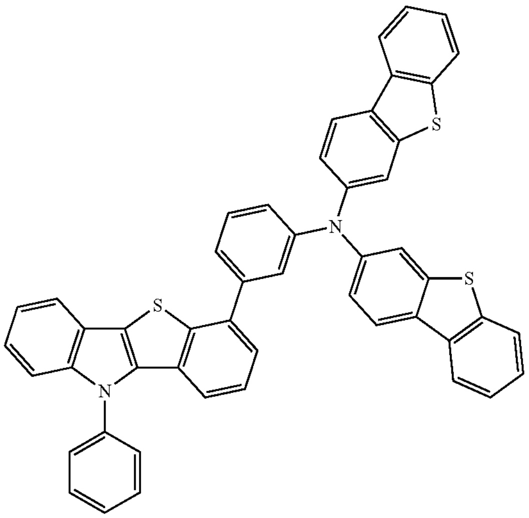
B148
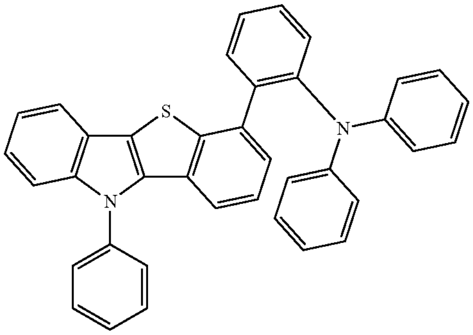
B149
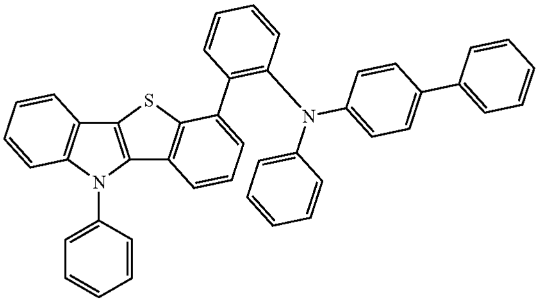
B150
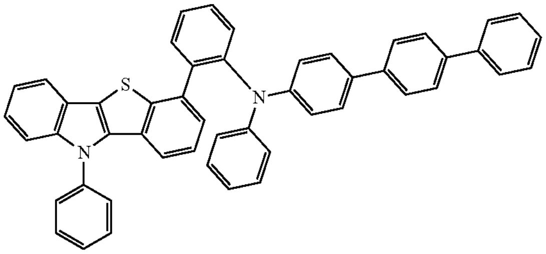
-continued
B151
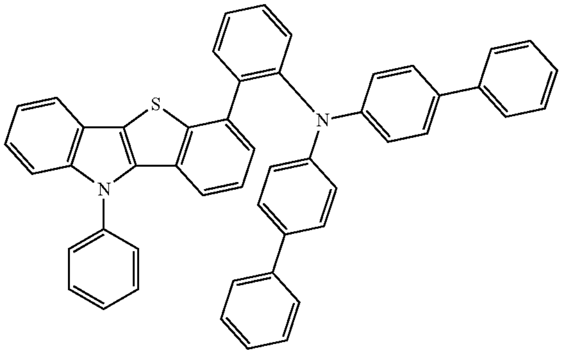
B152
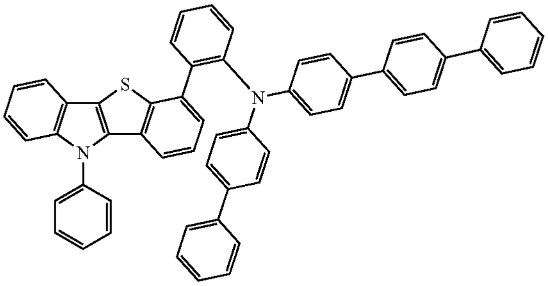
B153
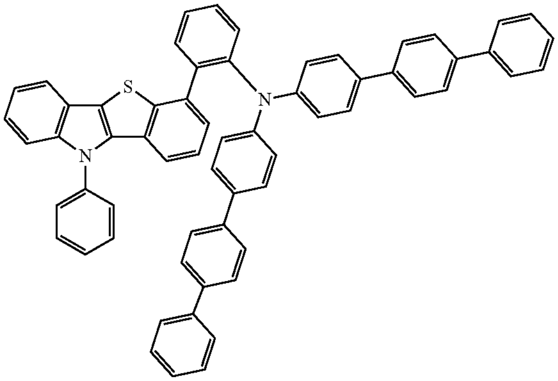
B154
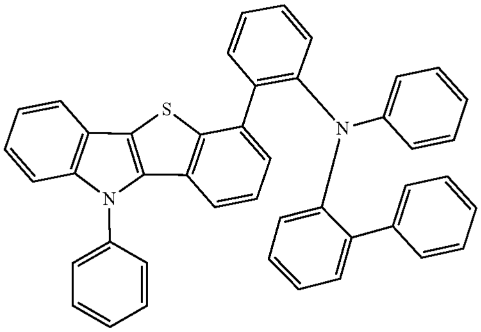

-continued
B155
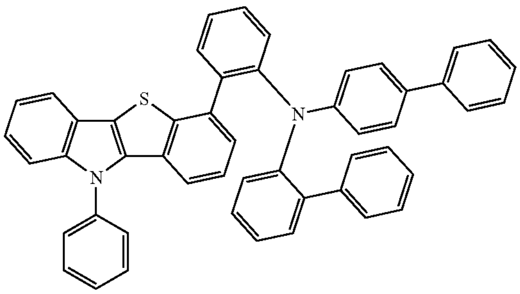
B156
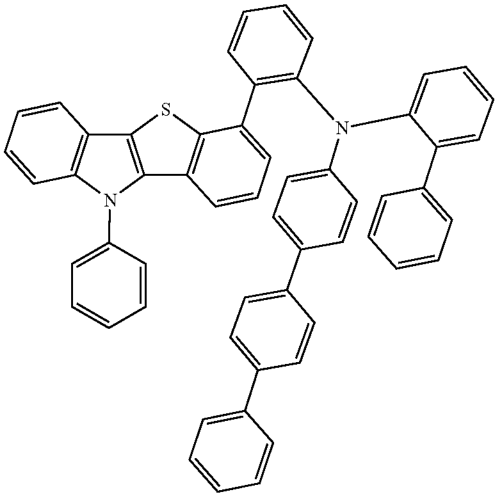
B157
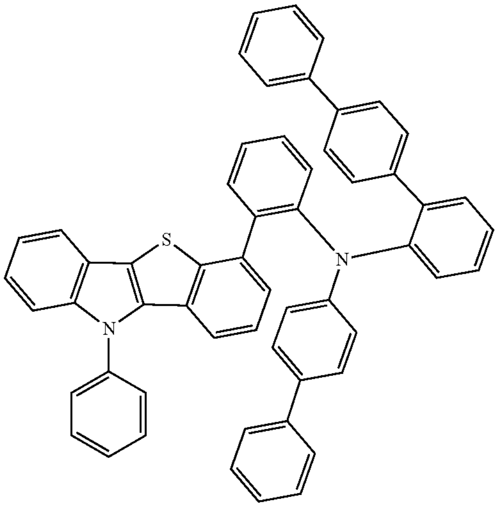
-continued
B158
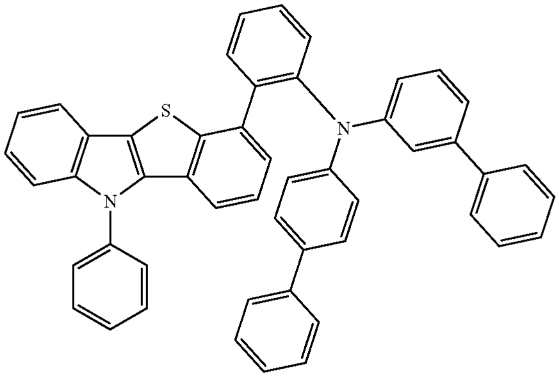
B159
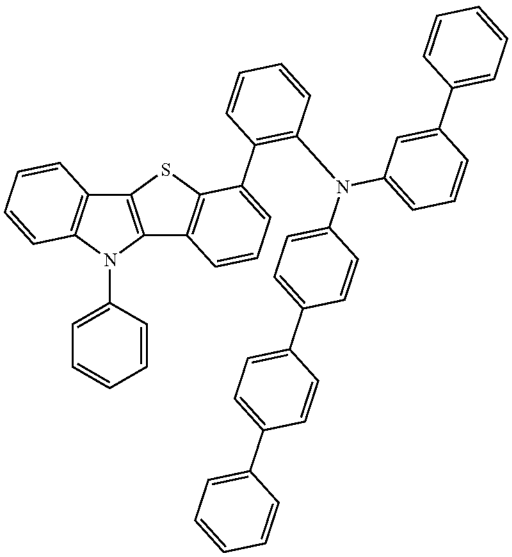
B160
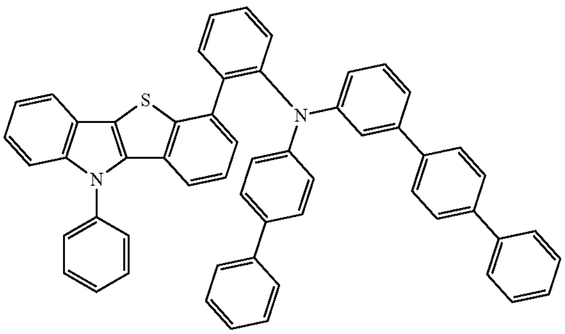

-continued
B161
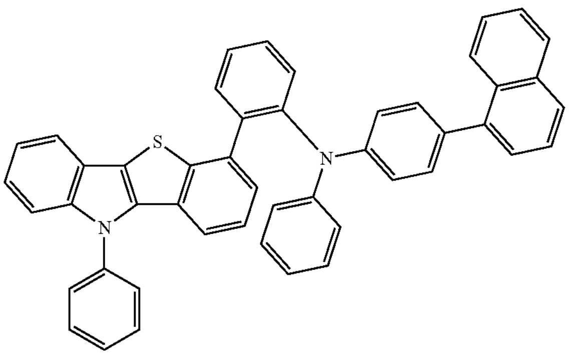
B162
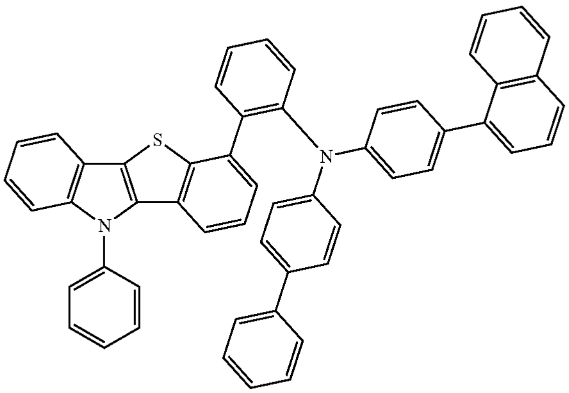
B163
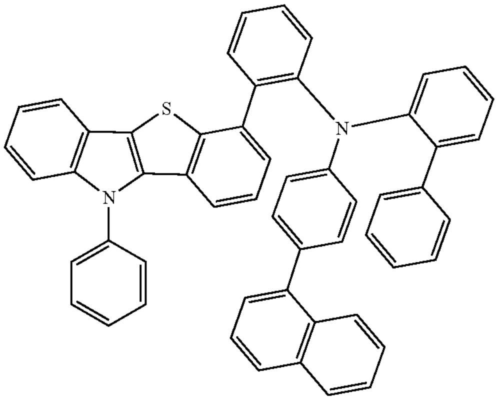
B164
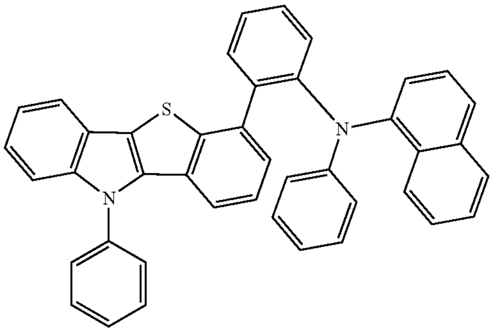
-continued
B165
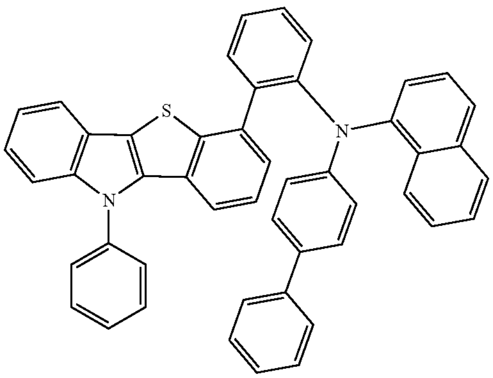
B166
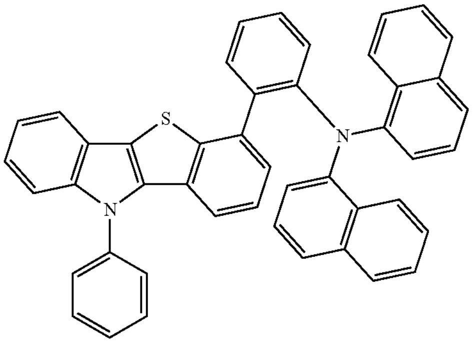
B167
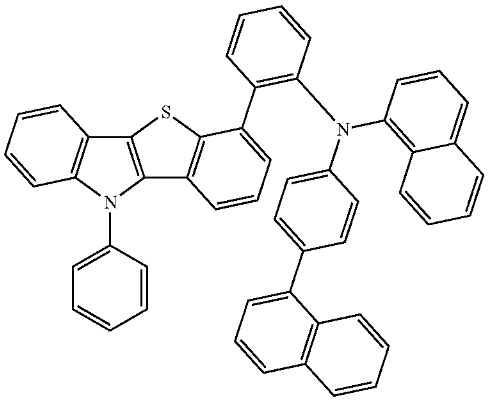
B168
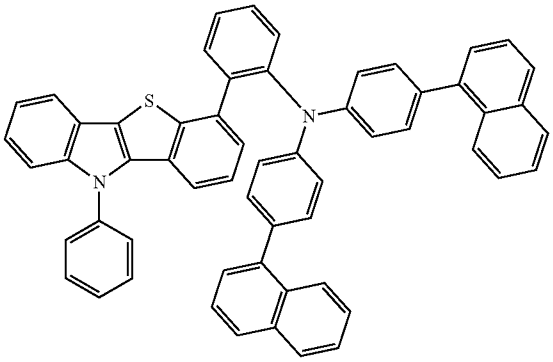

-continued
B169
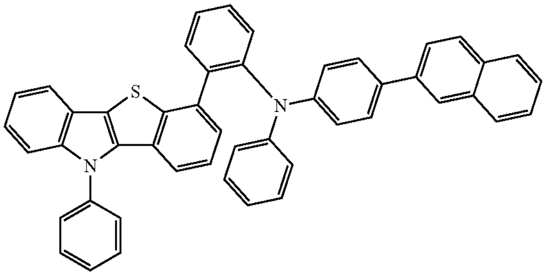
B170
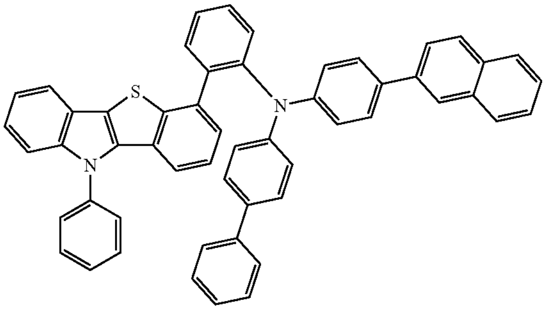
B171
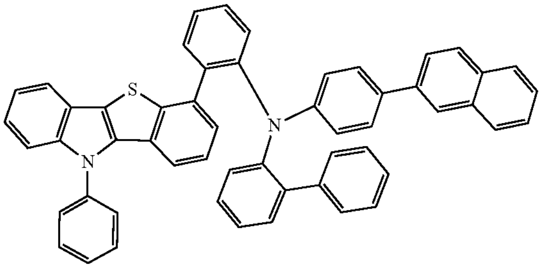
B172
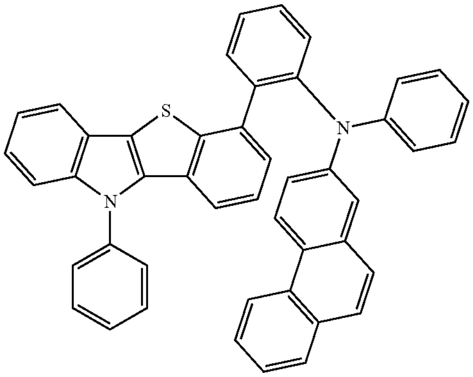
-continued
B173
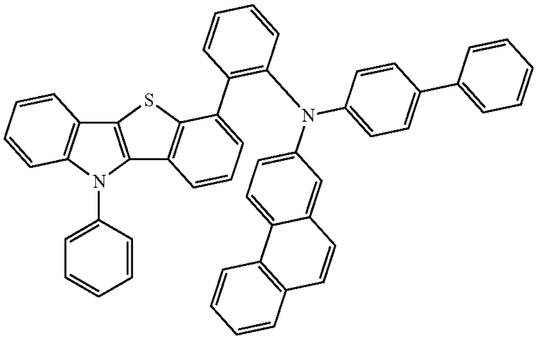
B174
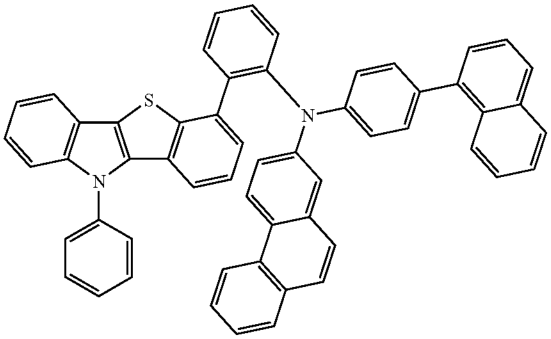
B175
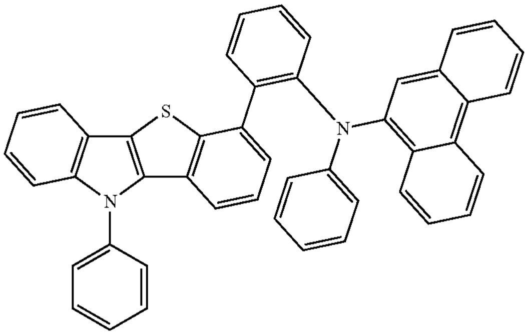
B176
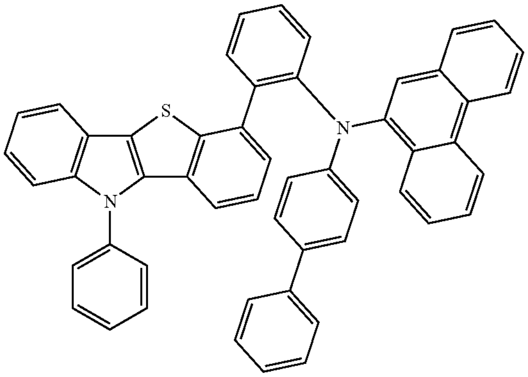

-continued
B177
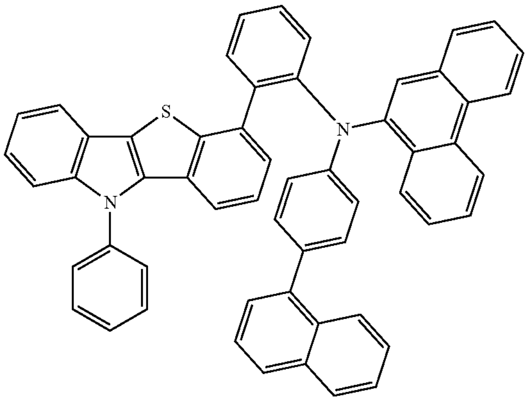
B179
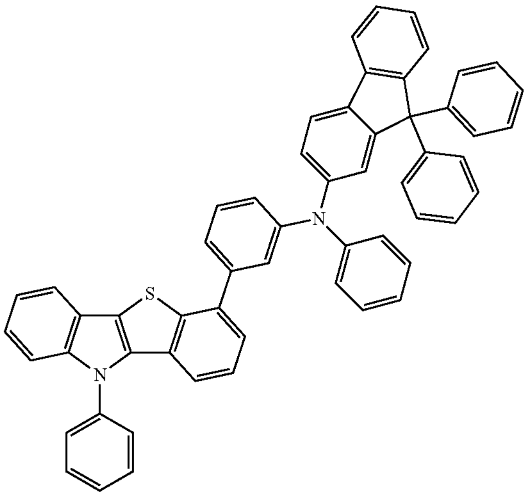
B180
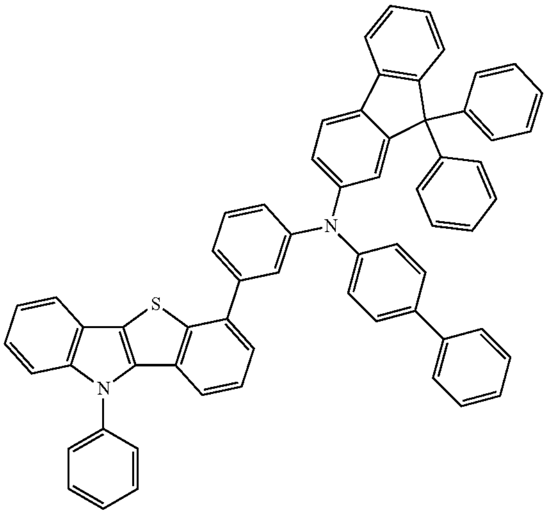
-continued
B181
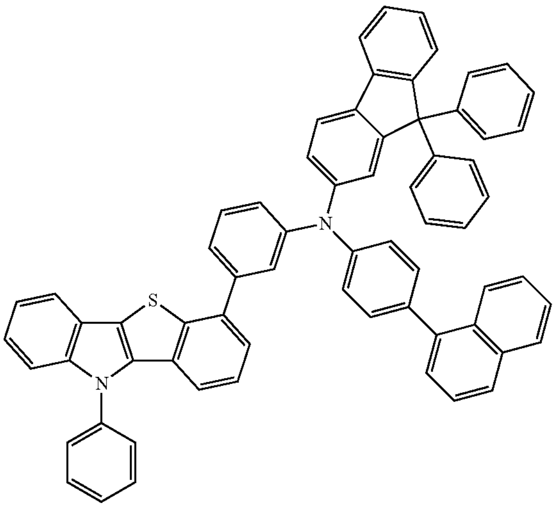
B182
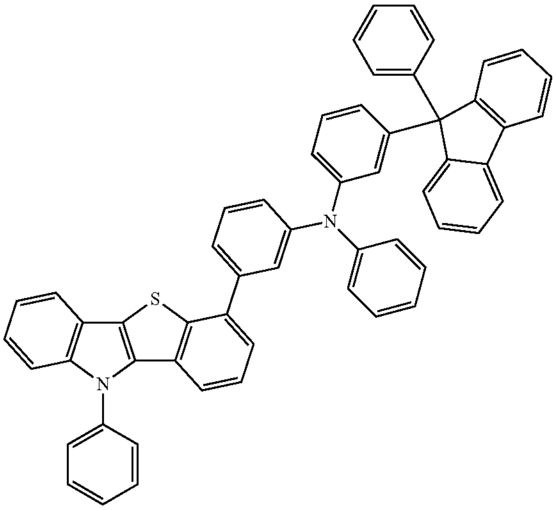
B183
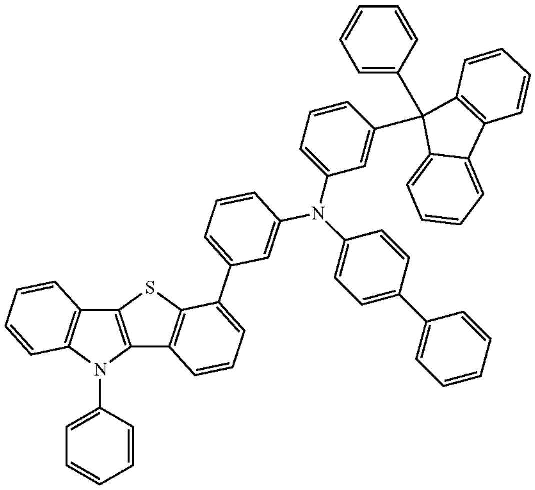

-continued
B184
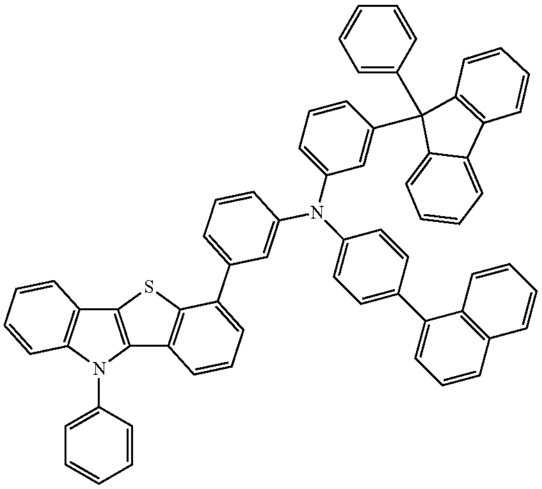
B185
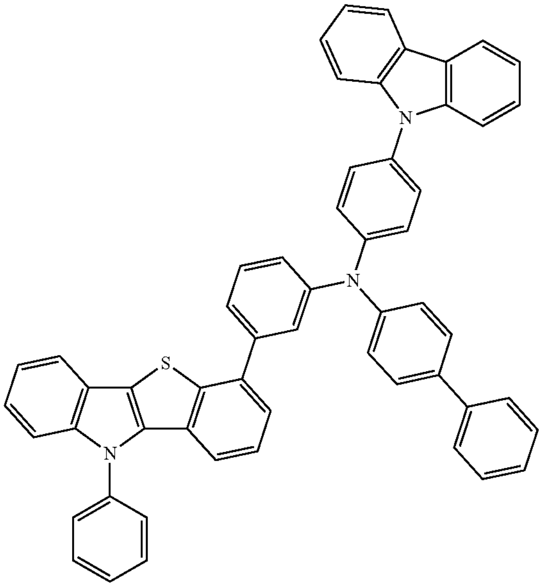
B186
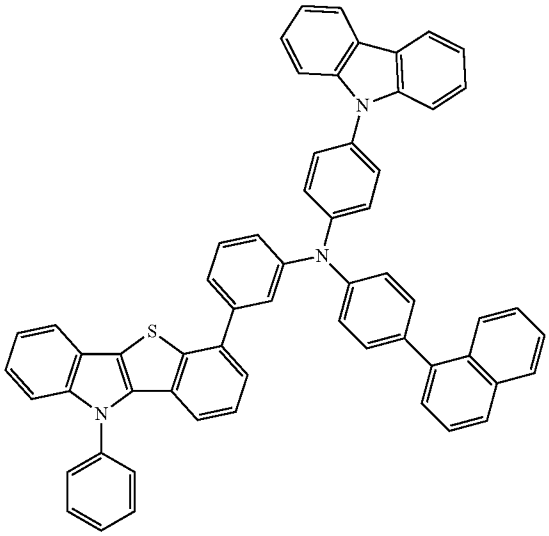
-continued
B187
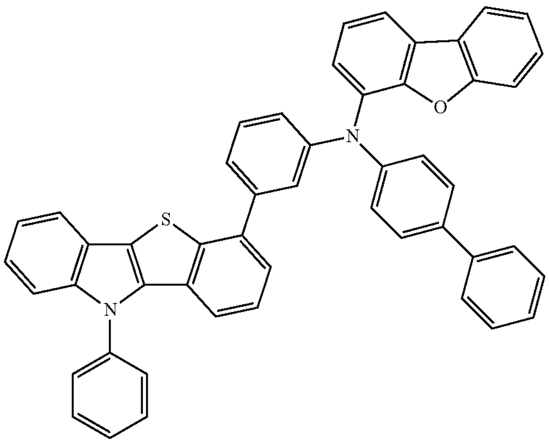
B188
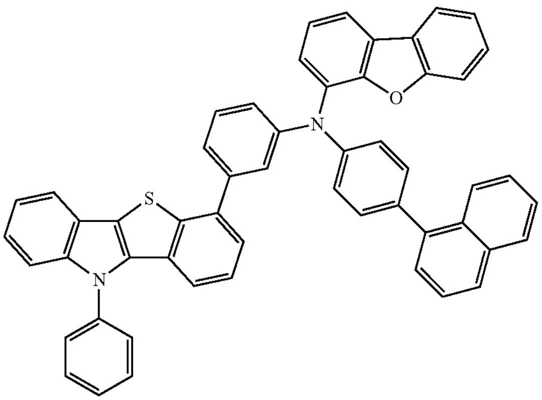
B189
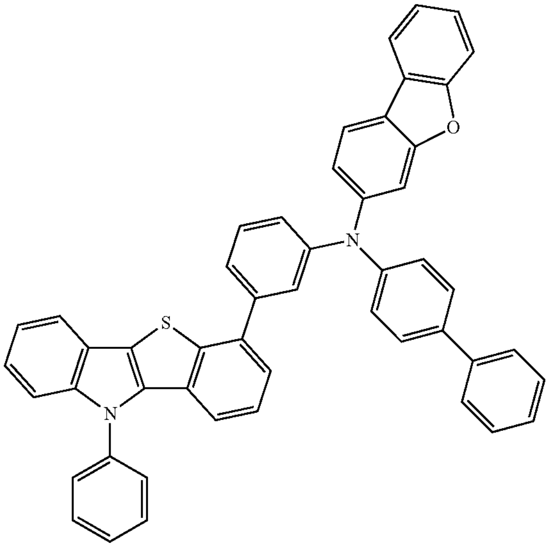

-continued
B190
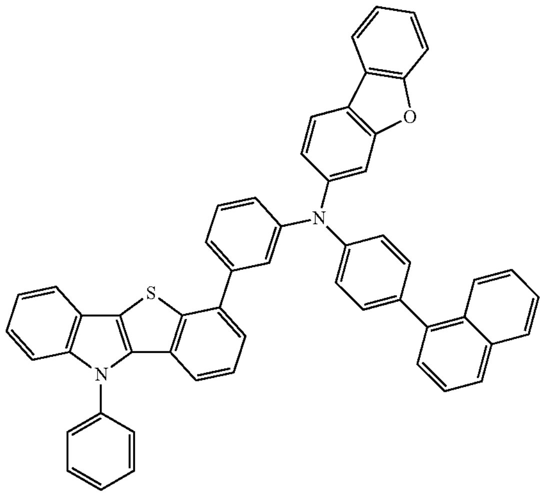
B191
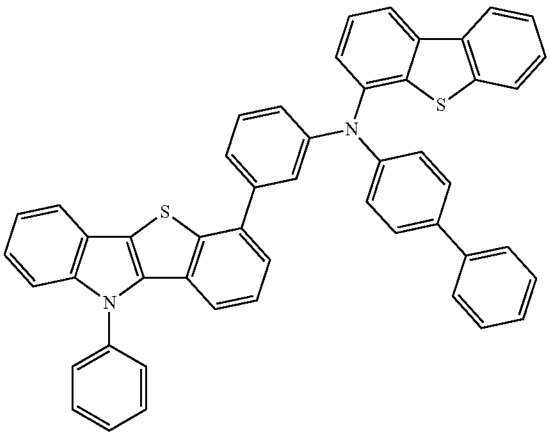
B192
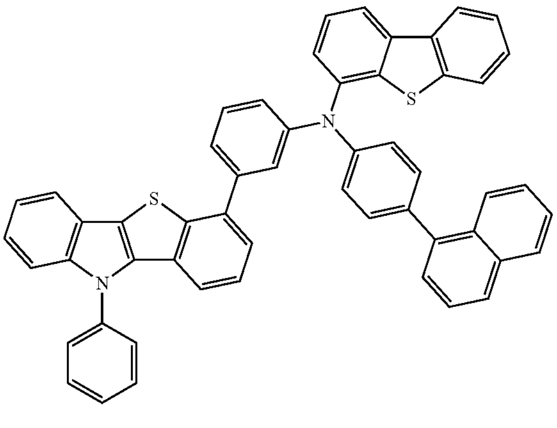
B193
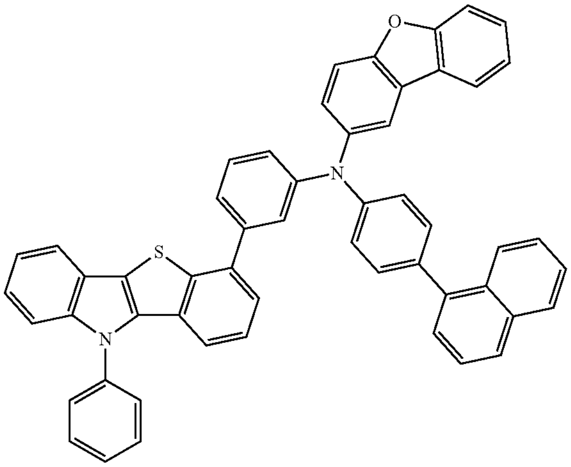
B194
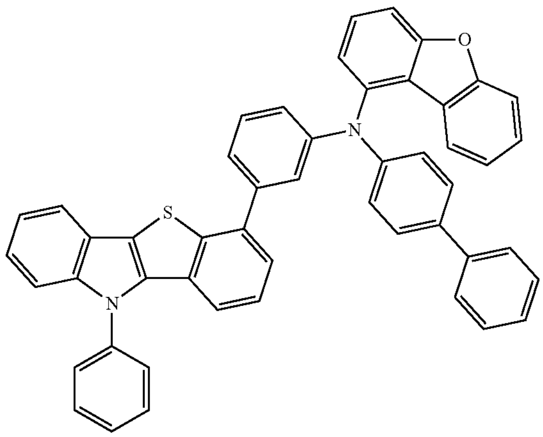
B195
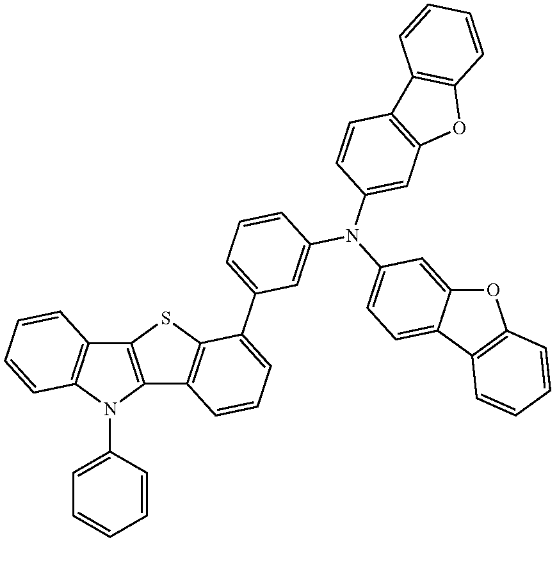

-continued

B196

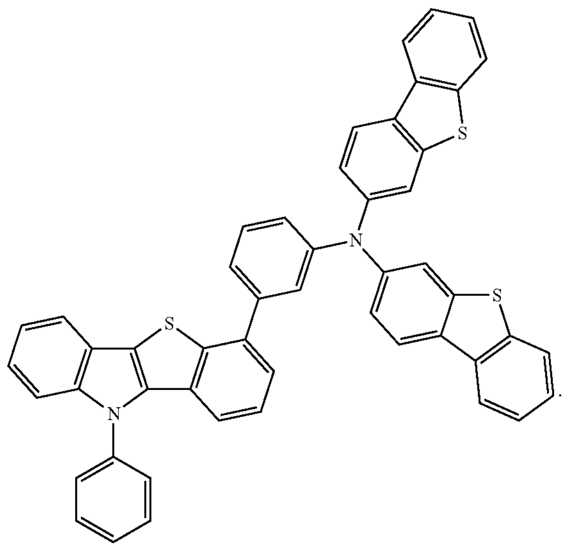

10. A polycyclic compound represented by the following Formula 1:

Formula 1

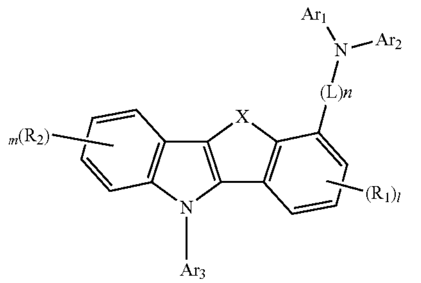

in Formula 1,

X is O, or S, $R_1$ and $R_2$ are a hydrogen atom, wherein $Ar_1$ and $Ar_2$ are each independently represented by Formula 2:

$$*-(Ar_{11})_p-Ar_{12}$$ Formula 2 in Formula 2, $Ar_{11}$ is an unsubstituted phenylene group, or an unsubstituted divalent biphenyl group, $Ar_{12}$ is an unsubstituted phenyl group, an unsubstituted biphenyl group, an unsubstituted terphenyl group, an unsubstituted phenanthryl group, an unsubstituted fluorenyl group, a fluorenyl group substituted with a substituted or unsubstituted aryl group of 6 to 30 ring carbon atoms, an unsubstituted naphthyl group, an unsubstituted carbazolyl group, an unsubstituted dibenzofuranyl group, or an or unsubstituted dibenzothiophenyl group, and p is 0 or 1, $Ar_3$ is an unsubstituted aryl group of 6 to 30 ring carbon atoms, L is an unsubstituted arylene group of 6 to 30 ring carbon atoms, 1 is an integer of 0 to 3, m is an integer of 0 to 4, and n is 1.

11. The polycyclic compound of claim 10, wherein the polycyclic compound comprises one acyclic amine.

12. The polycyclic compound of claim 10, wherein Formula 1 is represented by the following Formula 1-1 or Formula 1-2:

Formula 1-1

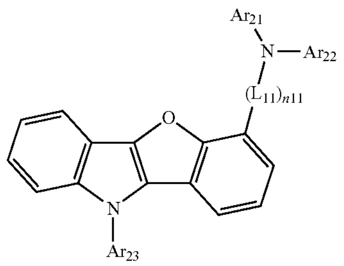

Formula 1-2

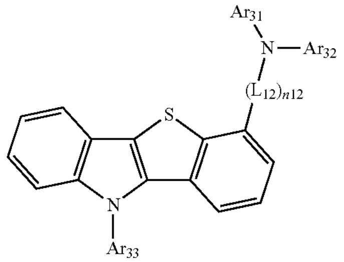

in Formula 1-1 and Formula 1-2, $Ar_{21}$ to $Ar_{23}$, and $Ar_{31}$ to $Ar_{33}$ are each independently represented by Formula 2, $L_{11}$, and $L_{12}$ are each independently an unsubstituted arylene group of 6 to 30 ring carbon atoms, and n11, and n12 are each 1.

13. The polycyclic compound of claim 10, wherein $Ar_3$ of Formula 1 is an unsubstituted phenyl group.

14. The polycyclic compound of claim 10, wherein L of Formula 1 is an unsubstituted phenylene group.

15. The polycyclic compound of claim 10, wherein $Ar_1$ and $Ar_2$ are each independently represented by the following 1-1 to 1-8 or 1-10:

1-1

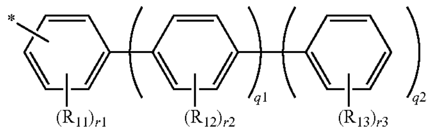

1-2

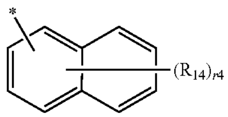

1-3

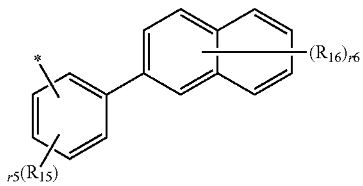

-continued 1-4

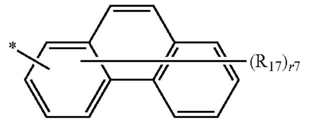

1-5

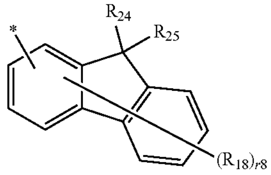

1-6

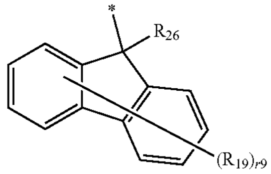

1-7

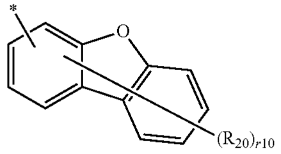

1-8

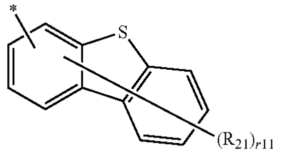

1-10

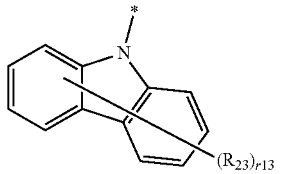

in 1-1 to 1-8 and 1-10 above, $R_{11}$ to $R_{17}$, $R_{20}$, $R_{21}$, and $R_{23}$ are hydrogen atom, $R_{18}$, $R_{19}$, $R_{24}$, $R_{25}$ and $R_{26}$ are each independently a hydrogen atom, or a substituted or unsubstituted aryl group of 6 to 30 ring carbon atoms, r1, r2, and r5 are each independently an integer of 0 to 4, r3 is an integer of 0 to 5, r4, r6, and r8 to r11 are each independently an integer of 0 to 7, r7 is an integer of 0 to 9, r13 is an integer of 0 to 8, and q1 and q2 are each independently 0 or 1.

16. The polycyclic compound of claim 10, wherein Formula 1 is represented by the following Formula 1-5:

Formula 1-5

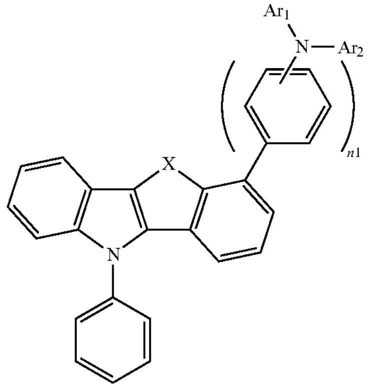

in Formula 1-5, n1 is 1, and

X, $Ar_1$, and $Ar_2$ are the same as defined in Formula 1.

17. The polycyclic compound of claim 10, wherein Formula 1 is any one selected among Compound Group 1 or Compound Group 2:

A50

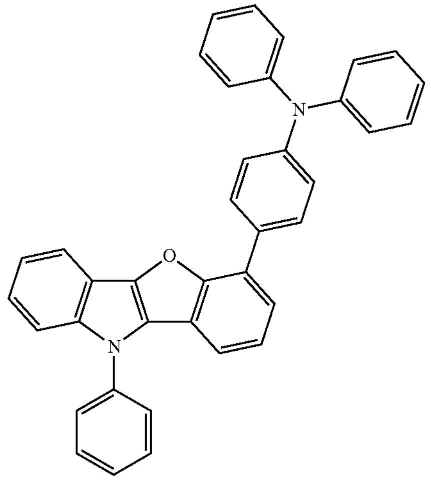

A51

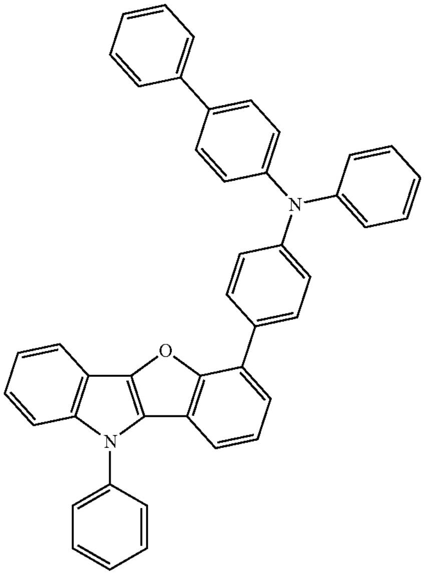

-continued
A52
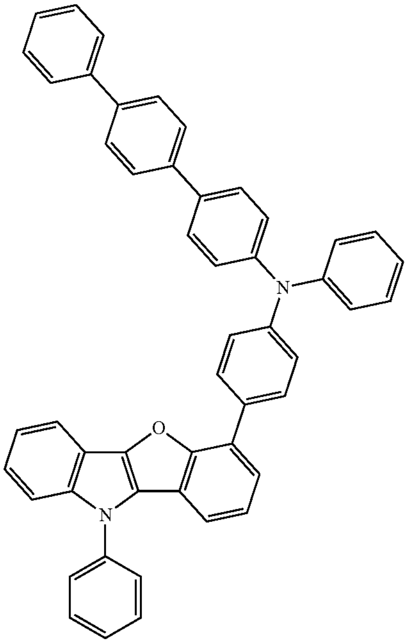
A53
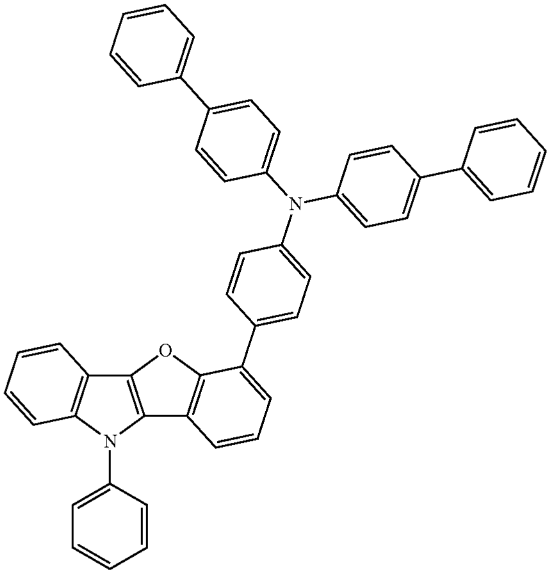
-continued
A54
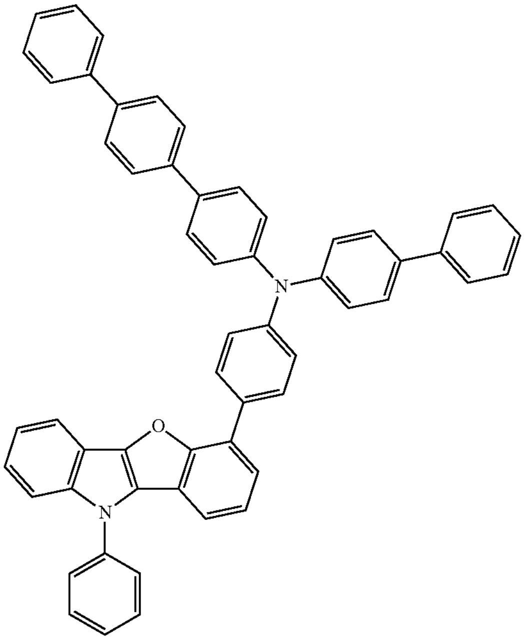
A55
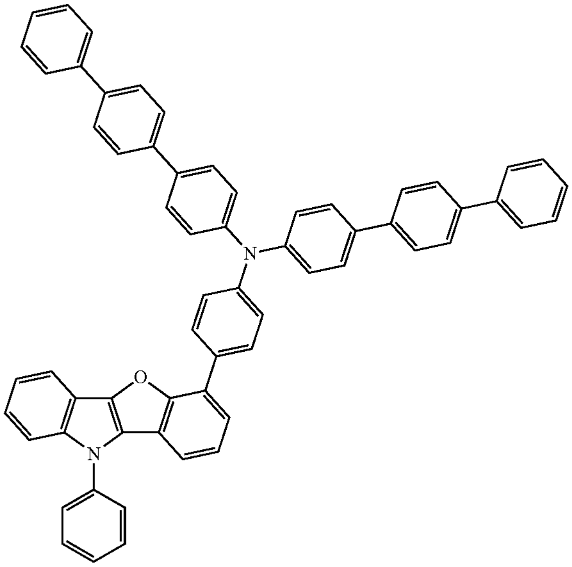

-continued
A56
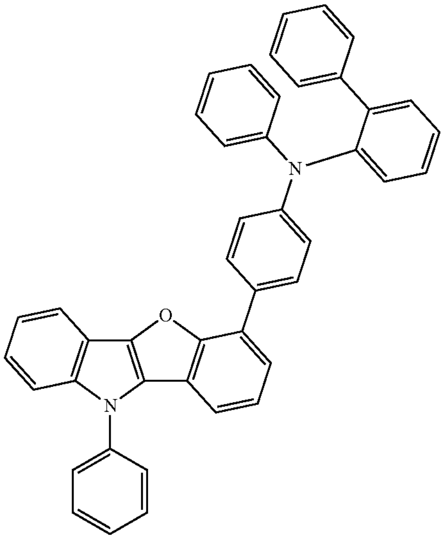
A57
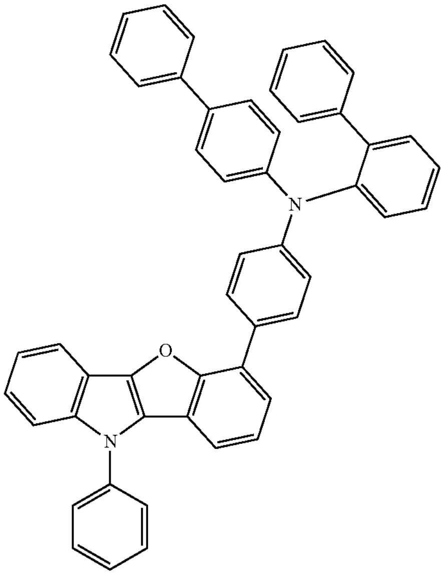
A58
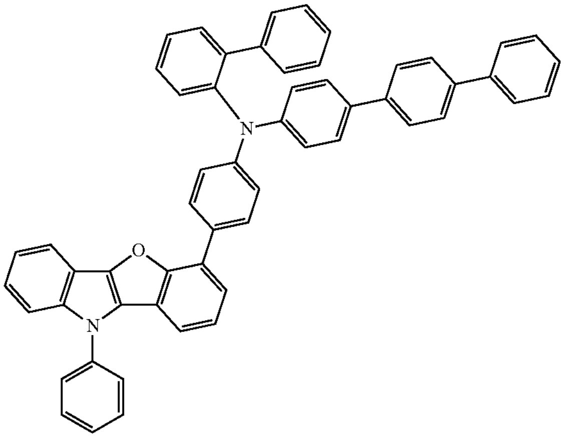
-continued
A59
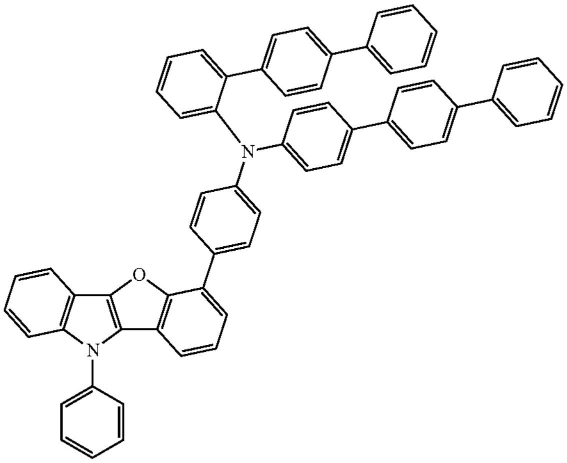
A60
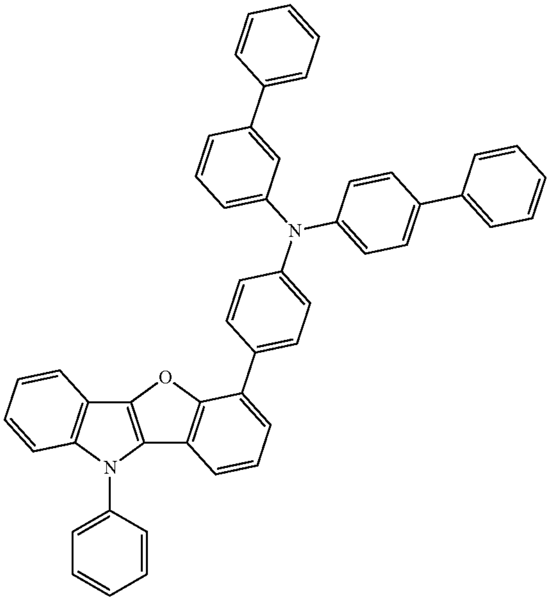
A61
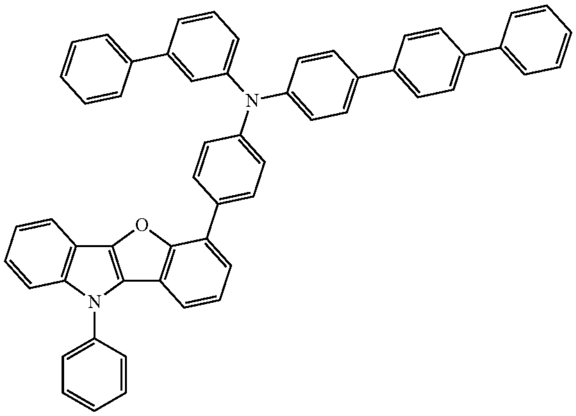

-continued
A62
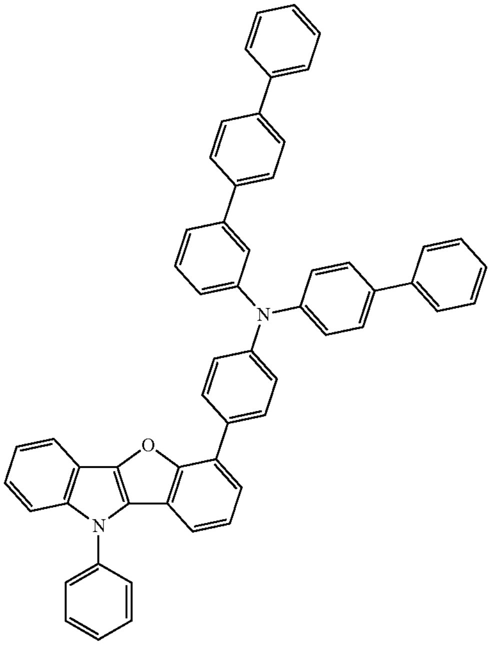
-continued
A64
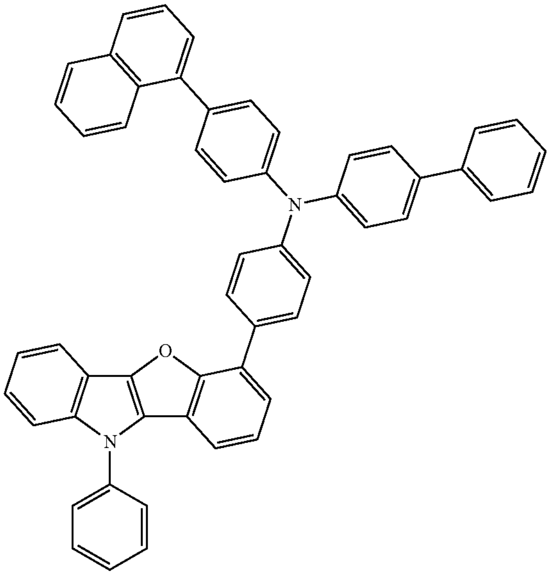
A63
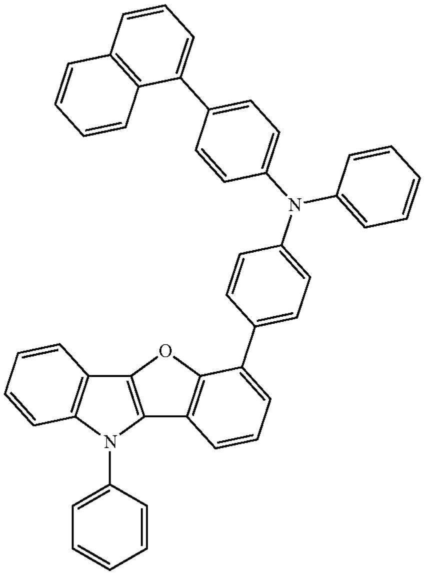
A65
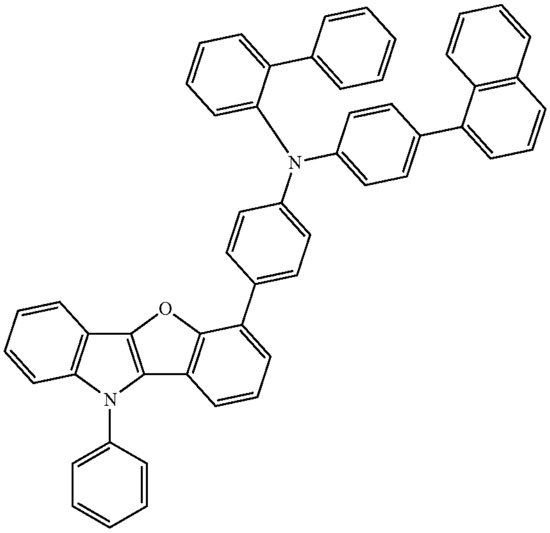

-continued
A66
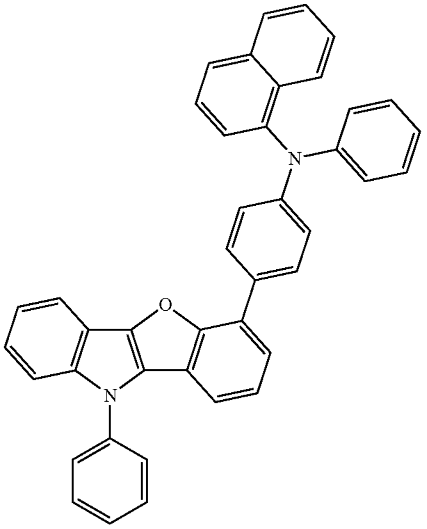
A67
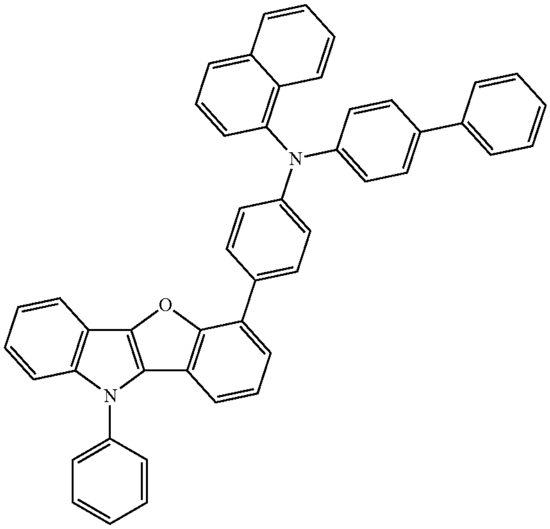
A68
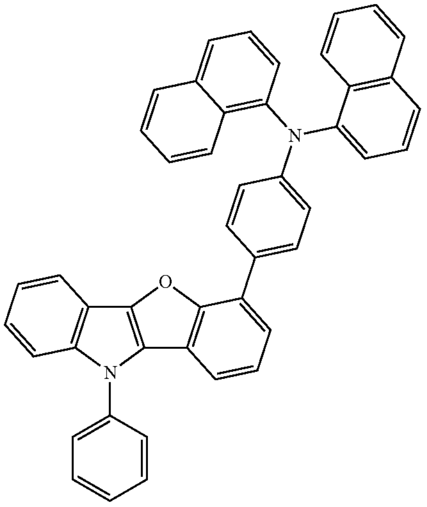
-continued
A69
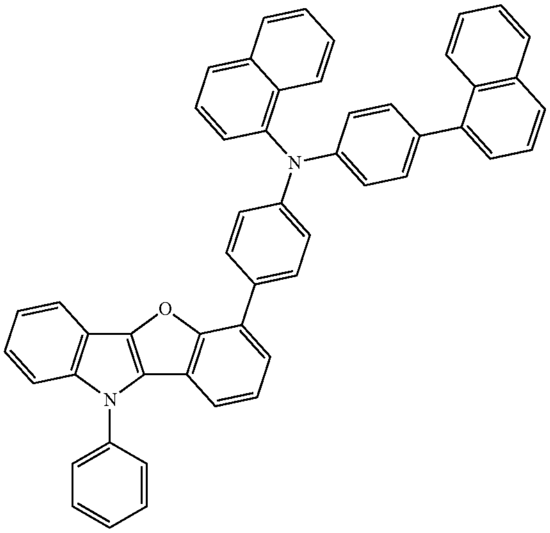
A70
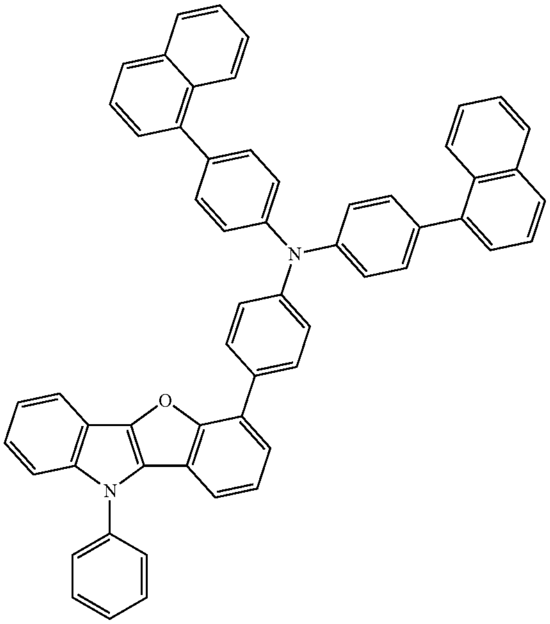

-continued
A71
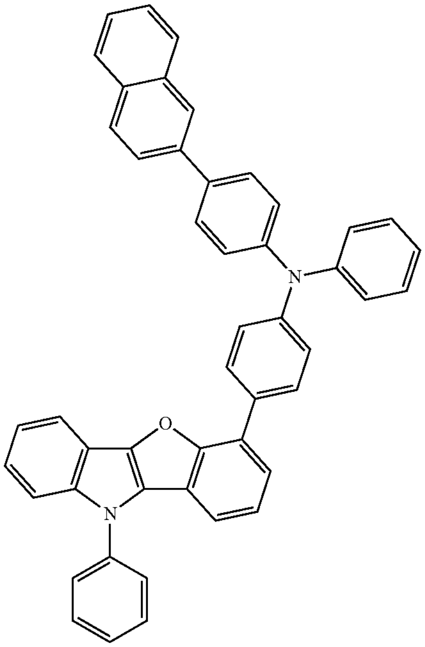
A72
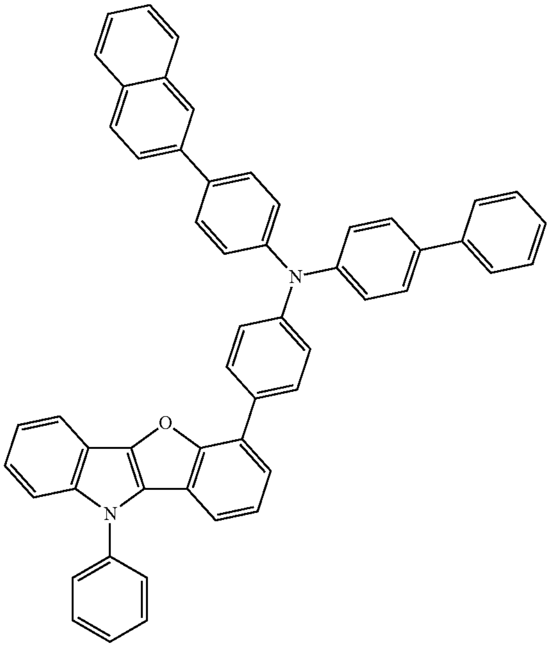
-continued
A73
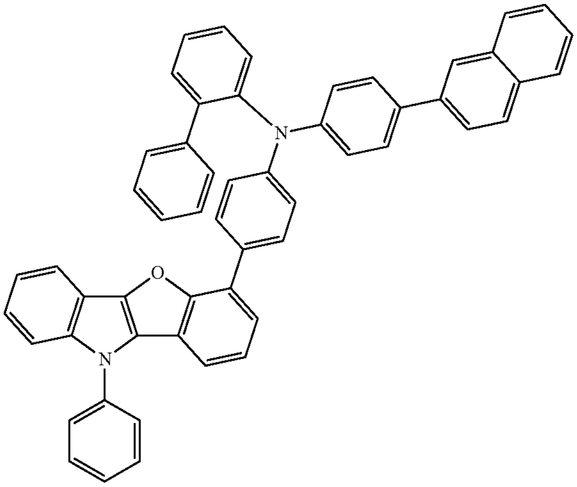
A74
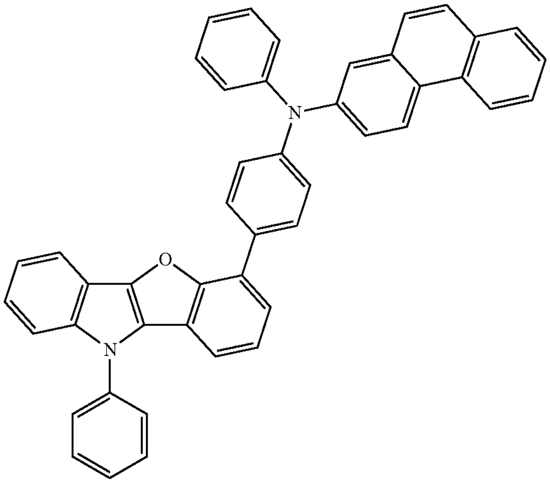
A75
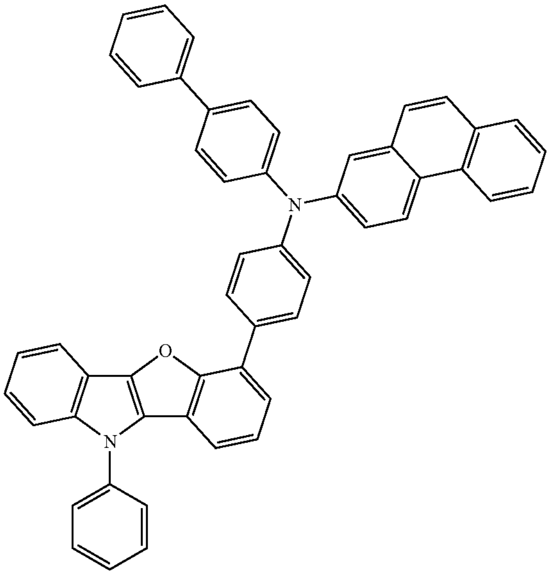

A76
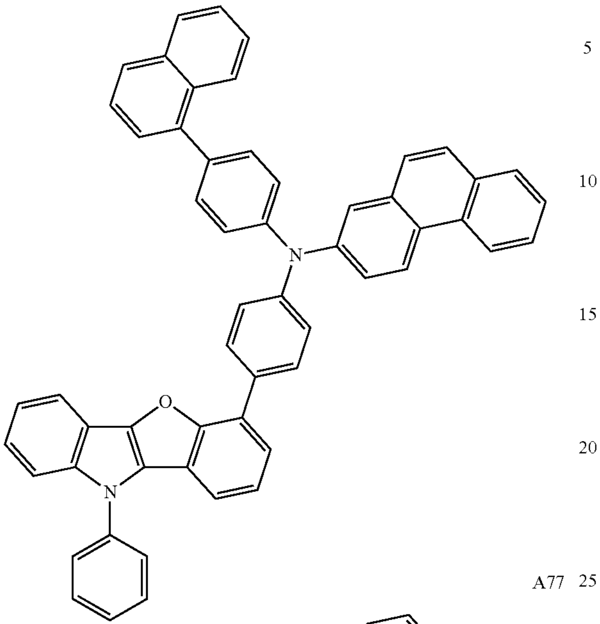
A77
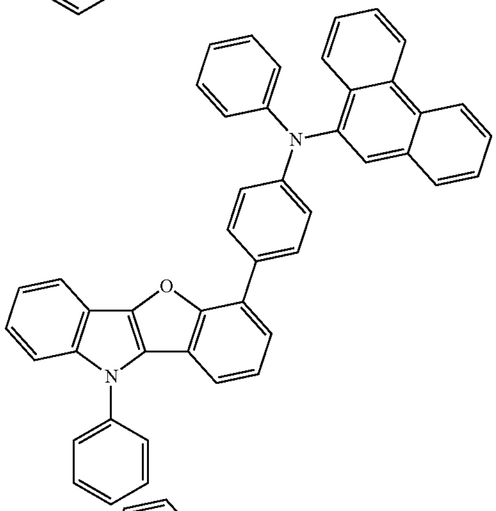
A78
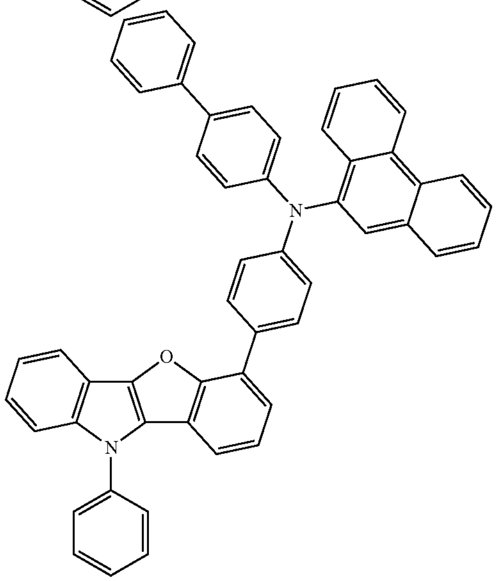
A79
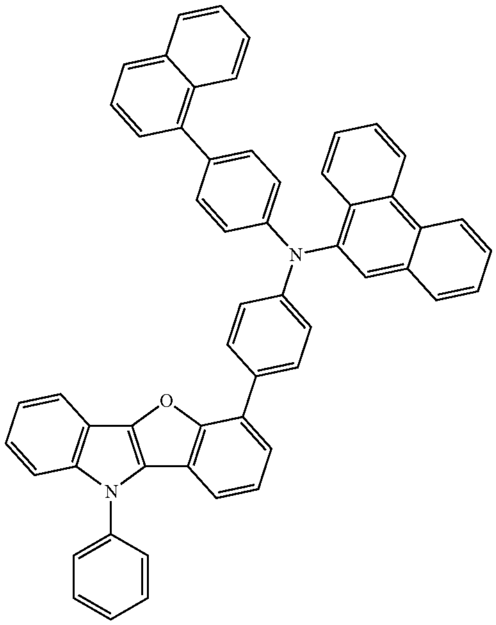
A81
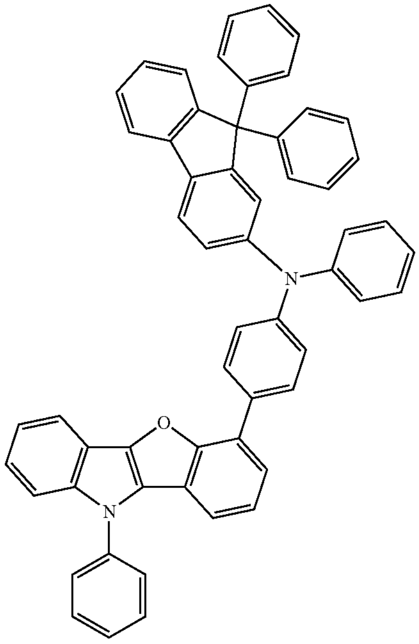

-continued
A82
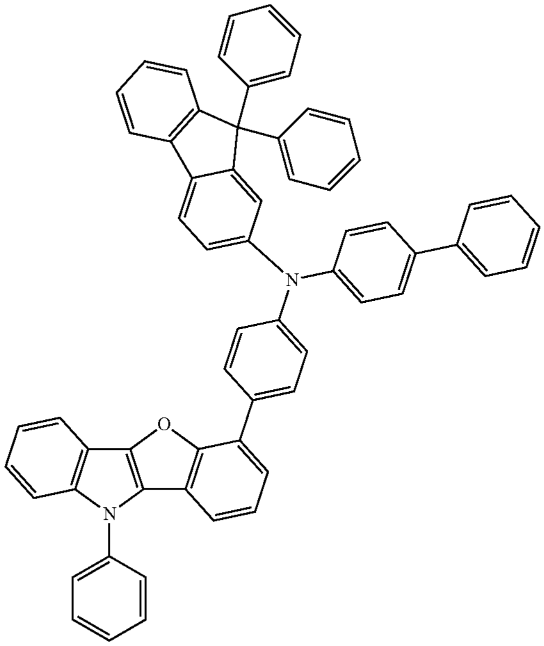
A83
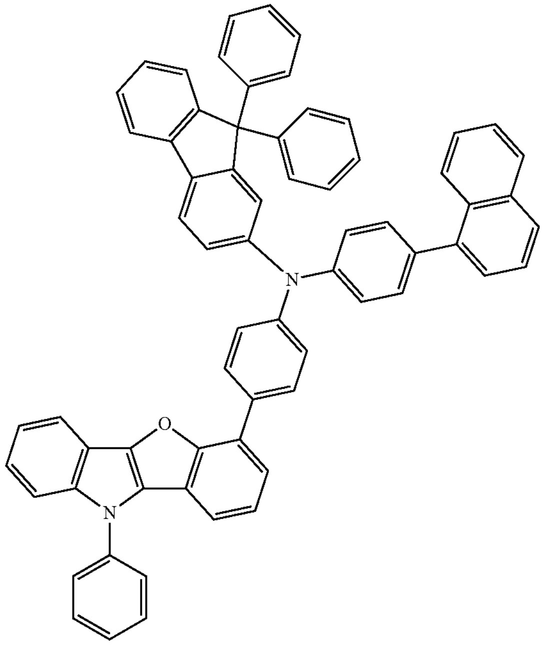
-continued
A84
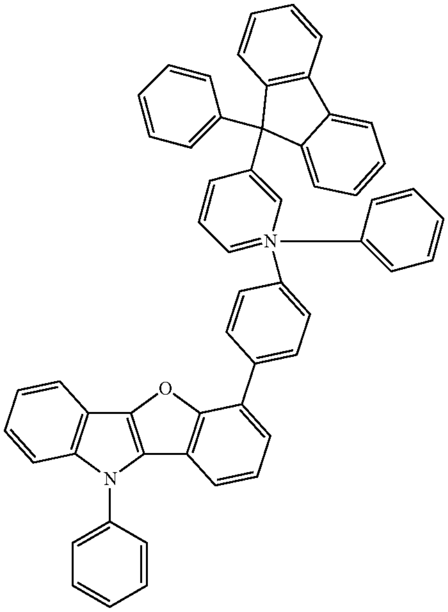
A85
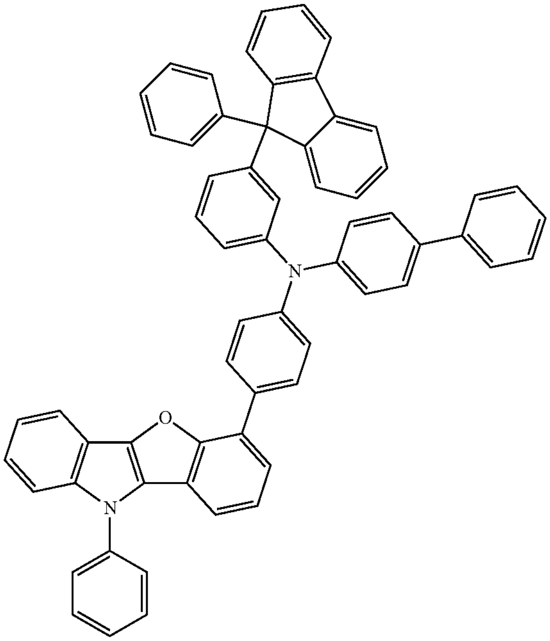

-continued
A86
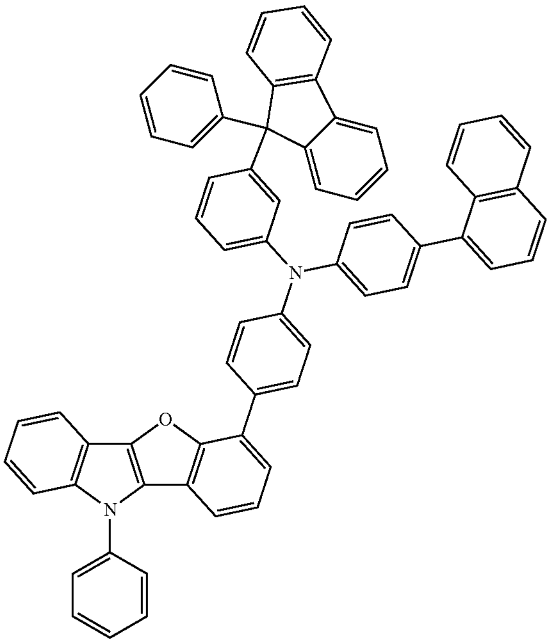
A87
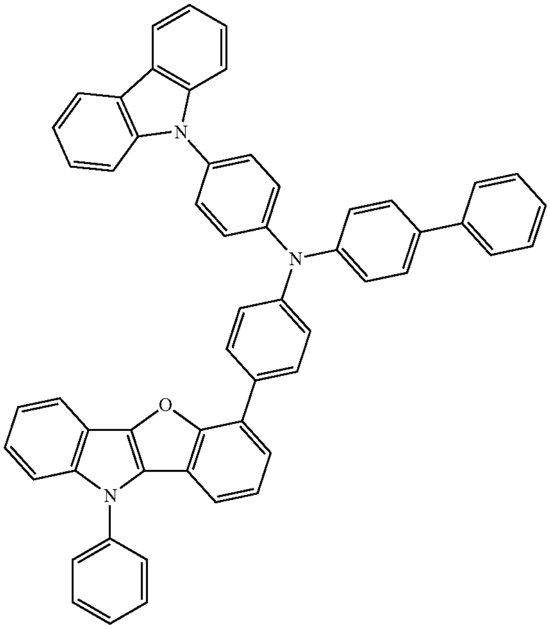
-continued
A88
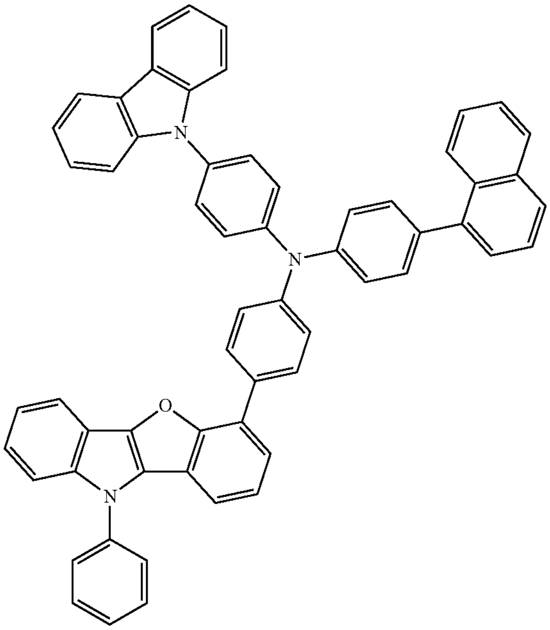
A89
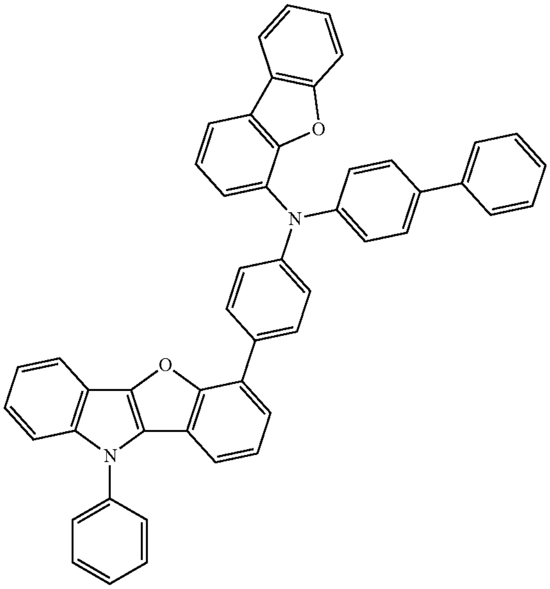

-continued
A90
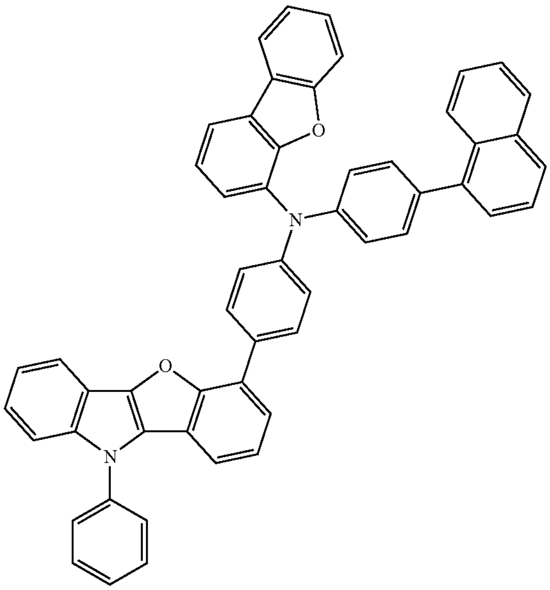
A91
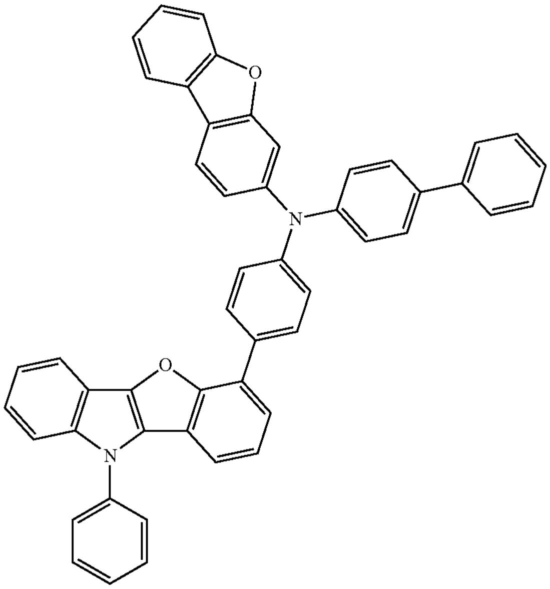
-continued
A92
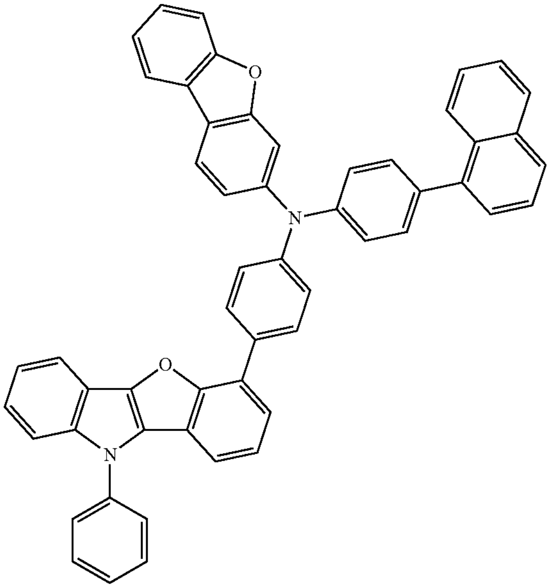
A93
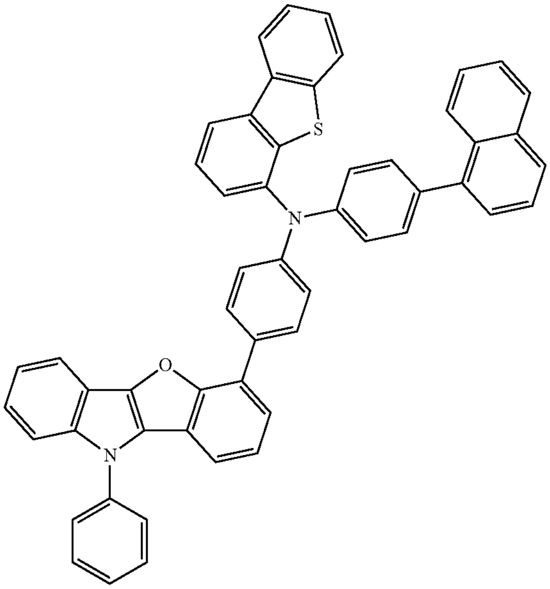

-continued
A94
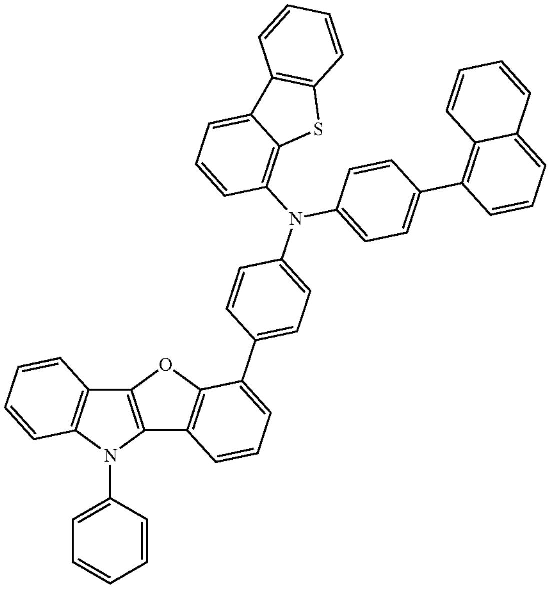
A95
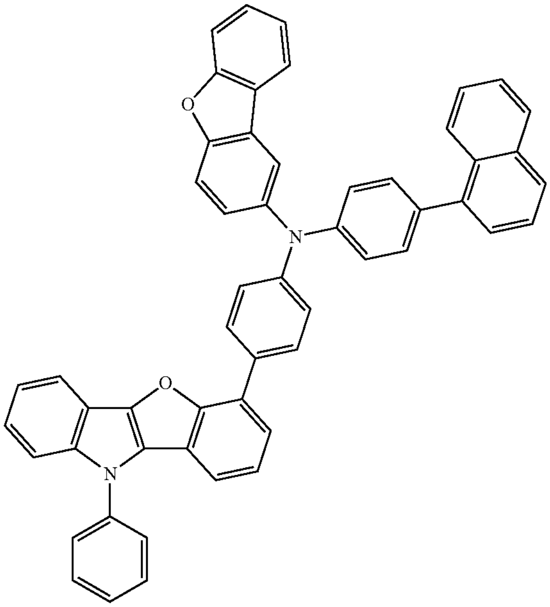
-continued
A96
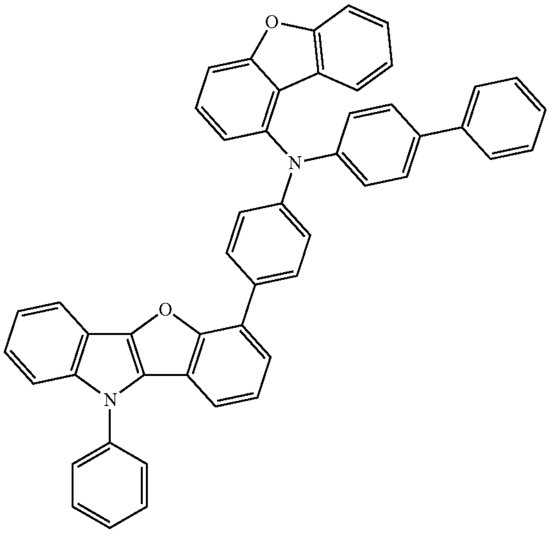
A97
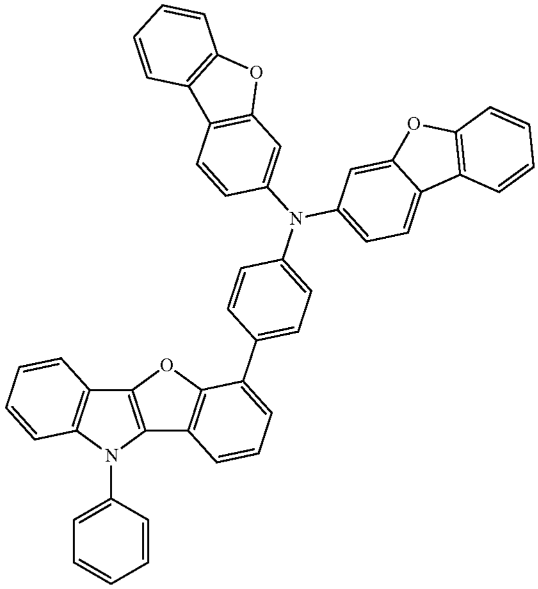

-continued
A98
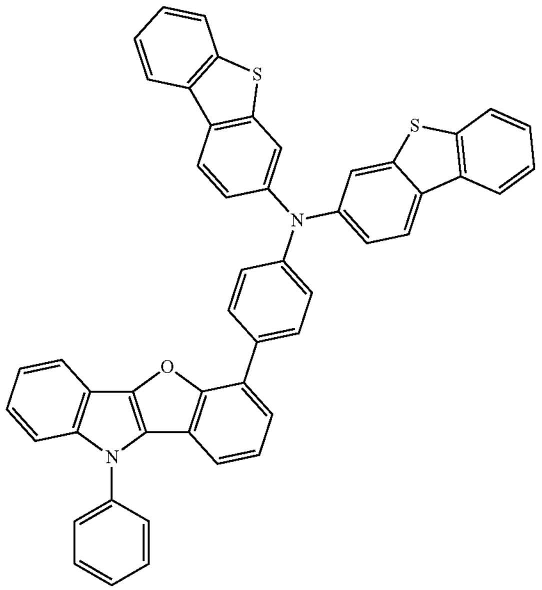
A99
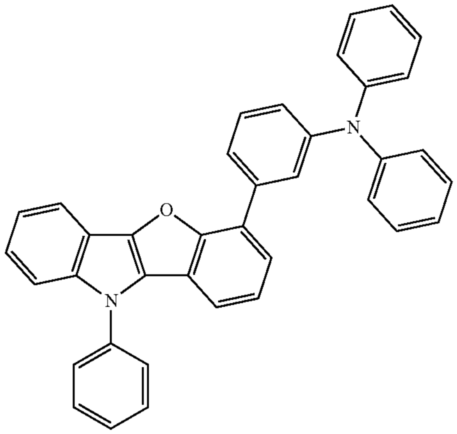
A100
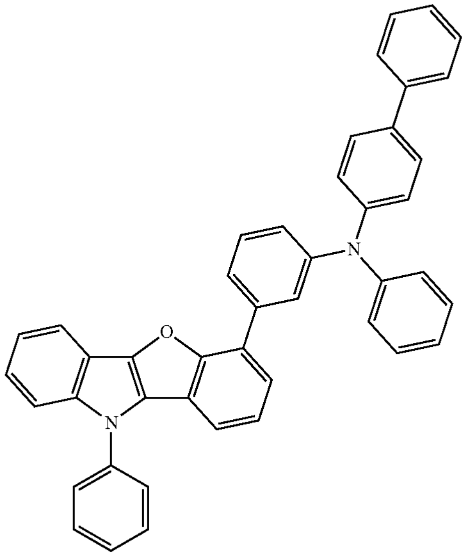
-continued
A101
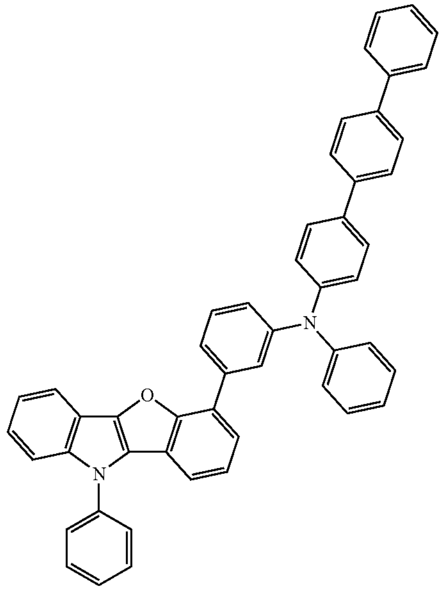
A102
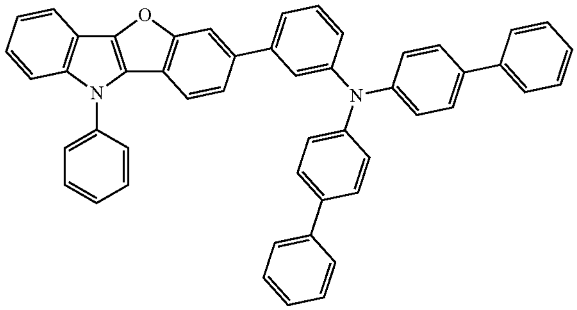
A103
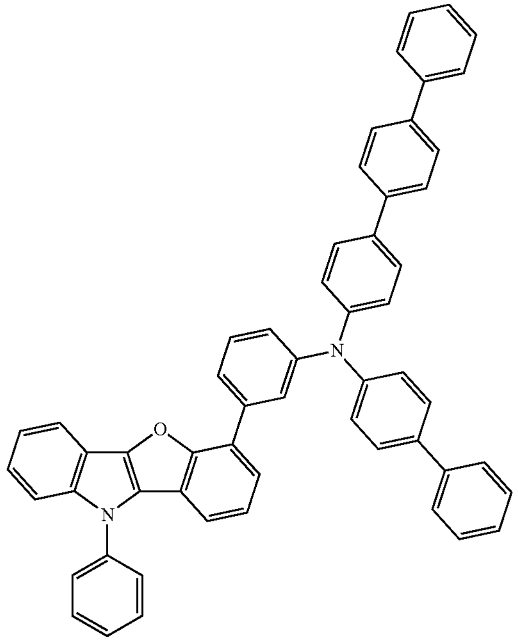

-continued
A104
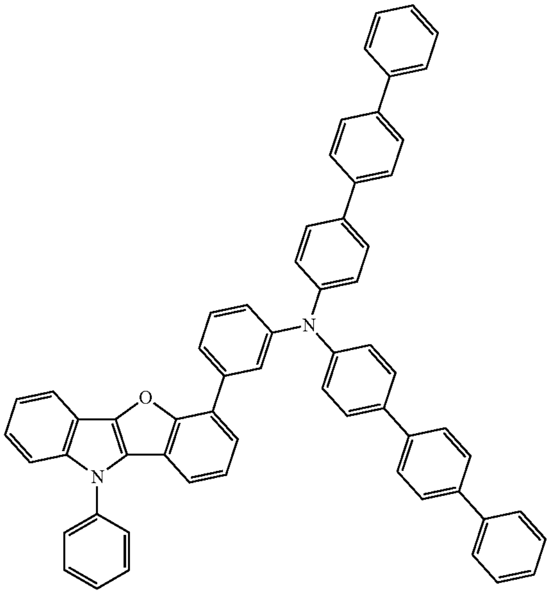
A105
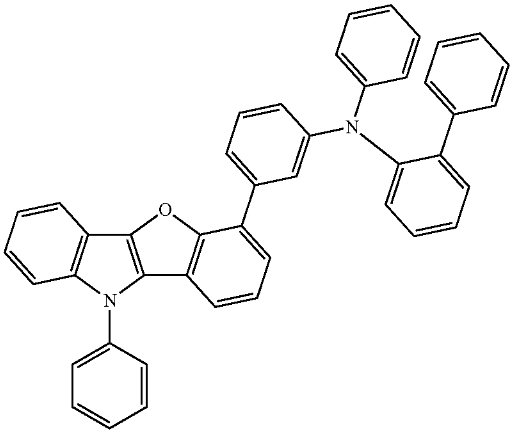
A106
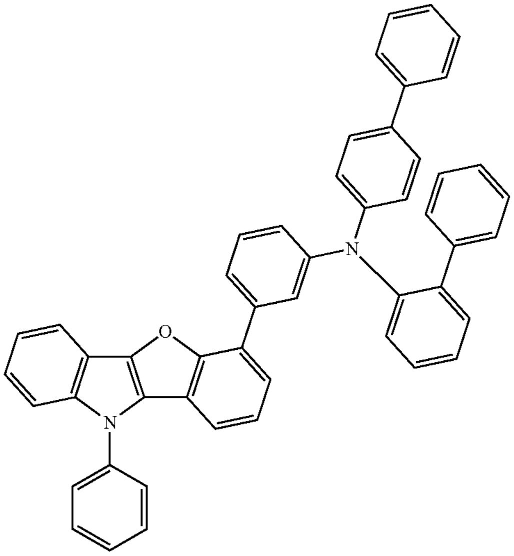
-continued
A107
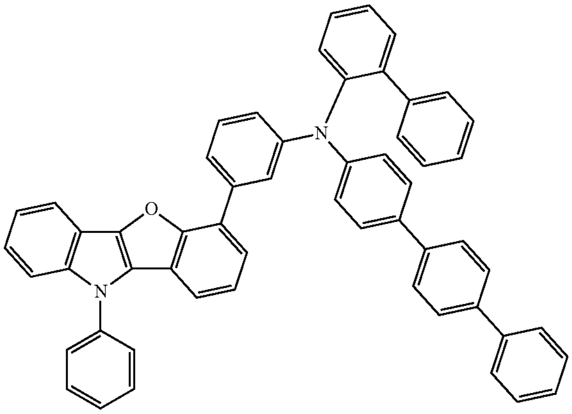
A108
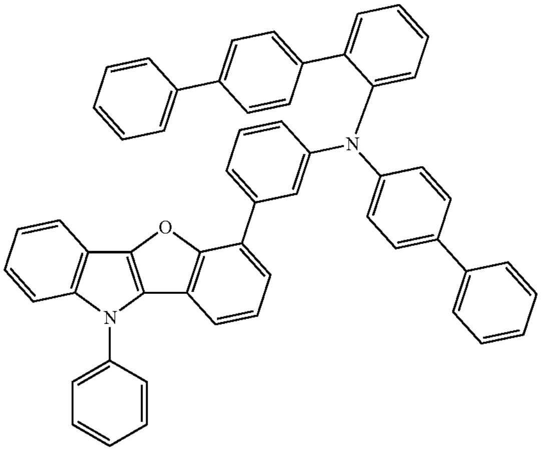
A109
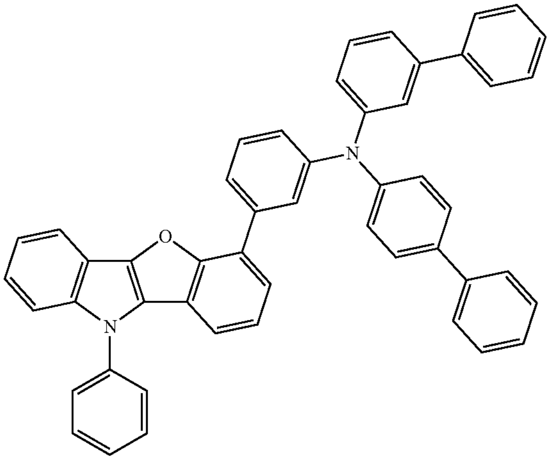

-continued
A110
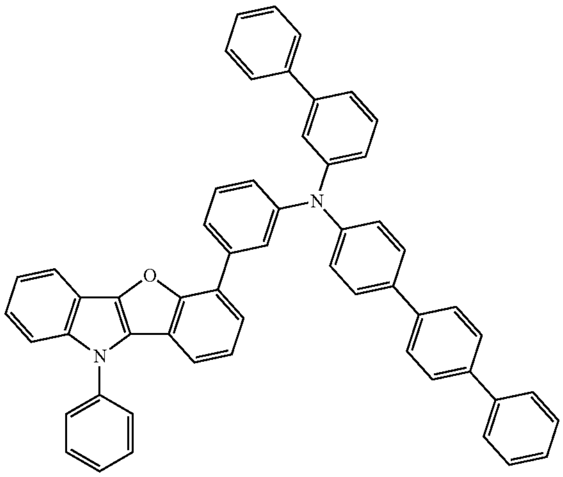
A111
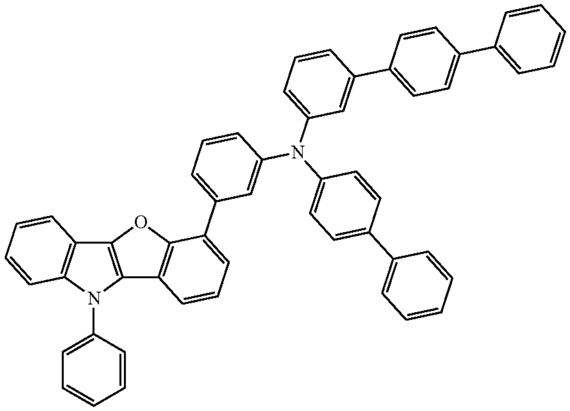
A112
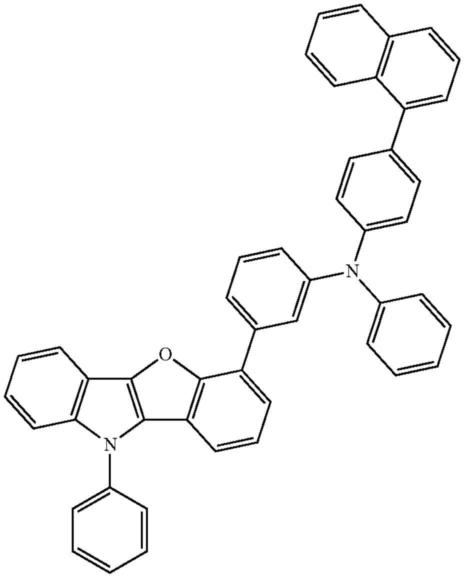
-continued
A113
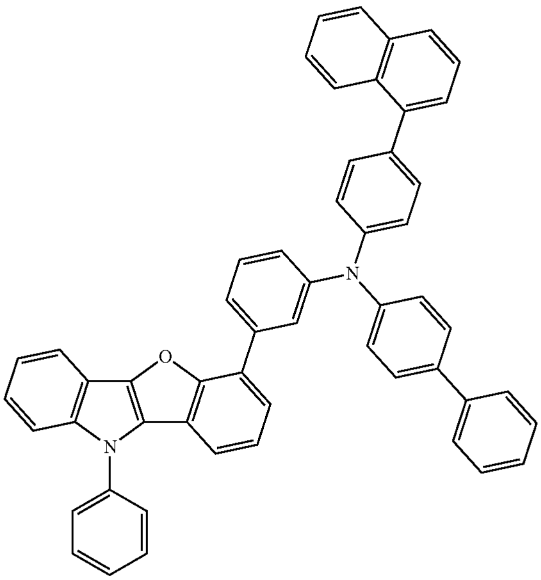
A114
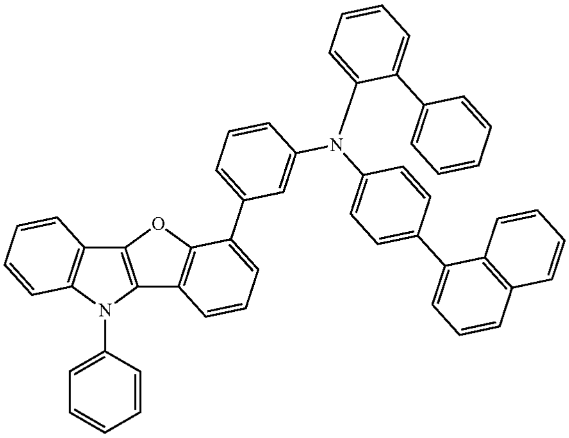
A115
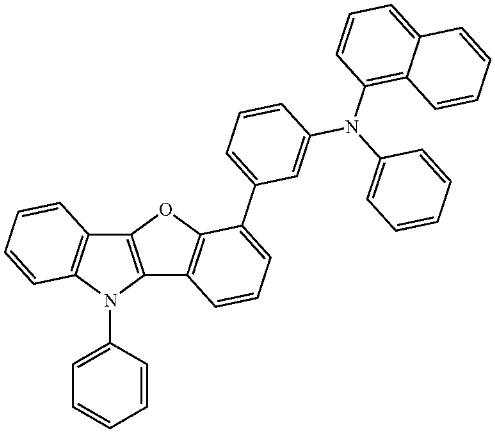

-continued
A116
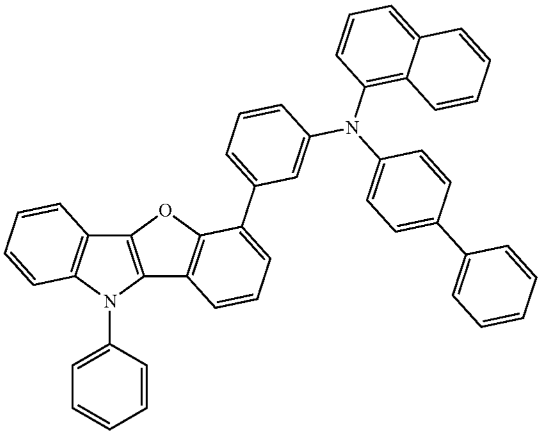
A117
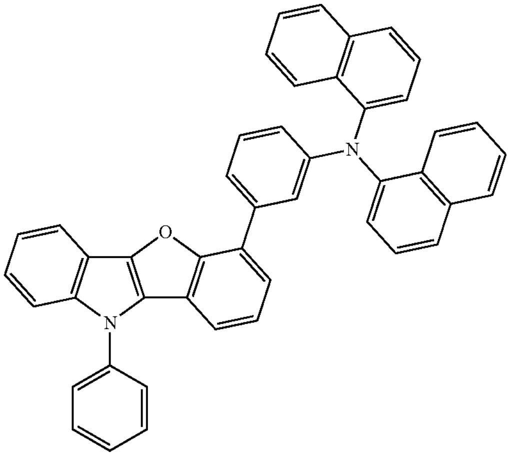
A118
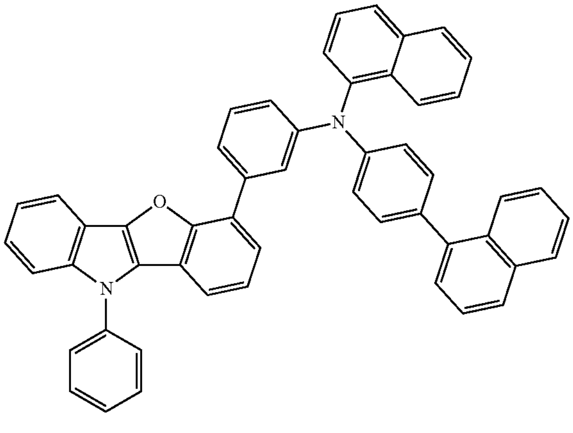
-continued
A119
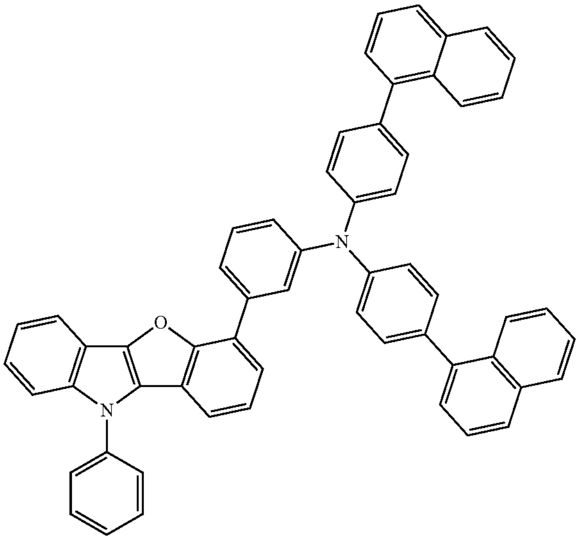
A120
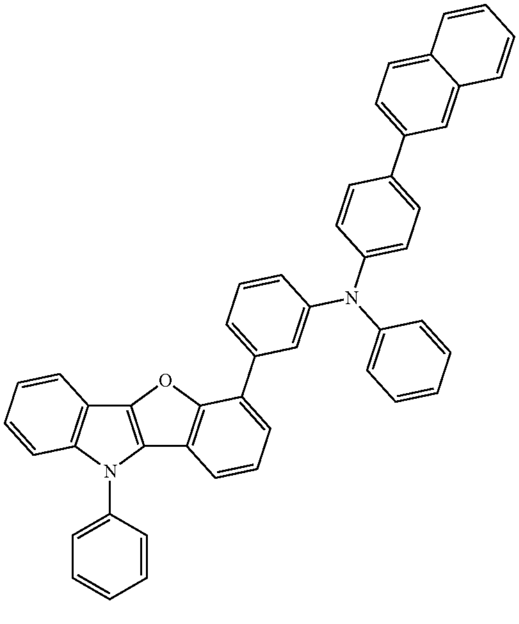

-continued
A121
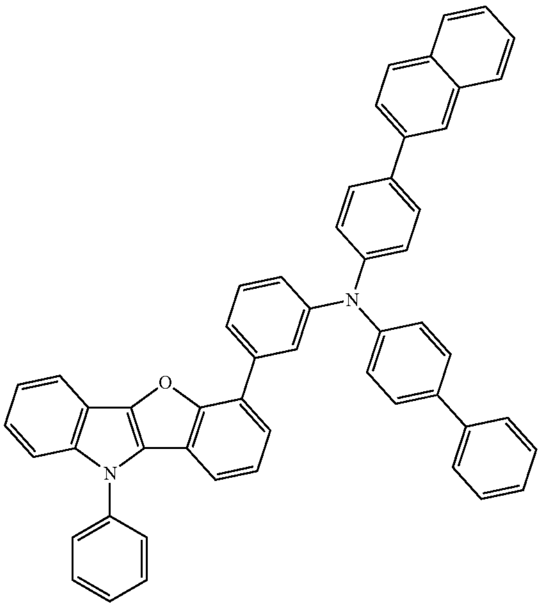
A122
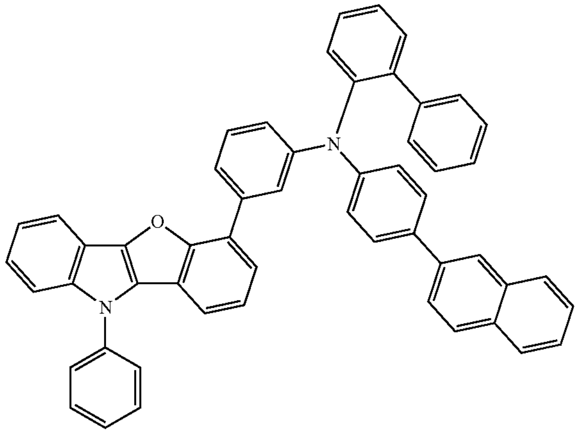
A123
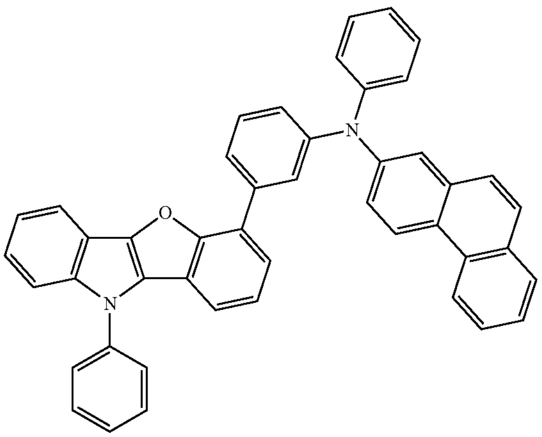
-continued
A124
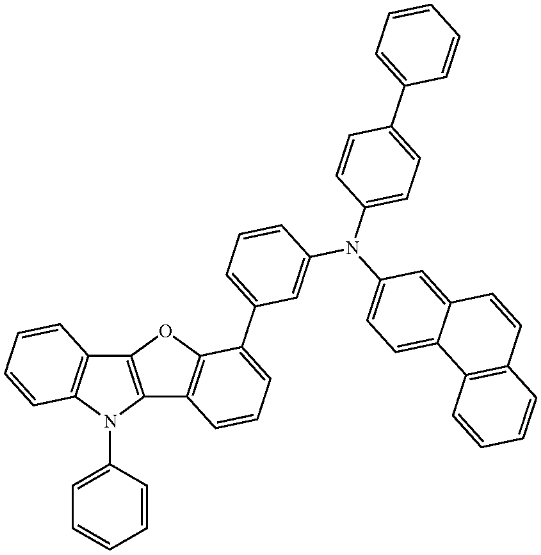
A125
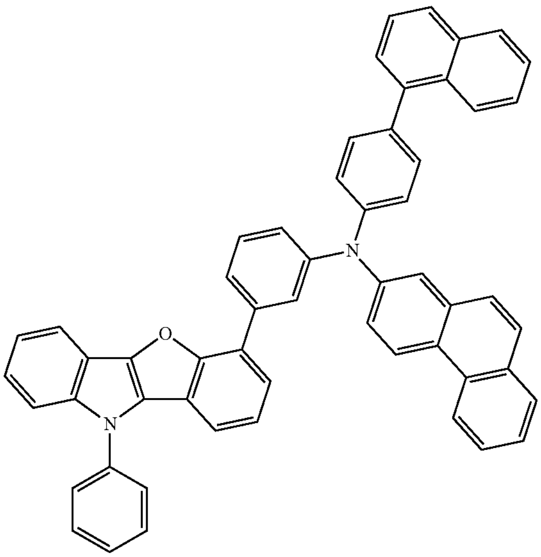
A126
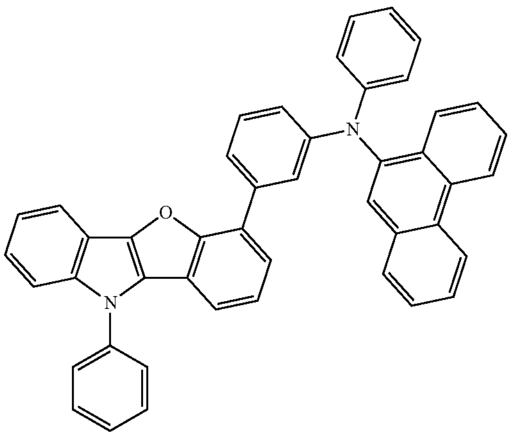

-continued
A127
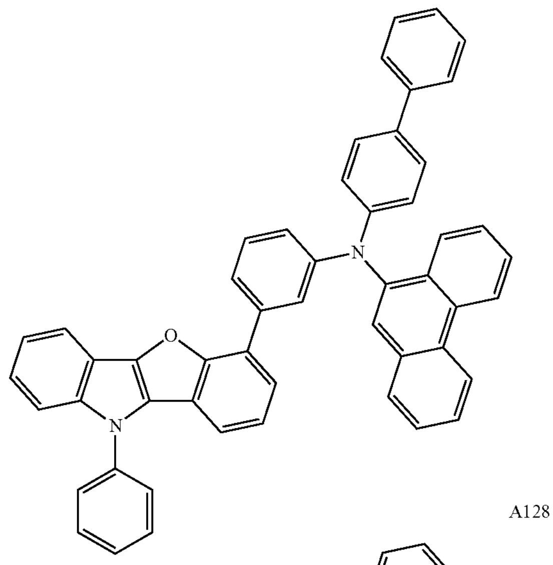
A128
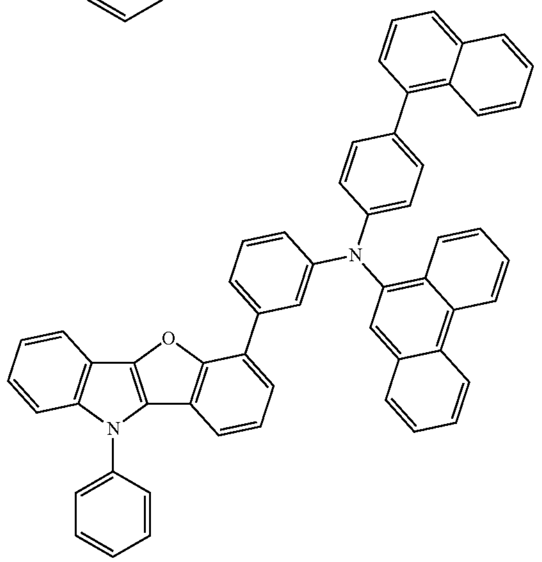
A130
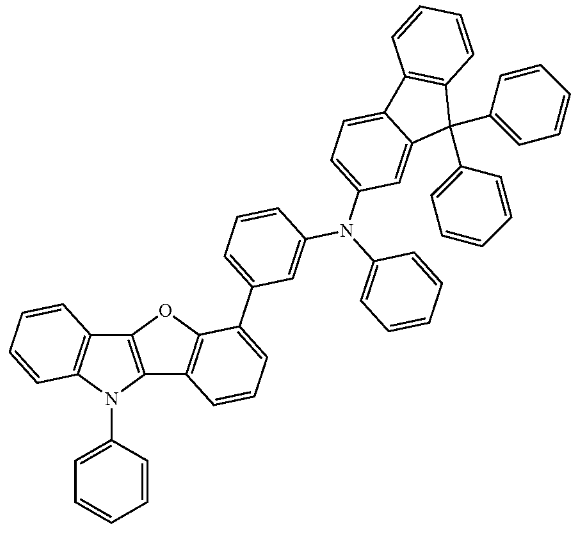
-continued
A131
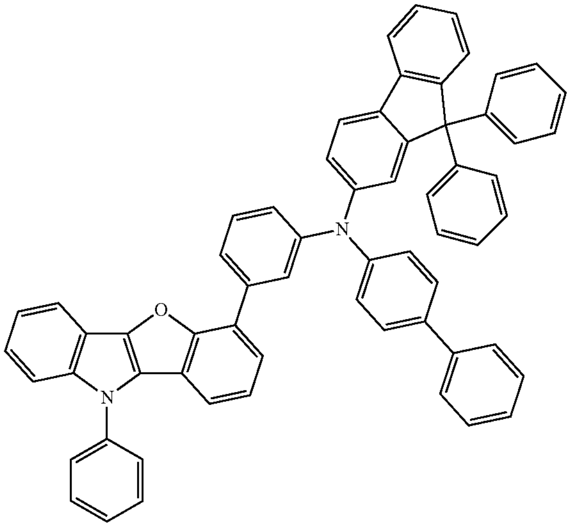
A132
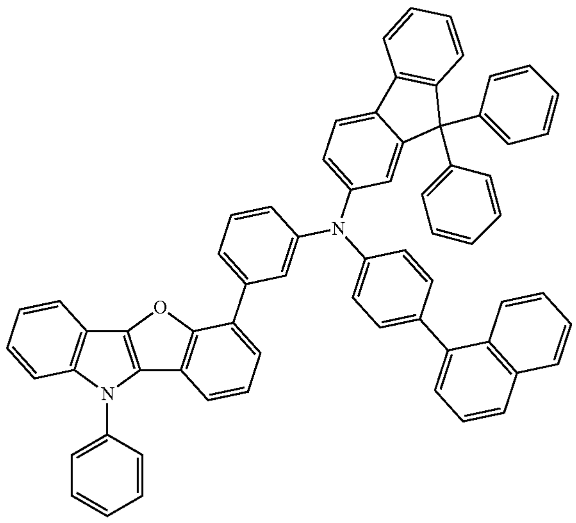
A133
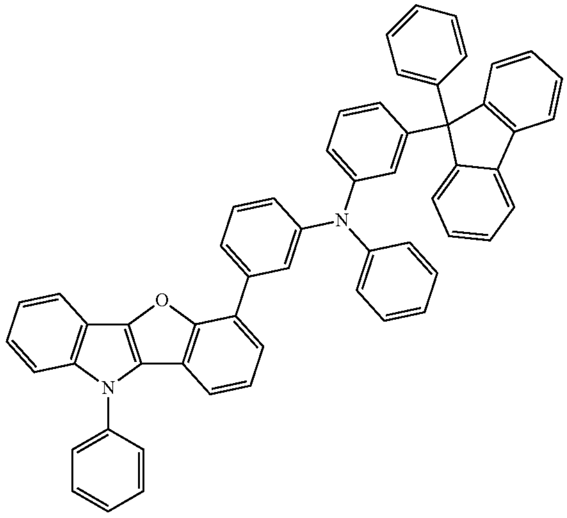

-continued
A134
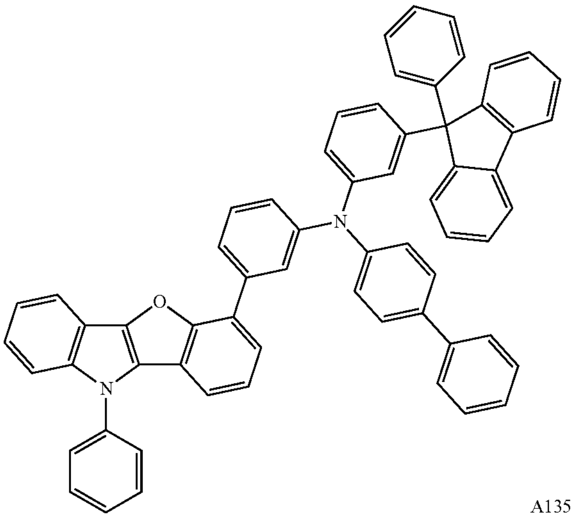
A135
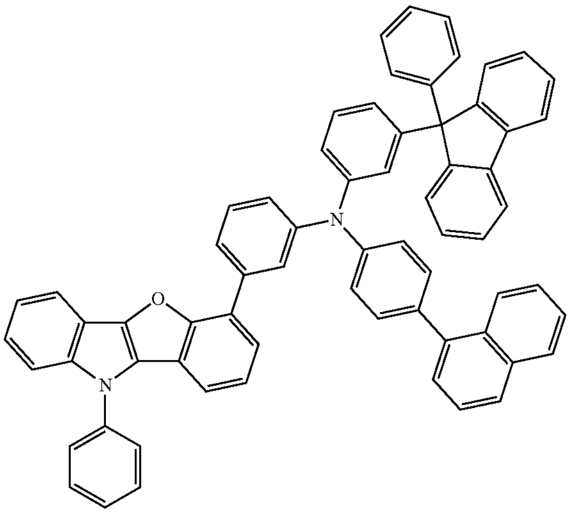
A136
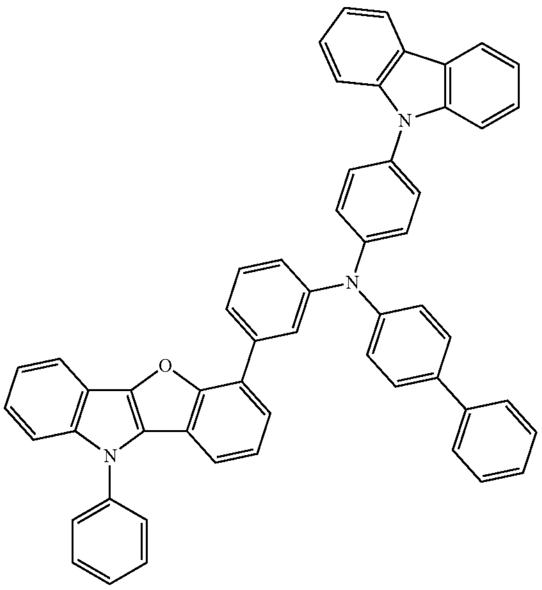
-continued
A137
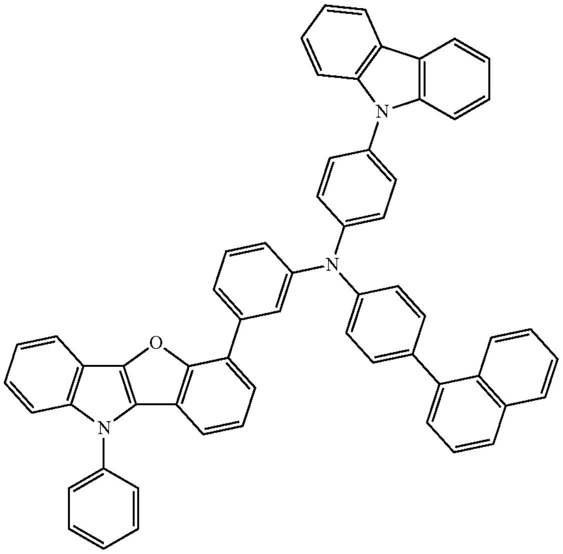
A138
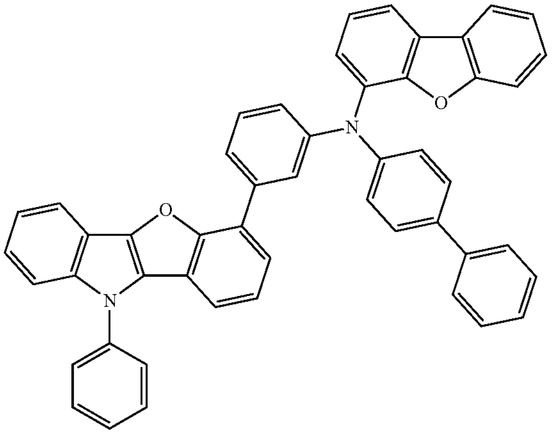
A139
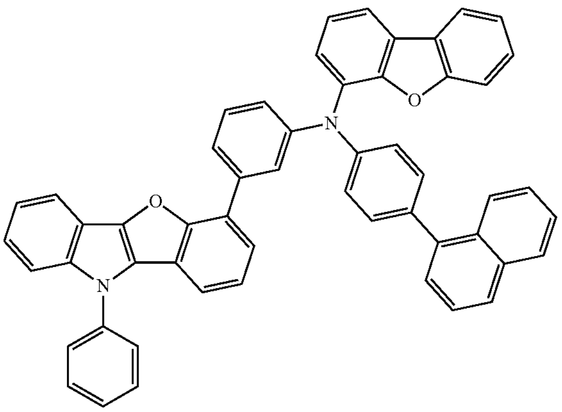

-continued
A140
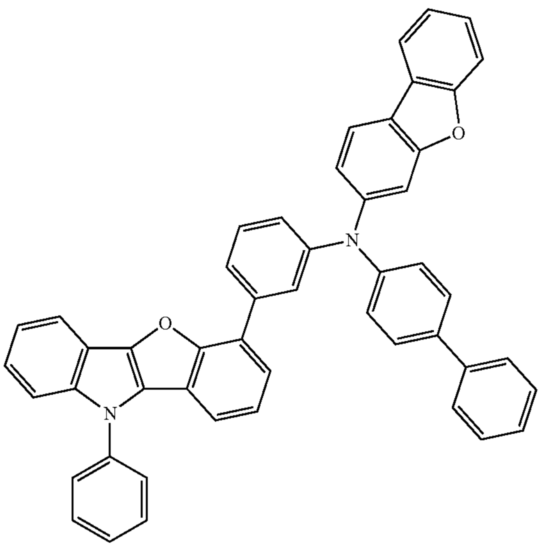
A141
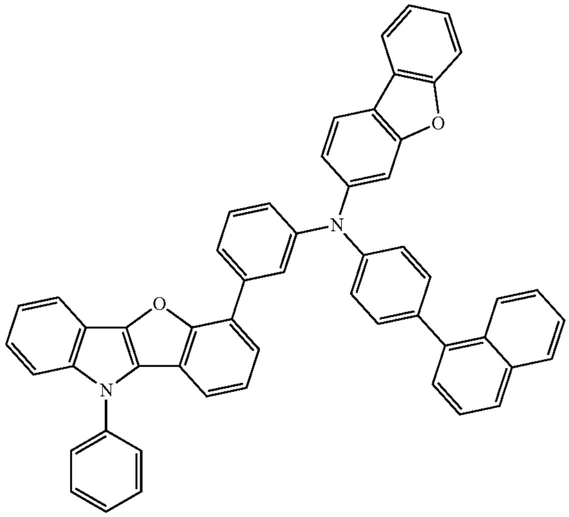
A142
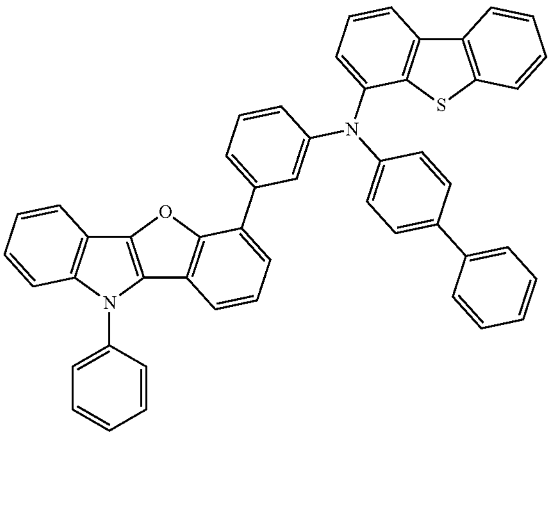
-continued
A143
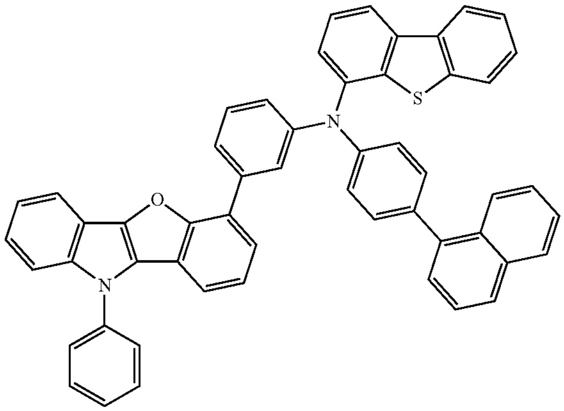
A144
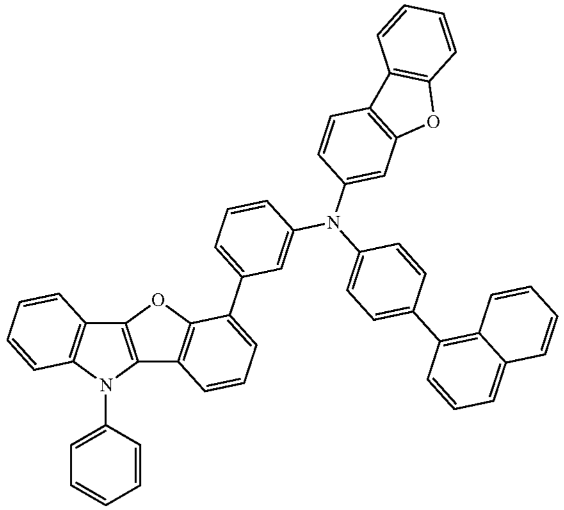
A145
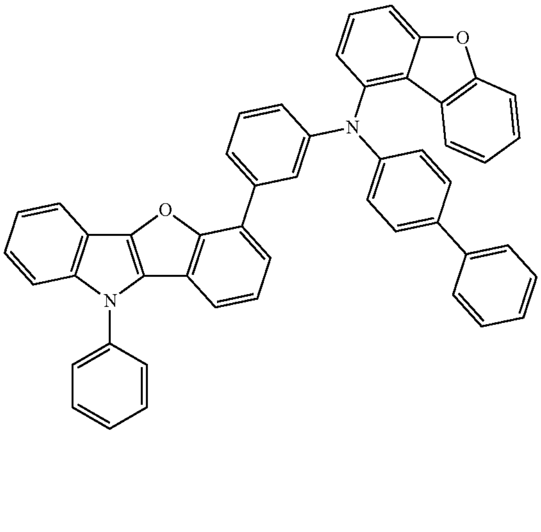

-continued
A146
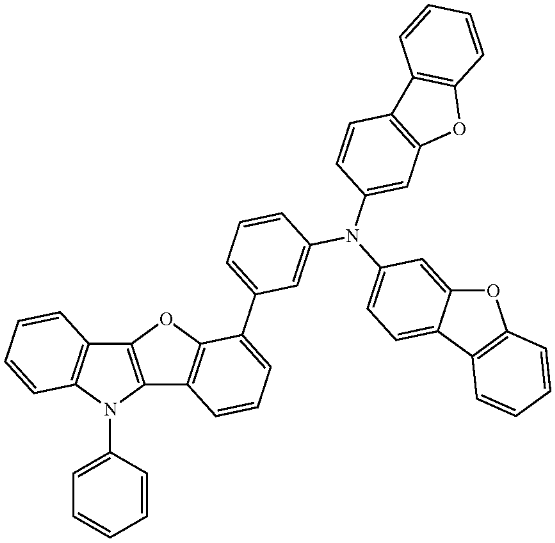
A147
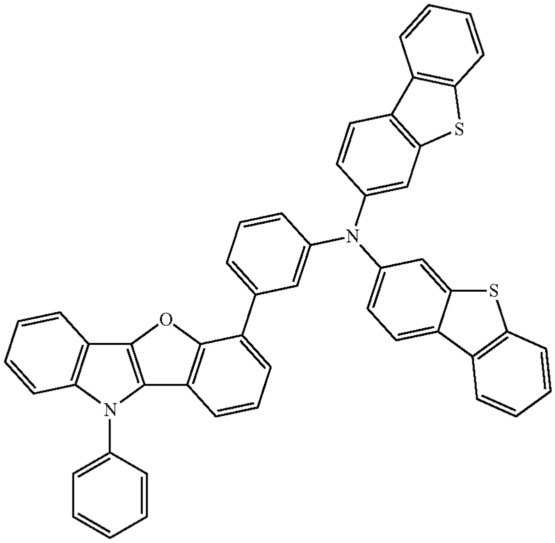
A148
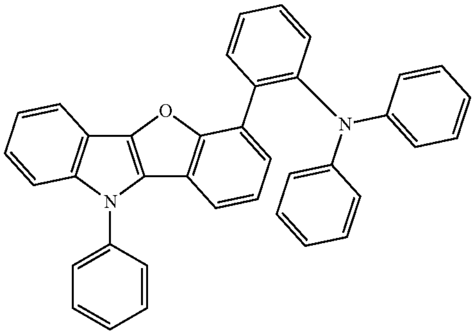
-continued
A149
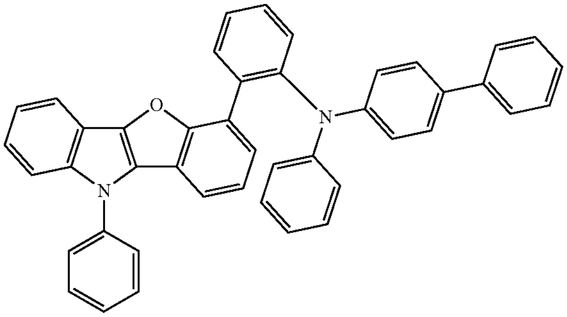
A150
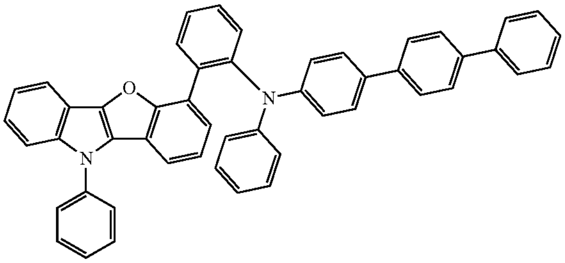
A151
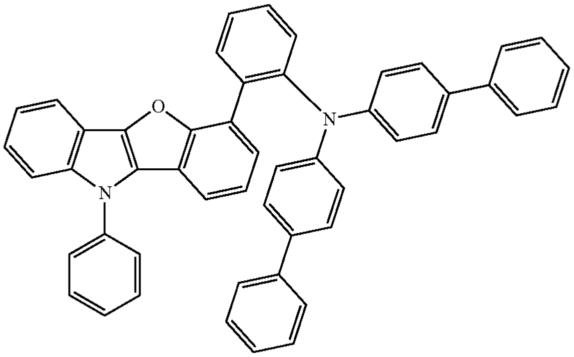
A152
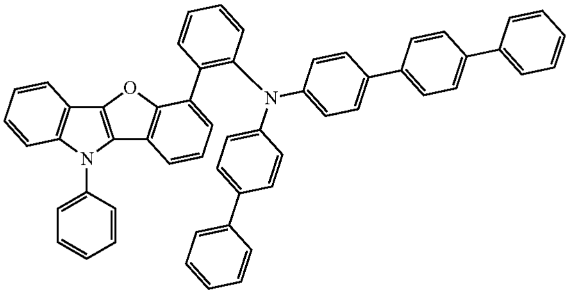

-continued
A153
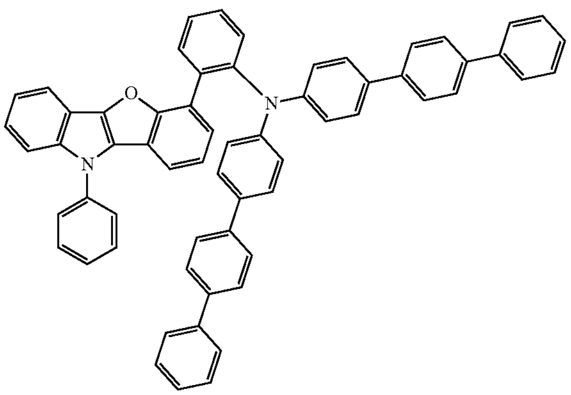
A154
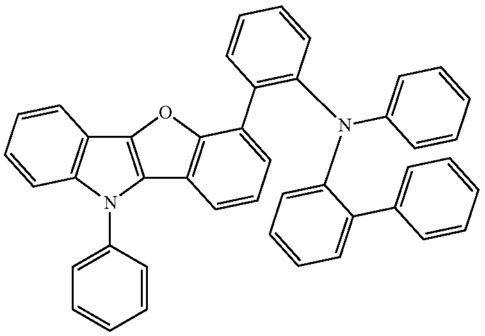
A155
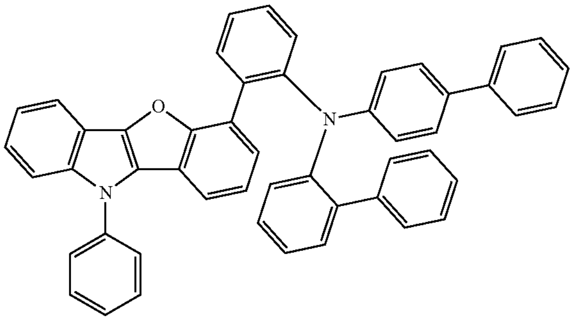
A156
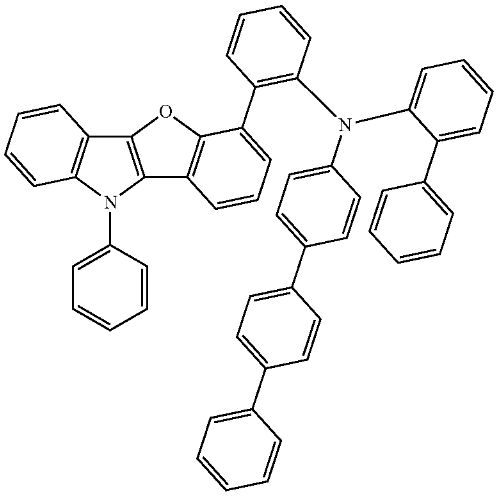
-continued
A157
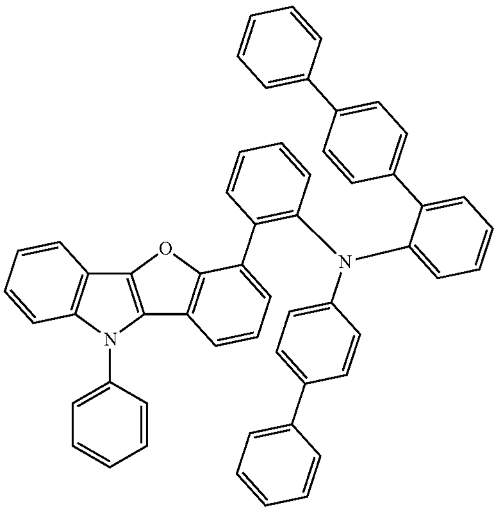
A158
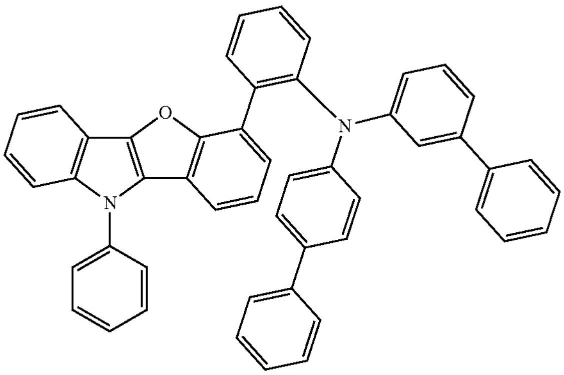
A159
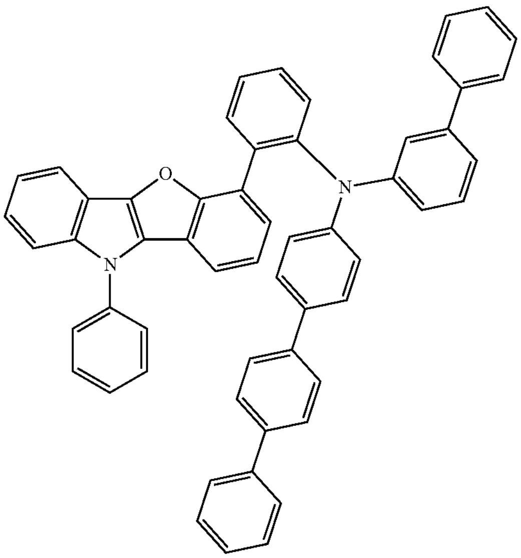

-continued
A160
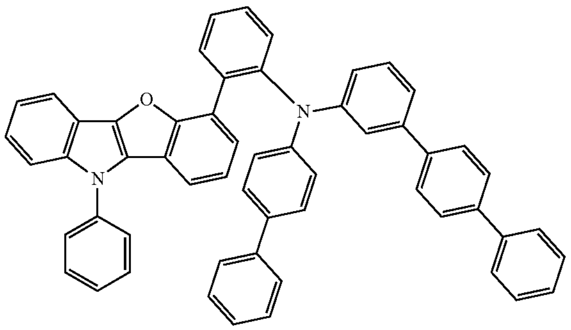
A161
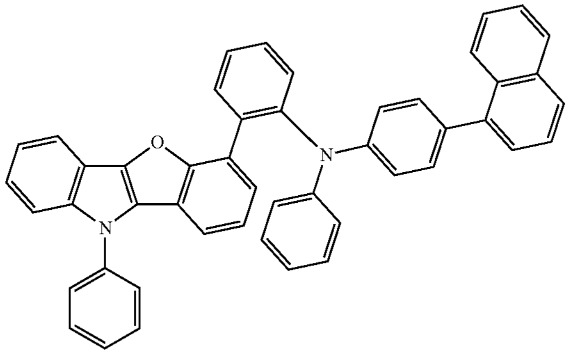
A162
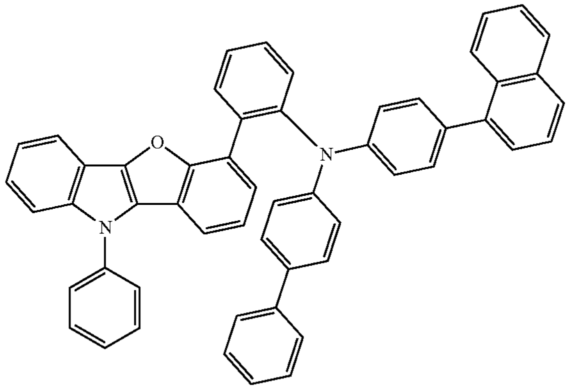
A163
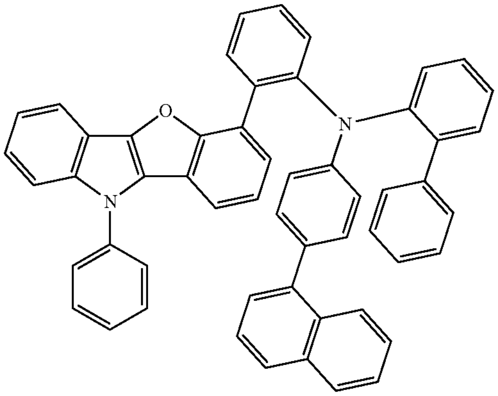
-continued
A164
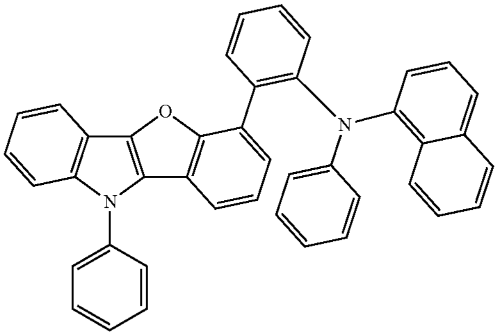
A165
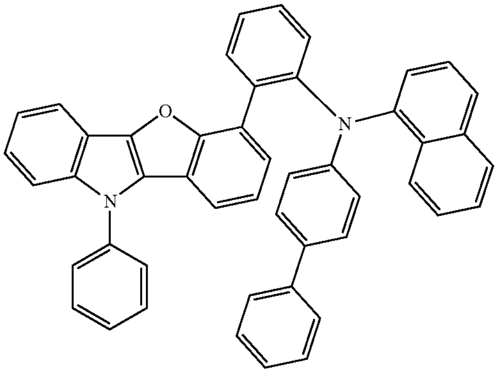
A166
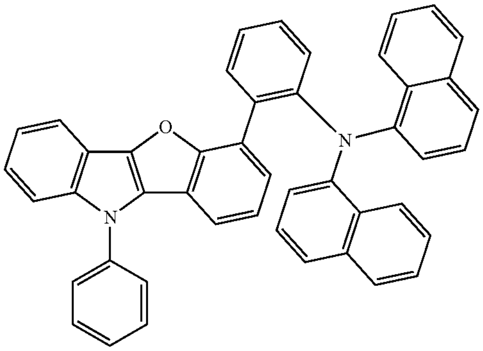
A167
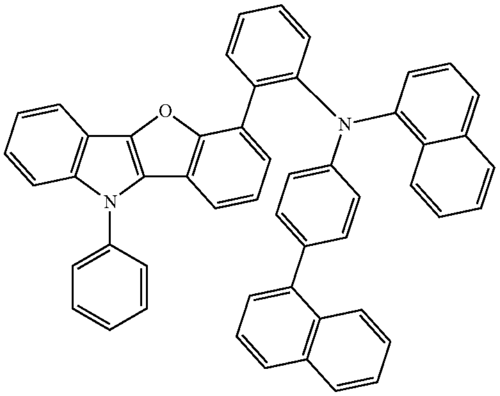

-continued
A168
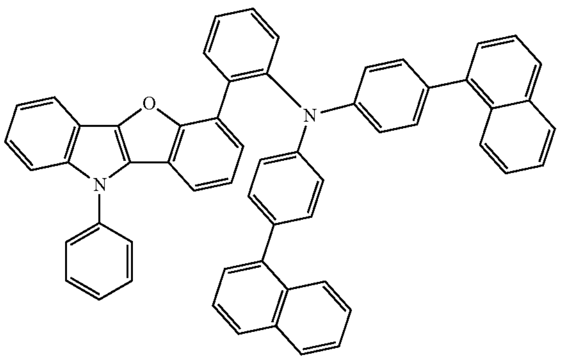
A169
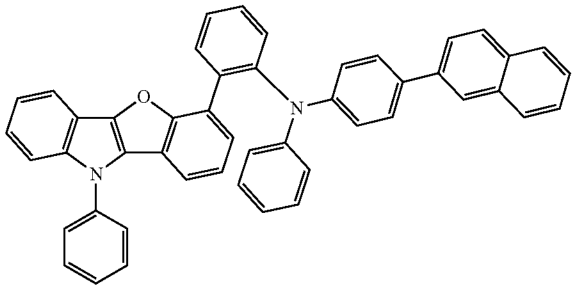
A170
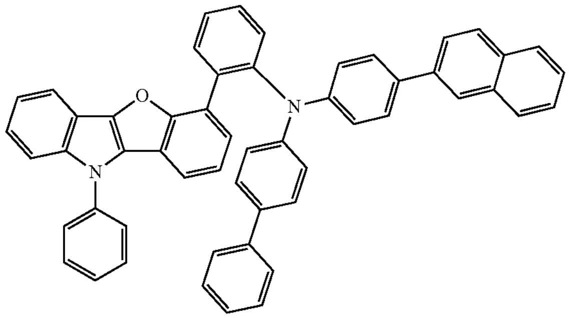
A171
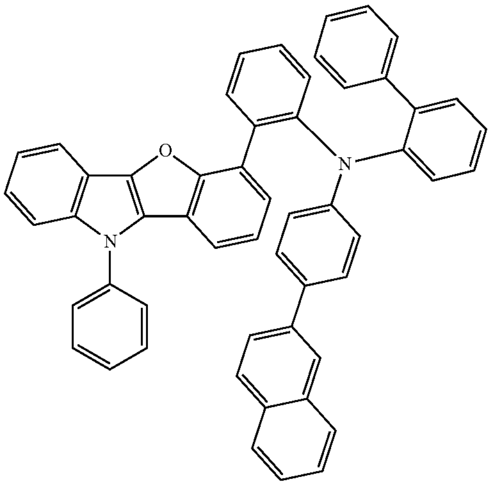
-continued
A172
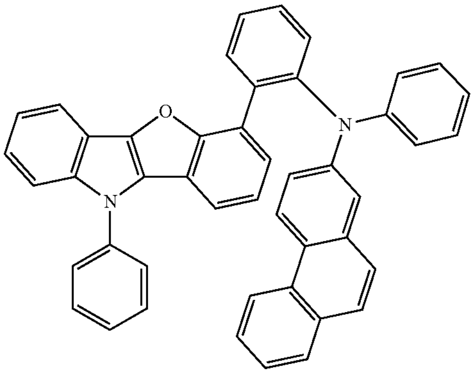
A173
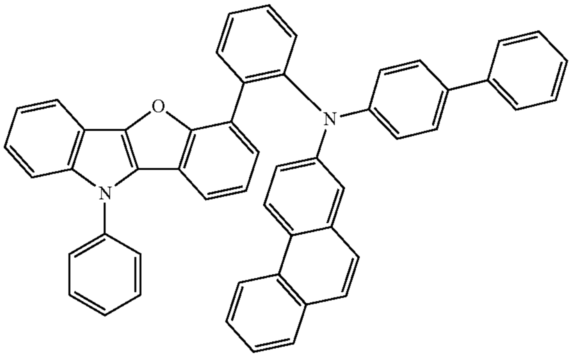
A174
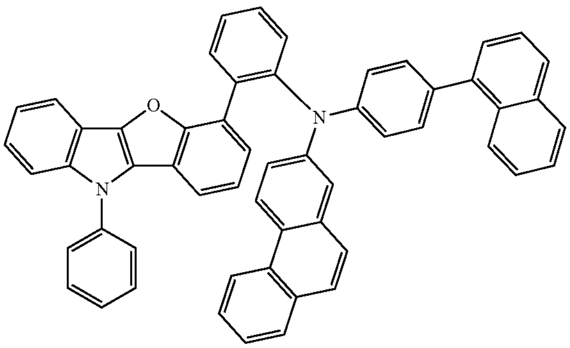
A175
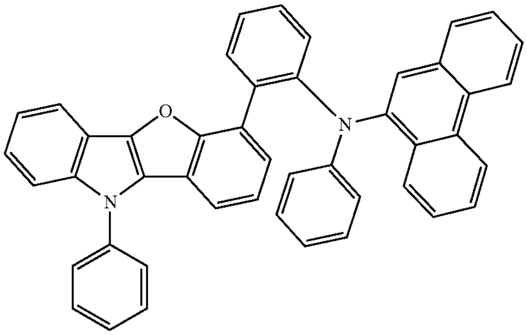

-continued
A176
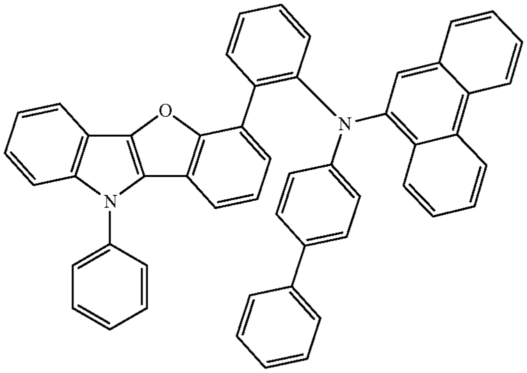
A177
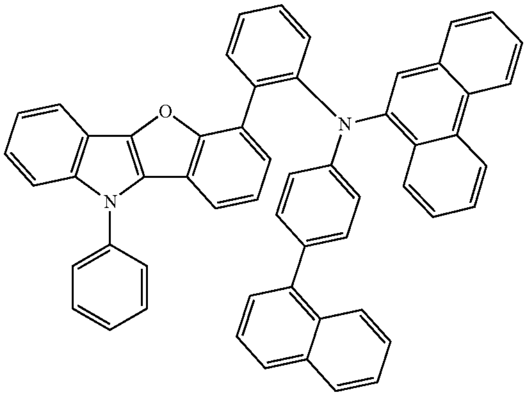
A179
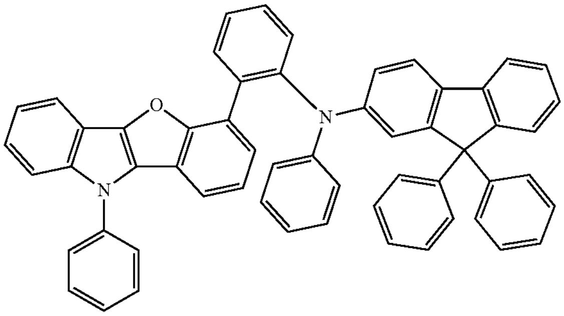
A180
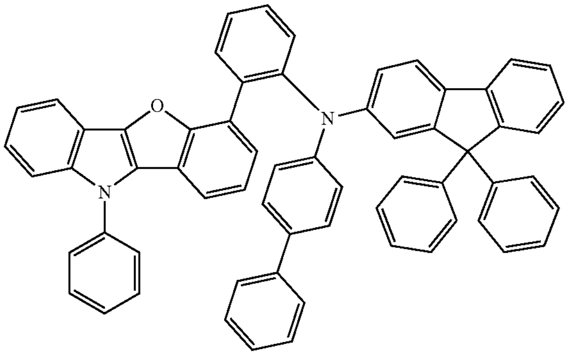
-continued
A181
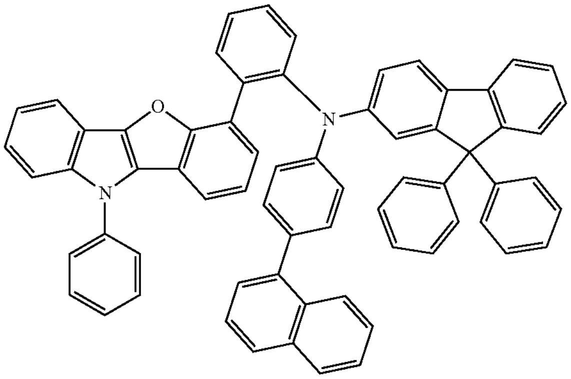
A182
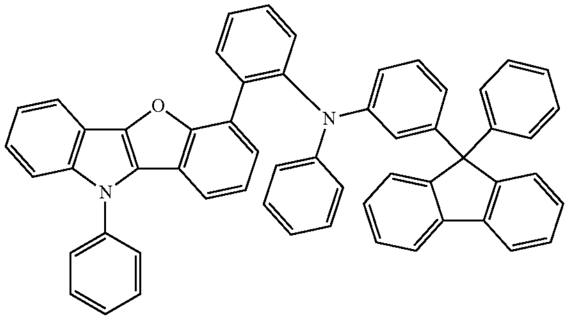
A183
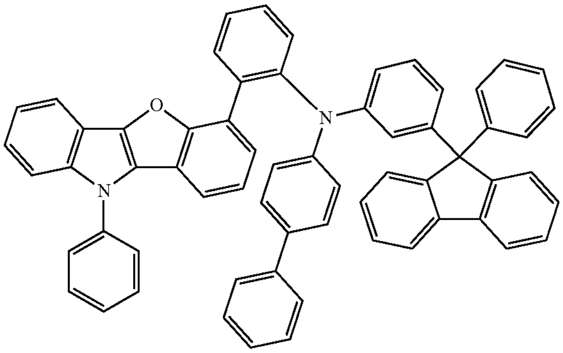
A184
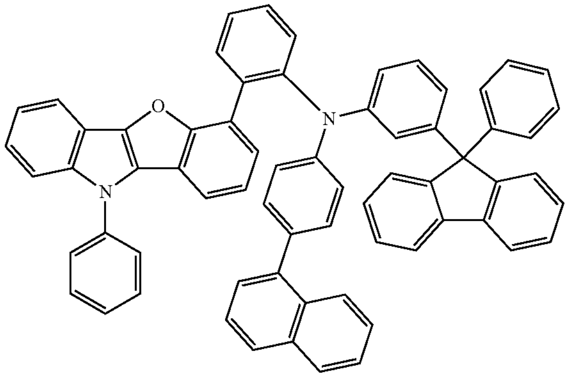

-continued
A185
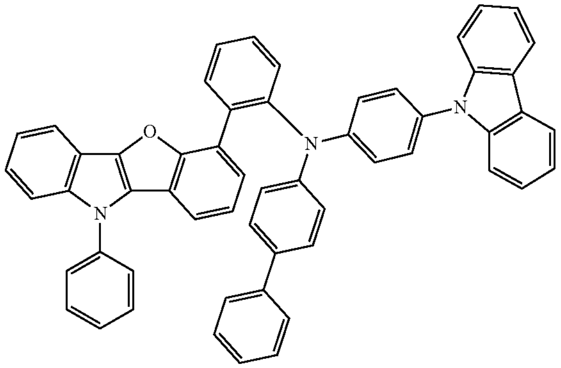
A186
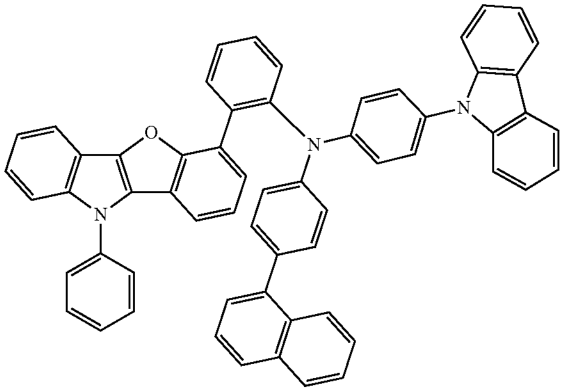
A187
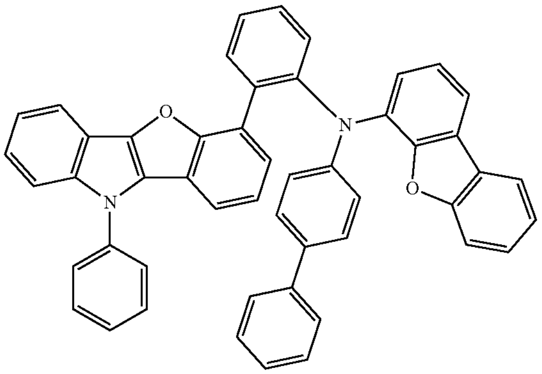
A188
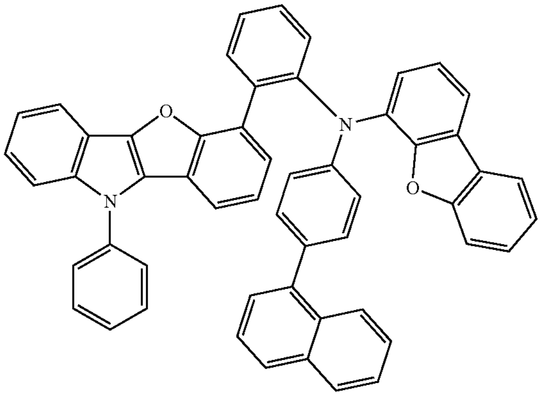
-continued
A189
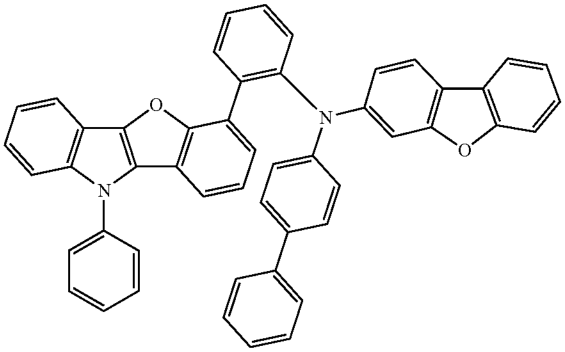
A190
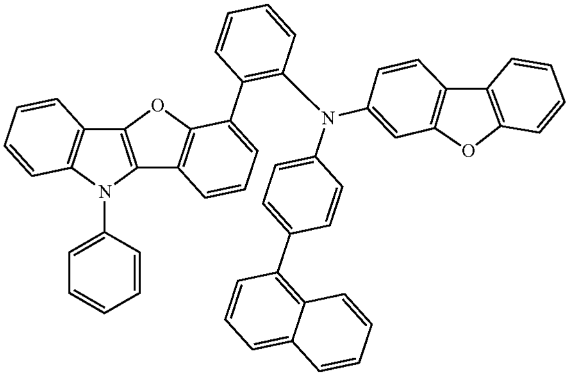
A191
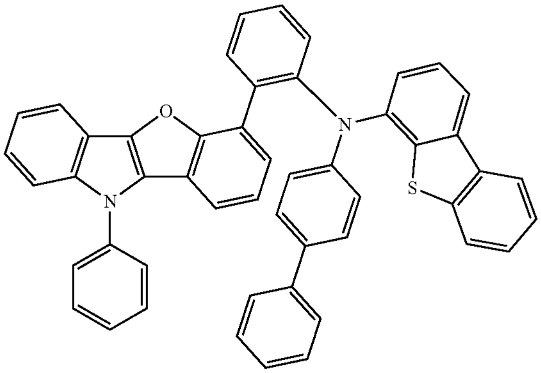
A192
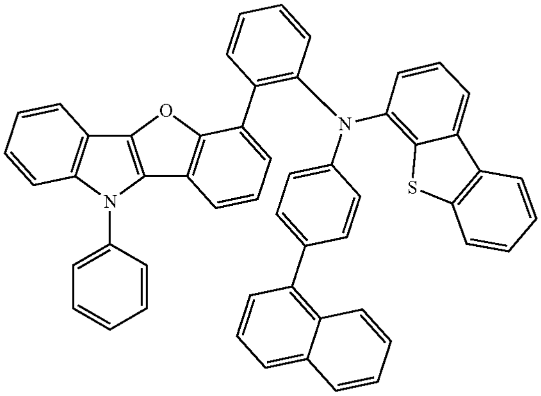

-continued
A193
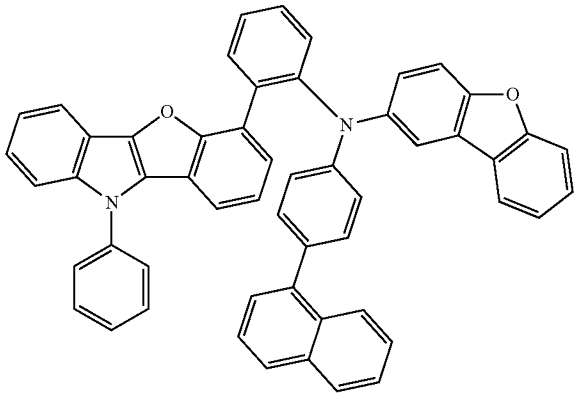
A194
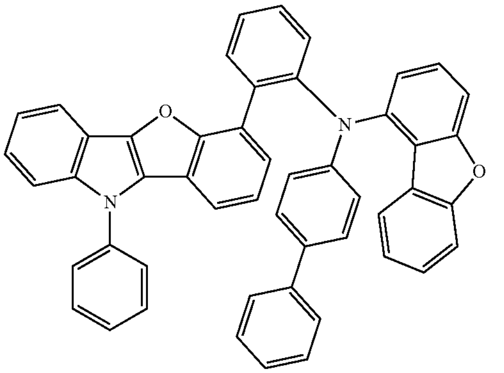
A195
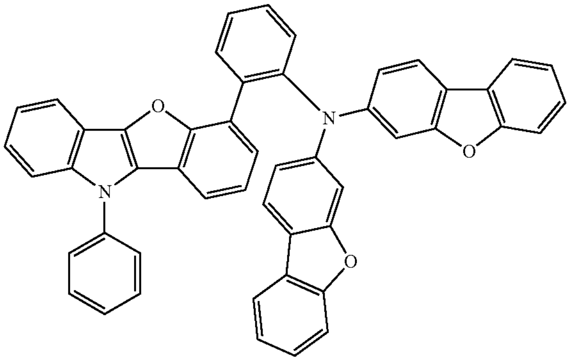
-continued
A196
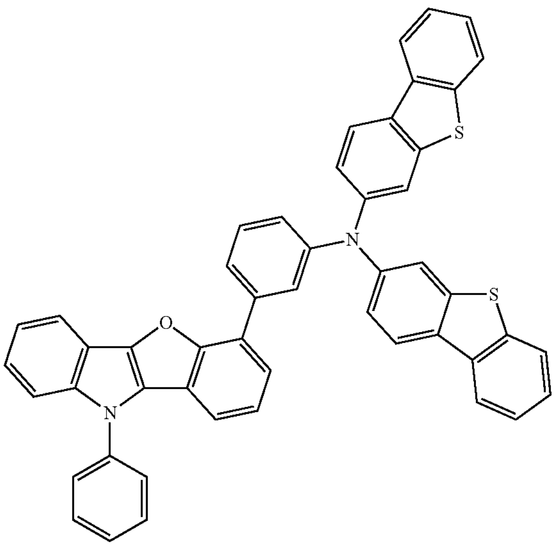
Compound Group 2
B50
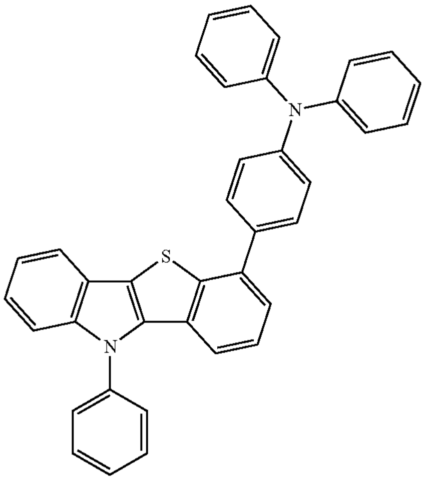
B51
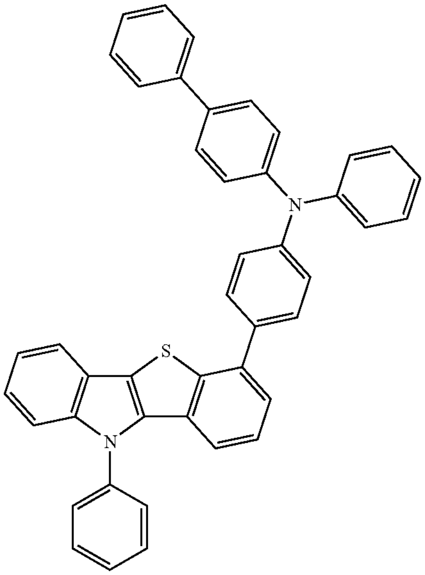

-continued
B52
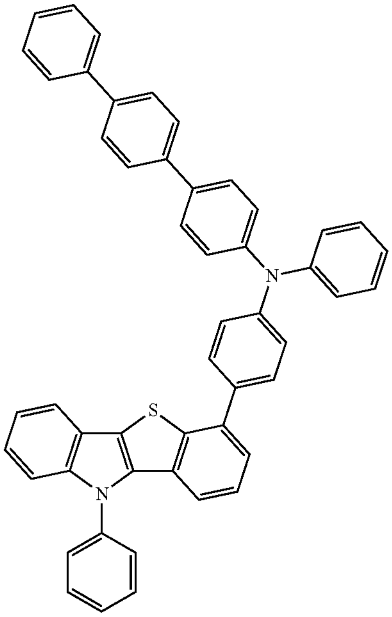
B53
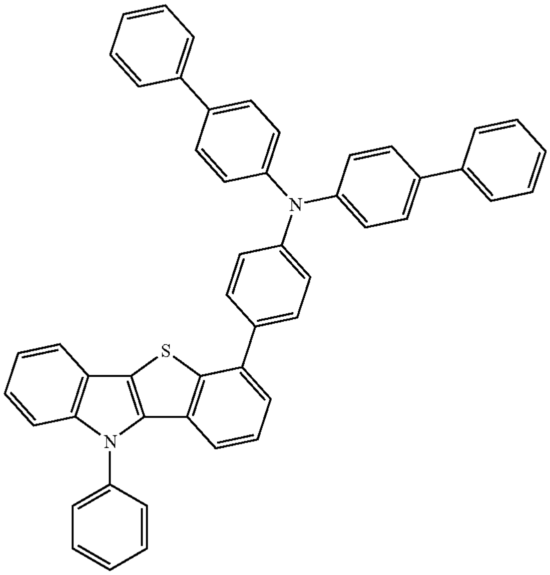
-continued
B54
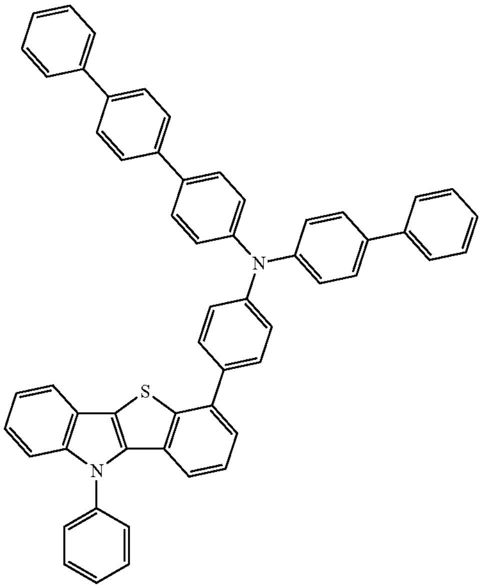
B55
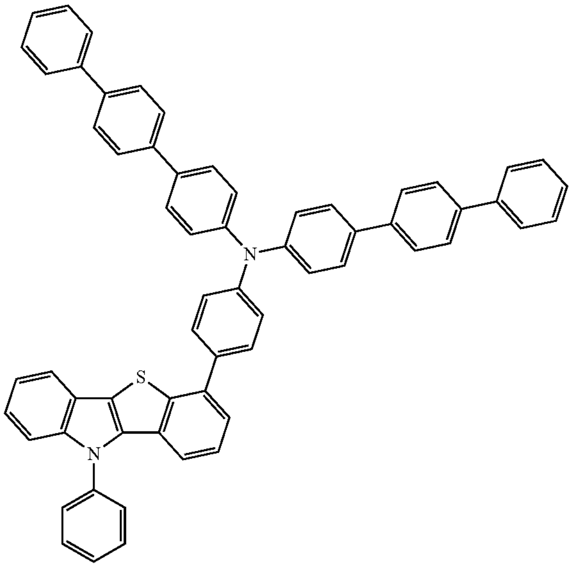

-continued
B56
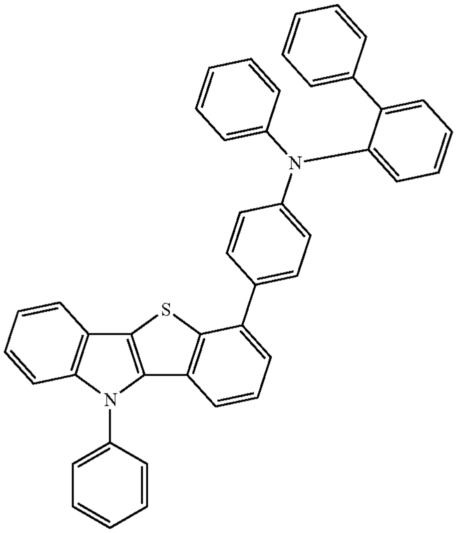
B57
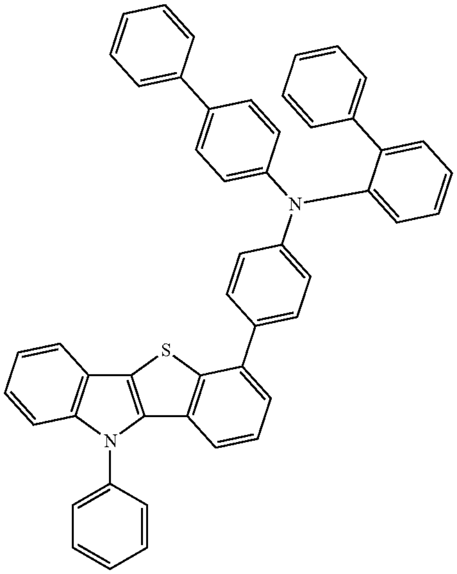
B58
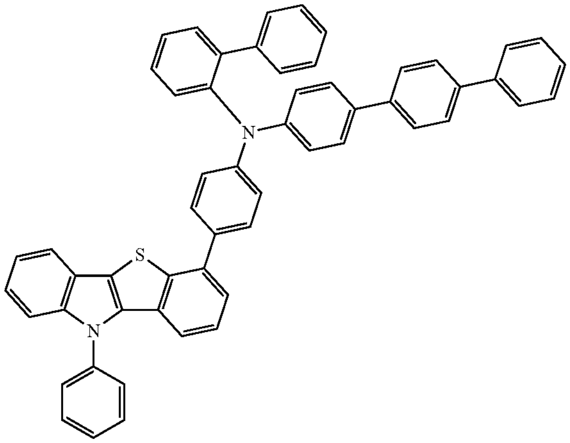
-continued
B59
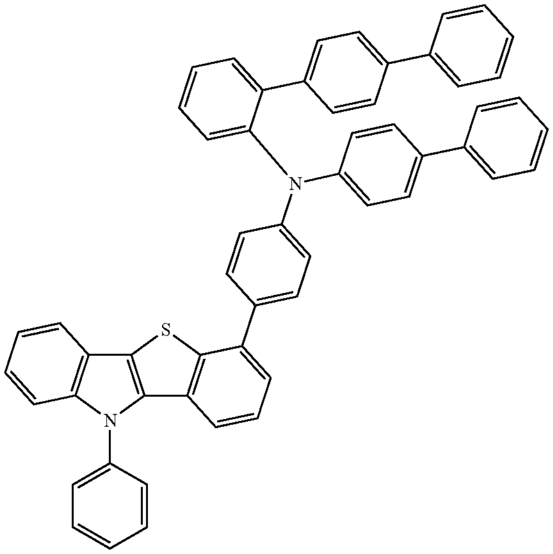
B60
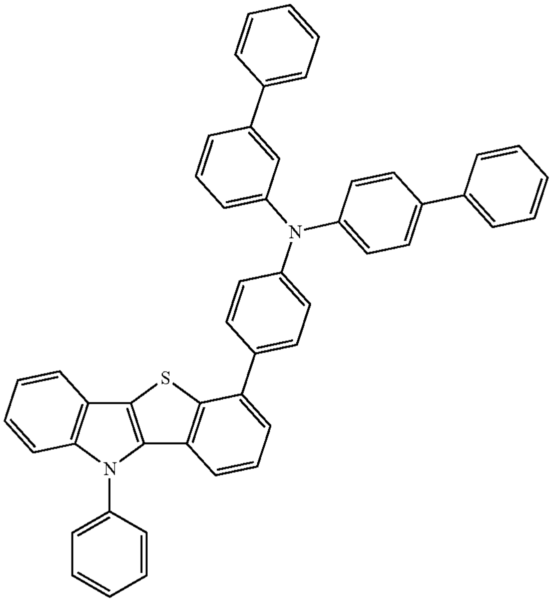
B61
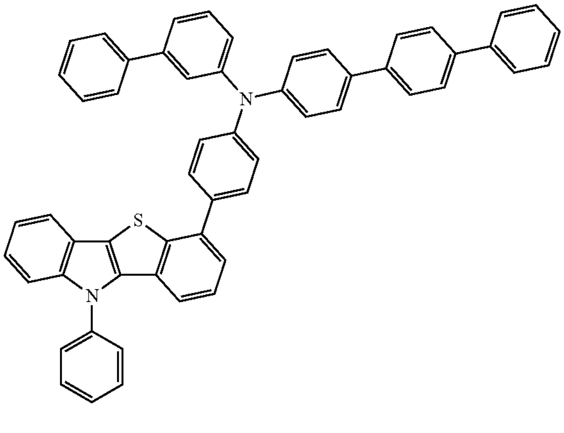

-continued
B62
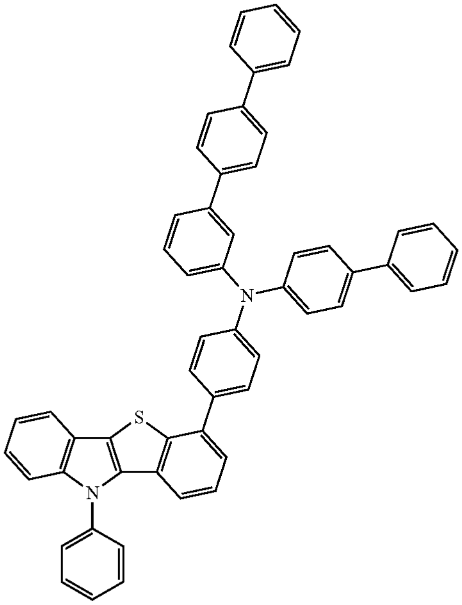
B63
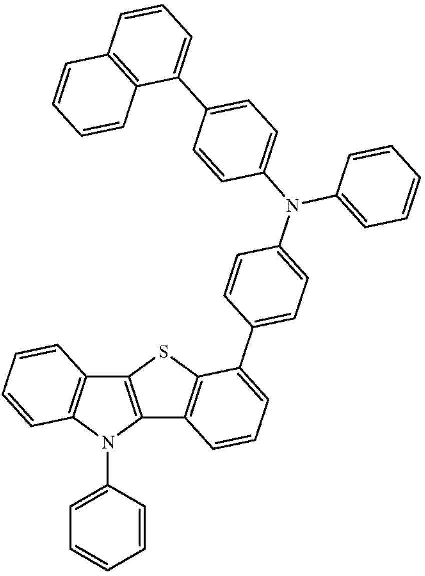
-continued
B64
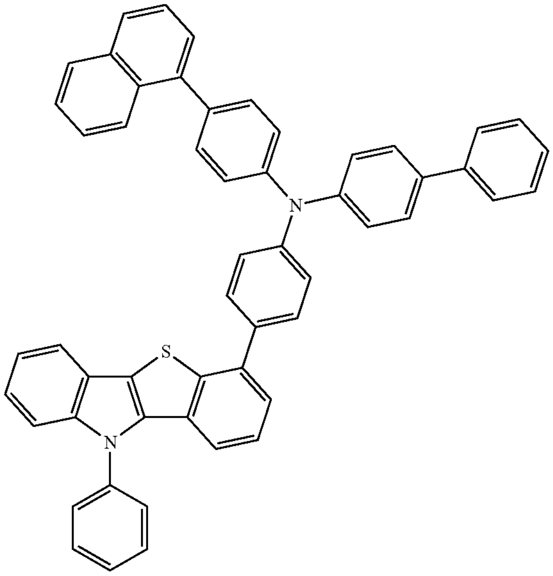
B65
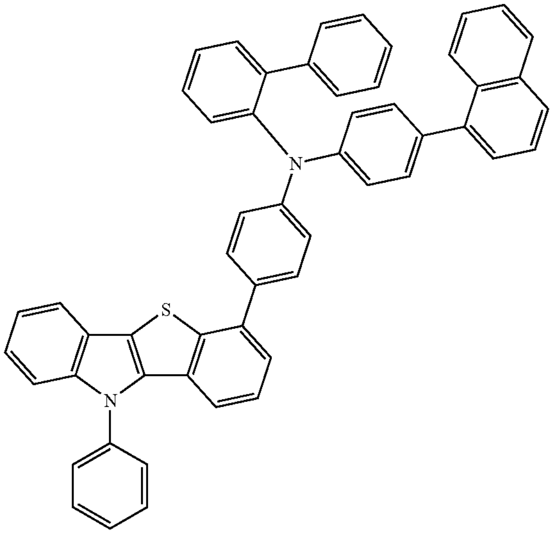

-continued
B66
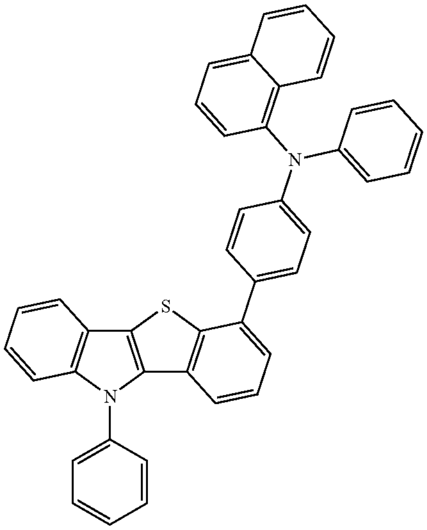
B67
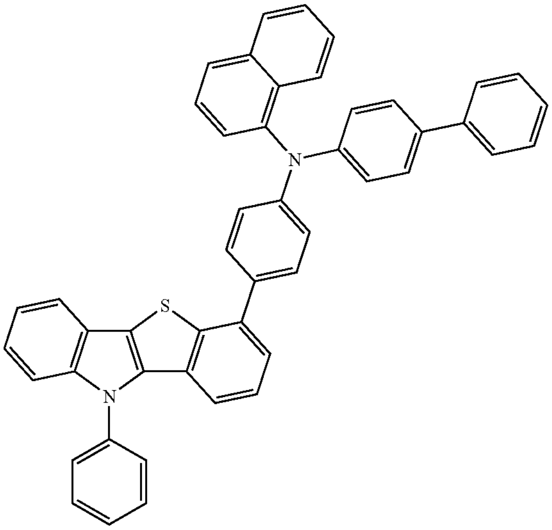
B68
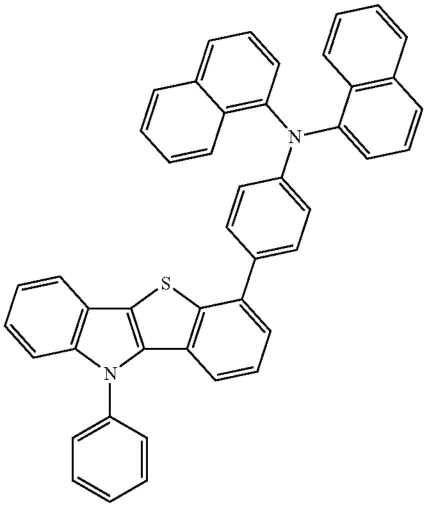
-continued
B69
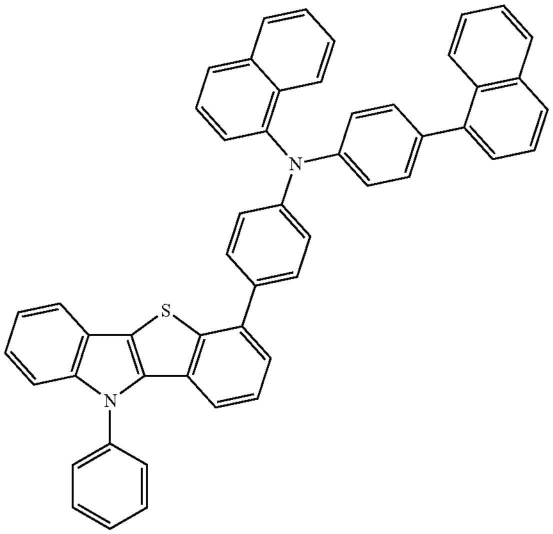
B70
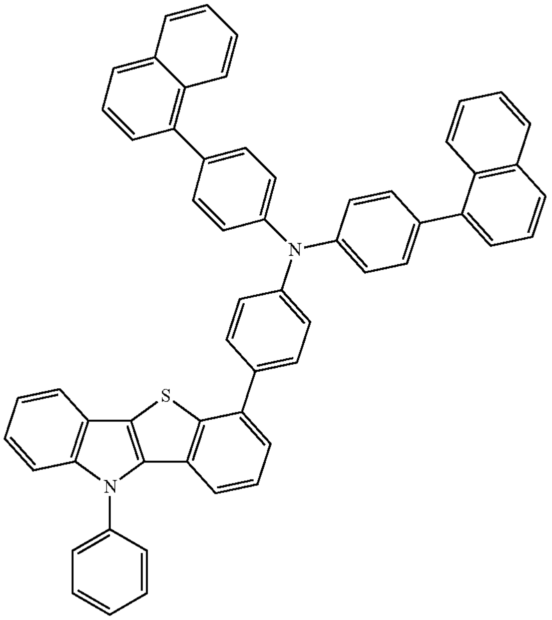

-continued
B71
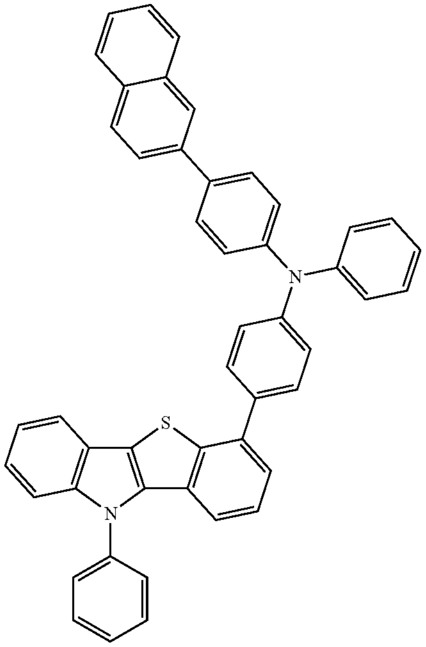
B72
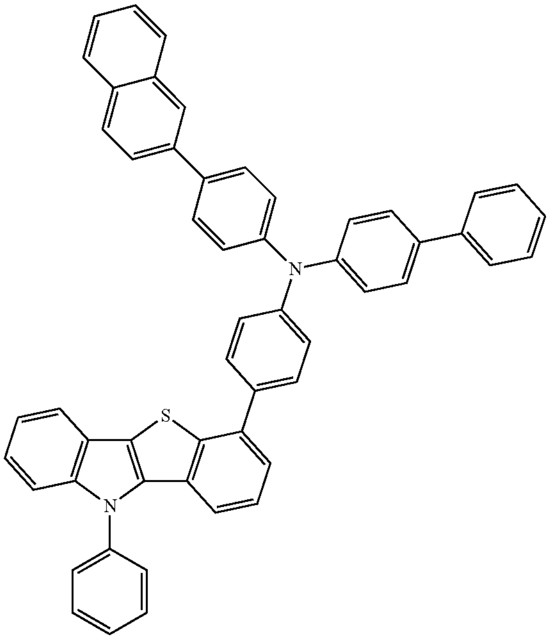
-continued
B73
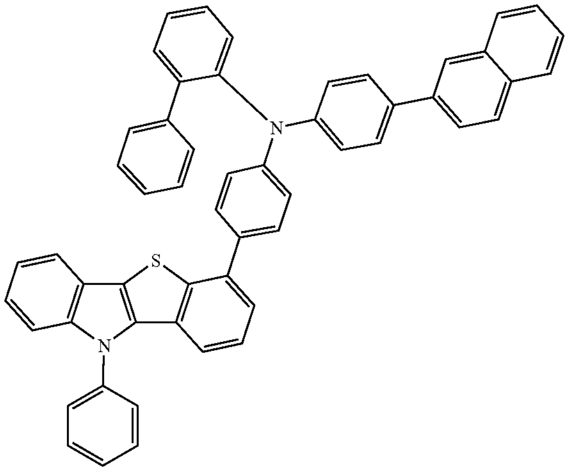
B74
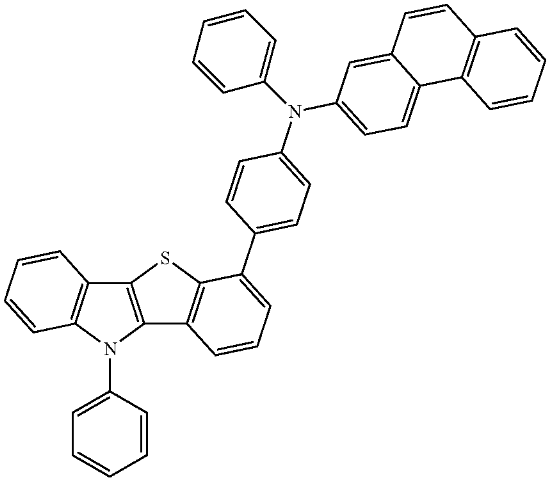
B75
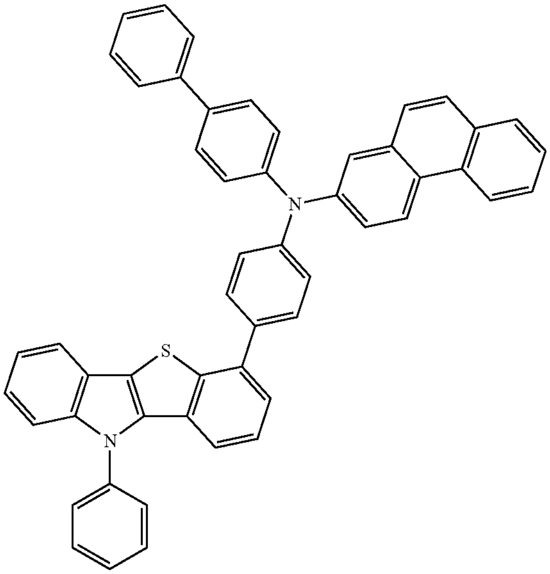

-continued
B76
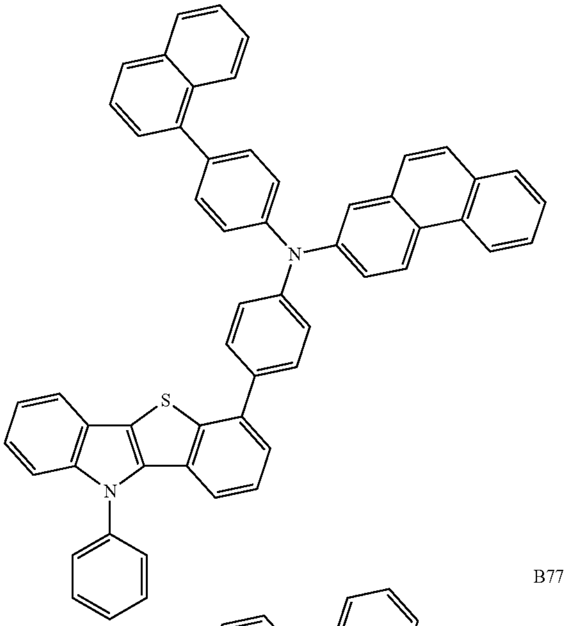
B77
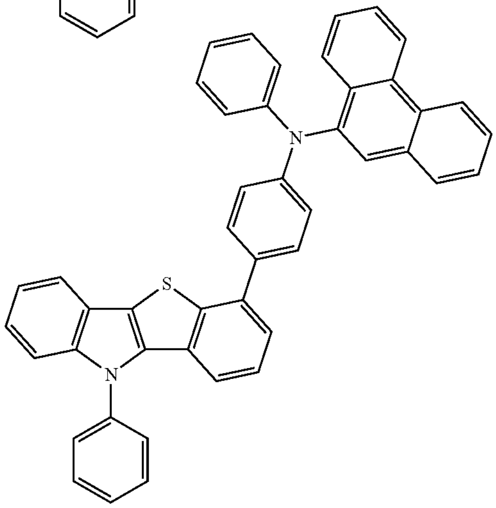
B78
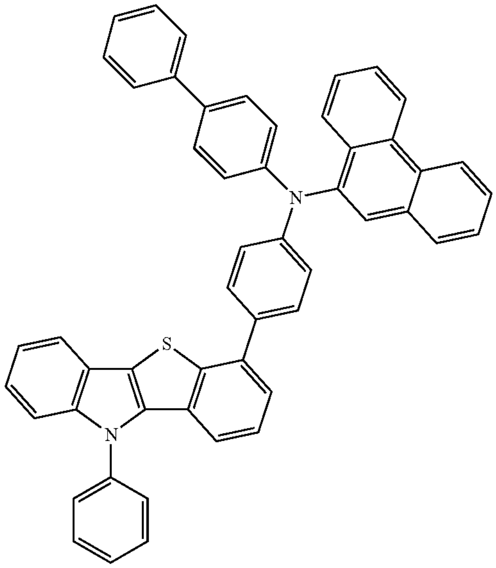
-continued
B79
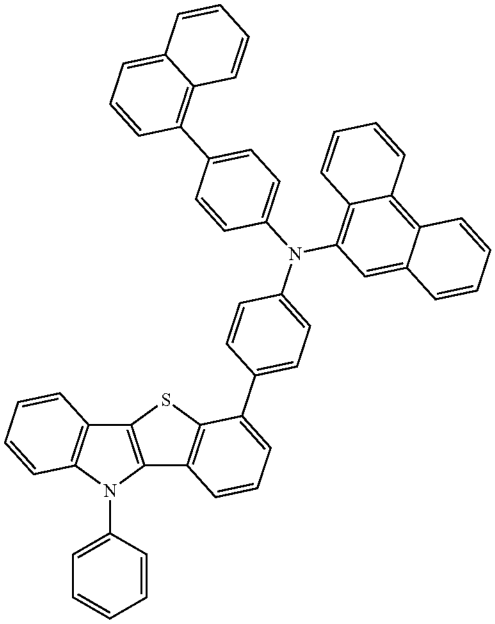
B81
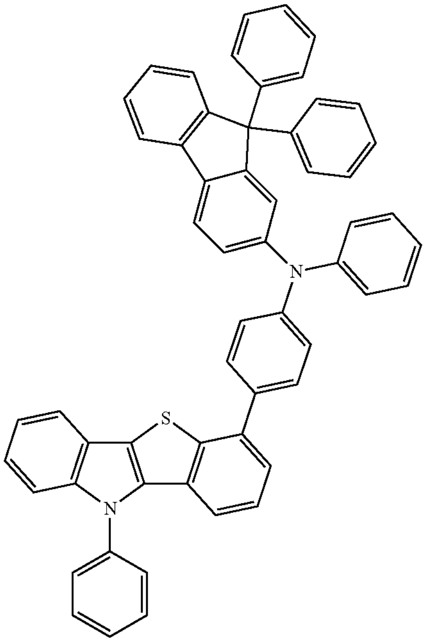

-continued
B82
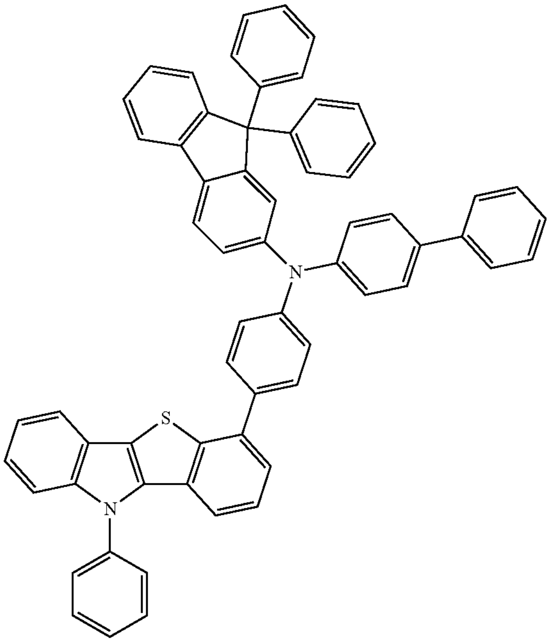
B83
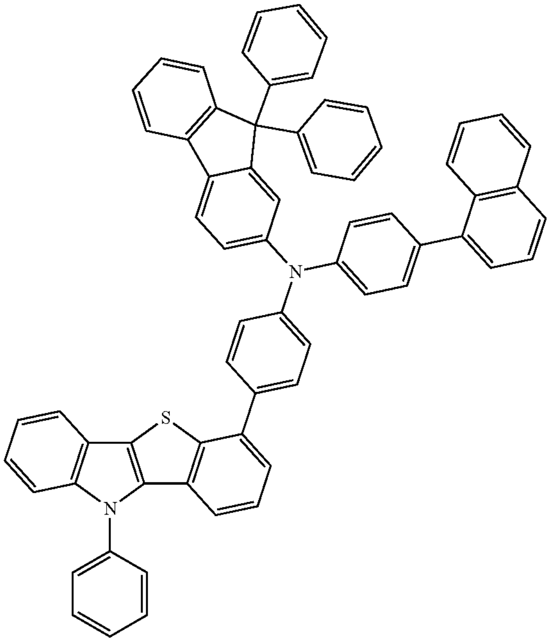
-continued
B84
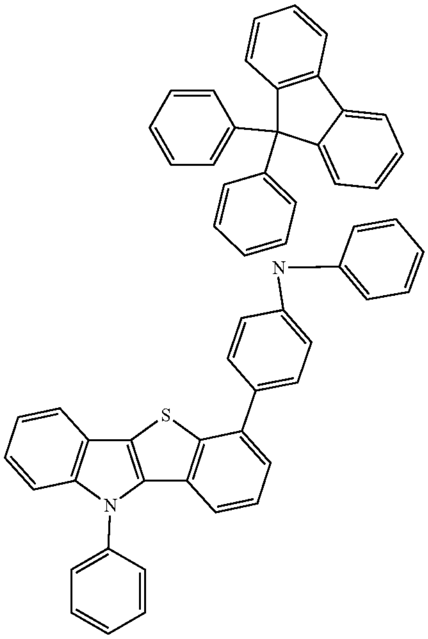
B85
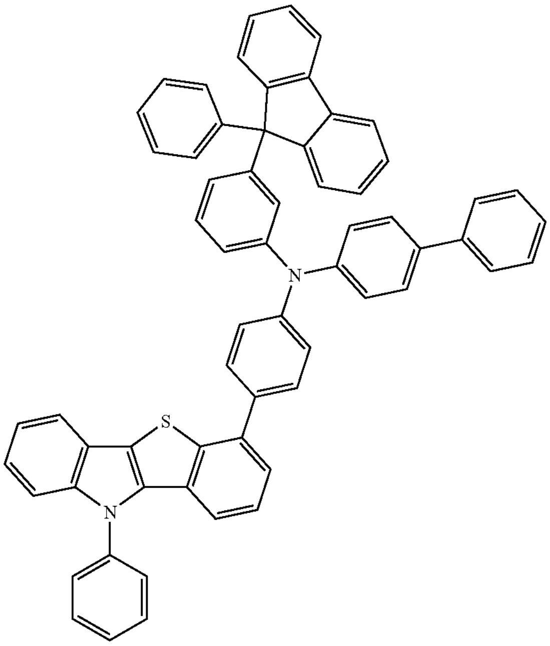

-continued
B86
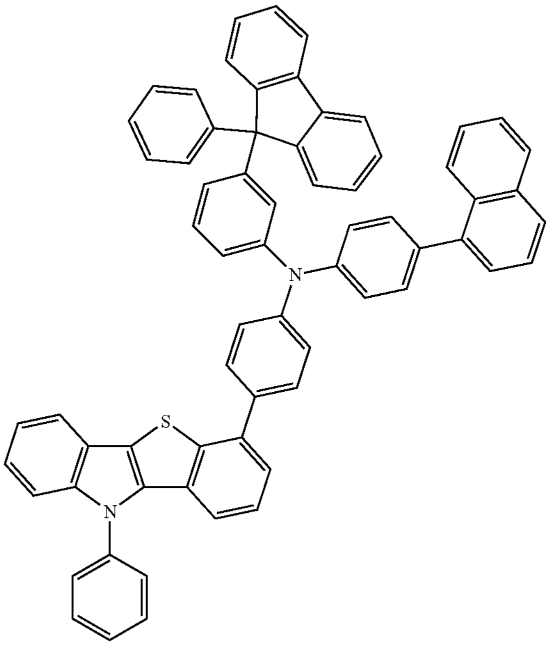
B87
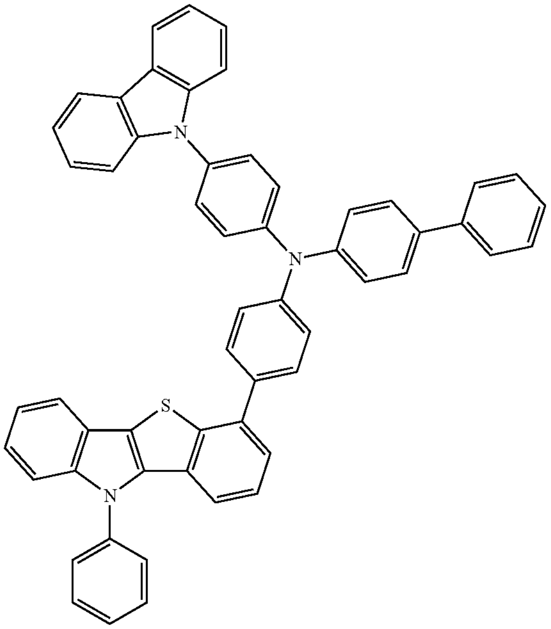
-continued
B88
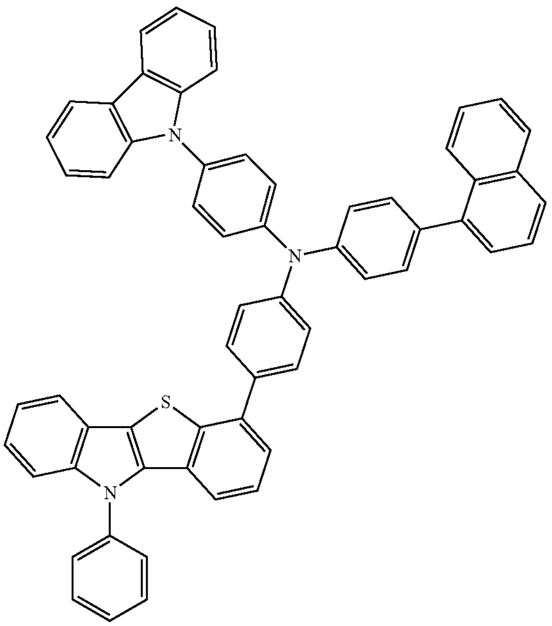
B89
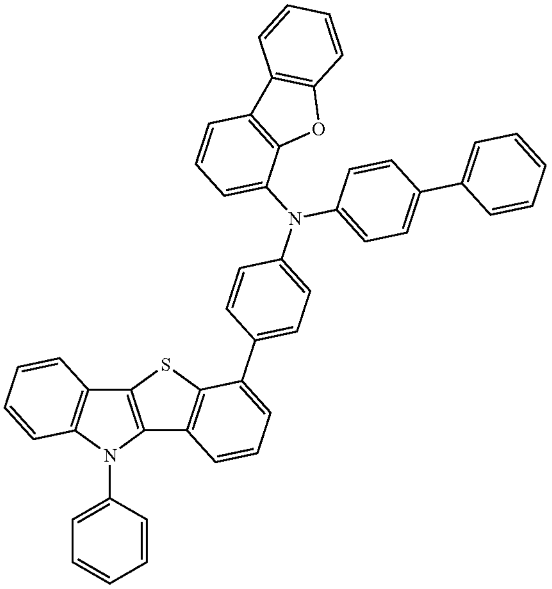

-continued
B90
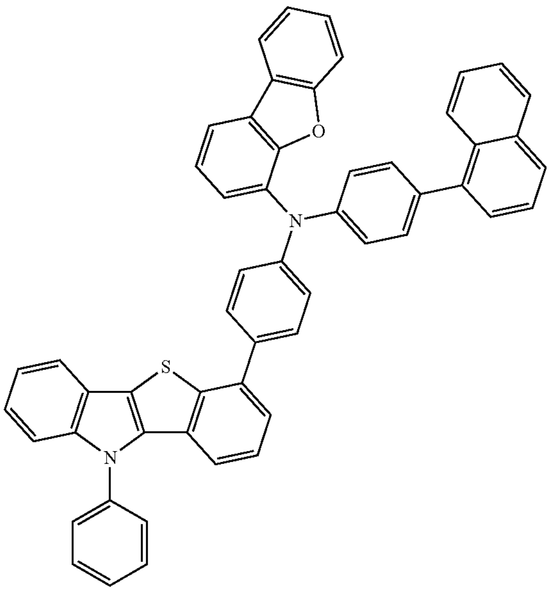
B91
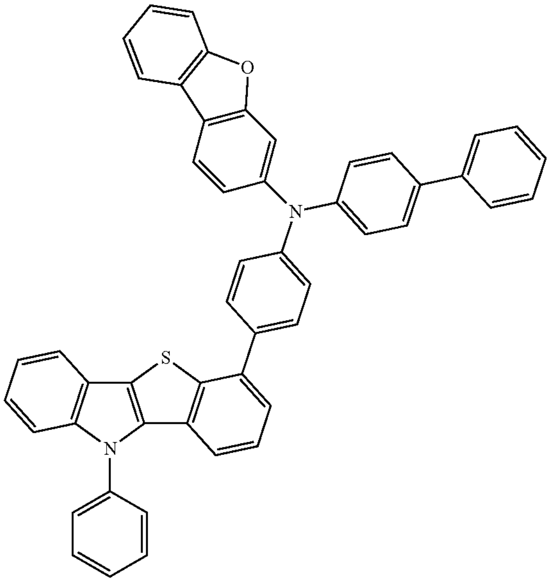
-continued
B92
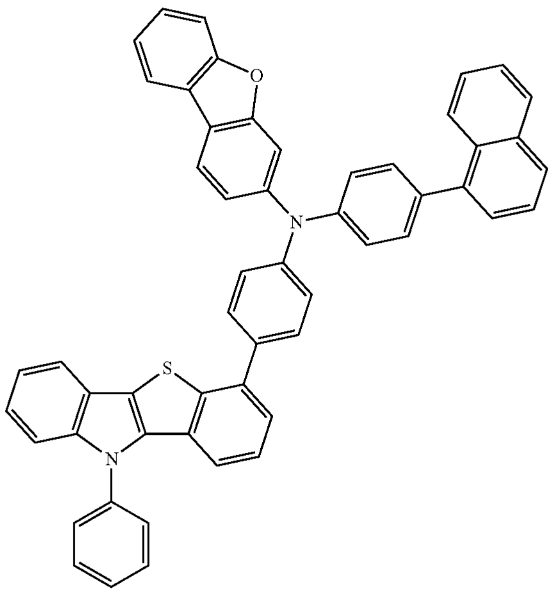
B93
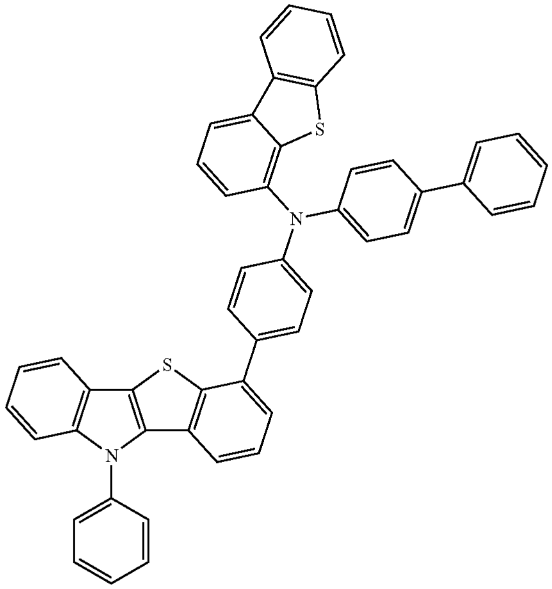

-continued
B94
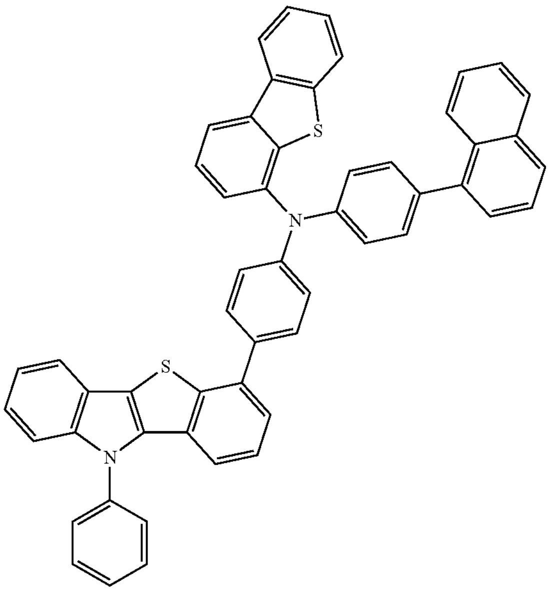
B95
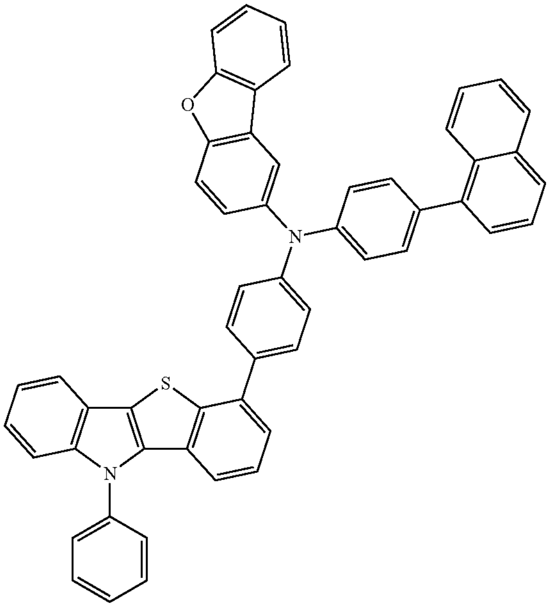
-continued
B96
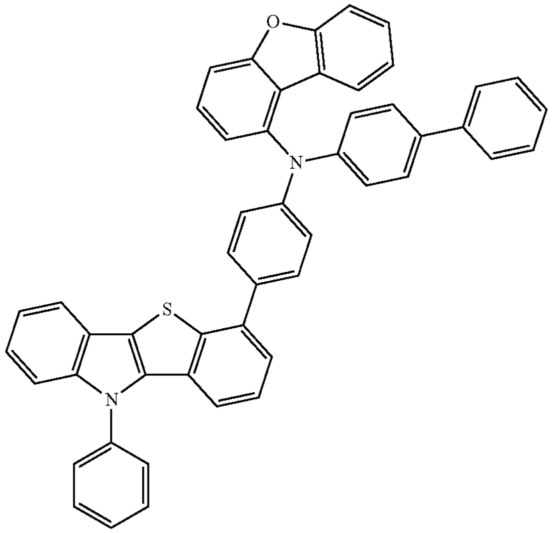
B97
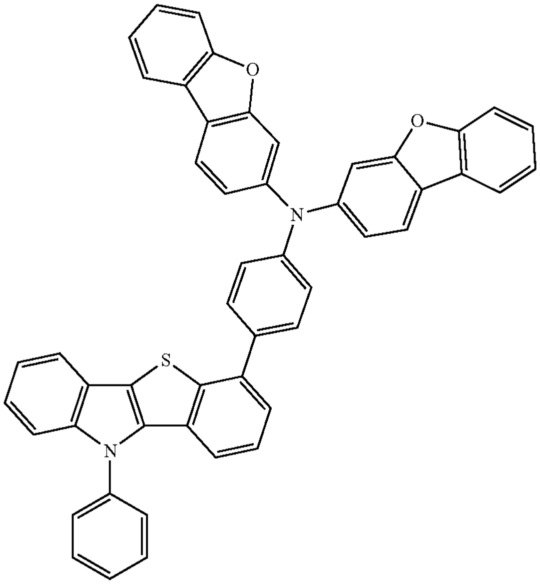

-continued
B98
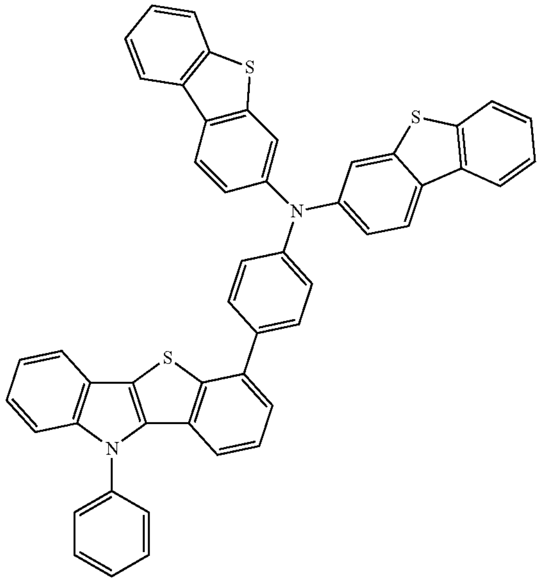
B99
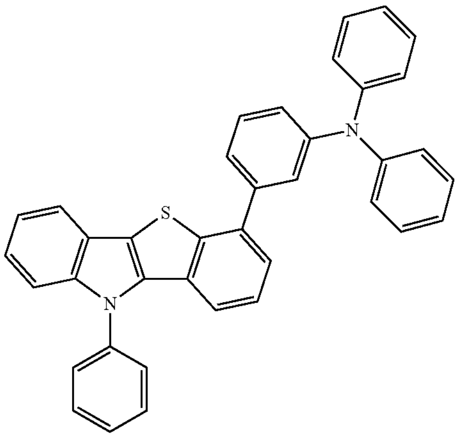
B100
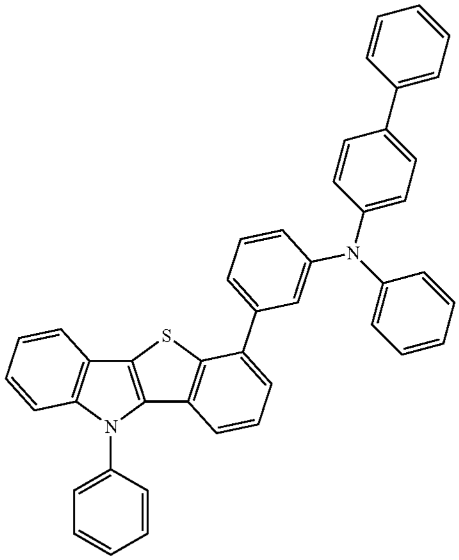
-continued
B101
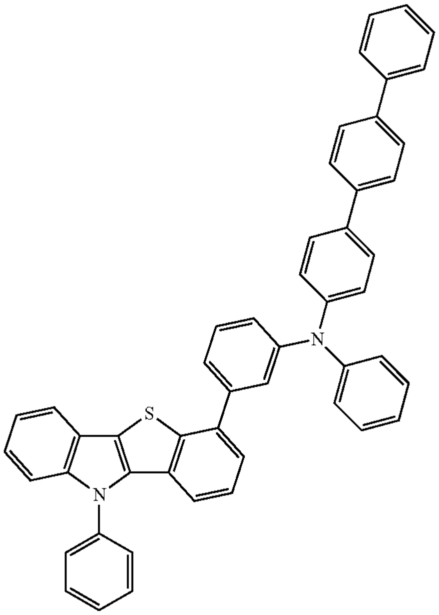
B102
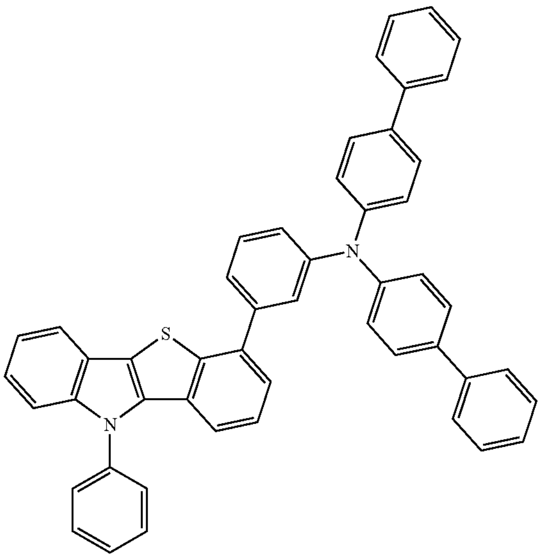

-continued
B103
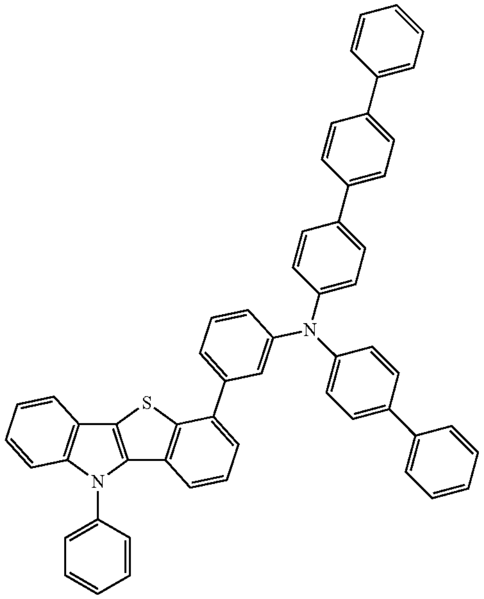
B104
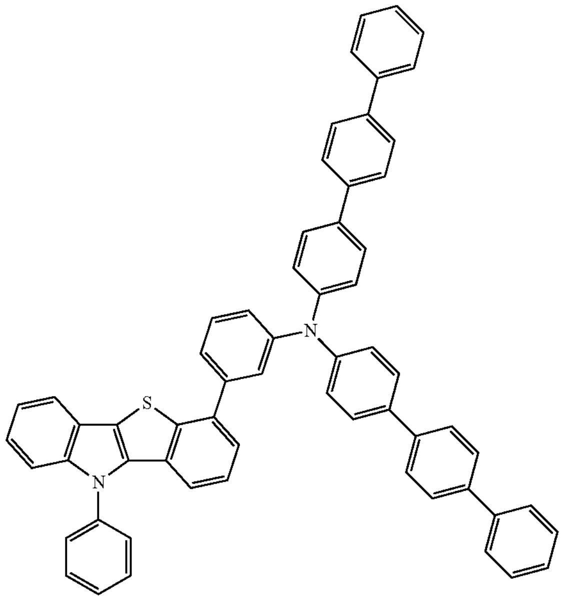
B105
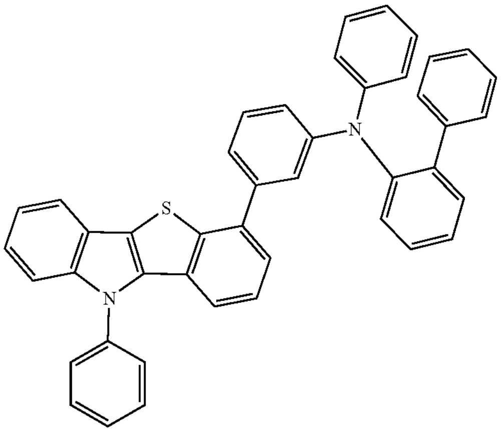
-continued
B106
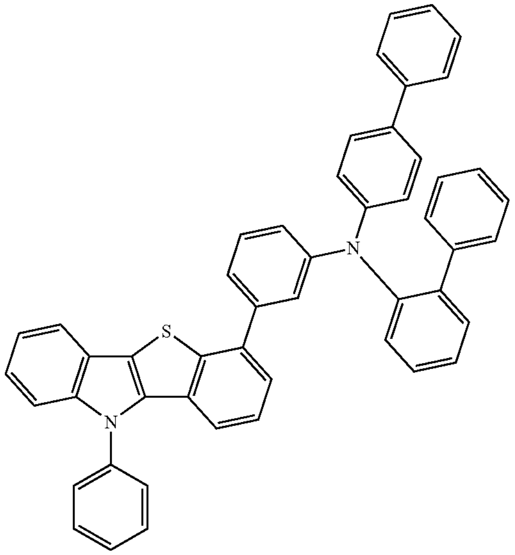
B107
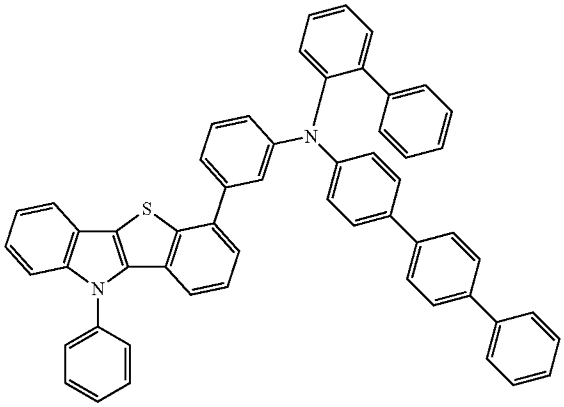
B108
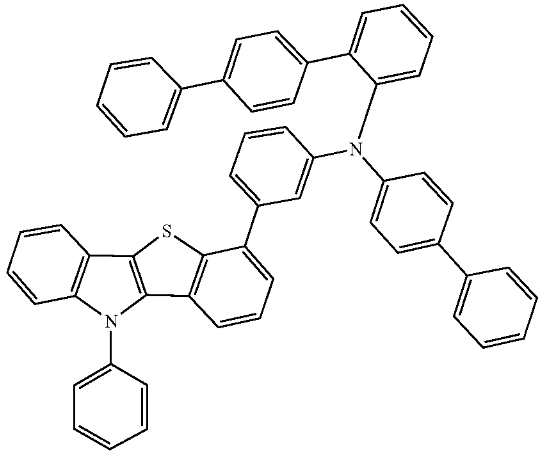

-continued
B109
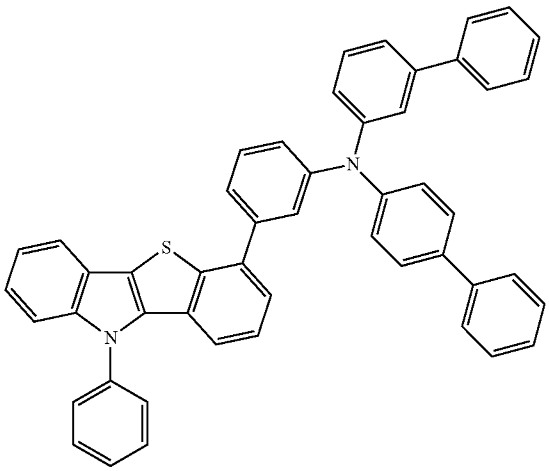
B110
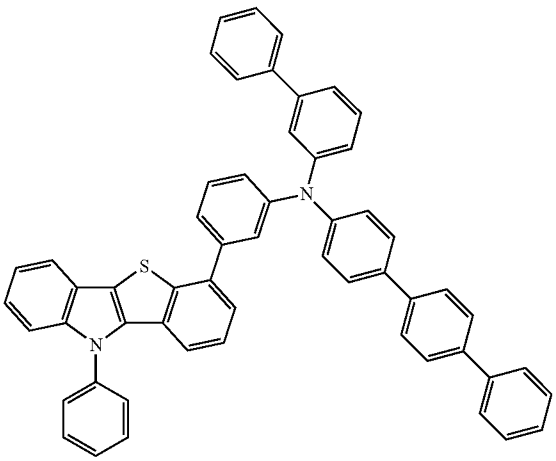
B111
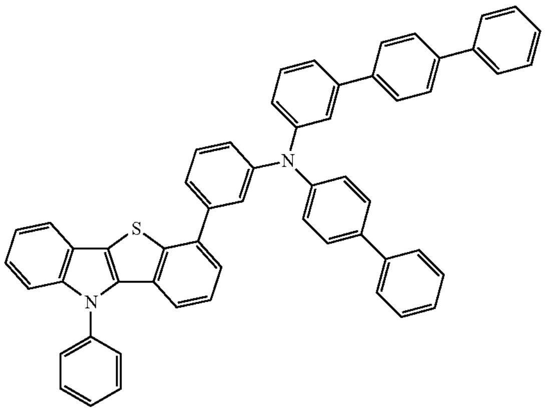
-continued
B112
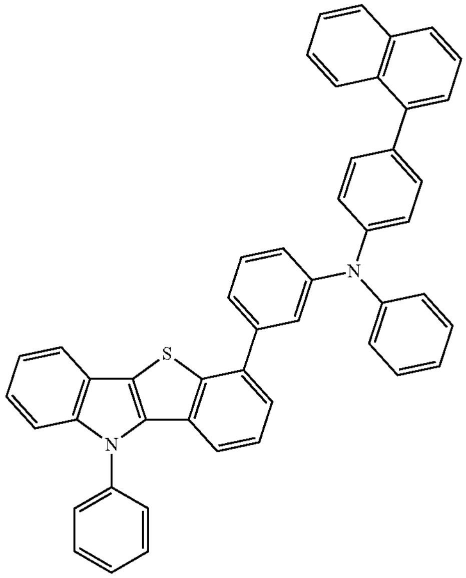
B113
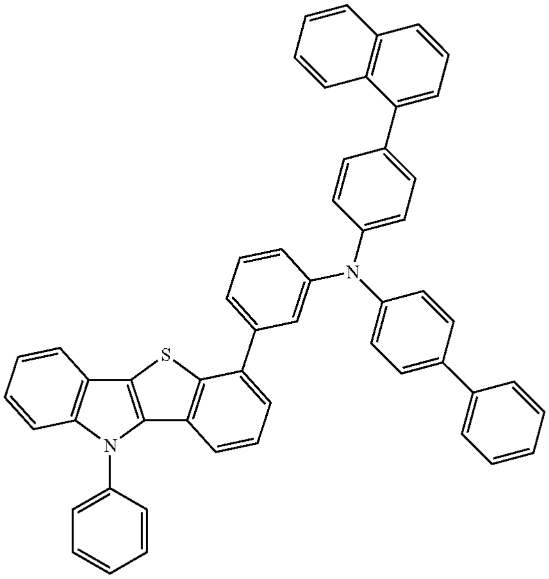
B114
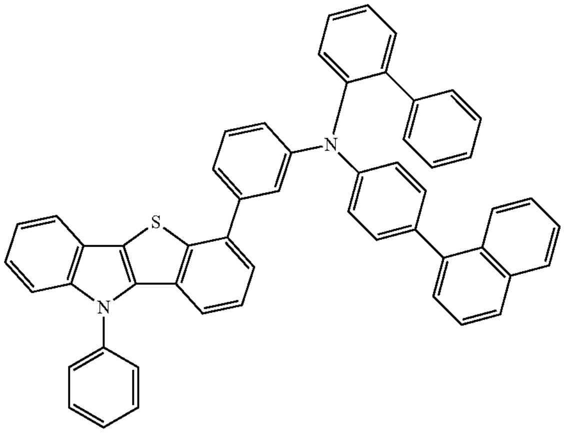

-continued
B115
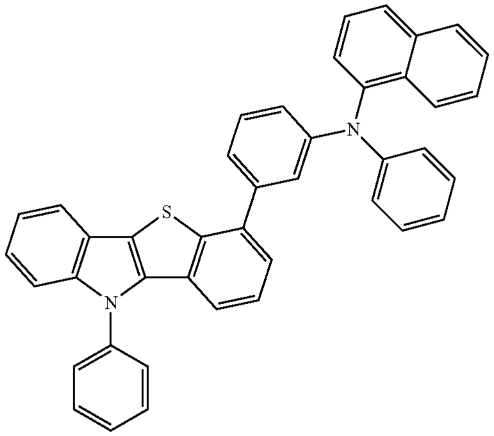
B116
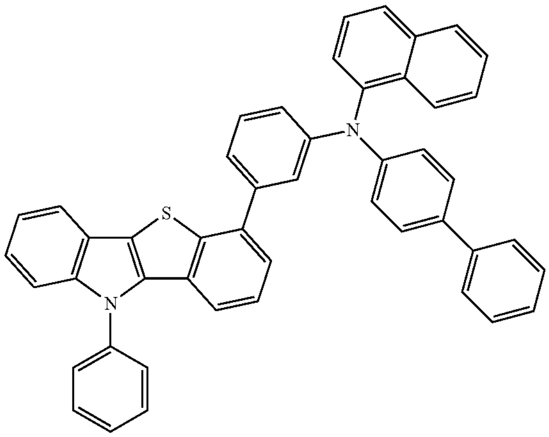
B117
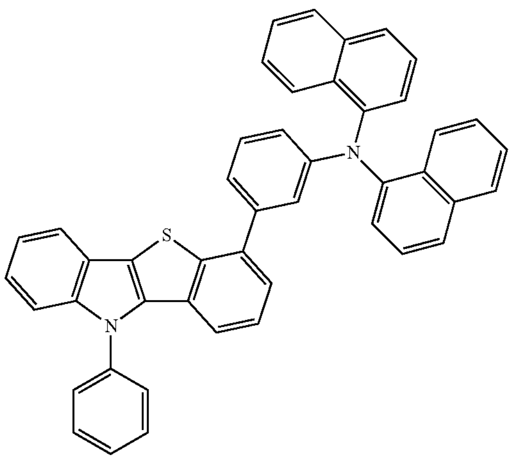
-continued
B118
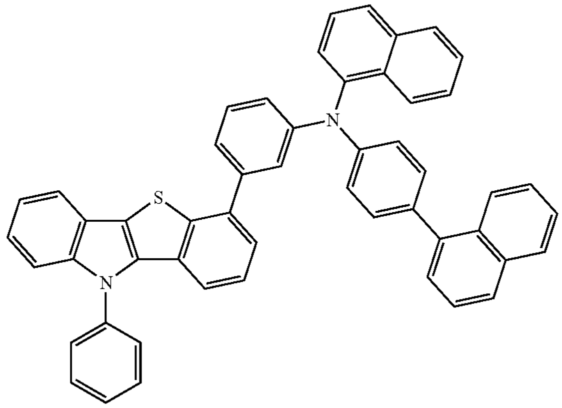
B119
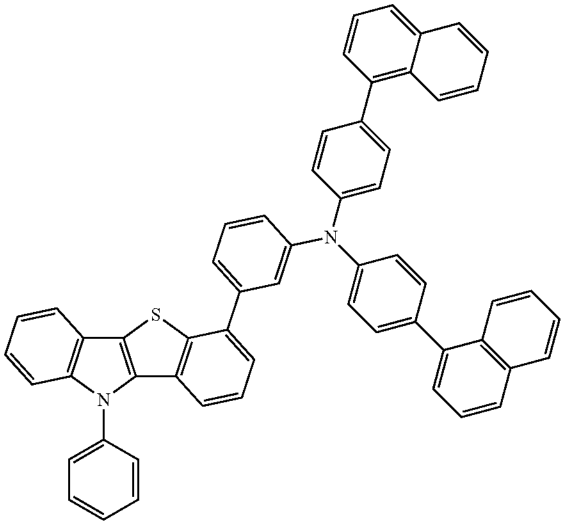
B120
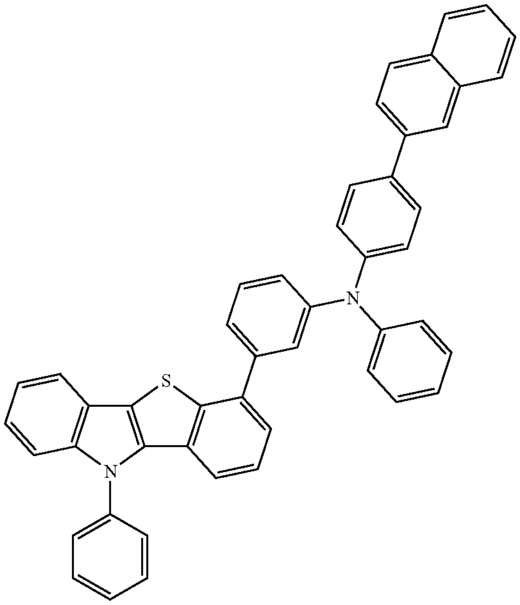

-continued
B121
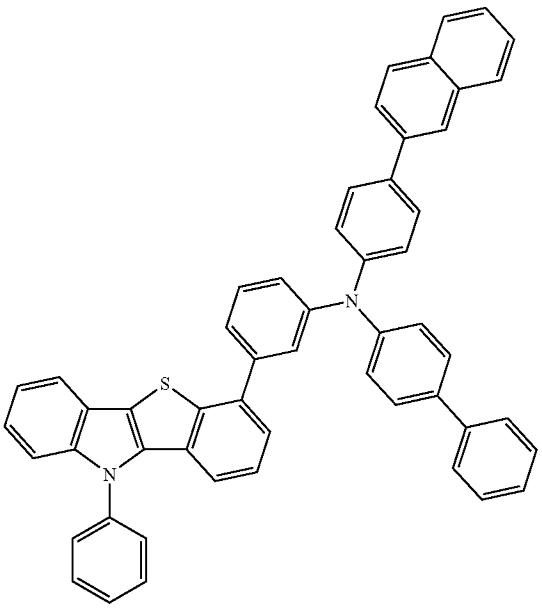
B122
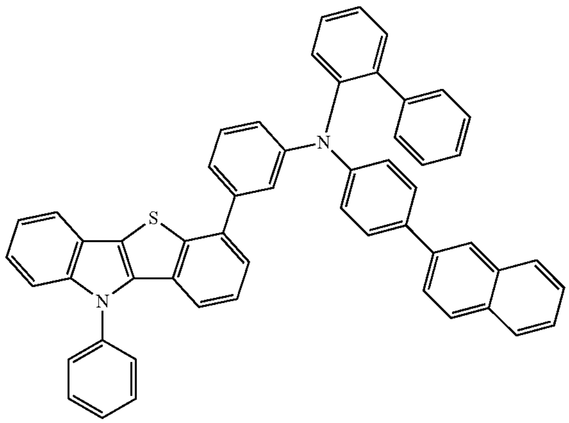
B123
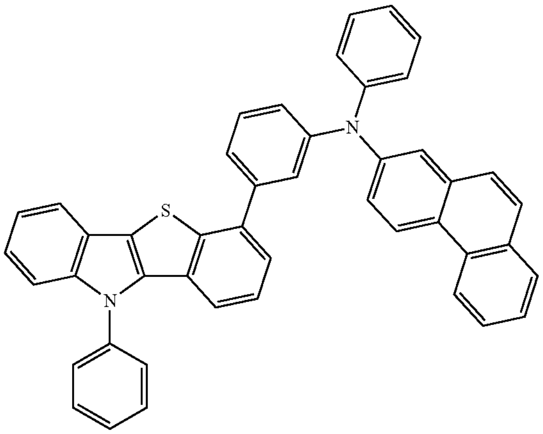
-continued
B124
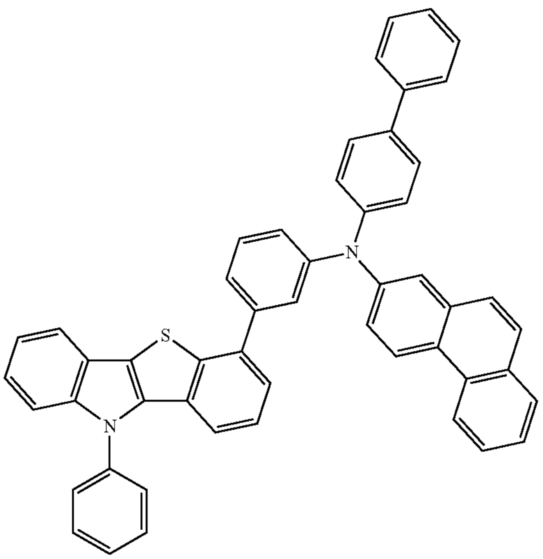
B125
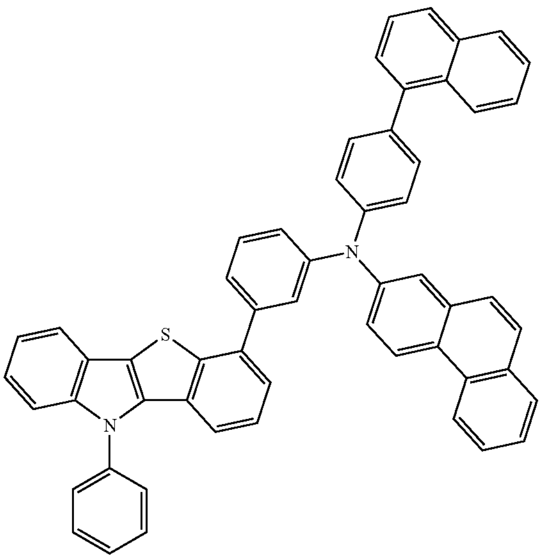
B126
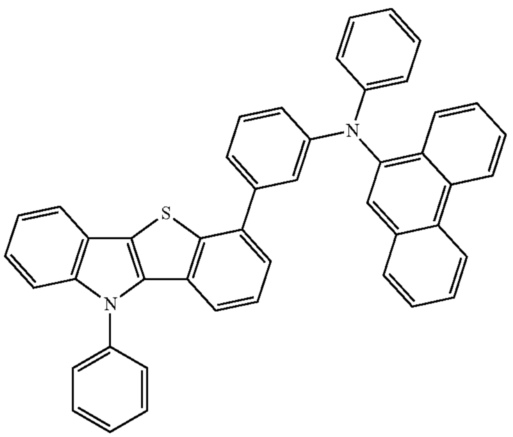

-continued
B127
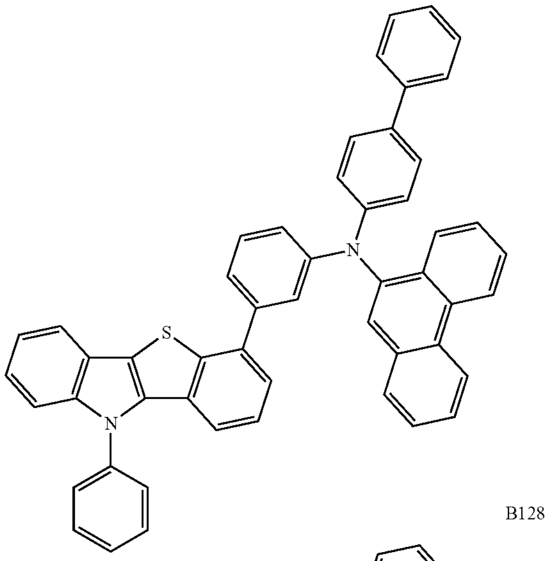
B128
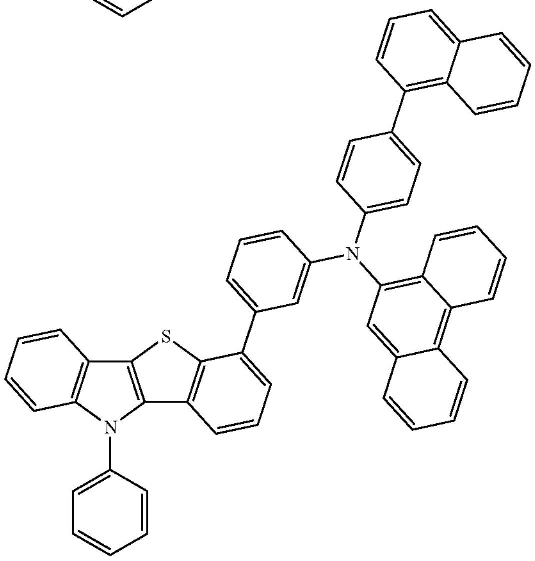
B130
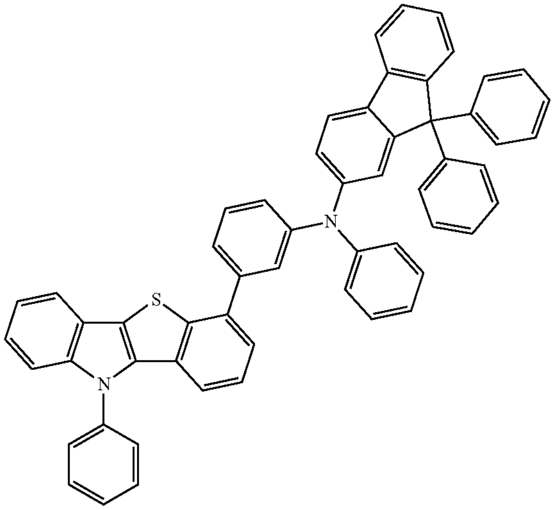
-continued
B131
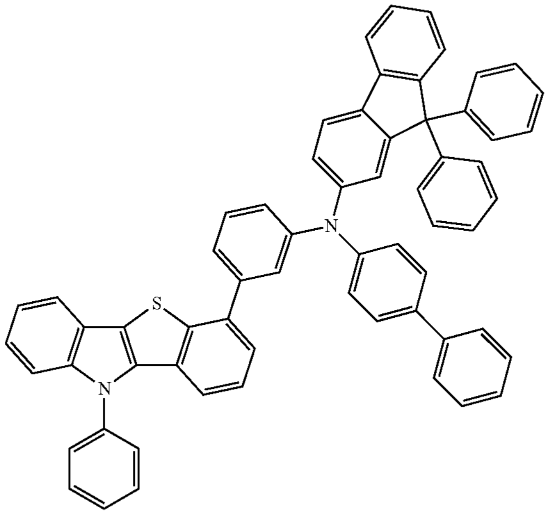
B132
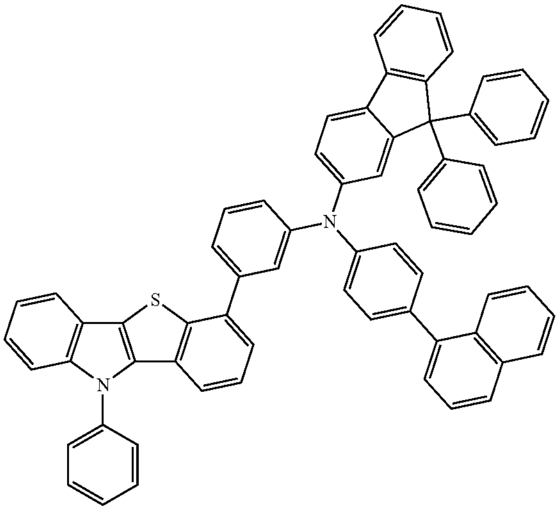
B133
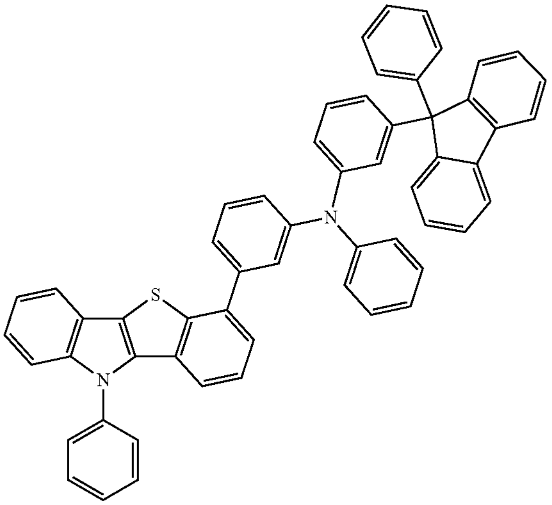

-continued
B134
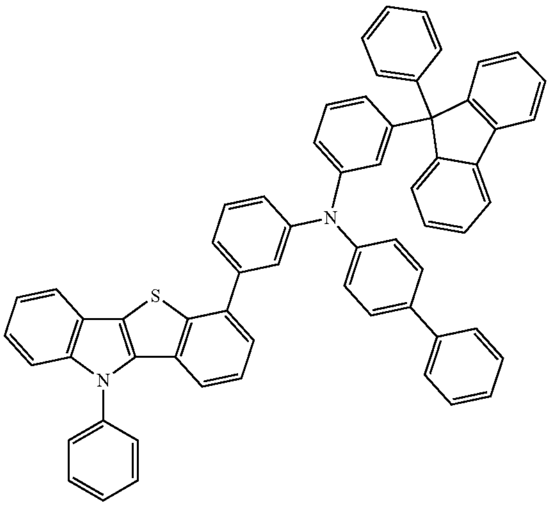
B135
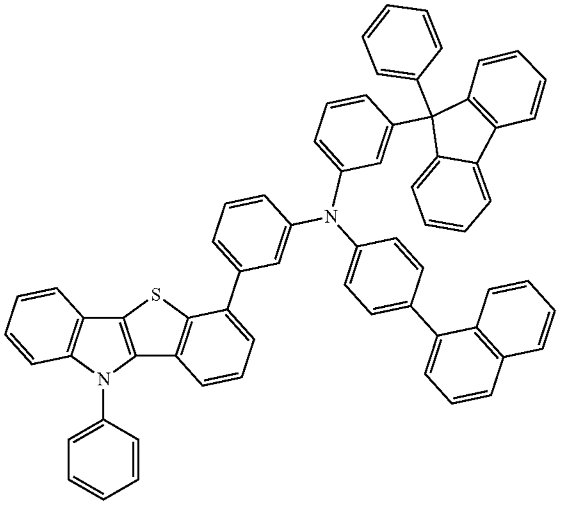
B136
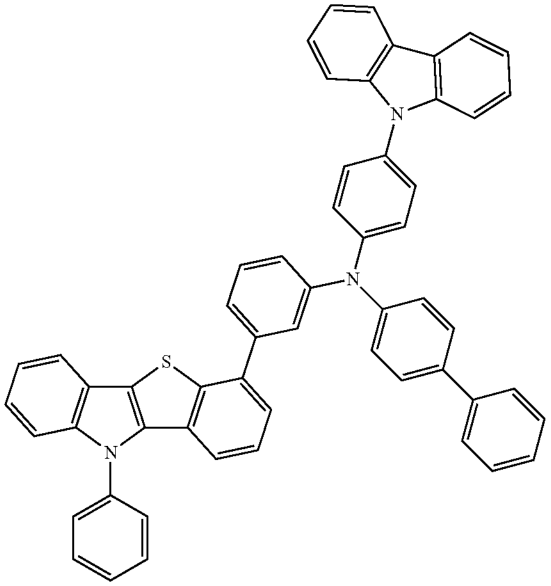
-continued
B137
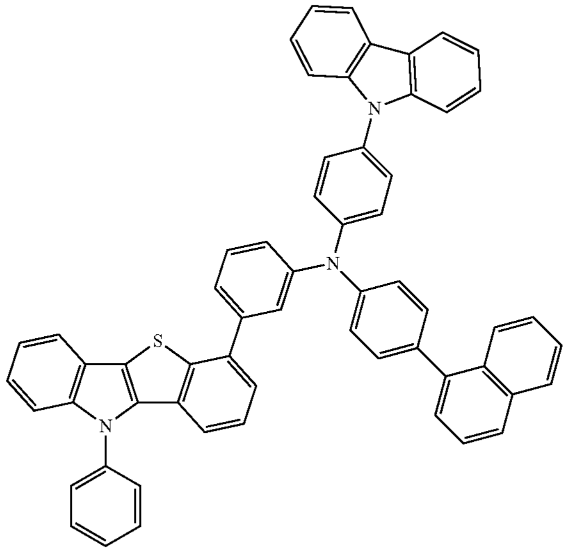
B138
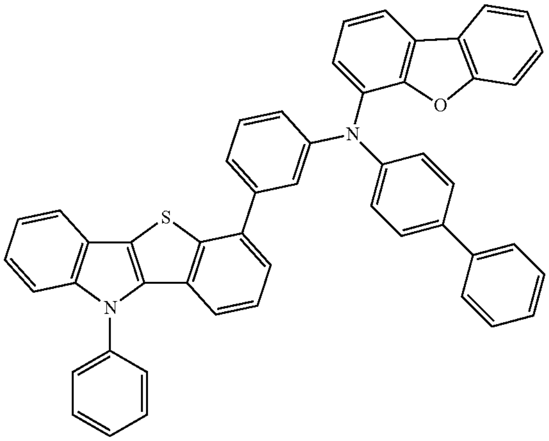
B139
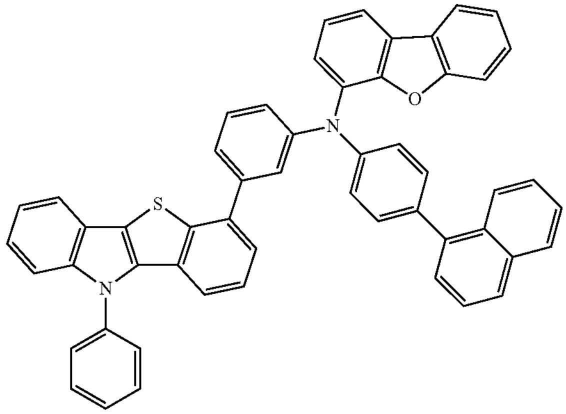

-continued
B140
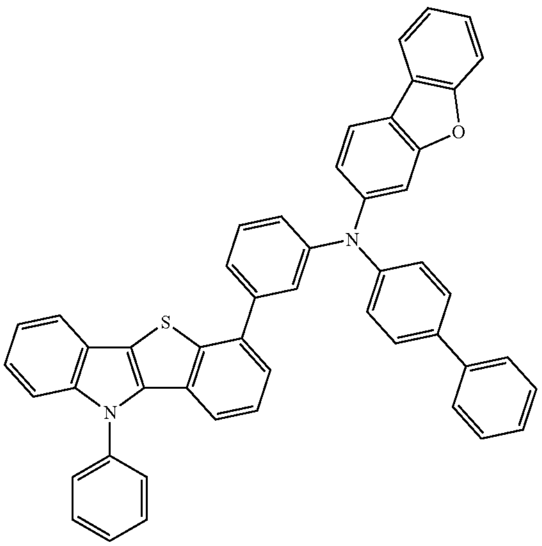
B141
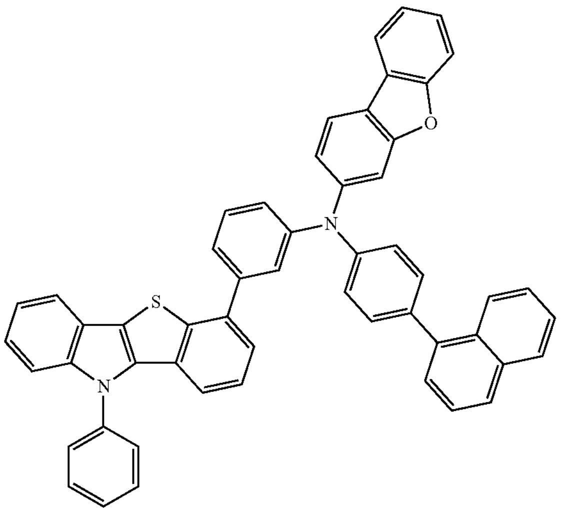
B142
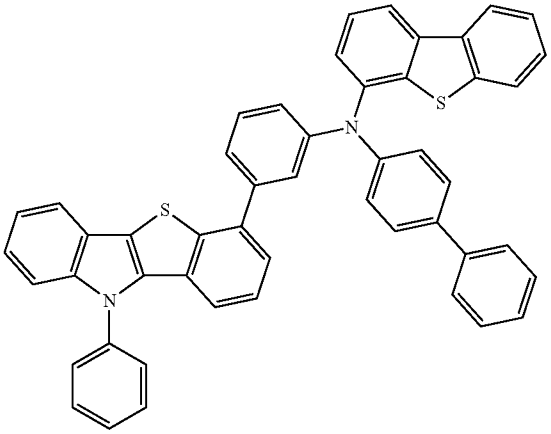
-continued
B143
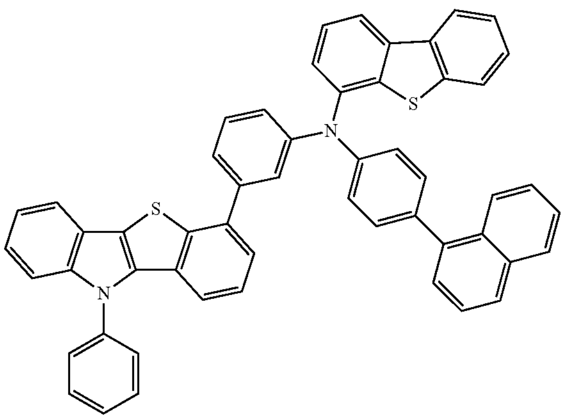
B144
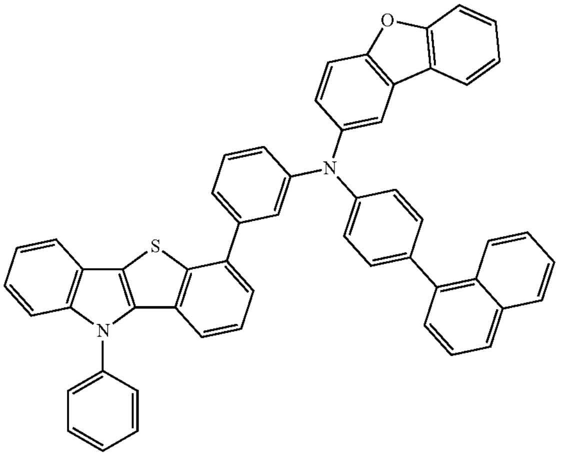
B145
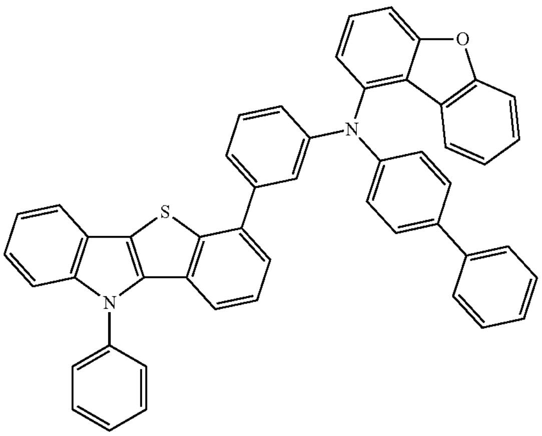

-continued
B146
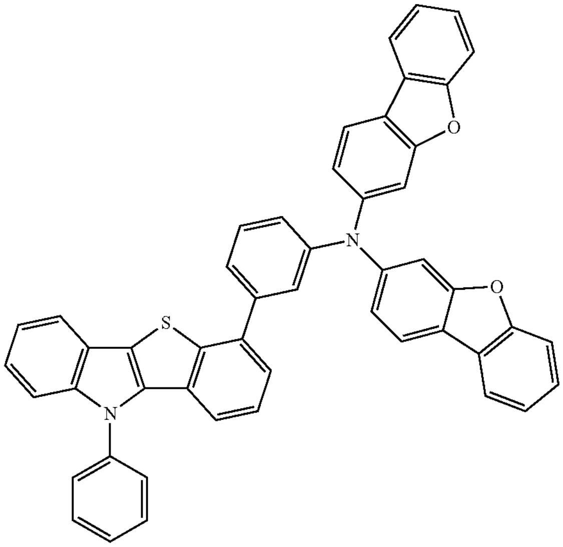
B147
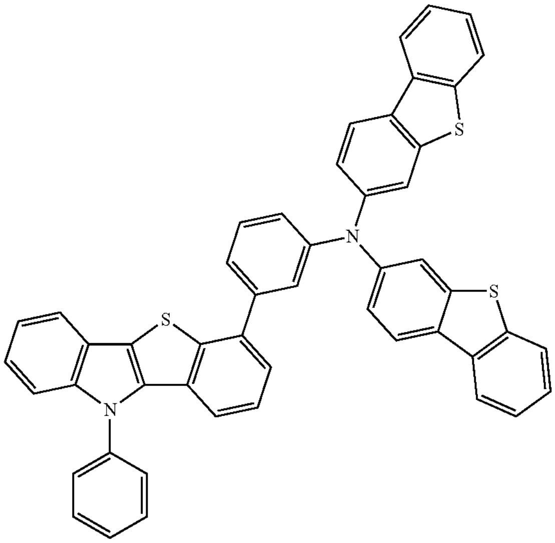
B148
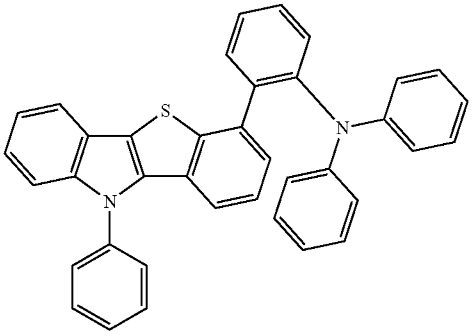
-continued
B149
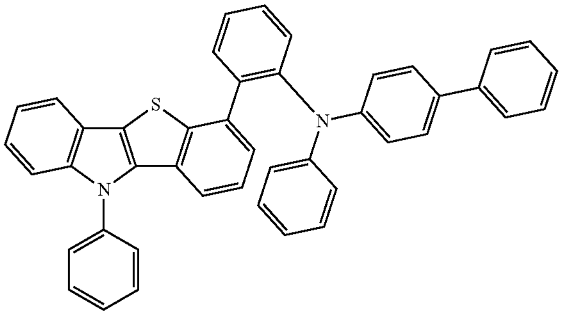
B150
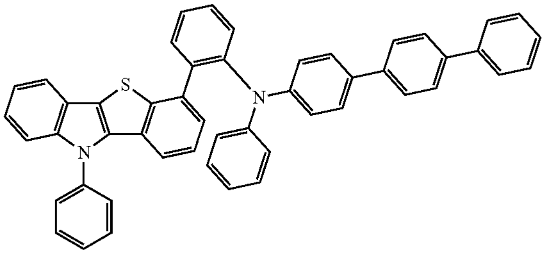
B151
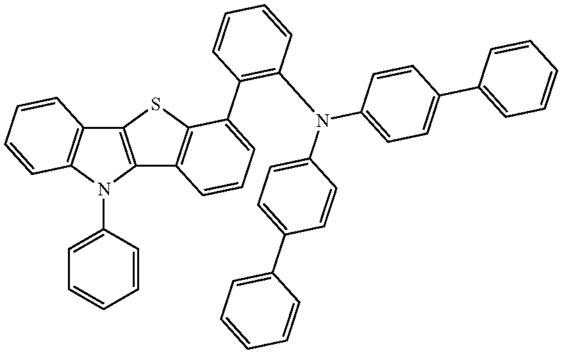
B152
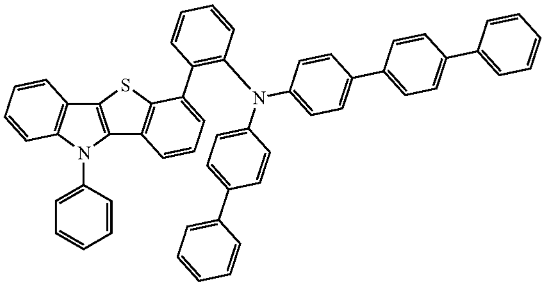

-continued
B153
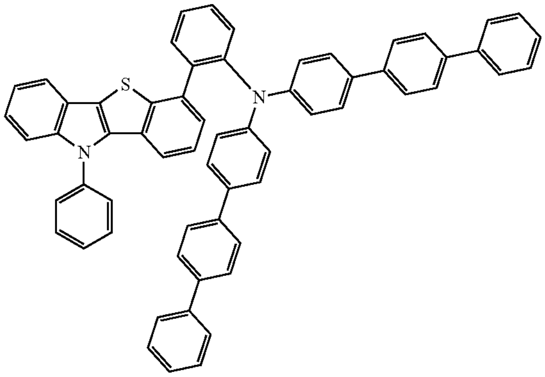
B154
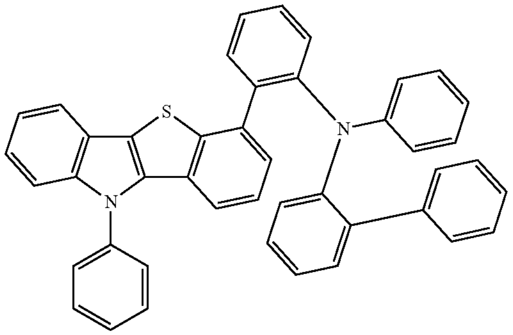
B155
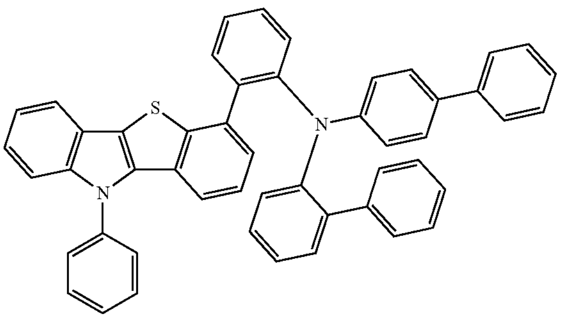
B156
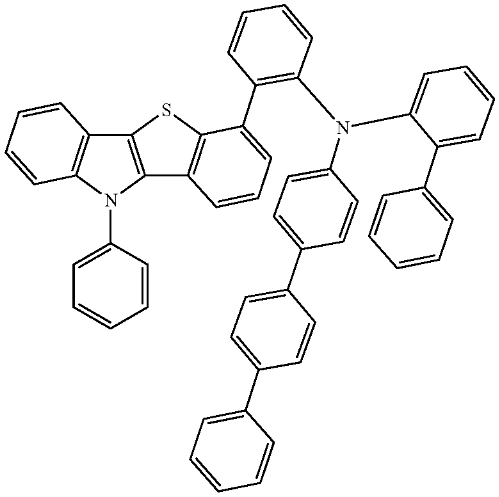
-continued
B157
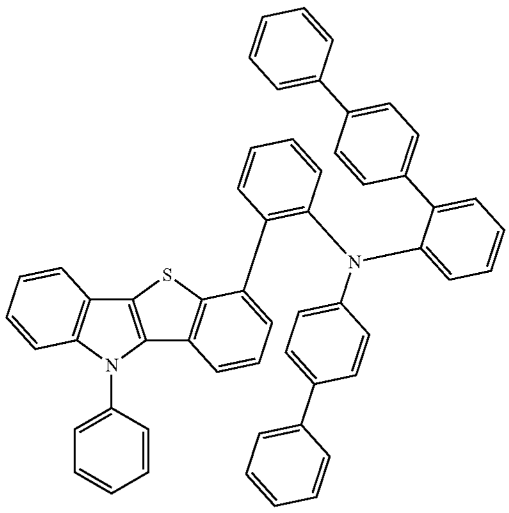
B158
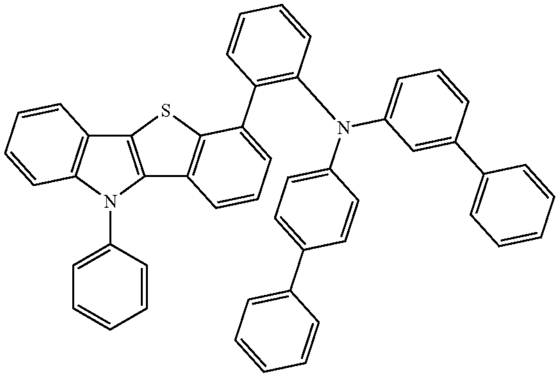
B159
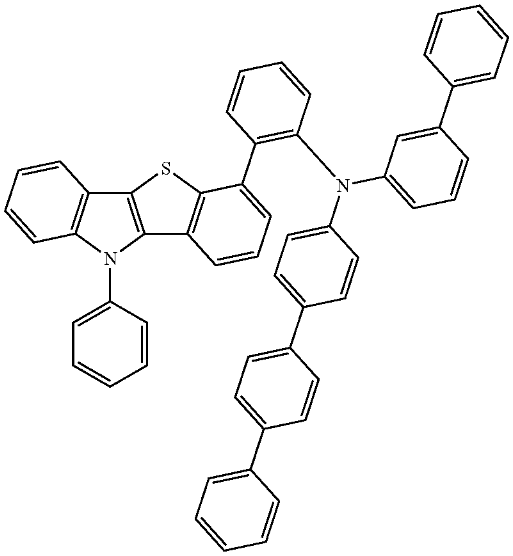

-continued
B160
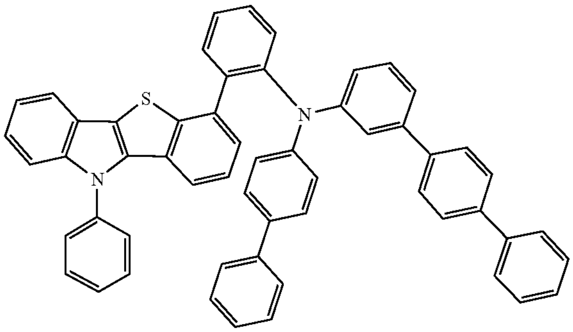
B161
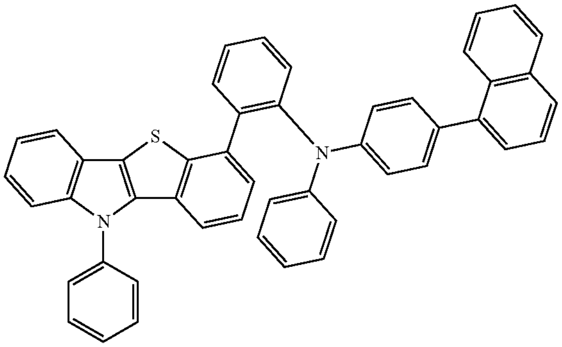
B162
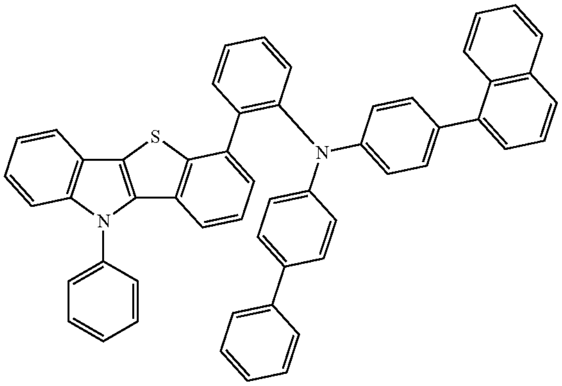
B163
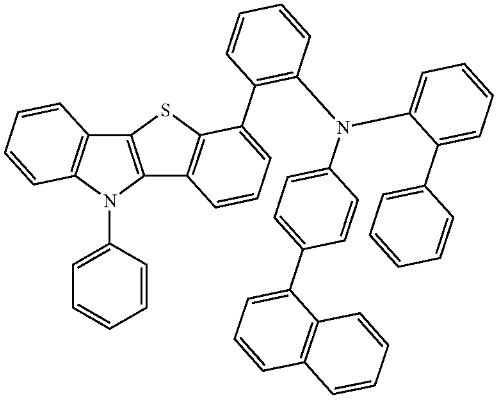
-continued
B164
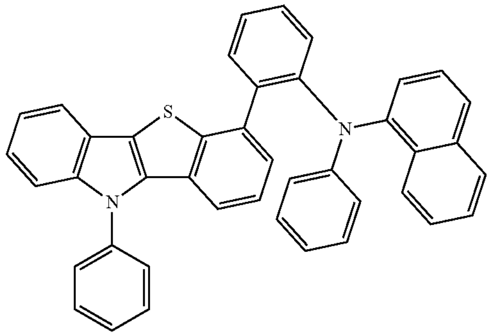
B165
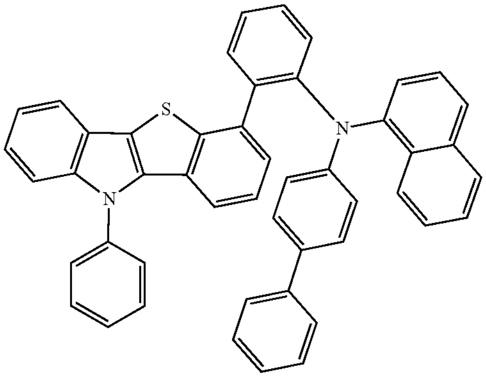
B166
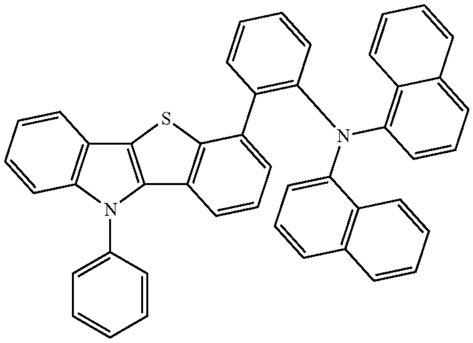
B167
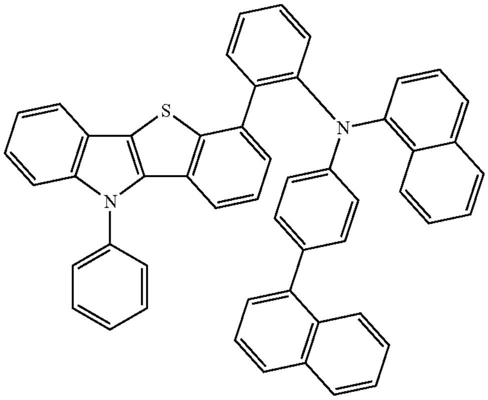

-continued
B168
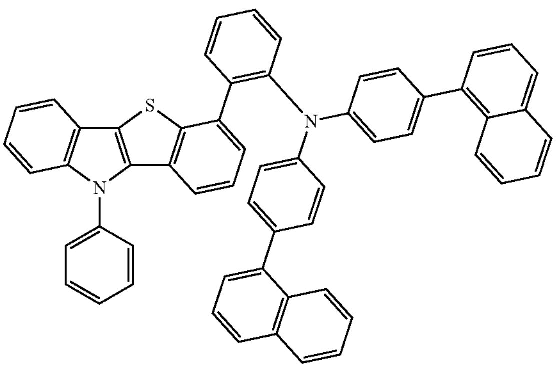
B169
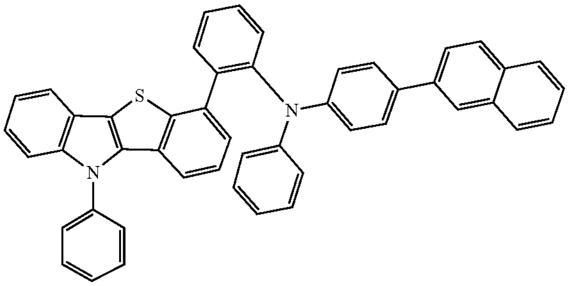
B170
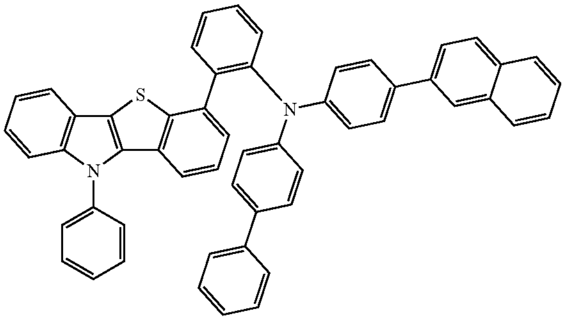
B171
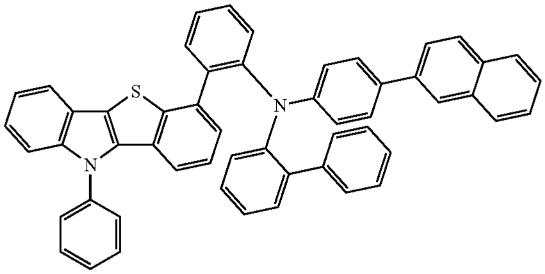
-continued
B172
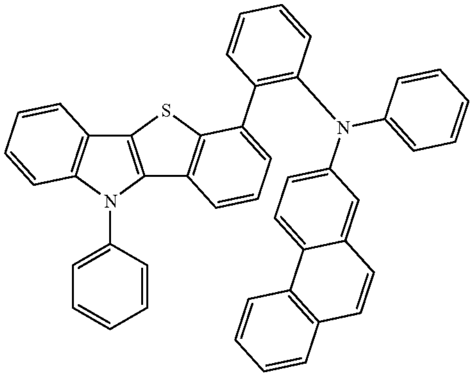
B173
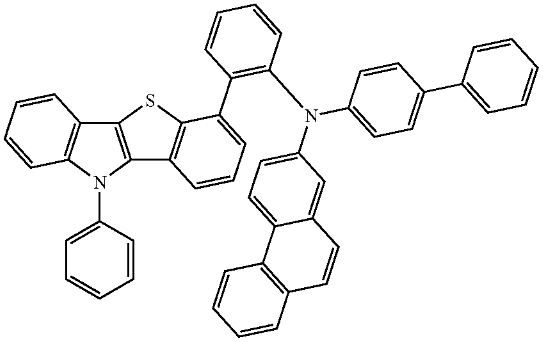
B174
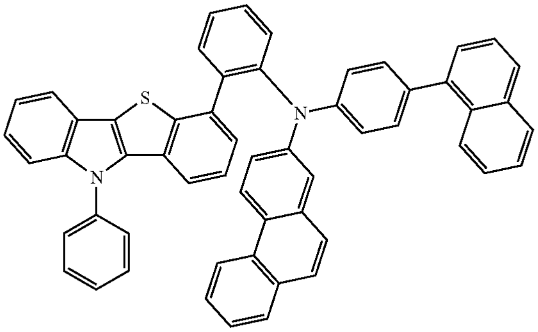
B175
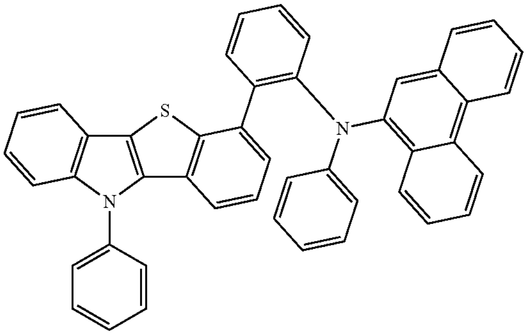

-continued
B176
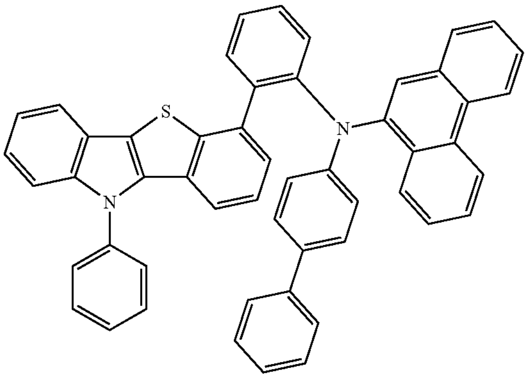
B177
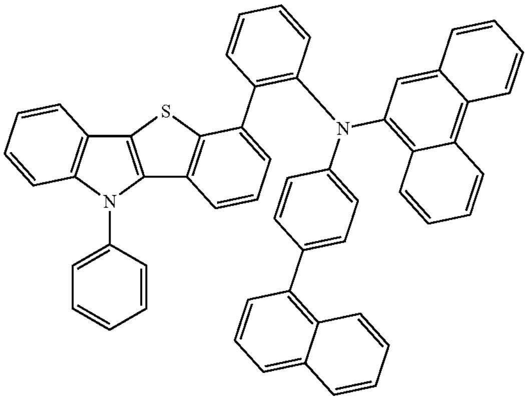
B179
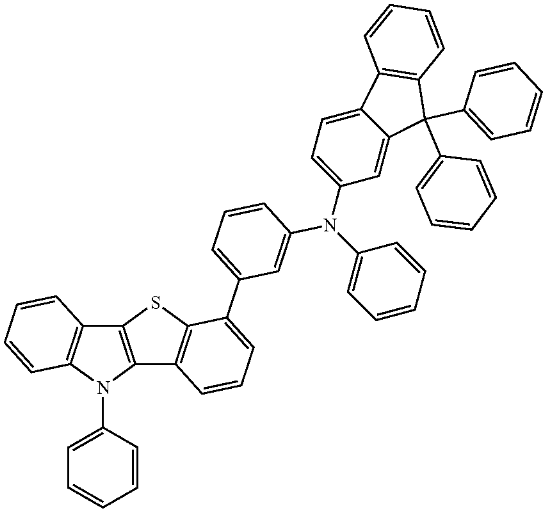
-continued
B180
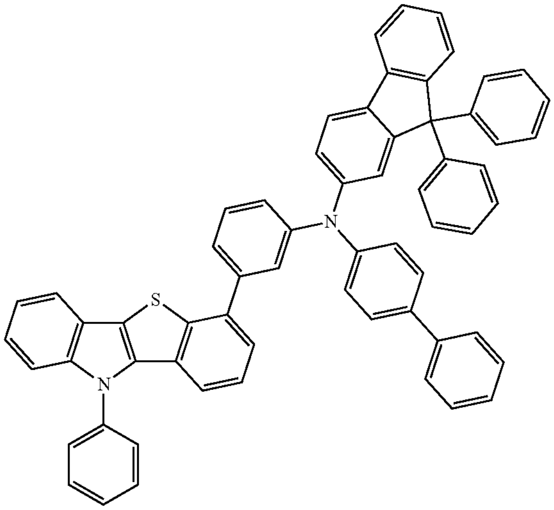
B181
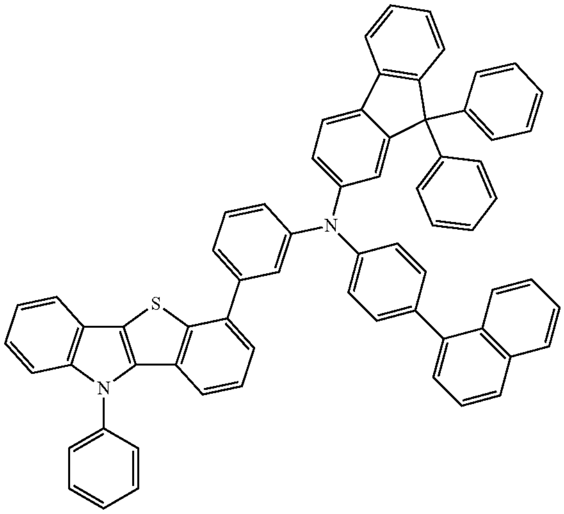
B182
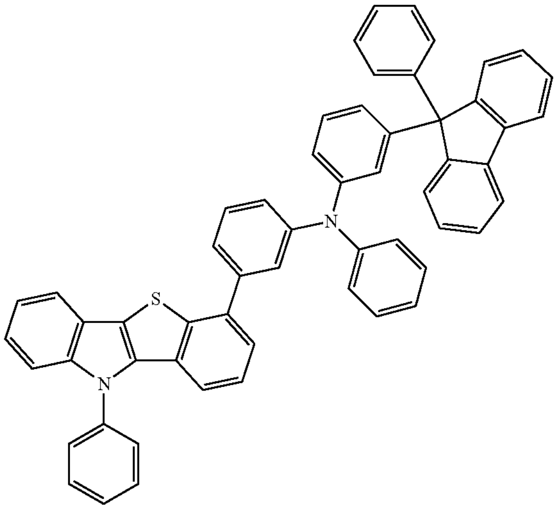

-continued
B183
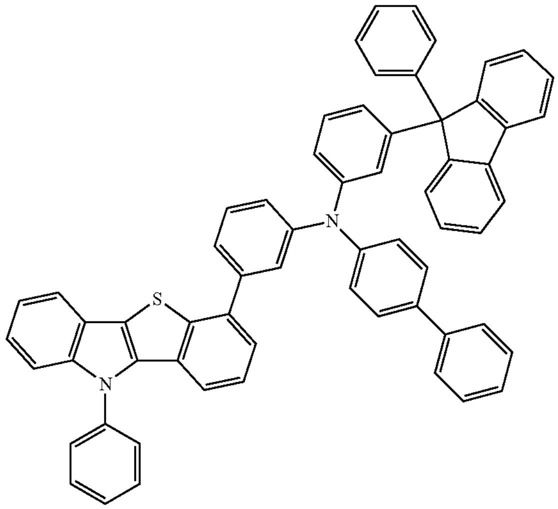
B184
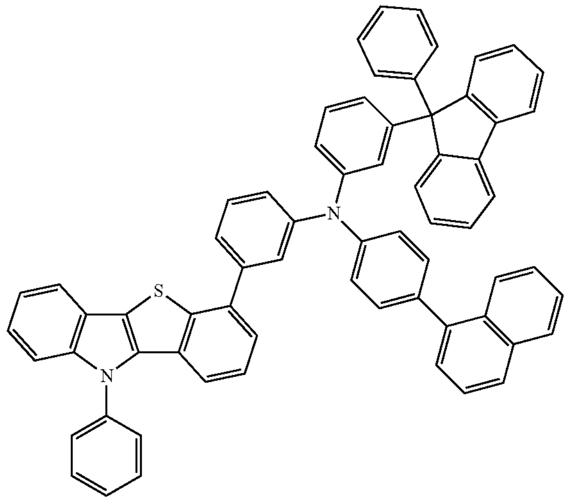
B185
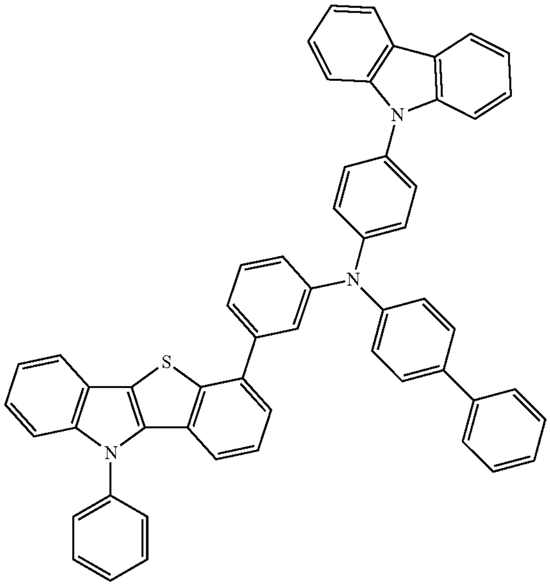
-continued
B186
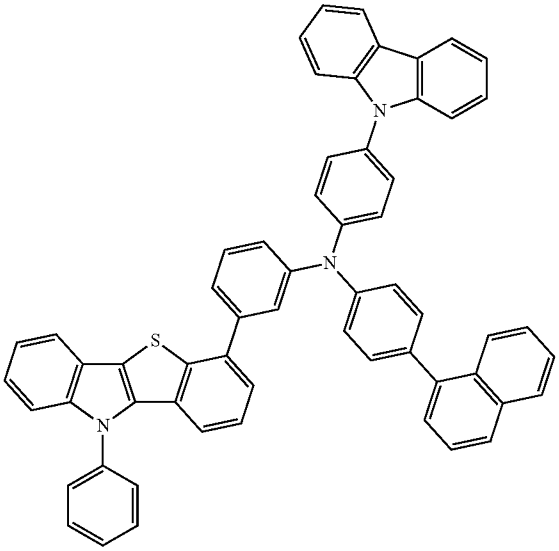
B187
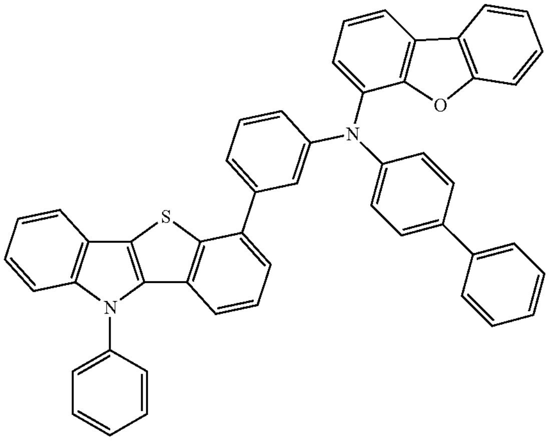
B188
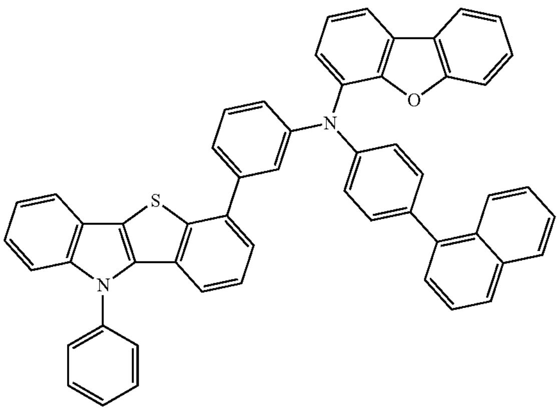

-continued
B189
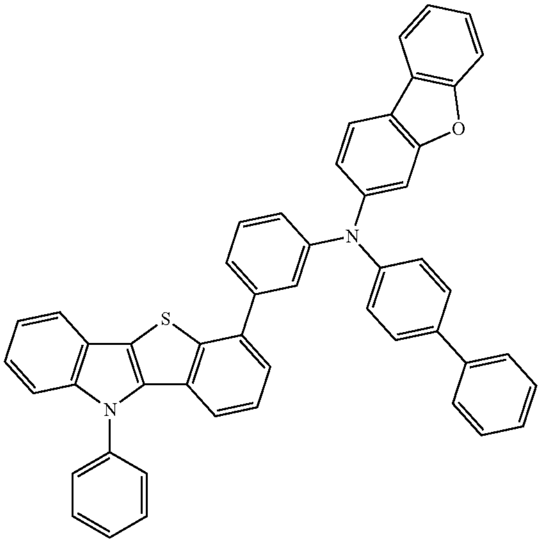
B190
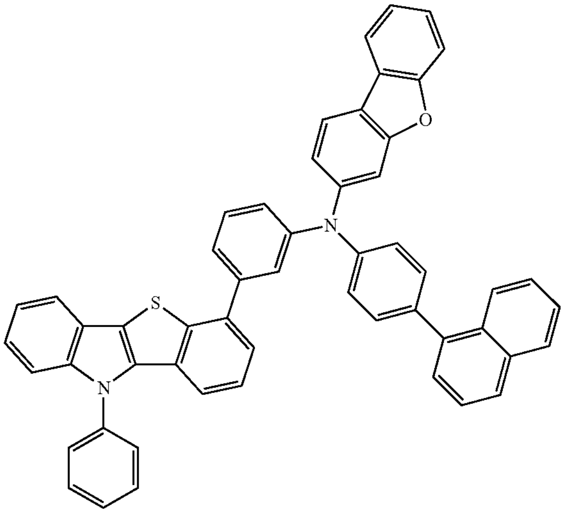
B191
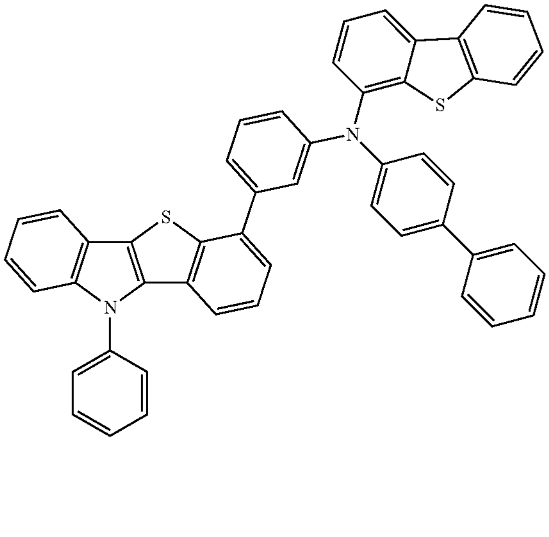
-continued
B192
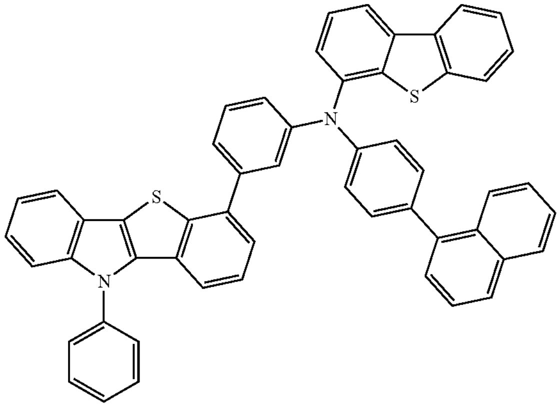
B193
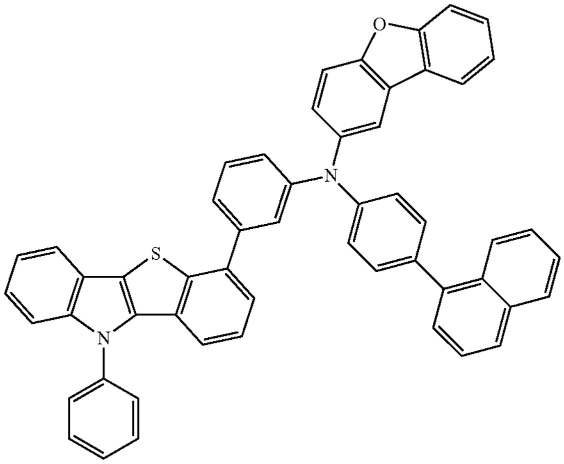
B194
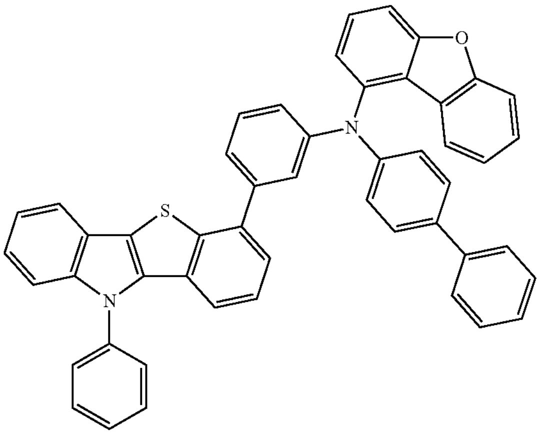

-continued
B195
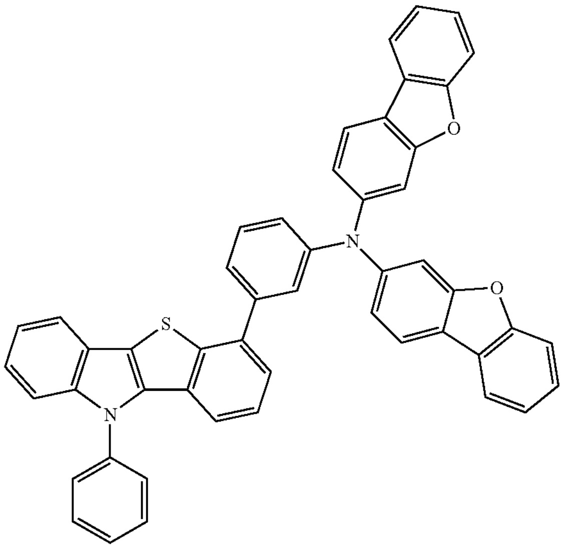
.
-continued
B196
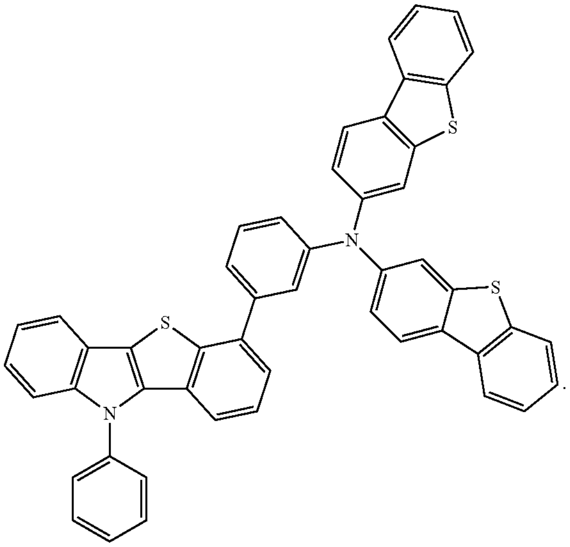
.
* * * * *